(12) United States Patent
Zhou et al.

(10) Patent No.: US 12,358,932 B2
(45) Date of Patent: Jul. 15, 2025

(54) CHEMICAL COMPOUNDS

(71) Applicant: BORAH, INC., Nashville, TN (US)

(72) Inventors: Yasheen Zhou, Moraga, CA (US);
Chun Yu Liu, Durham, NC (US);
Chunliang Liu, Cary, NC (US);
Yong-Kang Zhang, San Jose, CA (US)

(73) Assignee: BORAH, INC., Nashville, TN (US)

( * ) Notice: Subject to any disclaimer, the term of this patent is extended or adjusted under 35 U.S.C. 154(b) by 123 days.

(21) Appl. No.: 17/623,961

(22) PCT Filed: Jul. 2, 2020

(86) PCT No.: PCT/US2020/070234
§ 371 (c)(1),
(2) Date: Dec. 30, 2021

(87) PCT Pub. No.: WO2021/003501
PCT Pub. Date: Jan. 7, 2021

(65) Prior Publication Data
US 2024/0368196 A1    Nov. 7, 2024

Related U.S. Application Data

(60) Provisional application No. 62/949,301, filed on Dec. 17, 2019, provisional application No. 62/949,280, filed on Dec. 17, 2019, provisional application No. 62/916,697, filed on Oct. 17, 2019, provisional application No. 62/916,700, filed on Oct. 17, 2019, provisional application No. 62/870,537, filed on Jul. 3, 2019.

(51) Int. Cl.
*C07F 5/02* (2006.01)
*A61K 31/69* (2006.01)
*A61P 29/00* (2006.01)

(52) U.S. Cl.
CPC .............. *C07F 5/025* (2013.01); *A61K 31/69* (2013.01); *A61P 29/00* (2018.01)

(58) Field of Classification Search
CPC ............ C07F 5/02; A61K 31/69; A61P 29/00
USPC ........................................................... 514/64
See application file for complete search history.

(56) References Cited

U.S. PATENT DOCUMENTS

| 8,470,803 B2 | 6/2013 | Akama |
| 9,346,788 B2 | 5/2016 | Akama |
| 2015/0291629 A1 | 10/2015 | Akama |

FOREIGN PATENT DOCUMENTS

| CN | 106478700 A | 3/2017 |
| CN | 108329274 A | 7/2018 |
| CN | 108341835 A | 7/2018 |
| WO | 2010/027975 A1 | 3/2010 |
| WO | 2011/017125 A1 | 2/2011 |
| WO | 2014/066659 A1 | 5/2014 |

OTHER PUBLICATIONS

Dong, C., et al., "Treatment of skin inflammation with benzoxaborole phosphodiesterase inhibitors: selectivity, cellular activity, and effect on cytokines associated with skin inflammation and skin architecture changes", The Journal of Pharmacology and Experimental Therapeutics, (Sep. 2016), vol. 358, pp. 413-422.
Grimster, N.P., et al.,. "Discovery and optimization of a novel series of highly selective JAK1 kinase inhibitors", Journal of Medicinal Chemistry, (2018), vol. 61, pp. 5235-5244.
Nazarian, R., et al., "AN-2728, a PDE4 inhibitor for the potential topical treatment of psoriasis and atopic dermatitis", Current Opinion in Investigational Drugs, (2009), vol. 10, No. 11, pp. 1236-1242.
Patel, A.A., et al., "The next generation of JAK inhibitors: an update on Fedratinib, Momelotonib, and Pacritinib", Current Hematologic Malignancy Reports, (Dec. 2020), vol. 15, No. 6, pp. 409-418.
Ren, J., et al., "Design and synthesis of boron-containing diphenylpyrimidines as potent BTK and JAK3 dual Inhibitors", Bioorganic & Medicinal Chemistry, (2020), vol. 28, No. 2, pp. 1-12.
Roblin, D., et al., "Topical TrkA kinase inhibitor CT327 is an effective, novel therapy for the treatment of pruritus due to psoriasis: results from experimental studies, and efficacy and safety of CT327 in a phase 2b clinical trial in patients with psoriasis", Acta Derm. Venereol., (2015), vol. 95, pp. 542-548.
Kisseleva, T., et al., "Signaling through the JAK/STAT pathway, recent advances and future challenges", Gene (2002), vol. 285, pp. 1-24.
Yamaoka, K., et al., "The Janus kinases (JAKs)", Genome Biology, (2004), vol. 5, pp. 253.1-253.6.
Li, H., et al., "Phosphodiesterase-4 inhibitors for the treatment of inflammatory diseases", Frontiers in Pharmacology, (Oct. 2018), vol. 9, pp. 1-21.
Mata, P., et al., "The CIP sequence rules: analysis and proposal for a revision", Tetrahedron: Asymmetry, (1993), vol. 4, No. 4, pp. 657-668.
Schwartz, D.M., et al., "JAK inhibition as a therapeutic strategy for immune and inflammatory diseases", Nature Reviews Drug Discovery, (2017), vol. 16, pp. 843-862.
Cahn, R.S., et al., (1966), Angew. Chem. 78: 413-447, Angew. Chem., Int. Ed. Engl. 5: 385-414 (errata: Angew. Chem., Int. Ed. Engl. 5:511).

(Continued)

*Primary Examiner* — Raymond J Henley, III
(74) *Attorney, Agent, or Firm* — Barnes & Thornburg LLP

(57) ABSTRACT

The present disclosure describes novel compounds, or their pharmaceutically acceptable salts, pharmaceutical compositions containing them, and their medical uses. Compounds of the disclosure have activity as dual modulators of Janus kinase (JAK), alone, or in combination with one or more of an additional mechanism, including a tyrosine kinase, such as TrkA or Syk, and PDE4, and are useful in the in the treatment or control of inflammation, auto-immune diseases, cancer, and other disorders and indications where modulation of JAK would be desirable. Also described herein are methods of treating inflammation, auto-immune diseases, cancer, and other conditions susceptible to inhibition of JAK and PDE4 by administering a compound herein described.

18 Claims, 21 Drawing Sheets

(56) References Cited

OTHER PUBLICATIONS

Prelog, et al., (1982), Angew. Chem. 94: 614-631, Angew. Chem. Internat. Ed. Eng. 21:567-583.
International search report for PCT/US2020/070234, dated Oct. 23, 2020.

| Structure | EC50: GM-CSF/pSTAT5 _nM | EC50: IL-4/pSTAT6 _nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|
| 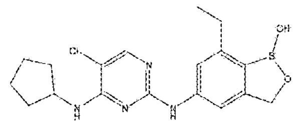 | 7704 | 256.4 | 0.373 | 65.4 |  | 52.8 | 12.5 |  |  |  |  |  |
| 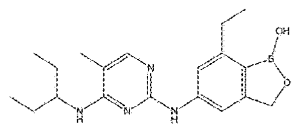 | 270.3 | 107 | 0.41 | 40.5 |  | 216 | 9.4 |  |  |  |  |  |
|  |  |  | 0.54 | 2.74 |  |  |  |  |  |  |  |  |
| 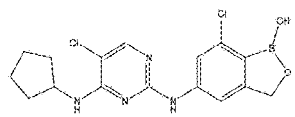 | 4779 | >10000 | 0.857 | >1000 |  | 398 | 1.88 |  |  |  |  |  |
| 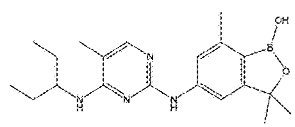 | 1691.5 | 488.6 | 0.676 | 50.2 |  | 213 | 28 | >10000 |  |  |  |  |
| 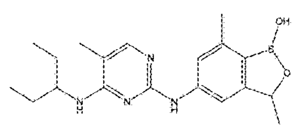 | 1599 | 202 | 0.939 | 30.8 |  |  |  |  | 1700 |  |  |  |
| 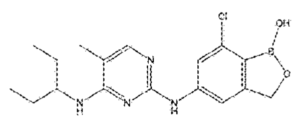 | 1699 | 154.7 | 1.08 | 95.7 | >1000 | 275 | 2.19 |  |  |  |  |  |

FIGURE 1A

| Structure | EC50: GM-CSF/pSTAT5 _nM | EC50: IL-4/pSTAT6 _nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|
| | >10000 | 118 | 1.13 | 41 | >10000 | 391 | 8.46 | | >10000 | 0.946 | 0.023 | 5 |
| | | | 1.2 | 7.17 | | 289 | 10.1 | | 69.5 | | | |
| | | 257 | 1.28 | 54.6 | >1000 | 579 | 18.6 | | 1720 | 0.165 | 0.069 | 2.2 |
| | | | 1.43 | 16.6 | | 69.6 | 2.72 | | | | | |
| 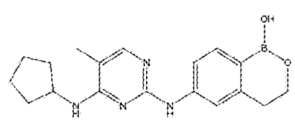 | 7329 | 196 | 1.63 | 64.7 | >1000 | 304 | 10.3 | | 375 | | | |
| 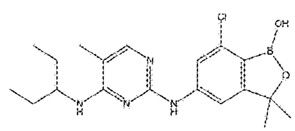 | 1887 | 126.7 | 1.86 | 38.8 | | 300 | | | | | | |
| | | | 1.93 | 14.2 | | 163 | 10.3 | | 87.3 | 0.13 | 0.081 | 1.1 |

FIGURE 1B

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|
| 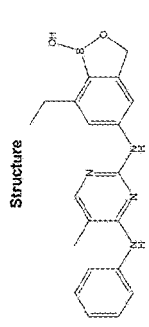 | | | 2.02 | 22.3 | | | | | | | | |
| 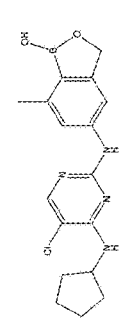 | >10000 | 688 | 2.13 | 663 | | >1000 | 22 | | | | | |
| 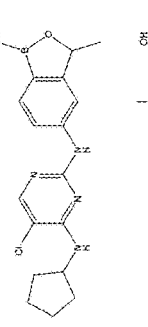 | | | 2.28 | 73.2 | | 65.6 | 14.1 | | | | 0.319 | 0.976 |
| 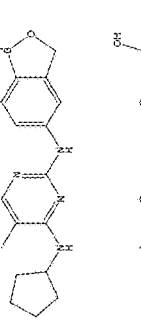 | 3333.5 | 972.8 | 2.31 | 59.3 | | 208 | 12.3 | | | 1 | | |
| 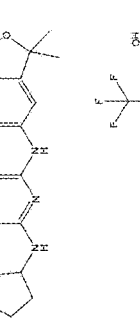 | 3940 | 218 | 2.41 | 83.9 | 761 | 432 | 20.9 | | 477 | | | |
| 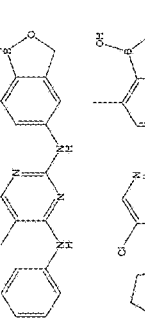 | | 1072 | 2.46 | 46.8 | | 889 | 17.4 | | | 0.688 | 0.111 | 1.32 |
| 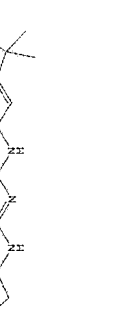 | >10000 | | 2.52 | 274 | | >1000 | 148 | | | | | |
FIGURE 1C

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|
| | | | 2.6 | 62 | >1000 | 353 | 13.5 | | | | | |
| 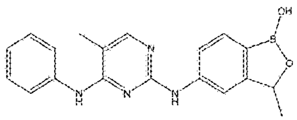 | 1718 | 223 | 2.61 | 10.4 | | 157 | 11.9 | | | | | |
| | | | 3.14 | 9.74 | | 94.9 | 23.4 | 94.9 | | | | |
| | | | 3.25 | 103 | >1000 | | | 194 | 73.2 | | | |
| 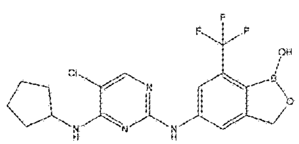 | >10000 | 2445 | 3.48 | 899 | | 34.2 | 755 | | | | | |
| | | | 3.71 | >1000 | | 212 | 31.9 | | 773 | | | |
| | | | 5.28 | 135 | | 171 | 70.5 | | | | | |

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|
| | | | 960 | >1000 | | | | | | | | |
| | | | >1000 | | | | | | | | | |
| 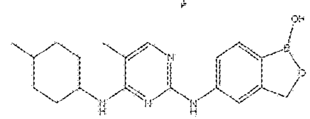 | 5354 | 956 | 0.643 | 6.56 | 40.7 | 76.3 | 1.07 | | 80.8 | | 0.085 | 0.796 |
| 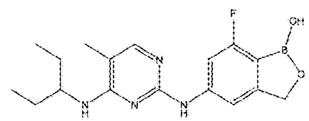 | 1379 | 125 | 0.653 | 43.7 | 212 | | | | | 0.125 | 0.049 | 0.493 |
| | | | 0.665 | 1.5 | | 9.43 | 1.4 | | 171 | | | |
| | | | 0.875 | 4.1 | | 46.2 | 1.5 | | >10000 | | | |

FIGURE 1G

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFα_24hr_µM |
|---|---|---|---|---|---|---|---|---|---|---|---|---|
| 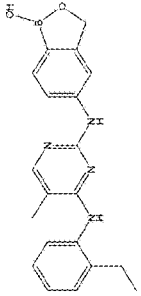 | | | 0.698 | 3.34 | | 17.5 | 1.43 | | | | | |
| 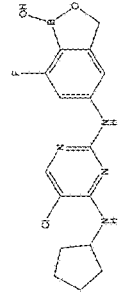 | >10000 | 6119 | 0.786 | 26.5 | | 24.9 | | | | 1.4 | 0.584 | 0.972 |
| 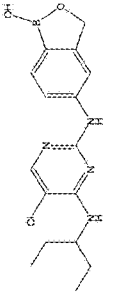 | | | 1.09 | 33.3 | 379 | 11.3 | 3.83 | | >10000 | | 0.218 | 0.583 |
| 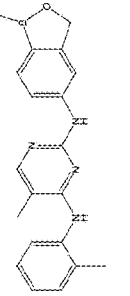 | | | 1.11 | 11.7 | | 71.6 | | | | | | |
|  | | | 1.22 | 13.6 | >1000 | 95.8 | 1.58 | | | | | |
| 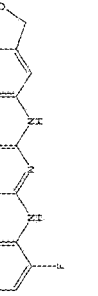 | | | 1.29 | 10.6 | | 94.8 | 4.4 | | | | | |
FIGURE 1H

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|
| 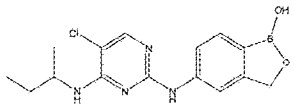 | 2734 | 381.2 | 1.61 | 31.2 | 29.2 | 19.9 | 3.87 | | 218 | | 0.175 | 0.521 |
| 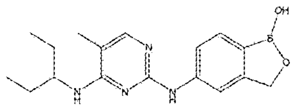 | >10000 | 115 | 1.64 | 60.2 | 85.5 | | | | 2740 | | | 0.96 |
| 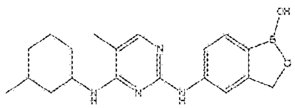 | 3470 | 637.4 | 1.88 | 19.8 | 22.8 | 96.5 | 2.69 | | | | | |
| | | | 1.89 | 65.1 | 220 | 23.7 | 15 | | | | | |
| 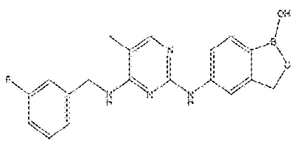 | 940.2 | 111 | 2 | 6.57 | | 21.5 | 20.5 | | 786 | | | |
| 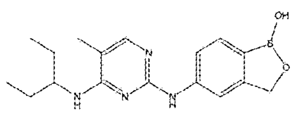 | 6726 | 122 | 2.04 | 61 | 92.2 | 281 | 5.05 | 5780 | 2340 | 0.251 | 0.109 | 0.694 |
| | | | 2.46 | 5.85 | | | | | | | | |

FIGURE 1I

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|
| 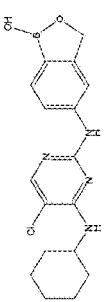 |  |  | 6.09 | 118 |  |  |  |  |  |  |  |  |
| 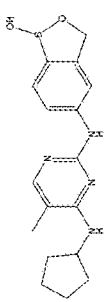 |  | 293 | 6.54 | 154 |  |  |  |  | >100000 |  |  |  |
| 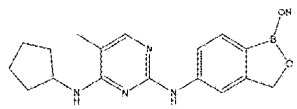 | 7967 |  | 8.34 | 149 | 114 | 504 | 20.4 | 1280 | 728 |  |  |  |
|  |  |  | 10.2 | 36.1 |  |  |  |  | 892 | 0.654 | 0.192 | 0.481 |
| 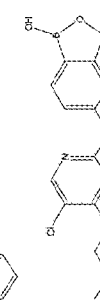 |  |  | 10.3 | 74.3 | 42.7 |  |  |  | 1260 |  |  |  |
| 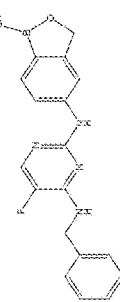 |  |  | 10.5 | 21.8 |  |  |  |  | 859 |  |  |  |
FIGURE 1K

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_μM | IC50: PHA_IL-4_24hr_μM | IC50: PHA_TNFa_24hr_μM |
|---|---|---|---|---|---|---|---|---|---|---|---|---|
| 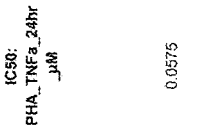 | >10000 | 1232 | 11 | 42.2 | 2.59 | 10 | 4.94 | | 108 | 0.09 | 0.065 | 0.0575 |
|  | >10000 | 1638 | 11.2 | 1850 | | >1000 | 4.8 | | >100000 | | | |
| 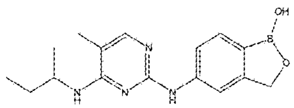 | 108 | 104.8 | 11.4 | 193 | 31.9 | 921 | 21.3 | | 3830 | | 0.169 | 0.332 |
|  | | | 11.5 | 41.2 | | | | | 475 | | | |
|  | | | 13.5 | 233 | | | | | >100000 | | | |
|  | | | 13.9 | 194 | | | | | 1670 | | | |
|  | >10000 | >10000 | 14.3 | 870 | 6.73 | 25.4 | 13.1 | | >100000 | | | |
FIGURE 1L

| Structure | EC50: GM-CSF/pSTAT5_nM | EC50: IL-4/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFα_24hr_µM |
|---|---|---|---|---|---|---|---|---|---|---|---|---|
| structure 1 | >10000 | >10000 | 18.1 | 8250 | 293 | | | | 20000 | | | 3 |
| structure 2 | | | 18.2 | 63.5 | 110 | 507 | 42.1 | | 245 | | 0.534 | 0.831 |
| structure 3 | | | 18.6 | 317 | | | | | | | | |
| structure 4 | >10000 | 2876 | 18.7 | 123 | 3.23 | | | | 436 | | | |
| structure 5 | >10000 | >10000 | 18.8 | 985 | 687 | | | | 53900 | | | |
| structure 6 | >10000 | >10000 | 21.1 | 889 | | | | | 885 | | | |

FIGURE 1N

| Structure | EC50: GM-CSF/pSTAT5_nM | EC50: IL-4/pSTAT5_nM | EC50: IL/pSTAT6_nM | IC50: JAK1_nM | IC50: JAK2_nM | IC50: PDE4B_nM | IC50: JAK3_nM | IC50: TYK2_nM | IC50: SYK_nM | IC50: TRKA_nM | IC50: PHA_IL-13_24hr_µM | IC50: PHA_IL-4_24hr_µM | IC50: PHA_TNFa_24hr_µM |
|---|---|---|---|---|---|---|---|---|---|---|---|---|---|
| | | | | 136 | 505 | | | | | | | | |
| | | | | 166 | >10000 | | | | | 4270 | | | |
| | | | | 485 | >1000 | | | | | 20000 | | | |
| | | | | 1920 | 14900 | | | | | | | | |
| | | | | 1960 | 4200 | | | | | 12900 | | | |
| | | | | >10000 | >10000 | | | | | 2270 | | | |
| | | | | >10000 | >10000 | >1000 | | | | | | | |

FIGURE 1S

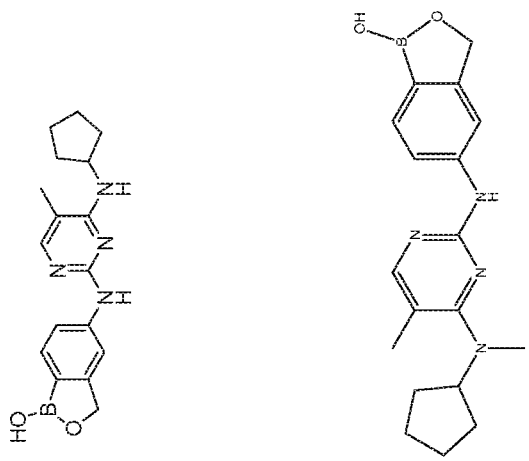
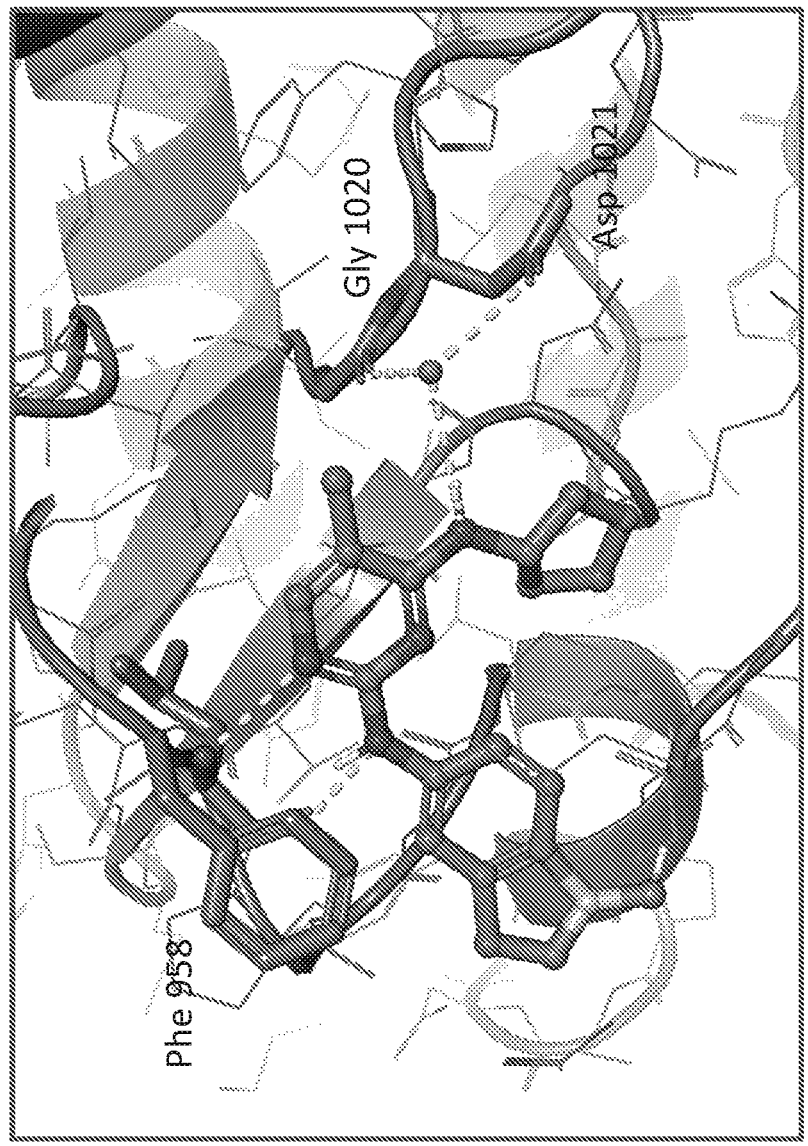
A docking model of compounds of the disclosure at the active site of JAK1 shows the NH(X) forming hydrogen bonds with Gly1020 and Asp1021 through a crystal water. Alkylation of the NH group abolishes the hydrogen bond and decreases its binding affinity to JAK1.
FIGURE 2

CHEMICAL COMPOUNDS

CROSS-REFERENCE TO RELATED APPLICATIONS

The present application claims priority to each of U.S. Provisional Application Ser. No. 62/870,537 filed Jul. 3, 2019, U.S. Provisional Application Ser. No. 62/916,697 filed Oct. 17, 2019, U.S. Provisional Application Ser. No. 62/916,700 filed Oct. 17, 2019, U.S. Provisional Application Ser. No. 62/949,280 filed Dec. 17, 2019, and U.S. Provisional Application Ser. No. 62/949,301 filed Dec. 17, 2019, each of which is herein incorporated by reference in its entirety.

FIELD OF THE INVENTION

The present disclosure describes novel boron-containing compounds, or their pharmaceutically acceptable salts, pharmaceutical compositions containing them, and their medical uses. In one embodiment, the compounds of the disclosure have activity as inhibitors of Janus kinases (JAK), either alone or in combination with at least one additional mechanism, such as inhibition of another tyrosine kinase, including Tropomyosin-receptor kinase A (TrkA) inhibitors or spleen tyrosine kinase (Syk) inhibitors, and are useful in the in the treatment or control of inflammation, auto-immune diseases, cancer, and other disorders and indications where modulation of JAK optionally in conjunction with one or more other mechanism, such as inhibition of a tyrosine kinase, including TrkA, and Syk, would be desirable. Also described herein are methods of treating inflammation, auto-immune diseases, cancer, and other conditions susceptible to inhibition of JAK optionally in conjunction with one or more other mechanism, such as inhibition of a tyrosine kinase, including TrkA and Syk by administering a compound of the disclosure. In one embodiment, the compounds of the disclosure have activity as dual inhibitors of Janus kinases (JAK) and phosphodiesterase-4 (PDE4) and are useful in the in the treatment or control of inflammation, auto-immune diseases, cancer, and other disorders and indications where modulation of JAK in conjunction with PDE4 would be desirable. Also described herein are methods of treating inflammation, auto-immune diseases, cancer, and other conditions susceptible to inhibition of JAK in conjunction with PDE4 by administering a compound of the disclosure. Similarly, where the compounds of the present disclosure have additional inhibitory mechanisms, the present disclosure includes methods of treating other conditions susceptible to such inhibition.

BACKGROUND

Atopic dermatitis (AD), also known as eczema, is a common chronic inflammatory skin disease, affecting approximately 20% of children and up to 10% of adults and it imposes a significant financial and societal burden because of the direct medical costs and decreased productivity of individuals with AD. The burden of AD appears to be related mainly to the limited methods of treatment. Furthermore, according to the AD treatment guidelines, there is no standard of care and treatment may be tailored to an individual's needs. Topical interventions are the mainstay of AD therapy. Until now, topical corticosteroids have been the first-line treatment. Their use, however, may be limited by potential local and systemic adverse effects. Topical calcineurin inhibitors are classified as second-line anti-inflammatory therapy for AD, with advantages in long-term maintenance and application to special sites. Topical calcineurin inhibitors inhibit calcineurin-dependent T-cell activation; however, a black box warning regarding the potential for developing malignant neoplasms with the use of topical calcineurin inhibitors reduces patients' adherence to treatment.

Protein kinases are families of enzymes that catalyze the phosphorylation of specific residues in proteins, broadly classified into tyrosine and serine/threonine kinases. Inappropriate kinase activity, arising from mutation, over-expression, or inappropriate regulation, dys-regulation, or de-regulation, as well as over- or under-production of growth factors or cytokines has been implicated in many diseases, including but not limited to cancer, cardiovascular diseases, allergies, asthma and other respiratory diseases, autoimmune diseases, inflammatory diseases, bone diseases, metabolic disorders, and neurological and neurodegenerative disorders such as Alzheimer's disease. Inappropriate kinase activity triggers a variety of biological cellular responses relating to cell growth, cell differentiation, survival, apoptosis, mitogenesis, cell cycle control, and cell mobility, which are implicated in the aforementioned and related diseases. Thus, protein kinases have emerged as an important class of enzymes as targets for therapeutic intervention.

In particular, the JAK family of cellular protein tyrosine kinases (JAK-1, JAK-2, JAK-3, and Tyk-2) play a central role in cytokine signaling (Kisseleva et al, Gene, 2002, 285, 1; Yamaoka et al. Genome Biology 2004, 5, 253)). Upon binding to their receptors, cytokines activate JAK which then phosphorylate the cytokine receptor, thereby creating docking sites for signaling molecules, notably, members of the signal transducer and activator of transcription (STAT) family that ultimately lead to gene expression, which stimulates biologic responses such as an itch signal. Activation of the JAK-STAT pathway also results in several other ancillary biologic activities that contribute to the inflammation and pruritic processes that contribute to acute allergy in animals but can also exacerbate clinical signs and contribute to chronic allergy. Selectivity amongst the JAK sub-types may prove helpful in treating certain diseases or disorders.

The TrkA family are receptor tyrosine kinases (TrkA, TrkB, and TrkC) involved in a variety of intracellular signal transduction pathways implicated in psoriasis and associated pruritus, pain signaling, and cancer. TrkA receptor activity is initiated upon binding of a family of neurotrophin ligands, including Nerve Growth Factor (NGF) (Roblin et al., Acta Derm Venereol, 2015, 95, 542). Increased expression of NGF and TrkA in the epidermis is associated with formation of psoriatic lesions. Furthermore, it is believed that NGF stimulates expression and sensitivity of a co-receptor Transient Receptor Potential cation channel subfamily V member 1 (TRPV1) and that NGF-TrkA-TRPV1 signaling is involved in these dermatological conditions.

The phosphodiesterase (PDE) family of enzymes plays a role in the degradation of cyclic adenosine monophosphate, an important intracellular second messenger central to multiple signalling pathways. PDE inhibitors have been developed and evaluated for the treatment of a variety of conditions, including asthma, chronic obstructive pulmonary disease, erectile dysfunction, Alzheimer's disease, and chronic inflammatory skin diseases. A phosphodiesterase type 4 inhibitor, commonly referred to as a PDE4 inhibitor, is a drug used to block the degradative action of phosphodiesterase 4 (PDE4) on cyclic adenosine monophosphate (cAMP). The PDE4 family of enzymes are the most prevalent PDE in immune cells and are predominantly responsible for hydrolyzing cAMP within both immune cells and cells in the central nervous system.

As noted hereinabove, phosphodiesterase-4 (PDE4), mainly present in immune cells, epithelial cells, and brain cells, manifests as an intracellular non-receptor enzyme that modulates inflammation and epithelial integrity. Inhibition of PDE4 is predicted to have diverse effects via the elevation of the level of cyclic adenosine monophosphate (cAMP) and the subsequent regulation of a wide array of genes and proteins. As such, PDE4 may be a promising therapeutic target for the treatment of diverse pulmonary, dermatological, and severe neurological diseases. Numerous PDE4 inhibitors have been designed and synthesized, among which roflumilast, apremilast, and crisaborole are indicated for the treatment of inflammatory airway diseases, psoriatic arthritis, and atopic dermatitis, respectively. The dramatic efficacies of a drug, however, may be accompanied by adverse effects, such as nausea, emesis, and gastrointestinal reactions.

In addition to dermatological utilities, PDE4 inhibitors may hold potential as treatments for a diverse group of different diseases, including central nervous system disorders such as major depressive disorder, depression, anxiety disorders, schizophrenia, Parkinson's disease, Alzheimer's disease, multiple sclerosis, attention deficit-hyperactivity disorder, Huntington's disease, stroke, autism and inflammatory conditions such as chronic obstructive pulmonary disease (COPD), asthma, and rheumatoid arthritis. PDE4 inhibition is also known to attenuate ethanol seeking and consumption in rats, and may be useful in the treatment of alcohol dependence.

Inflammation underlies the pathogenesis of various human diseases, which includes infection, immune-mediated disorders, metabolic disturbance, neurodegeneration, and cancer. Inflammatory diseases affect a certain population worldwide and possess extremely complicated pathogenic mechanisms (Kazatchkine and Kaveri, 2001). To date, numerous therapeutic strategies have emerged in the treatment of inflammatory diseases (Tabas and Glass, 2013; Siebert et al., 2015). Although non-steroidal anti-inflammatory drugs (NSAIDs) and corticosteroids have made tremendous contributions for inflammation intervention, the serious long-term adverse effects and the multiple manifestations of diseases drive some patients away from these therapeutic options (Hart and Huskisson, 1984). Hence, there remains a great need for the discovery of novel therapeutic drugs for controlling inflammation with various anti-inflammation spectra (Uguccioni et al., 2017). Cyclic guanosine monophosphate (cGMP) and cyclic adenosine monophosphate (cAMP) function as the fundamental second messengers in the regulation of multiple cellular metabolisms. Phosphodiesterases (PDEs), consisting of 11 families (PDE1-PDE11), are available for the degradation of cyclic nucleotides (Kumar et al., 2013). Distributions of PDE subfamilies are diverse in different cells and tissues, which may provide a substantial support for their pharmacological research in the field of inflammation, cognition, lipogenesis, proliferation, apoptosis, and differentiation. The cAMP-specific PDE4 is highly expressed in the brain, cardiovascular tissues, smooth muscles, keratinocytes, and immunocytes (including T cells, monocytes, macrophages, neutrophils, dendritic cells, eosinophils) (Chiricozzi et al., 2016). The inhibition of PDE4 can elevate the intracellular level of cAMP and subsequently modulate the inflammatory responses and maintain the immune balance (Maurice et al., 2014). Targeting PDE4 has been verified as an effective therapeutic strategy for inflammatory conditions, including asthma, chronic obstructive pulmonary disease (COPD), psoriasis, atopic dermatitis (AD), inflammatory bowel diseases (IBD), rheumatic arthritis (RA), lupus, and neuroinflammation. Several products such as, roflumilast, apremilast, and crisaborole, were approved in succession for the treatment of inflammatory airway or skin diseases. Moreover, a series of novel PDE4 inhibitors have also been developed for the regulation of inflammation, and have shown satisfactory therapeutic efficacies. Increasing evidence demonstrated that patients who suffered from inflammatory diseases showed higher expression of PDE4 than the healthy individuals (Schafer et al., 2016). There are four subtypes of PDE4, namely PDE4A-PDE4D, which are highly specific for cAMP degradation but not for cGMP. Inhibition of PDE4 results in the accumulation of intracellular cAMP and subsequently activates PKA, cyclic nucleotide-gated ion channels, and Epac1/2. These are involved in the regulation of pro-inflammatory and anti-inflammatory cytokines synthesis, activation of T cells, neutrophil degranulation, performance of antigen-presentation, and epithelial integrity via initiation of multiple downstream elements. Release of catalytic subunit from regulatory subunit upon PKA activation could subsequently increase the phosphorylation of cAMP-responsive element binding protein (CREB), activating transcription factor 1 (ATF-1) and cAMP responsive element modulator (CREM) and recruit the CREB binding protein (CBP) or the homologous protein p300, leading to the reduction of inflammatory cytokines and the increase of anti-inflammatory cytokines (Schafer, 2012). A previous study demonstrated that the transcriptional activity of classic nuclear factor kappa-lightchain-enhancer of activated B cells (NF-kB) can be stimulated upon the phosphorylation of p65 on Ser276 by PKA (Christian et al., 2016). The CBP/p300 is closely associated with NF-kB p65, and PKA activation could regulate the transcriptional activity of NF-kB through the modulation of its interaction with CBP/p300 without IkBa degradation or NF-kB DNA binding activity, which results in the downregulation of inflammatory responses (Zhong et al., 1998; Schafer, 2012). Additionally, PKA activation could interfere with B-cell lymphoma 6 protein (Bcl-6)-mediated synthesis of pro-inflammatory cytokines and proliferation of immune cells (Page, 2014; Hernández-Flórez and Valor, 2016). Activation of Epac1/2 in the wake of cAMP elevation serves as a promising alternative mechanism to target inflammation and proliferation (Lehrke et al., 2015). Compartmentalization of intracellular cAMP in space and time contributes to the Epac signalosome of transcription factors, small GTPases (Rap1), which do well in the optimization of the treatment of inflammatory airway diseases, renal failure, vasculature disturbance, and neuroinflammation (Schmidt et al., 2013). Given the role of cAMP in diverse physiological metabolisms in various kinds of cells, cAMP elevation following PDE4 inhibition is closely associated with the suppression of the overactivity of immune responses or intermediates. Accumulating research indicates that PDE4 inhibition could modulate both innate and adaptive responses. Inhibition of PDE4 showed regulatory activities in macrophages, neutrophils, monocytes, and dendritic cells (Crilly et al., 2011; Schafer, 2012). In addition, PDE4 inhibition showed excellent effects on T cell receptor (TCR)-induced activation of T cells, manifesting in the reduction of release of cytokines and chemokines from T helper-1 (Th1), Th2, and Th17 cells (Sakkas et al., 2017), whereas PDE4 inhibition might have little effect on the phenotype and function of B cells (Schafer et al., 2014). Furthermore, elevated cAMP in keratinocytes and epithelial cells could also inhibit the inflammatory responses and regulate the cell growth and barrier functions (Page, 2014). See, Li H, et al., Phosphodiesterase-4 Inhibitors for the Treatment of Inflammatory Diseases. Front. Pharmacol. 9:1048 (2018), within which the sub-references are cited, and all of which are herein incorporated by reference with regard to background biological teachings.

Therefore, PDE4 represents a more upstream anti-inflammatory target than JAK that regulates cytokines through JAK-STATS pathway. Thus, PDE4 inhibitors have complementary biological effects to JAK inhibitors. A combination of both JAK and PDE4 inhibition activities in one molecule results in drugs of a unique and attractive anti-inflammation profile and spectrum for the treatment of inflammation diseases with extremely complicated pathogenic mechanisms. So far, no such drugs have been reported in the literature.

The central role played by Syk (spleen tyrosine kinase) in the immune system in mediating inflammatory responses, coupled with its more recently identified association with malignancy, has made this kinase a popular target for the development of therapeutic agents for the treatment of multiple disease states ranging from arthritis and asthma to leukemia and lymphoma. Syk is a cytoplasmic protein-tyrosine kinase well known for its ability to couple immune cell receptors to intracellular signaling pathways that regulate cellular responses to extracellular antigens and antigen-immunoglobulin complexes of particular importance to the initiation of inflammatory responses. Thus, Syk is an attractive target for therapeutic kinase inhibitors designed to ameliorate symptoms and consequences of acute and chronic inflammation. Given the central role of SYK in transmission of activating signals within B-cells, a suppression of this tyrosine kinase might aid in the treatment of B cell malignancies and autoimmune diseases.

Syk inhibition has been proposed as a therapy for both lymphoma and chronic lymphocytic leukemia. Syk inhibitors are in clinical development, including cerdulatinib and entospletinib. Other inhibitors of B-cell receptor (BCR) signaling including ibrutinib (PCI-32765) which inhibits BTK, and idelalisib (PI3K inhibitor—CAL-101/GS-1101) showed activity in the diseases as well. The orally active SYK inhibitor fostamatinib (R788) is being developed in the treatment of rheumatoid arthritis. The Syk inhibitor nilvadipine has been shown to regulate amyloid-β production and Tau phosphorylation and hence has been proposed as a treatment for Alzheimer's Disease.

Thus, JAK inhibitors, with or without additional tyrosine kinase activity, and with our without PDE4 a dual inhibitory mechanism may provide a novel therapeutic strategy for various immune and inflammatory diseases, including rheumatoid arthritis (RA), arthritis, ulcerative colitis, Crohn's disease, inflammatory bowel disease (IBD), psoriasis, alopecia areata, atopic dermatitis, vitiligo, palmoplantar pustulosis, mucocutaneous disease erythema multiforme, mycosis fungoides, graft-versus-host disease, cutaneous lupus, transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, arterosclerosis, and cancer. Reference is made to Schwartz et al., *JAK inhibition as a therapeutic strategy for immune and inflammatory diseases*, Nat Rev Drug Discov., 2017 Dec. 28., 17(1):78, herein incorporated by reference with regard to the rationale for targeting JAKs.

Psoriasis and psoriatic arthritis are associated with aberrant inflammation and the production of proinflammatory mediators. Psoriasis and psoriatic arthritis are inflammatory diseases with overlapping features and shared immunologic mechanisms. Psoriasis is a systemic disease in that it primarily affects the skin but up to 40% of individuals with psoriasis may go on to develop psoriatic arthritis. Psoriatic arthritis typically affects the peripheral joints and may occasionally affect the spine and sacroiliac area. Enthesitis, dactylitis, and nail changes such as pitting and discoloration are also common manifestations of psoriatic disease in patients with joint involvement.

Thus, there a need for therapies targeting and modulating JAK alone or JAK and one or more of an additional mechanism, such as inhibition of a tyrosine kinase, including TrkA and Syk, and further optionally in combination with PDE4, for the treatment or control of inflammation, auto-immune diseases, cancer, and other disorders and indications where modulation would be desirable. Additionally, compounds with additional activity to modulate one of more additional tyrosine kinase, including inhibition of Tropomyosin receptor kinase A (TrkA) or Spleen tyrosine kinase (Syk), would also be desirable.

SUMMARY

One embodiment of the present disclosure includes a compound of formula (I):

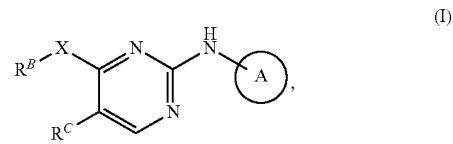

wherein:

A is selected from the group consisting of:

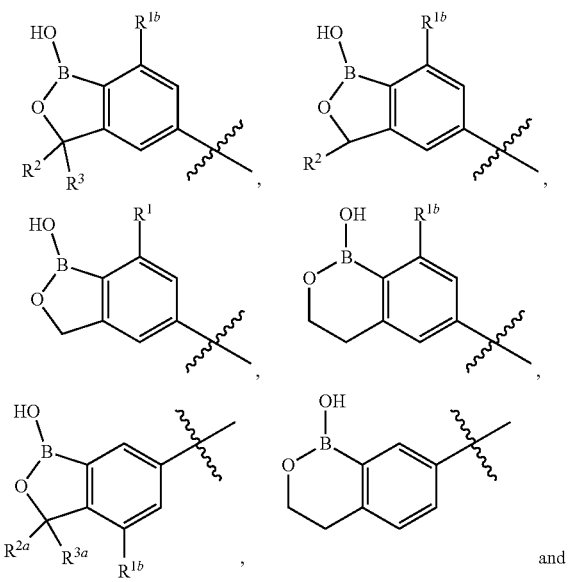

-continued

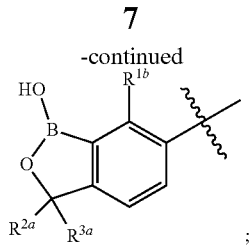

X is selected from the group consisting of: NH, O, and S;
when present, $R^1$ selected from the group consisting of: hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, O($C_1$-$C_3$ alkyl), and O($C_1$-$C_3$ haloalkyl);

when present, each $R^{1b}$ independently is selected from the group consisting of: hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, O($C_1$-$C_3$ alkyl), and O($C_1$-$C_3$ haloalkyl);

when present, each of $R^2$ and $R^3$ independently is selected from the group consisting of: $C_1$-$C_3$ alkyl, $C_2$-$C_3$ alkenyl, $C_2$-$C_3$ alkynyl, and, when present, $R^2$ and $R^3$ taken together form a 3 membered cycloalkyl ring; and when present, each of $R^{2a}$ and $R^{3a}$, independently is selected from the group consisting of: hydrogen, $C_1$-$C_3$ alkyl, $C_2$-$C_3$ alkenyl, $C_2$-$C_3$ alkynyl, and $R^{2a}$ and $R^{3a}$ taken together form a 3 membered cycloalkyl ring, $R^B$ is selected from the group consisting of: substituted phenyl, unsubstituted phenyl, unsubstituted $C_1$-$C_6$ alkyl, substituted $C_1$-$C_6$ alkyl, unsubstituted $C_1$-$C_6$ alkenyl, substituted $C_1$-$C_6$ alkenyl, unsubstituted $C_1$-$C_6$ alkynyl, substituted $C_1$-$C_6$ alkynyl, unsubstituted $C_3$-$C_6$ cycloalkyl, substituted $C_3$-$C_6$ cycloalkyl, and unsubstituted arylalkyl, substituted arylalkyl; and $R^C$ is selected from the group consisting of: hydrogen, halogen, $C_1$-$C_3$ alkyl, $C_2$-$C_3$ alkenyl, $C_2$-$C_3$ alkynyl, —CHO, cyclopropyl, $C_1$-$C_3$ haloalkyl, $C_2$-$C_3$ haloalkenyl, $C_2$-$C_3$ haloalkynyl, and partially or fully halogenated cyclopropyl, or a stereoisomer, enantiomer, or tautomer thereof, or a veterinary or pharmaceutically acceptable salt thereof.

In one aspect, when present, $R^1$ is selected from the group consisting of: hydrogen and fluorine; or selected from the group consisting of: chlorine, bromine, iodine, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, O($C_1$-$C_3$ alkyl), and O($C_1$-$C_3$ haloalkyl).

One embodiment of the present disclosure incudes a compound of formula (IA):

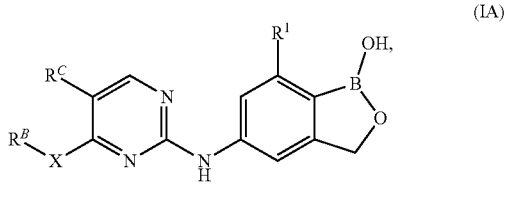

wherein:

X is selected from the group consisting of: NH, O, and S;

$R^1$ is selected from the group consisting of: hydrogen and fluorine;

$R^B$ is selected from the group consisting of: substituted phenyl, unsubstituted phenyl, unsubstituted $C_1$-$C_6$ alkyl, substituted $C_1$-$C_6$ alkyl, unsubstituted $C_1$-$C_6$ alkenyl, substituted $C_1$-$C_6$ alkenyl, unsubstituted $C_1$-$C_6$ alkynyl, substituted $C_1$-$C_6$ alkynyl, unsubstituted $C_3$-$C_6$ cycloalkyl, substituted $C_3$-$C_6$ cycloalkyl, unsubstituted arylalkyl, and substituted arylalkyl; and $R^C$ is selected from the group consisting of: hydrogen, halogen, $C_1$-$C_3$ alkyl, $C_2$-$C_3$ alkenyl, $C_2$-$C_3$ alkynyl, —CHO, cyclopropyl, $C_1$-$C_3$ haloalkyl, $C_2$-$C_3$ haloalkenyl, $C_2$-$C_3$ haloalkynyl, and partially or fully halogenated cyclopropyl, or a stereoisomer, enantiomer, or tautomer thereof, or a veterinary or pharmaceutically acceptable salt thereof.

In one aspect, $R^C$ is selected from the group consisting of: halogen, $C_1$-$C_3$ alkyl, and $C_1$-$C_3$ haloalkyl. In one aspect, $R^C$ is selected from the group consisting of: $CH_3$, $CF_3$, F, and Cl. In one aspect, X is NH. In one aspect, $R^B$ is selected from the group consisting of: unsubstituted phenyl, substituted phenyl, unsubstituted $C_1$-$C_6$ alkyl, substituted $C_1$-$C_6$ alkyl, unsubstituted $C_3$-$C_6$ cycloalkyl, substituted $C_3$-$C_6$ cycloalkyl, unsubstituted arylalkyl, and substituted arylalkyl In one aspect, $R^B$ is selected from the group consisting of: unsubstituted phenyl, substituted phenyl, unsubstituted $C_1$-$C_6$ alkyl, substituted $C_1$-$C_6$ alkyl, unsubstituted $C_3$-$C_6$ cycloalkyl, substituted $C_3$-$C_6$ cycloalkyl, unsubstituted benzyl, and substituted benzyl. In one aspect, each of the substituted phenyl, the substituted $C_1$-$C_6$ alkyl, the substituted $C_3$-$C_6$ cycloalkyl, or the substituted benzyl are independently substituted with one or more substituent selected from the group consisting of: —C(O)O($C_1$-$C_3$), OH, $CH_2OH$, $C_3$-$C_6$ cycloalkyl, $C_1$-$C_3$ alkyl, $C_1$-$C_3$ haloalkyl, halogen, O($C_1$-$C_3$ alkyl), and O($C_1$-$C_3$ haloalkyl). In one aspect, $R^B$ is selected from the group consisting of: unsubstituted $C_1$-$C_6$ alkyl, and unsubstituted $C_3$-$C_6$ cycloalkyl. In one aspect, $R^1$ is hydrogen. In one aspect, $R^1$ is fluorine.

One embodiment of the present disclosure includes a compound selected from the group consisting of:

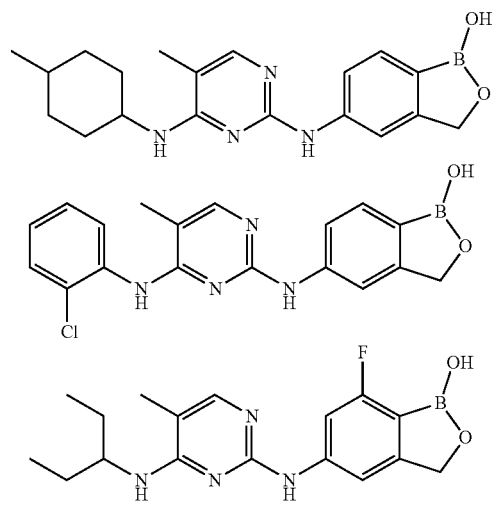

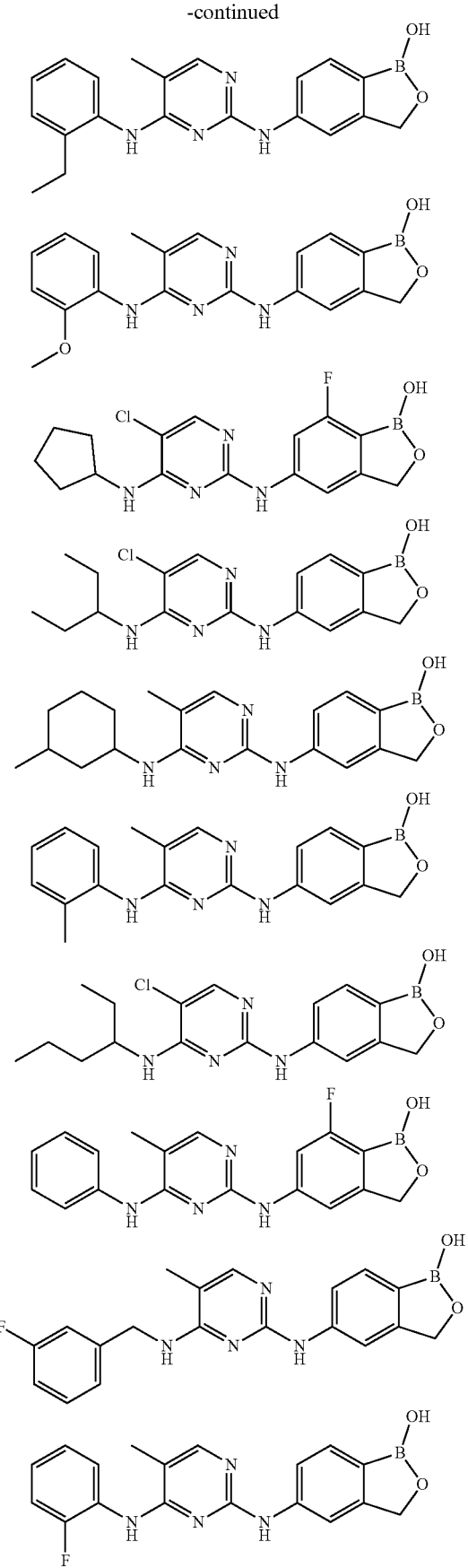
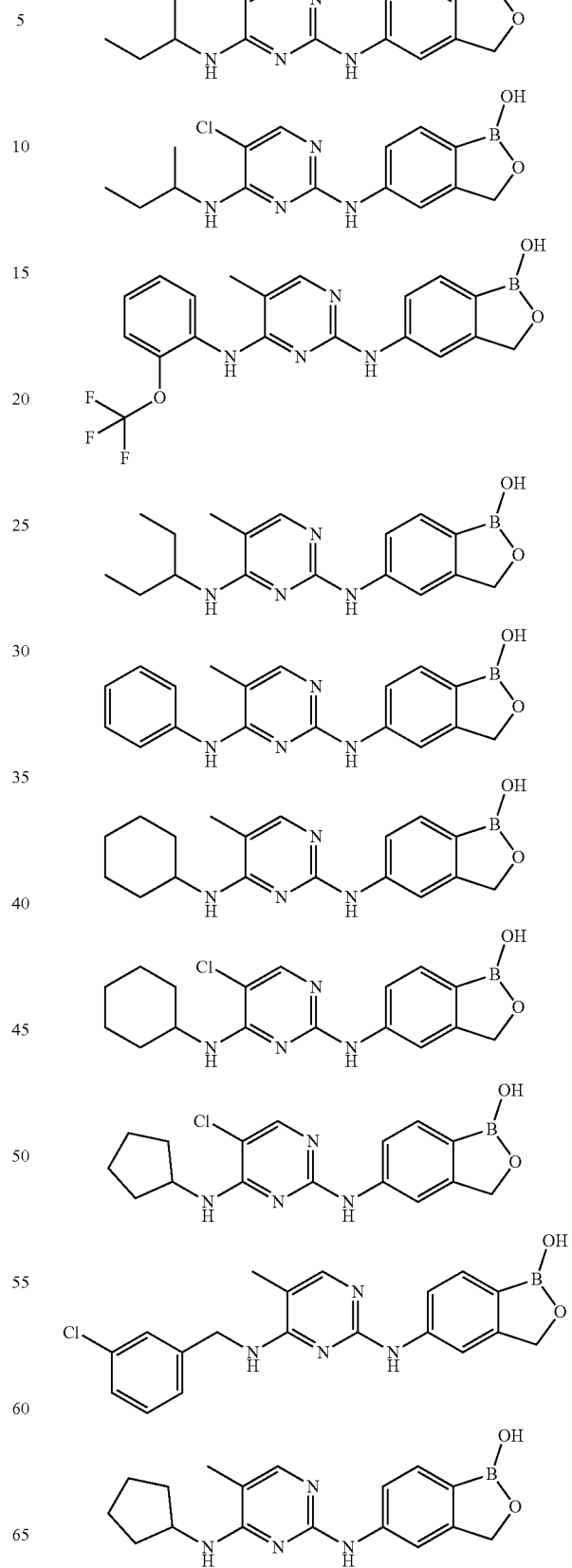

-continued
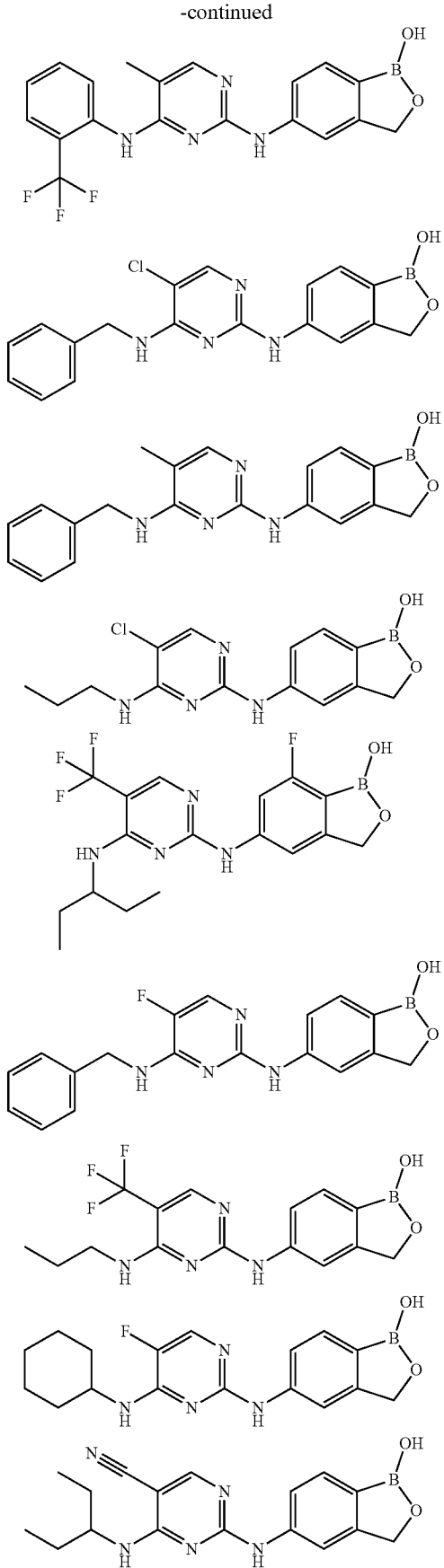
-continued
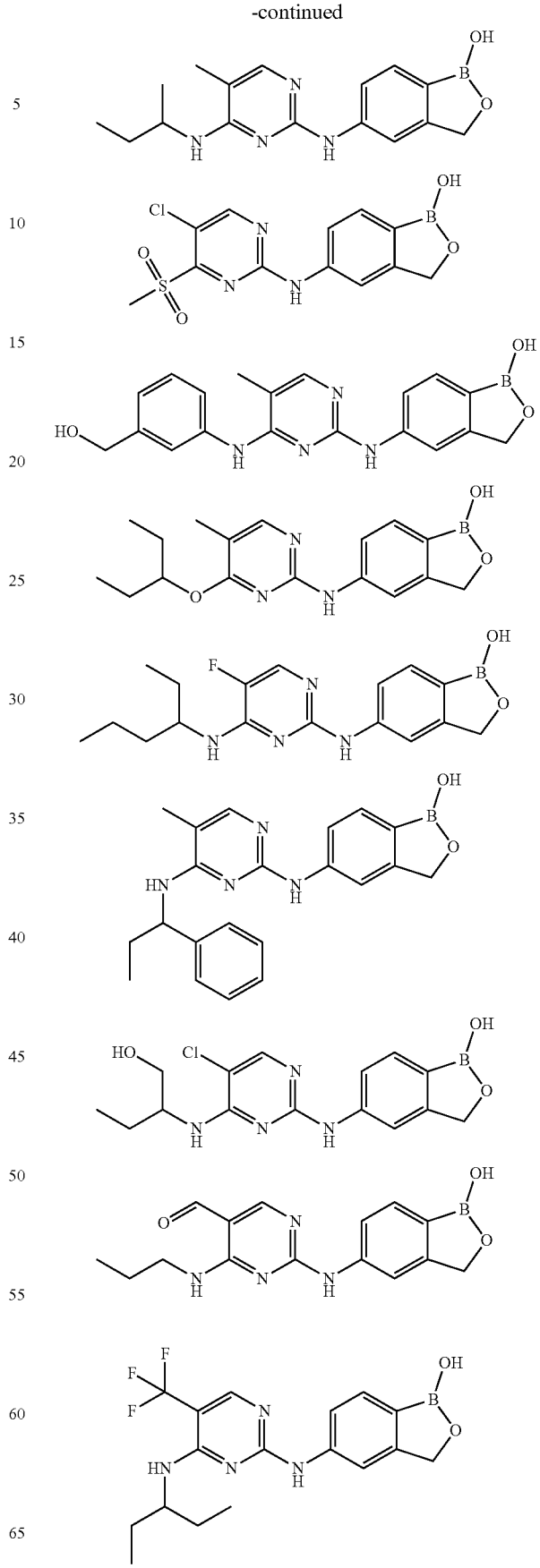

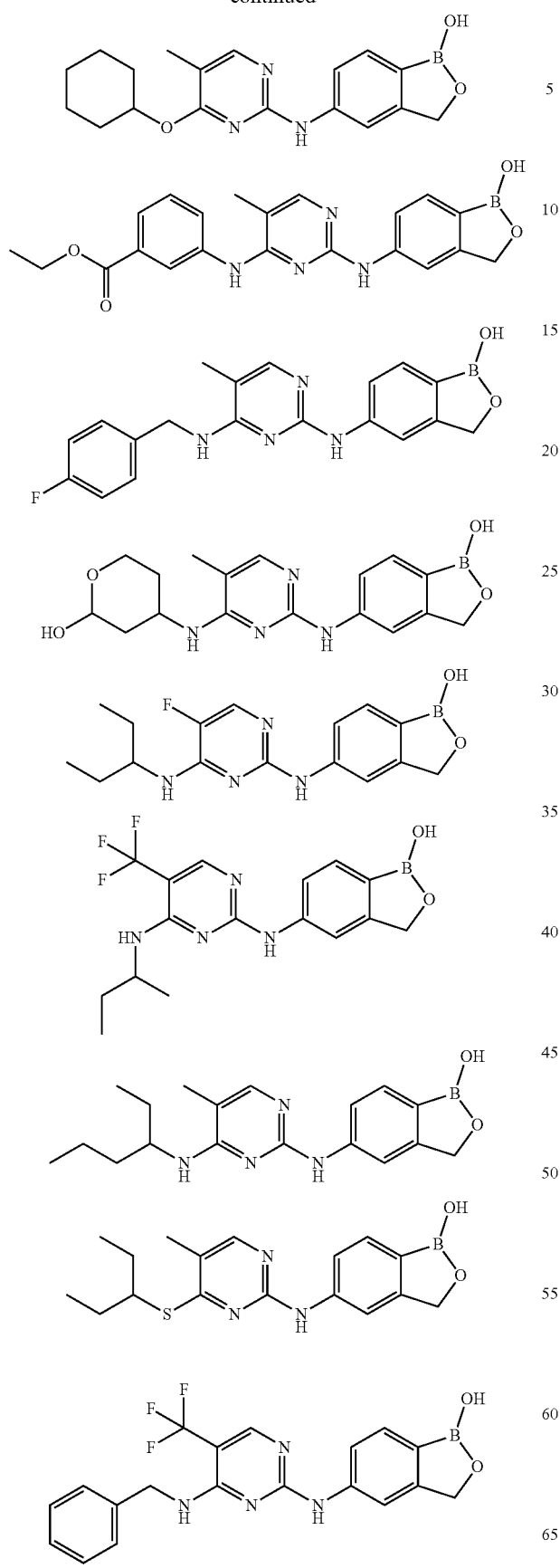
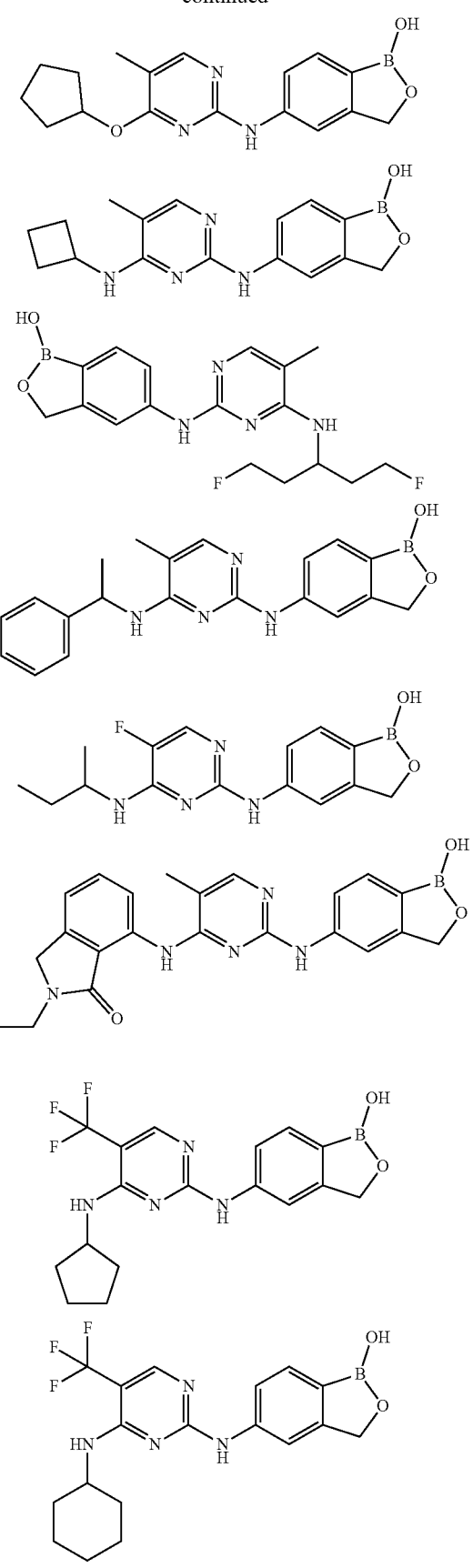

-continued
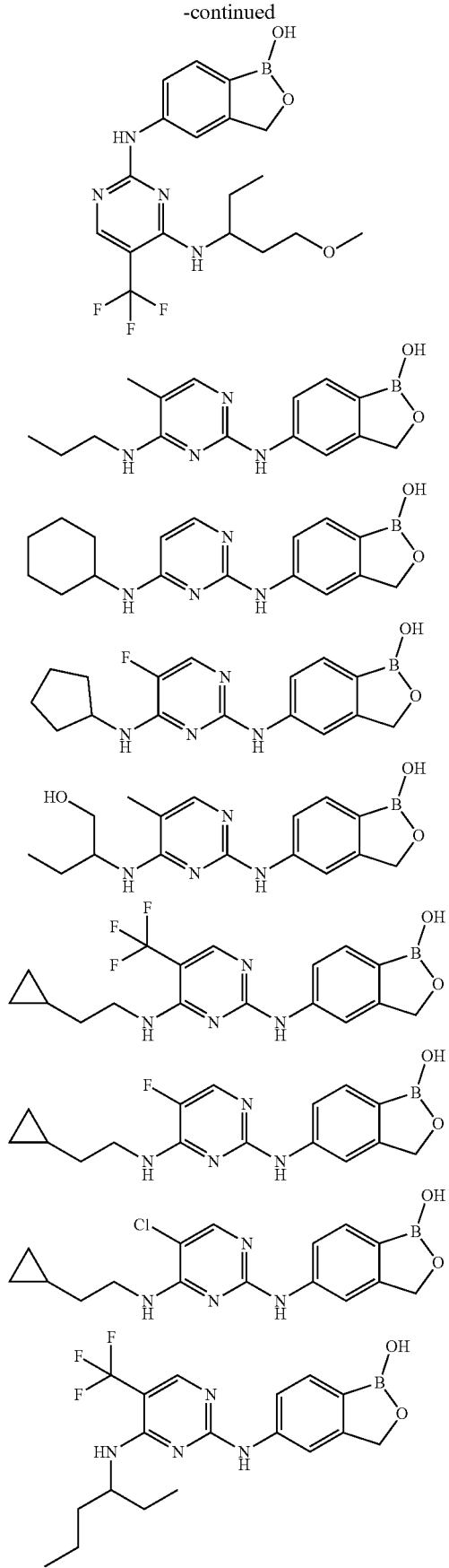
-continued
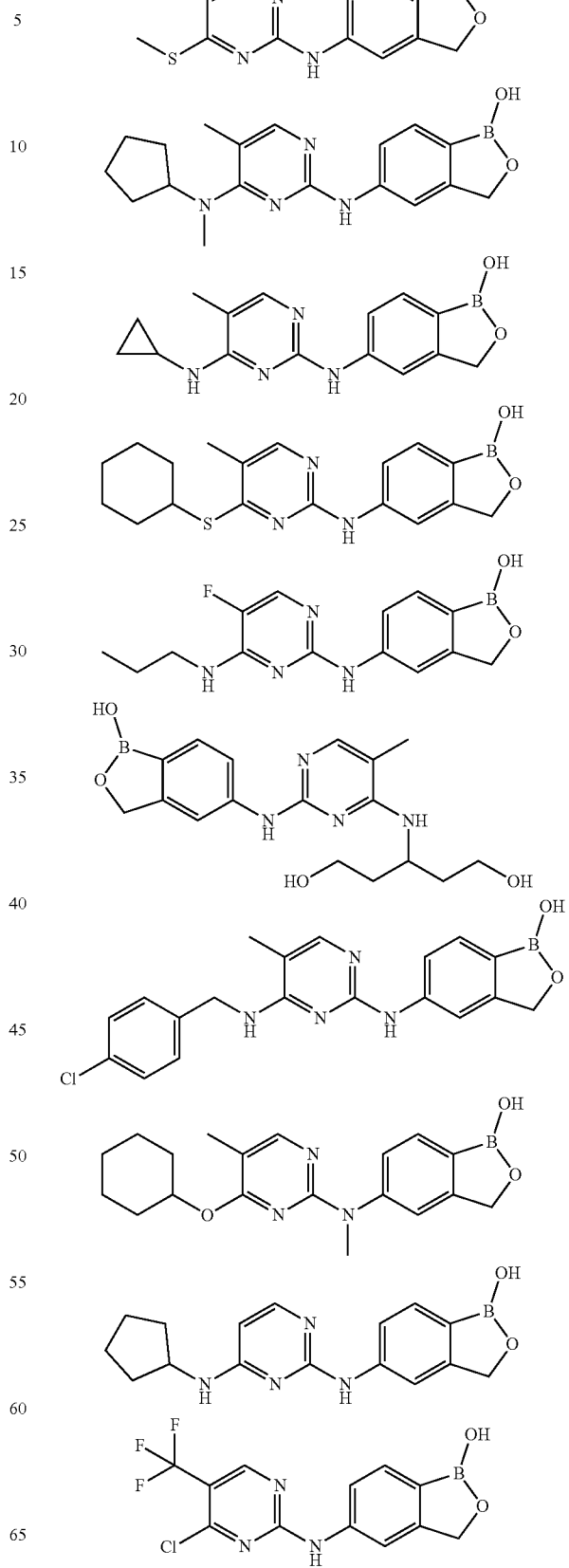

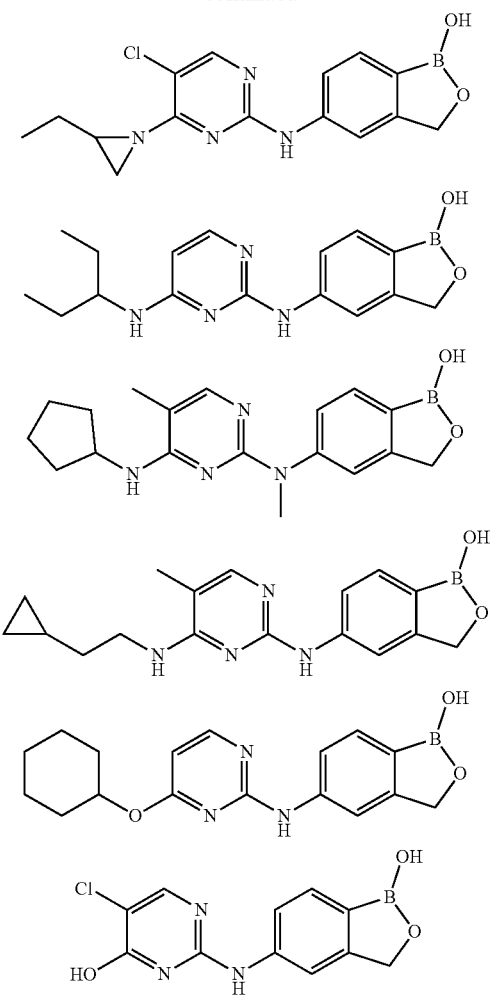
or a stereoisomer, enantiomer, or tautomer thereof, or a veterinary or pharmaceutically acceptable salt thereof.
One embodiment of the present disclosure includes a compound selected from the group consisting of:
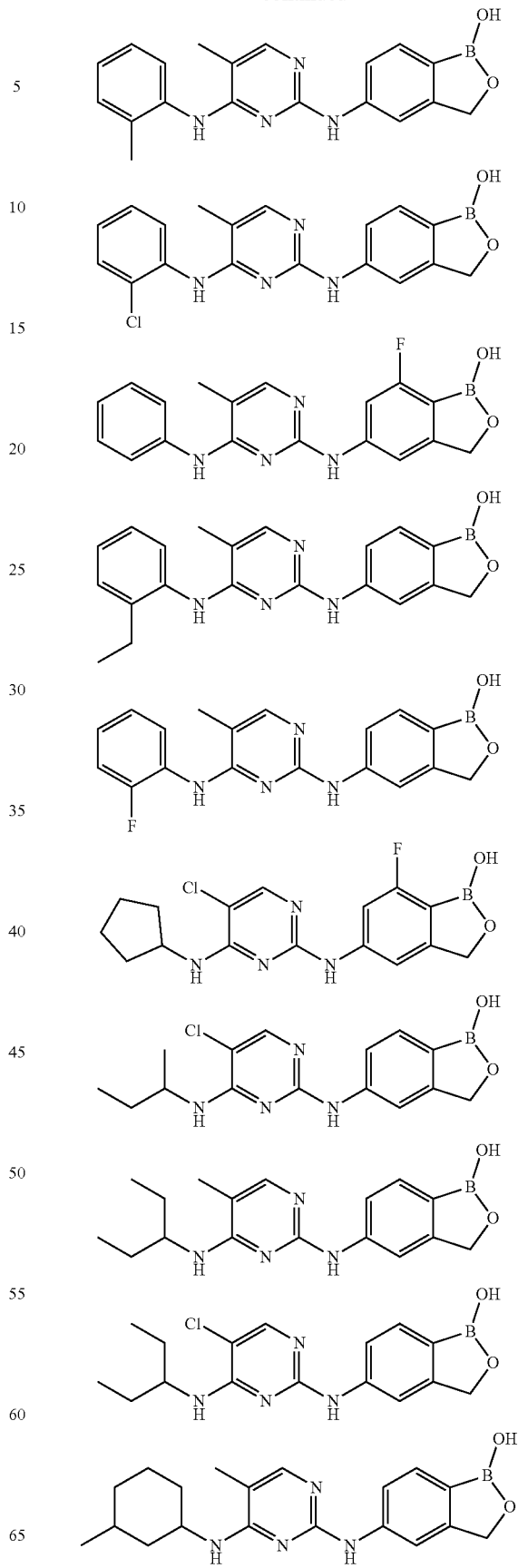

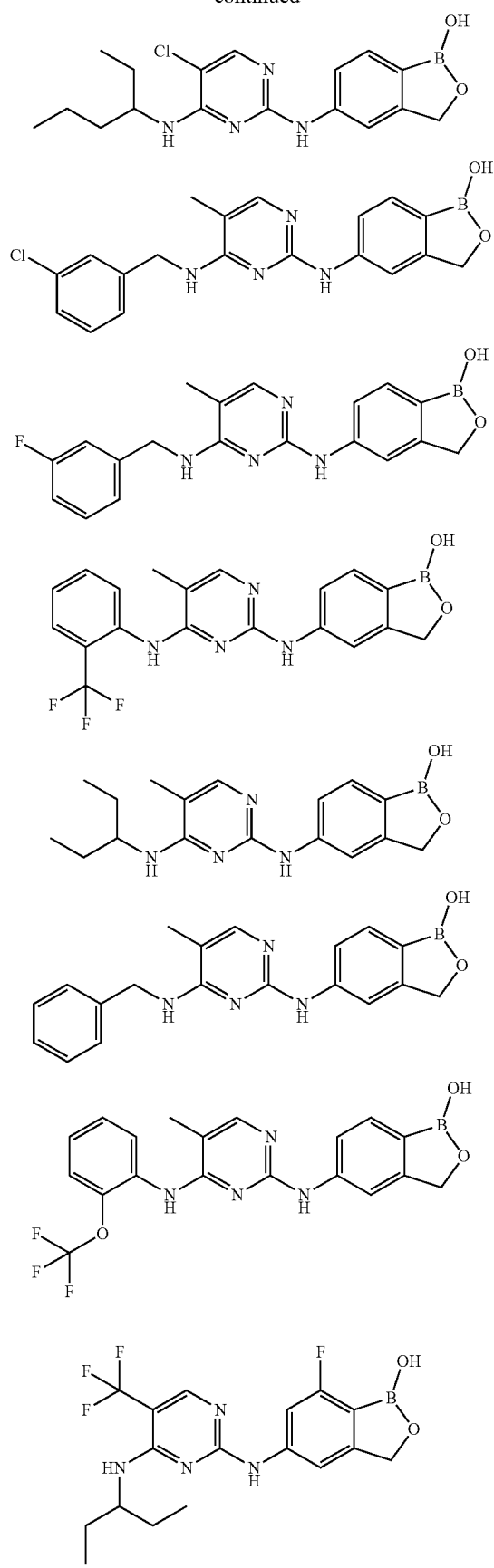
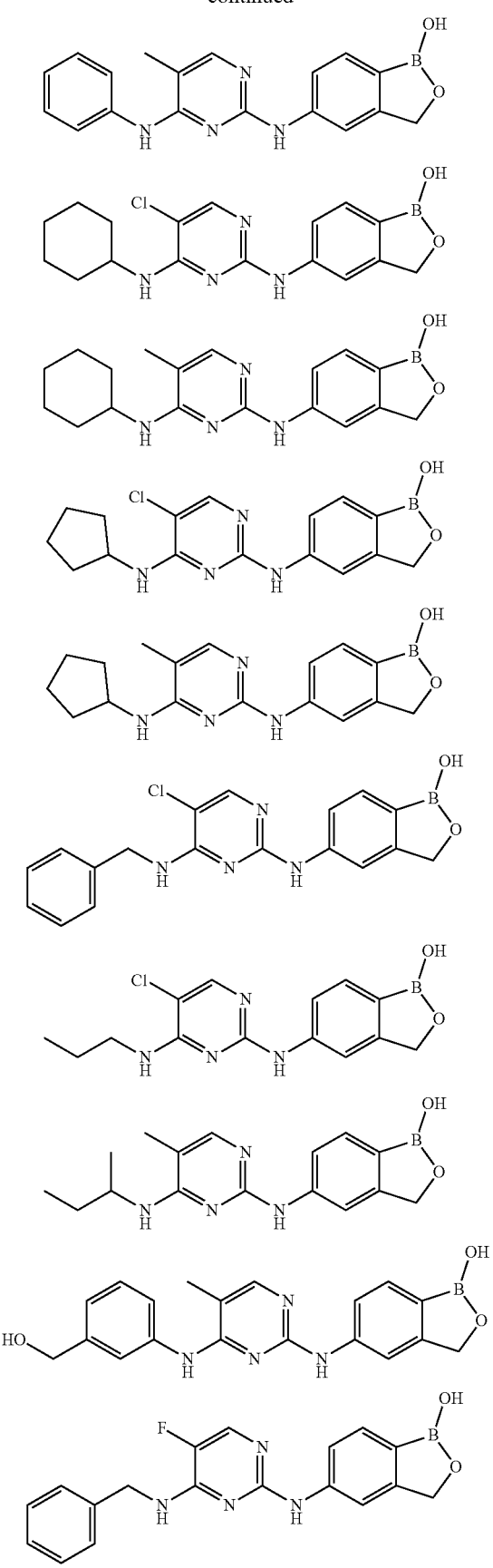

21
-continued

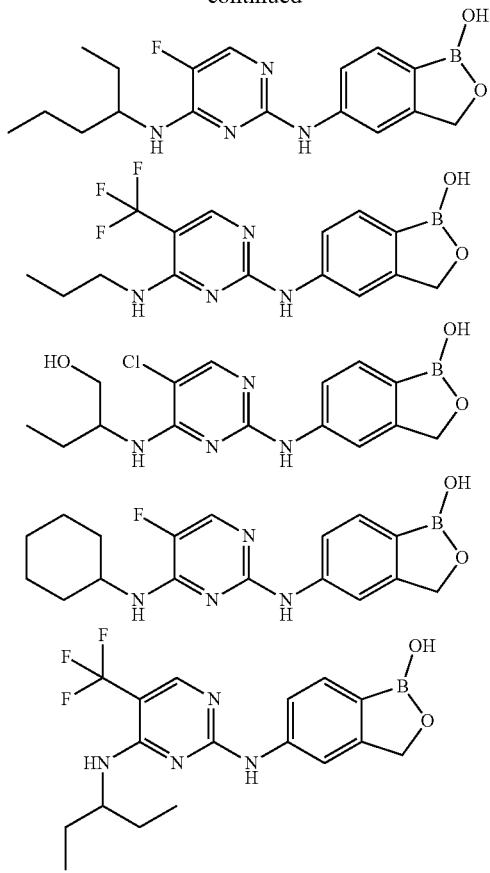

or a stereoisomer, enantiomer, or tautomer thereof, or a veterinary or pharmaceutically acceptable salt thereof.

One embodiment of the present disclosure includes a compound of formula (IB):

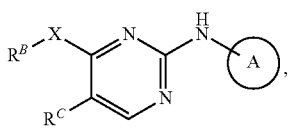

(IB)

wherein:
A is selected from the group consisting of:

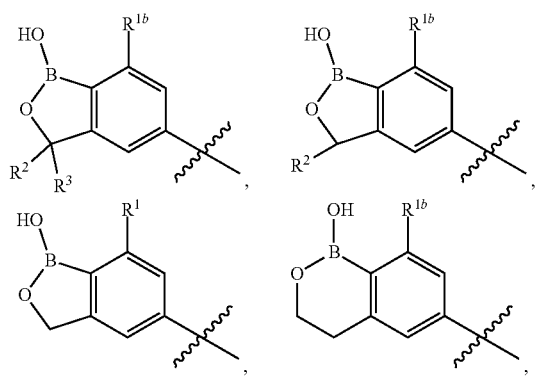

22
-continued

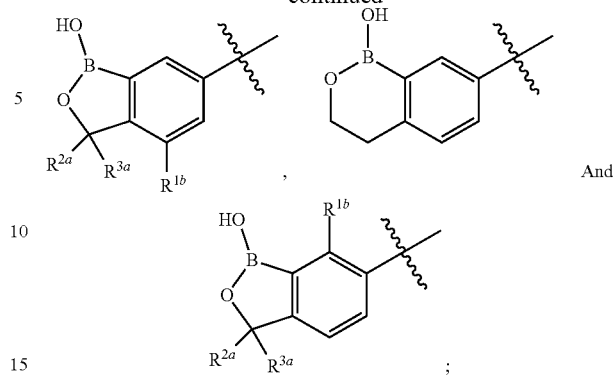

X is selected from the group consisting of: NH, O, and S;

$R^B$ is selected from the group consisting of: unsubstituted phenyl, substituted phenyl, unsubstituted $C_1$-$C_6$ alkyl, substituted $C_1$-$C_6$ alkyl, unsubstituted $C_2$-$C_6$ alkenyl, substituted $C_2$-$C_6$ alkenyl, unsubstituted $C_2$-$C_6$ alkynyl, substituted $C_2$-$C_6$ alkynyl, unsubstituted $C_3$-$C_6$ cycloalkyl, substituted $C_3$-$C_6$ cycloalkyl, and unsubstituted arylalkyl, substituted arylalkyl;

$R^C$ is selected from the group consisting of: hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, and partially or fully halogenated cyclopropyl;

each $R^1$, when present, is selected from the group consisting of: chlorine, bromine, iodine, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, $O(C_1$-$C_3$ alkyl), and $O(C_1$-$C_3$ haloalkyl);

each $R^{1b}$, when present, independently is selected from the group consisting of: hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, $O(C_1$-$C_3$ alkyl), and $O(C_1$-$C_3$ haloalkyl);

each of $R^2$ and $R^3$, when present, independently is selected from the group consisting of: $C_1$-$C_3$ alkyl, $C_2$-$C_3$ alkenyl, $C_2$-$C_3$ alkynyl, and, when present, $R^2$ and $R^3$ taken together form a 3 membered cycloalkyl ring; and each of $R^{2a}$ and $R^{3a}$, when present, independently is selected from the group consisting of: hydrogen, $C_1$-$C_3$ alkyl, $C_2$-$C_3$ alkenyl, $C_2$-$C_3$ alkynyl, and $R^{2a}$ and $R^{3a}$ taken together form a 3 membered cycloalkyl ring, or a stereoisomer, enantiomer, or tautomer thereof, or a veterinary or pharmaceutically acceptable salt thereof.

In one aspect, A is selected from the group consisting of

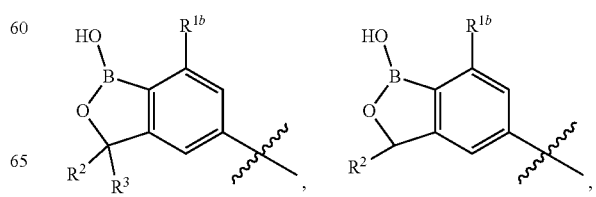

-continued

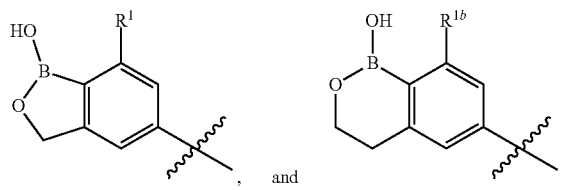
, and

In one aspect, A is selected from the group consisting of:

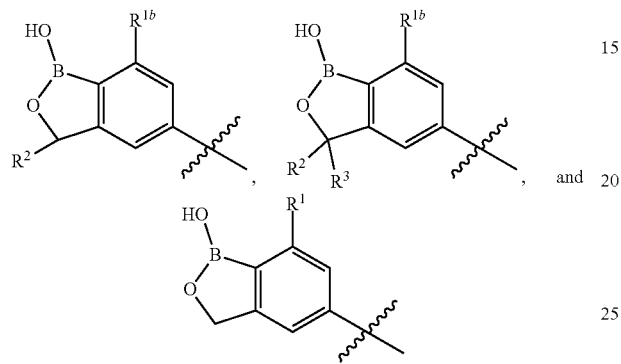
, and

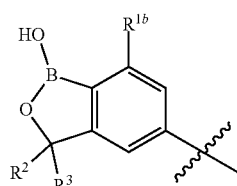
.

In one aspect, when present, $R^1$ is selected from the group consisting of: chlorine, bromine, iodine, $C_1$-$C_3$ alkyl, and $C_1$-$C_3$ haloalkyl. In one aspect, when present $R^{1b}$ is selected from the group consisted of hydrogen, halogen, $C_1$-$C_3$ alkyl, and $C_1$-$C_3$ haloalkyl. In one aspect, when present, $R^{1b}$ is selected from the group consisted of halogen, $C_1$-$C_3$ alkyl, and $C_1$-$C_3$ haloalkyl.

In one aspect, when present, each of $R^2$ and $R^3$ is methyl. In one aspect, A is:

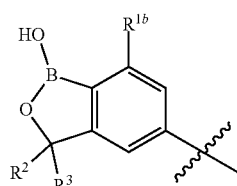
.

In one aspect, X is NH. In one aspect, $R^B$ is unsubstituted phenyl, substituted phenyl, unsubstituted $C_1$-$C_6$ alkyl, substituted $C_1$-$C_6$ alkyl, unsubstituted $C_3$-$C_6$ cycloalkyl, or substituted $C_3$-$C_6$ cycloalkyl. In one aspect, $R^B$ is unsubstituted phenyl, unsubstituted $C_1$-$C_6$ alkyl, or unsubstituted $C_3$-$C_6$ cycloalkyl. In one aspect, $R^B$ is unsubstituted $C_1$-$C_6$ alkyl, or unsubstituted $C_3$-$C_6$ cycloalkyl. In one aspect, $R^B$ is unsubstituted $C_1$-$C_6$ alkyl, substituted $C_1$-$C_6$ alkyl, unsubstituted $C_2$-$C_6$ alkenyl, substituted $C_2$-$C_6$ alkenyl, unsubstituted $C_2$-$C_6$ alkynyl, substituted $C_2$-$C_6$ alkynyl, unsubstituted $C_3$-$C_6$ cycloalkyl, or substituted $C_3$-$C_6$ cycloalkyl. In one aspect, substituted is selected from one or more of $CH_2OH$, $C_1$-$C_3$ alkyl, $C_1$-$C_3$ haloalkyl, and $SO_2(C_1$-$C_3$ alkyl). In one aspect, $R^C$ is selected from the group consisting of: halogen, $C_1$-$C_3$ alkyl, and partially or fully halogenated $C_1$-$C_3$ alkyl. In one aspect, $R^C$ is selected from the group consisting of: $CH_3$, $CF_3$, F, and $C_1$.

One embodiment of the present disclosure includes a compound selected from the group consisting of:

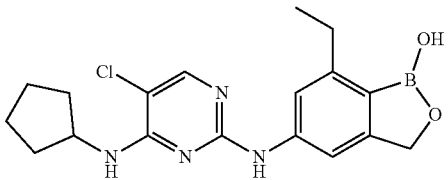 [SMILES: CCc1cc(Nc2ncc(Cl)c(NC3CCCC3)n2)cc2c1B(O)OC2]

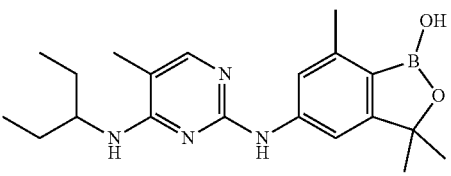 [SMILES: CCC(CC)Nc1nc(Nc2cc(C)c3c(c2)C(C)(C)OB3O)ncc1C]

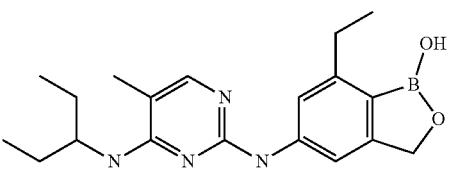

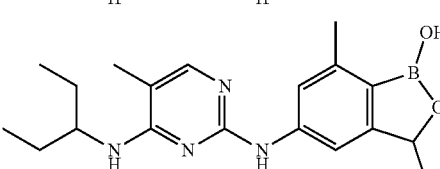

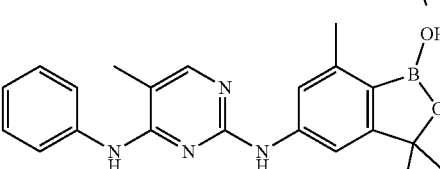

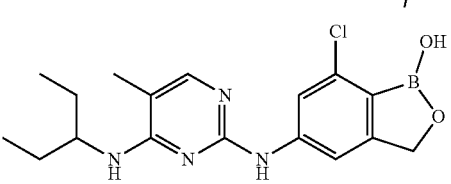

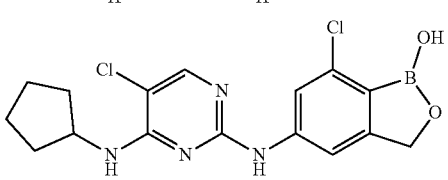

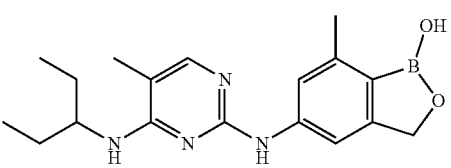 [SMILES: CCC(CC)Nc1nc(Nc2cc(C)c3c(c2)COB3O)ncc1C]

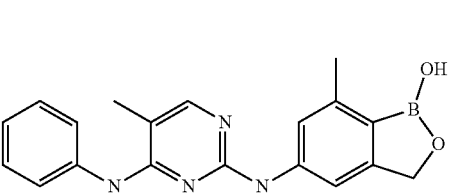


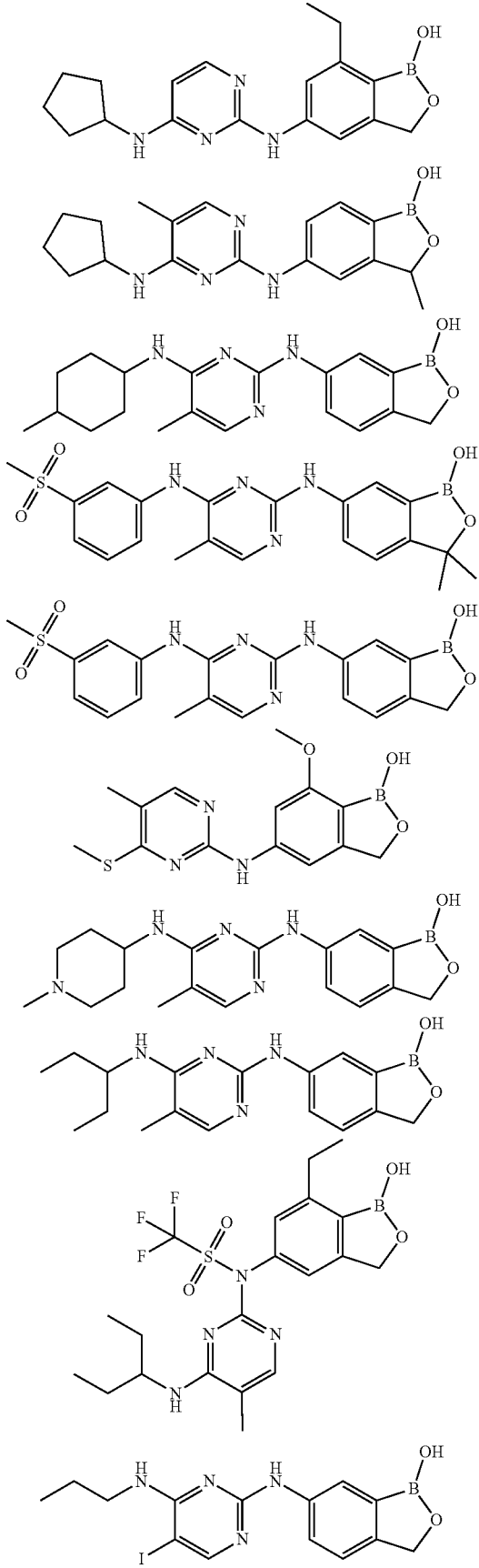
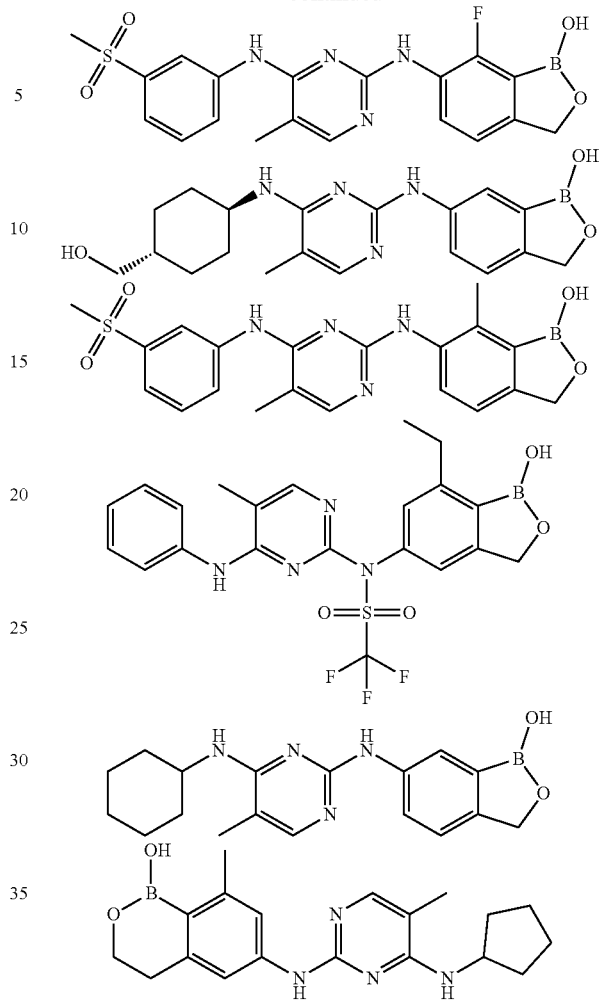
or a stereoisomer, enantiomer, or tautomer thereof, or a veterinary or pharmaceutically acceptable salt thereof.
One embodiment of the present disclosure includes a compound selected from the group consisting of:
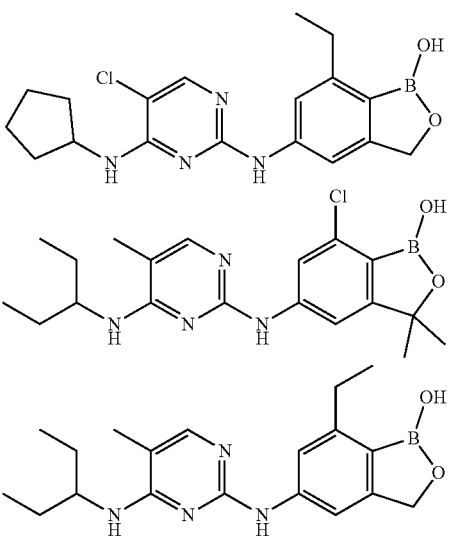

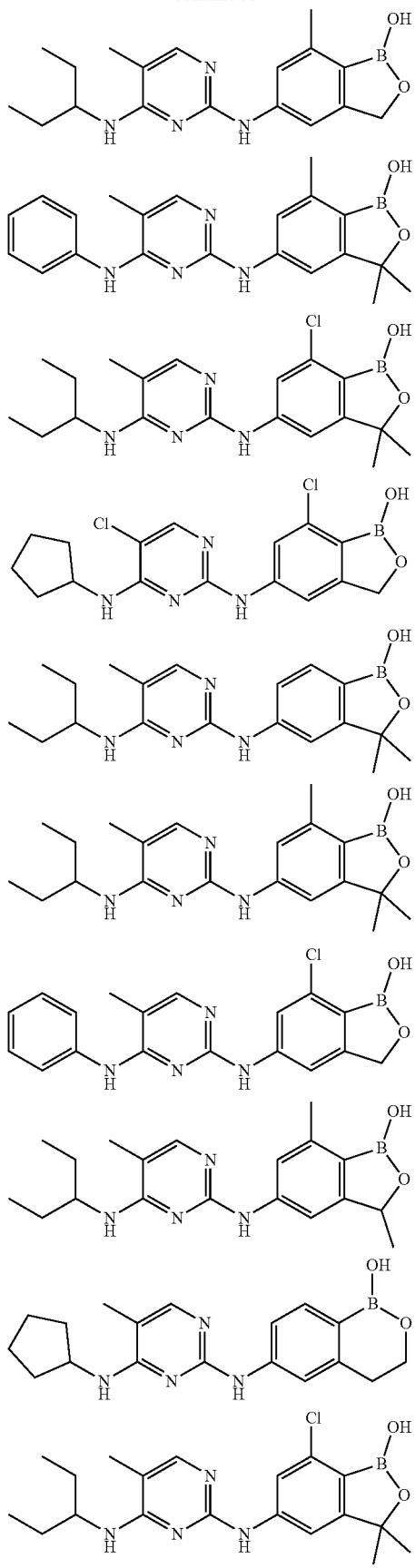
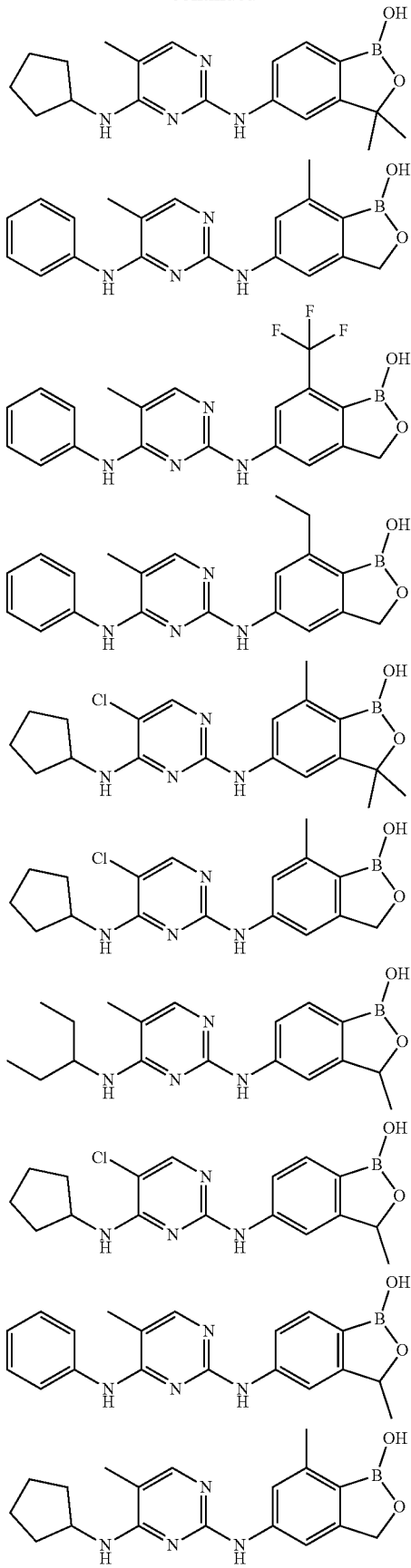

-continued

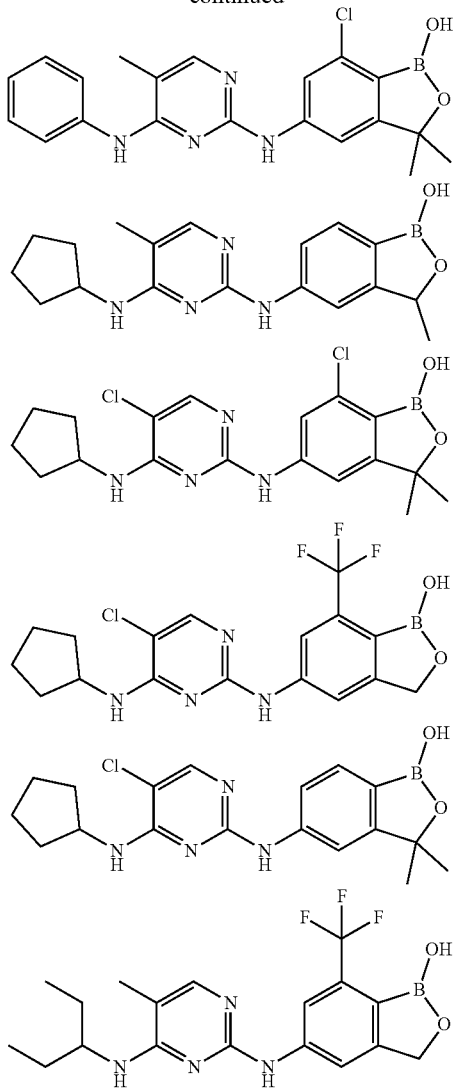

One embodiment of the present disclosure includes a method for treating a patient having a disease or disorder susceptible to modulation of one or more of (i) JAK, and (ii) JAK and an additional enzyme, comprising administering a therapeutically effective amount of a compound of the present disclosure. In one aspect, the additional enzyme is also a tyrosine kinase. In one aspect, the additional tyrosine kinase is one or more of TrkA and Syk. In one aspect, the additional enzyme is PDE4.

One embodiment of the present invention includes a method for treating a patient having a disease or disorder susceptible to modulation of JAK, either alone or with dual- or multi-modulation with one or more of an additional enzyme inhibitor, comprising administering a therapeutically effective amount of a compound of the present disclosure. In one aspect, the additional enzyme inhibitor is a tyrosine kinase inhibitor. In one aspect, the additional tyrosine kinase inhibitor inhibits one or more of TrkA and Syk. In one aspect, the additional enzyme inhibitor is a PDE4 inhibitor. In one aspect, the disease or disorder is one or more of atopic dermatitis, psoriasis, psoriatic arthritis, Bechet's disease, *pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer. In one aspect, the disease or disorder is one or more of atopic dermatitis, psoriasis, and rheumatoid arthritis. In one aspect, the compound is administered in an amount to perturb an immune regulatory pathway in a cell. In one aspect, the perturbation results in an effect on the JAK-STAT pathway.

One embodiment of the present invention includes a method of inhibiting JAK either alone or in combination with inhibition of one or more additional mechanism in a mammalian cell comprising contacting the mammalian cell with a compound of the present disclosure. In one aspect, an additional mechanism is also inhibition of a tyrosine kinase. In one aspect, the tyrosine kinase is one or more TrkA and Syk. In one aspect, the additional mechanism is inhibition of PDE4.

One embodiment of the present invention includes a method for treating a patient having a disease or disorder susceptible to modulation of JAK, either alone or in dual modulation with PDE4, comprising administering a therapeutically effective amount of a compound of the present disclosure. In one aspect, the disease or disorder is one or more of atopic dermatitis, psoriasis, psoriatic arthritis, Bechet's disease, *pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer. In one aspect, the disease or disorder is one or more of atopic dermatitis, psoriasis, and rheumatoid arthritis. In one aspect, the compound is administered in an amount to perturb an immune regulatory pathway in a cell. In one aspect, the perturbation results in an effect on the JAK-STAT pathway.

One embodiment of the present invention includes a method of inhibiting JAK in combination with PDE4, in a mammalian cell comprising contacting the mammalian cell with a compound of the present disclosure. In one aspect, the JAK is JAK-1. In one aspect, the inhibition is selective for JAK-1. In one aspect, the mammalian cell is a cell from a subject having an inflammatory condition. In one aspect, the method further comprises modulation of one or more of TrkA and Syk.

One embodiment of the present invention includes a method for treating one or more diseases or disorders of inflammation, auto-immune dysfunction, and cancer comprising administering to a subject in need thereof an effective amount of a compound of the present disclosure. In one aspect, the disease or disorder is atopic dermatitis, psoriasis, or rheumatoid arthritis. In one aspect, the subject is a mammal. In one aspect, the mammal is selected from humans, livestock mammals, domestic mammals, or companion mammals. In one aspect, the mammal is human. In one aspect, the mammal is one or more of cattle, sheep, goats, llamas, alpacas, pigs, horses, donkeys, dogs, and cats.

One embodiment of the present invention includes a composition comprising a compound of the present disclosure, and a pharmaceutically or veterinary acceptable carrier.

One embodiment of the present invention includes a combination comprising a compound of the present disclosure, and one or more other pharmaceutical or veterinary active substances.

One embodiment of the present invention includes a compound of the present disclosure, for use in medicine.

One embodiment of the present invention includes a compound of the present disclosure, for the manufacture of a medicament for the treatment of one or more diseases or disorder of inflammation, auto-immune dysfunction, and cancer. In one aspect, the disease or disorder is atopic dermatitis, psoriasis, or rheumatoid arthritis.

One embodiment of the present invention includes use of a compound of the present disclosure, for the treatment of one or more diseases or disorders of inflammation, auto-immune dysfunction, and cancer. In one aspect, the disease or disorder is atopic dermatitis, psoriasis, or rheumatoid arthritis.

Surprisingly, when structural modifications are made to the depicted core pyrimdine, including the number and placement of one or more nitrogen atoms in that ring, but where the variables are otherwise consistent with compounds of the present disclosure, the modified core is characterized by substantially different biological activity. Such compounds appear to have no JAK activity or significantly decreased JAK activity as compared to compounds of the present disclosure. Interestingly, however, such compounds maintain a level of PDE4 activity.

In addition, unexpectedly, when the compound is a compound of formula (IA) and when the depicted NH linker is alkylated, e.g., N—CH$_3$, the compound has no JAK activity or significantly decreased JAK activity. Furthermore, the alkylated NH linker causes the compounds to diminish in PDE4 activity as well. A non-limiting hypothesis is that the alkylation of the NH group abolishes the hydrogen bond and decreases its binding affinity to JAK1. Examples include Comparative Compounds A and B herein described.

In addition, unexpectedly, when the compound is a compound of formula (I) and X is N-alkyl, e.g. N—CH$_3$, the compound has much decreased JAK activity. A non-limiting hypothesis is that NH is key pharmacophore providing an important hydrogen bond donor to the hinge domain of the kinase.

In addition, unexpectedly, when the regiochemistry of (IA) is modified as shown in a compound of formula (III) as shown below, JAK and PDE4 activity is decreased. This is exemplified in the data shown below:

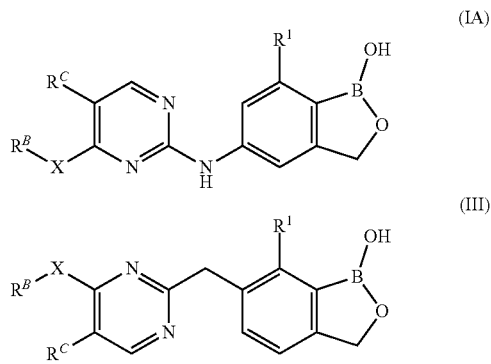

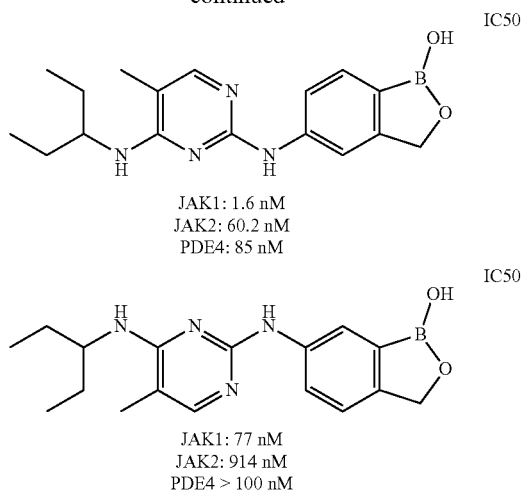

One or more aspects and embodiments may be incorporated in a different embodiment although not specifically described. That is, all aspects and embodiments may be combined in any way or combination.

BRIEF DESCRIPTION OF THE DRAWINGS

FIG. 2 illustrates the results of a docking model with compounds of the present disclosure at the active site of JAK1 showing the NH(X) forming hydrogen bonds with Gly1020 and Asp1021 through a crystal water. Alkylation of the NH group abolishes the hydrogen bond and decreases its binding affinity to JAK1.

DETAILED DESCRIPTION

Definitions

Figure 1D:
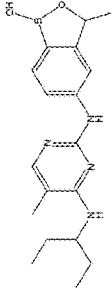
FIG. 1A-T is a table, providing results of biological testing for the compounds of the present disclosure, as described herein in more detail.
Figure 1E:
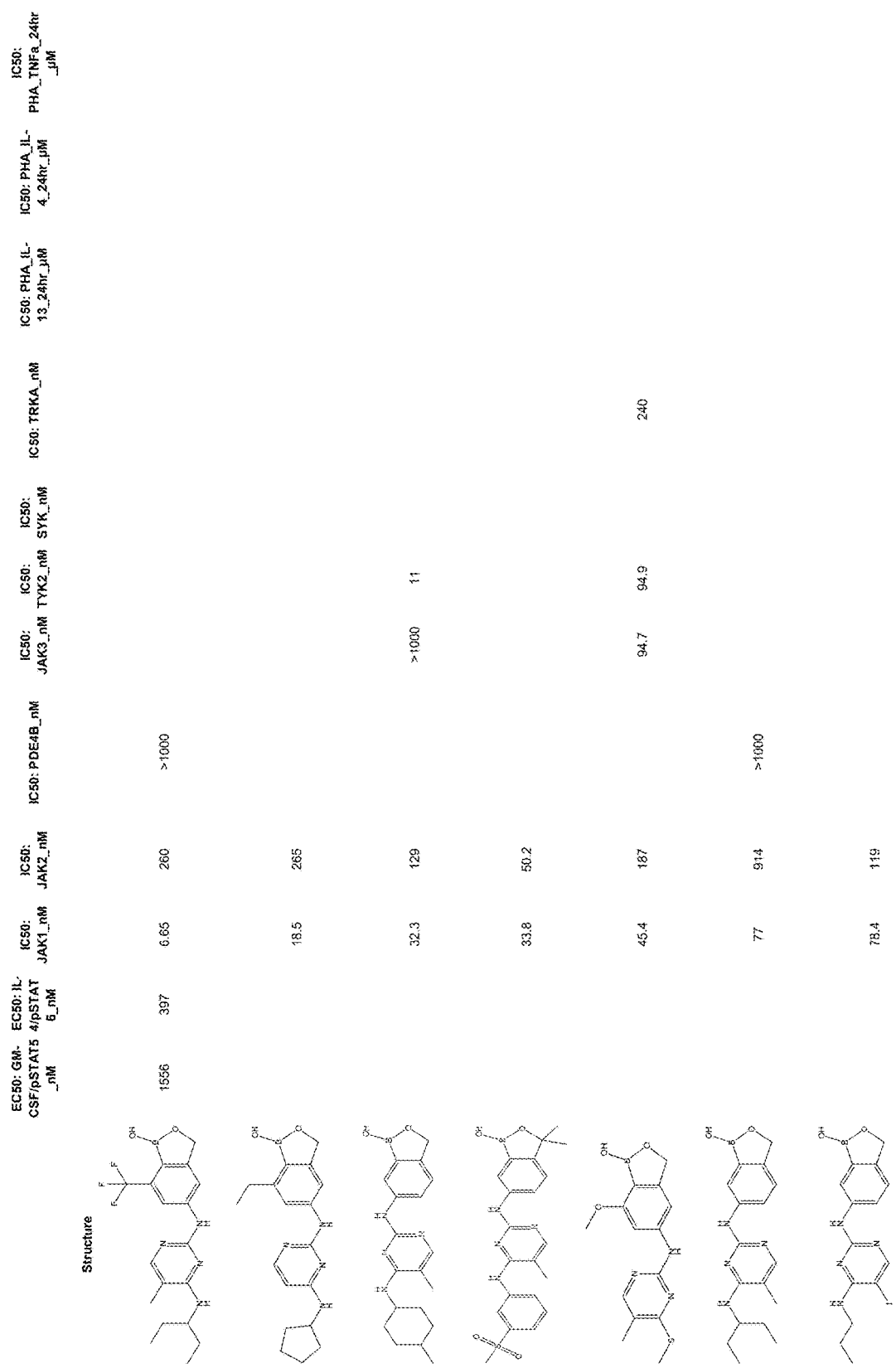
Figure 1F:
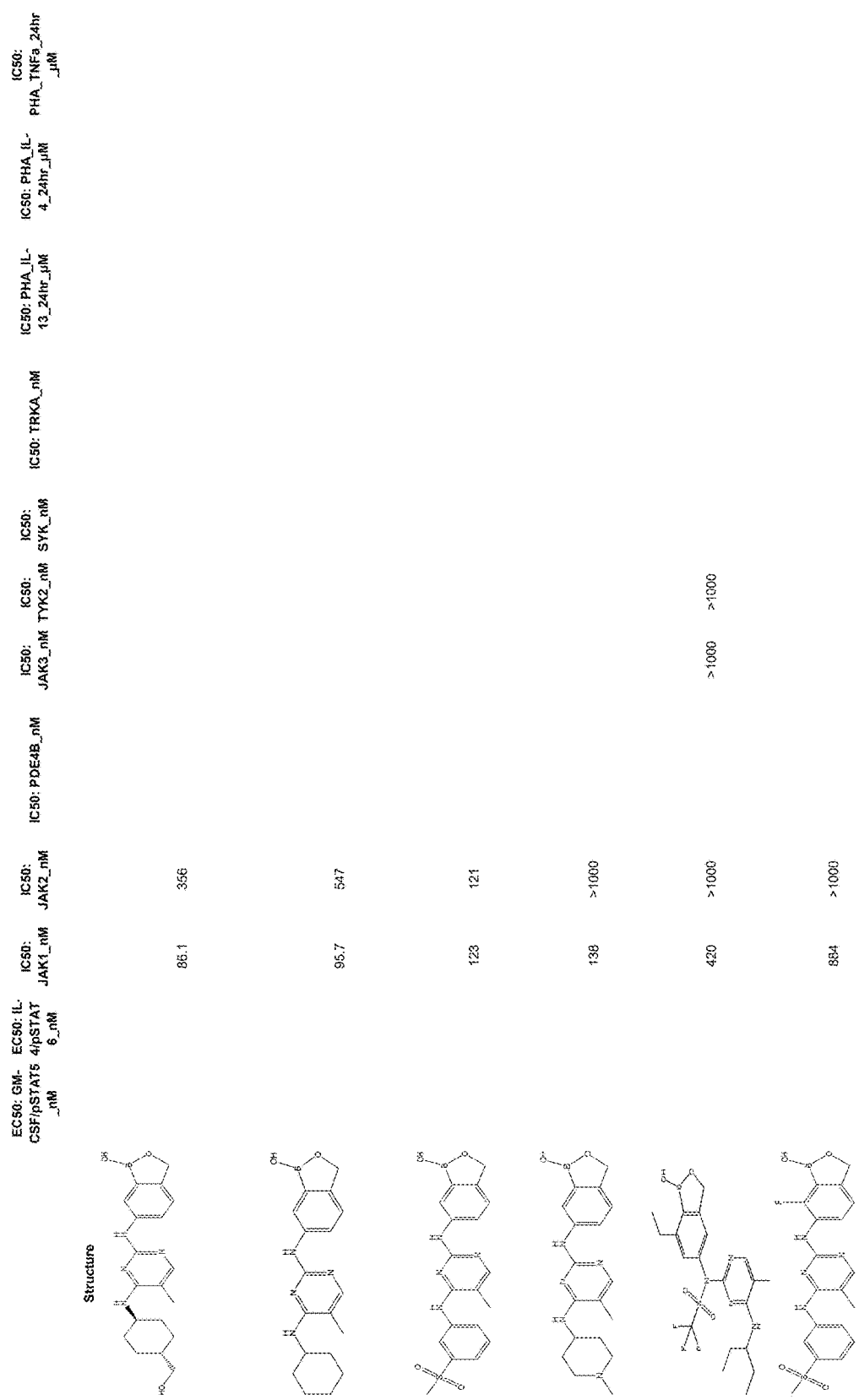
Figure 1J:
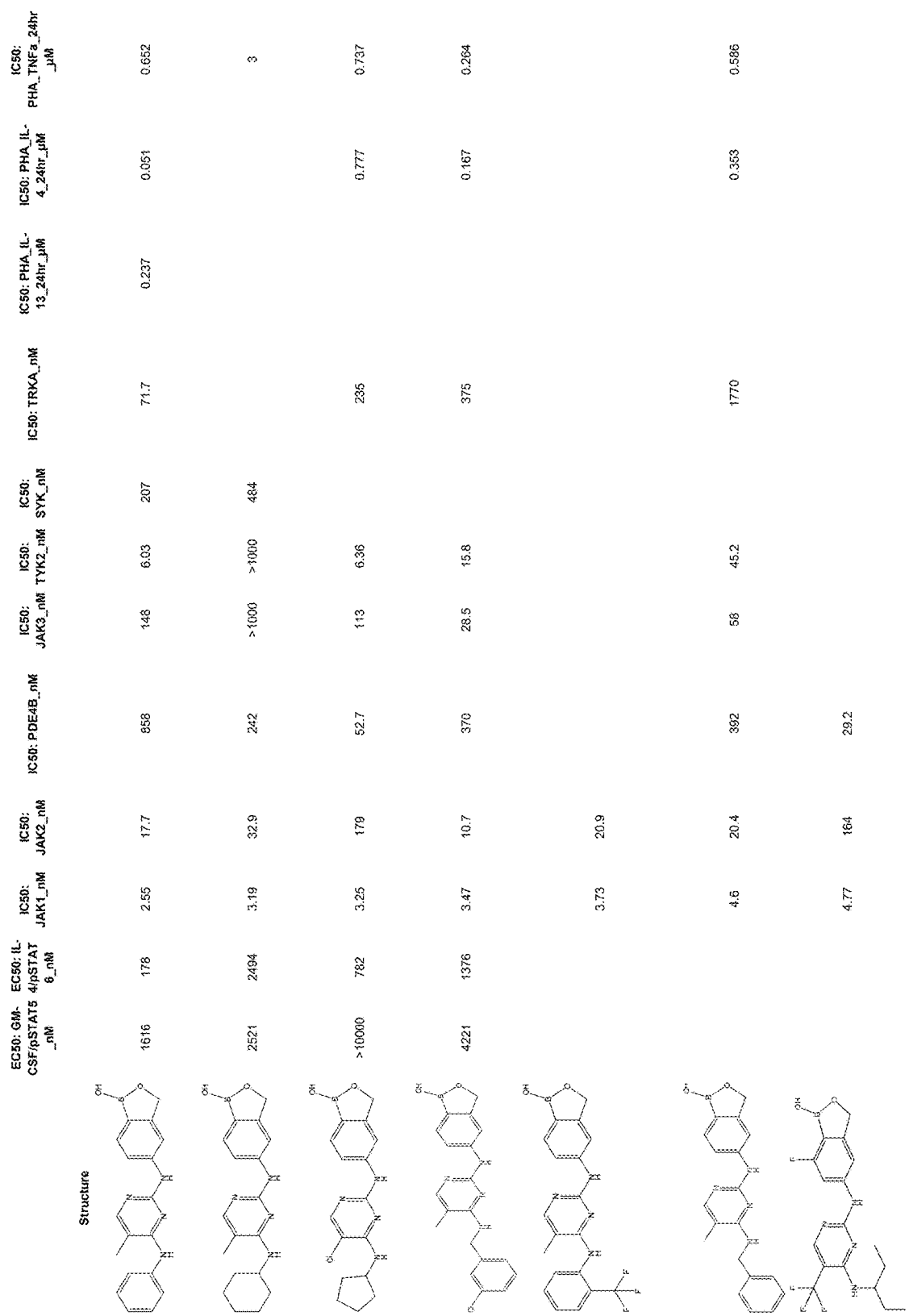
Figure 1M:
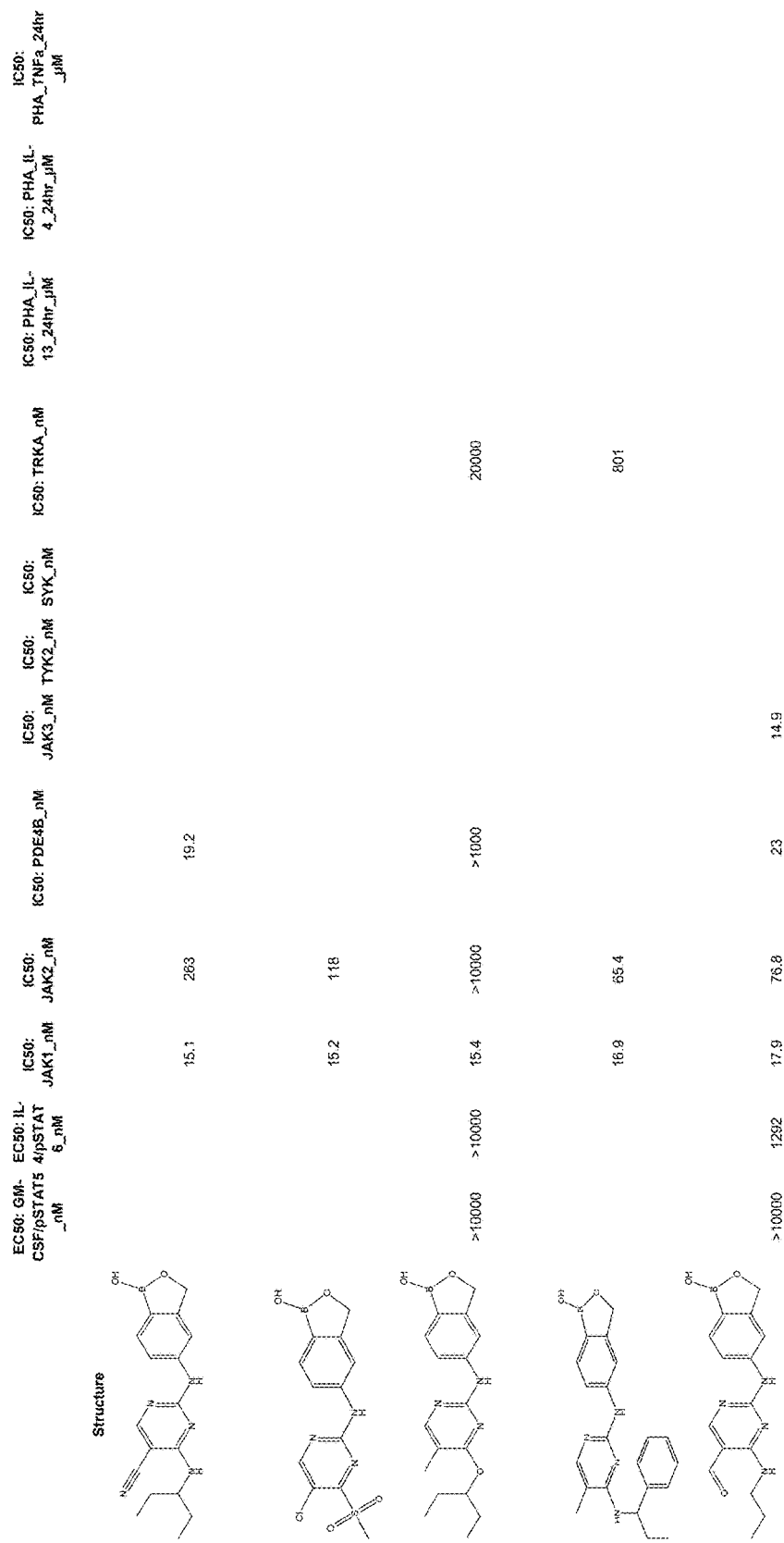
Figure 10:
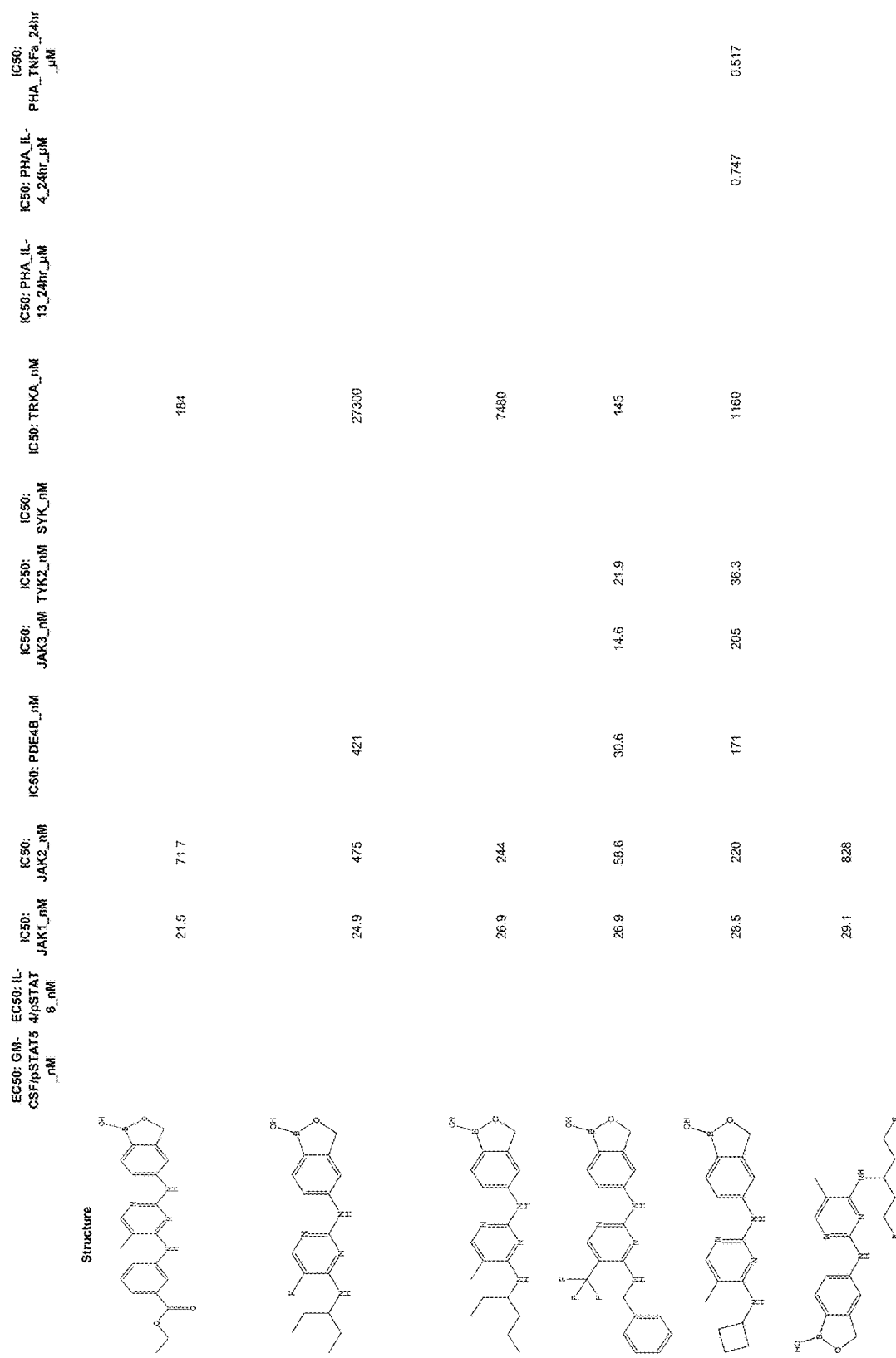
Figure 1P:
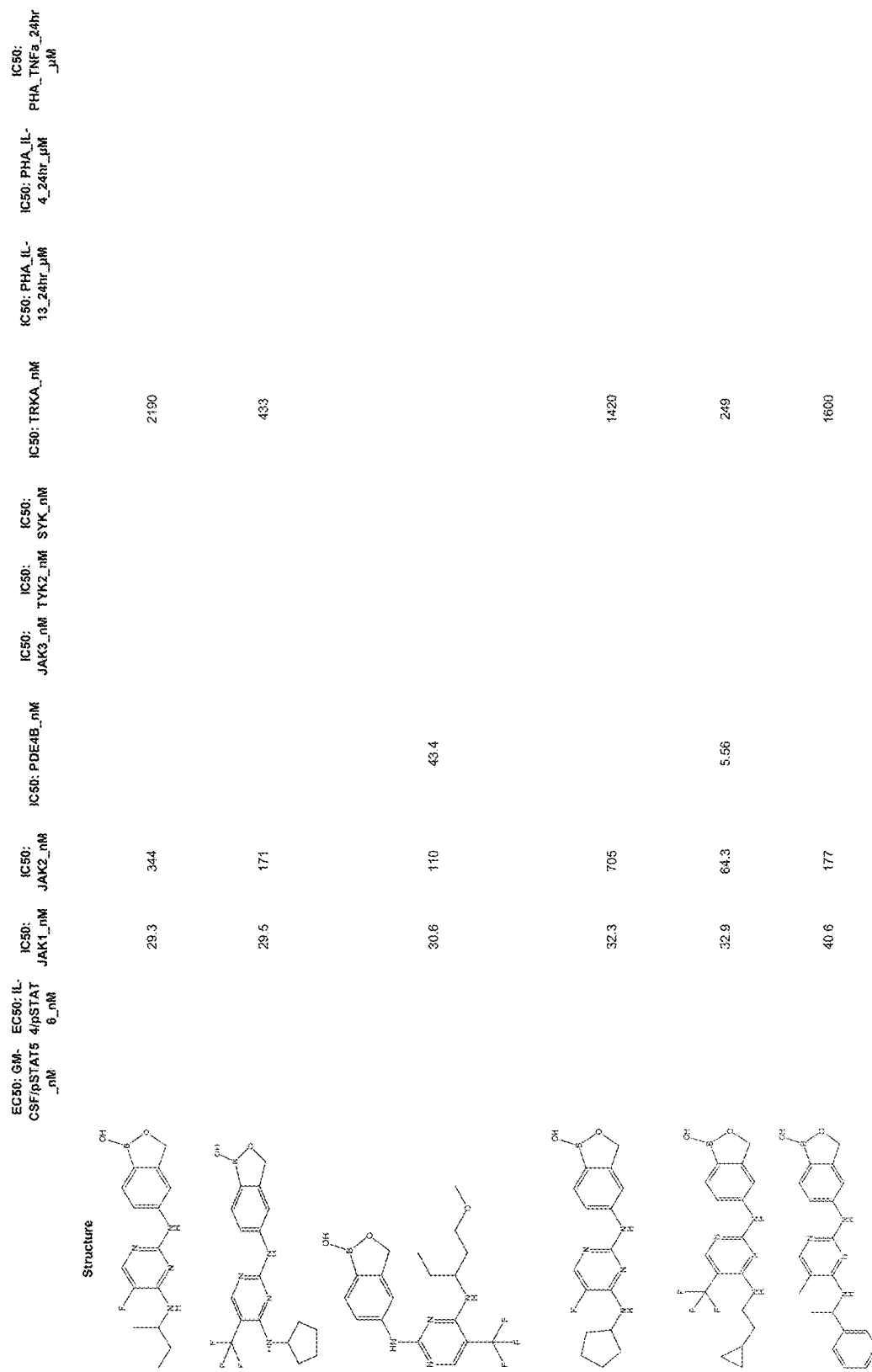
Figure 1Q:
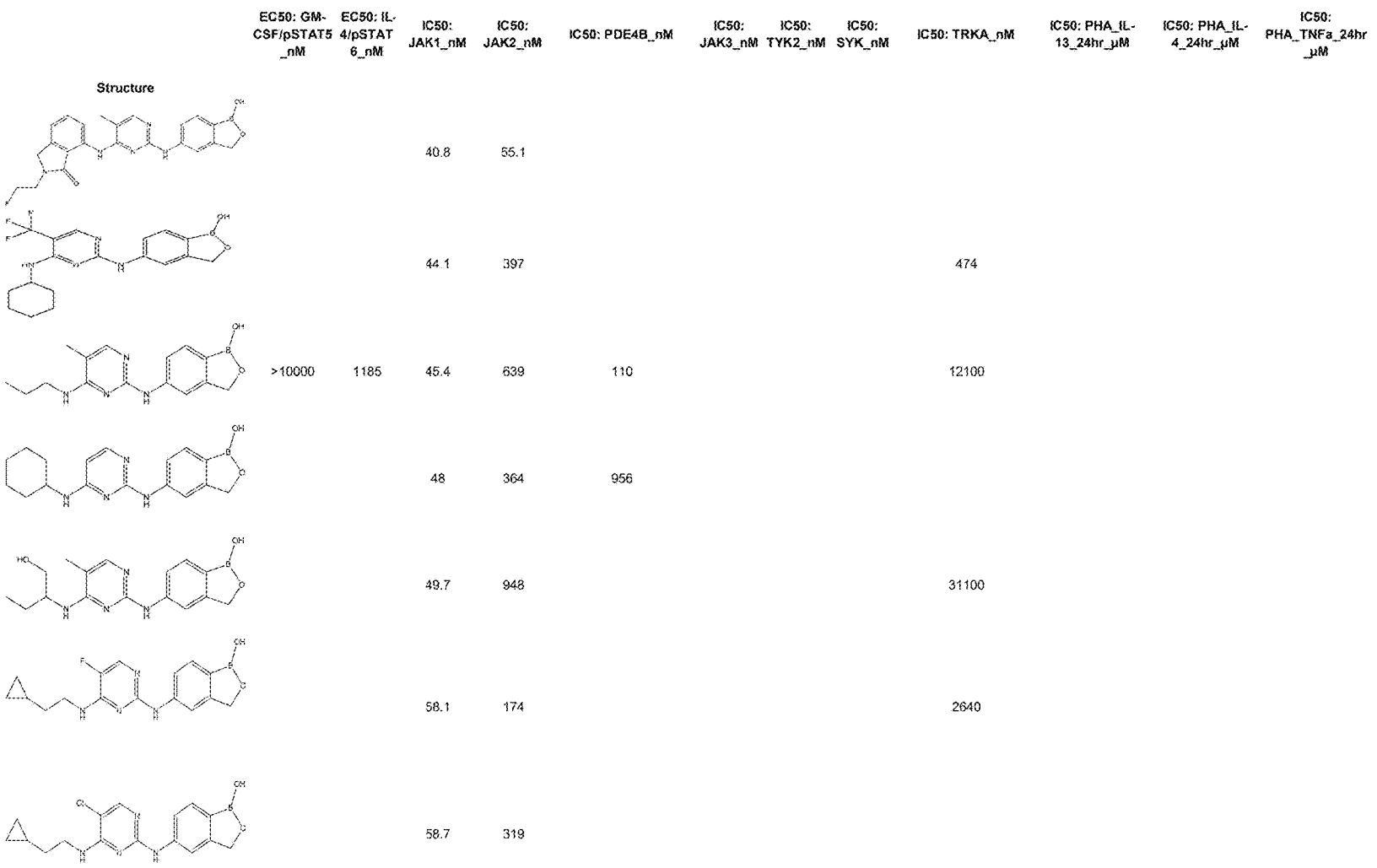
Figure 1R:
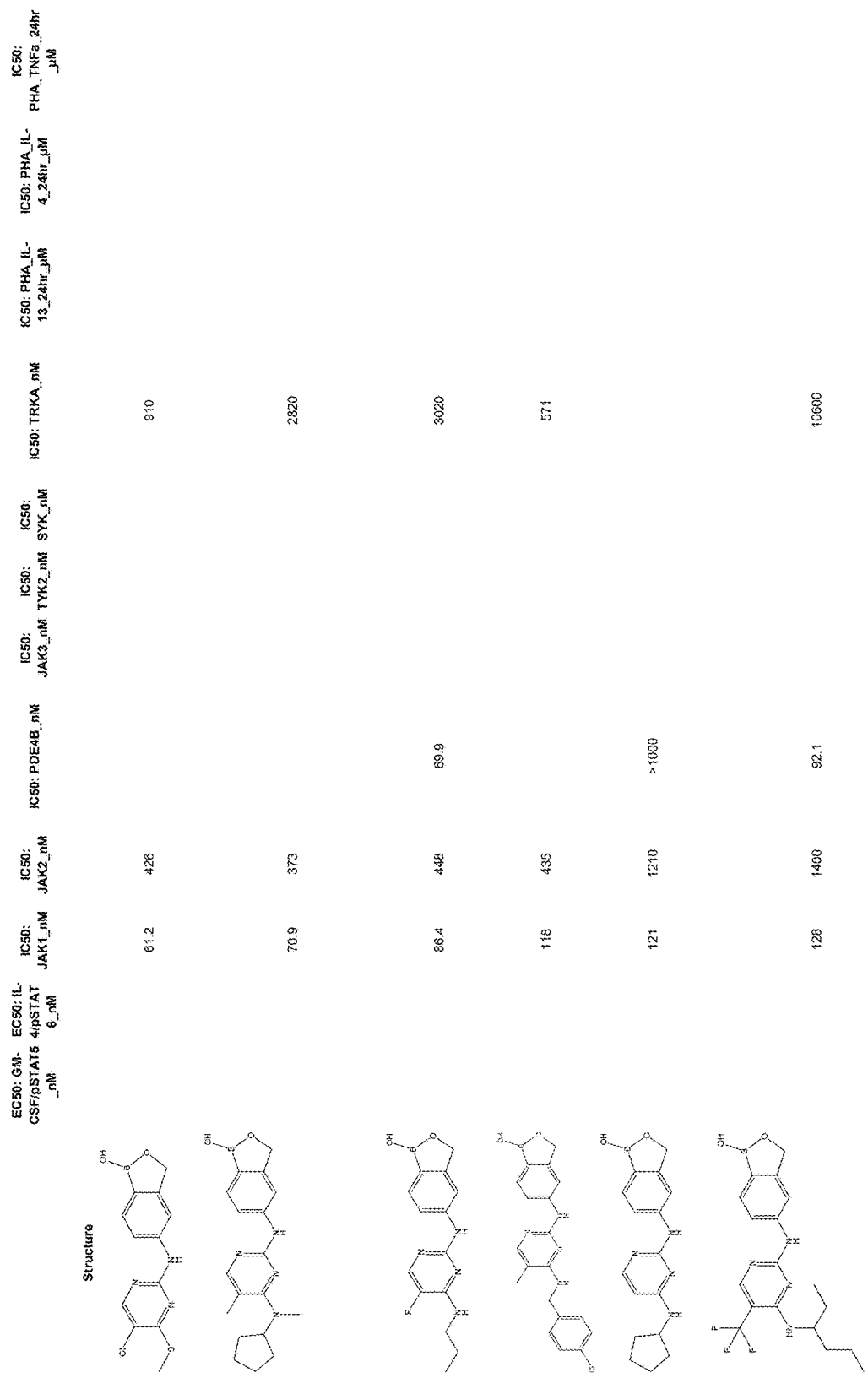
Figure 1T:
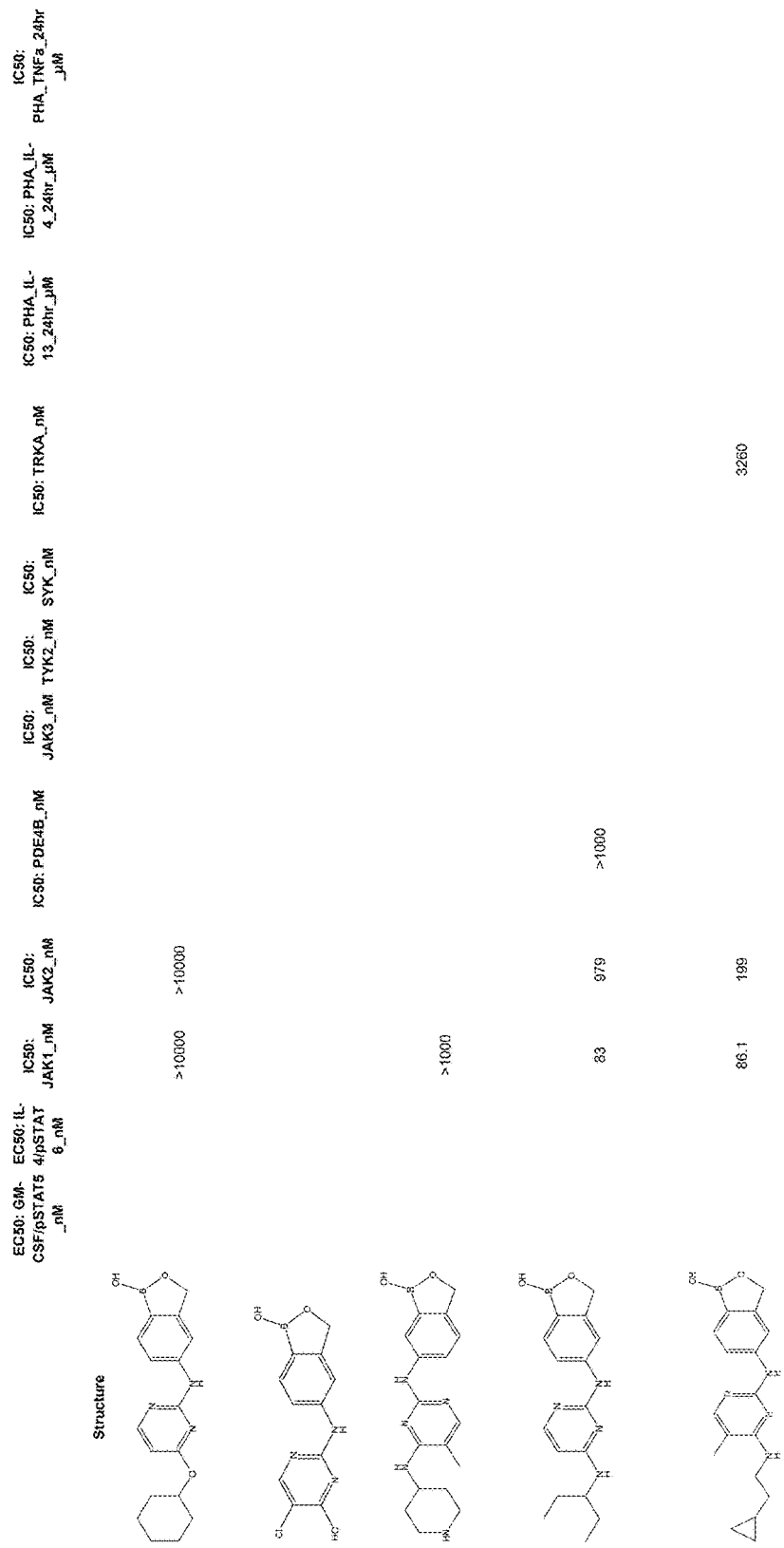

Any reference in the specification to "one embodiment" or "an embodiment" or "another embodiment" or a similar phrase means that a particular feature, structure, characteristic, operation, or function being described is included in at least one embodiment. Thus, any appearance of the phrases "in one embodiment" or "in an embodiment" in the specification is not necessarily referring to the same embodiment. Further, the particular features, structures, characteristics, operations, or functions may be combined in any suitable manner in one or more embodiments, and it is intended that embodiments of the described subject matter can and do cover modifications and variations of the described embodiments. Particular aspects, as used herein, should be treated in a similar manner.

The phrases "at least one", "one or more", and "and/or" are open-ended expressions that are both conjunctive and disjunctive in operation. For example, each of the expressions "at least one of A, B, and C", "at least one of A, B, or C", "one or more of A, B, and C", "one or more of A, B, or C" and "A, B, and/or C" means A alone, B alone, C alone, A and B together, A and C together, B and C together, or A, B, and C together.

The term "a" or "an" entity refers to one or more of that entity. As such, the terms "a" (or "an"), "one or more" and "at least one" may be used interchangeably herein. It is also to be noted that the terms "comprising", "including", and "having" may be used interchangeably.

A compound of this disclosure includes those described generally, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, "*Handbook of Chemistry and Physics*", 75th Ed., CRC Press, New York, NY (1995). Additionally, general principles of organic chemistry are described in "*Organic Chemistry*", Thomas Sorrell, University Science Books, Sausalito, CA (1999), and "*March's Advanced Organic Chemistry*", 5th Ed., Ed.: Smith, M. B. and March, J., John Wiley & Sons, New York, NY (2001), the entire contents of which are hereby incorporated by reference.

When referring to the compounds disclosed herein, the following terms have the following meanings unless indicated otherwise. The following definitions are meant to clarify, but not limit, the terms defined. If a particular term used herein is not specifically defined, such term should not be considered indefinite. Rather, terms are used within their accepted meanings.

As used herein, "alkyl" refers substituted or unsubstituted to monovalent saturated aliphatic hydrocarbyl groups having from 1 to 20 carbon atoms, preferably 1-8 carbon atoms, preferably 1-6 carbon atoms. The hydrocarbon chain may be either straight-chained or branched. Illustrative alkyl groups include methyl, ethyl, n-propyl, iso-propyl, n-butyl, iso-butyl, and tert-butyl. Similarly, an "alkenyl" group refers to an alkyl group having one or more double bonds present in the chain, and an "alkynyl" group refers to an alkyl group having one or more triple bonds present in the chain. Alkyl groups may be substituted or unsubstituted. Alkenyl groups may be substituted or unsubstituted. Alkynyl groups may be substituted or unsubstituted.

As used herein, "aryl" refers to a substituted or unsubstituted carbocyclic aromatic ring system, either pendent or fused, such as phenyl, naphthyl, anthracenyl, phenanthryl, tetrahydronaphthyl, indane, or biphenyl. A preferred aryl is phenyl.

As used herein, "cycloalkyl" refers to a substituted or unsubstituted, unsaturated or partially saturated hydrocarbon ring, containing from 3 to 15 ring atoms. Illustrative cycloalkyl groups include cyclopropyl, cyclobutyl, cyclopentyl, cyclohexyl, as well as partially saturated versions thereof, such as cyclohexenyl, and cyclohexadienyl. Cycloalkyl groups may be substituted or unsubstituted.

As used herein "halogen" or "halo" refers to a halogen. In some embodiments, the halogen is preferably Cl (chlorine), or F (fluorine).

As used herein, "haloalkyl" refers to monovalent saturated aliphatic hydrocarbyl groups having from 1 to 20 carbon atoms, preferably 1-8 carbon atoms, preferably 1-6 carbon atoms, wherein at least one hydrogen atom is substituted by a halogen, including but not limited to perhalo groups where all hydrogen atoms are replaced with halogen atoms. A preferred perhalo group is a perfluoro group. The haloalkyl chain can be either straight-chained or branched. Illustrative haloalkyl groups include trifluoromethyl, trichloromethyl, trifluoroethyl, trifluoropropyl, trifluorobutyl, and pentafluoroethyl. Similarly, a "haloalkenyl" group refers to a haloalkyl group having one or more double bonds present in the chain and a "haloalkynyl" refers to a haloalkyl group having one or more triple bonds present in the chain.

As used herein, the term "heterocyclyl" refers to a substituted or unsubstituted, unsaturated or partially saturated hydrocarbon ring, containing from 3 to 15 ring atoms, wherein one or more carbon atom is replaced with a heteroatom selected from O, N, S, or Si, where each N, S, or Si may be oxidized, and where each N may be quaternized. A heterocyclyl group may be attached to the remainder of the molecule through a heteroatom.

As used herein, the term "heteroaryl" or "heteroaromatic" refers to substituted or unsubstituted aromatic ring groups having 5 to 14 ring atoms selected from carbon and at least one (typically 1-4, more typically 1 or 2) heteroatom (e.g., oxygen, nitrogen, sulfur, or silicon). They include monocyclic rings and polycyclic rings in which a monocyclic heteroaromatic ring is fused to one or more other carbocyclic aromatic or heteroaromatic rings. Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl) and thienyl (e.g., 2-thienyl, 3-thienyl. Examples of monocyclic six-membered nitrogen-containing heteroaryl groups include pyrimidinyl, pyridinyl and pyridazinyl. Examples of polycyclic aromatic heteroaryl groups include carbazolyl, benzimidazolyl, benzothienyl, benzofuranyl, indolyl, quinolinyl, benzotriazolyl, benzothiazolyl, benzoxazolyl, benzimidazolyl, isoquinolinyl, indolyl, isoindolyl, acridinyl, or benzisoxazolyl. A heteroaryl group may be attached to the remainder of the molecule through a heteroatom.

The terms "arylalkyl" refers to those radicals in which an aryl group, such as a phenyl (Ph), is linked through an alkyl group. Examples includes benzyl, phenethyl, and the like. The term "benzyl" as used herein is a radical in which a phenyl group is attached to a CH$_2$ group, thus, a CH$_2$Ph group. The term substituted benzyl refers to radicals in which the benzyl group contains one or more substituents. In a preferred embodiment, the phenyl group has one substituent. In another preferred embodiment, the phenyl group has zero substituents (is unsubstituted). In one embodiment, the phenyl group may have 1 to 5 substituents, or in another embodiment 2 to 3 substituents. Moreover, the alkylene linking group may carry at least one substituent as well.

As used herein, "substituted" or "optionally substituted" refers to a substitution of a hydrogen atom, which would otherwise be present for the substituent. When discussing ring systems, the optional substitution is typically with 1, 2, or 3 substituents replacing the normally-present hydrogen. When referencing straight and branched moieties, however, the number of substitutions may be more, occurring wherever hydrogen is present. The substitutions may be the same or different.

As used herein, with reference to activity of a compound of the present invention, "selectivity" refers to a greater than 10-fold differential in activity. In one embodiment, compounds of the present disclosure may be characterized as selective for JAK1 over other JAK sub-types. In one embodiment, the compounds of the present disclosure may be characterized as having a JAK2:JAK1 ratio of about 10 to about 1000. In one embodiment, the compounds of the present disclosure may be characterized as having a JAK3:JAK1 ratio of about 0.5 to about 800. In one embodiment, upon administration to subject in need thereof, the compounds of the present disclosure preferentially inhibits activity of Jak1 over activity of Jak2, activity of Jak3, and activity of Tyk2, and inhibits less than 50%, 40%, 30%, 25%, 20%, 15%, 10%, or 5% of one or more of Jak2, Jak3, or Tyk2 activity in the subject. In certain embodiments, Jak1 activity is preferentially inhibited over activity of Jak2, activity of Jak3, and activity of Tyk2. In certain embodiments, more than 40%, 50%, 55%, 60%, 65%, 70%, 75%, 80%, 85%, 90%, 95%, 99% of Jak1 activity is inhibited in the mammal subject. In certain embodiments, activity of Jak1 is preferentially inhibited over activity of Jak2. For example, preferential inhibition can be measured by Jak1/Jak2 potency ratio, defined as the inverse ratio of $IC_{50}$ of Jak1 inhibition over $IC_{50}$ of Jak2 inhibition. In certain embodiments, the Jak1/Jak2 potency ratio is at least about 30, 35, 40, 45, 50, 55, 60, 65, 66, 67, 68, 69, 70, 71, 72, 73, 74, 75, 76, 77, 78, 79, 80, 85, or more. In certain embodiments, the $IC_{50}$ of Jak1 inhibition is measured by inhibition of IL6 stimulated STAT3 phosphorylation ex vivo, for example, using a sample (e.g., a blood example) from a subject administered with a compound of the present disclosure. In certain embodiments, the $IC_{50}$ of Jak2 inhibition is measured by inhibition of EPO stimulated STAT5 phosphorylation ex vivo, for example, using a sample (e.g., a blood example) from a subject administered with a compound of the present disclosure. In certain embodiments, activity of Jak1 is preferentially inhibited over activity of Jak3. For example, preferential inhibition can be measured by Jak1/Jak3 potency ratio, defined as the inverse ratio of $IC_{50}$ of Jak1 inhibition over $IC_{50}$ of Jak3 inhibition. In certain embodiments, the Jak1/Jak3 potency ratio is at least about 3, 5, 10, 15, 20, 25, 30, 35, 40, 45, 50, 55, 56, 57, 58, 59, 60, 65, 70 or more. In certain embodiments, the $IC_{50}$ of Jak1 inhibition is measured by inhibition of IL6 stimulated STAT3 phosphorylation ex vivo, for example, using a sample (e.g., a blood example) from a subject administered with a compound of the present disclosure.

Illustrative substitutions, which with multiple substituents can be the same or different, include halogen, such as fluoro, chloro, bromo or iodo, haloalkyl, such as —$CF_3$, —$CF_2CF_3$, —$CHF_2$, —$CH_2F$ and the like, R', OR', OH, SH, SR', $NO_2$, CN, C(O)R', C(O)OR', OC(O)R', CON(R')$_2$, OC(O)N(R')$_2$, $NH_2$, NHR', N(R')$_2$, NHCOR', NHCOH, NHCON$H_2$, NHCONHR', NHCON(R')$_2$, NRCOR', NRCOH, NHCO$_2$H, NHCO$_2$R', NHC(S)N$H_2$, NHC(S)NHR', NHC(S)N(R')$_2$, CO$_2$R', CO$_2$H, CHO, CON$H_2$, CONHR', CON(R')$_2$, S(O)$_2$H, S(O)$_2$R', SO$_2$N$H_2$, S(O)H, S(O)R', SO$_2$NHR', SO$_2$N(R')$_2$, NHS(O)$_2$H, NR'S(O)$_2$H, NHS(O)$_2$R', NR'S(O)$_2$R', and Si(R')$_3$, wherein each of the preceding may be linked through an alkylene linker, namely (CH$_2$)$_x$, where x is 1, 2, or 3. In embodiments where a saturated carbon atom is optionally substituted with one or more substituent groups, the substituents may be the same or different and may also include =O, =S, =NNHR', =NN$H_2$, =NN(R')$_2$, =N—OR', =N—OH, =NNHCOR', =NNHCOH, =NNHCO$_2$R', =NNHCO$_2$H, =NNHSO$_2$R', =NNHSO$_2$H, =N—CN, =NH, or =NR'. Each occurrence of R' is the same or different and represents hydrogen, alkyl, alkenyl, alkynyl, cycloalkyl, haloalkyl, aryl, heterocyclyl, or heteroaryl, or when two R' are each attached to a nitrogen atom, they may form a saturated or unsaturated heterocyclic ring containing from 4 to 6 ring atoms.

In some embodiments of the present disclosure, particularly preferred embodiments of substituents include —C(O) O($C_1$-$C_3$), OH, CH$_2$OH, $C_3$—C cycloalkyl, $C_1$-$C_3$ alkyl, $C_1$-$C_3$ haloalkyl, halogen, O($C_1$-$C_3$ alkyl), and O($C_1$-$C_3$ haloalkyl).

As used herein, the phrase veterinary or veterinarily, or pharmaceutical or pharmaceutically acceptable salt refers to any salt of a compound disclosed herein which retains its biological properties and which is not toxic or otherwise undesirable for veterinary or pharmaceutical use. Such salts may be derived from a variety of organic and inorganic counter-ions known in the art. Such salts include acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid, and like acids.

Salts further include, by way of example only, salts of non-toxic organic or inorganic acids, such as halides, such as, chloride and bromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like.

Examples of inorganic bases that may be used to form base addition salts include, but are not limited to, metal hydroxides, such as lithium hydroxide, sodium hydroxide, and potassium hydroxide; metal amides, such as lithium amide and sodium amide; metal carbonates, such as lithium carbonate, sodium carbonate, and potassium carbonate; and ammonium bases such as ammonium hydroxide and ammonium carbonate.

Examples of organic bases that may be used to form base addition salts include, but are not limited to, metal alkoxides, such as lithium, sodium, and potassium alkoxides including lithium methoxide, sodium methoxide, potassium methoxide, lithium ethoxide, sodium ethoxide, potassium ethoxide, and potassium tert-butoxide; quaternary ammonium hydroxides, such as choline hydroxide; and amines including, but not limited to, aliphatic amines (i.e., alkylamines, alkenylamines, alkynylamines, and alicyclic amines), heterocyclic amines, arylamines, heteroarylamines, basic amino acids, amino sugars, and polyamines.

According to embodiments of the present disclosure, the base may be a quaternary ammonium hydroxide, wherein one or more of the alkyl groups of the quaternary ammonium ion are optionally substituted with one or more suitable substituents. Preferably, at least one alkyl group is substituted with one or more hydroxyl groups. Non-limiting examples of quaternary ammonium hydroxides that may be used in accordance with the present disclosure include choline hydroxide, trimethylethylammonium hydroxide, tetramethylammonium hydroxide, and is preferably choline hydroxide. According to embodiments of the present disclosure, an alkylamine base may be substituted or unsubstituted. Non-limiting examples of unsubstituted alkylamine bases that may be used in accordance with the present disclosure include methylamine, ethylamine, diethylamine, and triethylamine. A substituted alkylamine base is preferably substituted with one or more hydroxyl groups, and preferably one to three hydroxyl groups. Non-limiting examples of substituted alkylamine bases that may be used in accordance with the present disclosure include 2-(diethylamino)ethanol, N,N-dimethylethanolamine (deanol), tromethamine, ethanolamine, and diolamine.

In certain cases, the depicted substituents may contribute to optical isomers and/or stereoisomerism. Compounds having the same molecular formula but differing in the nature or sequence of bonding of their atoms or in the arrangement of their atoms in space are termed "isomers." Isomers that differ in the arrangement of their atoms in space are termed "stereoisomers." Stereoisomers that are not mirror images of one another are termed "diastereomers" and those that are non-superimposable mirror images of each other are termed "enantiomers". When a compound has an asymmetric center, for example when it is bonded to four different groups, a pair of enantiomers is possible. A molecule with at least one stereocenter may be characterized by the absolute configuration of its asymmetric center and is designated (R) or (S) according to the rules of Cahn and Prelog (Cahn et al., 1966, *Angew. Chem.* 78: 413-447, *Angew. Chem., Int. Ed. Engl.* 5: 385-414 (errata: *Angew. Chem., Int. Ed. Engl.* 5:511); Prelog and Helmchen, 1982, *Angew. Chem.* 94: 614-631, *Angew. Chem. Internat. Ed. Eng.* 21: 567-583; Mata and Lobo, 1993, *Tetrahedron: Asymmetry* 4: 657-668) or may be characterized by the manner in which the molecule rotates the plane of polarized light and is designated dextrorotatory or levorotatory (namely, as (+)- or (−)-isomers, respectively). A chiral compound may exist as either an individual enantiomer or as a mixture thereof. A mixture containing equal proportions of enantiomers is called a "racemic mixture".

In certain embodiments, the compounds disclosed herein may possess one or more asymmetric centers, and such compounds may therefore be produced as a racemic mixture, an enantiomerically enriched mixture, or as an individual enantiomer. Unless indicated otherwise, for example by designation of stereochemistry at any position of a formula, the description or naming of a particular compound in the specification and claims is intended to include both individual enantiomers and mixtures, racemic or otherwise, thereof. Methods for determination of stereochemistry and separation of stereoisomers are well-known in the art.

In certain embodiments, the compounds disclosed herein are "stereochemically pure". A stereochemically pure compound has a level of stereochemical purity that would be recognized as "pure" by those of skill in the art. Of course, this level of purity may be less than 100%. In certain embodiments, "stereochemically pure" designates a compound that is substantially free, i.e. at least about 85% or more, of alternate isomers. In particular embodiments, the compound is at least about 85%, about 90%, about 91%, about 92%, about 93%, about 94%, about 95%, about 96%, about 97%, about 98%, about 99%, about 99.5% or about 99.9% free of other isomers.

As used herein, the terms "subject" and "patient" may be used interchangeably herein. In one embodiment, the subject is a human. In one embodiment, the subject is a companion animal such as a dog or cat. In a further embodiment, the subject is an animal such as a sheep, cow, horse, goat, fish, pig, or domestic fowl (e.g., chicken, turkey, duck, or goose). In another embodiment, the subject is a primate such as a monkey such as a cynomolgus monkey or a chimpanzee.

In addition, a pharmaceutically acceptable prodrug of the compound represented by the formula (I) is also included in the present disclosure. The pharmaceutically acceptable prodrug refers to a compound having a group which may be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198. The term prodrug is used throughout the specification to describe any pharmaceutically acceptable form of a compound which, upon administration to a patient, provides the active compound. Pharmaceutically acceptable prodrugs refer to a compound that is metabolized, for example hydrolyzed or oxidized, in the host to form the compound of the present disclosure. Typical examples of prodrugs include compounds that have biologically labile protecting groups on a functional moiety of the active compound. Prodrugs include compounds that may be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The present disclosure includes all pharmaceutically acceptable isotopically-labelled compounds of the disclosure wherein one or more atoms are replaced by atoms having the same atomic number, but an atomic mass or mass number different from the atomic mass or mass number usually found in nature. Examples of isotopes suitable for inclusion in the compounds of the disclosure include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$ nitrogen, such as $^{13}N$ and $^{15}N$, oxygen, such as $^{15}O$, $^{17}O$ and $^{18}O$, phosphorus, such as $^{32}P$, and sulfur, such as $^{35}S$. Certain isotopically-labelled compounds of the disclosure, such as those incorporating a radioactive isotope, may be useful in drug or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, may be useful in Positron Emission Topography (PET) studies for examining substrate receptor occupancy. Isotopically-labeled compounds of the disclosure may generally be prepared by conventional techniques known to those skilled in the art or by processes analogous to those described in the accompanying Examples using an appropriate isotopically-labeled reagent in place of the non-labeled reagent previously employed.

Compositions and Methods of Administration

The compounds of the present disclosure used in the methods disclosed herein may be administered in certain embodiments using veterinary or pharmaceutical compositions including at least one compound of the present disclosure, if appropriate in the salt form, either used alone or in the form of a combination with one or more compatible and veterinary or pharmaceutically acceptable carriers, such as diluents or adjuvants, or with another agent. There are provided compositions which comprise a derivative of the present disclosure or a salt thereof, and an acceptable excipient, carrier or diluent. The composition may also be in a variety of forms which include, but are not limited to, oral formulations, injectable formulations, and topical, dermal or subdermal formulations.

The composition may be in a form suitable for oral use, for example, as dietary supplements, troches, lozenges, chewables, tablets, hard or soft capsules, emulsions, aqueous or oily suspensions, aqueous or oily solutions, dispersible powders or granules, syrups, or elixirs. Compositions intended for oral use may be prepared according to any method known in the art for the manufacture of veterinary or pharmaceutical compositions and such compositions may contain one or more agents selected from the group consisting of sweetening agents, bittering agents, flavoring agents, coloring agents and preserving agents in order to provide elegant and palatable preparations.

Lozenges are solid compositions containing one or more active ingredients intended to dissolve or disintegrate slowly in the oral cavity by passive incubation in the oral cavity, or actively by sucking or chewing. They may be used for systemic effect if the drug is absorbed through the buccal or esophageal lining or is swallowed. In particular, soft lozenges may be chewed or allowed to dissolve slowly in the mouth. These dosage forms have the advantage of being flavored and thus easy to administer to both human and animal patients; have formulas that are easy to change and may be patient specific; may deliver accurate amounts of the active ingredient to the oral cavity and digestive system; and allow for the drug to remain in contact with the oral or esophageal cavity for an extended period of time.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period.

Formulations for oral use may be hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example, peanut oil, liquid paraffin, or olive oil.

The compositions may also be in the form of oil-in-water or water-in-oil emulsions. The oily phase may be a vegetable oil, for example, olive oil or *arachis* oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monoleate, and condensation products of the said partial esters with ethylene oxide, for example, polyoxyethylene sorbitan monooleate. The emulsions may also contain sweetening agents, bittering agents, flavoring agents, and preservatives.

In one embodiment of the formulation, the composition is in the form of a microemulsion. Microemulsions are well suited as the liquid carrier vehicle. Microemulsions are quaternary systems comprising an aqueous phase, an oily phase, a surfactant and a cosurfactant. They are translucent and isotropic liquids. Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously. In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase comprises of triglycerides; in another embodiment of the oily phase, the triglycerides are medium-chain triglycerides, for example, $C_8$-$C_{10}$ caprylic/capric triglyceride. In another embodiment, the oily phase will represent a % v/v range selected from the group consisting of about 2 to about 15%; about 7 to about 10%; and about 8 to about 9% v/v of the microemulsion. The aqueous phase includes, for example, water or glycol derivatives, such as propylene glycol, glycol ethers, polyethylene glycols, or glycerol. In one embodiment of the glycol derivatives, the glycol is selected from the group consisting of propylene glycol, diethylene glycol monoethyl ether, dipropylene glycol monoethyl ether and mixtures thereof. Generally, the aqueous phase will represent a proportion from about 1 to about 4% v/v in the microemulsion. Surfactants for the microemulsion include diethylene glycol monoethyl ether, dipropylene glycol monomethyl ether, polyglycolyzed $C_8$-$C_{10}$ glycerides or polyglyceryl-6 dioleate. In addition to these surfactants, the cosurfactants include short-chain alcohols, such as ethanol and propanol. Some compounds are common to the three components discussed above, for example, aqueous phase, surfactant, and cosurfactant. However, different compounds may be substituted for each component of the same formulation. In one embodiment for the amount of surfactant/cosurfactant, the cosurfactant to surfactant ratio may be from about 1/7 to about 1/2.

In another embodiment for the amount of cosurfactant, there will be from about 25 to about 75% v/v of surfactant and from about 10 to about 55% v/v of cosurfactant in the microemulsion.

Oily suspensions may be formulated by suspending the active ingredient in a vegetable oil, for example, atachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients are suspending agents, for example, sodium carboxymethylcellulose, methylcellulose, hydroxypropylmethylcellulose, sodium alginate, polvinylpyrrolidone, gum tragacanth and gum acacia;

dispersing or wetting agents may be a naturally-occurring phosphatide, for example, lecithin, or condensation products of an alkylene oxide with fatty acids, for example, polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example, polyethylene sorbitan monooleate. The aqueous suspensions may also contain one or more preservatives, for example, ethyl, or n-propyl, p-hydroxybenzoate, one or more coloring agents, one or more flavoring agents, and one or more sweetening agents and/or bittering agents, such as those herein described.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such formulations may also contain a demulcent, a preservative, flavoring agent(s) and coloring agent(s).

The compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. Preservatives, such as phenol or benzyl alcohol, may be used.

In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Topical, dermal and subdermal formulations may include emulsions, creams, ointments, gels or pastes.

Organic solvents that may be used in the disclosure include but are not limited to: acetyltributyl citrate, fatty acid esters such as the dimethyl ester, diisobutyl adipate, acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone (e.g. N-methylpyrrolidone), diethylene glycol monoethyl ether, ethylene glycol and diethyl phthalate, or a mixture of at least two of these solvents.

As vehicle or diluent, compositions of the present disclosure may include plant oils such as, but not limited to soybean oil, groundnut oil, castor oil, corn oil, cotton oil, olive oil, grape seed oil, sunflower oil, etc.; mineral oils such as, but not limited to, petrolatum, paraffin, silicone, etc.; aliphatic or cyclic hydrocarbons or alternatively, for example, medium-chain (such as $C_8$-$C_{12}$) triglycerides.

Dosage forms may contain from about 0.5 mg to about 5 g of an active agent.

In one embodiment of the disclosure, the active agent is present in the formulation at a concentration of about 0.05 to 10% weight/volume.

A compound of the present disclosure may be employed as such or in the form of their preparations or formulations as combinations.

A compound of the present disclosure according to the disclosure may be combined with one or more agents having the same sphere of activity, for example, to increase activity, or with substances having another sphere of activity, for example, to broaden the range of activity. As an example, a combination of a compound of the present disclosure with one or more of an additional JAK inhibitor or a JAK/Signal Transducer and Activator of Transcription (JAK/STAT) modulator may offer therapeutic advantage. Examples of JAK inhibitors that may be useful as combination agents include Baricitinib, Ruxolitinib, Filgotinib, CYT387, Upadacitinib, Fedratinib, Peficitinib, Lestaurtinib, Pacritinib, Oclacitinib, Cerdulatinib, and Tofacitinib.

The compounds of the present disclosure according to the disclosure may be combined with one or more additional active agents. Further additional active agents which may be used in the methods provided herein in combination with a compound of the present disclosure include, but are not limited to, disease-modifying anti-rheumatic drugs (DMARDs such as cyclosporine A and methotrexate), anti-inflammatory agents such as nonsteroidal anti-inflammatory drugs (NSAIDs), immnunosuppressants, mycophenolate mofetil, biologic agents, TNF-α inhibitors (such as etanercept), Cox-2 inhibitors, and analgesics. These agents may include but are not limited to cyclosporin A, e.g. Sandimmune® or Neoral®, rapamycin, FK-506 (tacrolimus), leflunomide, deoxyspergualin, mycophenolate, e.g., Cellcept®, azathioprine, e.g. Imuran®, daclizumab, e.g. Zenapax®, OKT3, e.g. Orthocolone®, AtGam, aspirin, acetaminophen, ibuprofen, naproxen, piroxicam, and anti-inflammatory steroids, e.g. prednisolone or dexamethasone.

In some embodiments, the second active agents may include, but are not limited to, anti-inflammatories such as NSAIDs including, but not limited to, diclofenac (e.g., ARTHROTEC®), diflunisal (e.g., DOLOBID®), etodolac (e.g., LODINE®), fenoprofen (e.g., NALFON®), ibuprofen (e.g., ADVIL®, CHILDREN'S ADVIL/MOTRIN®, MEDIPREN®, MOTRIN®, NUPRIN®, or PEDIACARE FEVER®), indomethacin (e.g., ARTHREXIN®), ketoprofen (e.g., ORUVAIL®), ketorolac (e.g., TORADOL®), fosfomycin tromethamine (e.g., MONURAL®), meclofenamate (e.g., MECLOMEN®), nabumetone (e.g., RELAFEN®), naproxen (e.g., ANAPROX®, ANAPROX® DS, EC-NAPROSYN®, NAPRELAN® or NAPROSYN®), oxaprozin (e.g., DAY PRO®), piroxicam (e.g., FELDENE®), sulindac (e.g., CLINORIL®), and tolmetin (e.g., TOLECTIN® DS or TOLECTIN®).

In other embodiments, the second active agents may include, but are not limited to, disease-modifying antirheumatic drugs (e.g., DMARDs) or immnunosuppressants such as, but not limited to, methotrexate (e.g., RHEUMATREX®), sulfasalazine (e.g., AZULFIDINE®), and cyclosporine (e.g., SANDIMMUNE® or NEROAL®; and including cyclosporine A).

In other embodiments, the second active agents may include, but are not limited to, mycophenolate mofetil (e.g., CellCept®), an immunosuppressive agent widely used in organ transplantation and gaining favor in treating autoimmune and inflammatory skin disorders.

In further embodiments, the second active agents may include, but are not limited to, biologic agents such as etanercept (ENBREL®), infliximab (REMICADE®) and adalimumab (HUMIRA®).

In further embodiments of interest, the second active agents may include, but are not limited to. Cox-2 inhibitors such as celecoxib (CELEBREX®), valdecoxib (BEXTRA®) and meloxicam (MOBIC®).

These one or more additional active agents may be administered as part of the same or separate dosage forms, via the same or different routes of administration, and on the same or different administration schedules according to standard pharmaceutical practice.

The pharmaceutical preparation comprising the compounds of the present disclosure, for delivery to a human or other mammal, is preferably in unit dosage form, in which the preparation is subdivided into unit doses containing an appropriate quantity of the active component. The unit dosage form may be a packaged preparation containing discrete quantities of the preparation, such as packaged tablets, capsules, and powders in vials or ampoules. Also, the unit dosage form may be a capsule, tablet or lozenge itself, or it may be an appropriate number of any of these in packaged form.

The quantity of active component in a unit dose preparation may be varied or adjusted from about 0.1 mg to about 1000 mg, according to the particular application and the potency of the active component. The composition may, if desired, also contain other compatible therapeutic agents.

In therapeutic use for the treatment or alleviation of inflammation, auto-immune diseases, and cancer in a human or other mammal, the compounds utilized in the method of treatment are administered at an initial dosage of about 0.1 mg/kg to about 100 mg/kg per interval, about 0.1 mg/kg to about 50.0 mg/kg per interval, about 0.1 mg/kg to about 10.0 mg/kg per interval, about 0.1 mg/kg to about 5.0 mg/kg per interval, about 0.1 mg/kg to about 2.5 mg/kg per interval, about 0.1 mg/kg to about 2.0 mg/kg per interval, about 0.1 mg/kg to about 1.0 mg/kg per interval, about 0.4 mg/kg to about 1.0 mg/kg per interval, or about 0.4 mg/kg to about 0.6 mg/kg per interval. Preferred intervals may be daily, weekly, monthly, quarterly, semi-annually, or annually. The dosages may be varied depending on the requirements of the patient, for example, the size of the human or mammal being treated, the severity of the condition being treated, the route of administration, and the potency of the compound(s) being used. Determination of the proper dosage and route of administration for a particular situation is within the skill of the practitioner. Generally, the treatment will be initiated with smaller dosages, which are less than the optimum dose of the compound, which may be increased in small increments until the optimum effect under the particular circumstances of the condition is reached. For convenience, the total daily dosage may be divided and administered in portions during the day if desired.

In therapeutic use, embodiments of the compounds of the present disclosure are useful in manufacture of a medicament for a method of the treating any indication where inhibition of JAK, optionally in dual modulation PDE4 and, optionally, with one or more of TykA and Syk would be desirable, including but not limited to cancer, neuroinflammation, inflammatory airway diseases, ankylosing spondylitis, inflammatory bowel diseases, rheumatoid arthritis, psoriasis, and atopic dermatitis. In one or more embodiment, a compound of the present disclosure is useful in the treatment of one or more of atopic dermatitis, psoriasis, psoriatic arthritis, Bechet's disease, *pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, asthma, vasculitis, multiple sclerosis, diabetic nephropathy, cardiovascular disease, artherosclerosis, and cancer.

In therapeutic use, the compounds of the present disclosure are useful in manufacture of a medicament for a method of the treating any indication including but not limited to cancer, neuroinflammation, inflammatory airway diseases, ankylosing spondylitis, inflammatory bowel diseases, rheumatoid arthritis, psoriasis, or atopic dermatitis. In one or more embodiment, a compound of the present disclosure is useful in the treatment of one or more of atopic dermatitis, psoriasis, psoriatic arthritis, Bechet's disease, *pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, asthma, vasculitis, multiple sclerosis, diabetic nephropathy, cardiovascular disease, artherosclerosis, and cancer.

The present disclosure explicitly encompasses those compounds presented below in Compound Lists, including salt forms thereof. A composition comprising a therapeutically acceptable amount of any of these compounds is also within the scope of the disclosure. The composition may further comprise a pharmaceutically or veterinary acceptable excipient, diluent, carrier, or mixture thereof. Such a composition may be administered to a subject in need thereof to treat or control a disease or disorder mediated, in whole or in part, directly or indirectly, by JAK, alone or in combination with inhibition of Tropomyosin receptor kinase A (TrkA) or Spleen tyrosine kinase (Syk), and, optionally, with inhibition of PDE4. The composition may further comprise an additional active agent, as described herein.

Compound List

It is to be understood that when in aqueous media, some contemplated compounds of the present disclosure may be present in a reversible equilibrium with water due the Lewis acidic nature of the trigonal planar boron center. This dynamic equilibrium may be important for the biological activity of the compounds of the present disclosure. Compounds in the present disclosure in this dynamic equilibrium are another aspect of the present disclosure.

Embodiments of the present disclosure are provided in the following list, where an aspect of compound activity is noted. For each list, this disclosure includes a stereoisomer, enantiomer, or tautomer of each compound, as well as a veterinary or pharmaceutically acceptable salt thereof. The (+) symbols identify a compound of the present disclosure with the noted target activity. The (*) symbols indicate preferential activity, where the greater number identifies the most preferred compounds.

| Activity Note | Structure | IUPAC |
|---|---|---|
| JAK+*** | | 5-((5-chloro-4-(cyclopentylamino)pyrimidin-2-yl)amino)-7-ethylbenzo[c][1,2]oxaborol-1(3H)-ol |
| JAK+*** | | 7-ethyl-5-((5-methyl-4-(pentan-3-ylamino)pyrimidin-2-yl)amino)benzo[c][1,2]oxaborol-1(3H)-ol |
| JAK+*** | | 3,3,7-trimethyl-5-((5-methyl-4-(phenylamino)pyrimidin-2-yl)amino)benzo[c][1,2]oxaborol-1(3H)-ol |
| JAK+*** | | 7-chloro-5-((5-chloro-4-(cyclopentylamino)pyrimidin-2-yl)amino)benzo[c][1,2]oxaborol-1(3H)-ol |
| JAK+*** | | 3,3,7-trimethyl-5-((5-methyl-4-(pentan-3-ylamino)pyrimidin-2-yl)amino)benzo[c][1,2]oxaborol-1(3H)-ol |
| JAK+*** | | 3,7-dimethyl-5-((5-methyl-4-(pentan-3-ylamino)pyrimidin-2-yl)amino)benzo[c][1,2]oxaborol-1(3H)-ol |
| JAK+*** | | 7-chloro-5-((5-methyl-4-(pentan-3-ylamino)pyrimidin-2-yl)amino)benzo[c][1,2]oxaborol-1(3H)-ol |
| JAK+*** | | 7-methyl-5-((5-methyl-4-(pentan-3-ylamino)pyrimidin-2-yl)amino)benzo[c][1,2]oxaborol-1(3H)-ol |
| JAK+*** | | 3,3-dimethyl-5-((5-methyl-4-(phenylamino)pyrimidin-2-yl)amino)benzo[c][1,2]oxaborol-1(3H)-ol |

-continued

| Activity Note | Structure | IUPAC |
|---|---|---|
| JAK+*** | | 3,3-dimethyl-5-((5-methyl-4-(pentan-3-ylamino)pyrimidin-2-yl)amino)benzo[c][1,2]oxaborol-1(3H)-ol |
| JAK+*** | | 7-chloro-5-((5-methyl-4-(phenylamino)pyrimidin-2-yl)amino)benzo[c][1,2]oxaborol-1(3H)-ol |
| JAK+*** | | 6-((4-(cyclopentylamino)-5-methylpyrimidin-2-yl)amino)-3,4-dihydro-1H-benzo[c][1,2]oxaborinin-1-ol |
| JAK+*** | | 7-chloro-3,3-dimethyl-5-((5-methyl-4-(pentan-3-ylamino)pyrimidin-2-yl)amino)benzo[c][1,2]oxaborol-1(3H)-ol |
| JAK+*** | | 7-methyl-5-((5-methyl-4-(phenylamino)pyrimidin-2-yl)amino)benzo[c][1,2]oxaborol-1(3H)-ol |
| JAK+*** | | 7-ethyl-5-((5-methyl-4-(phenylamino)pyrimidin-2-yl)amino)benzo[c][1,2]oxaborol-1(3H)-ol |
| JAK+*** | | 5-((5-chloro-4-(cyclopentylamino)pyrimidin-2-yl)amino)-7-methylbenzo[c][1,2]oxaborol-1(3H)-ol |
| JAK+*** | | 5-((5-chloro-4-(cyclopentylamino)pyrimidin-2-yl)amino)-3-methylbenzo[c][1,2]oxaborol-1(3H)-ol |

-continued

| Activity Note | Structure | IUPAC |
|---|---|---|
| JAK+*** | | 5-((4-(cyclopentylamino)-5-methylpyrimidin-2-yl)amino)-7-methylbenzo[c][1,2]oxaborol-1(3H)-ol |
| JAK+*** | | 5-((4-(cyclopentylamino)-5-methylpyrimidin-2-yl)amino)-3,3-dimethylbenzo[c][1,2]oxaborol-1(3H)-ol |
| JAK+*** | | 5-((5-methyl-4-(phenylamino)pyrimidin-2-yl)amino)-7-(trifluoromethyl)benzo[c][1,2]oxaborol-1(3H)-ol |
| JAK+*** | | 5-((5-chloro-4-(cyclopentylamino)pyrimidin-2-yl)amino)-3,3,7-trimethylbenzo[c][1,2]oxaborol-1(3H)-ol |
| JAK+*** | | 3-methyl-5-((5-methyl-4-(pentan-3-ylamino)pyrimidin-2-yl)amino)benzo[c][1,2]oxaborol-1(3H)-ol |
| JAK+*** | | 3-methyl-5-((5-methyl-4-(phenylamino)pyrimidin-2-yl)amino)benzo[c][1,2]oxaborol-1(3H)-ol |
| JAK+*** | | 7-chloro-3,3-dimethyl-5-((5-methyl-4-(phenylamino)pyrimidin-2-yl)amino)benzo[c][1,2]oxaborol-1(3H)-ol |
| JAK+*** | | 5-((4-(cyclopentylamino)-5-methylpyrimidin-2-yl)amino)-3-methylbenzo[c][1,2]oxaborol-1(3H)-ol |

| Activity Note | Structure | IUPAC |
|---|---|---|
| JAK+*** | | 7-chloro-5-((5-chloro-4-(cyclopentylamino)pyrimidin-2-yl)amino)-3,3-dimethylbenzo[c][1,2]oxaborol-1(3H)-ol |
| JAK+*** | | 5-((5-chloro-4-(cyclopentylamino)pyrimidin-2-yl)amino)-7-(trifluoromethyl)benzo[c][1,2]oxaborol-1(3H)-ol |
| JAK+*** | | 5-((5-chloro-4-(cyclopentylamino)pyrimidin-2-yl)amino)-3,3-dimethylbenzo[c][1,2]oxaborol-1(3H)-ol |
| JAK+*** | | 5-((5-methyl-4-(pentan-3-ylamino)pyrimidin-2-yl)amino)-7-(trifluoromethyl)benzo[c][1,2]oxaborol-1(3H)-ol |
| JAK+** | | 5-((4-(cyclopentylamino)pyrimidin-2-yl)amino)-7-ethylbenzo[c][1,2]oxaborol-1(3H)-ol |
| JAK+** | | 6-((5-methyl-4-((4-methylcyclohexyl)amino)pyrimidin-2-yl)amino)benzo[c][1,2]oxaborol-1(3H)-ol |
| JAK+** | | 3,3-dimethyl-6-((5-methyl-4-((3-(methylsulfonyl)phenyl)amino)pyrimidin-2-yl)amino)benzo[c][1,2]oxaborol-1(3H)-ol |
| JAK+** | | 7-methoxy-5-((5-methyl-4-(methylthio)pyrimidin-2-yl)amino)benzo[c][1,2]oxaborol-1(3H)-ol |

| Activity Note | Structure | IUPAC |
|---|---|---|
| JAK+* | 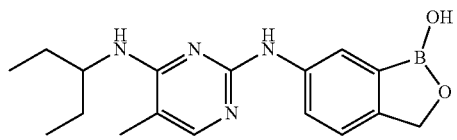 [SMILES: CCC(CC)Nc1nc(Nc2ccc3c(c2)B(O)OC3)ncc1C] | 6-((5-methyl-4-(pentan-3-ylamino)pyrimidin-2-yl)amino)benzo[c][1,2]oxaborol-1(3H)-ol |
| JAK+* | 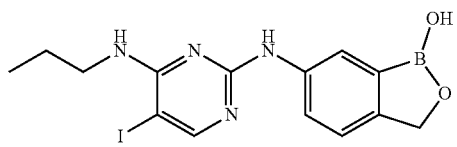 [SMILES: CCCNc1nc(Nc2ccc3c(c2)B(O)OC3)ncc1I] | 6-((5-iodo-4-(propylamino)pyrimidin-2-yl)amino)benzo[c][1,2]oxaborol-1(3H)-ol |
| JAK+* | 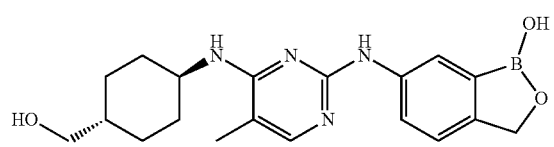 [SMILES: Cc1cnc(Nc2ccc3c(c2)B(O)OC3)nc1N[C@H]1CC[C@H](CO)CC1] | 6-((4-(((1r,4r)-4-(hydroxymethyl)cyclohexyl)amino)-5-methylpyrimidin-2-yl)amino)benzo[c][1,2]oxaborol-1(3H)-ol |
| JAK+* | 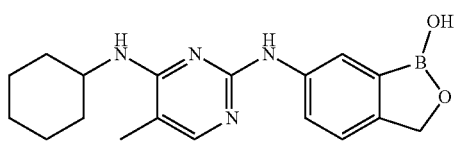 [SMILES: Cc1cnc(Nc2ccc3c(c2)B(O)OC3)nc1NC1CCCCC1] | 6-((4-(cyclohexylamino)-5-methylpyrimidin-2-yl)amino)benzo[c][1,2]oxaborol-1(3H)-ol |
| JAK+* | 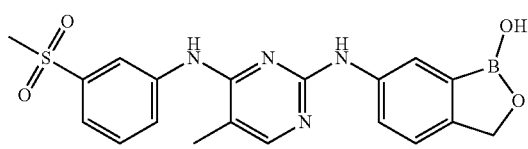 [SMILES: Cc1cnc(Nc2ccc3c(c2)B(O)OC3)nc1Nc1cccc(S(C)(=O)=O)c1] | 6-((5-methyl-4-((3-(methylsulfonyl)phenyl)amino)pyrimidin-2-yl)amino)benzo[c][1,2]oxaborol-1(3H)-ol |
| JAK+* | 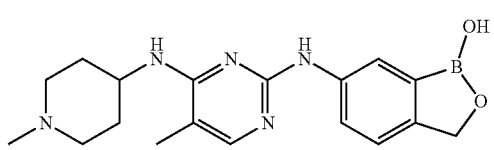 [SMILES: Cc1cnc(Nc2ccc3c(c2)B(O)OC3)nc1NC1CCN(C)CC1] | 6-((5-methyl-4-((1-methylpiperidin-4-yl)amino)pyrimidin-2-yl)amino)benzo[c][1,2]oxaborol-1(3H)-ol |
| JAK+* | 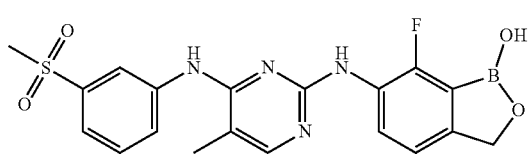 [SMILES: Cc1cnc(Nc2ccc3c(c2F)B(O)OC3)nc1Nc1cccc(S(C)(=O)=O)c1] | 7-fluoro-6-((5-methyl-4-((3-(methylsulfonyl)phenyl)amino)pyrimidin-2-yl)amino)benzo[c][1,2]oxaborol-1(3H)-ol |
| JAK+* | 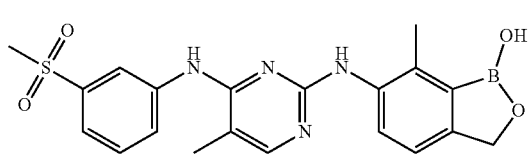 [SMILES: Cc1cnc(Nc2ccc3c(c2C)B(O)OC3)nc1Nc1cccc(S(C)(=O)=O)c1] | 7-methyl-6-((5-methyl-4-((3-(methylsulfonyl)phenyl)amino)pyrimidin-2-yl)amino)benzo[c][1,2]oxaborol-1(3H)-ol |
| JAK+* | 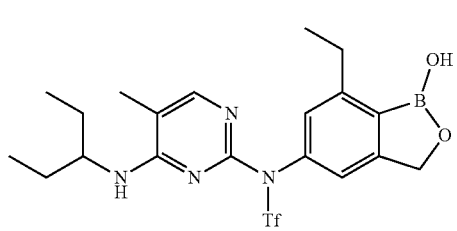 | N-(7-ethyl-1-hydroxy-1,3-dihydrobenzo[c][1,2]oxaborol-5-yl)-1,1,1-trifluoro-N-(5-methyl-4-(pentan-3-ylamino)pyrimidin-2-yl)methanesulfonamide |

-continued

| Activity Note | Structure | IUPAC |
|---|---|---|
| | | N-(4-anilino-5-methyl-pyrimidin-2-yl)-N-(7-ethyl-1-hydroxy-3H-2,1-benzoxaborol-5-yl)-1,1,1-trifluoro-methanesulfonamide |
| JAK+* | 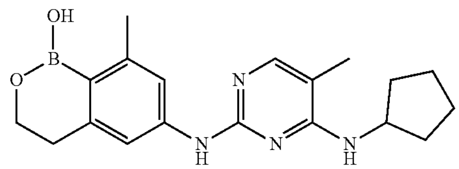 [SMILES: Cc1cnc(Nc2cc(C)c3c(c2)CCOB3O)nc1NC1CCCC1] | 6-((4-(cyclopentylamino)-5-methylpyrimidin-2-yl)amino)-8-methyl-3,4-dihydro-1H-benzo[c][1,2]oxaborinin-1-ol |
| PDE4+ JAK+*** | | 5-((5-methyl-4-((4-methylcyclohexyl)amino)pyrimidin-2-yl)amino)benzo[c][1,2]oxaborol-1(3H)-ol |
| PDE4+ JAK+*** | | 7-fluoro-5-((5-methyl-4-(pentan-3-ylamino)pyrimidin-2-yl)amino)benzo[c][1,2]oxaborol-1(3H)-ol |
| PDE4+ JAK+*** | | 5-((4-((2-methoxyphenyl)amino)-5-methylpyrimidin-2-yl)amino)benzo[c][1,2]oxaborol-1(3H)-ol |
| PDE4+ JAK+*** | | 5-((4-((2-chlorophenyl)amino)-5-methylpyrimidin-2-yl)amino)benzo[c][1,2]oxaborol-1(3H)-ol |
| PDE4+ JAK+*** | | 5-((4-((2-ethylphenyl)amino)-5-methylpyrimidin-2-yl)amino)benzo[c][1,2]oxaborol-1(3H)-ol |
| PDE4+ JAK+*** | | 5-((5-chloro-4-(cyclopentylamino)pyrimidin-2-yl)amino)-7-fluorobenzo[c][1,2]oxaborol-1(3H)-ol |

| Activity Note | Structure | IUPAC |
|---|---|---|
| PDE4+ JAK+*** | | 5-((5-chloro-4-(pentan-3-ylamino)pyrimidin-2-yl)amino)benzo[c][1,2]oxaborol-1(3H)-ol |
| PDE4+ JAK+*** | | 5-((5-methyl-4-(o-tolylamino)pyrimidin-2-yl)amino)benzo[c][1,2]oxaborol-1(3H)-ol |
| PDE4+ JAK+*** | | 7-fluoro-5-((5-methyl-4-(phenylamino)pyrimidin-2-yl)amino)benzo[c][1,2]oxaborol-1(3H)-ol |
| PDE4+ JAK+*** | | 5-((4-((2-fluorophenyl)amino)-5-methylpyrimidin-2-yl)amino)benzo[c][1,2]oxaborol-1(3H)-ol |
| PDE4+ JAK+*** | | 5-((4-(sec-butylamino)-5-chloropyrimidin-2-yl)amino)benzo[c][1,2]oxaborol-1(3H)-ol |
| PDE4+ JAK+*** | | 5-((5-methyl-4-(pentan-3-ylamino)pyrimidin-2-yl)amino)benzo[c][1,2]oxaborol-1(3H)-ol |
| PDE4+ JAK+*** | | 5-((5-methyl-4-((3-methylcyclohexyl)amino)pyrimidin-2-yl)amino)benzo[c][1,2]oxaborol-1(3H)-ol |
| PDE4+ JAK+*** | | 5-((5-chloro-4-(hexan-3-ylamino)pyrimidin-2-yl)amino)benzo[c][1,2]oxaborol-1(3H)-ol |
| PDE4+ JAK+*** | | 5-((4-((3-fluorobenzyl)amino)-5-methylpyrimidin-2-yl)amino)benzo[c][1,2]oxaborol-1(3H)-ol |

| Activity Note | Structure | IUPAC |
|---|---|---|
| PDE4+ JAK+*** | | 5-((5-methyl-4-(pentan-3-ylamino)pyrimidin-2-yl)amino)benzo[c][1,2]oxaborol-1(3H)-ol |
| PDE4+ JAK+*** | | 5-((5-methyl-4-((2-(trifluoromethoxy)phenyl)amino)pyrimidin-2-yl)amino)benzo[c][1,2]oxaborol-1(3H)-ol |
| PDE4+ JAK+*** | | 5-((5-methyl-4-(phenylamino)pyrimidin-2-yl)amino)benzo[c][1,2]oxaborol-1(3H)-ol |
| PDE4+ JAK+*** | | 5-((4-(cyclohexylamino)-5-methylpyrimidin-2-yl)amino)benzo[c][1,2]oxaborol-1(3H)-ol |
| PDE4+ JAK+*** | | 5-((5-chloro-4-(cyclopentylamino)pyrimidin-2-yl)amino)benzo[c][1,2]oxaborol-1(3H)-ol |
| PDE4+ JAK+*** | | 5-((4-((3-chlorobenzyl)amino)-5-methylpyrimidin-2-yl)amino)benzo[c][1,2]oxaborol-1(3H)-ol |
| PDE4+ JAK+*** | | 5-((5-methyl-4-((2-(trifluoromethyl)phenyl)amino)pyrimidin-2-yl)amino)benzo[c][1,2]oxaborol-1(3H)-ol |
| PDE4+ JAK+*** | | 5-((4-(benzylamino)-5-methylpyrimidin-2-yl)amino)benzo[c][1,2]oxaborol-1(3H)-ol |

-continued

| Activity Note | Structure | IUPAC |
|---|---|---|
| PDE4+ JAK+*** | | 7-fluoro-5-((4-(pentan-3-ylamino)-5-(trifluoromethyl)pyrimidin-2-yl)amino)benzo[c][1,2]oxaborol-1(3H)-ol |
| PDE4+ JAK+*** | | 5-((5-chloro-4-(cyclohexylamino)pyrimidin-2-yl)amino)benzo[c][1,2]oxaborol-1(3H)-ol |
| PDE4+ JAK+*** | | 5-((4-(cyclopentylamino)-5-methylpyrimidin-2-yl)amino)benzo[c][1,2]oxaborol-1(3H)-ol |
| PDE4+ JAK+*** | | 5-((4-(cyclopentylamino)-5-methylpyrimidin-2-yl)amino)benzo[c][1,2]oxaborol-1(3H)-ol |
| PDE4+ JAK+*** | | 5-((4-(benzylamino)-5-chloropyrimidin-2-yl)amino)benzo[c][1,2]oxaborol-1(3H)-ol |
| PDE4+ JAK+*** | | 5-((5-chloro-4-(propylamino)pyrimidin-2-yl)amino)benzo[c][1,2]oxaborol-1(3H)-ol |
| PDE4+ JAK+*** | | 5-((4-(benzylamino)-5-fluoropyrimidin-2-yl)amino)benzo[c][1,2]oxaborol-1(3H)-ol |
| PDE4+ JAK+*** | | 5-((4-(propylamino)-5-(trifluoromethyl)pyrimidin-2-yl)amino)benzo[c][1,2]oxaborol-1(3H)-ol |

-continued

| Activity Note | Structure | IUPAC |
|---|---|---|
| PDE4+ JAK+*** | | 5-((4-(cyclohexylamino)-5-fluoropyrimidin-2-yl)amino)benzo[c][1,2]oxaborol-1(3H)-ol |
| PDE4+ JAK+*** | | 5-((4-(sec-butylamino)-5-methylpyrimidin-2-yl)amino)benzo[c][1,2]oxaborol-1(3H)-ol |
| PDE4+ JAK+*** | | 5-((4-((3-(hydroxymethyl)phenyl)amino)-5-methylpyrimidin-2-yl)amino)benzo[c][1,2]oxaborol-1(3H)-ol |
| PDE4+ JAK+*** | | 5-((5-fluoro-4-(hexan-3-ylamino)pyrimidin-2-yl)amino)benzo[c][1,2]oxaborol-1(3H)-ol |
| PDE4+ JAK+*** | | 5-((5-chloro-4-((1-hydroxybutan-2-yl)amino)pyrimidin-2-yl)amino)benzo[c][1,2]oxaborol-1(3H)-ol |
| PDE4+ JAK+*** | | 5-((4-(pentan-3-ylamino)-5-(trifluoromethyl)pyrimidin-2-yl)amino)benzo[c][1,2]oxaborol-1(3H)-ol |
| PDE4+ JAK+** | | 2-((1-hydroxy-1,3-dihydrobenzo[c][1,2]oxaborol-5-yl)amino)-4-(pentan-3-ylamino)pyrimidine-5-carbonitrile |
| PDE4+ JAK+** | | 5-((5-chloro-4-(methylsulfonyl)pyrimidin-2-yl)amino)benzo[c][1,2]oxaborol-1(3H)-ol |
| PDE4+ JAK+** | | 5-((5-methyl-4-(pentan-3-yloxy)pyrimidin-2-yl)amino)benzo[c][1,2]oxaborol-1(3H)-ol |

| Activity Note | Structure | IUPAC |
|---|---|---|
| PDE4+ JAK+** | | 5-((5-methyl-4-((1-phenylpropyl)amino)pyrimidin-2-yl)amino)benzo[c][1,2]oxaborol-1(3H)-ol |
| PDE4+ JAK+** | | 2-((1-hydroxy-1,3-dihydrobenzo[c][1,2]oxaborol-5-yl)amino)-4-(propylamino)pyrimidine-5-carbaldehyde |
| PDE4+ JAK+** | | 5-((4-(cyclohexyloxy)-5-methylpyrimidin-2-yl)amino)benzo[c][1,2]oxaborol-1(3H)-ol |
| PDE4+ JAK+** | | 5-((4-((4-fluorobenzyl)amino)-5-methylpyrimidin-2-yl)amino)benzo[c][1,2]oxaborol-1(3H)-ol |
| PDE4+ JAK+** | | 5-((4-((2-hydroxytetrahydro-2H-pyran-4-yl)amino)-5-methylpyrimidin-2-yl)amino)benzo[c][1,2]oxaborol-1(3H)-ol |
| PDE4+ JAK+** | | 5-((4-(sec-butylamino)-5-(trifluoromethyl)pyrimidin-2-yl)amino)benzo[c][1,2]oxaborol-1(3H)-ol |
| PDE4+ JAK+** | | 5-((5-methyl-4-(pentan-3-ylthio)pyrimidin-2-yl)amino)benzo[c][1,2]oxaborol-1(3H)-ol |
| PDE4+ JAK+** | | 5-((4-(cyclopentyloxy)-5-methylpyrimidin-2-yl)amino)benzo[c][1,2]oxaborol-1(3H)-ol |

| Activity Note | Structure | IUPAC |
|---|---|---|
| PDE4+ JAK+** | | ethyl 3-((2-((1-hydroxy-1,3-dihydrobenzo[c][1,2]oxaborol-5-yl)amino)-5-methylpyrimidin-4-yl)amino)benzoate |
| PDE4+ JAK+** | | 5-((5-fluoro-4-(pentan-3-ylamino)pyrimidin-2-yl)amino)benzo[c][1,2]oxaborol-1(3H)-ol |
| PDE4+ JAK+** | | 5-((4-(hexan-3-ylamino)-5-methylpyrimidin-2-yl)amino)benzo[c][1,2]oxaborol-1(3H)-ol |
| PDE4+ JAK+** | | 5-((4-(benzylamino)-5-(trifluoromethyl)pyrimidin-2-yl)amino)benzo[c][1,2]oxaborol-1(3H)-ol |
| PDE4+ JAK+** | | 5-((4-(cyclobutylamino)-5-methylpyrimidin-2-yl)amino)benzo[c][1,2]oxaborol-1(3H)-ol |
| PDE4+ JAK+** | | 5-((4-((1,5-difluoropentan-3-yl)amino)-5-methylpyrimidin-2-yl)amino)benzo[c][1,2]oxaborol-1(3H)-ol |
| PDE4+ JAK+** | | 5-((4-(sec-butylamino)-5-fluoropyrimidin-2-yl)amino)benzo[c][1,2]oxaborol-1(3H)-ol |
| PDE4+ JAK+** | | 5-((4-(cyclopentylamino)-5-(trifluoromethyl)pyrimidin-2-yl)amino)benzo[c][1,2]oxaborol-1(3H)-ol |

-continued

| Activity Note | Structure | IUPAC |
|---|---|---|
| PDE4+ JAK+** | | 5-((4-((1-methoxypentan-3-yl)amino)-5-(trifluoromethyl)pyrimidin-2-yl)amino)benzo[c][1,2]oxaborol-1(3H)-ol |
| PDE4+ JAK+** | | 5-((4-(cyclopentylamino)-5-fluoropyrimidin-2-yl)amino)benzo[c][1,2]oxaborol-1(3H)-ol |
| PDE4+ JAK+** | | 5-((4-((2-cyclopropylethyl)amino)-5-(trifluoromethyl)pyrimidin-2-yl)amino)benzo[c][1,2]oxaborol-1(3H)-ol |
| PDE4+ JAK+** | | 5-((5-methyl-4-((1-phenylethyl)amino)pyrimidin-2-yl)amino)benzo[c][1,2]oxaborol-1(3H)-ol |
| PDE4+ JAK+** | | 2-(2-fluoroethyl)-7-((2-((1-hydroxy-1,3-dihydrobenzo[c][1,2]oxaborol-5-yl)amino)-5-methylpyrimidin-4-yl)amino)isoindolin-1-one |
| PDE4+ JAK+** | | 5-((4-(cyclohexylamino)-5-(trifluoromethyl)pyrimidin-2-yl)amino)benzo[c][1,2]oxaborol-1(3H)-ol |

-continued

| Activity Note | Structure | IUPAC |
|---|---|---|
| PDE4+ JAK+** | | 5-((5-methyl-4-(propylamino)pyrimidin-2-yl)amino)benzo[c][1,2]oxaborol-1(3H)-ol |
| PDE4+ JAK+** | | 5-((4-(cyclohexylamino)pyrimidin-2-yl)amino)benzo[c][1,2]oxaborol-1(3H)-ol |
| PDE4+ JAK+** | | 5-((4-((1-hydroxybutan-2-yl)amino)-5-methylpyrimidin-2-yl)amino)benzo[c][1,2]oxaborol-1(3H)-ol |
| PDE4+ JAK+** | | 5-((4-((2-cyclopropylethyl)amino)-5-fluoropyrimidin-2-yl)amino)benzo[c][1,2]oxaborol-1(3H)-ol |
| PDE4+ JAK+* | | 5-((5-chloro-4-((2-cyclopropylethyl)amino)pyrimidin-2-yl)amino)benzo[c][1,2]oxaborol-1(3H)-ol |
| PDE4+ JAK+* | | 5-((5-chloro-4-(methylthio)pyrimidin-2-yl)amino)benzo[c][1,2]oxaborol-1(3H)-ol |
| PDE4+ JAK+* | | 5-((4-(cyclopentyl(methyl)amino)-5-methylpyrimidin-2-yl)amino)benzo[c][1,2]oxaborol-1(3H)-ol |
| PDE4+ JAK+* | | 5-((5-fluoro-4-(propylamino)pyrimidin-2-yl)amino)benzo[c][1,2]oxaborol-1(3H)-ol |
| PDE4+ JAK+* | | 5-((4-((4-chlorobenzyl)amino)-5-methylpyrimidin-2-yl)amino)benzo[c][1,2]oxaborol-1(3H)-ol |

| Activity Note | Structure | IUPAC |
|---|---|---|
| PDE4+ JAK+* | | 5-((4-(cyclopentylamino)pyrimidin-2-yl)amino)benzo[c][1,2]oxaborol-1(3H)-ol |
| PDE4+ JAK+* | | 5-((4-(hexan-3-ylamino)-5-(trifluoromethyl)pyrimidin-2-yl)amino)benzo[c][1,2]oxaborol-1(3H)-ol |
| PDE4+ JAK+* | | 5-((4-(cyclopropylamino)-5-methylpyrimidin-2-yl)amino)benzo[c][1,2]oxaborol-1(3H)-ol |
| PDE4+ JAK+* | | 5-((4-(cyclohexylthio)-5-methylpyrimidin-2-yl)amino)benzo[c][1,2]oxaborol-1(3H)-ol |
| PDE4+ JAK+* | | 3-((2-((1-hydroxy-1,3-dihydrobenzo[c][1,2]oxaborol-5-yl)amino)-5-methylpyrimidin-4-yl)amino)pentane-1,5-diol |
| PDE4+ JAK+* | | 5-((4-(cyclohexyloxy)-5-methylpyrimidin-2-yl)(methyl)amino)benzo[c][1,2]oxaborol-1(3H)-ol |
| PDE4+ JAK+* | | 5-((4-chloro-5-(trifluoromethyl)pyrimidin-2-yl)amino)benzo[c][1,2]oxaborol-1(3H)-ol |
| | | 5-((5-chloro-4-(2-ethylaziridin-1-yl)pyrimidin-2-yl)amino)benzo[c][1,2]oxaborol-1(3H)-ol |

-continued

| Activity Note | Structure | IUPAC |
|---|---|---|
| | 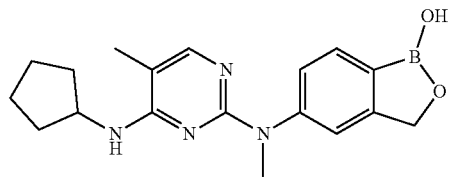 [SMILES: Cc1cnc(N(C)c2ccc3c(c2)COB3O)nc1NC1CCCC1] | 5-((4-(cyclopentylamino)-5-methylpyrimidin-2-yl)(methyl)amino)benzo[c][1,2]oxaborol-1(3H)-ol |
| | 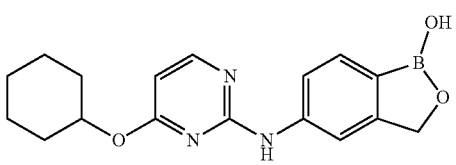 [SMILES: OB1OCc2cc(Nc3nccc(OC4CCCCC4)n3)ccc21] | 5-((4-(cyclohexyloxy)pyrimidin-2-yl)amino)benzo[c][1,2]oxaborol-1(3H)-ol |
| | 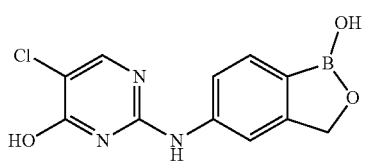 [SMILES: OB1OCc2cc(Nc3ncc(Cl)c(O)n3)ccc21] | 5-chloro-2-((1-hydroxy-1,3-dihydrobenzo[c][1,2]oxaborol-5-yl)amino)pyrimidin-4-ol |
| PDE4+ JAK+* | 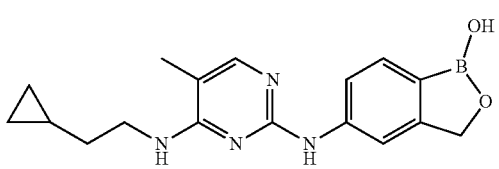 [SMILES: Cc1cnc(Nc2ccc3c(c2)COB3O)nc1NCCC1CC1] | 5-((4-((2-cyclopropylethyl)amino)-5-methylpyrimidin-2-yl)amino)benzo[c][1,2]oxaborol-1(3H)-ol |
| PDE4+ JAK+* | 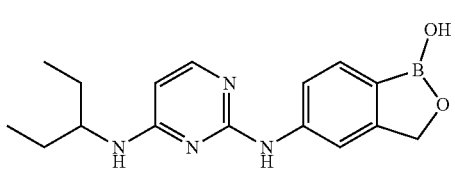 [SMILES: CCC(CC)Nc1ccnc(Nc2ccc3c(c2)COB3O)n1] | 5-((4-(pentan-3-ylamino)pyrimidin-2-yl)amino)benzo[c][1,2]oxaborol-1(3H)-ol |

Additional Compound List A1: Additional embodiments of the present disclosure include a compound selected from the group consisting of:

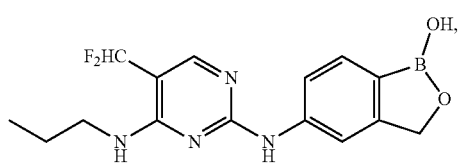

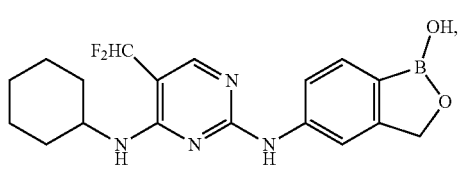

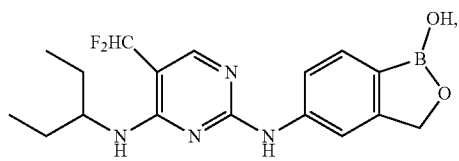

-continued

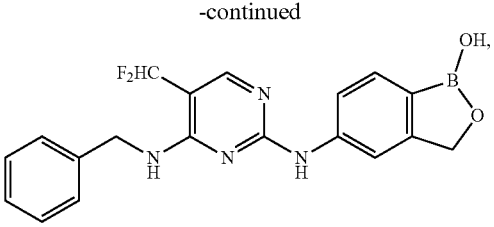

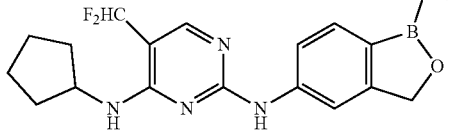

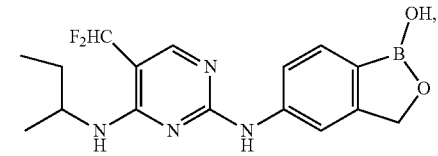

-continued

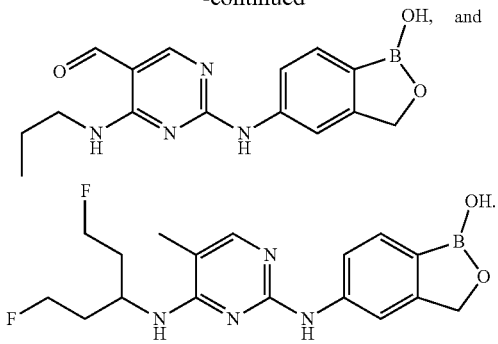

Additional Compound List 1: Additional embodiments of the present disclosure include a compound selected from the group consisting of

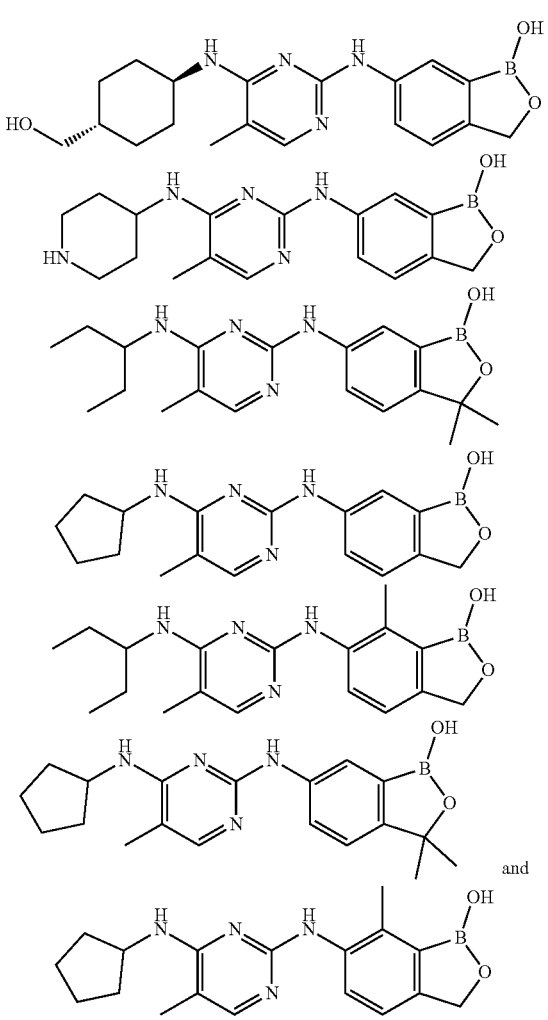

EXAMPLES

Example numbering is coordinated within each designated section and is not continuous between sections. Additionally, different naming conventions may be used throughout the present disclosure. A compound, therefore, may be referred to with different chemical names, depending on the convention used. Those skilled in the art will appreciate the differences and the chemical names, although different, are, nevertheless, clear. Variables provided in the following exemplary schemes may not coincide with the variables elsewhere in the present disclosure. In context, however, the description remains clear.

Part 1-1: General Synthetic Teachings for Compounds of Formula (IB)

General Synthetic Scheme A

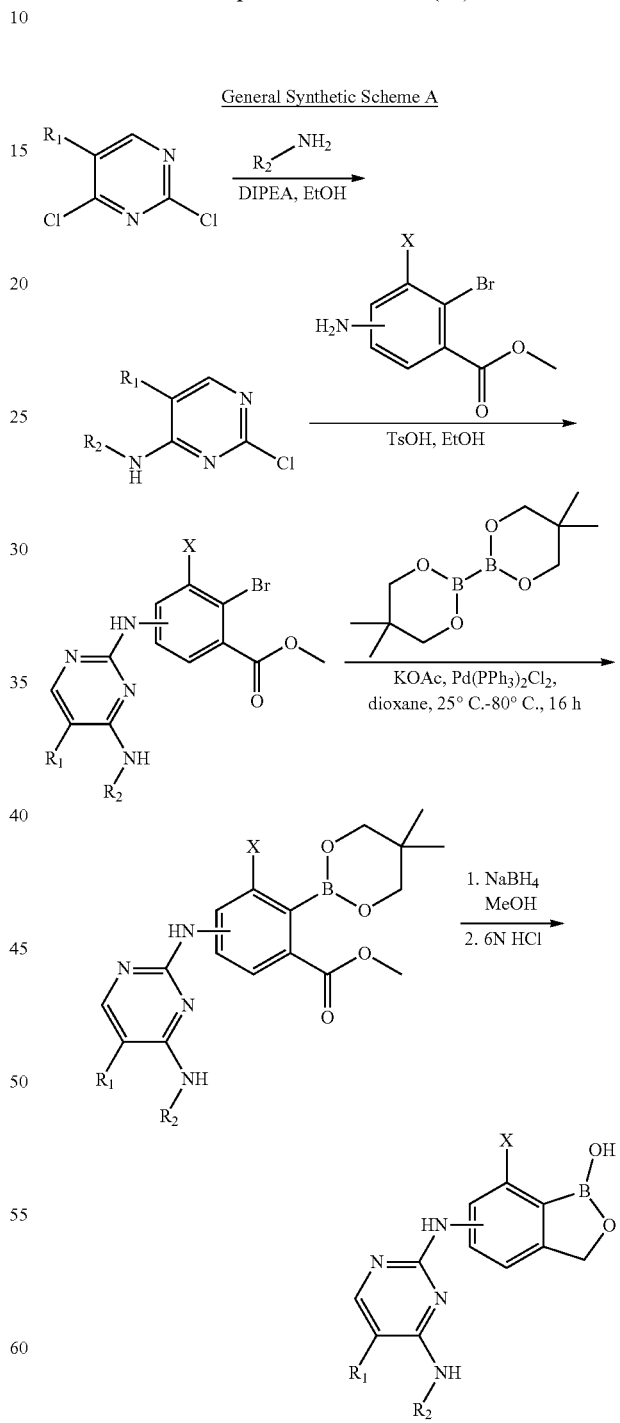

The detailed procedure is as shown in the preparation of 7-methyl-5-((5-methyl-4-(pentan-3-ylamino)pyrimidin-2-yl)amino)benzo[c][1,2]oxaborol-1(3H)-ol.

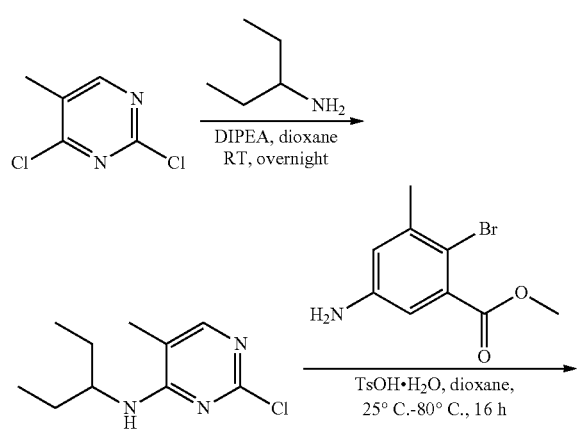

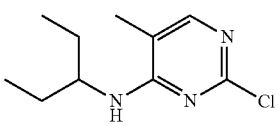

A mixture of pentan-3-amine (1.3 g, 15 mmol), 2,4-dichloro-5-methylpyrimidine (3.67 g, 22.5 mmol) and DIPEA (3.87 g, 30 mmol) in 1,4-dioxane (30 mL) was stirred at room temperature overnight. The reaction mixture was concentrated and purified by column chromatography eluted with PE/EA: 8/1 to give 2-chloro-5-methyl-N-(pentan-3-yl)pyrimidin-4-amine (1.45 g, 45% yield) as a white powder. MS: m/z=214.0 (M+H)$^+$.

A.2 Preparation of methyl 2-bromo-5-[[4-(1-ethyl-propylamino)-5-methyl-pyrimidin-2-yl]amino]-3-methyl-benzoate

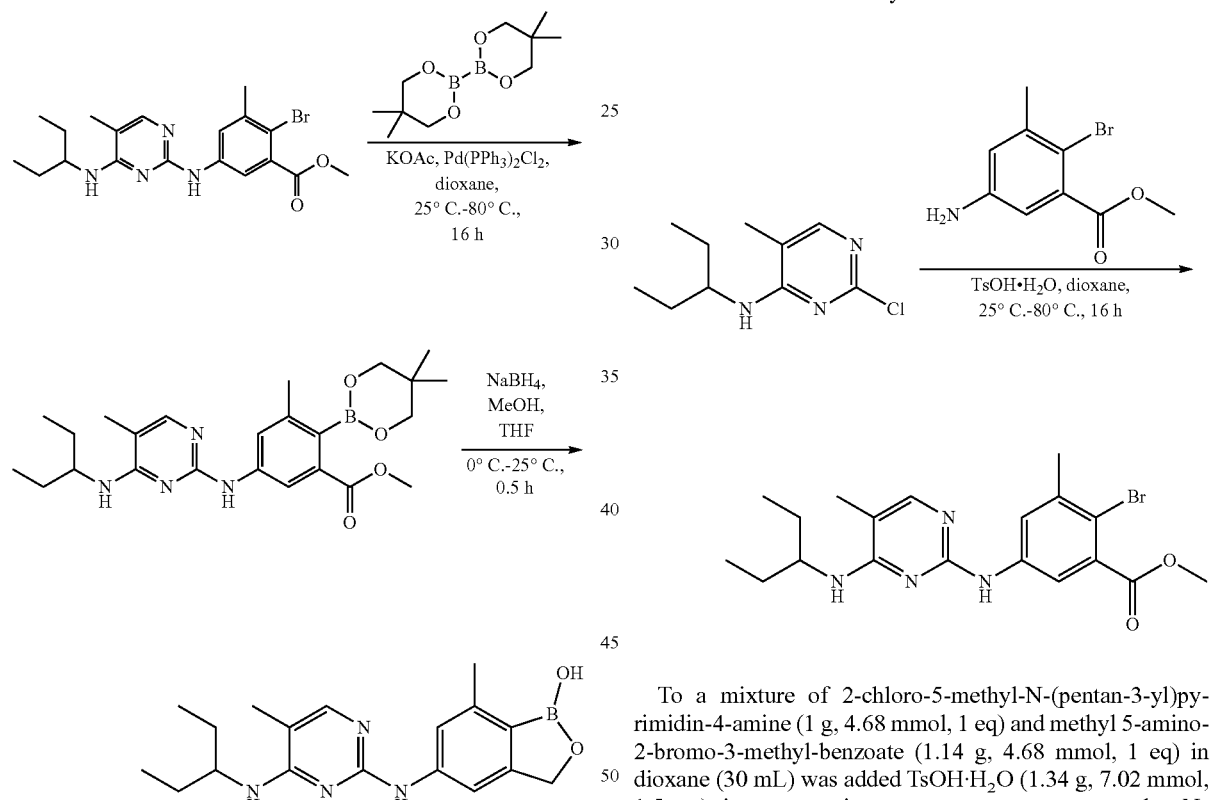

A.1 Preparation of 2-chloro-5-methyl-N-(pentan-3-yl)pyrimidin-4-amine

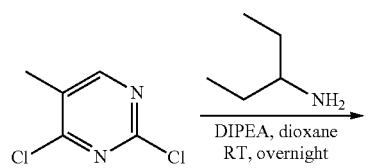

To a mixture of 2-chloro-5-methyl-N-(pentan-3-yl)pyrimidin-4-amine (1 g, 4.68 mmol, 1 eq) and methyl 5-amino-2-bromo-3-methyl-benzoate (1.14 g, 4.68 mmol, 1 eq) in dioxane (30 mL) was added TsOH·H$_2$O (1.34 g, 7.02 mmol, 1.5 eq) in one portion at room temperature under N$_2$ atmosphere. The resulting mixture was heated to 80° C. and stirred for 16 h. Then the reaction mixture was poured into sat. NaHCO$_3$ solution (50 mL), and the aqueous phase was extracted with ethyl acetate (30 mL×3). The combined organic phase was washed with brine (30 mL×2), dried over anhydrous Na$_2$SO$_4$, filtered and concentrated in vacuo to give a residue, which was purified by column chromatography (SiO$_2$, Petroleum ether/Ethyl acetate=3/1 to 1/1) to give methyl 2-bromo-5-[[4-(1-ethylpropylamino)-5-methyl-pyrimidin-2-yl]amino]-3-methyl-benzoate (1.5 g, 3.56 mmol, 76.08% yield) as a brown solid. $^1$H NMR (DMSO, 400 MHz) δ 9.10 (s, 1H), 8.13 (d, J=2.4 Hz, 1H), 7.74 (d, J=2.4 Hz, 1H), 7.66 (s, 1H), 6.17 (d, J=8.4 Hz, 1H), 4.08-4.05 (m, 1H), 3.83 (s, 3H), 2.33 (s, 3H), 1.94 (s, 3H), 1.62-1.51 (m, 4H), 0.85 (t, J=7.6 Hz, 6H).

A.3 Preparation of methyl 2-(5,5-dimethyl-1,3,2-dioxaborinan-2-yl)-5-[[4-(1-ethylpropylamino)-5-methyl-pyrimidin-2-yl]amino]-3-methyl-benzoate

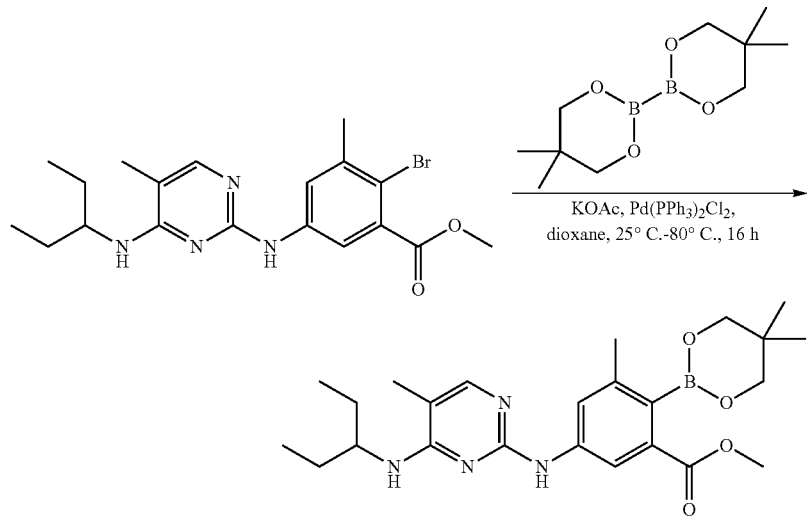

To a mixture of methyl 2-bromo-5-[[4-(1-ethylpropylamino)-5-methyl-pyrimidin-2-yl]amino]-3-methyl-benzoate (500 mg, 1.19 mmol, 1 eq) in dioxane (10 mL) was added KOAc (291 mg, 2.97 mmol, 2.5 eq), Pd(PPh$_3$)$_2$Cl$_2$ (83.30 mg, 118.67 μmol, 0.1 eq) and 2-(5,5-dimethyl-1,3,2-dioxaborinan-2-yl)-5,5-dimethyl-1,3,2-dioxaborinane (600 mg, 2.66 mmol, 2.24 eq) in one portion at 25° C. under N$_2$ atmosphere, the resulting reaction mixture was heated to 80° C. and stirred for 16 hours. The reaction mixture was filtered, concentrated in vacuo to give a residue, which was purified by column chromatography (SiO$_2$, Petroleum ether/Ethyl acetate=3/1 to 1/1) to give methyl 2-(5,5-dimethyl-1,3,2-dioxaborinan-2-yl)-5-[[4-(1-ethylpropylamino)-5-methyl pyrimidin-2-yl]amino]-3-methyl-benzoate (700 mg, crude) as a brown oil, which was used directly in the next step without further purification. MS (ESI): mass calcd. For C$_{24}$H$_{25}$BN$_4$O$_4$, 454.28, m/z found 455.2 [M+H]$^+$.

A.4 Preparation of N4-(1-ethylpropyl)-N2-(1-hydroxy-7-methyl-3H-2,1-benzoxaborol-5-yl)-5-methyl-pyrimidine-2,4-diamine

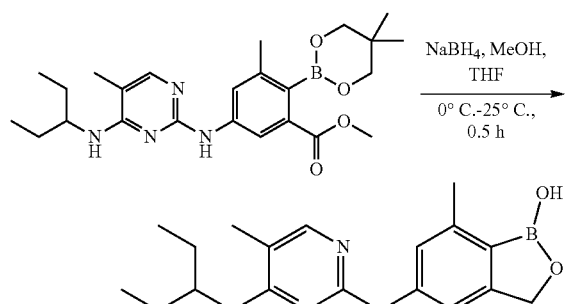

To a mixture of methyl 2-(5,5-dimethyl-1,3,2-dioxaborinan-2-yl)-5-[[4-(1-ethylpropylamino)-5-methyl-pyrimidin-2-yl]amino]-3-methyl-benzoate (700 mg, crude, 1 eq) and MeOH (0.1 mL) in THF (8 mL) was added NaBH$_4$ (174 mg, 4.62 mmol, 3 eq) in portions at 0° C., the resulting mixture was stirred at 0-25° C. for 30 min. The mixture was then poured into ice-water (w/w=1/1) (8 mL), pH of the aqueous phase was adjusted to 3-4 using aq. HCl (2N), and extracted with ethyl acetate (5 mL×3). The combined organic phase was washed with brine (5 mL×2), dried over anhydrous Na$_2$SO$_4$, filtered and concentrated in vacuo to give a residue, which was purified by prep-HPLC (column: Welch Xtimate C18 150*25 mm*5 um; mobile phase: [water(0.1% TFA)-ACN]; B %: 25%-45%, 10.5 min). After freeze-drying, the TFA salt was poured into ice-water (w/w=1/1) (8 mL), and the pH of the aqueous phase was adjusted 6-7 using aq. NaHCO$_3$ (2N), extracted with EtOAc (5 mL×3). The combined organic phase was washed with brine (5 mL×2), dried over anhydrous Na$_2$SO$_4$, filtered and concentrated in vacuo to give N4-(1-ethylpropyl)-N2-(1-hydroxy-7-methyl-3H-2,1-benzoxaborol-5-yl)-5-methyl-pyrimidine-2,4-diamine (46 mg, 116.46 μmol, 7.56% yield, 86.14% purity) as a yellow solid. $^1$H NMR (DMSO-de, 400 MHz) δ 8.89 (s, 1H), 8.58 (s, 1H), 7.67 (s, 1H), 7.65 (s, 1H), 7.46 (s, 1H), 6.11 (d, J=8.4 Hz, 1H), 4.86 (s, 2H), 4.10-4.04 (m, 1H), 2.36 (s, 3H), 1.94 (s, 3H), 1.61-1.55 (m, 4H), 0.88 (t, J=7.2 Hz, 6H). MS (ESI): mass calcd. For C$_{18}$H$_{25}$BN$_4$O$_2$, 340.21, m/z found 341.1 [M+H]$^+$. HPLC: 86.14% (220 nm), 93.84% (254 nm).

General Synthetic Scheme B

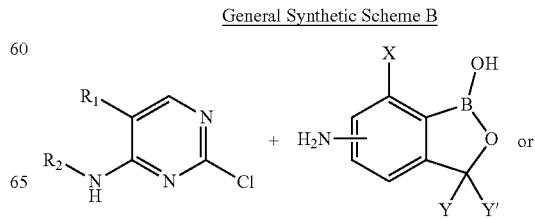

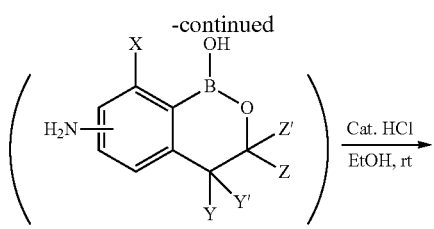

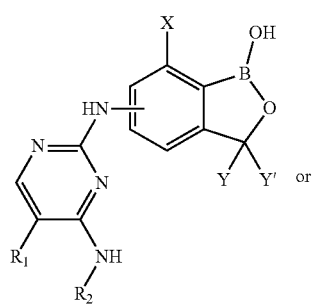

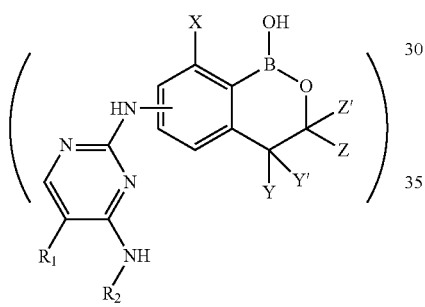

The detailed procedure is as shown in the preparation of 5-((4-(cyclopentylamino)-5-methylpyrimidin-2-yl)amino)-7-methylbenzo[c][1,2]oxaborol-1(3H)-ol

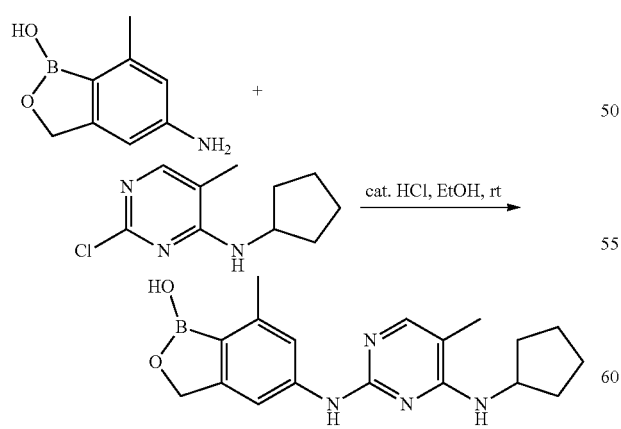

To a solution of 5-amino-7-methylbenzo[c][1,2]oxaborol-1(3H)-ol (450 mg, 2.8 mmol) in EtOH (10 mL) was added 2-chloro-N-cyclopentyl-5-methylpyrimidin-4-amine (591 mg, 2.8 mmol) and two drop of concentrated HCl at room temperature, the resulting reaction mixture was kept stirring at room temperature overnight. It was then neutralized by adding aq. NaHCO₃, extracted with EtOAc. The combined organic phase was washed with brine, concentrated in vacuo to give a residue, which was purified by silica chromatography eluting with DCM/MeOH (100/1 to 10/1) to give the crude product, which was then triturated with MeCN and water to give 5-((4-(cyclopentylamino)-5-methylpyrimidin-2-yl)amino)-7-methylbenzo[c][1,2]oxaborol-1(3H)-ol (69 mg, yield 7%) as a white solid. $^1$H NMR (400 MHz, DMSO-$d_6$): δ 8.97 (s, 1H), 8.59 (s, 1H), 7.69 (s, 1H), 7.66 (s, 1H), 7.50 (s, 1H), 6.37 (d, J=6.8 Hz, 1H), 4.86 (s, 2H), 4.41-4.39 (m, 1H), 2.36 (s, 3H), 2.01-1.99 (m, 2H), 1.73 (s, 3H), 1.60-1.53 (m, 2H), 1.24-1.22 (m, 4H) ppm. HPLC purity: 98.51% at 210 nm and 98.35% at 254 nm. MS: (M+H)+: m/z=339.2. HPLC purity: 98.51% at 210 nm and 98.35% at 254 nm. MS: (M+H)$^+$: m/z=339.2.

General Synthetic Scheme C

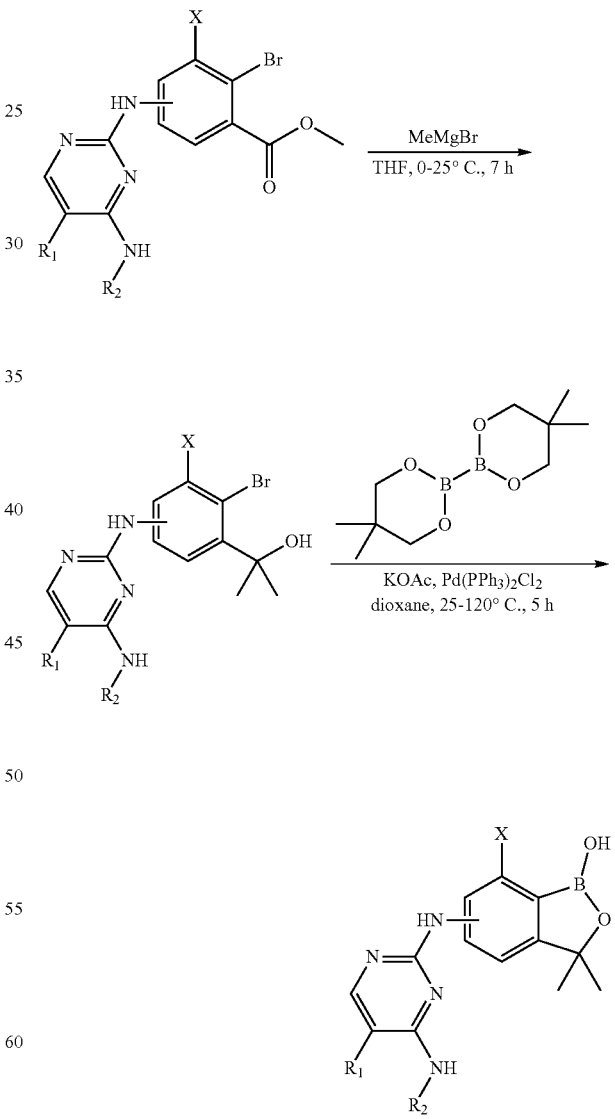

The detailed procedure is as shown in the preparation of N2-(1-hydroxy-3,3,7-trimethyl-2,1-benzoxaborol-5-yl)-5-methyl-N4-phenyl-pyrimidine-2,4-diamine

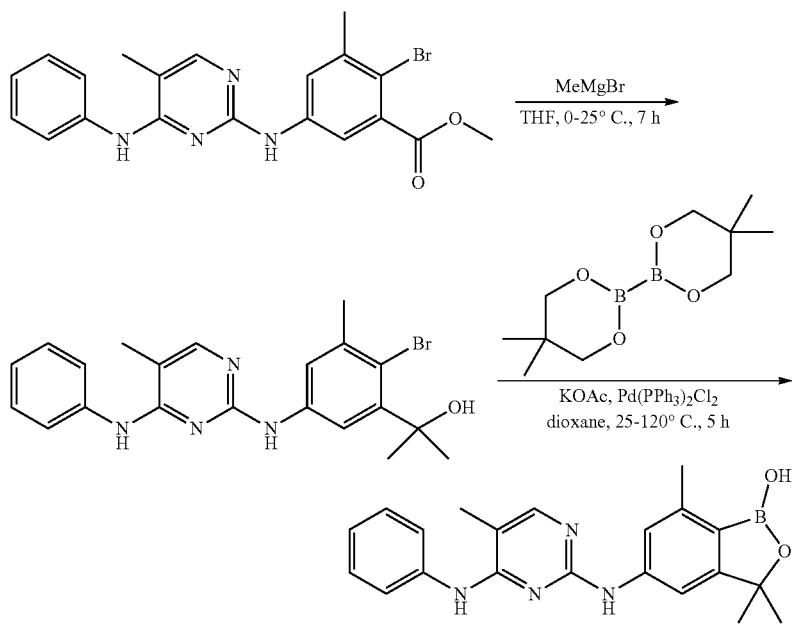

C.1 Preparation of 2-[5-[(4-anilino-5-methyl-pyrimidin-2-yl)amino]-2-bromo-3-methyl-phenyl]propan-2-ol

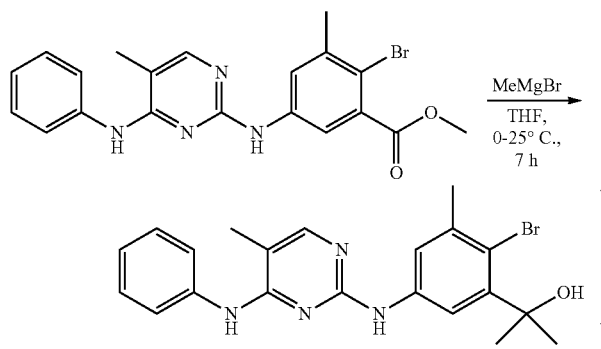

Methyl 5-[(4-anilino-5-methyl-pyrimidin-2-yl)amino]-2-bromo-3-methyl-benzoate (500 mg, 1.17 mmol, 1 eq) was added to MeMgBr (3 M, 7.80 mL, 20 eq) at 0° C. over a period of 30 min, the resulting mixture was stirred at 25° C. for 6.5 h. Then the reaction mixture was poured into sat. aq. NH$_4$Cl (15 mL), and the aqueous phase was extracted with EtOAc (8 mL×3). The combined organic layers were washed with brine (5 mL×3), dried over Na$_2$SO$_4$, filtered and concentrated in vacuo to give a residue. The residue was purified by flash silica gel chromatography (ISCO®; 12 g SepaFlash® Silica Flash Column, Eluent of 0~100% Ethyl acetate/Petroleum ethergradient @ 36 mL/min) to give 2-[5-[(4-anilino-5-methyl-pyrimidin-2-yl)amino]-2-bromo-3-methyl-phenyl]propan-2-ol (250 mg, 585 μmol, 49.99% yield) as a yellow solid.

C.2 Preparation of N2-(1-hydroxy-3,3,7-trimethyl-2,1-benzoxaborol-5-yl)-5-methyl-N4-phenyl-pyrimidine-2,4-diamine

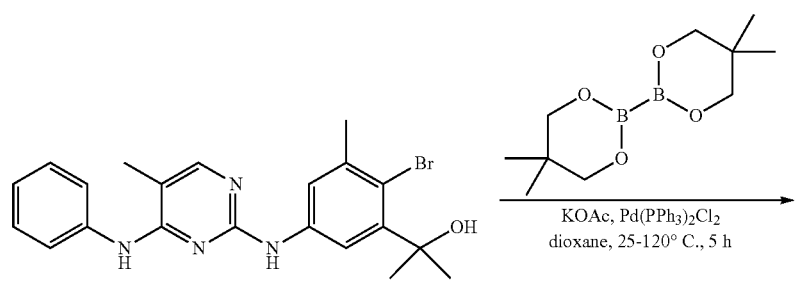

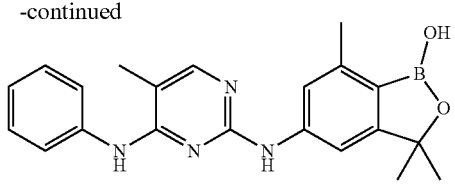

To a solution of 2-[5-[(4-anilino-5-methyl-pyrimidin-2-yl)amino]-2-bromo-3-methyl-phenyl]propan-2-ol (50 mg, 117 μmol, 1 eq) and 2-(5,5-dimethyl-1,3,2-dioxaborinan-2-yl)-5,5-dimethyl-1,3,2-dioxaborinane (66.1 mg, 293 μmol, 2.5 eq) in dioxane (3 mL) was added KOAc (23.0 mg, 234 μmol, 2 eq), Pd(PPh$_3$)$_2$Cl$_2$ (8.21 mg, 11.7 μmol, 0.1 eq) at 25° C. under N$_2$ atmosphere, the resulting mixture was stirred at 120° C. for 5 h. Then the reaction mixture was filtered, and the filtrate was concentrated in vacuo to give a residue. The residue was purified by prep-HPLC (column: Welch Xtimate C18 100*25 mm*3 um; mobile phase: [water(0.1% TFA)-ACN]; B %: 15%-35%, 12 min) to give N2-(1-hydroxy-3,3,7-trimethyl-2,1-benzoxaborol-5-yl)-5-methyl-N4-phenyl-pyrimidine-2,4-diamine (8.4 mg, 19.18% yield) as a white solid. $^1$H NMR (DMSO-d$_6$, 400 MHz) δ 10.00 (s, 1H), 9.49 (s, 1H), 8.66 (s, 1H), 7.91 (s, 1H), 7.58-7.56 (m, 2H), 7.42-7.38 (m, 2H), 7.26-7.25 (m, 2H), 7.23-7.16 (m, 1H), 2.29 (s, 3H), 2.17 (s, 3H), 3.83 (s, 6H). MS (ESI): mass calcd. For C$_{21}$H$_{23}$BN$_4$O$_2$ 374.19, m/z found 375.1 [M+H]$^+$. HPLC: 100.00% (220 nm), 100.00% (254 nm).

General Synthetic Scheme D

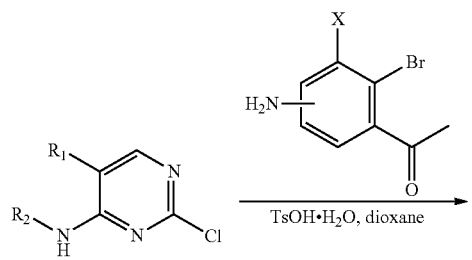

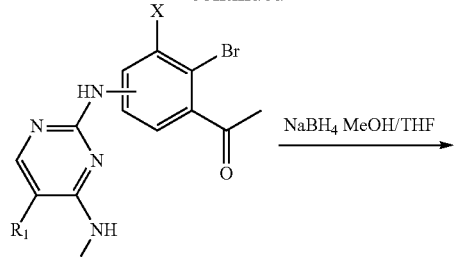

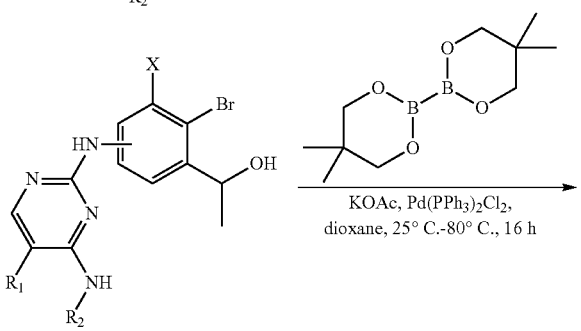

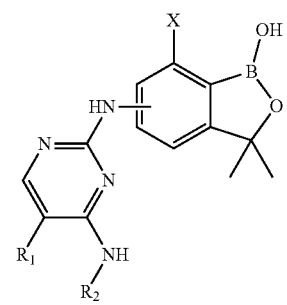

The detailed procedure is as shown in the preparation of 3-methyl-5-((5-methyl-4-(pentan-3-ylamino)pyrimidin-2-yl)amino)benzo [c][1,2]oxaborol-1(3H)-ol

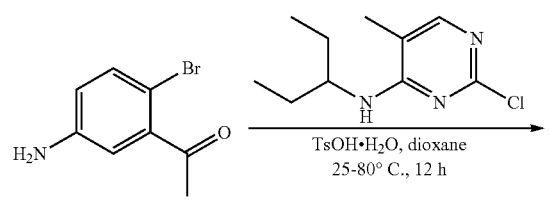

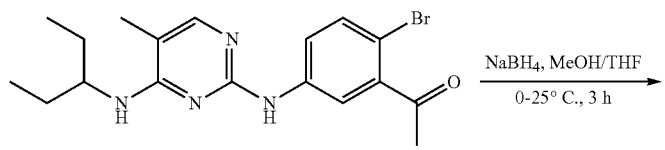

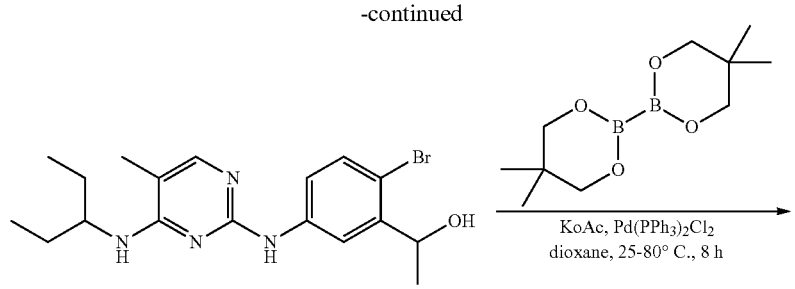

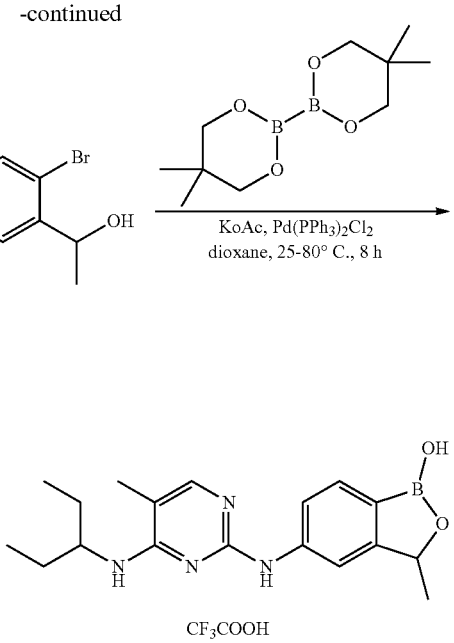

CF₃COOH

D.1 Preparation of 1-[2-bromo-5-[[4-(1-ethylpropylamino)-5-methyl-pyrimidin-2-yl]amino]phenyl]ethanone D.2 Preparation of 1-[2-bromo-5-[[4-(1-ethylpropylamino)-5-methyl-pyrimidin-2-yl]amino] phenyl]ethanol

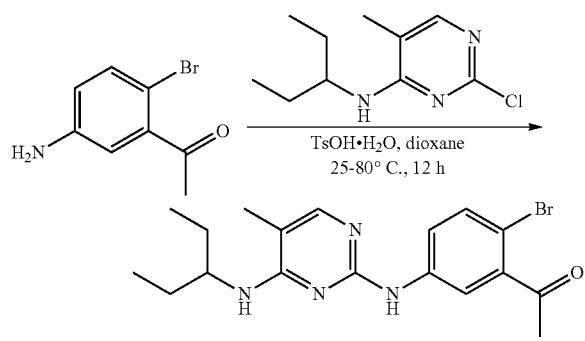

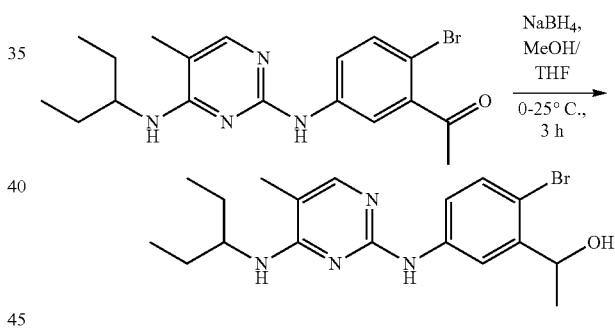

To a solution of 2-chloro-N-(1-ethylpropyl)-5-methyl-pyrimidin-4-amine (1.5 g, 7.02 mmol, 1 eq) and 1-(5-amino-2-bromo-phenyl)ethanone (1.50 g, 7.02 mmol, 1 eq) in dioxane (50 mL) was added TsOH·H₂O (2.00 g, 10.5 mmol, 1.5 eq) at 25° C., the resulting mixture was heated to 80° C. and stirred for 12 h. H₂O (30 mL) was poured into the above mixture, and its pH was adjusted to 9 with sat. aq. NaHCO₃, extracted with EtOAc (10 mL×3). The combined organic layers were washed with brine (50 mL×3), dried over Na₂SO₄, filtered and concentrated in vacuo to give a residue. The residue was purified by flash silica gel chromatography (ISCO®; 40 g SepaFlash® Silica Flash Column, Eluent of 0~100% Ethyl acetate/Petroleum ethergradient @ 75 mL/min) to give 1-[2-bromo-5-[[4-(1-ethylpropylamino)-5-methyl-pyrimidin-2-yl]amino]phenyl]ethanone (1.3 g, 3.32 mmol, 47.33% yield) as brown oil. $^1$H NMR (DMSO-d₆, 400 MHz) δ 9.11 (s, 1H), 8.14 (d, J=2.8 Hz, 1H), 7.73 (dd, J=8.8, 2.8 Hz, 1H), 7.67 (s, 1H), 7.48 (d, J=8.8 Hz, 1H), 6.15 (d, J=8.8 Hz, 1H), 4.08-4.04 (m, 1H), 2.54 (s, 3H), 1.94 (m, 3H), 1.62-1.49 (m, 4H), 0.85 (t, J=7.6 Hz, 6H).

To a solution of 1-[2-bromo-5-[[4-(1-ethylpropylamino)-5-methyl-pyrimidin-2-yl]amino]phenyl]ethanone (700 mg, 1.79 mmol, 1 eq) and MeOH (1.79 mmol, 72.4 μL, 1 eq) in THF (5 mL) was added NaBH₄ (102 mg, 2.69 mmol, 1.5 eq) at 0° C., the resulting mixture was stirred at 25° C. for 3 h. The reaction mixture was poured into H₂O (10 mL), its pH was adjusted to 5 with 2N HCl, and extracted with EtOAc (5 mL×3). The combined organic layers were washed with brine (5 mL×3), dried over Na₂SO₄, filtered and concentrated in vacuo to give a residue. The residue was purified by short column to give 1-[2-bromo-5-[[4-(1-ethylpropylamino)-5-methyl-pyrimidin-2-yl]amino]phenyl]ethanol (400 mg, 1.02 mmol, 56.98% yield) as a white solid. $^1$H NMR (DMSO-d₆, 400 MHz) δ 8.91 (s, 1H), 8.16 (d, J=2.8 Hz, 1H), 7.63 (s, 1H), 7.53 (dd, J=8.8, 2.8 Hz, 1H), 7.29 (d, J=8.8 Hz, 1H), 6.06 (d, J=8.8 Hz, 1H), 5.23 (d, J=3.6 Hz, 1H), 4.93-4.88 (m, 1H), 4.26-4.13 (m, 1H), 1.93 (s, 3H), 1.62-1.53 (m, 4H), 1.28 (d, J=6.4 Hz, 3H), 0.87 (q, J=7.6 Hz, 6H)

D.3 Preparation of N4-(1-ethylpropyl)-N2-(1-hydroxy-3-methyl-3H-2,1-benzoxaborol-5-yl)-5-methyl-pyrimidine-2,4-diamine

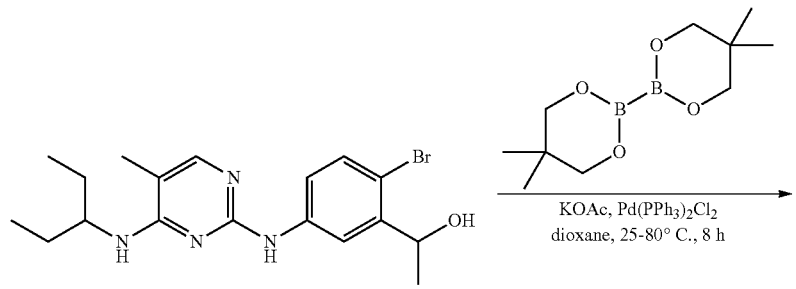

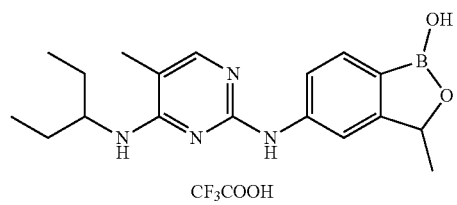

CF₃COOH

To a solution of 1-[2-bromo-5-[[4-(1-ethylpropylamino)-5-methyl-pyrimidin-2-yl]amino]phenyl]ethanol (300 mg, 763 μmol, 1 eq) and 2-(5,5-dimethyl-1,3,2-dioxaborinan-2-yl)-5,5-dimethyl-1,3,2-dioxaborinane (431 mg, 1.91 mmol, 2.5 eq) in dioxane (10 mL) was added Pd(PPh₃)₂Cl₂ (53.5 mg, 76.3 μmol, 0.1 eq), KOAc (150 mg, 1.53 mmol, 2 eq) at 25° C. under N₂ atmosphere, the resulting mixture was stirred at 80° C. for 8 h. The reaction mixture was filtered, and the filtrate was concentrated in vacuo to give a residue, which was dissolved in H₂O (10 mL), and its pH was adjusted to 5 with 2N HCl, extracted with EtOAc (8 mL×3). The combined organic layers were washed with brine (5 mL×3), dried over Na₂SO₄, filtered and concentrated in vacuo to give a residue. The residue was purified by prep-HPLC (column: Welch Xtimate C18 100*25 mm*3 um; mobile phase: [water(0.1% TFA)-MeOH]; B %: 40%-60%, 12 min) to give N4-(1-ethylpropyl)-N2-(1-hydroxy-3-methyl-3H-2,1-benzoxaborol-5-yl)-5-methyl-pyrimidine-2,4-diamine (96 mg, 211 μmol, 27.65% yield, 99.80% purity, TFA) as a white solid. ¹H NMR (DMSO-d₆, 400 MHz) δ 12.06 (s, 1H), 10.19 (s, 1H), 9.06 (s, 1H), 7.82 (s, 1H), 7.72 (s, 2H), 7.67 (d, J=8.0 Hz, 1H), 7.40 (d, J=8.0 Hz, 1H), 5.20 (q, J=6.8 Hz, 1H), 4.12-4.03 (m, 1H), 2.03 (s, 3H), 1.64-1.59 (m, 4H), 1.40 (d, J=6.8 Hz, 3H), 0.88-0.82 (m, 6H). MS (ESI): mass calcd. For C₂₀H₂₆BF₃N₄O₄ 454.20, m/z found 341.0 [M+H]⁺. HPLC: 99.80% (220 nm), 99.74% (254 nm).

Part 1-2: Synthetic Examples for Compounds of Formula (IB)

Example 1: 7-methoxy-5-((5-methyl-4-(methylthio)pyrimidin-2-yl)amino)benzo[c][1,2]oxaborol-1(3H)-ol

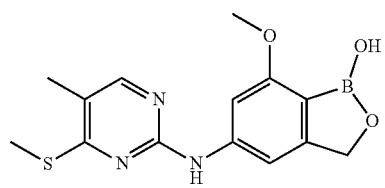 [SMILES: COc1cc(Nc2ncc(C)c(SC)n2)cc2c1B(O)OC2]

This substance was prepared by following General Synthetic Scheme A. ¹H NMR (DMSO-d6, 400 MHz) δ (ppm) 9.60 (s, 1H), 8.58 (br, 1H), 8.05 (s, 1H), 7.50 (s, 1H), 7.22 (s, 1H), 4.87 (s, 2H), 3.78 (s, 3H), 2.59 (s, 3H), 2.06 (s, 3H). MS (ESI): m/z found 318.0 [M+H]⁺. Purity by HPLC: 98.8% (220 nm), 98.93% (254 nm).

Example 2: 5-((4-(cyclopentylamino)-5-methylpyrimidin-2-yl)amino)-3-methylbenzo[c][1,2]oxaborol-1(3H)-ol

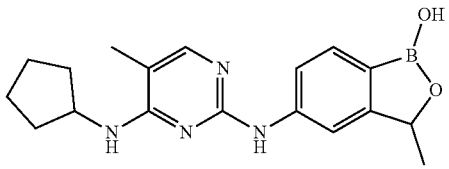 [SMILES: Cc1cnc(Nc2ccc3c(c2)C(C)OB3O)nc1NC1CCCC1]

This substance was prepared by following General Synthetic Scheme D. ¹H NMR (DMSO-d6, 400 MHz) δ (ppm) 9.05 (s, 1H), 8.77 (s, 1H), 8.07 (s, 1H), 7.67 (s, 1H), 7.50-7.48 (m, 2H), 6.36 (d, J=7.2 Hz, 1H), 5.11 (q, J=6.4 Hz, 1H), 4.45-4.43 (m, 1H), 2.01-1.99 (m, 2H), 1.93 (s, 3H), 1.74-1.73 (m, 2H), 1.60-1.57 (m, 4H), 1.37 (d, J=6.4 Hz, 1H). MS (ESI): m/z found 339.2 [M+H]⁺. Purity by HPLC: 97.16% (220 nm), 97.78% (254 nm).

Example 3: 5-((4-(cyclopentylamino)-5-methylpyrimidin-2-yl)amino)-3,3-dimethylbenzo[c][1,2]oxaborol-1(3H)-ol

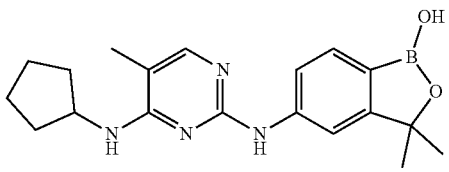 [SMILES: Cc1cnc(Nc2ccc3c(c2)C(C)(C)OB3O)nc1NC1CCCC1]

This substance was prepared by following General Synthetic Scheme C. ¹H NMR (DMSO-d6, 400 MHz) δ (ppm) 9.09 (s, 1H), 8.73 (s, 1H), 8.12 (s, 1H), 7.68 (s, 1H), 7.46 (d, J=8.0 Hz, 1H), 7.39 (dd, J=8.0, 1.6 Hz, 1H), 6.44 (d, J=7.2 Hz, 1H), 4.53-4.47 (m, 1H), 2.03-2.01 (m, 2H), 1.93 (s, 3H), 1.76-1.73 (m, 2H), 1.61-1.57 (m, 4H), 1.42 (s, 6H). MS (ESI): m/z found 353.2 [M+H]⁺. Purity by HPLC: 95.93% (220 nm), 94.50% (254 nm).

Example 4: 6-((4-(cyclopentylamino)-5-methylpyrimidin-2-yl)amino)-3,4-dihydro-1H-benzo[c][1,2]oxaborinin-1-ol

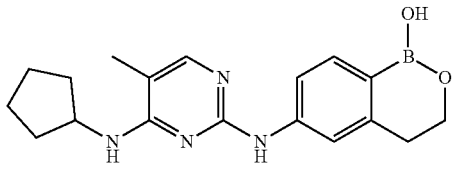 [SMILES: Cc1cnc(Nc2ccc3c(c2)CCOB3O)nc1NC1CCCC1]

This substance was prepared by following General Synthetic Scheme B. ¹H NMR (DMSO-d6, 400 MHz) δ (ppm) 8.95 (s, 1H), 8.11 (s, 1H), 7.78 (s, 1H), 7.66 (s, 1H), 7.51 (s, 2H), 6.35 (d, J=7.2 Hz, 1H), 4.44-4.38 (m, 1H), 4.04 (t, J=5.6 Hz, 2H), 2.77 (t, J=5.6 Hz, 2H), 2.01-1.99 (m, 2H), 1.92 (s, 3H), 1.75-1.73 (m, 2H), 1.59-1.57 (m, 4H). MS (ESI): m/z found 339.2 [M+H]⁺. Purity by HPLC: 96.64% (220 nm), 98.79% (254 nm).

Example 5: 7-methyl-5-((5-methyl-4-(pentan-3-ylamino)pyrimidin-2-yl)amino)benzo[c][1,2]oxaborol-1(3H)-ol

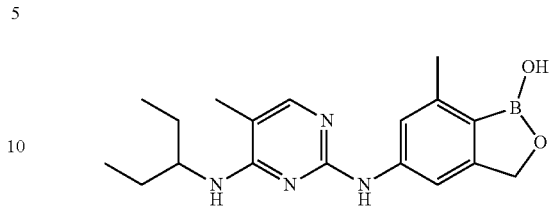

This substance was prepared by following the General Synthetic Scheme A. ¹H NMR (DMSO-d6, 400 MHz) δ 8.89 (s, 1H), 8.58 (s, 1H), 7.67 (s, 1H), 7.65 (s, 1H), 7.46 (s, 1H), 6.11 (d, J=8.4 Hz, 1H), 4.86 (s, 2H), 4.10-4.04 (m, 1H), 2.36 (s, 3H), 1.94 (s, 3H), 1.61-1.55 (m, 4H), 0.88 (t, J=7.2 Hz, 6H) ppm. HPLC purity: 86.14% at 210 nm and 93.84% at 254 nm. MS: (M+H)⁺: m/z=341.1.

Example 6: 3,3-dimethyl-5-((5-methyl-4-(pentan-3-ylamino)pyrimidin-2-yl)amino)benzo[c][1,2]oxaborol-1(3H)-ol

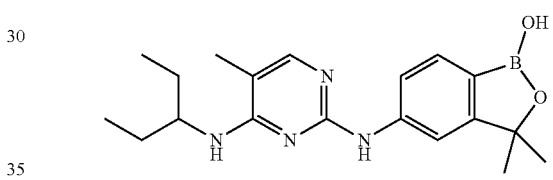

This substance was prepared by following General Synthetic Scheme B. ¹H NMR (DMSO-d6, 400 MHz) δ 11.86 (br, 1H), 10.13 (br, 1H), 8.99 (br, 1H), 7.91-7.86 (m, 1H), 7.79 (s, 1H), 7.72 (s, 1H), 7.64 (d, J=8.0 Hz, 1H), 7.33 (dd, J=8.0, 1.6 Hz, 1H), 4.16-4.11 (m, 1H), 2.03 (s, 3H), 1.64-1.58 (m, 4H), 1.45 (s, 6H), 0.84 (t, J=7.2 Hz, 6H) ppm. HPLC purity: 99.8% at 210 nm and 99.99% at 254 nm. MS: (M+H)⁺: m/z=355.2.

Example 7: 5-((4-(cyclopentylamino)-5-methylpyrimidin-2-yl)amino)-7-methylbenzo[c][1,2]oxaborol-1(3H)-ol

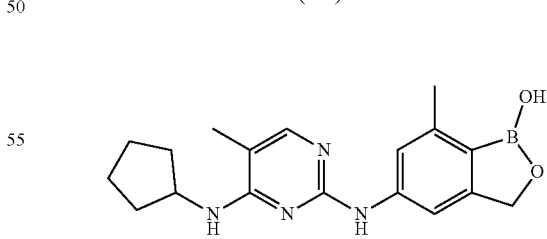

This substance was prepared by following General Synthetic Scheme B. ¹H NMR (DMSO-d6, 400 MHz) δ 8.97 (s, 1H), 8.59 (s, 1H), 7.69 (s, 1H), 7.66 (s, 1H), 7.50 (s, 1H), 6.37 (d, J=6.8 Hz, 1H), 4.86 (s, 2H), 4.41-4.39 (m, 1H), 2.36 (s, 3H), 2.01-1.99 (m, 2H), 1.73 (s, 3H), 1.60-1.53 (m, 2H), 1.24-1.22 (m, 4H) ppm. HPLC purity: 98.51% at 210 nm and 98.35% at 254 nm. MS: (M+H)⁺: m/z=339.2.

Example 8: 5-((5-chloro-4-(cyclopentylamino)pyrimidin-2-yl)amino)-7-methylbenzo[c][1,2]oxaborol-1(3H)-ol

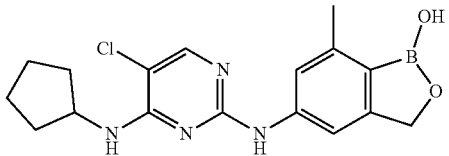 [SMILES: Cc1cc(Nc2ncc(Cl)c(NC3CCCC3)n2)cc2c1B(O)OC2]

This substance was prepared by following General Synthetic Scheme A. $^1$H NMR (DMSO-d6, 400 MHz) δ (ppm) 9.33 (s, 1H), 8.65 (s, 1H), 7.95 (s, 1H), 7.64 (s, 1H), 7.48 (s, 1H) 6.87 (d, J=7.2 Hz, 1H), 4.88 (s, 2H), 4.42-4.36 (m, 1H), 2.37 (s, 3H), 2.01-1.98 (m, 2H), 1.74-1.73 (m, 2H), 1.61-1.56 (m, 4H). MS (ESI): m/z found 359.1 [M+H]$^+$. Purity by HPLC: 93.73% (220 nm), 94.52% (254 nm).

Example 9: 6-((4-(cyclopentylamino)-5-methylpyrimidin-2-yl)amino)-8-methyl-3,4-dihydro-1H-benzo[c][1,2]oxaborinin-1-ol

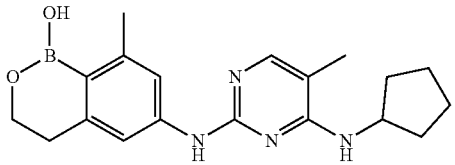 [SMILES: Cc1cnc(Nc2cc(C)c3c(c2)CCOB3O)nc1NC1CCCC1]

This substance was prepared by following General Synthetic Scheme B. It was obtained as a TFA salt. $^1$H NMR (DMSO-d6, 400 MHz) δ 11.78 (br s, 1H), 9.40 (br s, 1H), 8.36 (s, 1H), 8.06 (br s, 1H), 7.74 (s, 1H), 7.41-7.39 (m, 2H), 4.03-4.01 (m, 3H), 2.83 (t, J=6 Hz, 2H), 2.50 (s, 3H), 2.12 (s, 3H), 1.96-1.90 (m, 2H), 1.68-1.69 (m, 2H), 1.55-1.52 (m, 4H) ppm. HPLC purity: 98.72% at 210 nm and 95.12% at 254 nm. MS: (M+H)$^+$: m/z=353.2.

Example 10: 7-chloro-3,3-dimethyl-5-((5-methyl-4-(pentan-3-ylamino)pyrimidin-2-yl)amino)benzo[c][1,2] oxaborol-1(3H)-ol

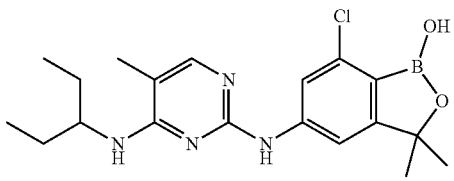 [SMILES: CCC(CC)Nc1nc(Nc2cc(Cl)c3c(c2)C(C)(C)OB3O)ncc1C]

This substance was prepared by following General Synthetic Scheme C. $^1$H NMR (DMSO-d6, 400 MHz) δ (ppm) 10.63 (s, 1H), 8.96 (s, 1H), 7.95 (d, J=8.4 Hz, 1H), 7.79 (s, 1H), 7.60 (s, 1H), 7.59 (s, 1H), 4.17-4.08 (m, 1H), 2.04 (s, 3H), 1.67-1.46 (m, 4H), 1.46 (s, 6H), 0.85 (t, J=7.4 Hz, 6H). MS (ESI): m/z found 389.2 [M+H]$^+$. Purity by HPLC: 99.84% (220 nm), 99.83% (254 nm).

Example 11: 5-((5-chloro-4-(cyclopentylamino)pyrimidin-2-yl)amino)-3,3,7-trimethylbenzo[c][1,2]oxaborol-1(3H)-ol

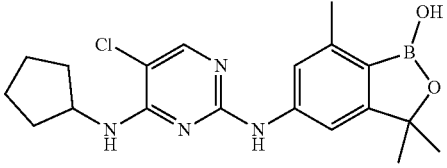 [SMILES: Cc1cc(Nc2ncc(Cl)c(NC3CCCC3)n2)cc2c1B(O)OC2(C)C]

This substance was prepared by following General Synthetic Scheme C. $^1$H NMR (DMSO-d6, 400 MHz) δ (ppm) 9.77 (br, 1H), 8.78 (br, 1H), 8.07 (s, 1H), 7.66 (s, 1H), 7.26 (s, 1H), 4.51-4.45 (m, 1H), 2.39 (s, 3H), 1.99-1.97 (m, 2H), 1.77-1.75 (m, 2H), 1.68-1.66 (m, 2H), 1.56-1.54 (m, 2H), 1.43 (s, 6H). MS (ESI): m/z found 387.1 [M+H]$^+$. Purity by HPLC: 97.21% (220 nm), 88.55% (254 nm).

Example 12: 7-chloro-5-((5-chloro-4-(cyclopentylamino)pyrimidin-2-yl)amino)-3,3-dimethylbenzo[c][1,2] oxaborol-1(3H)-ol

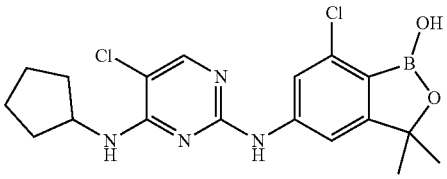 [SMILES: CC1(C)OB(O)c2c(Cl)cc(Nc3ncc(Cl)c(NC4CCCC4)n3)cc21]

This substance was prepared by following General Synthetic Scheme C. $^1$H NMR (DMSO-d6, 400 MHz) δ (ppm) 9.61 (s, 1H), 8.76 (s, 1H), 7.99 (s, 1H), 7.77 (s, 1H), 7.71 (s, 1H), 7.02 (d, J=7.6 Hz, 1H), 4.46-4.41 (m, 1H), 2.50-1.99 (m, 2H), 1.76-1.74 (m, 2H), 1.65-1.55 (m, 4H), 1.43 (s, 6H). MS (ESI): m/z found 407.1 [M+H]$^+$. Purity by HPLC: 98.76% (220 nm), 98.54% (254 nm).

Example 13: 5-((5-chloro-4-(cyclopentylamino)pyrimidin-2-yl)amino)-3-methylbenzo[c][1,2]oxaborol-1(3H)-ol

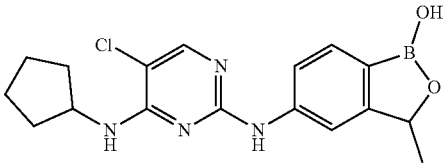 [SMILES: CC1OB(O)c2ccc(Nc3ncc(Cl)c(NC4CCCC4)n3)cc21]

This substance was prepared by following General Synthetic Scheme D. $^1$H NMR (DMSO-d6, 400 MHz) δ (ppm) 9.74 (s, 1H), 8.04 (s, 1H), 7.92 (s, 1H), 7.58 (d, J=8.0 Hz, 1H), 7.46-7.41 (m, 2H), 5.15 (q, J=6.4 Hz, 1H), 4.45-4.40 (m, 1H), 1.97-1.96 (m, 2H), 1.74-1.73 (m, 2H), 1.64-4.63 (m, 2H), 1.55-1.53 (m, 2H), 1.38 (d, J=6.4 Hz, 3H). MS (ESI): m/z found 359.1 [M+H]$^+$. Purity by HPLC: 98.84% (220 nm), 97.83% (254 nm).

Example 14: 3-methyl-5-((5-methyl-4-(pentan-3-ylamino)pyrimidin-2-yl)amino)benzo[c][1,2]oxaborol-1(3H)-ol

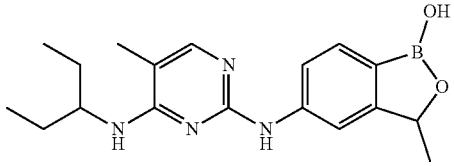 [SMILES: CCC(CC)Nc1nc(Nc2ccc3c(c2)C(C)OB3O)ncc1C]

This substance was prepared by following General Synthetic Scheme D. $^1$H NMR (DMSO-d6, 400 MHz) δ (ppm) 12.06 (br, 1H), 10.19 (s, 1H), 9.06 (s, 1H), 7.82 (br, 1H), 7.72 (s, 2H), 7.67 (d, J=8.0 Hz, 1H), 7.41 (d, J=8.0 Hz, 1H), 5.20 (q, J=6.4 Hz, 1H), 4.12-4.03 (m, 1H), 2.03 (s, 3H), 1.64-1.59 (m, 4H), 1.40 (d, J=6.4 Hz, 3H), 0.88-0.82 (m, 6H). MS (ESI): m/z found 341.1 [M+H]$^+$. Purity by HPLC: 99.8% (220 nm), 99.74% (254 nm).

Example 15: 3,3-dimethyl-5-((5-methyl-4-(phenylamino)pyrimidin-2-yl)amino)benzo[c][1,2]oxaborol-1(3H)-ol

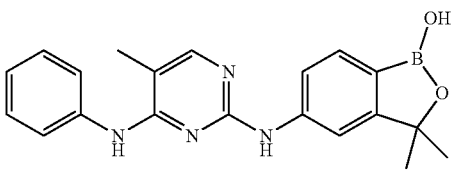 [SMILES: Cc1cnc(Nc2ccc3c(c2)C(C)(C)OB3O)nc1Nc1ccccc1]

This substance was prepared by following General Synthetic Scheme C. $^1$H NMR (DMSO-d6, 400 MHz) δ (ppm) 10.18 (s, 1H), 9.64 (s, 1H), 8.91 (br, 1H), 7.93 (s, 1H), 7.56-7.51 (m, 3H), 7.43-7.38 (m, 4H), 7.27-7.25 (m, 1H), 2.18 (s, 3H), 1.29 (s, 6H). MS (ESI): m/z found 361.0 [M+H]$^+$. Purity by HPLC: 100% (220 nm), 99.77% (254 nm).

Example 16: 5-((5-methyl-4-(pentan-3-ylamino)pyrimidin-2-yl)amino)-7-(trifluoromethyl)benzo[c][1,2] oxaborol-1(3H)-ol

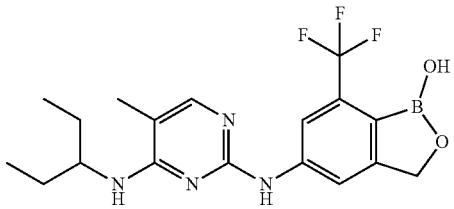 [SMILES: CCC(CC)Nc1nc(Nc2cc3c(c(C(F)(F)F)c2)B(O)OC3)ncc1C]

This substance was prepared by following General Synthetic Scheme A. $^1$H NMR (DMSO-d6, 400 MHz) δ (ppm) 10.52 (s, 1H), 9.13 (s, 1H), 8.23 (s, 1H), 7.81 (br, 1H), 7.80 (s, 1H), 7.71 (s, 1H), 5.06 (s, 2H), 4.11-4.06 (m, 1H), 2.04 (s, 1H), 1.65-1.55 (m, 4H), 0.83 (t, J=7.4 Hz, 6H). MS (ESI): m/z found 395.1 [M+H]$^+$. Purity by HPLC: 98.77% (220 nm), 99.23% (254 nm).

Example 17: 7-methyl-5-((5-methyl-4-(phenylamino)pyrimidin-2-yl)amino)benzo[c][1,2]oxaborol-1(3H)-ol

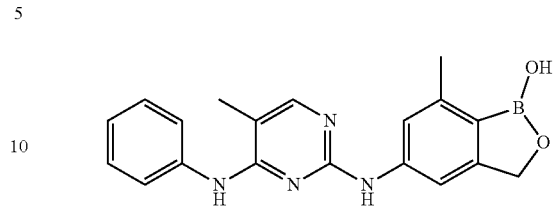

This substance was prepared by following General Synthetic Scheme A. $^1$H NMR (DMSO-d6, 400 MHz) δ (ppm) 9.78 (br, 1H), 9.01 (br, 1H), 8.70 (s, 1H), 7.94 (s, 1H), 7.60 (d, J=7.6 Hz, 2H), 7.52 (s, 1H), 7.42-7.38 (m, 2H), 7.22-7.17 (m, 2H), 6.54 (br, 1H), 4.76 (s, 2H), 2.30 (s, 3H), 2.14 (s, 3H). MS (ESI): m/z found 347.1 [M+H]$^+$. Purity by HPLC: 90.25% (220 nm), 88.74% (254 nm).

Example 18: 5-((5-methyl-4-(phenylamino)pyrimidin-2-yl)amino)-7-(trifluoromethyl)benzo[c][1,2] oxaborol-1(3H)-ol

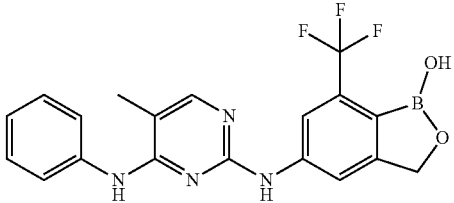 [SMILES: Cc1cnc(Nc2cc3c(c(C(F)(F)F)c2)B(O)OC3)nc1Nc1ccccc1]

This substance was prepared by following General Synthetic Scheme A. $^1$H NMR (DMSO-d6, 400 MHz) δ (ppm) 9.71 (br, 1H), 8.91 (s, 1H), 8.66 (br, 1H), 8.13 (s, 1H), 7.96 (s, 1H), 7.77 (s, 1H), 7.62 (d, J=8.4 Hz, 2H), 7.40-7.36 (m, 2H), 7.16 (t, J=7.6 Hz, 1H), 4.86 (s, 2H), 2.15 (s, 3H). MS (ESI): m/z found 401.1 [M+H]$^+$. Purity by HPLC: 99.28% (220 nm), 99.8% (254 nm).

Example 19: 3-methyl-5-((5-methyl-4-(phenylamino)pyrimidin-2-yl)amino)benzo[c][1,2]oxaborol-1(3H)-ol

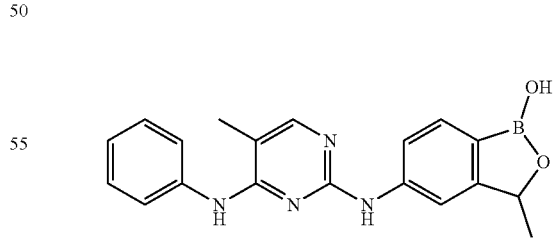

This substance was prepared by following General Synthetic Scheme D. $^1$H NMR (DMSO-d6, 400 MHz) δ (ppm) 10.26 (s, 1H), 9.69 (s, 1H), 8.98 (br, 1H), 7.93 (s, 1H), 7.56-7.53 (m, 4H), 7.45-7.41 (m, 2H), 7.32-7.31 (m, 2H), 5.02 (q, J=6.4 Hz, 1H), 2.18 (s, 3H), 1.17 (d, J=6.4 Hz, 3H). MS (ESI): m/z found 347.1 [M+H]$^+$. Purity by HPLC: 94.91% (220 nm), 93.77% (254 nm).

Example 20: 5-((5-chloro-4-(cyclopentylamino) pyrimidin-2-yl)amino)-3,3-dimethylbenzo[c][1,2] oxaborol-1(3H)-ol

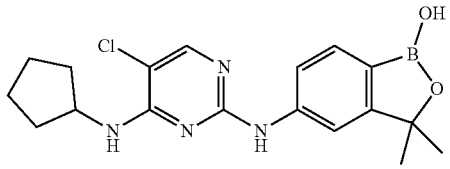 [SMILES: CC1(C)OB(O)c2ccc(Nc3ncc(Cl)c(NC4CCCC4)n3)cc21]

This substance was prepared by following General Synthetic Scheme C. $^1$H NMR (DMSO-d6, 400 MHz) δ (ppm) 9.75 (s, 1H), 8.04 (s, 1H), 7.96 (s, 1H), 7.51 (d, J=8.0 Hz, 1H), 7.49 (br, 1H), 7.38 (d, J=8.0 Hz, 1H), 4.50-4.44 (m, 1H), 1.98-1.97 (m, 2H), 1.75-1.73 (m, 2H), 1.65-1.64 (m, 2H), 1.53-1.51 (m, 2H), 1.43 (s, 6H). MS (ESI): m/z found 373.1 [M+H]$^+$. Purity by HPLC: 96.66% (220 nm), 95.82% (254 nm).

Example 21: 5-((5-chloro-4-(cyclopentylamino) pyrimidin-2-yl)amino)-7-(trifluoromethyl)benzo[c] [1,2] oxaborol-1(3H)-ol

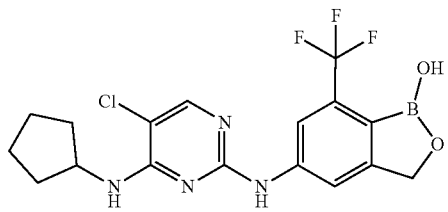 [SMILES: OB1OCc2cc(Nc3ncc(Cl)c(NC4CCCC4)n3)cc(C(F)(F)F)c21]

This substance was prepared by following General Synthetic Scheme A. $^1$H NMR (DMSO-d6, 400 MHz) δ (ppm) 9.92 (s, 1H), 8.98 (br, 1H), 8.24 (s, 1H), 8.04 (s, 1H), 7.93 (s, 1H), 7.23 (d, J=7.2 Hz, 1H), 5.01 (s, 2H), 4.43-4.38 (m, 1H), 1.98-1.96 (m, 2H), 1.74-1.72 (m, 2H), 1.63-1.55 (m, 4H). MS (ESI): m/z found 413.0 [M+H]$^+$. Purity by HPLC: 98.46% (220 nm), 98.87% (254 nm).

Example 22: 7-chloro-5-((5-methyl-4-(pentan-3-ylamino)pyrimidin-2-yl)amino)benzo[c][1,2]oxaborol-1(3H)-ol

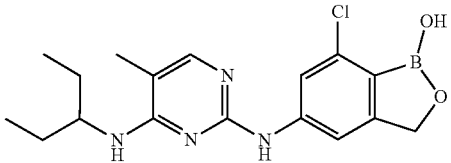 [SMILES: CCC(CC)Nc1nc(Nc2cc(Cl)c3c(c2)COB3O)ncc1C]

This substance was prepared by following General Synthetic Scheme A. $^1$H NMR (DMSO-d6, 400 MHz) δ (ppm) 10.47 (s, 1H), 9.10 (s, 1H), 7.85 (s, 1H), 7.79 (s, 1H), 7.78 (s, 1H), 7.45 (s, 1H), 4.99 (s, 2H), 4.09-4.02 (m, 1H), 2.03 (s, 3H), 1.68-1.56 (m, 4H), 0.87 (t, J=7.4 Hz, 6H). MS (ESI): m/z found 361.1 [M+H]$^+$. Purity by HPLC: 99.83% (220 nm), 99.82% (254 nm).

Example 23: 7-ethyl-5-((5-methyl-4-(pentan-3-ylamino)pyrimidin-2-yl)amino)benzo[c][1,2]oxaborol-1(3H)-ol

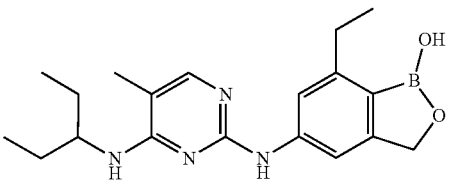 [SMILES: CCc1cc(Nc2ncc(C)c(NC(CC)CC)n2)cc2c1B(O)OC2]

This substance was prepared by following General Synthetic Scheme A. $^1$H NMR (DMSO-d6, 400 MHz) δ (ppm) 10.25 (s, 1H), 8.89 (s, 1H), 7.92 (d, J=8.0 Hz, 1H), 7.73 (s, 1H), 7.41 (s, 1H), 7.36 (s, 1H), 4.95 (s, 2H), 4.12-4.07 (m, 1H), 2.79 (q, J=7.6 Hz, 2H), 2.03 (s, 3H), 1.64-1.57 (m, 4H), 1.19 (t, J=6.8 Hz, 3H), 0.85 (t, J=7.4 Hz, 6H). MS (ESI): m/z found 355.1 [M+H]$^+$. Purity by HPLC: 93.05% (220 nm), 95.97% (254 nm).

Example 24: 3,3,7-trimethyl-5-((5-methyl-4-(pentan-3-ylamino)pyrimidin-2-yl)amino)benzo[c][1,2] oxaborol-1(3H)-ol

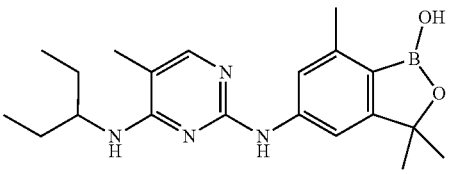 [SMILES: CCC(CC)Nc1nc(Nc2cc(C)c3c(c2)C(C)(C)OB3O)ncc1C]

This substance was prepared by following General Synthetic Scheme C. $^1$H NMR (DMSO-d6, 400 MHz) δ (ppm) 8.93 (s, 1H), 8.45 (s, 1H), 7.85 (s, 1H), 7.67 (s, 1H), 7.25 (s, 1H), 6.17 (d, J=8.8 Hz, 1H), 4.23-4.21 (m, 1H), 2.35 (s, 3H), 1.96 (s, 3H), 1.68-1.54 (m, 4H), 1.42 (s, 6H), 0.88 (t, J=7.4 Hz, 6H). MS (ESI): m/z found 369.2 [M+H]$^+$. Purity by HPLC: 98.87% (220 nm), 99.07% (254 nm).

Example 25: 7-chloro-5-((5-methyl-4-(phenylamino)pyrimidin-2-yl)amino)benzo[c][1,2]oxaborol-1(3H)-ol

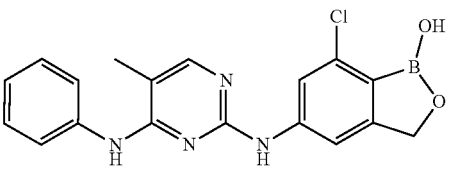 [SMILES: Cc1cnc(Nc2cc(Cl)c3c(c2)COB3O)nc1Nc1ccccc1]

This substance was prepared by following General Synthetic Scheme A. $^1$H NMR (DMSO-d6, 400 MHz) δ (ppm) 9.98 (br, 1H), 9.31 (br, 1H), 8.98 (br, 1H), 7.94 (s, 1H), 7.56-7.54 (m, 3H), 7.45-7.41 (m, 3H), 7.27-7.25 (m, 1H), 4.80 (s, 2H), 2.17 (s, 3H). MS (ESI): m/z found 367.1 [M+H]$^+$. Purity by HPLC: 96% (220 nm), 98.16% (254 nm).

Example 26: 7-chloro-3,3-dimethyl-5-((5-methyl-4-(phenylamino)pyrimidin-2-yl)amino)benzo[c][1,2]oxaborol-1(3H)-ol

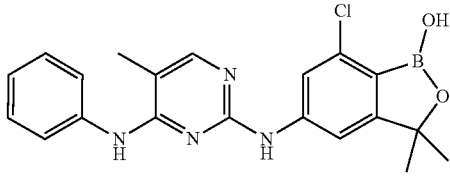 [SMILES: Cc1cnc(Nc2cc(Cl)c3c(c2)C(C)(C)OB3O)nc1Nc1ccccc1]

This substance was prepared by following General Synthetic Scheme C. ¹H NMR (DMSO-d6, 400 MHz) δ (ppm) 10.03 (br, 1H), 9.30 (br, 1H), 8.83 (br, 1H), 7.95 (s, 1H), 7.59-7.57 (m, 3H), 7.42-7.38 (m, 2H), 7.35 (s, 1H), 7.23-7.19 (m, 1H), 2.17 (s, 3H), 1.32 (s, 6H). MS (ESI): m/z found 395.1 [M+H]⁺. Purity by HPLC: 96.13% (220 nm), 98.95% (254 nm).

Example 27: 5-((5-chloro-4-(cyclopentylamino)pyrimidin-2-yl)amino)-7-ethylbenzo[c][1,2]oxaborol-1(3H)-ol

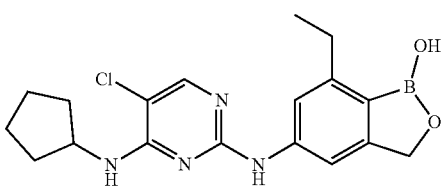 [SMILES: CCc1cc(Nc2ncc(Cl)c(NC3CCCC3)n2)cc2c1B(O)OC2]

This substance was prepared by following General Synthetic Scheme A. ¹H NMR (DMSO-d6, 400 MHz) δ (ppm) 9.77 (s, 1H), 8.77 (br, 1H), 8.05 (s, 1H), 7.53-7.50 (m, 3H), 4.91 (s, 2H), 4.46-4.37 (m, 1H), 2.73 (q, J=7.4 Hz, 2H), 1.98-1.96 (m, 2H), 1.74-1.72 (m, 2H), 1.64-1.54 (m, 4H), 1.17 (t, J=7.8 Hz, 3H). MS (ESI): m/z found 373.1 [M+H]⁺. Purity by HPLC: 98.74% (220 nm), 98.68% (254 nm).

Example 28: 7-chloro-5-((5-chloro-4-(cyclopentylamino)pyrimidin-2-yl)amino)benzo[c][1,2]oxaborol-1(3H)-ol

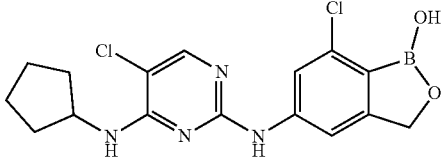 [SMILES: OB1OCc2cc(Nc3ncc(Cl)c(NC4CCCC4)n3)cc(Cl)c21]

This substance was prepared by following General Synthetic Scheme A. ¹H NMR (DMSO-d6, 400 MHz) δ (ppm) 9.65 (s, 1H), 8.90 (br, 1H), 7.99 (s, 1H), 7.92 (s, 1H), 7.66 (s, 1H), 7.01 (d, J=7.2 Hz, 1H), 4.93 (s, 2H), 4.41-4.35 (m, 1H), 2.01-1.99 (m, 2H), 1.74-1.73 (m, 2H), 1.62-1.57 (m, 4H). MS (ESI): m/z found 379.1 [M+H]⁺. Purity by HPLC: 94.64% (220 nm), 97.36% (254 nm).

Example 29: 3,7-dimethyl-5-((5-methyl-4-(pentan-3-ylamino)pyrimidin-2-yl)amino)benzo[c][1,2]oxaborol-1(3H)-ol

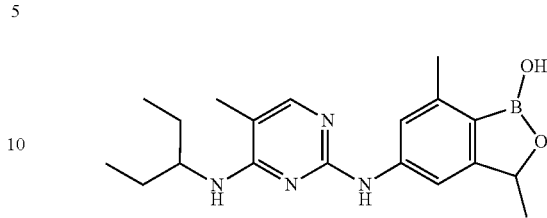

This substance was prepared by following General Synthetic Scheme D. ¹H NMR (DMSO-d6, 400 MHz) δ (ppm) 8.92 (s, 1H), 8.54 (s, 1H), 7.50 (s, 1H), 7.67 (s, 1H), 7.37 (s, 1H), 6.16 (d, J=8.4 Hz, 1H), 5.09 (q, J=6.4 Hz, 2H), 4.17-4.14 (m, 1H), 2.36 (s, 3H), 1.95 (s, 3H), 1.64-1.54 (m, 4H), 1.37 (d, J=6.4 Hz, 3H), 0.91-0.86 (m, 6H). MS (ESI): m/z found 355.2 [M+H]⁺. Purity by HPLC: 97.41% (220 nm), 96.99% (254 nm).

Example 30: 3,3,7-trimethyl-5-((5-methyl-4-(phenylamino)pyrimidin-2-yl)amino)benzo[c][1,2]oxaborol-1(3H)-ol

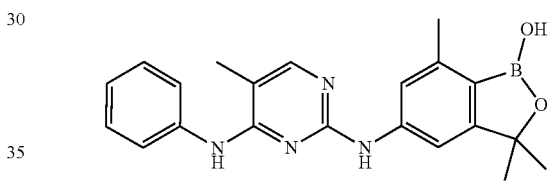

This substance was prepared by following General Synthetic Scheme C. ¹H NMR (DMSO-d6, 400 MHz) δ (ppm) 9.99 (br, 1H), 9.5 (br, 1H), 8.67 (s, 1H), 7.91 (s, 1H), 7.57 (d, J=7.2 Hz, 2H), 7.42-7.38 (m, 2H), 7.27-7.23 (m, 2H), 7.15 (s, 1H), 2.29 (s, 3H), 2.17 (s, 3H), 1.30 (s, 6H). MS (ESI): m/z found 375.1 [M+H]⁺. Purity by HPLC: 99.84% (220 nm), 99.82% (254 nm).

Example 31: 5-((4-(cyclopentylamino)pyrimidin-2-yl)amino)-7-ethylbenzo[c][1,2]oxaborol-1(3H)-ol

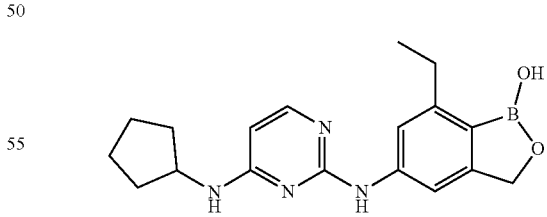

This substance was prepared by following General Synthetic Scheme A. ¹H NMR (DMSO-d6, 400 MHz) δ (ppm) 10.43 (br, 1H), 8.98 (br, 1H), 8.90 (s, 1H), 7.78 (d, J=7.2 Hz, 1H), 7.44-7.42 (m, 2H), 6.19 (d, J=7.2 Hz, 2H), 4.98 (s, 2H), 4.30-4.25 (m, 1H), 2.77 (q, J=7.2 Hz, 2H), 1.99-1.97 (m, 2H), 1.72-1.71 (m, 2H), 1.59-1.55 (m, 4H), 1.19 (t, J=7.6 Hz, 3H). MS (ESI): m/z found 339.2 [M+H]⁺. Purity by HPLC: 98.52% (220 nm), 98.84% (254 nm).

Example 32: 7-ethyl-5-((5-methyl-4-(phenylamino) pyrimidin-2-yl)amino)benzo[c][1,2]oxaborol-1(3H)-ol

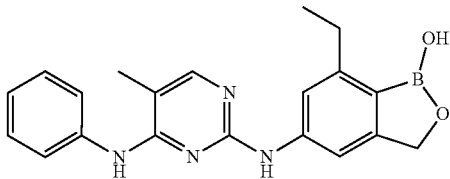 [SMILES: CCc1cc(Nc2ncc(C)c(Nc3ccccc3)n2)cc2c1B(O)OC2]

This substance was prepared by following General Synthetic Scheme A. $^1$H NMR (DMSO-d6, 400 MHz) δ (ppm) 9.13 (s, 1H), 8.61 (s, 1H), 8.33 (s, 1H), 7.91 (s, 1H), 7.73 (s, 1H), 7.66 (d, J=8.0 Hz, 2H), 7.35 (t, J=8.0 Hz, 2H), 7.24 (s, 1H), 7.13-7.11 (m, 1H), 4.78 (s, 2H), 2.64 (q, J=7.4 Hz, 2H), 2.12 (s, 3H), 1.10 (t, J=7.4 Hz, 3H). MS (ESI): m/z found 361.1 [M+H]$^+$. Purity by HPLC: 92.87% (220 nm), 94.53% (254 nm).

Example 34: 6-((5-methyl-4-((4-methylcyclohexyl)amino)pyrimidin-2-yl)amino)benzo[c][1,2]oxaborol-1(3H)-ol

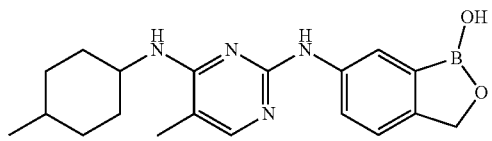 [SMILES: Cc1cnc(Nc2ccc3c(c2)B(O)OC3)nc1NC1CCC(C)CC1]

This substance was prepared by following General Synthetic Scheme B. The analytical data of this compound are shown as following. $^1$H NMR (400 MHz, DMSO-d$_6$): δ 9.01 (s, 1H), 8.83 (s, 1H), 8.03 & 8.00 (two s, 1H), 7.86 (s, 1H), 7.64 (s, 1H), 7.23 (d, J=7.6 Hz, 1H), 6.20 (d, J=4.8 Hz, partial 1H), 6.01 (s, partial 1H), 4.91 (s, 2H), 4.08 (s, partial 1H), 3.97 (d, J=4.0 Hz, partial 1H), 1.98-1.90 (m, 4H), 1.80-1.50 (m, 4H), 1.50-1.30 (m, 3H), 1.20-1.05 (m, 1H), 0.97 & 0.91 (two s, 3H) ppm. HPLC purity: 97.30% at 210 nm and 98.22% at 254 nm. MS: m/z=353.2 (M+H)$^+$.

Example 51: 6-((5-methyl-4-((3-(methylsulfonyl)phenyl)amino)pyrimidin-2-yl)amino)benzo[c][1,2]oxaborol-1(3H)-ol

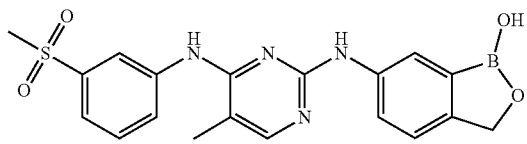 [SMILES: Cc1cnc(Nc2ccc3c(c2)B(O)OC3)nc1Nc1cccc(S(C)(=O)=O)c1]

This substance was prepared by following General Synthetic Scheme B. The analytical data of this compound are shown as following. $^1$H NMR (400 MHz, DMSO-d$_6$): δ 10.18 (br s, 1H), 9.67 (br s, 1H), 9.24 (s, 1H), 8.15 (d, J=8.4 Hz, 1H), 8.03-8.02 (m, 1H), 7.95 (s, 1H), 7.71-7.67 (m, 2H), 7.64-7.56 (m, 1H), 7.35 (d, J=8.4 Hz, 1H), 4.98 (s, 2H), 3.18 (s, 3H), 2.19 (s, 3H) ppm. HPLC purity: 98.73% at 210 nm and 99.38% at 254 nm. MS: (M+H)$^+$: m/z=411.1.

Example 52: 3,3-dimethyl-6-((5-methyl-4-((3-(methylsulfonyl)phenyl)amino)pyrimidin-2-yl)amino)benzo[c][1,2]oxaborol-1(3H)-ol

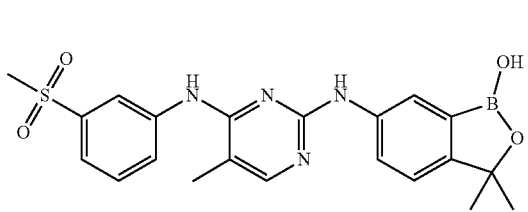 [SMILES: Cc1cnc(Nc2ccc3c(c2)B(O)OC3(C)C)nc1Nc1cccc(S(C)(=O)=O)c1]

This substance was prepared by following General Synthetic Scheme B. The analytical data of this compound are shown as following. $^1$H NMR (400 MHz, DMSO-d$_6$): δ 10.38 (s, 1H), 9.84 (s, 1H), 9.11 (br s, 1H), 8.11 (d, J=8.4 Hz, 1H), 8.02 (d, J=1.6 Hz, 1H), 7.95 (s, 1H), 7.73 (d, J=8.4 Hz, 1H), 7.62-7.46 (m, 3H), 7.40 (d, J=8.4 Hz, 1H), 3.19 (s, 3H), 2.19 (s, 3H), 1.45 (s, 6H) ppm. HPLC purity: 98.30% at 210 nm and 99.14% at 254 nm. MS: m/z=438.9 (M+H)$^+$.

Example 55: 7-methyl-6-((5-methyl-4-((3-(methylsulfonyl)phenyl)amino)pyrimidin-2-yl)amino)benzo[c][1,2]oxaborol-1(3H)-ol

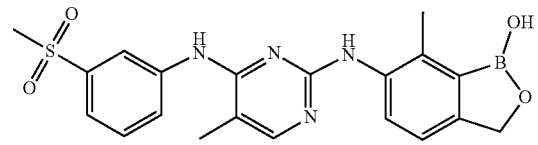 [SMILES: Cc1cnc(Nc2ccc3c(c2C)B(O)OC3)nc1Nc1cccc(S(C)(=O)=O)c1]

This substance was prepared by following General Synthetic Scheme B. The analytical data of this compound are shown as following. $^1$H NMR (400 MHz, DMSO-d$_6$): δ 9.74 (br s, 1H), 9.66 (br s, 1H), 9.07 (s, 1H), 8.05 (s, 2H), 7.84 (s, 1H), 7.66 (d, J=7.7 Hz, 1H), 7.44 (d, J=8.0 Hz, 2H), 7.29 (d, J=8.0 Hz, 1H), 5.00 (s, 2H), 3.18 (s, 3H), 2.33 (s, 3H), 2.17 (s, 3H) ppm. HPLC purity: 99.60% at 210 nm and 99.63% at 254 nm. MS: m/z=425.1 (M+H)$^+$.

Example 59: 6-((4-(((1r,4r)-4-(hydroxymethyl)cyclohexyl)amino)-5-methylpyrimidin-2-yl)amino)benzo[c][1,2]oxaborol-1(3H)-ol

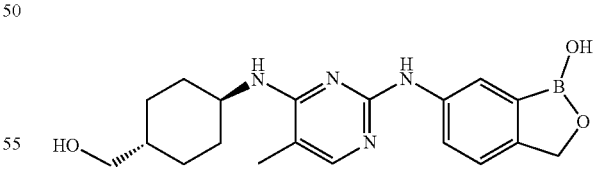

This substance was prepared by following General Synthetic Scheme B. The analytical data of this compound are shown as following. $^1$H NMR (400 MHz, DMSO-d$_6$): δ 12.11 (br s, 1H), 10.20 (s, 1H), 9.20 (s, 1H), 7.96 (d, J=7.2 Hz, 1H), 7.84 (d, J=1.5 Hz, 1H), 7.72-7.61 (m, 2H), 7.42 (d, J=8.2 Hz, 1H), 5.00 (s, 2H), 4.40 (br s, 1H), 4.02-3.90 (m, 1H), 3.22 (d, J=6.3 Hz, 2H), 1.99 (s, 3H), 1.88 (d, J=11.4 Hz, 2H), 1.79 (d, J=11.1 Hz, 1H), 1.54-1.25 (m, 4H), 1.04-0.88 (m, 2H) ppm. HPLC purity: 94.70% at 210 nm and 94.29% at 254 nm. MS: m/z=369.2 (M+H)$^+$.

Example 62: 7-fluoro-6-((5-methyl-4-((3-(methyl-sulfonyl)phenyl)amino)pyrimidin-2-yl)amino)benzo[c][1,2]oxaborol-1(3H)-ol

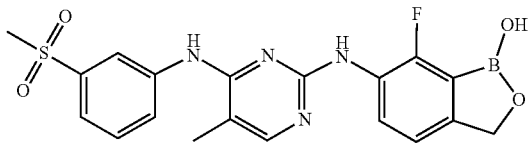 [SMILES: Cc1cnc(Nc2ccc3c(c2F)B(O)OC3)nc1Nc1cccc(S(C)(=O)=O)c1]

This substance was prepared by following General Synthetic Scheme B. The analytical data of this compound are shown as following. $^1$H NMR (300 MHz, DMSO-$d_6$): δ 9.64 (br s, 1H), 9.58 (brs, 1H), 9.36 (s, 1H), 8.07 (d, J=8.0 Hz, 1H), 8.02 (s, 1H), 7.93 (s, 1H), 7.67-7.64 (m, 2H), 7.47-7.43 (m, 1H), 7.22 (d, J=7.6 Hz, 1H), 5.02 (s, 2H), 3.18 (s, 3H), 2.18 (s, 3H) ppm; HPLC purity: 98.33% at 210 nm and 98.04% at 254 nm; MS: m/z=429.1 [M+H]$^+$.

Example 63: 6-((5-methyl-4-((1-methylpiperidin-4-yl)amino)pyrimidin-2-yl)amino)benzo[c][1,2]oxaborol-1(3H)-ol

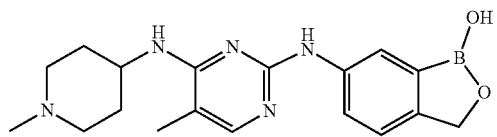 [SMILES: Cc1cnc(Nc2ccc3c(c2)B(O)OC3)nc1NC1CCN(C)CC1]

This substance was prepared by following General Synthetic Scheme B. The analytical data of this compound are shown as following. $^1$H NMR (400 MHz, DMSO-$d_6$): δ 9.01 (br s, 1H), 8.81 (s, 1H), 8.00 (d, J=1.6 Hz, 1H), 7.86 (dd, J=8.0 & 2.0 Hz, 1H), 7.64 (s, 1H), 7.22 (d, J=8.4 Hz, 1H), 6.22 (d, J=7.6 Hz, 1H), 4.92 (s, 2H), 4.05-3.90 (m, 1H), 2.78 (d, J=11.2 Hz, 2H), 2.18 (s, 3H), 2.01 (t, J=7.8 Hz, 2H), 1.91 (s, 3H), 1.84 (d, J=7.8 Hz, 2H), 1.70-1.50 (m, 2H) ppm. HPLC purity: 94.22% at 210 nm and 97.13% at 254 nm. MS: m/z=354.2 (M+H)$^+$.

Example 64: 6-((5-methyl-4-(piperidin-4-ylamino)pyrimidin-2-yl)amino)benzo[c][1,2]oxaborol-1(3H)-ol

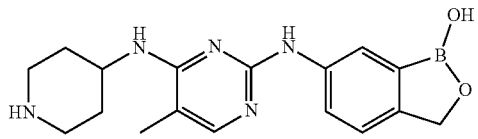 [SMILES: Cc1cnc(Nc2ccc3c(c2)B(O)OC3)nc1NC1CCNCC1]

This substance was prepared by following General Synthetic Scheme B. It was obtained as 2·HCl salt. The analytical data of this compound are shown as following. $^1$H NMR (400 MHz, DMSO-$d_6$): δ 12.61 (br s, 1H), 10.85 (br s, 1H), 9.60 (br s, 1H), 9.41 (s, 1H), 9.34 (br s, 1H), 8.34 (br s, 1H), 7.95 (d, J=1.6 Hz, 1H), 7.84 (s, 1H), 7.67 (dd, J=8.4 & 2.0 Hz, 1H), 7.43 (d, J=8.4 Hz, 1H), 4.98 (s, 2H), 4.30-4.20 (m, 1H), 3.31-3.28 (m, 2H), 2.95-2.80 (m, 2H), 2.03 (s, 3H), 2.01-1.98 (m, 4H) ppm. HPLC purity: 99.46% at 210 nm and 99.18% at 254 nm. MS: m/z=340.2 (M+H)$^+$.

Example 65: 6-((4-(cyclohexylamino)-5-methylpyrimidin-2-yl)amino)benzo[c][1,2]oxaborol-1(3H)-ol

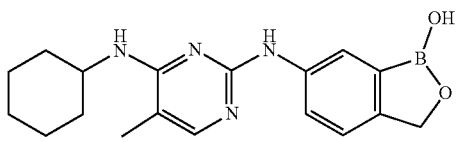 [SMILES: Cc1cnc(Nc2ccc3c(c2)B(O)OC3)nc1NC1CCCCC1]

The title compound was prepared by using the scheme and procedures shown below:

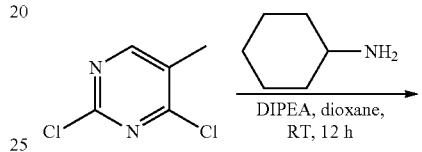

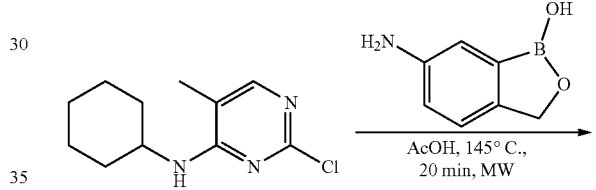

A mixture of cyclohexanamine (1.5 g, 15 mmol), 2,4-dichloro-5-methylpyrimidine (3.67 g, 22.5 mmol) and DIPEA (3.87 g, 30 mmol) in 1,4-dioxane (30 mL) was stirred at room temperature overnight. The reaction mixture was concentrated and purified by column chromatography eluted with PE/EA: 8/1 to give 2-chloro-N-cyclohexyl-5-methylpyrimidin-4-amine (1.4 g, 41% yield) as a white powder. MS: m/z=225.9 (M+H)$^+$. A mixture of 2-chloro-N-cyclohexyl-5-methylpyrimidin-4-amine (562.5 mg, 2.5 mmol) and 6-aminobenzo[c][1,2]oxaborol-1(3H)-ol (372.5 mg, 2.5 mmol) in AcOH (10 mL) was stirred at 145° C. under microwave for 20 min. The reaction mixture was concentrated and purified by prep-HPLC to obtain 6-((4-(cyclohexylamino)-5-methylpyrimidin-2-yl)amino)benzo[c][1,2]oxaborol-1(3H)-ol (40 mg) as a white powder. $^1$H NMR (400 MHz, DMSO-$d_6$): δ 8.86 (s, 1H), 8.15 (s, 1H), 8.00-7.99 (d, 1H), 7.90 (dd, J=8 & 4 Hz, 1H), 7.64 (d, 1H), 7.24 (d, J=12.0 Hz, 1H), 6.19 (d, J=8.0 Hz, 1H). 4.92 (s, 2H), 4.02-4.00 (m, 1H), 1.93-1.91 (m, 2H), 1.91 (s, 3H), 1.76-1.73 (m, 2H), 1.66-1.62 (m, 1H), 1.37-1.27 (m, 4H), 1.18-1.12 (m, 1H) ppm. HPLC purity: 96.2% at 214 nm and 95.4% at 254 nm. MS: m/z=339.1 [M+H]$^+$.

Example 66: 6-((5-methyl-4-(pentan-3-ylamino)pyrimidin-2-yl)amino)benzo[c][1,2]oxaborol-1(3H)-ol

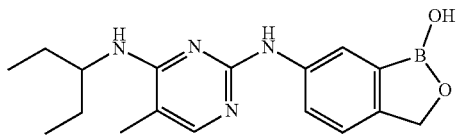 [SMILES: CCC(CC)Nc1nc(Nc2ccc3c(c2)B(O)OC3)ncc1C]

The title compound was prepared by using the scheme and procedures shown below:

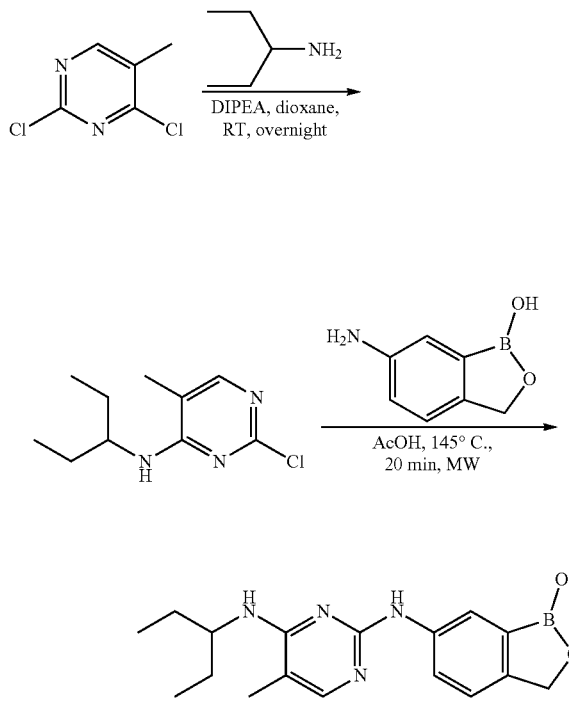

A mixture of pentan-3-amine (1.3 g, 15 mmol), 2,4-dichloro-5-methylpyrimidine (3.67 g, 22.5 mmol) and DIPEA (3.87 g, 30 mmol) in 1,4-dioxane (30 mL) was stirred at room temperature overnight. The reaction mixture was concentrated and purified by column chromatography eluted with PE/EA: 8/1 to give 2-chloro-5-methyl-N-(pentan-3-yl)pyrimidin-4-amine (1.45 g, 45% yield) as a white powder. MS: m/z=214.0 (M+H)$^+$. A mixture of 2-chloro-5-methyl-N-(pentan-3-yl)pyrimidin-4-amine (213 mg, 1.0 mmol) and 6-aminobenzo[c][1,2]oxaborol-1(3H)-ol (150 mg, 1.0 mmol) in AcOH (5 mL) was stirred at 145° C. under microwave for 20 min. The reaction mixture was concentrated and purified by prep-TLC and prep-HPLC to provide 6-((5-methyl-4-(pentan-3-ylamino)pyrimidin-2-yl)amino)benzo[c][1,2]oxaborol-1(3H)-ol (8 mg) as a white powder. $^1$H NMR (300 MHz, DMSO-d$_6$): δ 8.77 (s, 1H), 8.13 (s, 1H), 7.95 (s, 1H), 7.87 (d, J=9.0 Hz, 1H), 7.61 (s, 1H), 7.22 (d, J=9.0 Hz, 1H), 6.05 (d, J=9.0 Hz, 1H), 4.90 (s, 2H), 4.10-4.04 (m, 1H), 1.93 (s, 3H), 1.61-1.54 (m, 4H), 0.88 (t, J=7.5 Hz, 6H) ppm. HPLC purity: 96.1% at 214 nm and 95.3% at 254 nm. MS: m/z=327.1 [M+H]$^+$.

Part 1-3: Synthetic Examples for Compounds of Formula (IB)

3. 5-amino-3-methylbenzo[c][1,2]oxaborol-1(3H)-ol

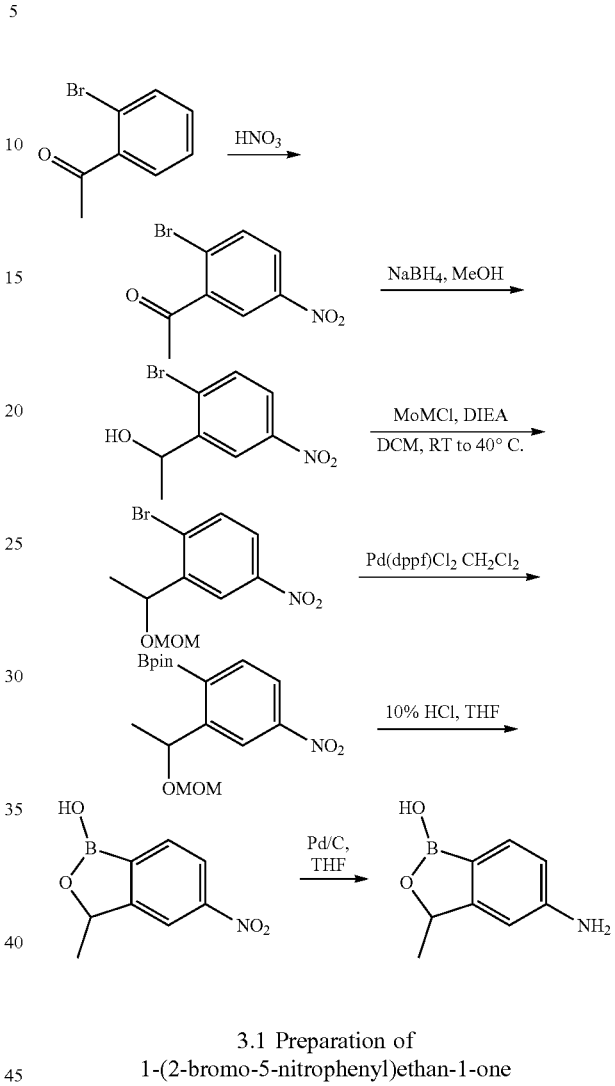

3.1 Preparation of 1-(2-bromo-5-nitrophenyl)ethan-1-one

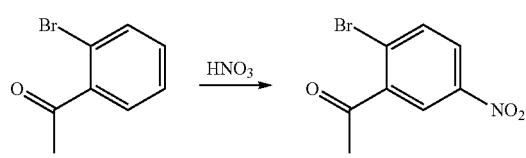

To a solution of potassium nitrate (12.5 g, 125 mmol) in concentrated sulfuric acid (100 mL) was added 1-(2-bromophenyl)ethan-1-one (20.0 g, 100 mmol) at 0° C., the resulting mixture was then allowed to warm to room temperature, and stirred for 1.5 h. The reaction was quenched by pouring into ice-water (500 mL), the aqueous phase was extracted with dichloromethane (2×150 mL). The combined organic phase was dried over anhydrous MgSO$_4$, filtered and concentrated in vacuo to give a residue, which was purified by silica gel flash chromatography (eluting with 10% EA in PE) to give 1-(2-bromo-5-nitrophenyl)ethan-1-one (13.9 g, 54%) as a white powder. $^1$H NMR (400 MHz, DMSO-d$_6$):

δ 8.49 (d, J=2.7 Hz, 1H), 8.22 (dd, J=8.7, 2.7 Hz, 1H), 8.02 (d, J=8.8 Hz, 1H), 2.65 (s, 3H) ppm.

3.2 Preparation of 1-(2-bromo-5-nitrophenyl)ethan-1-ol

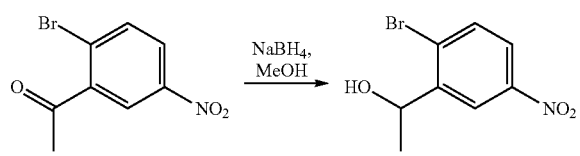

To a solution of 1-(2-bromo-5-nitrophenyl)ethan-1-one (4.8 g, 20 mmol) in MeOH (30 mL) was added NaBH$_4$ (1.15 g, 30 mmol) in portions at 0° C. The resulting mixture was stirred at room temperature for 2 h. Then the reaction was quenched by water, extracted with EA, and the combined organic phase was washed with water, brine, concentrated in vacuo to give a residue, which was purified by silica gel chromatography (PE/EA (100/1 to 10/1)) to give 1-(2-bromo-5-nitrophenyl)ethan-1-ol (3.7 g, yield 77%) as a white solid. $^1$H NMR (300 MHz, DMSO-d$_6$): δ 8.37 (d, J=2.9 Hz, 1H), 8.02 (dd, J=8.7, 2.9 Hz, 1H), 7.87 (d, J=8.7 Hz, 1H), 5.80 (d, J=4.4 Hz, 1H), 5.09-4.84 (m, 1H), 1.35 (d, J=6.4 Hz, 3H) ppm.

3.3 Preparation of 1-bromo-2-(1-(methoxymethoxy)ethyl)-4-nitrobenzene

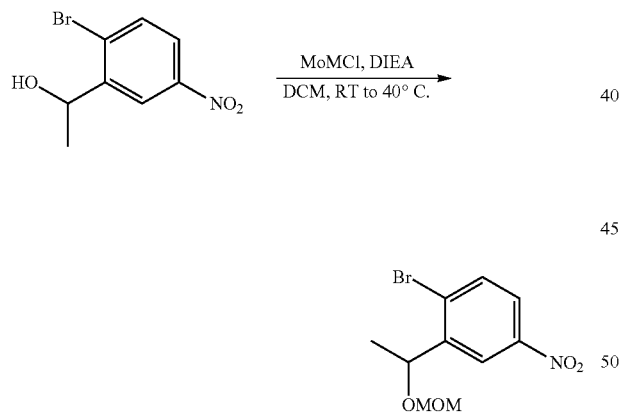

To a solution of 1-(2-bromo-5-nitrophenyl)ethan-1-ol (3.7 g, 15 mmol) in DMC (30 mL) was added DIEA (5.2 mL, 30 mmol). Then MOMCl (2.4 g, 30 mmol) was added dropwise to the mixture. The resulting mixture was heated to 40° C. for 2 h, then cooled to room temperature, washed with sat. NaHCO$_3$, brine, concentrated in vacuo to give a residue, which was purified by silica gel chromatography (PE/EA (30/1 to 10/1)) to give 1-bromo-2-(1-(methoxymethoxy)ethyl)-4-nitrobenzene (4.1 g, yield 90%) as a colorless oil. $^1$H NMR (400 MHz, CDCl$_3$): δ 8.34 (d, J=2.6 Hz, 1H), 7.91 (dd, J=8.7, 2.1 Hz, 1H), 7.63 (d, J=8.7 Hz, 1H), 5.2-5.0 (m, 1H), 4.62 (d, J=6.4 Hz, 1H), 4.50 (dd, J=6.8, 0.6 Hz, 1H), 3.31 (s, 3H), 1.40 (d, J=6.4 Hz, 3H) ppm.

3.4. Preparation of 2-(2-(1-(methoxymethoxy)ethyl)-4-nitrophenyl)-4,4,5,5-tetramethyl-1,3,2-dioxaborolane

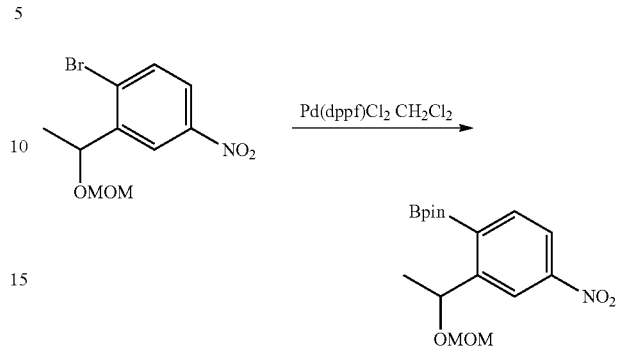

To a solution of compound 1-bromo-2-(1-(methoxymethoxy)ethyl)-4-nitrobenzene (3.1 g, 10 mmol) in dioxane (30 mL) was added KOAc (1.96 g, 20 mol), B$_2$Pin$_2$ (3.0 g, 12 mmol) and (dpp)PdCl$_2$-DCM (816 mg, 1 mmol) at room temperature under nitrogen atmosphere. The mixture was heated to 100° C. overnight. Then the precipitate from the reaction mixture was removed by filtration, the filtrate was concentrated in vacuo to give a residue, which was purified by silica chromatography (PE/EA (20/1 to 5/1)) to give 2-(2-(1-(methoxymethoxy)ethyl)-4-nitrophenyl)-4,4,5,5-tetramethyl-1,3,2-dioxaborolane (2.4 g, crude) as a white solid. $^1$H NMR (400 MHz, CDCl$_3$): δ 8.29 (d, J=2.2 Hz, 1H), 7.97 (dd, J=8.2, 2.3 Hz, 1H), 7.79 (d, J=8.2 Hz, 1H), 5.35 (q, J=6.4 Hz, 1H), 4.59 (d, J=6.8, 1.0 Hz, 1H), 4.48 (d, J=6.8, 3.2 Hz, 1H), 3.28 (s, 3H), 1.40 (d, J=6.5 Hz, 3H), 1.30 (s, 12H) ppm.

3.5 Preparation of 3-methyl-5-nitrobenzo[c][1,2]oxaborol-1(3H)-ol

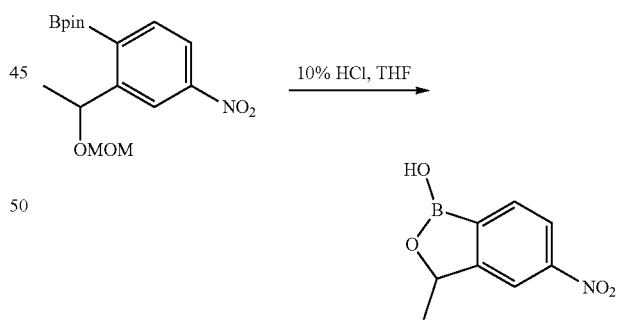

To a solution of 2-(2-(1-(methoxymethoxy)ethyl)-4-nitrophenyl)-4,4,5,5-tetramethyl-1,3,2-dioxaborolane (2.4 g, 6.4 mmol) in THF (6 mL) was added 6N HCl (3 mL). The reaction was stirred at room temperature overnight. Then the reaction mixture was diluted with water, and the aqueous phase was extracted with EtOAc. The combined organic layer was washed with water, brine, concentrated in vacuo to give a residue, which was purified by prep-HPLC (eluting with 0.1% TFA in water and ACN) to give 3-methyl-5-nitrobenzo[c][1,2]oxaborol-1(3H)-ol (1.0 g, yield 81%) as a white solid. $^1$H NMR (400 MHz, DMSO-d$_6$): δ 9.56 (s, 1H), 8.30 (d, J=1.8 Hz, 1H), 8.20 (dd, J=8.0, 1.7 Hz, 1H), 7.95 (d, J=8.0 Hz, 1H), 5.35 (q, J=6.6 Hz, 1H), 1.48 (d, J=6.6 Hz, 3H) ppm.

3.6 Preparation of 5-amino-3-methylbenzo[c][1,2]oxaborol-1(3H)-ol

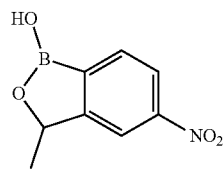

To a solution of 3-methyl-5-nitrobenzo[c][1,2]oxaborol-1(3H)-ol (1.0 g, 5.1 mmol) in THF (6 mL) was added Pd/C (100 mg, 10% mmol). The reaction was degassed and flushed with H₂ three times, then stirred at room temperature overnight. The reaction mixture was passed through a pad of Celite, the filtrate was concentrated in vacuo to give a residue, which was purified by prep-HPLC (eluting with ACN and water) to give 5-amino-3-methylbenzo[c][1,2]oxaborol-1(3H)-ol (400 mg, yield 54%) as a yellow solid. $^1$H NMR (400 MHz, DMSO-d$_6$): δ 8.53 (s, 1H), 7.31 (d, J=7.9 Hz, 1H), 6.50 (dd, J=7.9, 1.8 Hz, 1H), 6.44 (s, 1H), 5.43 (s, 2H), 4.99 (q, J=6.5 Hz, 1H), 1.31 (d, J=6.6 Hz, 3H) ppm.

4. 5-((4-(cyclopentylamino)-5-methylpyrimidin-2-yl)amino)-3-methylbenzo[c][1,2]oxaborol-1(3H)-ol

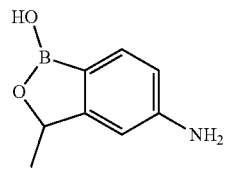

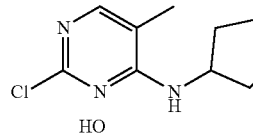

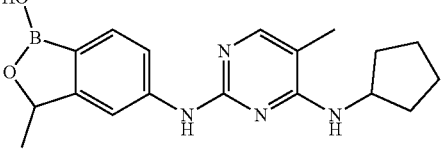

This substance was prepared by using General Synthetic Scheme B and following the procedure employed for the synthesis of 5-((4-(cyclopentylamino)-5-methylpyrimidin-2-yl)amino)-7-methylbenzo[c][1,2]oxaborol-1(3H)-ol as a white solid. Yield: 8%. $^1$H NMR (DMSO-d6, 400 MHz) δ (ppm) 9.05 (s, 1H), 8.77 (s, 1H), 8.07 (s, 1H), 7.67 (s, 1H), 7.50-7.48 (m, 2H), 6.36 (d, J=7.2 Hz, 1H), 5.11 (q, J=6.4 Hz, 1H), 4.45-4.43 (m, 1H), 2.01-1.99 (m, 2H), 1.93 (s, 3H), 1.74-1.73 (m, 2H), 1.60-1.57 (m, 4H), 1.37 (d, J=6.4 Hz, 1H). MS (ESI): m/z found 339.2 [M+H]⁺. Purity by HPLC: 97.16% (220 nm), 97.78% (254 nm).

5. 5-amino-3,3-dimethylbenzo[c][1,2]oxaborol-1(3H)-ol

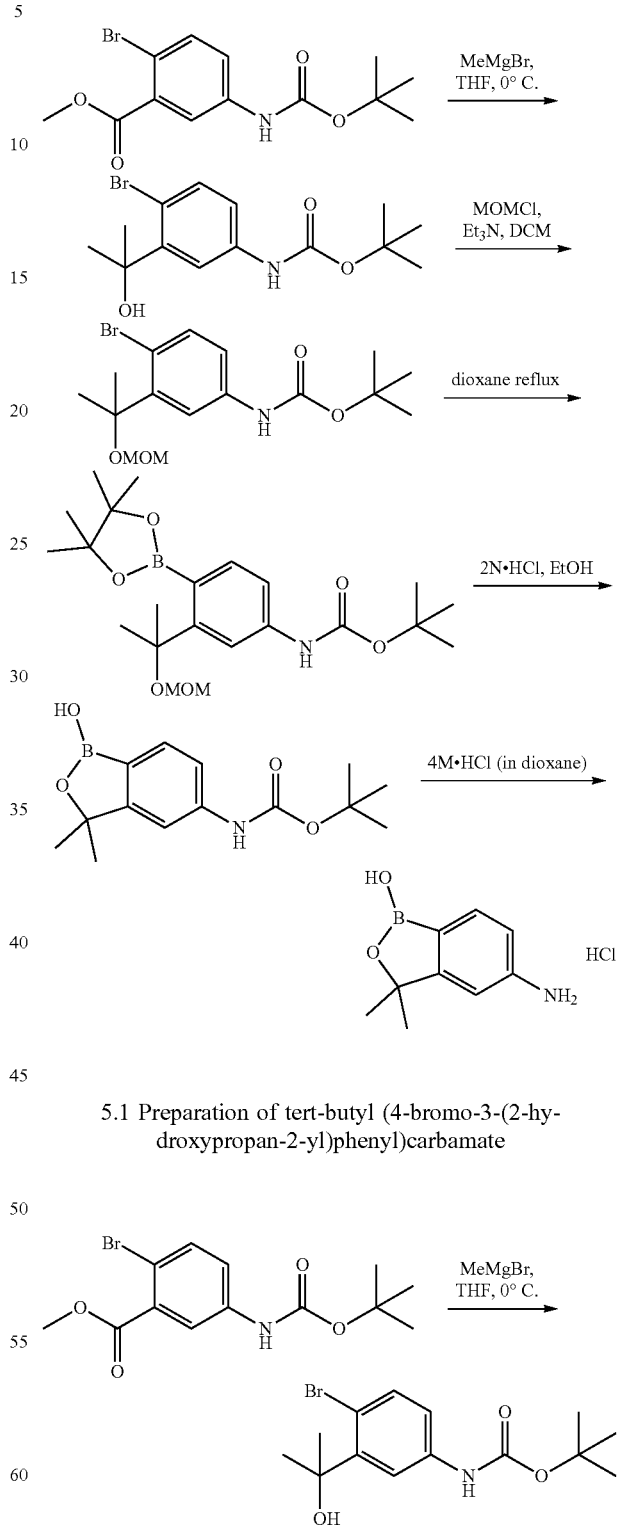

5.1 Preparation of tert-butyl (4-bromo-3-(2-hydroxypropan-2-yl)phenyl)carbamate

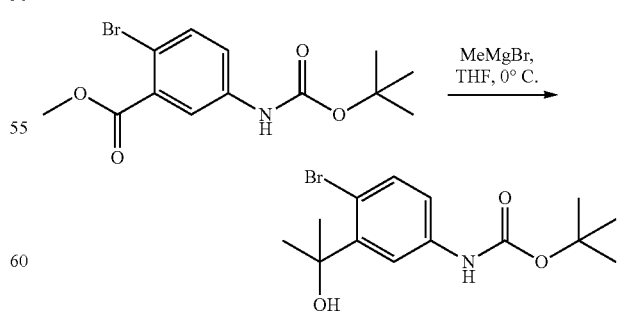

To a solution of methyl 2-bromo-5-((tert-butoxycarbonyl)amino)benzoate (10.0 g, 30.4 mmol) in dry THF (50 mL) was added MeMgBr (50 mL, 150 mmol) dropwise at 0° C. The resulting reaction mixture was stirred at room temperature overnight. The reaction was then quenched by water, extracted with EtOAc. The combined organic phase was washed with water, brine, dried over anhydrous Na$_2$SO$_4$, concentrated in vacuo to give a residue, which was purified by silica chromatography eluting with PE/EA (100/1 to 10/1) to give tert-butyl (4-bromo-3-(2-hydroxypropan-2-yl)phenyl)carbamate (7.5 g, yield 75%) as a yellow oil. $^1$H NMR (300 MHz, DMSO-d$_6$): δ 9.42 (s, 1H), 8.02 (d, J=2.6 Hz, 1H), 7.41 (d, J=8.6 Hz, 1H), 7.23 (dd, J=8.6, 2.6 Hz, 1H), 5.18 (s, 1H), 1.59 (s, 6H), 1.47 (s, 9H) ppm.

5.2 Preparation of tert-butyl (4-bromo-3-(2-(methoxymethoxy)propan-2-yl)phenyl)carbamate

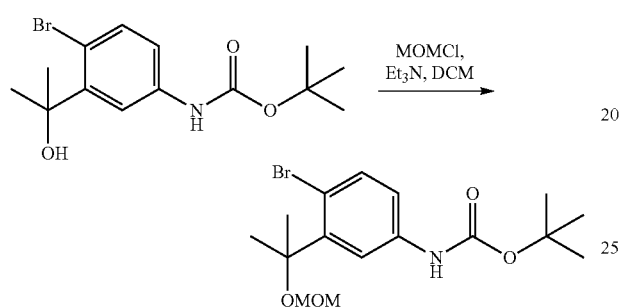

To a solution of tert-butyl (4-bromo-3-(2-hydroxypropan-2-yl)phenyl)carbamate (7.5 g, 22.8 mmol) in DCM (80 mL) was added DIPEA (5.2 mL, 30 mmol). Then MOMCI (2.4 g, 30 mmol) was added dropwise to the mixture. The resulting mixture was heated up to 40° C. for 2 h. Then the reaction mixture was cooled to room temperature, washed with sat.NaHCO$_3$, brine, concentrated in vacuo to give a residue, which was purified by silica chromatography (PE/EA (30/1 to 10/1)) to give tert-butyl (4-bromo-3-(2-(methoxymethoxy)propan-2-yl)phenyl)carbamate (6.5 g, crude) as a yellow oil, which was used directly in the next step without further purification.

5.3 Preparation of tert-butyl (3-(2-(methoxymethoxy)propan-2-yl)-4-(4,4,5,5-tetramethyl-1,3,2-dioxaborolan-2-yl)phenyl) carbamate

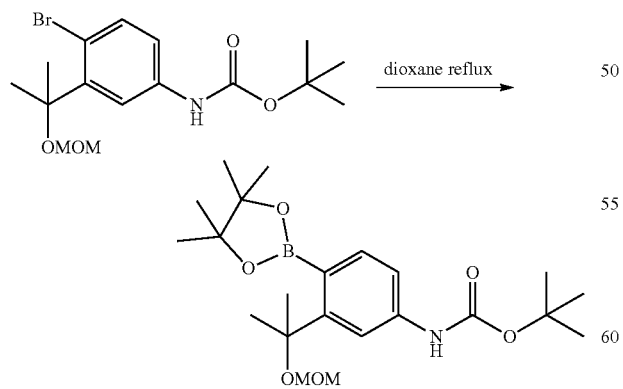

To a solution of tert-butyl (4-bromo-3-(2-(methoxymethoxy)propan-2-yl)phenyl)carbamate (6.5 g, 17 mmol) in dioxane (50 mL) was added KOAc (5.1 g, 52 mol), B$_2$Pin$_2$ (5.1 g, 20.4 mmol) and (dpp)PdCl$_2$-DCM (1.4 g, 1.7 mmol) at room temperature under nitrogen atmosphere. The resulting mixture was heated up to 100° C. for 4 h, then cooled to room temperature. The solid from the mixture was removed by filtration, and the filtrate was concentrated in vacuo to give a residue, which was purified by silica chromatography (PE/EA (20/1 to 5/1)) to give tert-butyl (3-(2-(methoxymethoxy)propan-2-yl)-4-(4,4,5,5-tetramethyl-1,3,2-dioxaborolan-2-yl)phenyl) carbamate (2.4 g, crude) as a yellow oil, which was used directly in the next step without further purification.

5.4 Preparation of tert-butyl (1-hydroxy-3,3-dimethyl-1,3-dihydrobenzo[c][1,2]oxaborol-5-yl)carbamate

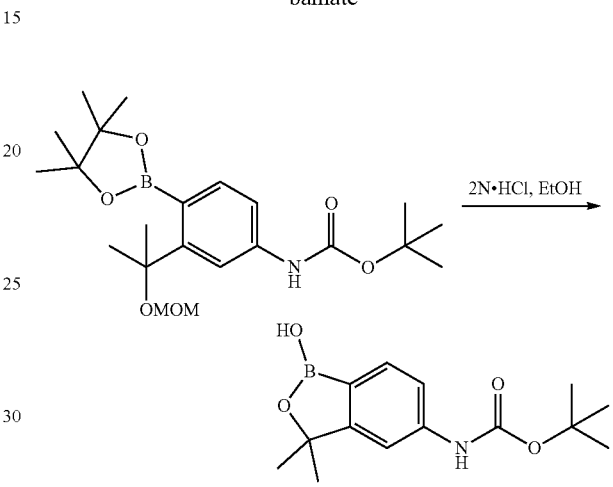

To a solution of tert-butyl (3-(2-(methoxymethoxy)propan-2-yl)-4-(4,4,5,5-tetramethyl-1,3,2-dioxaborolan-2-yl) phenyl) carbamate (2.4 g, 5.7 mmol) in EtOH (15 mL) was added 2N. HCl (5 mL, 10 mol), the resulting reaction mixture was stirred at room temperature for 30 min, then the mixture was diluted by EtOAc, and the organic phase was washed with brine, dried over anhydrous Na$_2$SO$_4$, filtered and concentrated in vacuo to give a residue, which was purified by column chromatography (PE/EtOAc=10:1) afforded tert-butyl (1-hydroxy-3,3-dimethyl-1,3-dihydrobenzo[c][1,2]oxaborol-5-yl)carbamate (1.0 g, crude) as a yellow oil, which is used directly in the next step without further purification. MS: (M−H)$^-$: m/z=276.0.

5.5 Preparation of 5-amino-3,3-dimethylbenzo[c][1,2]oxaborol-1(3H)-ol HCl salt

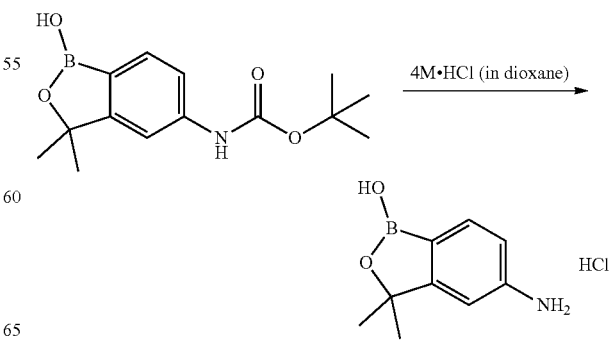

To a solution of tert-butyl (1-hydroxy-3,3-dimethyl-1,3-dihydrobenzo[c][1,2]oxaborol-5-yl)carbamate (1.0 g, 3.6 mmol) in dioxane (4M HCl in dioxane, 6 mL) was stirred at room temperature for 3 h, the precipitate was collected by filtration, dried in vacuo to give (280 mg, 37%) 5-amino-3,3-dimethylbenzo[c][1,2]oxaborol-1(3H)-ol HCl salt as a white solid. ¹H NMR (400 MHz, DMSO-d₆): δ 7.43 (d, J=7.8 Hz, 1H), 6.77-6.67 (m, 2H), 1.39 (s, 6H) ppm.

6. 5-((4-(cyclopentylamino)-5-methylpyrimidin-2-yl)amino)-3,3-dimethylbenzo[c][1,2] oxaborol-1(3H)-ol

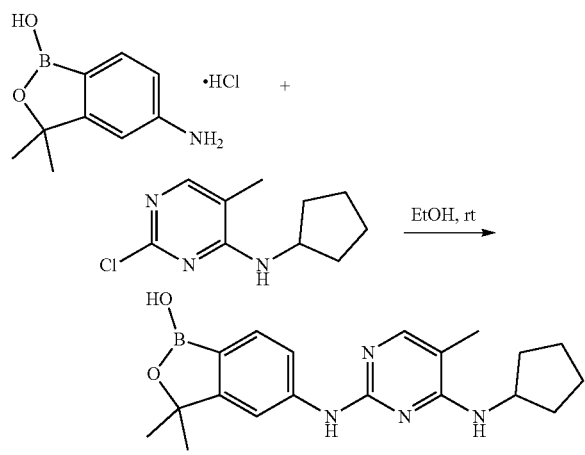

This substance was prepared by using General Synthetic Scheme B and following the procedure employed for the synthesis of 5-((4-(cyclopentylamino)-5-methylpyrimidin-2-yl)amino)-7-methylbenzo[c][1,2]oxaborol-1(3H)-ol. Yield: 26%. ¹H NMR (DMSO-d6, 400 MHz) δ (ppm) 9.09 (s, 1H), 8.73 (s, 1H), 7.68 (s, 1H), 7.46 (d, J=8.0 Hz, 1H), 7.39 (dd, J=8.0, 1.6 Hz, 1H), 6.44 (d, J=7.2 Hz, 1H), 4.53-4.47 (m, 1H), 2.03-2.01 (m, 2H), 1.93 (s, 3H), 1.76-1.73 (m, 2H), 1.61-1.57 (m, 4H), 1.42 (s, 6H). MS (ESI): m/z found 353.2 [M+H]⁺. Purity by HPLC: 95.93% (220 nm), 94.50% (254 nm).

7. Preparation of 5-((5-chloro-4-(cyclopentylamino)pyrimidin-2-yl)amino)-7-ethylbenzo[c][1,2]oxaborol-1(3H)-ol and 5-((4-(cyclopentylamino)pyrimidin-2-yl)amino)-7-ethylbenzo[c][1,2]oxaborol-1(3H)-ol

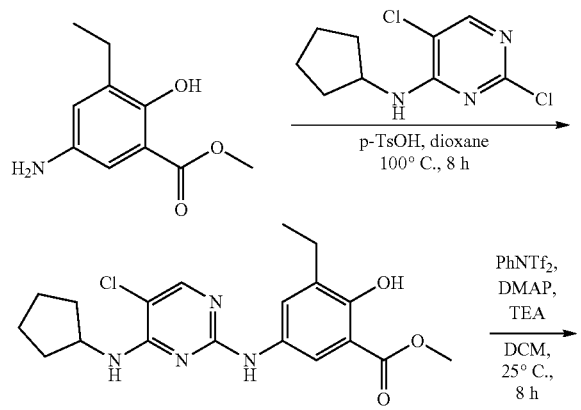

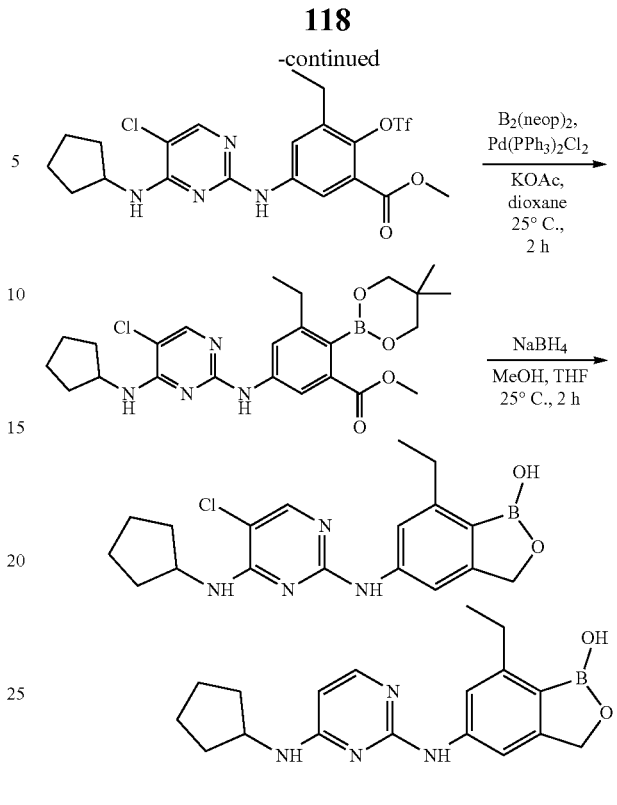

7.1 Preparation of methyl 5-[[5-chloro-4-(cyclopentylamino)pyrimidin-2-yl]amino]-3-ethyl-2-hydroxybenzoate

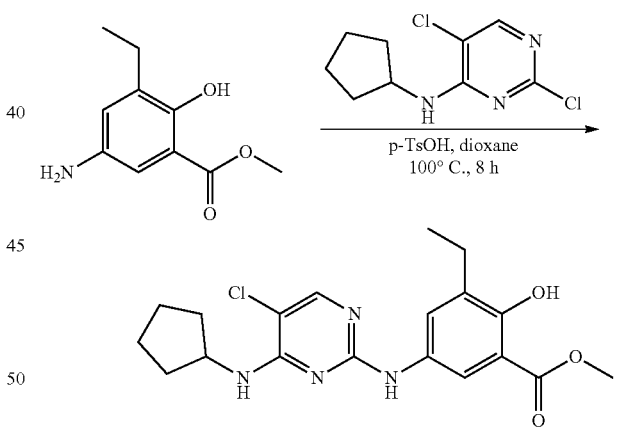

To a solution of methyl 5-amino-3-ethyl-2-hydroxy-benzoate (600 mg, 3.07 mmol, 1 eq) and 2,5-dichloro-N-cyclopentyl-pyrimidin-4-amine (713 mg, 3.07 mmol, 1 eq) in dioxane (20 mL) was added p-TsOH (794 mg, 4.61 mmol, 1.5 eq) at 20° C. The reaction mixture was stirred at 100° C. for 8 h. The reaction mixture was filtered, and the filtrate was concentrated in vacuo to give a residue, to which sat. NaHCO₃ (30 mL) was added at 0° C., extracted with EtOAc (30 mL×3). The combined organic layers were washed with brine (100 mL), dried over anhydrous Na₂SO₄, filtered and concentrated in vacuo to yield a residue, which was purified by column chromatography (SiO₂, Petroleum ether/Ethyl acetate=1/0 to 5/1) to give methyl 5-[[5-chloro-4-(cyclopentylamino)pyrimidin-2-yl]amino]-3-ethyl-2-hydroxy-benzoate (700 mg, 1.79 mmol, 58.27% yield) as a yellow solid. ¹H NMR (DMSO-d₆, 400 MHz) δ 10.59 (s, 1H), 9.10 (s, 1H), 8.16 (s, 1H), 7.89 (s, 1H), 7.70 (d, J=2.8 Hz, 1H), 6.77 (d, J=7.6 Hz, 1H), 4.46-4.40 (m, 1H), 3.89 (s, 3H), 2.57 (q, J=7.6 Hz, 2H), 1.99-1.85 (m, 2H), 1.73-1.61 (m, 2H), 1.60-1.45 (m, 4H), 1.16 (t, J=7.6 Hz, 3H).

7.2 Preparation of methyl 5-[[5-chloro-4-(cyclopentylamino)pyrimidin-2-yl]amino]-3-ethyl-2-(trifluoromethylsulfonyloxy)benzoate

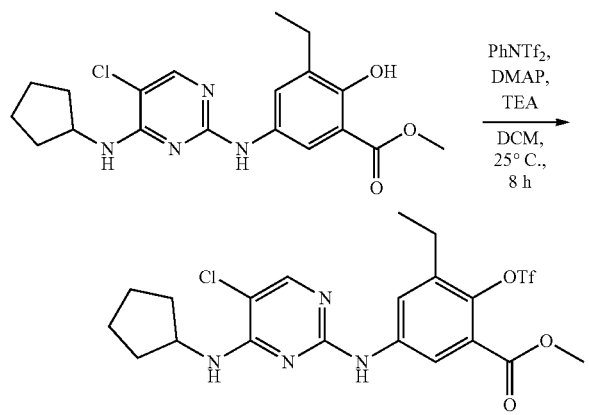

To a solution of 1,1,1-trifluoro-N-phenyl-N-(trifluoromethylsulfonyl)methanesulfonamide (658 mg, 1.84 mmol, 1.2 eq) and methyl 5-[[5-chloro-4-(cyclopentylamino)pyrimidin-2-yl] amino]-3-ethyl-2-hydroxy-benzoate (600 mg, 1.54 mmol, 1 eq) in DCM (30 mL) was added DMAP (56 mg, 461 μmol, 0.3 eq) and TEA (311 mg, 3.07 mmol, 427 μL, 2 eq) at 0° C. The mixture was stirred at 25° C. for 8 h. The reaction mixture was filtered, and the filtrate was concentrated in vacuo to give a residue, which was purified by column chromatography (SiO2, Petroleum ether/Ethyl acetate=1/0 to 3/1) to give methyl 5-[[5-chloro-4-(cyclopentylamino)pyrimidin-2-yl]amino]-3-ethyl-2-(trifluoromethylsulfonyloxy)benzoate (600 mg, 1.15 mmol, 74.75% yield) as a white solid. ¹H NMR (CDCl₃, 400 MHz) δ 8.16 (d, J=3.2 Hz, 1H), 7.92 (s, 1H), 7.73 (d, J=3.2 Hz, 1H), 7.26 (s, 1H), 5.28 (d, J=7.2 Hz, 1H), 4.48-4.42 (m, 1H), 3.93 (s, 3H), 2.81-2.74 (q, J=7.6 Hz, 2H), 2.21-2.08 (m, 2H), 1.85-1.65 (m, 4H), 1.61-1.47 (m, 2H), 1.29 (t, J=7.6 Hz, 3H).

7.3. Preparation of methyl 5-[[5-chloro-4-(cyclopentylamino)pyrimidin-2-yl]amino]-2-(5,5-dimethyl-1,3,2-dioxaborinan-2-yl)-3-ethyl-benzoate

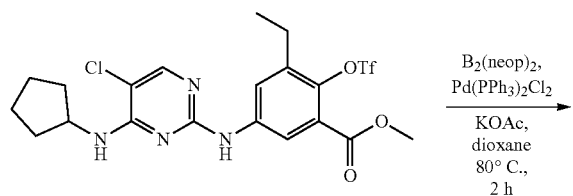

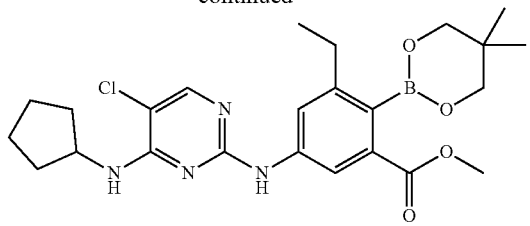

A mixture of methyl 5-[[5-chloro-4-(cyclopentylamino)pyrimidin-2-yl]amino]-3-ethyl-2-(trifluoromethylsulfonyloxy)benzoate (150 mg, 287 μmol, 1 eq), 2-(5,5-dimethyl-1,3,2-dioxaborinan-2-yl)-5,5-dimethyl-1,3,2-dioxaborinane (194 mg, 860 μmol, 3 eq), KOAc (84 mg, 861 μmol, 3 eq) and Pd(PPh₃)₂Cl₂ (20 mg, 29 μmol, 0.1 eq) in dioxane (10 mL) was degassed and purged with N₂ for 3 times, then the mixture was stirred at 80° C. for 2 h under N₂ atmosphere. The reaction mixture was filtered, and the filtrate was concentrated in vacuo to give a residue, which was purified by column chromatography (SiO₂, Petroleum ether/Ethyl acetate=1/0 to 3/1) to give methyl 5-[[5-chloro-4-(cyclopentylamino)pyrimidin-2-yl]amino]-2-(5,5-dimethyl-1,3,2-dioxaborinan-2-yl)-3-ethyl-benzoate (450 mg, 924 μmol, 80.57% yield) as white solid. ¹H NMR (CDCl₃, 400 MHz) δ 8.19 (d, J=2 Hz, 1H), 7.87 (s, 1H), 7.54 (d, J=2 Hz, 1H), 7.45 (s, 1H), 5.23 (d, J=7.2 Hz, 1H), 4.51-4.45 (m, 1H), 3.91 (s, 3H), 3.83 (s, 4H), 2.75 (q, J=7.6 Hz, 2H), 2.16-2.05 (m, 2H), 1.78-1.47 (m, 6H), 1.30-1.25 (t, J=7.6 Hz, 3H), 1.14 (s, 6H).

7.4 Preparation of N4-cyclopentyl-N2-(7-ethyl-1-hydroxy-3H-2,1-benzoxaborol-5-yl) pyrimidine-2,4-diamine and 5-chloro-N4-cyclopentyl-N2-(7-ethyl-1-hydroxy-3H-2,1-benzoxaborol-5-yl)pyrimidine-2,4-diamine

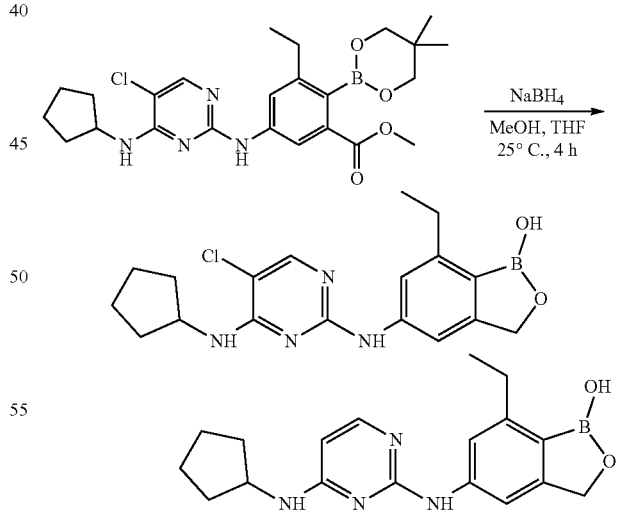

To a mixture of methyl 5-[[5-chloro-4-(cyclopentylamino)pyrimidin-2-yl]amino]-2-(5,5-dimethyl-1,3,2-dioxaborinan-2-yl)-3-ethyl-benzoate (150 mg, 308 μmol, 1 eq, 3 batch) in THF (10 mL) and MeOH (0.5 mL) was added NaBH₄ (58 mg, 1.54 mmol, 5 eq) in portions at 0° C., then the mixture was stirred at 25° C. for 4 h under N₂ atmosphere. The reaction was quenched by 1 N HCl (1 mL) at 0°

C., concentrated in vacuo to give a residue, which was purified by prep-HPLC (column: Xtimate C18 100*30 mm*3 um; mobile phase: [water(0.1% TFA)-ACN]; B %: 30%-50%, 10 min) to give N4-cyclopentyl-N2-(7-ethyl-1-hydroxy-3H-2,1-benzoxaborol-5-yl)pyrimidine-2,4-diamin (195 mg, 577 μmol, 62.37% yield). $^1$H NMR (DMSO-$d_6$, 400 MHz) δ 9.77 (s, 1H), 8.76 (br s, 1H), 8.05 (s, 1H), 7.53-7.50 (m, 3H), 4.91 (s, 2H), 4.47-4.36 (m, 1H), 2.73 (q, J=7.6 Hz, 2H), 1.98-1.96 (m, 2H), 1.74-1.72 (m, 2H), 1.64-1.54 (m, 4H), 1.18 (t, J=7.6 Hz, 3H). MS (ESI): mass calcd. For $C_{18}H_{22}BClN_4O_2$ 372.15, m/z found 373.1 [M+H]$^+$. HPLC: 98.74% (220 nm), 98.68% (254 nm). And 5-chloro-N4-cyclopentyl-N2-(7-ethyl-1-hydroxy-3H-2,1-benzoxaborol-5-yl)pyrimidine-2,4-diamine (51 mg, 137 μmol, 14.80% yield) as white solid. $^1$H NMR (DMSO-$d_6$, 400 MHz) δ 10.43 (s, 1H), 8.98 (d, J=2.0 Hz, 1H), 8.90 (s, 1H), 7.78 (d, J=7.2 Hz, 1H), 7.44 (s, 1H), 7.42 (s, 1H), 6.19 (d, J=7.2 Hz, 1H), 4.95 (s, 2H), 4.30-4.24 (m, 1H), 2.76 (q, J=7.6 Hz, 2H), 2.00-1.90 (m, 2H), 1.76-1.65 (m, 2H), 1.64-1.48 (m, 4H), 1.19 (t, J=7.6 Hz, 3H). MS (ESI): mass calcd. For $C_{18}H_{23}BN_4O_2$ 338.19, m/z found 339.2 [M+H]$^+$. HPLC: 98.52% (220 nm), 98.84% (254 nm).

8. Preparation of 3,3-dimethyl-5-((5-methyl-4-(pentan-3-ylamino)pyrimidin-2-yl)amino)benzo[c][1,2]oxaborol-1(3H)-ol

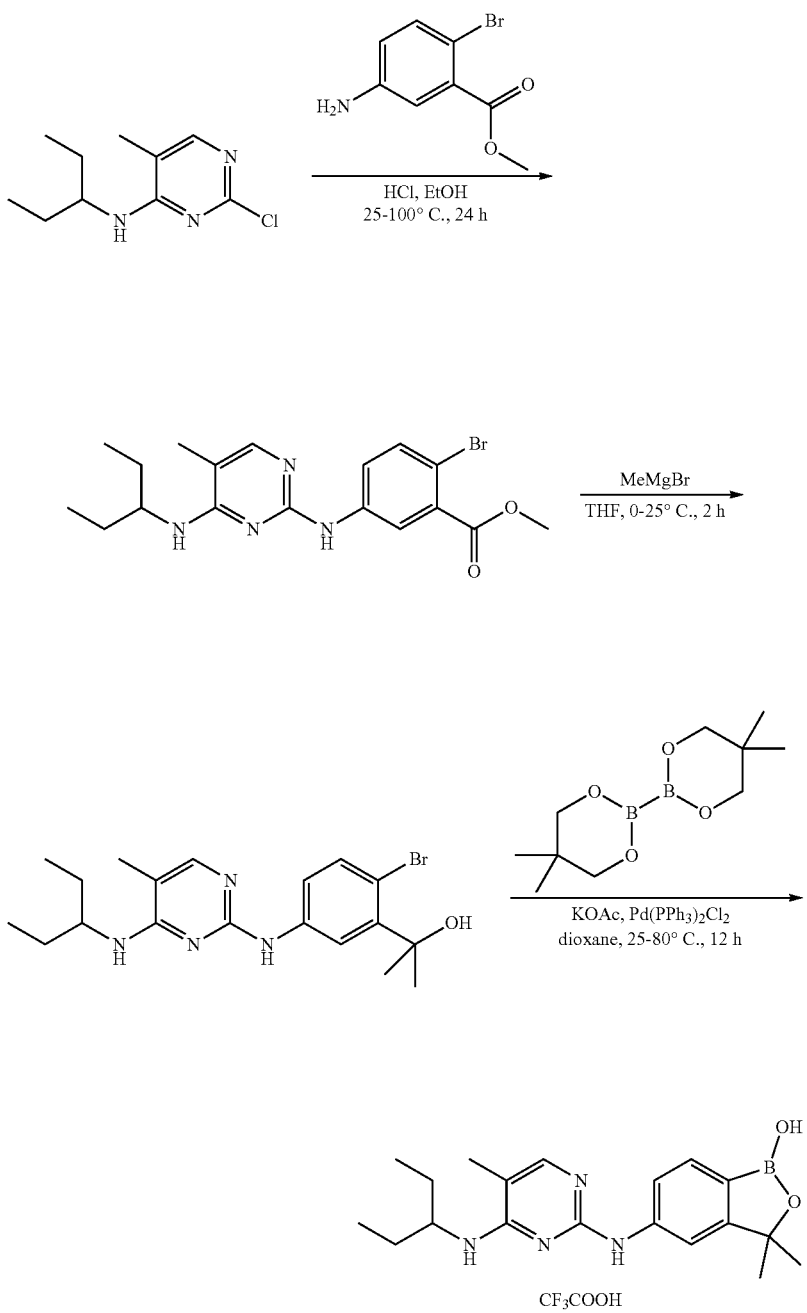

8.1. Preparation of methyl 2-bromo-5-[[4-(1-ethyl-propylamino)-5-methyl-pyrimidin-2-yl]amino]benzoate

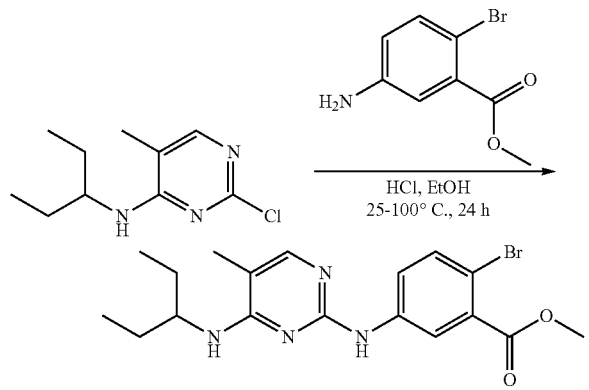

To a solution of 2-chloro-N-(1-ethylpropyl)-5-methyl-pyrimidin-4-amine (2 g, 9.36 mmol, 1 eq) and methyl 5-amino-2-bromo-benzoate (2.15 g, 9.36 mmol, 1 eq) in EtOH (50 mL) was added HCl (37.4 mmol, 3.72 mL, 36% purity, 4 eq) at 25° C., the reaction mixture was heated to 100° C. and stirred for 24 h. Then the solvent was removed to yield a residue, to which H$_2$O (20 mL) was added, and its pH was adjusted to 5 with sat. aq. NaHCO$_3$, extracted with EtOAc (20 mL×3). The combined organic layers were washed with brine (20 mL×3), dried over anhydrous Na$_2$SO$_4$, filtered and concentrated in vacuo to give a residue. The residue was triturated with MTBE (10 mL) to give the crude product, then the crude product was triturated with EtOAc (10 mL) to give methyl 2-bromo-5-[[4-(1-ethylpropylamino)-5-methyl-pyrimidin-2-yl]amino]benzoate (2.3 g, 5.65 mmol, 60.33% yield) as a white solid. $^1$H NMR (DMSO-d$_6$, 400 MHz) δ 8.22 (d, J=2.4 Hz, 1H), 7.69 (d, J=4.0 Hz, 1H), 7.50 (s, 1H), 7.37-7.35 (m, 1H), 3.99-3.93 (m, 1H), 3.81 (s, 3H), 1.94 (s, 3H), 1.54-1.49 (m, 4H), 0.75 (t, J=7.2 Hz, 6H).

8.2. Preparation of 2-[2-bromo-5-[[4-(1-ethylpropylamino)-5-methyl-pyrimidin-2-yl]amino]phenyl]propan-2-ol A solution of methyl 2-bromo-5-[[4-(1-ethylpropylamino)-5-methyl-pyrimidin-2-yl]amino]benzoate (500 mg, 1.23 mmol, 1 eq) in THF (10 mL) was added MeMgBr (3 M, 2.05 mL, 5 eq) dropwise at 0° C. over a period of 10 min, the resulting mixture was stirred at 25° C. for 2 h. Then the reaction mixture was poured into H$_2$O (30 mL), and the aqueous phase was extracted with EtOAc (10 mL×3). The combined organic layers were washed with brine (5 mL×3), dried over anhydrous Na$_2$SO$_4$, filtered and concentrated in vacuo to give a residue. The residue was purified by short column to give 2-[2-bromo-5-[[4-(1-ethylpropylamino)-5-methyl-pyrimidin-2-yl]amino]phenyl]propan-2-ol (400 mg, 982 μmol, 79.83% yield) as yellow oil. $^1$H NMR (DMSO-d$_6$, 400 MHz) δ 8.86 (s, 1H), 8.11 (d, J=2.4 Hz, 1H), 7.66 (s, 1H), 7.62 (s, 1H), 7.34 (d, J=8.4 Hz, 1H), 5.05 (s, 1H), 4.19-4.12 (m, 1H), 1.99 (s, 3H), 1.58-1.48 (m, 10H), 0.86 (t, J=7.6 Hz, 6H).

8.3. Preparation of N4-(1-ethylpropyl)-N2-(1-hydroxy-3,3-dimethyl-2,1-benzoxaborol-5-yl)-5-methyl-pyrimidine-2,4-diamine

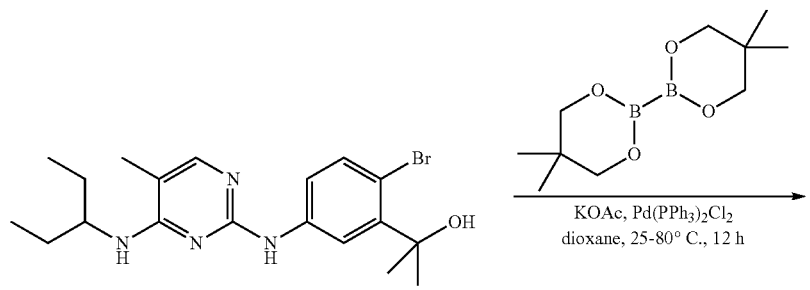

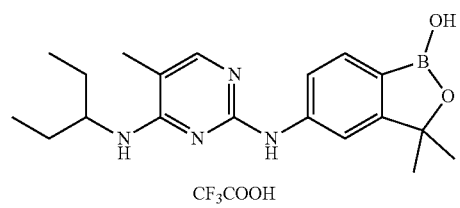

CF$_3$COOH

To a solution of 2-[2-bromo-5-[[4-(1-ethylpropylamino)-5-methyl-pyrimidin-2-yl]amino]phenyl] propan-2-ol (350 mg, 859 µmol, 1 eq) and 2-(5,5-dimethyl-1,3,2-dioxaborinan-2-yl)-5,5-dimethyl-1,3,2-dioxaborinane (485 mg, 2.15 mmol, 2.5 eq) in dioxane (7 mL) was added Pd(PPh$_3$)$_2$Cl$_2$ (60.3 mg, 85.9 µmol, 0.1 eq), KOAc (169 mg, 1.72 mmol, 2 eq) at 25° C. under N$_2$ atmosphere, the resulting mixture was stirred at 80° C. for 12 h. Then the reaction mixture was filtered, concentrated in vacuo to give a residue. The residue was purified by prep-HPLC (column: Xtimate C18 100*30 mm*3 um; mobile phase: [water(0.1% TFA)-ACN]; B %: 25%-45%, 10 min) to give N4-(1-ethylpropyl)-N2-(1-hydroxy-3-methyl-3H-2,1-benzoxaborol-5-yl)-5-methyl-pyrimidine-2,4-diamine (30 mg, 65.9 µmol, 7.67% yield, 99.8% purity, TFA) as a white solid. $^1$H NMR (DMSO-d$_6$, 400 MHz) δ 11.86 (s, 1H), 10.13 (s, 1H), 8.99 (s, 1H), 7.91-7.86 (m, 1H), 7.79 (s, 1H), 7.72 (s, 1H), 7.64 (d, J=8.0 Hz, 1H), 7.32 (d, J=8.0 Hz, 1H), 4.16-4.11 (m, 1H), 2.03 (s, 3H), 1.64-1.58 (m, 4H), 1.45 (s, 6H), 0.84 (t, J=7.2 Hz, 6H). MS (ESI): mass calcd. For C$_{21}$H$_{28}$BF$_3$N$_4$O$_4$ 468.22, m/z found 355.2 [M+H]$^+$. HPLC: 99.80% (220 nm), 99.99% (254 nm)

9. Preparation of 3-methyl-5-((5-methyl-4-(pentan-3-ylamino)pyrimidin-2-yl)amino)benzo [c][1,2]oxaborol-1(3H)-ol

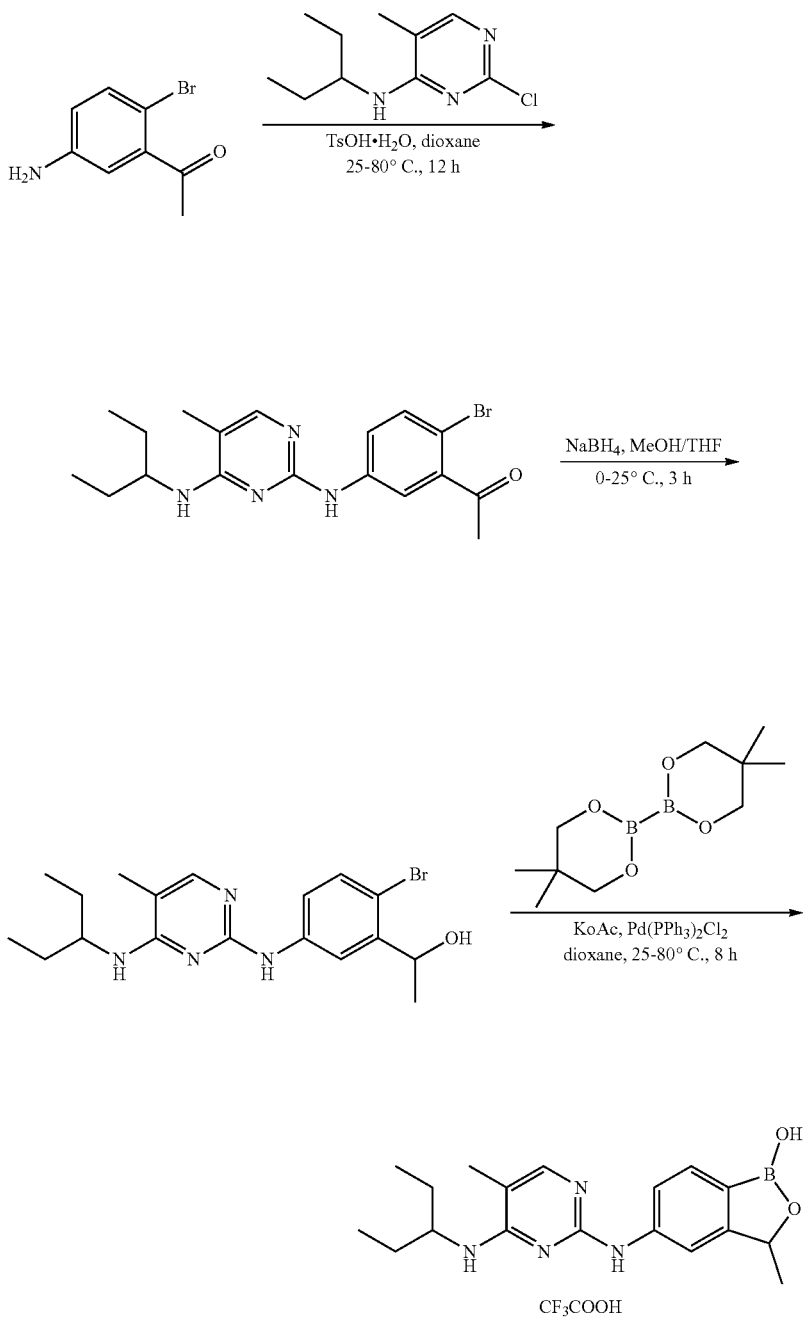

9.1 Preparation of 1-[2-bromo-5-[[4-(1-ethylpropylamino)-5-methyl-pyrimidin-2-yl]amino]phenyl]ethanone

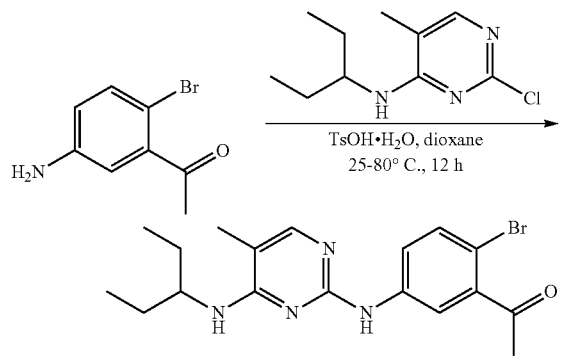

To a solution of 2-chloro-N-(1-ethylpropyl)-5-methyl-pyrimidin-4-amine (1.5 g, 7.02 mmol, 1 eq) and 1-(5-amino-2-bromo-phenyl)ethanone (1.50 g, 7.02 mmol, 1 eq) in dioxane (50 mL) was added TsOH·H₂O (2.00 g, 10.5 mmol, 1.5 eq) at 25° C., the resulting mixture was heated to 80° C. and stirred for 12 h. H₂O (30 mL) was poured into the above mixture, and its pH was adjusted to 9 with sat. aq. NaHCO₃, extracted with EtOAc (10 mL×3). The combined organic layers were washed with brine (50 mL×3), dried over Na₂SO₄, filtered and concentrated in vacuo to give a residue. The residue was purified by flash silica gel chromatography (ISCO®; 40 g SepaFlash® Silica Flash Column, Eluent of 0-100% Ethyl acetate/Petroleum ethergradient @ 75 mL/min) to give 1-[2-bromo-5-[[4-(1-ethylpropylamino)-5-methyl-pyrimidin-2-yl]amino]phenyl]ethanone (1.3 g, 3.32 mmol, 47.33% yield) as brown oil. $^1$H NMR (DMSO-$d_6$, 400 MHz) δ 9.11 (s, 1H), 8.14 (d, J=2.8 Hz, 1H), 7.73 (dd, J=8.8, 2.8 Hz, 1H), 7.67 (s, 1H), 7.48 (d, J=8.8 Hz, 1H), 6.15 (d, J=8.8 Hz, 1H), 4.08-4.04 (m, 1H), 2.54 (s, 3H), 1.94 (m, 3H), 1.62-1.49 (m, 4H), 0.85 (t, J=7.6 Hz, 6H).

9.2 Preparation of 1-[2-bromo-5-[[4-(1-ethylpropylamino)-5-methyl-pyrimidin-2-yl]amino] phenyl]ethanol

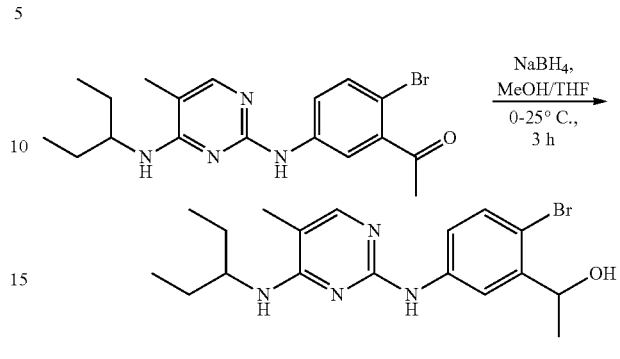

To a solution of 1-[2-bromo-5-[[4-(1-ethylpropylamino)-5-methyl-pyrimidin-2-yl]amino]phenyl]ethanone (700 mg, 1.79 mmol, 1 eq) and MeOH (1.79 mmol, 72.4 μL, 1 eq) in THF (5 mL) was added NaBH₄ (102 mg, 2.69 mmol, 1.5 eq) at 0° C., the resulting mixture was stirred at 25° C. for 3 h. The reaction mixture was poured into H₂O (10 mL), its pH was adjusted to 5 with 2N HCl, and extracted with EtOAc (5 mL×3). The combined organic layers were washed with brine (5 mL×3), dried over Na₂SO₄, filtered and concentrated in vacuo to give a residue. The residue was purified by short column to give 1-[2-bromo-5-[[4-(1-ethylpropylamino)-5-methyl-pyrimidin-2-yl]amino]phenyl]ethanol (400 mg, 1.02 mmol, 56.98% yield) as a white solid. $^1$H NMR (DMSO-$d_6$, 400 MHz) δ 8.91 (s, 1H), 8.16 (d, J=2.8 Hz, 1H), 7.63 (s, 1H), 7.53 (dd, J=8.8, 2.8 Hz, 1H), 7.29 (d, J=8.8 Hz, 1H), 6.06 (d, J=8.8 Hz, 1H), 5.23 (d, J=3.6 Hz, 1H), 4.93-4.88 (m, 1H), 4.26-4.13 (m, 1H), 1.93 (s, 3H), 1.62-1.53 (m, 4H), 1.28 (d, J=6.4 Hz, 3H), 0.87 (q, J=7.6 Hz, 6H)

9.3 Preparation of N4-(1-ethylpropyl)-N2-(1-hydroxy-3-methyl-3H-2,1-benzoxaborol-5-yl)-5-methyl-pyrimidine-2,4-diamine

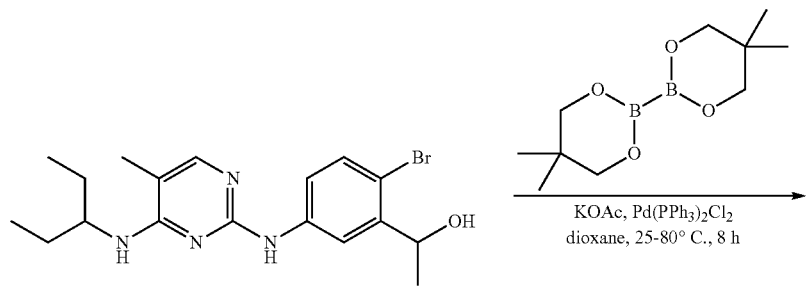

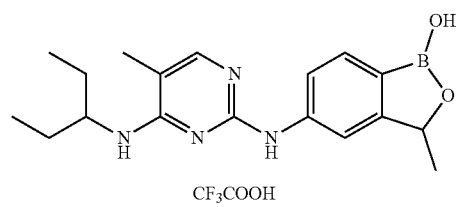

CF₃COOH

To a solution of 1-[2-bromo-5-[[4-(1-ethylpropylamino)-5-methyl-pyrimidin-2-yl]amino]phenyl]ethanol (300 mg, 763 μmol, 1 eq) and 2-(5,5-dimethyl-1,3,2-dioxaborinan-2-yl)-5,5-dimethyl-1,3,2-dioxaborinane (431 mg, 1.91 mmol, 2.5 eq) in dioxane (10 mL) was added Pd(PPh$_3$)$_2$Cl$_2$ (53.5 mg, 76.3 μmol, 0.1 eq), KOAc (150 mg, 1.53 mmol, 2 eq) at 25° C. under N$_2$ atmosphere, the resulting mixture was stirred at 80° C. for 8 h. The reaction mixture was filtered, and the filtrate was concentrated in vacuo to give a residue, which was dissolved in H$_2$O (10 mL), and its pH was adjusted to 5 with 2N HCl, extracted with EtOAc (8 mL×3). The combined organic layers were washed with brine (5 mL×3), dried over Na$_2$SO$_4$, filtered and concentrated in vacuo to give a residue. The residue was purified by prep-HPLC (column: Welch Xtimate C18 100*25 mm*3 um; mobile phase: [water(0.1% TFA)-MeOH]; B %: 40%-60%, 12 min) to give N4-(1-ethylpropyl)-N2-(1-hydroxy-3-methyl-3H-2,1-benzoxaborol-5-yl)-5-methyl-pyrimidine-2,4-diamine (96 mg, 211 μmol, 27.65% yield, 99.80% purity, TFA) as a white solid. $^1$H NMR (DMSO-d$_6$, 400 MHz) δ 12.06 (s, 1H), 10.19 (s, 1H), 9.06 (s, 1H), 7.82 (s, 1H), 7.72 (s, 2H), 7.67 (d, J=8.0 Hz, 1H), 7.40 (d, J=8.0 Hz, 1H), 5.20 (q, J=6.8 Hz, 1H), 4.12-4.03 (m, 1H), 2.03 (s, 3H), 1.64-1.59 (m, 4H), 1.40 (d, J=6.8 Hz, 3H), 0.88-0.82 (m, 6H). MS (ESI): mass calcd. For C$_{20}$H$_{26}$BF$_3$N$_4$O$_4$ 454.20, m/z found 341.0 [M+H]$^+$. HPLC: 99.80% (220 nm), 99.74% (254 nm).

10. Preparation of N-(7-ethyl-1-hydroxy-1,3-dihydrobenzo[c][1,2]oxaborol-5-yl)-1,1,1-trifluoro-N-(5-methyl-4-(pentan-3-ylamino)pyrimidin-2-yl)methanesulfonamide

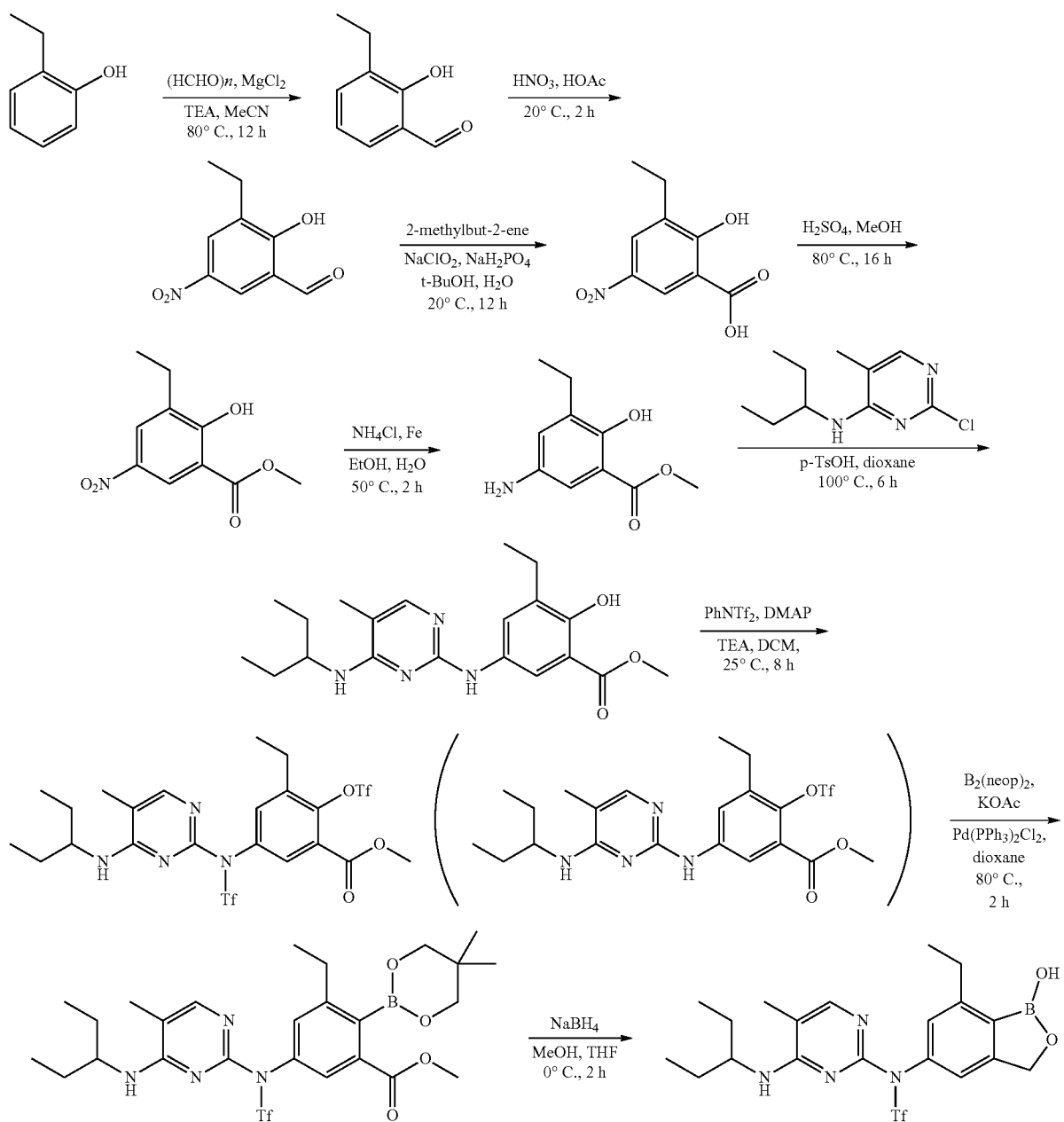

10.1 Preparation of 3-ethyl-2-hydroxy-benzaldehyde

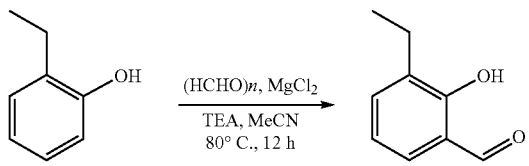

A mixture of 2-ethylphenol (10.0 g, 81.86 mmol, 9.62 mL, 1 eq), MgCl$_2$ (11.7 g, 122.79 mmol, 5.04 mL, 1.5 eq), TEA (33.1 g, 327.43 mmol, 45.57 mL, 4 eq) and (HCHO)n (4.9 g, 163.71 mmol, 2 eq) in MeCN (100 mL) was degassed and purged with N$_2$ 3 times, the reaction mixture was stirred at 80° C. for 12 h under N$_2$ atmosphere. Then the reaction mixture was poured into aq. HCl (200 mL, 1N), and the aqueous phase was extracted with EtOAc (50 mL×3). The combined organic layers were washed with brine (50 mL×2), dried over anhydrous Na$_2$SO$_4$, filtered and concentrated in vacuo to give a residue, which was purified by column chromatography (SiO$_2$, Petroleum ether/Ethyl acetate=1/0 to 10/1) to give 3-ethyl-2-hydroxy-benzaldehyde (16 g, 106.54 mmol, 65.08% yield, 2 batch) as yellow oil. $^1$H NMR (CDCl$_3$, 400 MHz) δ 11.29 (s, 1H), 9.89 (s, 1H), 7.43-7.40 (m, 2H), 6.97 (t, J=7.6 Hz, 1H), 2.71 (q, J=7.2 Hz, 2H), 1.25 (t, J=7.2 Hz, 3H).

10.2 Preparation of 3-ethyl-2-hydroxy-5-nitro-benzaldehyde

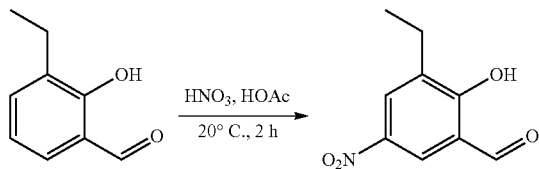

To a solution of 3-ethyl-2-hydroxy-benzaldehyde (10.0 g, 66.59 mmol, 1 eq) in AcOH (100 mL) was added HNO$_3$ (14.0 g, 199.97 mmol, 10 mL, 90% purity, 3.00 eq) slowly at 0° C. The solution was stirred at 20° C. for 2 h. The reaction mixture was poured into ice/water (250 mL) at 0° C., the formed yellow solid was collected by filtration, dried in vacuo to give 3-ethyl-2-hydroxy-5-nitro-benzaldehyde (8.60 g, 44.06 mmol, 66.17% yield) as a yellow solid. $^1$H NMR (CDCl$_3$, 400 MHz) δ 11.91 (s, 1H), 9.99 (s, 1H), 8.42 (d, J=2.8 Hz, 1H), 8.30 (d, J=2.8 Hz, 1H), 2.78 (q, J=7.6 Hz, 2H), 1.30 (t, J=7.6 Hz, 3H).

10.3 Preparation of 3-ethyl-2-hydroxy-5-nitro-benzoic Acid

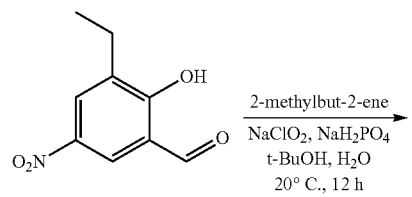

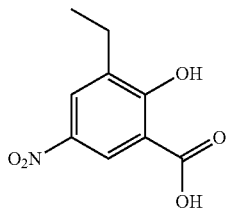

To a solution of 3-ethyl-2-hydroxy-5-nitro-benzaldehyde (5.00 g, 25.62 mmol, 1 eq) and 2-methyl-2-butene (12.6 g, 179.33 mmol, 19.00 mL, 7 eq) in t-BuOH (50 mL) and H$_2$O (30 mL) was added NaH$_2$PO$_4$ (13.8 g, 115.28 mmol, 4.5 eq) and NaClO$_2$ (7.00 g, 76.86 mmol, 3 eq) at 20° C. The reaction mixture was stirred at 20° C. for 12 h. The reaction mixture was filtered, and the filtrate was concentrated in vacuo to give a residue, which was poured into ice/water (100 mL) at 0° C. The aqueous phase was extracted with EtOAc (100 mL×3), and the combined organic layers were washed with brine (100 mL), dried over anhydrous Na$_2$SO$_4$, filtered and concentrated in vacuo to give 3-ethyl-2-hydroxy-5-nitro-benzoic acid (5.00 g, 18.94 mmol, 73.94% yield, 80% purity) as a yellow solid. $^1$H NMR (CDCl$_3$, 400 MHz) δ 11.45 (s, 1H), 8.74 (d, J=2.8 Hz, 1H), 8.28 (d, J=2.8 Hz, 1H), 2.78 (q, J=7.6 Hz, 2H), 1.30 (t, J=7.6 Hz, 3H).

10.4 Preparation of 3-ethyl-2-hydroxy-5-nitro-benzoate

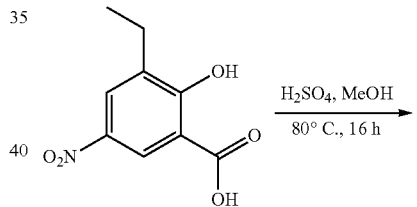

To a solution of 3-ethyl-2-hydroxy-5-nitro-benzoic acid (5.00 g, 18.94 mmol, 1 eq) in MeOH (50 mL) was added H$_2$SO$_4$ (7.4 g, 75.77 mmol, 4.0 mL, 4 eq) dropwise at 0° C. The mixture was stirred for 16 h at 80° C. The reaction mixture was poured into ice/water (100 mL) at 0° C., and the aqueous phase was extracted with EtOAc (50 mL×3). The combined organic layers were washed with brine (100 mL), dried over anhydrous Na$_2$SO$_4$, filtered and concentrated in vacuo to give a residue, which was purified by column (SiO$_2$, Petroleum ether/Ethyl acetate=1/0 to 10/1) to give methyl 3-ethyl-2-hydroxy-5-nitro-benzoate (3.60 g, 14.39 mmol, 75.95% yield, 90% purity) as yellow oil. $^1$H NMR (CDCl$_3$, 400 MHz) δ 11.74 (s, 1H), 8.66 (d, J=2.4 Hz, 1H), 8.22 (d, J=2.4 Hz, 1H), 4.03 (s, 3H), 2.76 (q, J=7.2 Hz, 2H), 1.28 (t, J=7.2 Hz, 3H).

10.5 Preparation of methyl 5-amino-3-ethyl-2-hydroxy-benzoate

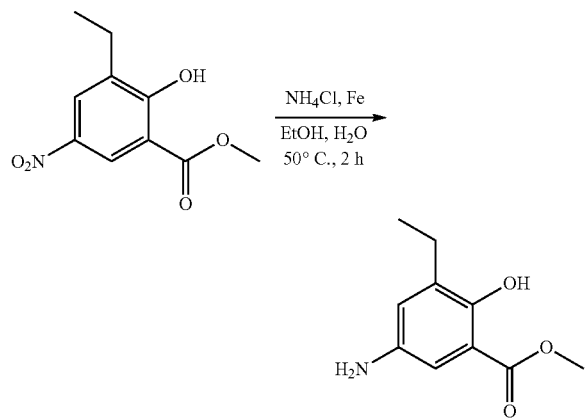

To a solution of methyl 3-ethyl-2-hydroxy-5-nitro-benzoate (3.50 g, 15.54 mmol, 1 eq) in EtOH (50 mL) and $H_2O$ (10 mL) was added $NH_4Cl$ (2.50 g, 46.63 mmol, 1.63 mL, 3 eq) and Fe (2.60 g, 46.63 mmol, 3 eq) at 20° C. The mixture was stirred at 50° C. for 2 h. The reaction mixture was filtered, and the filtrate was concentrated in vacuo to give a residue. The residue was poured into ice/water (100 mL) at 0° C., and the aqueous phase was extracted with EtOAc (50 mL×3). The combined organic layers were washed with brine (100 mL), dried over anhydrous $Na_2SO_4$, filtered and concentrated in vacuo to give methyl 5-amino-3-ethyl-2-hydroxy-benzoate (2.00 g, 10.25 mmol, 65.92% yield) as a yellow solid. $^1H$ NMR ($CDCl_3$, 400 MHz) δ 10.49 (s, 1H), 7.20 (d, J=2.8 Hz, 1H), 6.79 (d, J=2.8 Hz, 1H), 3.92 (s, 3H), 3.39 (s, 2H), 2.64 (q, J=7.2 Hz, 2H), 1.21 (t, J=7.2 Hz, 3H).

10.6 Preparation of methyl 3-ethyl-5-[[4-(1-ethyl-propylamino)-5-methyl-pyrimidin-2-yl] amino]-2-hydroxy-benzoate

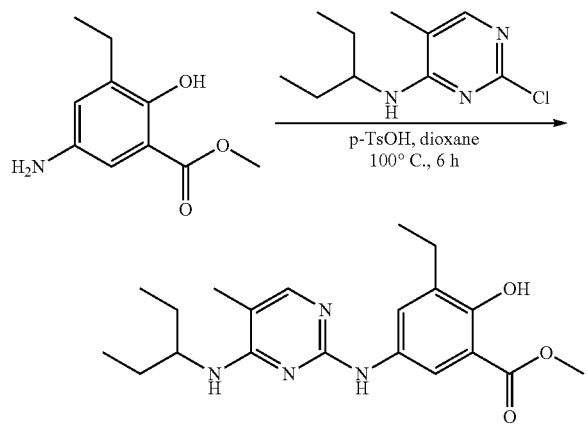

To a solution of methyl 5-amino-3-ethyl-2-hydroxy-benzoate (600 mg, 3.07 mmol, 1 eq) in dioxane (20 mL) was added p-TsOH (794 mg, 4.61 mmol, 1.5 eq) and 2-chloro-N-(1-ethylpropyl)-5-methyl-pyrimidin-4-amine (657 mg, 3.07 mmol, 1 eq) at 20° C. The mixture was stirred at 100° C. for 6 h. The reaction mixture was filtered, the filtrate was concentrated in vacuo to give a residue. The residue was poured into sat. $NaHCO_3$ (30 mL) at 0° C., extracted with EtOAc (30 mL×3). The combined organic layers were washed with brine (100 mL), dried over anhydrous $Na_2SO_4$, filtered and concentrated in vacuo to give a residue, which was purified by column chromatography ($SiO_2$, Petroleum ether/Ethyl acetate=1/0 to 2/1) to give methyl 3-ethyl-5-[[4-(1-ethylpropylamino)-5-methyl-pyrimidin-2-yl]amino]-2-hydroxy-benzoate (700 mg, 1.88 mmol, 61.15% yield) as a yellow solid. $^1H$ NMR (DMSO-$d_6$, 400 MHz) δ 10.55 (s, 1H), 8.68 (s, 1H), 8.32 (d, J=2.8 Hz, 1H), 7.65 (d, J=2.8 Hz, 1H), 7.61 (s, 1H), 6.03 (d, J=8.8 Hz, 1H), 4.20-4.16 (m, 1H), 3.89 (s, 3H), 2.59-2.51 (q, J=7.6 Hz, 2H), 1.92 (s, 3H), 1.65-1.45 (m, 4H), 1.16 (t, J=7.6 Hz, 3H), 0.85 (t, J=7.2 Hz, 6H).

10.7 Preparation of methyl 3-ethyl-5-[[4-(1-ethyl-propylamino)-5-methyl-pyrimidin-2-yl]-(trifluoromethylsulfonyl)amino]-2-(trifluoromethylsulfonyloxy) benzoate and methyl 3-ethyl-5-((5-methyl-4-(pentan-3-ylamino)pyrimidin-2-yl)amino)-2-(((trifluoromethyl)sulfonyl)oxy) benzoate

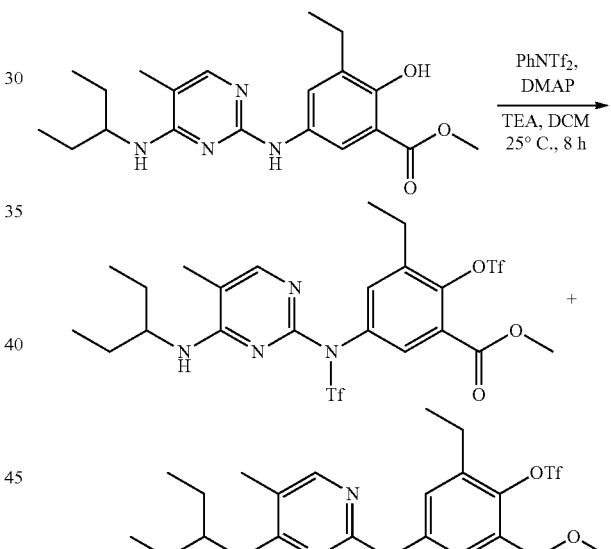

To a solution of 1,1,1-trifluoro-N-phenyl-N-(trifluoromethylsulfonyl)methanesulfonamide (748 mg, 2.09 mmol, 1.3 eq) and methyl 3-ethyl-5-[[4-(1-ethylpropylamino)-5-methyl-pyrimidin-2-yl]amino]-2-hydroxy-benzoate (600 mg, 1.61 mmol, 1 eq) in DCM (30 mL) was added DMAP (59 mg, 483 μmol, 0.3 eq) and TEA (326 mg, 3.22 mmol, 448 μL, 2 eq) at 0° C. The reaction mixture was stirred at 25° C. for 8 h. The reaction mixture was filtered, the filtrate was concentrated in vacuo to give a residue, which was purified by column chromatography ($SiO_2$, Petroleum ether/Ethyl acetate=1/0 to 3/1) to give methyl 3-ethyl-5-[[4-(1-ethylpropylamino)-5-methyl-pyrimidin-2-yl]-(trifluoromethylsulfonyl)amino]-2-(trifluoromethylsulfonyloxy)benzoate (300 mg, 471 μmol, 36.91% yield) and methyl 3-ethyl-5-((5-methyl-4-(pentan-3-ylamino)pyrimidin-2-yl)amino)-2-(((trifluoromethyl)sulfonyl)oxy)benzoate (300 mg, 595

μmol, 29.25% yield) as a white solid. $^1$H NMR (CDCl$_3$, 400 MHz) δ 11.24 (s, 1H), 7.84-7.79 (m, 4H), 7.60 (d, J=2.8 Hz, 1H), 7.36 (d, J=2.8 Hz, 1H), 4.41-4.35 (m, 2H), 4.05-3.97 (m, 1H), 3.93 (s, 6H), 3.87-3.83 (m, 1H), 2.82 (q, J=7.6 Hz, 2H), 2.68 (q, J=7.6 Hz, 2H), 1.99 (s, 6H), 1.65-1.51 (m, 3H), 1.49-1.35 (m, 5H), 1.33-1.21 (m, 7H), 0.90-0.80 (m, 14H).

10.8 Preparation of methyl 2-(5,5-dimethyl-1,3,2-dioxaborinan-2-yl)-3-ethyl-5-[[4-(1-ethyl propylamino)-5-methyl-pyrimidin-2-yl]-(trifluoromethylsulfonyl)amino]benzoate

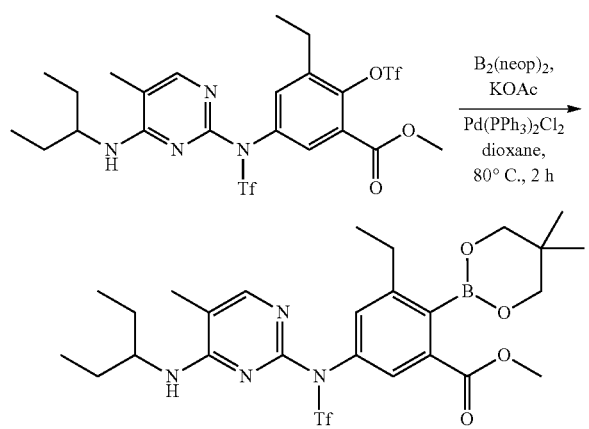

A mixture of methyl 3-ethyl-5-[[4-(1-ethylpropylamino)-5-methyl-pyrimidin-2-yl]-(trifluoro methylsulfonyl)amino]-2-(trifluoromethylsulfonyloxy)benzoate (100 mg, 157 μmol, 1 eq), 2-(5,5-dimethyl-1,3,2-dioxaborinan-2-yl)-5,5-dimethyl-1,3,2-dioxaborinane (106 mg, 471 μmol, 3 eq), KOAc (46 mg, 471 μmol, 3 eq) and Pd(PPh$_3$)$_2$Cl$_2$ (11 mg, 16 μmol, 0.1 eq) in dioxane (10 mL) was degassed and purged with N$_2$ 3 times, then the mixture was stirred at 80° C. for 2 h under N$_2$ atmosphere. The reaction mixture was filtered, the filtrate was concentrated in vacuo to give a residue, which was purified by column chromatography (SiO$_2$, Petroleum ether/ Ethyl acetate=1/0 to 3/1) to give methyl 2-(5,5-dimethyl-1,3,2-dioxaborinan-2-yl)-3-ethyl-5-[[4-(1-ethylpropylamino)-5-methyl-pyrimidin-2-yl]-(trifluoromethylsulfonyl)amino]benzoate (600 mg, crude) as colorless oil.

10.9 Preparation of N-(7-ethyl-1-hydroxy-3H-2,1-benzoxaborol-5-yl)-N-[4-(1-ethylpropylamino)-5-methyl-pyrimidin-2-yl]-1,1,1-trifluoro-methanesulfonamide

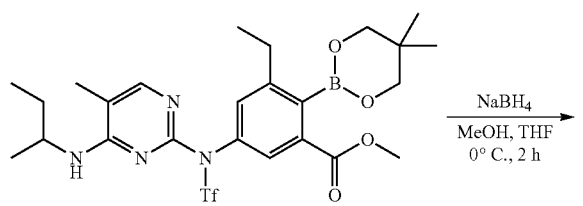

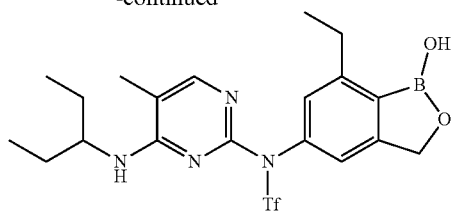

To a mixture of methyl 2-(5,5-dimethyl-1,3,2-dioxaborinan-2-yl)-3-ethyl-5-[[4-(1-ethylpropylamino)-5-methyl-pyrimidin-2-yl]-(trifluoromethylsulfonyl)amino]benzoate (80 mg, 133.23 μmol, 1 eq) in MeOH (0.1 mL) and THF (2 mL) was added NaBH$_4$ (20 mg, 532.93 μmol, 4 eq) at 0° C., and then the mixture was stirred at 20° C. for 2 h under N$_2$ atmosphere. The reaction was quenched by HCl (1 N, 0.5 mL), concentrated in vacuo to give a residue, which was purified by prep-HPLC (column: Nano-micro Kromasil C18 100*30 mm 8 um; mobile phase: [water(0.1% TFA)-ACN]; B %: 50%-60%, 10 min) to give N-(7-ethyl-1-hydroxy-3H-2,1-benzoxaborol-5-yl)-N-[4-(1-ethylpropylamino)-5-methyl-pyrimidin-2-yl]-1,1,1-trifluoro-methanesulfonamide (20 mg, 41.13 μmol, 30.87% yield) as a white solid. $^1$H NMR (DMSO-d$_6$, 400 MHz) δ 9.09 (br s, 1H), 7.77 (s, 1H), 7.24 (s, 1H), 7.12 (s, 1H), 6.73 (d, J=8.4 Hz, 1H), 4.97 (s, 2H), 3.87-3.81 (m, 1H), 2.80 (q, J=7.6 Hz, 2H), 1.97 (s, 3H), 1.50-1.39 (m, 4H), 1.15 (t, J=7.6 Hz, 3H), 0.75 (t, J=7.6 Hz, 6H). MS (ESI): mass calcd. For C$_{20}$H$_{26}$BF$_3$N$_4$O$_4$S 486.17, m/z found 487.1 [M+H]$^+$. HPLC: 96.15% (220 nm), 90.95% (254 nm).

11. Preparation of 7-ethyl-5-((5-methyl-4-(pentan-3-ylamino)pyrimidin-2-yl)amino)benzo[c][1,2]oxaborol-1(3H)-ol

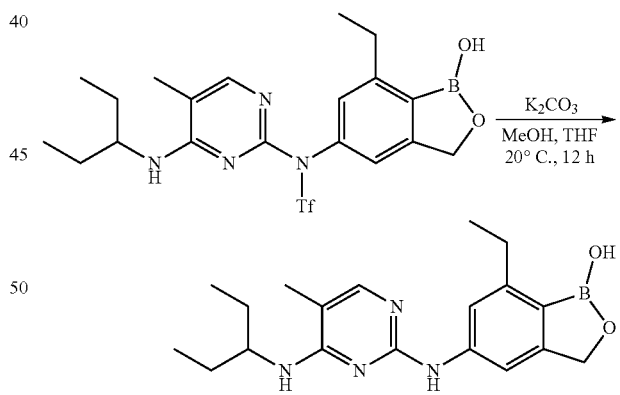

A mixture of N-(7-ethyl-1-hydroxy-3H-2,1-benzoxaborol-5-yl)-N-[4-(1-ethylpropylamino)-5-methyl-pyrimidin-2-yl]-1,1,1-trifluoro-methanesulfonamide (200 mg, 411 μmol, 1 eq) in THF (10 mL) and MeOH (10 mL) was added K$_2$CO$_3$ (142 mg, 1.03 mmol, 2.5 eq) at 0° C., then the mixture was stirred at 20° C. for 12 h under N$_2$ atmosphere. The reaction mixture was filtered, the filtrate was concentrated in vacuo to give a residue, which was purified by prep-HPLC (column: Nano-micro Kromasil C18 100*30 mm 8 um; mobile phase: [water(0.1% TFA)-ACN]; B %: 30%-50%, 10 min) to give N2-(7-ethyl-1-hydroxy-3H-2,1-benzoxaborol-5-yl)-N4-(1-ethylpropyl)-5-methyl-pyrimidine-2,4-diamine (45 mg, 127 μmol, 15.44% yield) as white solid. $^1$H NMR (DMSO-d$_6$, 400 MHz) δ 10.25 (s, 1H), 8.89 (s, 1H), 7.91 (d, J=8.0 Hz, 1H), 7.73 (s, 1H), 7.41 (s, 1H), 7.36 (s, 1H), 4.95 (s, 2H), 4.13-4.07 (m, 1H), 2.78 (q, J=7.6 Hz, 2H), 2.03 (s, 3H), 1.64-1.56 (m, 4H), 1.90 (t, J=7.6 Hz, 3H), 0.85 (t, J=7.6 Hz, 6H). MS (ESI): mass calcd. For C$_{19}$H$_{27}$BN$_4$O$_2$ 354.22, m/z found 355.1 [M+H]$^+$. HPLC: 93.05% (220 nm), 95.97% (254 nm).

12. Preparation of 5-((5-chloro-4-(cyclopentylamino)pyrimidin-2-yl)amino)-7-methylbenzo[c][1,2]oxaborol-1(3H)-ol

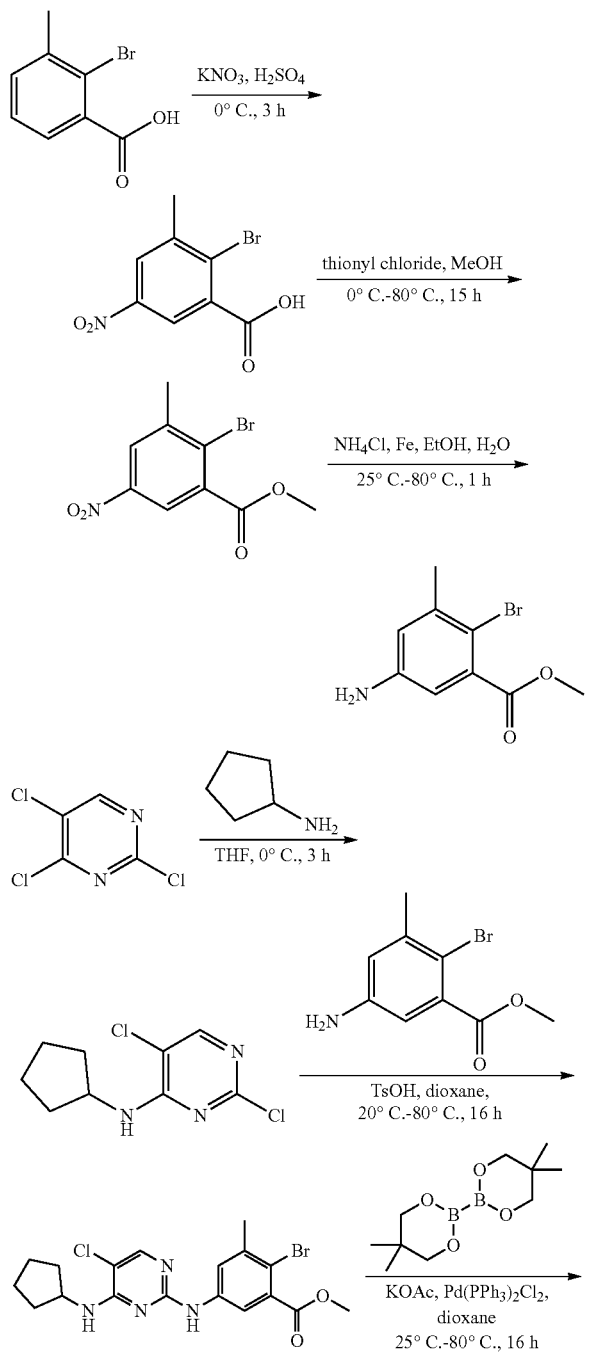

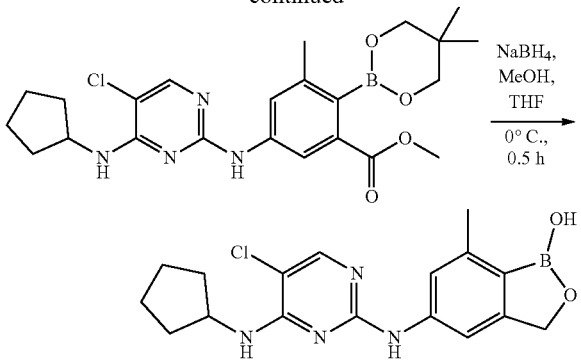

12.1 Preparation of 2-bromo-3-methyl-5-nitro-benzoic Acid

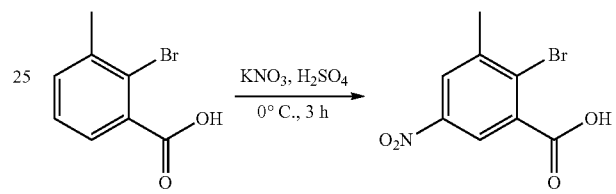

To a mixture of 2-Bromo-3-methyl-benzoic acid (10 g, 46.5 mmol, 1 eq) in concentrated H$_2$SO$_4$ (70 mL) was added a solution of KNO$_3$ (4.61 g, 45.5 mmol, 0.98 eq) in H$_2$SO$_4$ (30 mL), the resulting mixture was stirred for 3 h at 0° C. The reaction mixture was poured into ice-water (w/w=1/1) (200 mL), the mixture was filtered, and the filter cake was dissolved in ethyl acetate (200 mL). The resulting solution was washed with brine (50 mL×2), dried over anhydrous Na$_2$SO$_4$, filtered and concentrated in vacuo to give 2-bromo-3-methyl-5-nitro-benzoic acid (10.6 g, crude) as a brown solid. $^1$H NMR (CDCl$_3$, 400 MHz) δ 8.55 (d, J=2.8 Hz, 1H), 8.27 (d, J=2.8 Hz, 1H), 2.63 (s, 3H).

12.2 Preparation of methyl 2-bromo-3-methyl-5-nitro-benzoate

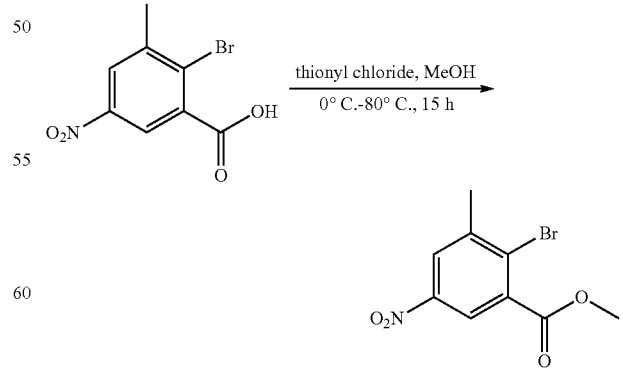

To a mixture of 2-bromo-3-methyl-5-nitro-benzoic acid (8.5 g, 32.7 mmol, 1 eq) in MeOH (100 mL) was added thionyl chloride (65.3 mmol, 4.7 mL, 2 eq) at 0° C., the resulting mixture was heated to 80° C. and stirred for 15 h. The reaction mixture was cooled to room temperature, concentrated in vacuo to give a residue, which was purified by column chromatography (SiO₂, Petroleum ether/Ethyl acetate=10/1 to 5/1) to give methyl 2-bromo-3-methyl-5-nitro-benzoate (8.5 g, 31.0 mmol, 94.9% yield) as an off-white solid. $^1$H NMR (CDCl₃, 400 MHz) δ 8.35 (d, J=2.4 Hz, 1H), 8.20 (d, J=2.4 Hz, 1H), 3.99 (s, 3H), 2.59 (s, 3H).

12.3 Preparation of methyl 5-amino-2-bromo-3-methyl-benzoate

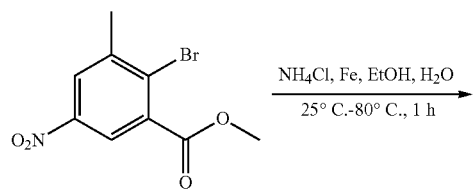

To a mixture of methyl 2-bromo-3-methyl-5-nitro-benzoate (7.5 g, 27.4 mmol, 1 eq) in EtOH (100 mL) and H₂O (20 mL) was added NH₄Cl (5.86 g, 109 mmol, 4 eq) and Fe (6.11 g, 109 mmol, 4 eq) in one portion at 25° C. under N₂ atmosphere, the resulting mixture was heated to 80° C. and stirred for 1 h. The reaction mixture was filtered, and the filtrate was concentrated in vacuo to give a residue. The residue was dissolved in DCM (100 mL), the resulting solution was dried over anhydrous Na₂SO₄, filtered and concentrated in vacuo to give methyl 5-amino-2-bromo-3-methyl-benzoate (6 g, 24.6 mmol, 89.8% yield) as brown oil. $^1$H NMR (CDCl₃, 400 MHz) δ 6.79 (s, 1H), 6.67 (s, 1H), 3.90 (s, 3H), 3.72 (br s, 2H), 2.34 (s, 3H).

12.4 Preparation of 2,5-dichloro-N-cyclopentyl-pyrimidin-4-amine

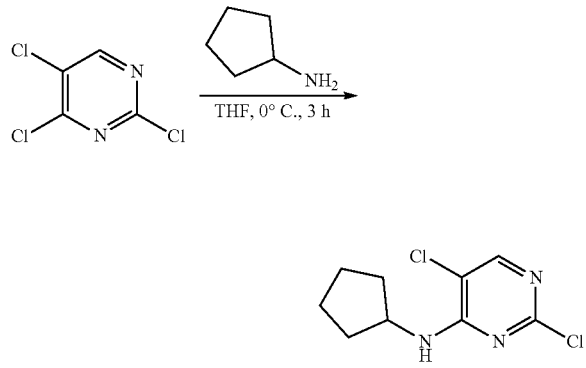

To a mixture of 2,4,5-trichloropyrimidine (13 g, 70.8 mmol, 1 eq) in THF (150 mL) was added cyclopentanamine (106 mmol, 10.5 mL, 1.5 eq) dropwise at 0° C., the mixture was stirred at 0° C. for 3 h. The reaction mixture was poured into ice-water (w/w=1/1) (200 mL), the aqueous phase was extracted with ethyl acetate (100 mL×2), the combined organic phase was washed with brine (50 mL×2), dried over anhydrous Na₂SO₄, filtered and concentrated in vacuo to give a residue, which was purified by column chromatography (SiO₂, Petroleum ether/Ethyl acetate=20/1 to 10/1) to give 2,5-dichloro-N-cyclopentyl-pyrimidin-4-amine (12.6 g, 54.2 mmol, 76.6% yield) as a white solid. $^1$H NMR (CDCl₃, 400 MHz) δ 7.97 (s, 1H), 5.43 (d, J=4.0 Hz, 1H), 4.44-4.38 (m, 1H), 2.14-2.11 (m, 2H), 1.75-1.66 (m, 4H), 1.49-1.45 (m, 2H).

12.5 Preparation of methyl 2-bromo-5-[[5-chloro-4-(cyclopentylamino)pyrimidin-2-yl]amino]-3-methyl-benzoate

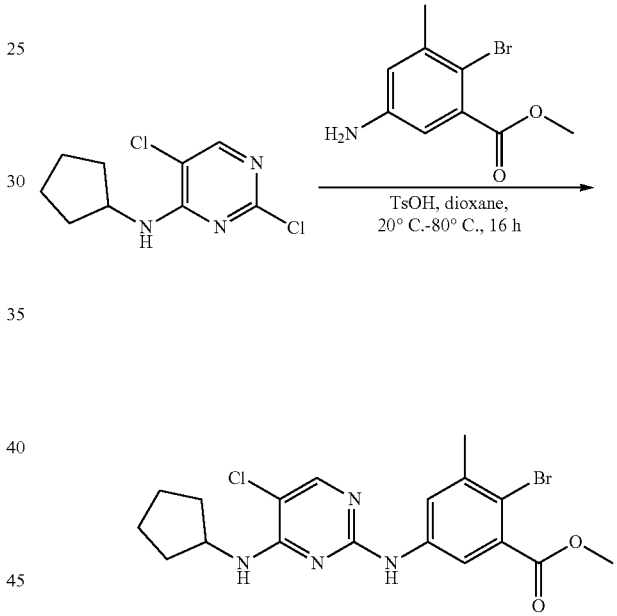

To a mixture of 2,5-dichloro-N-cyclopentyl-pyrimidin-4-amine (2 g, 8.62 mmol, 1 eq) and methyl 5-amino-2-bromo-3-methyl-benzoate (2.1 g, 8.62 mmol, 1 eq) in dioxane (50 mL) was added TsOH (2.23 g, 12.9 mmol, 1.5 eq) dropwise at 20° C. under N₂ atmosphere. The mixture was heated to 80° C. and stirred for 16 h. The reaction mixture was poured into sat. aq. NaHCO₃ (100 mL), the aqueous phase was extracted with ethyl acetate (50 mL×3), the combined organic phase was washed with brine (50 mL×2), dried over anhydrous Na₂SO₄, filtered and concentrated in vacuo to give a residue. The residue was purified by column chromatography (SiO₂, Petroleum ether/Ethyl acetate=3/1 to 1/1) to give methyl 2-bromo-5-[[5-chloro-4-(cyclopentylamino)pyrimidin-2-yl]amino]-3-methyl-benzoate (1.5 g, 3.41 mmol, 39.6% yield) as a white solid. $^1$H NMR (DMSO-d₆, 400 MHz) δ 9.49 (s, 1H), 8.02 (s, 1H), 7.96 (s, 1H), 7.78 (s, 1H), 6.92 (d, J=7.2 Hz, 1H), 4.38-4.33 (m, 1H), 3.83 (s, 3H), 2.34 (s, 3H), 1.98-1.93 (m, 2H), 1.72-1.70 (m, 2H), 1.62-1.54 (m, 4H).

12.6 Preparation of methyl 5-[[5-chloro-4-(cyclo-pentylamino)pyrimidin-2-yl]amino]-2-(5,5-dimethyl-1,3,2-dioxaborinan-2-yl)-3-methyl-benzoate

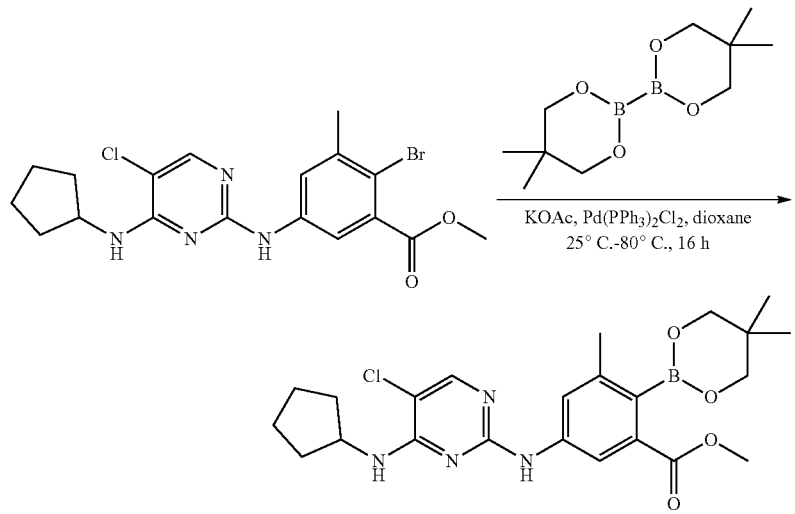

To a mixture of methyl 2-bromo-5-[[5-chloro-4-(cyclopentylamino) pyrimidin-2-yl]amino]-3-methyl-benzoate (500 mg, 1.14 mmol, 1 eq) in dioxane (15 mL) was added KOAc (279 mg, 2.84 mmol, 2.5 eq), Pd(PPh$_3$)$_2$Cl$_2$ (79 mg, 113 µmol, 0.1 eq) and 2-(5,5-dimethyl-1,3,2-dioxaborinan-2-yl)-5,5-dimethyl-1,3,2-dioxaborinane (513 mg, 2.27 mmol, 2 eq) in one portion at 25° C. under N$_2$ atmosphere, then the mixture was heated to 80° C. and stirred for 16 h. The reaction mixture was filtered, the filtrate was concentrated in vacuo to give methyl 5-[[5-chloro-4-(cyclopentylamino)pyrimidin-2-yl]amino]-2-(5,5-dimethyl-1,3,2-dioxaborinan-2-yl)-3-methyl-benzoate (700 mg, crude) as a brown solid. MS (ESI): mass calcd. For C$_{23}$H$_{30}$BClN$_4$O$_4$ 472.20, m/z found 473.2 [M+H]$^+$.

12.7 Preparation of 5-chloro-N4-cyclopentyl-N2-(1-hydroxy-7-methyl-3H-2,1-benzoxaborol-5-yl)pyrimidine-2,4-diamine

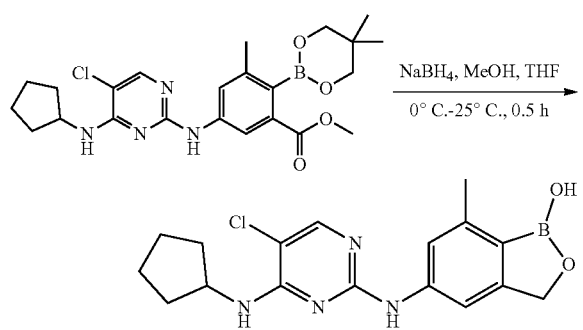 [SMILES: COC(=O)c1cc(Nc2ncc(Cl)c(NC3CCCC3)n2)cc(C)c1B1OCC(C)(C)CO1 ; Cc1cc(Nc2ncc(Cl)c(NC3CCCC3)n2)cc2c1B(O)OC2]

To a mixture of methyl 5-[[5-chloro-4-(cyclopentylamino)pyrimidin-2-yl]amino]-2-(5,5-dimethyl-1,3,2-dioxaborinan-2-yl)-3-methyl-benzoate (700 mg, crude) and MeOH (0.1 mL, 1.67 eq) in THF (8 mL) was added NaBH$_4$ (168 mg, 4.44 mmol, 3 eq) in portions at 0° C., then the reaction was stirred at 25° C. for 30 min. The reaction mixture was poured into ice-water (w/w=1/1) (8 mL), pH of the aqueous phase was adjusted to 3-4 with HCl (2N), which was extracted with ethyl acetate (5 mL×3). The combined organic phase was washed with brine (5 mL×2), dried over anhydrous Na$_2$SO$_4$, filtered and concentrated in vacuo to give a residue. The residue was purified by prep-HPLC (column: Nano-micro Kromasil C18 100*30 mm 8 um; mobile phase: [water (0.1% TFA)-ACN]; B %: 20%-50%, 10 min) to give the product with TFA residue. The product was dissolved in ice-water (w/w=1/1) (8 mL), and the pH of the aqueous phase was adjusted to 7 with NaHCO$_3$ (2N), extracted with ethyl acetate (5 mL×3), the combined organic phase was washed with brine (5 mL×2), dried over anhydrous Na$_2$SO$_4$, filtered and concentrated in vacuum to give 5-chloro-N4-cyclopentyl-N2-(1-hydroxy-7-methyl-3H-2,1-benzoxaborol-5-yl)pyrimidine-2,4-diamine (16 mg, 42 µmol, 2.82% yield, 93.73% purity) as a yellow solid. $^1$H NMR (DMSO-d$_6$, 400 MHz) δ 9.33 (s, 1H), 8.65 (s, 1H), 7.95 (s, 1H), 7.64 (s, 1H), 7.48 (s, 1H), 6.86 (d, J=7.2 Hz, 1H), 4.88 (s, 2H), 4.42-4.36 (m, 1H), 2.37 (s, 3H), 2.01-1.98 (m, 2H), 1.74-1.73 (m, 2H), 1.61-1.56 (m, 4H). MS (ESI): mass calcd. For C$_{17}$H$_{20}$BClN$_4$O$_2$ 358.14, m/z found 359.1 [M+H]$^+$. HPLC: 93.73% (220 nm), 94.52% (254 nm).

13. Preparation of 7-chloro-3,3-dimethyl-5-((5-methyl-4-(pentan-3-ylamino)pyrimidin-2-yl)amino) benzo[c][1,2] oxaborol-1(3H)-ol

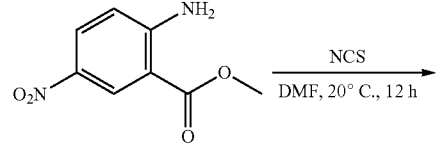

13.1 Preparation of methyl 2-amino-3-chloro-5-nitro-benzoate

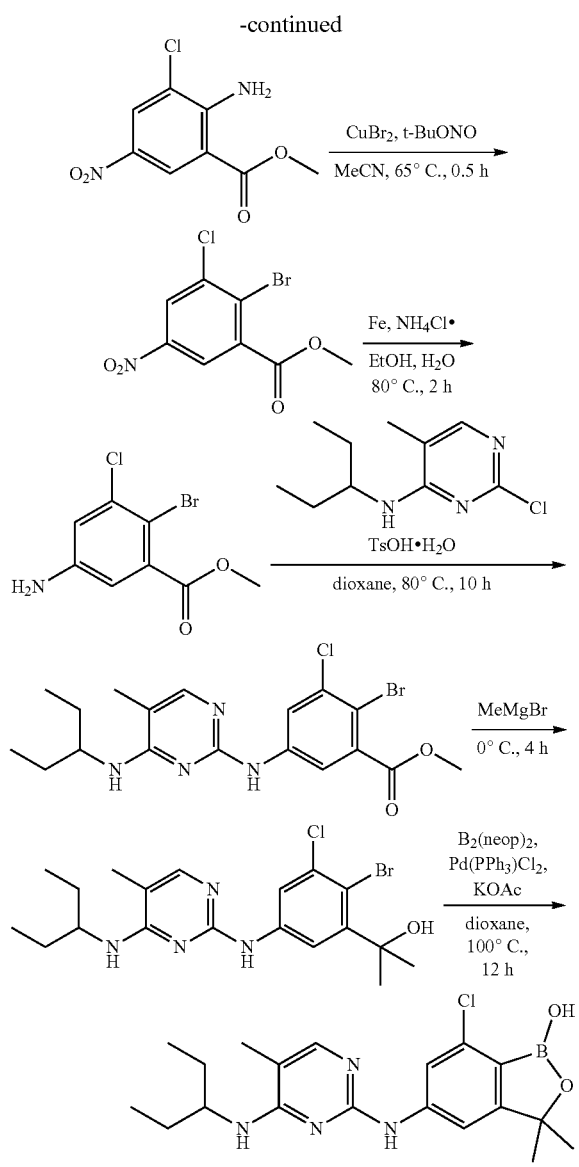

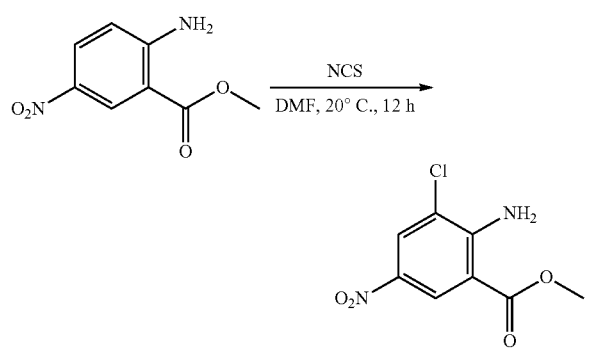

To a mixture of methyl 2-amino-5-nitro-benzoate (12 g, 61.17 mmol, 1 eq) in DMF (120 mL) was added NCS (10.6 g, 79.5 mmol, 1.3 eq) in portions at 20° C. The mixture was stirred at 20° C. for 12 h. The reaction mixture was poured into H₂O (200 mL), then yellow precipitate was collected by filtration, dried in vacuo to give methyl 2-amino-3-chloro-5-nitro-benzoate (13 g, 56.37 mmol, 92.15% yield) as a yellow solid. ¹H NMR (DMSO-d₆, 400 MHz) δ 8.52 (dd, J=6.8, 2.8 Hz, 1H), 8.29 (dd, J=7.6, 2.4 Hz, 1H), 3.88 (s, 3H).

13.2 Preparation of methyl 2-bromo-3-chloro-5-nitro-benzoate

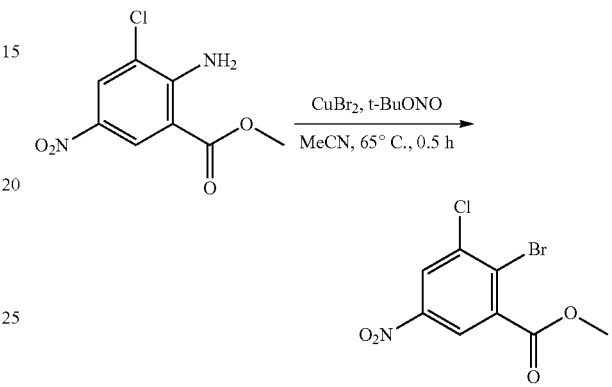

To a mixture of t-BuONO (8.94 g, 86.7 mmol, 10.3 mL, 2 eq) and CuBr₂ (14.53 g, 65.0 mmol, 3.0 mL, 1.5 eq) in MeCN (100 mL) was added methyl 2-amino-3-chloro-5-nitro-benzoate (10 g, 43.4 mmol, 1 eq) in portions at 65° C. The mixture was stirred at 65° C. for 30 min. The reaction mixture was poured into H₂O (150 mL), the aqueous phase was extracted with EtOAc (100 mL×3). The combined organic layers were washed with sat. aq. Na₂SO₃ (100 mL×3), the combined organic layers were washed with brine (100 mL×2), dried over anhydrous Na₂SO₄, filtered and concentrated in vacuo to give a residue, which was purified by flash silica gel chromatography (ISCO®; 120 g Sepa-Flash® Silica Flash Column, Eluent of 0-10% Ethyl acetate/ Petroleum ethergradient @ 100 mL/min) to give methyl 2-bromo-3-chloro-5-nitro-benzoate (11 g, 37.3 mmol, 86.14% yield) as a yellow solid. ¹H NMR (CDCl₃, 400 MHz) δ 8.43-8.42 (m, 2H), 4.01 (s, 3H).

13.3 Preparation of methyl 5-amino-2-bromo-3-chloro-benzoate

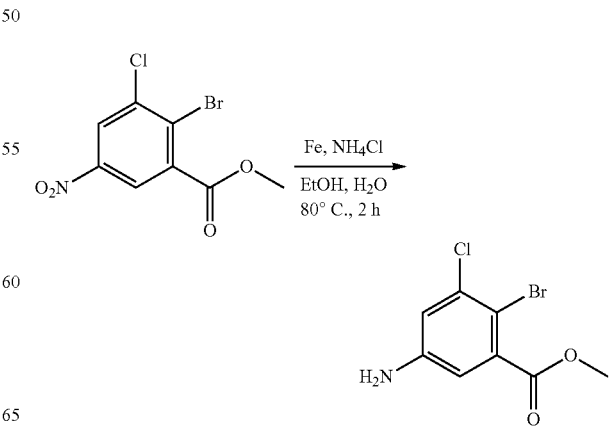

To a mixture of methyl 2-bromo-3-chloro-5-nitro-benzoate (11 g, 37.4 mmol, 1 eq) in EtOH (110 mL) and H$_2$O (30 mL) was added Fe (6.26 g, 112 mmol, 3 eq) and NH$_4$Cl (3.00 g, 56.0 mmol, 1.5 eq) in one portion at 20° C. The mixture was stirred at 80° C. for 2 h. The reaction mixture was filtered, the filtrate was concentrated in vacuo to give a residue, which was dissolved in DCM (100 mL), dried over anhydrous Na$_2$SO$_4$, filtered and concentrated in vacuo to give methyl 5-amino-2-bromo-3-chloro-benzoate (10 g, crude) as yellow oil. $^1$H NMR (CDCl$_3$, 400 MHz) δ 6.90-6.89 (m, 1H), 6.86-6.85 (m, 1H), 3.92 (s, 3H).

13.4 Preparation of methyl 2-bromo-3-chloro-5-[[4-(1-ethylpropylamino)-5-methyl-pyrimidin-2-yl]amino]benzoate

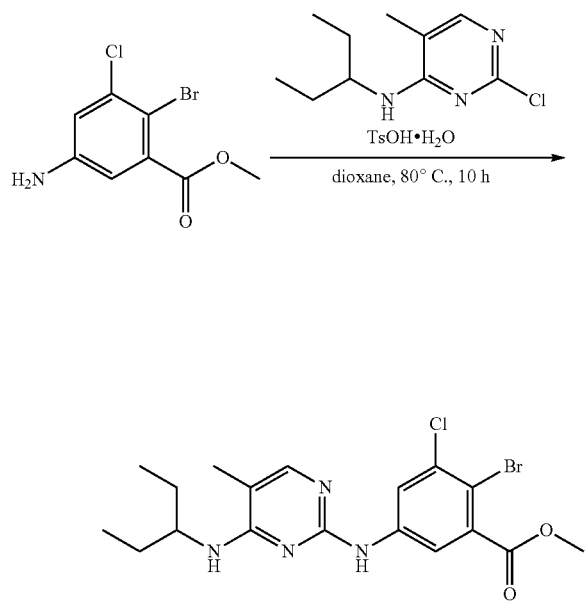

To a mixture of methyl 5-amino-2-bromo-3-chloro-benzoate (2.72 g, 10.3 mmol, 1.1 eq) and 2-chloro-N-(1-ethylpropyl)-5-methyl-pyrimidin-4-amine (2 g, 9.36 mmol, 1 eq) in dioxane (20 mL) was added TsOH·H$_2$O (2.67 g, 14.0 mmol, 1.5 eq) in one portion at 20° C. The mixture was heated up to 80° C. and kept stirring for 10 h. The reaction mixture was cooled to room temperature, and its pH was adjusted to 7 by sat. aq. NaHCO$_3$, the aqueous phase was extracted with EtOAc (20 mL×3). The combined organic layers were washed with brine (20 mL×2), dried over anhydrous Na$_2$SO$_4$, filtered and concentrated in vacuo to give a residue, which was purified by flash silica gel chromatography (ISCO®; 40 g SepaFlash® Silica Flash Column, Eluent of 0-40% Ethyl acetate/Petroleum ethergradient @ 75 mL/min) to give methyl 2-bromo-3-chloro-5-[[4-(1-ethylpropylamino)-5-methyl-pyrimidin-2-yl]amino]benzoate (2.1 g, 4.75 mmol, 50.80% yield) as a yellow solid. $^1$H NMR (DMSO-d$_6$, 400 MHz) δ 9.38 (s, 1H), 8.25 (s, 1H), 8.11 (s, 1H), 7.69 (s, 1H), 6.27 (d, J=7.6 Hz, 1H), 4.09-4.00 (m, 1H), 3.86 (s, 3H), 1.95 (s, 3H), 1.63-1.52 (m, 4H), 0.86 (t, J=7.6 Hz, 6H).

13.5 Preparation of 2-[2-bromo-3-chloro-5-[[4-(1-ethylpropylamino)-5-methyl-pyrimidin-2-yl]amino]phenyl]propan-2-ol

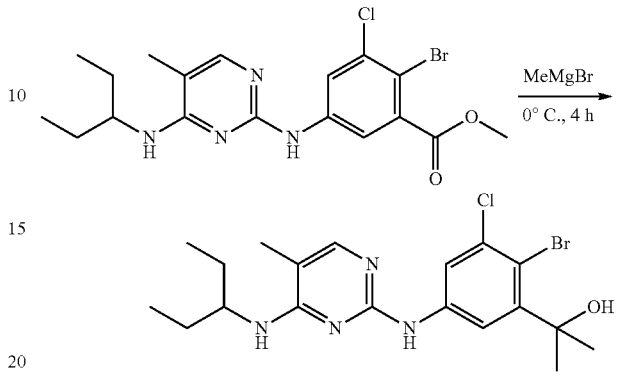

Methyl 2-bromo-3-chloro-5-[[4-(1-ethylpropylamino)-5-methyl-pyrimidin-2-yl]amino]benzoate (1 g, 2.26 mmol, 1 eq) was added to MeMgBr (3 M, 11.3 mL, 15 eq) in portions at 0° C., the resulting mixture was stirred at 0° C. for 4 h. The reaction mixture was poured into sat. aq. NH$_4$Cl (20 mL), and the aqueous phase was extracted with EtOAc (20 mL×3). The combined organic layer was washed with brine (20 mL×2), dried over anhydrous Na$_2$SO$_4$, filtered and concentrated in vacuo to give a residue, which was purified by flash silica gel chromatography (ISCO®; 20 g SepaFlash® Silica Flash Column, Eluent of 0-60% Ethyl acetate/Petroleum ethergradient @ 75 mL/min) to give 2-[2-bromo-3-chloro-5-[[4-(1-ethylpropylamino)-5-methyl-pyrimidin-2-yl]amino]phenyl] propan-2-ol (0.6 g, 1.36 mmol, 59.99% yield) as a yellow solid. $^1$H NMR (CDCl$_3$, 400 MHz) δ 8.33 (d, J=2.8 Hz, 1H), 7.73 (s, 1H), 7.49 (d, J=2.4 Hz, 1H), 4.28-4.26 (m, 1H), 4.20-4.16 (m, 1H), 1.97 (s, 3H), 1.78 (s, 6H), 1.71-1.68 (m, 2H), 1.57-1.53 (m, 2H), 0.96 (t, J=7.6 Hz, 6H).

13.6 Preparation of N2-(7-chloro-1-hydroxy-3,3-dimethyl-2,1-benzoxaborol-5-yl)-N4-(1-ethylpropyl)-5-methyl-pyrimidine-2,4-diamine

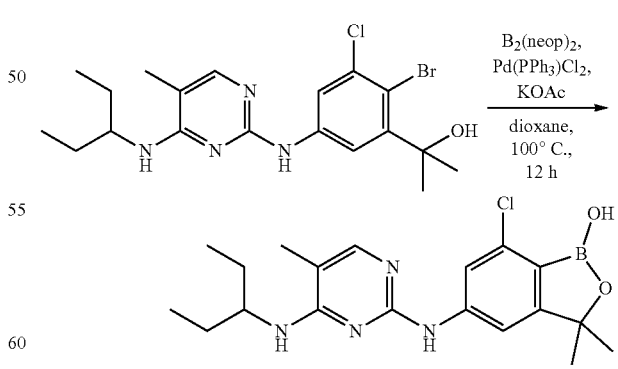

To a mixture of 2-[2-bromo-3-chloro-5-[[4-(1-ethylpropylamino)-5-methyl-pyrimidin-2-yl]amino]phenyl]propan-2-ol (0.6 g, 1.36 mmol, 1 eq) and 2-(5,5-dimethyl-1,3,2-dioxaborinan-2-yl)-5,5-dimethyl-1,3,2-dioxaborinane (614 mg, 2.72 mmol, 2 eq) in dioxane (10 mL) was added KOAc (333 mg, 3.40 mmol, 2.5 eq) and Pd(PPh$_3$)$_2$Cl$_2$ (95 mg, 135.81 μmol, 0.1 eq) in one portion at 20° C., the resulting mixture was stirred at 100° C. for 12 h under N$_2$ atmosphere. The reaction mixture was filtered, the filtrate was concentrated in vacuo to give a residue, which was purified by prep-HPLC (column: Nano-micro Kromasil C18 100*30 mm 8 um; mobile phase: [water(0.1% TFA)-ACN]; B %: 25%-50%, 10 min) to give N2-(7-chloro-1-hydroxy-3,3-dimethyl-2,1-benzoxaborol-5-yl)-N4-(1-ethylpropyl)-5-methyl-pyrimidine-2,4-diamine (202 mg, 519.68 μmol, 38.27% yield) as a white solid. $^1$H NMR (DMSO-d$_6$, 400 MHz) δ 10.63 (s, 1H), 8.96 (s, 1H), 7.95 (d, J=8.4 Hz, 1H), 7.79 (s, 1H), 7.60-7.59 (m, 2H), 4.17-4.08 (m, 1H), 2.04 (s, 3H), 1.67-1.56 (m, 4H), 1.46 (s, 6H), 0.86 (t, J=7.2 Hz, 6H). MS (ESI): mass calcd. For C$_{19}$H$_{26}$BClN$_4$O$_2$ 388.18, m/z found 389.2 [M+H]$^+$. HPLC: 99.84% (220 nm), 99.83% (254 nm).

14. Preparation of 7-chloro-5-((5-methyl-4-(pentan-3-ylamino)pyrimidin-2-yl)amino)benzo [c][1,2]oxaborol-1(3H)-ol

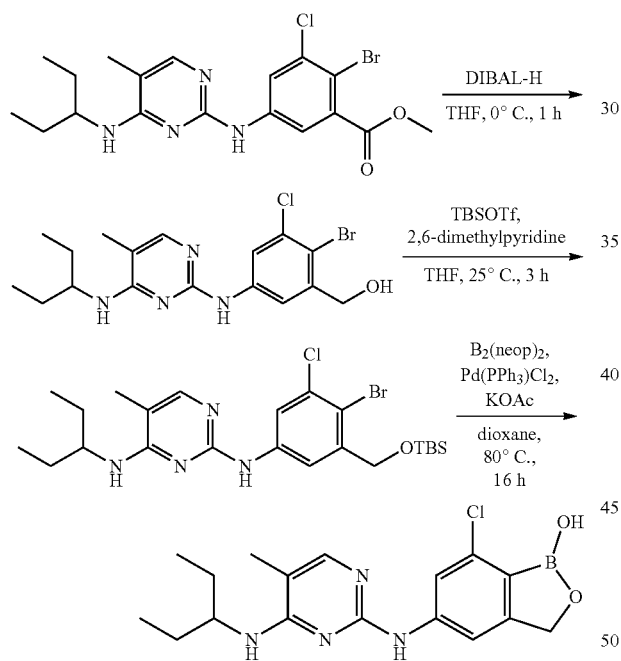

14.1 Preparation of [2-bromo-3-chloro-5-[[4-(1-ethylpropylamino)-5-methyl-pyrimidin-2-yl]amino]phenyl]methanol

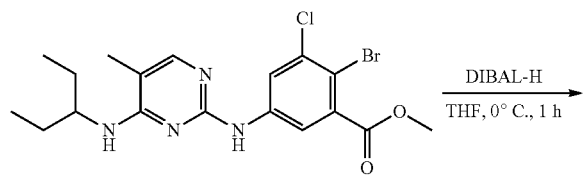

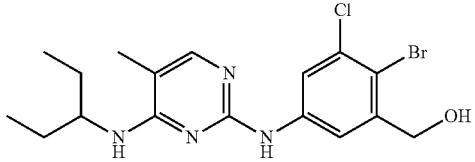

To a mixture of methyl 2-bromo-3-chloro-5-[[4-(1-ethylpropylamino)-5-methyl-pyrimidin-2-yl]amino]benzoate (1.5 g, 3.40 mmol, 1 eq) in THF (20 mL) was added DIBAL-H (1 M, 13.6 mL, 4 eq) dropwise at 0° C., the resulting mixture was stirred at 0° C. for 1 h. Then Na$_2$SO$_4$·10H$_2$O (5 g) was added to above mixture, the resulting mixture was stirred at 25° C. for 10 min. The mixture was filtered, and the filtrate was concentrated in vacuo to give [2-bromo-3-chloro-5-[[4-(1-ethylpropylamino)-5-methyl-pyrimidin-2-yl]amino]phenyl]methanol (1 g, 2.42 mmol, 71.18% yield) as a yellow solid. $^1$H NMR (DMSO-d$_6$, 400 MHz) δ 9.18 (s, 1H), 8.24 (d, J=2.8 Hz, 1H), 7.78 (d, J=2.8 Hz, 1H), 7.66 (s, 1H), 6.17 (d, J=8.8 Hz, 1H), 5.46 (t, J=6.0 Hz, 1H), 4.46 (d, J=5.6 Hz, 2H), 4.18-4.09 (m, 1H), 1.94 (s, 3H), 1.64-1.52 (m, 4H), 0.87 (t, J=7.2 Hz, 6H).

14.2 Preparation of N2-[4-bromo-3-[[tert-butyl(dimethyl)silyl]oxymethyl]-5-chloro-phenyl]-N4-(1-ethylpropyl)-5-methyl-pyrimidine-2,4-diamine

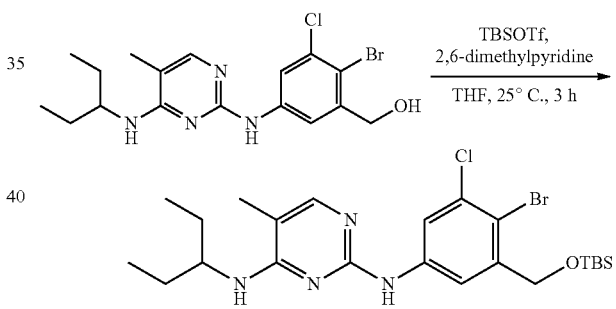

To a mixture of [2-bromo-3-chloro-5-[[4-(1-ethylpropylamino)-5-methyl-pyrimidin-2-yl]amino]phenyl]methanol (0.9 g, 2.18 mmol, 1 eq) in THF (10 mL) was added TBSOTf (863 mg, 3.26 mmol, 750 μL, 1.5 eq) and 2,6-dimethylpyridine (396 mg, 3.70 mmol, 430 μL, 1.7 eq) in one portion at 25° C. The mixture was stirred at 25° C. for 3 h. The reaction mixture was poured into H$_2$O (20 mL), and the aqueous phase was extracted with EtOAc (20 mL×3). The combined organic layers were washed with brine (20 mL×2), dried over anhydrous Na$_2$SO$_4$, filtered and concentrated in vacuo to give a residue, which was purified by flash silica gel chromatography (ISCO®; 20 g SepaFlash® Silica Flash Column, Eluent of 0-20% Ethyl acetate/Petroleum ethergradient @ 36 mL/min) to give N2-[4-bromo-3-[[tert-butyl(dimethyl)silyl]oxymethyl]-5-chloro-phenyl]-N4-(1-ethylpropyl)-5-methyl-pyrimidine-2,4-diamine (0.7 g, 1.33 mmol, 60.95% yield) as a yellow solid. $^1$H NMR (DMSO-d$_6$, 400 MHz) δ 9.30 (s, 1H), 8.34 (d, J=2.4 Hz, 1H), 7.69 (d, J=2.4 Hz, 1H), 7.66 (s, 1H), 6.19 (d, J=8.8 Hz, 1H), 4.64 (s, 2H), 4.14-4.07 (m, 1H), 1.94 (s, 3H), 1.63-1.49 (m, 4H), 0.93 (s, 9H), 0.87 (t, J=7.6 Hz, 6H), 0.12 (s, 6H).

14.3 Preparation of N2-(7-chloro-1-hydroxy-3H-2,1-benzoxaborol-5-yl)-N4-(1-ethylpropyl)-5-methyl-pyrimidine-2,4-diamine

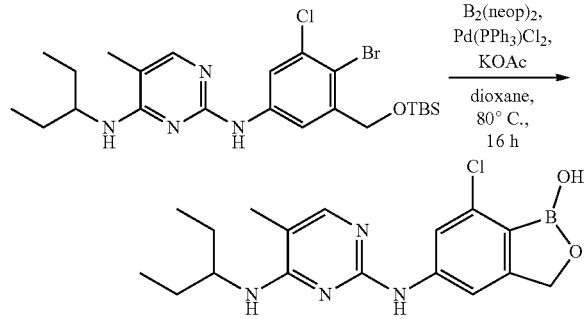 [SMILES: CCC(CC)Nc1nc(Nc2cc(Cl)c(Br)c(CO[Si](C)(C)C(C)(C)C)c2)ncc1C ; CCC(CC)Nc1nc(Nc2cc(Cl)c3c(c2)COB3O)ncc1C]

To a mixture of N2-[4-bromo-3-[[tert-butyl(dimethyl)silyl]oxymethyl]-5-chloro-phenyl]-N4-(1-ethylpropyl)-5-methyl-pyrimidine-2,4-diamine (0.6 g, 1.14 mmol, 1 eq) and 2-(5,5-dimethyl-1,3,2-dioxaborinan-2-yl)-5,5-dimethyl-1,3,2-dioxaborinane (513 mg, 2.27 mmol, 2 eq) in dioxane (10 mL) was added KOAc (335 mg, 3.41 mmol, 3 eq) and Pd(PPh$_3$)$_2$Cl$_2$ (80 mg, 114 μmol, 0.1 eq) in one portion at 25° C. The mixture was stirred at 80° C. for 16 h under N$_2$ atmosphere. The reaction mixture was filtered, HCl (2N, 1 mL) was added into the filtrate, which was concentrated in vacuo to give a residue. The residue was purified by prep-HPLC (column: Phenomenex Luna C18 150*30 mm*5 um; mobile phase: [water(0.1% TFA)-ACN]; B %: 20%-40%, 12 min) to give N2-(7-chloro-1-hydroxy-3H-2,1-benzoxaborol-5-yl)-N4-(1-ethylpropyl)-5-methyl-pyrimidine-2,4-diamine (103 mg, 285.60 μmol, 25.13% yield) as a white solid. $^1$H NMR (DMSO-d$_6$, 400 MHz) δ 10.47 (s, 1H), 9.10 (s, 1H), 7.85 (s, 1H), 7.78 (d, J=8.0 Hz, 2H), 7.45 (s, 1H), 4.99 (s, 2H), 4.09-4.02 (m, 1H), 2.03 (s, 3H), 1.68-1.52 (m, 4H), 0.87 (t, J=7.6 Hz, 6H). MS (ESI): mass calcd. For C$_{17}$H$_{22}$BClN$_4$O$_2$ 360.15, m/z found 361.1 [M+H]$^+$. HPLC: 99.83% (220 nm), 99.82% (254 nm).

15. Preparation of 5-((5-chloro-4-(cyclopentylamino)pyrimidin-2-yl)amino)-3,3,7-trimethylbenzo[c][1,2]oxaborol-1(3H)-ol

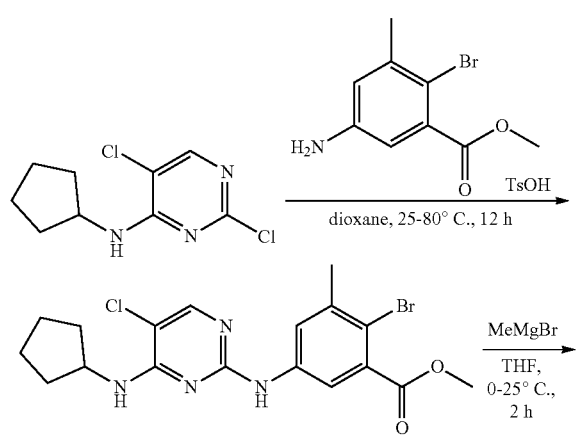

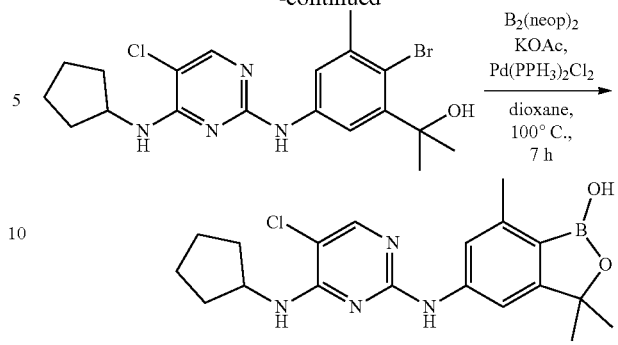

15.1 Preparation of methyl 2-bromo-5-[[5-chloro-4-(cyclopentylamino) pyrimidin-2-yl]amino]-3-methyl-benzoate

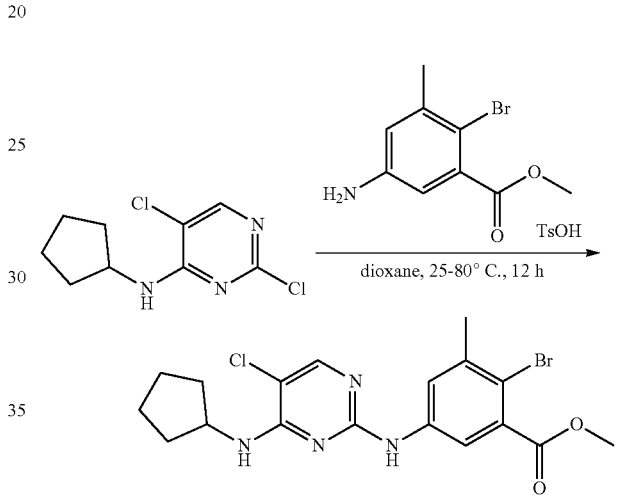

To a mixture of methyl 5-amino-2-bromo-3-methyl-benzoate (2.31 g, 9.45 mmol, 1 eq) and 2,5-dichloro-N-cyclopentyl-pyrimidin-4-amine (2.19 g, 9.45 mmol, 1 eq) in dioxane (60 mL) was added TsOH (1.79 g, 10.4 mmol, 1.1 eq) at 25° C. under N$_2$ atmosphere, the resulting mixture was heated to 80° C. for 12 h. The reaction mixture was filtered, and the filtrate was concentrated in vacuo to give a residue, which was purified by re-crystallization from MTBE (40 mL) at 25° C. to give methyl 2-bromo-5-[[5-chloro-4-(cyclopentylamino) pyrimidin-2-yl]amino]-3-methyl-benzoate (3.00 g, 6.82 mmol, 72.18% yield) as a white solid. $^1$H NMR (DMSO-d$_6$, 400 MHz) δ 9.49 (s, 1H), 8.03 (d, J=2.8 Hz, 1H), 7.97 (s, 1H), 7.79 (d, J=2.4 Hz, 1H), 6.93 (d, J=7.6 Hz, 1H), 4.37 (q, J=7.6 Hz, 1H), 3.84 (s, 3H), 2.36 (s, 3H), 1.99-1.96 (m, 2H), 1.74-1.73 (m, 2H), 1.62-1.54 (m, 4H).

15.2 Preparation of 2-[2-bromo-5-[[5-chloro-4-(cyclopentylamino)pyrimidin-2-yl]amino]-3-methyl-phenyl]propan-2-ol

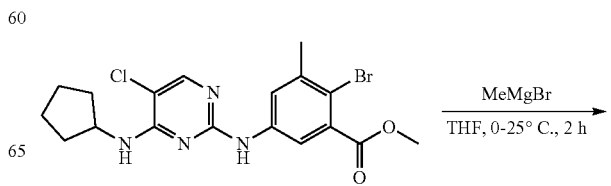

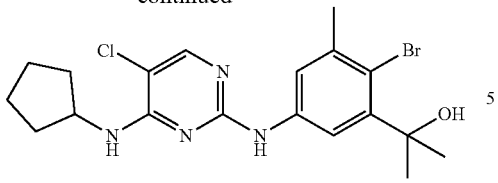

To a mixture of methyl 2-bromo-5-[[5-chloro-4-(cyclopentylamino)pyrimidin-2-yl]amino]-3-methyl-benzoate (1.00 g, 2.27 mmol, 1 eq) in THF (6 mL) was added MeMgBr (3 M, 4.60 mL, 6 eq) in one portion at 0° C. under N$_2$ atmosphere, the resulting mixture was stirred at 25° C. for 2 h. sat. NH$_4$Cl (50 mL) was added into above mixture, and the aqueous phase extracted with EtOAc (30 mL×3). The combined organic layers were washed with brine (20 mL×2), dried over anhydrous Na$_2$SO$_4$, filtered and concentrated in vacuo to give 2-[2-bromo-5-[[5-chloro-4-(cyclopentylamino) pyrimidin-2-yl]amino]-3-methyl-phenyl]propan-2-ol (0.85 g, 1.93 mmol, 84.99% yield) as yellow oil, which was used directly without further purification in the next step.

15.3 Preparation of 5-chloro-N4-cyclopentyl-N2-(1-hydroxy-3,3,7-trimethyl-2,1-benzo xaborol-5-yl) pyrimidine-2,4-diamine

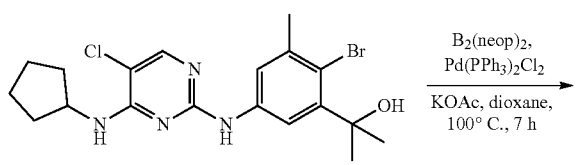

To a mixture of 2-[2-bromo-5-[[5-chloro-4-(cyclopentylamino)pyrimidin-2-yl]amino]-3-methyl-phenyl]propan-2-ol (0.85 g, 1.93 mmol, 1 eq) and 2-(5,5-dimethyl-1,3,2-dioxaborinan-2-yl)-5,5-dimethyl-1,3,2-dioxaborinane (1.09 g, 4.83 mmol, 2.5 eq) in dioxane (20 mL) was added KOAc (0.474 g, 4.83 mmol, 2.5 eq) and Pd(PPh$_3$)$_2$Cl$_2$ (0.135 g, 193.28 µmol, 0.1 eq) in one portion at 25° C. under N$_2$ atmosphere, the resulting mixture was heated to 100° C. and stirred for 7 h. The reaction mixture was filtered, and the filtrate was concentrated in vacuo to give a residue. The residue was purified by column chromatography (SiO$_2$, Petroleum ether/Ethyl acetate=10/1 to 2/1). to give 5-chloro-N4-cyclopentyl-N2-(1-hydroxy-3,3,7-trimethyl-2,1-benzoxaborol-5-yl) pyrimidine-2,4-diamine (0.09 g, 232.75 µmol, 12.04% yield) as a white solid. $^1$H NMR (DMSO-d$_6$, 400 MHz) δ 9.78 (s, 1H), 8.65 (s, 1H), 8.07 (s, 1H), 7.66 (s, 1H), 7.26 (s, 1H), 4.48 (q, J=6.8 Hz, 1H), 2.39 (s, 3H), 1.98-1.97 (m, 2H), 1.76-1.75 (m, 2H), 1.67-1.66 (m, 2H), 1.55-1.54 (m, 2H), 1.43 (s, 6H). MS (ESI): mass calcd. For C$_{19}$H$_{24}$BClN$_4$O$_2$ 386.17, m/z found 387.1 [M+H]$^+$. HPLC: 97.21% (220 nm), 88.55% (254 nm).

16. Preparation of 2-(2-bromo-3-methyl-5-((5-methyl-4-(pentan-3-ylamino)pyrimidin-2-yl)amino)phenyl)propan-2-ol and 1-(2-bromo-3-methyl-5-((5-methyl-4-(pentan-3-ylamino)pyrimidin-2-yl)amino)phenyl)ethanone

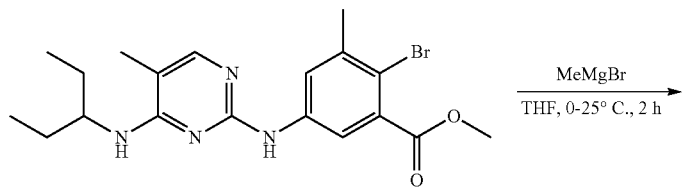

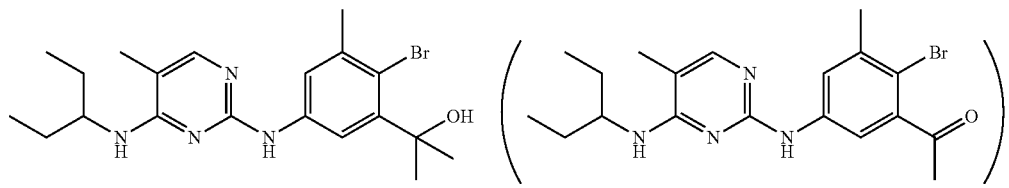

To a mixture of methyl 2-bromo-3-methyl-5-((5-methyl-4-(pentan-3-ylamino)pyrimidin-2-yl) amino)benzoate (2.00 g, 4.75 mmol, 1 eq) in THF (6 mL) was added MeMgBr (3 M, 9.50 mL, 6 eq) in one portion at 0° C. under $N_2$, the mixture was stirred at 25° C. for 2 h. The reaction mixture was quenched with sat. aq. $NH_4Cl$ (50 mL), and the aqueous phase was extracted with EtOAc (30 mL×3). The combined organic layers were washed with brine, dried over anhydrous $Na_2SO_4$, filtered and concentrated in vacuo to give a residue, which was purified by silica gel column chromatography (PE:EtOAc=5:1 to 1:1) to give 2-[2-bromo-5-[[4-(1-ethyl-propylamino)-5-methyl-pyrimidin-2-yl]amino]-3-methyl-phenyl]propan-2-ol (1.30 g, 3.09 mmol, 64.99% yield) as yellow oil. $^1$H NMR (DMSO-$d_6$, 400 MHz) δ 8.78 (s, 1H), 7.92 (s, 1H), 7.86 (s, 1H), 7.63 (s, 1H), 6.06 (d, J=8.8 Hz, 1H), 5.03 (s, 1H), 4.22-4.16 (m, 1H), 2.33 (s, 3H), 1.94 (s, 3H), 1.64-1.51 (m, 10H), 0.87 (t, J=7.2 Hz, 6H). And 1-[2-bromo-5-[[4-(1-ethylpropylamino)-5-methyl-pyrimidin-2-yl]amino]-3-methyl-phenyl] ethenone (0.400 g, 987 μmol, 20.79% yield) as yellow oil.

17. Preparation of 3,3,7-trimethyl-5-((5-methyl-4-(pentan-3-ylamino)pyrimidin-2-yl)amino)benzo[c][1,2]oxaborol-1(3H)-ol

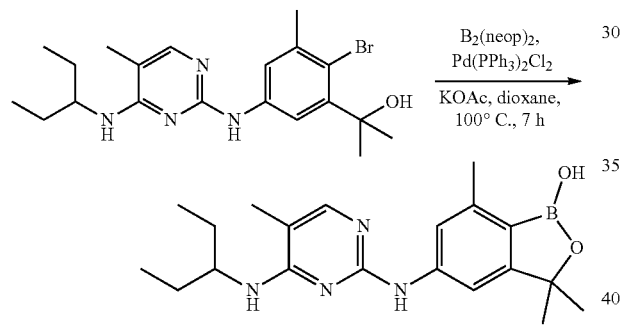

To a mixture of 2-[2-bromo-5-[[5-chloro-4-(1-ethylpropylamino)pyrimidin-2-yl]amino]-3-ethyl-phenyl]propan-2-ol (1.00 g, 2.26 mmol, 1 eq) and 2-(5,5-dimethyl-1,3,2-d ioxaborinan-2-yl) 5,5-dimethyl-1,3,2-dioxaborinane (1.28 g, 5.66 mmol, 2.5 eq) in dioxane (20 mL) was added KOAc (0.555 g, 5.66 mmol, 2.5 eq) and $Pd(PPh_3)_2Cl_2$ (0.159 g, 226 μmol, 0.1 eq) in one portion at 25° C. under $N_2$ atmosphere, the resulting mixture was heated to 100° C. and stirred for 7 h. The reaction mixture was filtered, and the filtrate was concentrated in vacuo to give a residue. The residue was purified by prep-HPLC (column: Welch Xtimate C18 100*25 mm*3 um; mobile phase: [water(10 mM $NH_4HCO_3$)-MeOH]; B %: 65%-85%, 12 min) to give 3,3,7-trimethyl-5-((5-methyl-4-(pentan-3-ylamino)pyrimidin-2-yl)amino)benzo[c][1,2] oxaborol-1(3H)-ol (0.111 g, 286 μmol, 12.62% yield) as a white solid. $^1$H NMR (DMSO-$d_6$, 400 MHz) δ 8.92 (s, 1H), 8.44 (s, 1H), 7.84 (s, 1H), 7.66 (s, 1H), 7.27 (s, 1H), 6.16 (d, J=8.8 Hz, 1H), 4.24-4.21 (m, 1H), 2.34 (s, 3H), 1.95 (s, 3H), 1.68-1.54 (m, 4H), 1.42 (s, 6H), 0.88 (t, J=7.2 Hz, 6H). MS (ESI): mass calcd. For $C_{20}H_{29}BN_4O_2$ 368.24, m/z found 369.2 [M+H]$^+$. HPLC: 98.87% (220 nm), 99.07% (254 nm).

18. Preparation of 3,7-dimethyl-5-((5-methyl-4-(pentan-3-ylamino)pyrimidin-2-yl)amino) benzo[c][1,2]oxaborol-1(3H)-ol

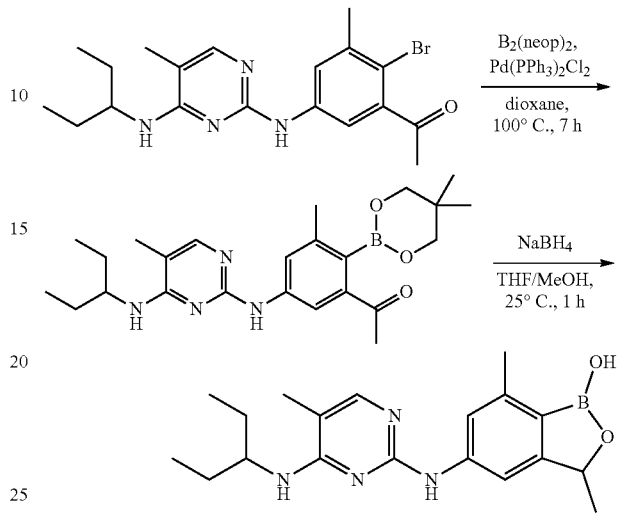

18.1 Preparation of 1-[5-[[5-chloro-4-(1-ethylpropylamino)pyrimidin-2-yl]amino]-2-(5,5-dimethyl-1,3,2-dioxaborinan-2-yl)-3-methyl-phenyl]ethanone

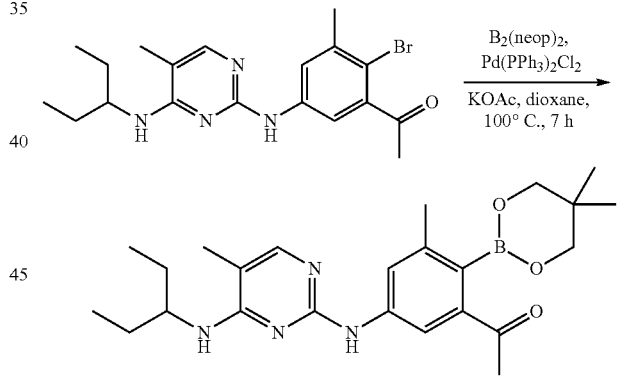

To a mixture of 1-[2-bromo-5-[[5-chloro-4-(1-ethylpropylamino)pyrimidin-2-yl]amino]-3-methyl-phenyl]ethanone (400 mg, 940 μmol, 1 eq) and 2-(5,5-dimethyl-1,3,2-dioxaborinan-2-yl)-5,5-dimethyl-1,3,2-dioxaborinane (531 mg, 2.35 mmol, 2.5 eq) in dioxane (20 mL) was added KOAc (231 mg, 2.35 mmol, 2.5 eq) and $Pd(PPh_3)_2Cl_2$ (66 mg, 94.0 μmol, 0.1 eq) in one portion at 25° C. under $N_2$ atmosphere, the resulting mixture was heated to 100° C. and stirred for 7 h. The reaction mixture was filtered, and the filtrate was concentrated in vacuo to give a residue. The residue was purified by column chromatography ($SiO_2$, Petroleum ether/Ethyl acetate=10/1 to 2/1) to give 1-[5-[[5-chloro-4-(1-ethylpropylamino)pyrimidin-2-yl]amino]-2-(5,5-dimethyl-1,3,2-dioxaborinan-2-yl)-3-methyl-phenyl]ethanone (350 mg, 763 μmol, 81.20% yield) as yellow oil, which was used directly in the next step.

18.2 Preparation of 3,7-dimethyl-5-((5-methyl-4-(pentan-3-ylamino)pyrimidin-2-yl)amino) benzo[c][1,2]oxaborol-1(3H)-ol

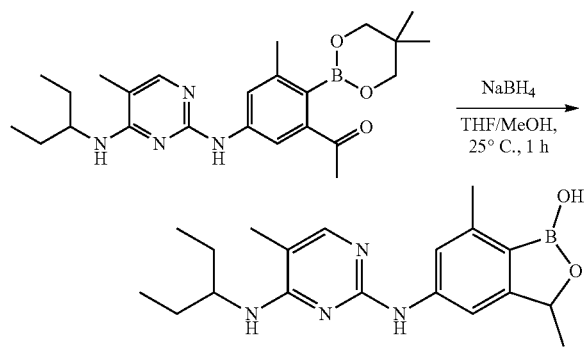

To a mixture of 1-[2-(5,5-dimethyl-1,3,2-dioxaborinan-2-yl)-5-[[4-(1-ethylpropylamino)-5-methyl-pyrimidin-2-yl]amino]-3-methyl-phenyl]ethanone (300 mg, 684 μmol, 1 eq) in THF (10 mL) and MeOH (1 mL) was added NaBH₄ (65 mg, 1.71 mmol, 2.5 eq) in one portion at 25° C. under N₂ atmosphere, the resulting mixture was stirred at 25° C. for 1 h. The reaction mixture was diluted with H₂O (10 mL), its pH was adjusted to 5 with 2N HCl, extracted with EtOAc (20 mL×3). The combined organic layers were washed with brine, dried over Na₂SO₄, filtered and concentrated in vacuo to give a residue. The residue was purified by prep-HPLC (column: Welch Xtimate C18 100*25 mm*3 um; mobile phase: [water(10 mM NH₄HCO₃)-MeOH]; B %: 60%-80%, 12 min) to give 3,7-dimethyl-5-((5-methyl-4-(pentan-3-ylamino)pyrimidin-2-yl)amino)benzo[c][1,2]oxaborol-1(3H)-ol (23 mg, 64.9 μmol, 9.49% yield) as a white solid. $^1$H NMR (DMSO-d$_6$, 400 MHz) δ 8.92 (s, 1H), 8.53 (s, 1H), 7.74 (s, 1H), 7.66 (s, 1H), 7.36 (s, 1H), 6.16 (d, J=8.4 Hz, 1H), 5.08 (q, J=6.8 Hz, 1H), 4.16-4.13 (m, 1H), 2.36 (s, 3H), 1.95 (s, 3H), 1.65-1.53 (m, 4H), 1.37 (d, J=6.4 Hz, 3H), 0.90-0.85 (m, 6H). MS (ESI): mass calcd. For C$_{19}$H$_{27}$BN$_4$O$_2$ 354.22, m/z found 355.2 [M+H]$^+$. HPLC: 97.41% (220 nm), 96.99% (254 nm).

19. Preparation of 5-chloro-N2-(7-chloro-1-hydroxy-3H-2,1-benzoxaborol-5-yl)-N4-cyclopentyl-pyrimidine-2,4-diamine

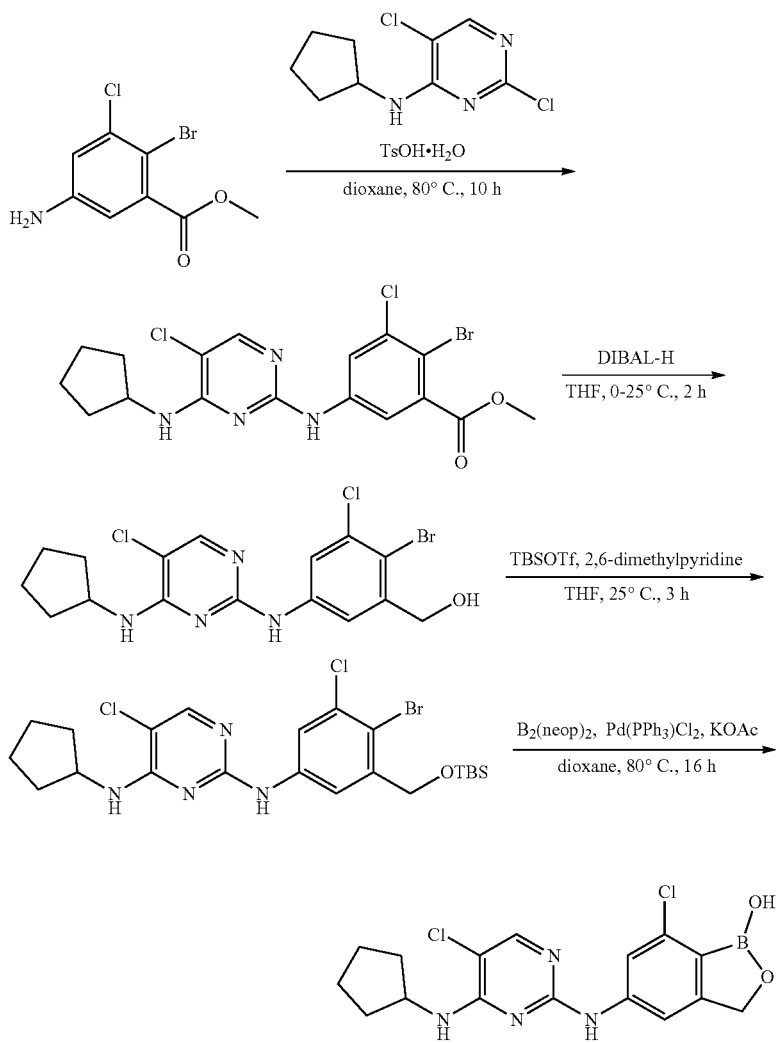

19.1 Preparation of methyl 2-bromo-3-chloro-5-[[5-chloro-4-(cyclopentylamino)pyrimidin-2-yl]amino]benzoate

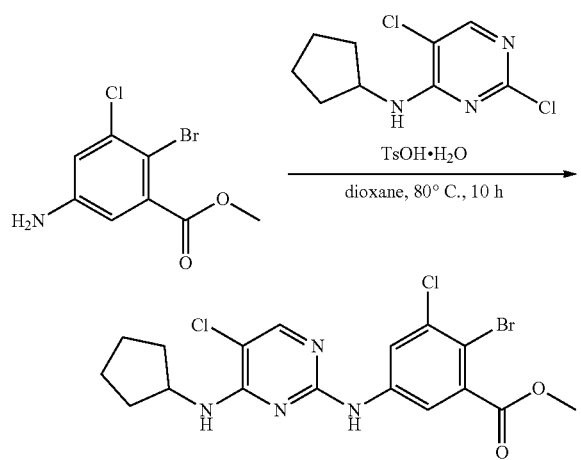

To a mixture of methyl 5-amino-2-bromo-3-chloro-benzoate (2.13 g, 8.06 mmol, 1.1 eq) and 2,5-dichloro-N-cyclopentyl-pyrimidin-4-amine (1.7 g, 7.32 mmol, 1 eq) in dioxane (20 mL) was added TsOH·H$_2$O (2.09 g, 10.99 mmol, 1.5 eq) in one portion at 20° C., the resulting mixture was stirred at 80° C. for 10 h. The reaction mixture was cooled to room temperature, and its pH was adjusted to 7 by sat. aq. NaHCO$_3$. The mixture was filtered, and the filter cake was dried in vacuo to give methyl 2-bromo-3-chloro-5-[[5-chloro-4-(cyclopentylamino)pyrimidin-2-yl]amino]benzoate (3 g, 6.52 mmol, 89.02% yield) as a yellow solid. $^1$H NMR (CDCl$_3$, 400 MHz) δ 8.28 (d, J=2.4 Hz, 1H), 7.98 (s, 1H), 7.92 (s, 1H), 7.68 (d, J=2.8 Hz, 1H), 5.30 (d, J=6.8 Hz, 1H), 4.42-4.33 (m, 1H), 3.94 (s, 3H), 2.18-2.15 (m, 2H), 1.81-1.71 (m, 4H), 1.55-1.53 (m, 2H).

19.2 Preparation of [2-bromo-3-chloro-5-[[5-chloro-4-(cyclopentylamino)pyrimidin-2-yl]amino]phenyl]methanol

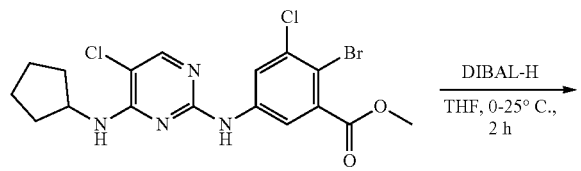

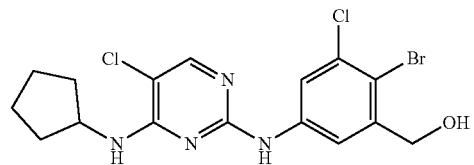

To a mixture of methyl 2-bromo-3-chloro-5-[[5-chloro-4-(cyclopentylamino) pyrimidin-2-yl]amino]benzoate (2 g, 4.35 mmol, 1 eq) in THF (20 mL) was added dropwise DIBAL-H (1 M, 22 mL, 5 eq) at 0° C., the resulting mixture was stirred at 25° C. for 2 h. The reaction mixture was poured into H$_2$O (150 mL), Na$_2$SO$_4$·10H$_2$O (5 g) was added to above mixture, the resulting mixture was filtered to remove the insoluble substance. The filtrate was dried in vacuo to give [2-bromo-3-chloro-5-[[5-chloro-4-(cyclopentylamino)pyrimidin-2-yl]amino]phenyl]methanol (1.1 g, 2.55 mmol, 58.56% yield) as a yellow solid. $^1$H NMR (DMSO-d$_6$, 400 MHz) δ 9.58 (s, 1H), 8.19 (d, J=2.4 Hz, 1H), 7.97 (s, 1H), 7.82 (d, J=2.4 Hz, 1H), 6.94 (d, J=7.2 Hz, 1H), 5.50 (t, J=5.6 Hz, 1H), 4.47 (d, J=5.6 Hz, 2H), 4.43 (t, J=8.0 Hz, 1H), 2.04-2.01 (m, 2H), 1.76-1.68 (m, 2H), 1.63-1.58 (m, 4H).

19.3 Preparation of N2-[4-bromo-3-[[tert-butyl(dimethyl)silyl]oxymethyl]-5-chloro-phenyl]-5-chloro-N4-cyclopentyl-pyrimidine-2,4-diamine

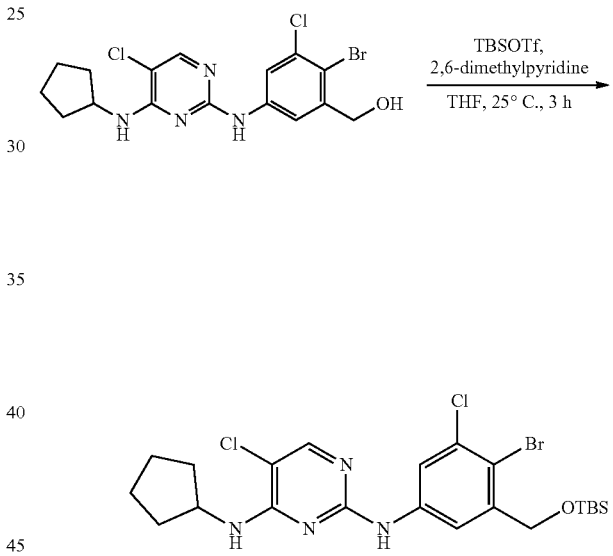

To a mixture of [2-bromo-3-chloro-5-[[5-chloro-4-(cyclopentylamino)pyrimidin-2-yl]amino]phenyl]methanol (1 g, 2.31 mmol, 1 eq) in THF (12 mL) was added TBSOTf (918 mg, 3.47 mmol, 800 µL, 1.5 eq) and 2,6-dimethylpyridine (422 mg, 3.93 mmol, 460 µL, 1.7 eq) in one portion at 25° C. The mixture was stirred at 25° C. for 3 h. The reaction mixture was poured into H$_2$O (20 mL), the aqueous phase was extracted with EtOAc (20 mL×3). The combined organic layers were washed with brine (20 mL×2), dried over anhydrous Na$_2$SO$_4$, filtered and concentrated in vacuo to yield the crude product, which was triturated with EtOAc at 25° C. for 10 min, then the crude product was collected by filtration, dried in vacuo to give N2-[4-bromo-3-[[tert-butyl(dimethyl)silyl]oxymethyl]-5-chloro-phenyl]-5-chloro-N4-cyclopentyl-pyrimidine-2,4-diamine (0.7 g, 1.28 mmol, 55.36% yield) as a white solid. $^1$H NMR (DMSO-d$_6$, 400 MHz) δ 9.72 (s, 1H), 8.33 (s, 1H), 7.96 (s, 1H), 7.66 (s, 1H), 6.97 (d, J=7.6 Hz, 1H), 4.65 (s, 2H), 4.40-4.38 (m, 1H), 1.98-1.97 (m, 2H), 1.74-1.71 (s, 2H), 1.64-1.59 (m, 4H), 0.94 (s, 9H), 0.12 (s, 6H).

19.4 Preparation of 5-chloro-N2-(7-chloro-1-hydroxy-3H-2,1-benzoxaborol-5-yl)-N4-cyclopentyl-pyrimidine-2,4-diamine

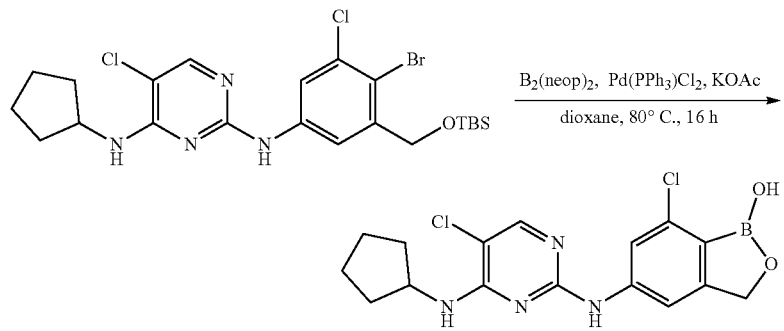

To a mixture of N2-[4-bromo-3-[[tert-butyl(dimethyl)silyl]oxymethyl]-5-chloro-phenyl]-5-chloro-N4-cyclopentyl-pyrimidine-2,4-diamine (0.6 g, 1.10 mmol, 1 eq) and 2-(5,5-dimethyl-1,3,2-dioxaborinan-2-yl)-5,5-dimethyl-1,3,2-dioxaborinane (496 mg, 2.20 mmol, 2 eq) in dioxane (10 mL) was added KOAc (323 mg, 3.29 mmol, 3 eq) and Pd(PPh$_3$)$_2$Cl$_2$ (77 mg, 109.81 μmol, 0.1 eq) in one portion at 25° C. The mixture was stirred at 80° C. for 16 h under N$_2$ atmosphere. The reaction mixture was filtered, and HCl (2N, 1 mL) was added to the filtrate. The resulting mixture was concentrated in vacuo to give a residue, which was purified by prep-HPLC (column: Welch Xtimate C18 100*25 mm*3 um; mobile phase: [water(0.1% TFA)-MeOH]; B %: 45%-65%, 12 min) to give 5-chloro-N2-(7-chloro-1-hydroxy-3H-2,1-benzoxaborol-5-yl)-N4-cyclopentyl-pyrimidine-2,4-diamine (25 mg, 65.95 μmol, 6.01% yield) as a white solid. $^1$H NMR (DMSO-d$_6$, 400 MHz) δ 9.65 (s, 1H), 8.90 (br s, 1H), 7.99 (s, 1H), 7.92 (s, 1H), 7.66 (s, 1H), 7.01 (d, J=7.2 Hz, 1H), 4.93 (s, 2H), 4.41-4.35 (m, 1H), 2.01-1.99 (m, 2H), 1.74-1.72 (m, 2H), 1.62-1.57 (m, 4H). MS (ESI): mass calcd. For C$_{16}$H$_{17}$BCl$_2$N$_4$O$_2$ 378.08, m/z found 379.1 [M+H]$^+$. HPLC: 94.64% (220 nm), 97.36% (254 nm).

20. Preparation of 5-chloro-N2-(7-chloro-1-hydroxy-3,3-dimethyl-2,1-benzoxaborol-5-yl)-N4-cyclopentyl-pyrimidine-2,4-diamine

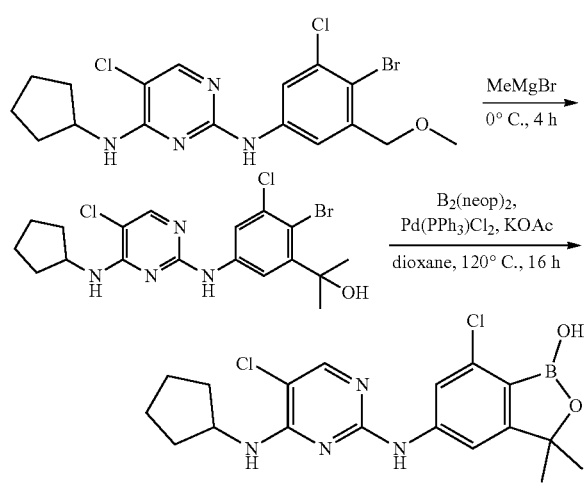

20.1 Preparation of 2-[2-bromo-3-chloro-5-[[5-chloro-4-(cyclopentylamino)pyrimidin-2-yl]amino]phenyl]propan-2-ol

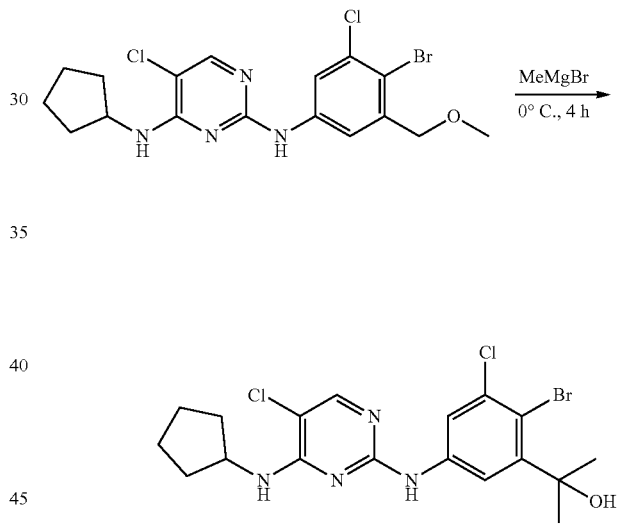

To a mixture of methyl 2-bromo-3-chloro-5-[[5-chloro-4-(cyclopentylamino)pyrimidin-2-yl]amino]benzoate (1 g, 2.17 mmol, 1 eq) was added to MeMgBr (3 M, 10.9 mL, 15 eq) in portions at 0° C., the resulting mixture was stirred at 0° C. for 4 h. The reaction mixture was poured into sat. aq. NH$_4$Cl (20 mL), and the aqueous phase was extracted with EtOAc (20 mL×3). The combined organic layers were washed with brine (20 mL×2), dried over anhydrous Na$_2$SO$_4$, filtered and concentrated in vacuo to give a residue, which was purified by flash silica gel chromatography (ISCO®; 20 g SepaFlash® Silica Flash Column, Eluent of 0-30% Ethyl acetate/Petroleum ethergradient @ 75 mL/min) to give 2-[2-bromo-3-chloro-5-[[5-chloro-4-(cyclopentylamino)pyrimidin-2-yl]amino]phenyl]propan-2-ol (0.6 g, 1.30 mmol, 59.99% yield) as a yellow solid. $^1$H NMR (CDCl$_3$, 400 MHz) δ 8.33 (d, J=2.8 Hz, 1H), 7.91 (s, 1H), 7.49 (d, J=2.4 Hz, 1H), 7.36 (s, 1H), 5.26 (d, J=7.2 Hz, 1H), 4.42 (q, J=6.8 Hz, 1H), 2.89 (s, 1H), 2.21-2.16 (m, 2H), 1.78 (s, 6H), 1.76-1.72 (m, 3H), 1.57-1.53 (m, 2H).

20.2 Preparation of 5-chloro-N2-(7-chloro-1-hydroxy-3,3-dimethyl-2,1-benzoxaborol-5-yl)-N4-cyclopentyl-pyrimidine-2,4-diamine

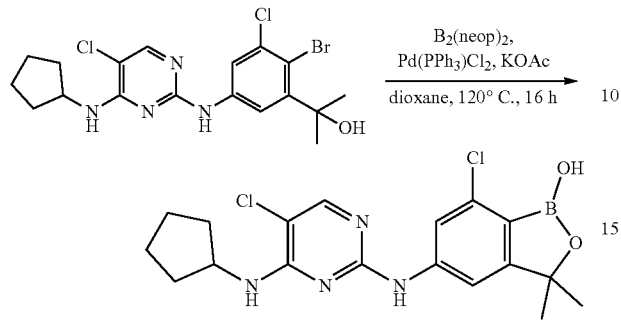

To a mixture of 2-[2-bromo-3-chloro-5-[[5-chloro-4-(cyclopentylamino)pyrimidin-2-yl]amino] phenyl]propan-2-ol (0.5 g, 1.09 mmol, 1 eq) and 2-(5,5-dimethyl-1,3,2-dioxaborinan-2-yl)-5,5-dimethyl-1,3,2-dioxaborinane (491 mg, 2.17 mmol, 2 eq) in dioxane (10 mL) was added KOAc (267 mg, 2.72 mmol, 2.5 eq) and Pd(PPh$_3$)$_2$Cl$_2$ (76 mg, 108.65 µmol, 0.1 eq) in one portion at 20° C., the resulting mixture was stirred at 120° C. for 16 h under N$_2$ atmosphere. The reaction mixture was filtered, HCl (2N, 1 mL) was added to the filtrate. The resulting mixture was concentrated in vacuo to give a residue, which was purified by prep-HPLC (column: Xtimate C18 100*30 mm*3 um; mobile phase: [water (0.1% TFA)-ACN]; B %: 30%-50%, 10 min) to give 5-chloro-N2-(7-chloro-1-hydroxy-3,3-dimethyl-2,1-benzoxaborol-5-yl)-N4-cyclopentyl-pyrimidine-2,4-diamine (53 mg, 130.19 µmol, 11.98% yield) as off-white solid. $^1$H NMR (DMSO-d$_6$, 400 MHz) δ 9.61 (s, 1H), 8.76 (s, 1H), 7.99 (s, 1H), 7.77 (s, 1H), 7.71 (s, 1H), 7.02 (d, J=7.6 Hz, 1H), 4.46-4.41 (m, 1H), 2.03-1.99 (m, 2H), 1.76-1.74 (m, 2H), 1.65-1.55 (m, 4H), 1.43 (s, 6H). MS (ESI): mass calcd. For C$_{18}$H$_{21}$BCl$_2$N$_4$O$_2$ 406.11, m/z found 407.1 [M+H]$^+$. HPLC: 98.76% (220 nm), 98.54% (254 nm).

21. Preparation of 5-((5-chloro-4-(cyclopentylamino)pyrimidin-2-yl)amino)-3-methylbenzo[c][1,2]oxaborol-1(3H)-ol

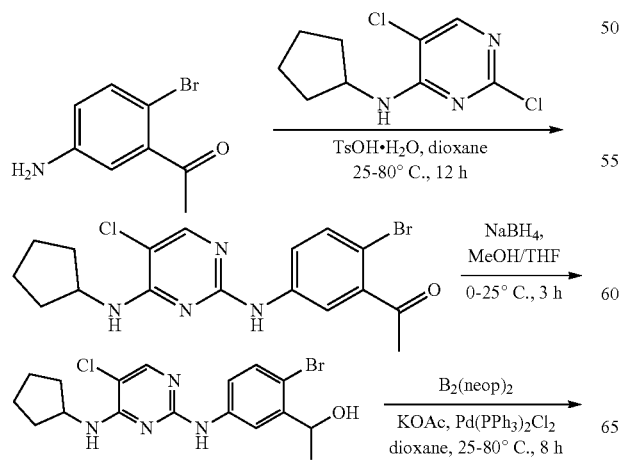

21.1 Preparation of 1-[2-bromo-5-[[5-chloro-4-(cyclopentylamino)pyrimidin-2-yl]amino]phenyl]ethanone

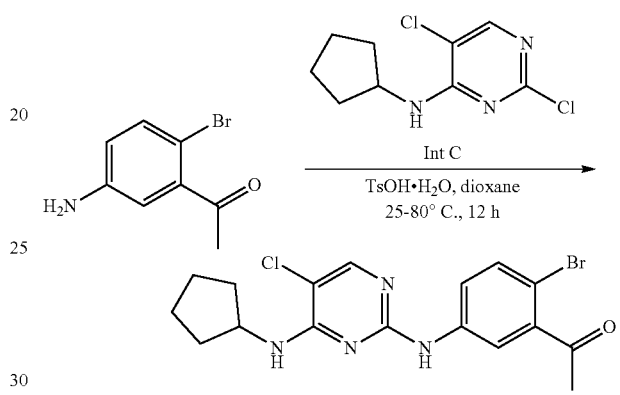

To a solution of 2,5-dichloro-N-cyclopentyl-pyrimidin-4-amine (2.00 g, 8.62 mmol, 1 eq) and 1-(5-amino-2-bromophenyl)ethanone (1.84 g, 8.62 mmol, 1 eq) in dioxane (60 mL) was added TsOH·H$_2$O (2.46 g, 12.9 mmol, 1.5 eq) at 25° C. under N$_2$ atmosphere, the resulting mixture was heated to 80° C. and stirred for 12 h. The reaction mixture was concentrated in vacuo to give a residue. The residue was dissolved in H$_2$O (30 mL), and its pH was adjusted to 9 with sat. aq NaHCO$_3$, and the aqueous phase was extracted with EtOAc (10 mL×3). The combined organic layers were washed with brine (5 mL×3), dried over Na$_2$SO$_4$, filtered and concentrated in vacuo to give the crude product, which was purified by flash silica gel chromatography (ISCO®; 40 g SepaFlash® Silica Flash Column, Eluent of 0~17% Ethyl acetate/Petroleum ethergradient @ 75 mL/min) to give 1-[2-bromo-5-[[5-chloro-4-(cyclopentylamino)pyrimidin-2-yl]amino]phenyl]ethanone (2.5 g, 6.10 mmol, 70.82% yield) as a yellow solid. $^1$H NMR (DMSO-d$_6$, 400 MHz) δ 9.52 (s, 1H), 8.13 (d, J=2.4 Hz, 1H), 7.96 (s, 1H), 7.66 (dd, J=9.2, 2.8 Hz, 1H), 7.53 (d, J=8.8 Hz, 1H), 6.93 (d, J=7.2 Hz, 1H), 4.40-4.34 (m, 1H), 2.54 (s, 3H), 1.96-1.93 (m, 2H), 1.71-1.67 (m, 2H), 1.62-1.53 (m, 4H).

21.2 Preparation of [1-[2-bromo-5-[[5-chloro-4-(cyclopentylamino)pyrimidin-2-yl]amino]phenyl]ethanol

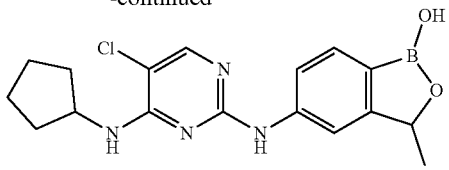

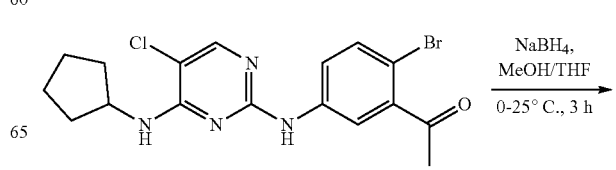

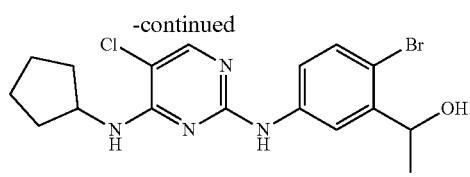

To a solution of 1-[2-bromo-5-[[5-chloro-4-(cyclopentylamino)pyrimidin-2-yl]amino]phenyl]ethanone (500 mg, 1.22 mmol, 1 eq) and MeOH (1.28 mmol, 51.7 μL, 1 eq) in THF (10 mL) was added NaBH₄ (72.5 mg, 1.92 mmol, 1.5 eq) at 0° C., the resulting mixture was stirred at 25° C. for 3 h. The reaction was quenched by adding 2N HCl, H₂O (10 mL) was poured into the above mixture, and its pH was adjusted to 5 with 2N HCl, then the aqueous phase was extracted with EtOAc (5 mL×3). The combined organic layers were washed with brine (5 mL×3), dried over Na₂SO₄, filtered and concentrated in vacuo to give a residue. The residue was purified by short column to give 1-[2-bromo-5-[[5-chloro-4-(cyclopentylamino)pyrimidin-2-yl]amino]phenyl]ethanol (400 mg, 972 μmol, 76.05% yield) as yellow oil. ¹H NMR (DMSO-d₆, 400 MHz) δ 9.34 (s, 1H), 8.22 (d, J=2.4 Hz, 1H), 7.92 (s, 1H), 7.42 (dd, J=8.8, 2.8 Hz, 1H), 7.34 (d, J=8.8 Hz, 1H), 6.84 (d, J=7.6 Hz, 1H), 5.28 (d, J=3.2 Hz, 1H), 4.94-4.88 (m, 1H), 4.56-4.50 (m, 1H), 1.98-1.97 (m, 2H), 1.69-1.66 (m, 2H), 1.62-1.53 (m, 4H), 1.27 (d, J=6.4 Hz, 3H).

21.3 Preparation of 5-chloro-N4-cyclopentyl-N2-(1-hydroxy-3-methyl-3H-2,1-benzoxaborol-5-yl)pyrimidine-2,4-diamine

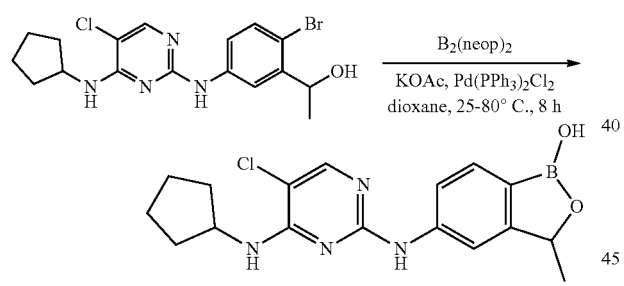

To a solution of 1-[2-bromo-5-[[5-chloro-4-(cyclopentylamino)pyrimidin-2-yl] amino]phenyl]ethanol (300 mg, 729 μmol, 1 eq) and 2-(5,5-dimethyl-1,3,2-dioxaborinan-2-yl)-5,5-dimethyl-1,3,2-dioxaborinane (411 mg, 1.82 mmol, 2.5 eq) in dioxane (10 mL) was added Pd(PPh₃)₂Cl₂ (51 mg, 72.9 μmol, 0.1 eq) and KOAc (143 mg, 1.46 mmol, 2 eq) at 25° C. under N₂ atmosphere, the resulting mixture was stirred at 80° C. for 8 h. The reaction mixture was filtered, and the filtrate was concentrated in vacuo to give a residue. The residue was dissolved in H₂O (10 mL), and its pH was adjusted to 5 with 2N HCl. EtOAc (10 mL) was added into the above mixture, the formed precipitate was collected by filtration, dried in vacuo to give the crude product, which was purified by prep-HPLC (column: Welch Xtimate C18 100*25 mm*3 um; mobile phase: [water(0.1% TFA)-MeOH]; B %: 40%-60%, 12 min) to give 5-chloro-N4-cyclopentyl-N2-(1-hydroxy-3-methyl-3H-2,1-benzoxaborol-5-yl)pyrimidine-2,4-diamine (147 mg, 405 μmol, 55.60% yield, 98.84% purity) as a white solid. ¹H NMR (DMSO-d₆, 400 MHz) δ 9.74 (s, 1H), 8.04 (s, 1H), 7.92 (s, 1H), 7.57 (d, J=8.0 Hz, 1H), 7.46-7.41 (m, 2H), 5.15 (q, J=6.4 Hz, 1H), 4.45-4.40 (m, 1H), 1.98-1.96 (m, 2H), 1.74-1.72 (m, 2H), 1.67-1.61 (m, 2H), 1.57-1.53 (m, 2H), 1.38 (d, J=6.4 Hz, 3H). MS (ESI): mass calcd. For C₁₇H₂₀BClN₄O₂ 358.14, m/z found 359.1 [M+H]⁺. HPLC: 98.84% (220 nm), 97.83% (254 nm).

22. Preparation of 5-chloro-N4-cyclopentyl-N2-(1-hydroxy-3,3-dimethyl-2,1-benzoxaborol-5-yl)pyrimidine-2,4-diamine

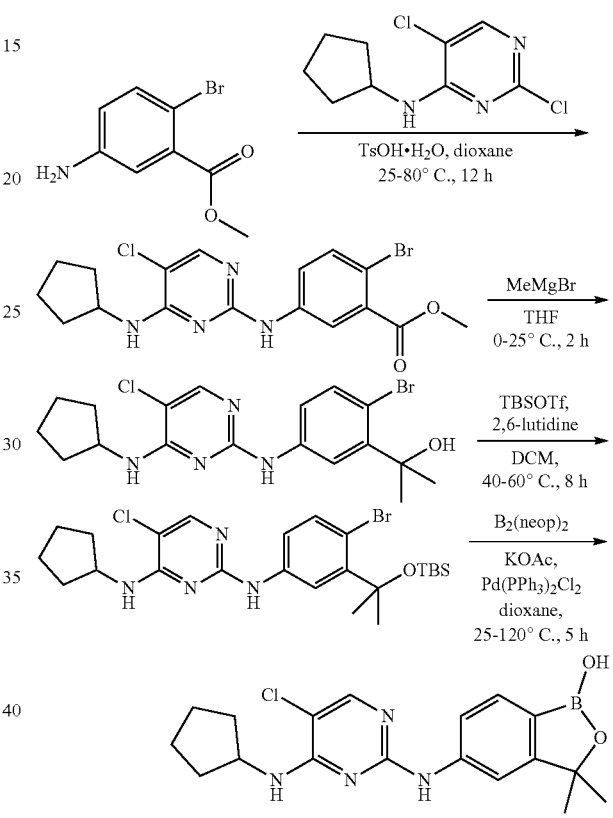

22.1 Preparation of methyl 2-bromo-5-[[5-chloro-4-(cyclopentylamino)pyrimidin-2-yl]amino]benzoate

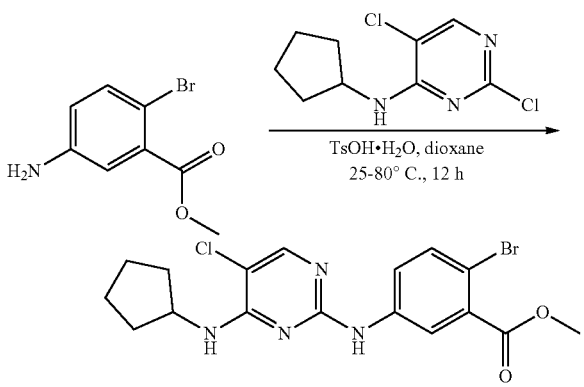

To a solution of 2,5-dichloro-N-cyclopentyl-pyrimidin-4-amine (2.00 g, 8.62 mmol, 1 eq) and methyl 5-amino-2-bromo-benzoate (2.38 g, 10.3 mmol, 1.2 eq) in dioxane (60 mL) was added TsOH·H₂O (2.46 g, 12.9 mmol, 1.5 eq) at 25° C. under N₂ atmosphere, the reaction was heated to 80° C. and stirred for 12 h. The reaction mixture was concentrated in vacuo to give a residue, which was dissolved in H₂O (30 mL), and its pH was adjusted to 9 with sat. aq. NaHCO₃, extracted with EtOAc (10 mL×3). The combined organic layers were washed with brine (5 mL×3), dried over Na₂SO₄, filtered and concentrated under reduced pressure to give the crude product, which was purified by flash silica gel chromatography (ISCO®; 40 g SepaFlash® Silica Flash Column, Eluent of 0~20% Ethyl acetate/Petroleum ether-gradient @75 mL/min) to give methyl 2-bromo-5-[[5-chloro-4-(cyclopentylamino)pyrimidin-2-yl]amino]benzoate (3.30 g, 7.75 mmol, 89.96% yield) as a yellow solid. ¹H NMR (DMSO-d₆, 400 MHz) δ 9.58 (s, 1H), 8.39 (d, J=2.8 Hz, 1H), 7.97 (s, 1H), 7.66 (dd, J=8.8, 2.8 Hz, 1H), 7.58 (d, J=8.8 Hz, 1H), 6.92 (d, J=7.6 Hz, 1H), 4.42-4.33 (m, 1H), 3.84 (s, 3H), 1.99-1.91 (m, 2H), 1.74-1.68 (m, 2H), 1.64-1.54 (m, 4H).

22.2 Preparation of methyl 2-[2-bromo-5-[[5-chloro-4-(cyclopentylamino)pyrimidin-2-yl] amino]phenyl]propan-2-ol

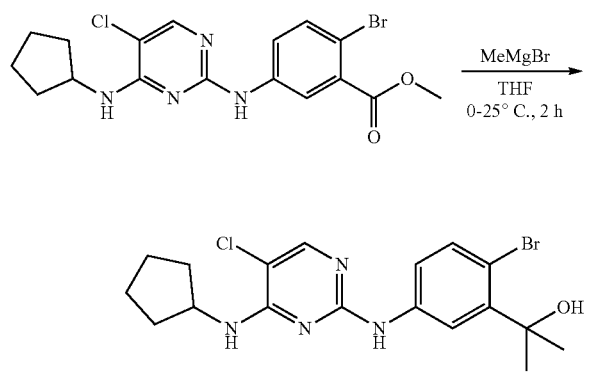 [SMILES: "MeMgBr" ; COC(=O)c1cc(Nc2ncc(Cl)c(NC3CCCC3)n2)ccc1Br ; CC(C)(O)c1cc(Nc2ncc(Cl)c(NC3CCCC3)n2)ccc1Br]

A solution of methyl 2-bromo-5-[[5-chloro-4-(cyclopentylamino)pyrimidin-2-yl]amino]benzoate (2.00 g, 4.70 mmol, 1 eq) in THF (20 mL) was added to the solution of MeMgBr (3 M, 7.90 mL, 5 eq) at 0° C. dropwise over a period of 30 min, the resulting mixture was stirred at 25° C. for 1.5 h. Then the reaction mixture was poured into a mixture of H₂O (15 mL) and sat. NH₄Cl (10 mL), the aqueous phase was extracted with EtOAc (8 mL×3). The combined organic layers were washed with brine (5 mL×3), dried over Na₂SO₄, filtered and concentrated in vacuo to give a residue. The residue was purified by flash silica gel chromatography (ISCO®; 20 g SepaFlash® Silica Flash Column, Eluent of 0-55% Ethyl acetate/Petroleum ethergradient @36 mL/min) to give 2-[2-bromo-5-[[5-chloro-4-(cyclopentylamino)pyrimidin-2-yl]amino]phenyl]propan-2-ol (1.3 g, 3.05 mmol, 64.99% yield) as yellow oil. ¹H NMR (DMSO-d₆, 400 MHz) δ 9.28 (s, 1H), 8.22 (d, J=2.4 Hz, 1H), 7.91 (s, 1H), 7.54 (dd, J=8.8, 2.8 Hz, 1H), 7.39 (d, J=8.8 Hz, 1H), 6.78-6.75 (m, 1H), 5.10 (s, 1H), 4.52-4.45 (m 1H), 1.96-1.63 (m, 4H), 1.60 (s, 6H), 1.58-1.52 (m, 4H).

22.3 Preparation of N2-[4-bromo-3-[1-[tert-butyl(dimethyl)silyl]oxy-1-methyl-ethyl]phenyl]-5-chloro-N4-cyclopentyl-pyrimidine-2,4-diamine

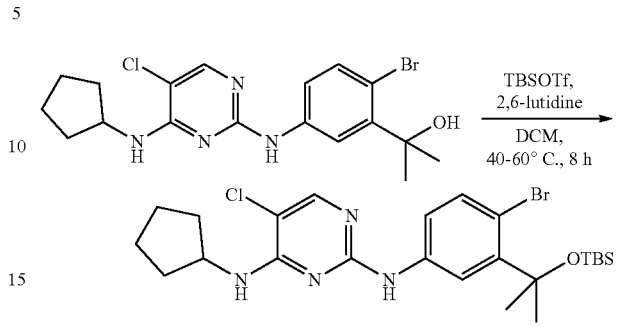

To a solution of 2-[2-bromo-5-[[5-chloro-4-(cyclopentylamino)pyrimidin-2-yl]amino]phenyl] propan-2-ol (300 mg, 705 μmol, 1 eq) and 2,6-dimethylpyridine (2.11 mmol, 246 μL, 3 eq) in DCM (10 mL) was added [tert-butyl(dimethyl)silyl] trifluoromethanesulfonate (1.76 mmol, 405 μL, 2.5 eq) at 25° C., the resulting mixture was stirred at 40° C. for 6 h. Then to the above mixture was added additional part of [tert-butyl(dimethyl)silyl] trifluoromethanesulfonate (352 μmol, 81.0 μL, 0.5 eq) in one portion at 25° C., the reaction mixture was stirred at 60° C. for 2 h. H₂O (15 mL) was added into the reaction mixture, and the aqueous phase was extracted with DCM (8 mL×3). The combined organic layers were washed with brine (5 mL×3), dried over Na₂SO₄, filtered and concentrated in vacuo to give a residue. The residue was purified by flash silica gel chromatography (ISCO®; 12 g SepaFlash® Silica Flash Column, Eluent of 0-10% Ethyl acetate/Petroleum ethergradient @36 mL/min) to give N2-[4-bromo-3-[1-[tert-butyl(dimethyl)silyl]oxy-1-methyl-ethyl]phenyl]-5-chloro-N4-cyclopentyl-pyrimidine-2,4-diamine (400 mg, 741 μmol, 52.56% yield) as yellow oil. ¹H NMR (DMSO-d₆, 400 MHz) δ 9.25 (s, 1H), 7.90 (s, 1H), 7.57 (dd, J=8.4, 2.4 Hz, 1H), 7.44 (d, J=8.8 Hz, 1H), 6.82 (d, J=8.0 Hz, 1H), 4.42-4.37 (m, 1H), 1.96-1.93 (m, 2H), 1.74-1.71 (m, 8H), 1.58-1.52 (m, 4H), 0.89 (s, 9H), 0.10 (s, 6H).

22.4 Preparation of 5-chloro-N4-cyclopentyl-N2-(1-hydroxy-3,3-dimethyl-2,1-benzoxaborol-5-yl)pyrimidine-2,4-diamine

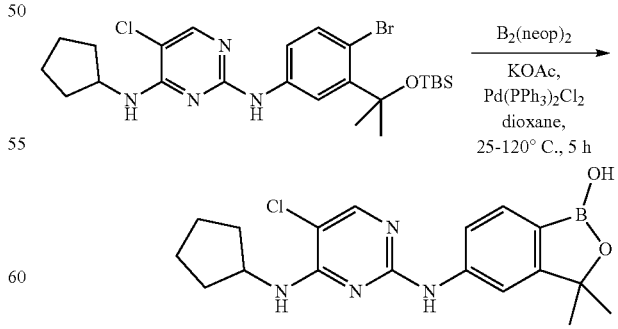

To a solution of N2-[4-bromo-3-[1-[tert-butyl(dimethyl)silyl]oxy-1-methyl-ethyl]phenyl]-5-chloro-N4-cyclopentyl-pyrimidine-2,4-diamine (400 mg, 741 μmol, 1 eq) and 2-(5,5-dimethyl-1,3,2-dioxaborinan-2-yl)-5,5-dimethyl-1,3, 2-dioxaborinane (418 mg, 1.85 mmol, 2.5 eq) in dioxane (10 mL) was added Pd(PPh$_3$)$_2$Cl$_2$ (52.0 mg, 74.1 μmol, 0.1 eq) and KOAc (145 mg, 1.48 mmol, 2 eq) at 25° C. under N$_2$ atmosphere, the resulting mixture was stirred at 120° C. for 5 h. The reaction mixture was cooled to room temperature, and filtered, the filtrate was concentrated in vacuo to give a residue. The residue was purified by prep-HPLC (column: Nano-micro Kromasil C18 100*30 mm 8 um; mobile phase: [water(0.1% TFA)-ACN]; B %: 25%-45%, 10 min) to give 5-chloro-N4-cyclopentyl-N2-(1-hydroxy-3,3-dimethyl-2,1-benzoxaborol-5-yl)pyrimidine-2,4-diamine (102 mg, 267 μmol, 36.04% yield, 97.54% purity) as a white solid. $^1$H NMR (DMSO-d$_6$, 400 MHz) δ 9.74 (s, 1H), 8.03 (s, 1H), 7.97 (s, 1H), 7.53 (d, J=8.0 Hz, 1H), 7.46-7.44 (m, 1H), 7.37 (d, J=8.0 Hz, 1H), 4.52-4.42 (m, 1H), 1.98-1.96 (m, 2H), 1.77-1.71 (m, 2H), 1.66-1.60 (m, 2H), 1.55-1.51 (m, 2H), 1.42 (s, 6H). MS (ESI): mass calcd. For C$_{18}$H$_{22}$BClN$_4$O$_2$ 372.15, m/z found 373.1 [M+H]$^+$. HPLC: 97.54% (220 nm), 96.29% (254 nm)

23. Preparation of 3,3-dimethyl-5-((5-methyl-4-(phenylamino)pyrimidin-2-yl)amino)benzo[c][1,2]oxaborol-1(3H)-ol

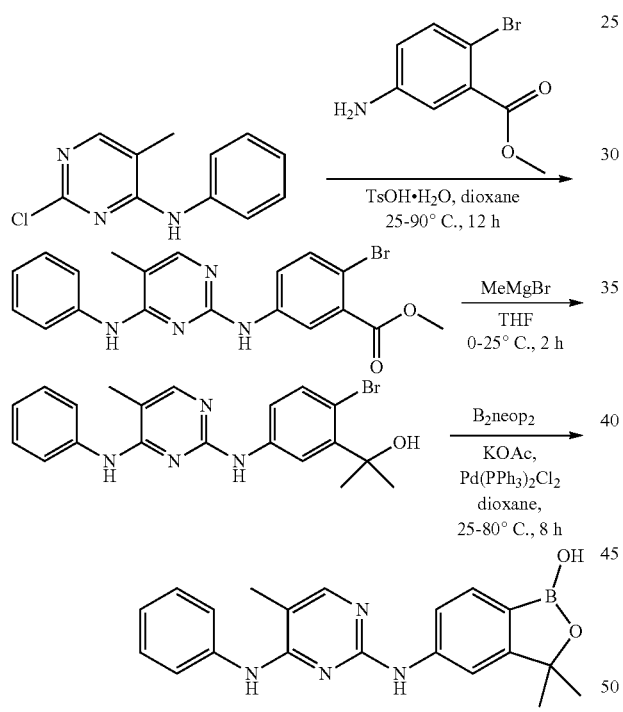

23.1 Preparation of 5-[(4-anilino-5-methyl-pyrimidin-2-yl)amino]-2-bromo-benzoate

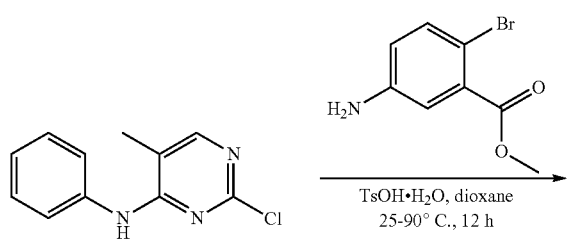

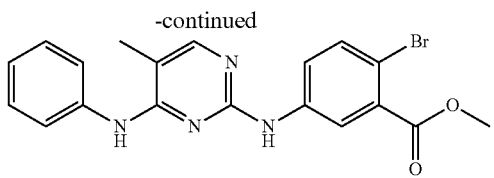

To a solution of 2-chloro-5-methyl-N-phenyl-pyrimidin-4-amine (1.50 g, 6.83 mmol, 1 eq) and methyl 5-amino-2-bromo-benzoate (1.73 g, 7.51 mmol, 1.1 eq) in dioxane (60 mL) was added TsOH·H$_2$O (1.95 g, 10.2 mmol, 1.5 eq) at 25° C. under N$_2$ atmosphere, the resulting mixture was stirred at 90° C. for 12 h. The reaction mixture was cooled to room temperature and filtered, the filter cake was dissolved in H$_2$O (30 mL), and its pH was adjusted to 9 with sat. NaHCO$_3$, and the aqueous phase was extracted with EtOAc (15 mL×3). The combined organic layers were washed with brine (5 mL×3), dried over anhydrous Na$_2$SO$_4$, filtered and concentrated in vacuo to give a residue, which was triturated with EtOAc (20 mL) to give methyl 5-[(4-anilino-5-methyl-pyrimidin-2-yl)amino]-2-bromo-benzoate (1.70 g, 4.11 mmol, 60.24% yield) as a Light yellow solid. $^1$H NMR (DMSO-d$_6$, 400 MHz) δ 9.36 (s, 1H), 8.36 (s, 1H), 8.11 (d, J=2.8 Hz, 1H), 7.93 (s, 1H), 7.79 (dd, J=8.8, 2.8 Hz, 1H), 7.68 (d, J=7.6 Hz, 2H), 7.46 (d, J=8.8 Hz, 1H), 7.31 (t, J=8.4 Hz, 2H), 7.08 (d, J=7.2 Hz, 1H), 3.78 (s, 3H), 2.13 (s, 3H).

23.2 Preparation of 2-[5-[(4-anilino-5-methyl-pyrimidin-2-yl)amino]-2-bromo-phenyl] propan-2-ol

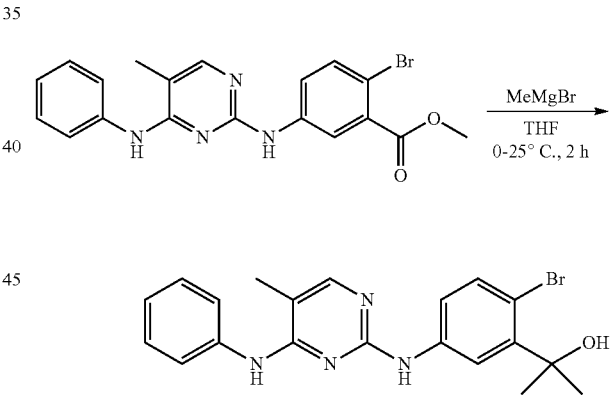

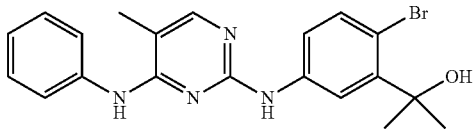

To a solution of methyl 5-[(4-anilino-5-methyl-pyrimidin-2-yl)amino]-2-bromo-benzoate (500 mg, 1.21 mmol, 1 eq) in THF (10 mL) was added MeMgBr (3 M, 2.10 mL, 5 eq) dropwise at 0° C. over a period of 30 min, the resulting mixture was stirred at 25° C. for 1.5 h. The reaction was quenched by adding sat. NH$_4$Cl (15 mL), and the aqueous phase was extracted with EtOAc (8 mL×3). The combined organic layers were washed with brine (5 mL×3), dried over anhydrous Na$_2$SO$_4$, filtered and concentrated in vacuo to give 2-[5-[(4-anilino-5-methyl-pyrimidin-2-yl)amino]-2-bromo-phenyl]propan-2-ol (350 mg, 847 μmol, 69.99% yield) as a yellow solid. $^1$H NMR (DMSO-d$_6$, 400 MHz) δ 9.11 (s, 1H), 8.25 (s, 1H), 7.89 (d, J=3.6 Hz, 2H), 7.79 (dd, J=8.8, 2.8 Hz, 1H), 7.77-7.75 (m, 1H), 7.74-7.73 (m, 1H), 7.35-7.28 (m, 3H), 7.06 (t, J=7.6 Hz, 1H), 5.09 (s, 1H), 2.11 (s, 3H), 1.58 (s, 6H).

23.3 Preparation of N2-(1-hydroxy-3,3-dimethyl-2,1-benzoxaborol-5-yl)-5-methyl-N4-phenyl-pyrimidine-2,4-diamine

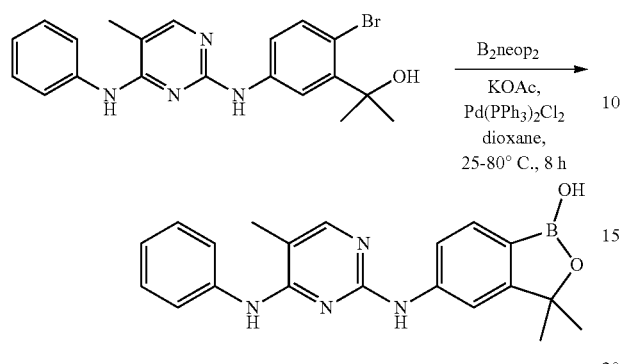

To a solution of 2-[5-[(4-anilino-5-methyl-pyrimidin-2-yl)amino]-2-bromo-phenyl]propan-2-ol (300 mg, 726 µmol, 1 eq) and 2-(5,5-dimethyl-1,3,2-dioxaborinan-2-yl)-5,5-dimethyl-1,3,2-dioxaborinane (401 mg, 1.81 mmol, 2.5 eq) in dioxane (10 mL) was added Pd(PPh$_3$)$_2$Cl$_2$ (51 mg, 72.6 µmol, 0.1 eq) and KOAc (143 mg, 1.45 mmol, 2 eq) at 25° C. under N$_2$ atmosphere, the resulting mixture was stirred at 80° C. for 8 h. The reaction mixture was filtered, and the filtrate was concentrated in vacuo to give a residue. The residue was dissolved in H$_2$O (10 mL), and its pH was adjusted to 5 with 2N HCl, and the aqueous phase was extracted with EtOAc (8 mL×3). The combined organic layers were washed with brine (5 mL×3), dried over Na$_2$SO$_4$, filtered and concentrated in vacuo to give the crude product, which was purified by prep-HPLC (column: Welch Xtimate C18 100*25 mm*3 um; mobile phase: [water (0.1% TFA)-ACN]; B %: 20%-30%, 12 min) to give N2-(1-hydroxy-3,3-dimethyl-2,1-benzoxaborol-5-yl)-5-methyl-N4-phenyl-pyrimidine-2,4-diamine (103 mg, 286 µmol, 39.39% yield, 100% purity) as a white solid. $^1$H NMR (DMSO-d$_6$, 400 MHz) δ 10.18 (s, 1H), 9.64 (s, 1H), 8.91 (br s, 1H), 7.93 (s, 1H), 7.56-7.51 (m, 3H), 7.43-7.38 (m, 4H), 7.27 (t, J=7.6 Hz, 1H), 2.18 (s, 3H), 1.29 (s, 6H). MS (ESI): mass calcd. For C$_{20}$H$_{21}$BN$_4$O$_2$ 360.18, m/z found 361.0 [M+H]$^+$. HPLC: 100.00% (220 nm), 99.77% (254 nm).

24. Preparation of 3-methyl-5-((5-methyl-4-(phenylamino)pyrimidin-2-yl)amino)benzo[c][1,2]oxaborol-1(3H)-ol

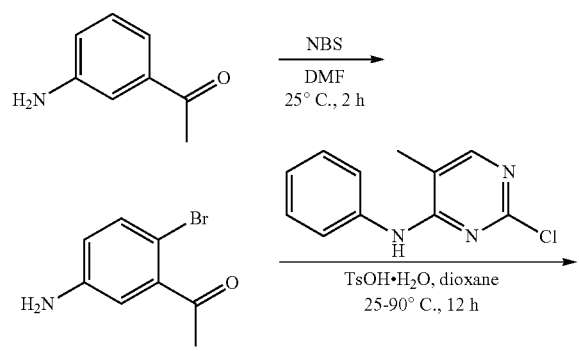

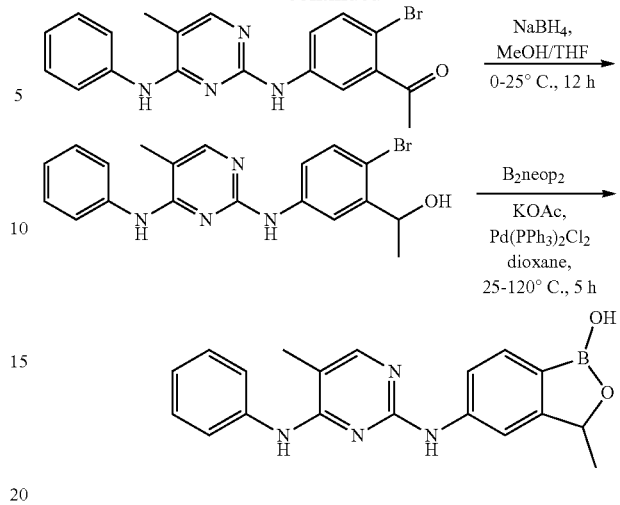

24.1 Preparation of 1-(5-amino-2-bromo-phenyl)ethanone

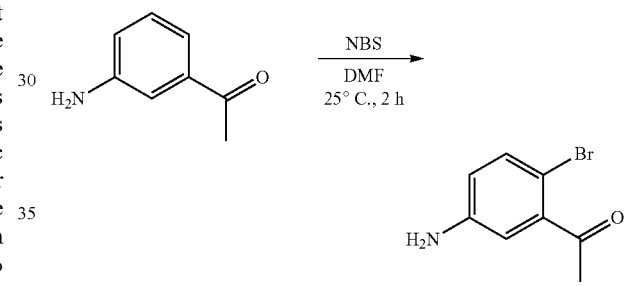

A solution of 1-(3-aminophenyl)ethanone (10.0 g, 74.0 mmol, 1 eq) in DMF (70 mL) was dropwise a solution of NBS (13.2 g, 74.0 mmol, 1 eq) in DMF (70 mL) at 25° C. over a period of 1 h, the resulting mixture was stirred at 25° C. for 1 h. The reaction mixture was poured into H$_2$O (100 mL), and the aqueous phase was extracted with EtOAc (40 mL×3). The combined organic layers were washed with sat. aq. NaHCO$_3$ (20 mL×3), H$_2$O (15 mL×3) and brine (10 mL×3), dried over Na$_2$SO$_4$, filtered and concentrated in vacuo to give 1-(5-amino-2-bromo-phenyl)ethanone (15.0 g, 70.1 mmol, 94.71% yield) was as brown oil. $^1$H NMR (CDCl$_3$, 400 MHz) δ 7.34 (d, J=8.4 Hz, 1H), 6.75 (d, J=2.8 Hz, 1H), 6.62 (dd, J=8.8, 2.8 Hz, 1H), 3.82 (br s, 2H).

24.2 Preparation of methyl 5-[(4-anilino-5-methyl-pyrimidin-2-yl)amino]-2-bromo-benzoate

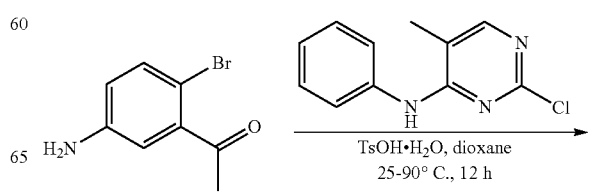

-continued

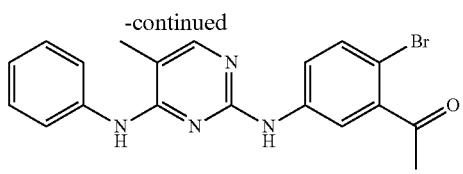

To a solution of 2-chloro-5-methyl-N-phenyl-pyrimidin-4-amine (2.00 g, 9.10 mmol, 1 eq) and methyl 5-amino-2-bromo-benzoate (2.30 g, 10.0 mmol, 1.1 eq) in dioxane (60 mL) was added TsOH·H₂O (2.60 g, 13.7 mmol, 1.5 eq) at 25° C. under N₂ atmosphere, the resulting mixture was stirred at 90° C. for 12 h. The reaction mixture was filtered, the filter cake was dissolved in H₂O (30 mL), and its pH was adjusted to 9 with sat. aq. NaHCO₃, extracted with EtOAc (15 mL×3). The combined organic layers were washed with brine (5 mL×3), dried over Na₂SO₄, filtered and concentrated in vacuo to give a residue. The residue was triturated with EtOAc (20 mL), the precipitate was collected by filtration, dried in vacuo to give methyl 5-[(4-anilino-5-methyl-pyrimidin-2-yl)amino]-2-bromo-benzoate (2.00 g, 4.84 mmol, 53.15% yield) as a brown solid. ¹H NMR (DMSO-d₆, 400 MHz) δ 9.31 (s, 1H), 8.38 (s, 1H), 7.98 (d, J=2.8 Hz, 1H), 7.93 (s, 1H), 7.74-7.71 (m, 1H), 7.64 (d, J=8.0 Hz, 2H), 7.42 (d, J=9.2 Hz, 1H), 7.32 (t, J=7.6 Hz, 2H), 7.08 (t, J=7.6 Hz, 1H), 2.37 (s, 3H), 2.12 (s, 3H).

24.3 Preparation of 1-[5-[(4-anilino-5-methyl-pyrimidin-2-yl)amino]-2-bromo-phenyl]ethanol

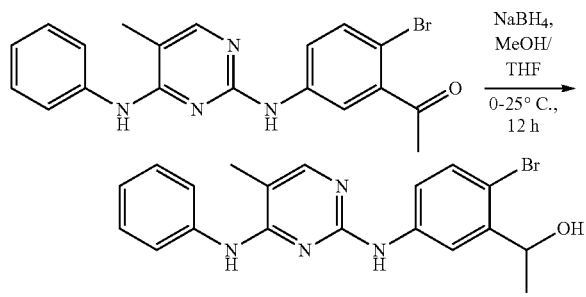

To a solution of 1-[5-[(4-anilino-5-methyl-pyrimidin-2-yl)amino]-2-bromo-phenyl]ethanone (1.60 g, 4.03 mmol, 1 eq) and MeOH (4.03 mmol, 163 µL, 1 eq) in THF (25 mL) was added NaBH₄ (229 mg, 6.04 mmol, 1.5 eq) at 0° C., the resulting mixture was stirred at 25° C. for 12 h. The reaction was quenched by adding 2N HCl, H₂O (25 mL) was added into the above mixture, its pH was adjusted to 5 with 2N HCl, the aqueous phase was extracted with EtOAc (8 mL×3). The combined organic layers were washed with brine (5 mL×3), dried over Na₂SO₄, filtered and concentrated in vacuo to give a residue. The residue was triturated with MTBE (10 mL) at 25° C., and the precipitate was collected by filtration, dried in vacuo to give 1-[5-[(4-anilino-5-methyl-pyrimidin-2-yl)amino]-2-bromo-phenyl]ethanol (1.00 g, 2.50 mmol, 62.18% yield) as a brown solid. ¹H NMR (CDCl₃, 400 MHz) δ 10.09 (br s, 1H), 7.89 (s, 1H), 7.57-7.55 (m, 2H), 7.53-7.47 (m, 2H), 7.41 (t, J=8.0 Hz, 3H), 7.36-7.32 (m, 1H), 7.30-7.24 (m, 2H) 4.88 (q, J=6.4 Hz, 1H), 2.17 (s, 3H), 1.25 (d, J=6.4 Hz, 3H)

24.4 Preparation of N2-(1-hydroxy-3-methyl-3H-2,1-benzoxaborol-5-yl)-5-methyl-N4-phenyl-pyrimidine-2,4-diamine

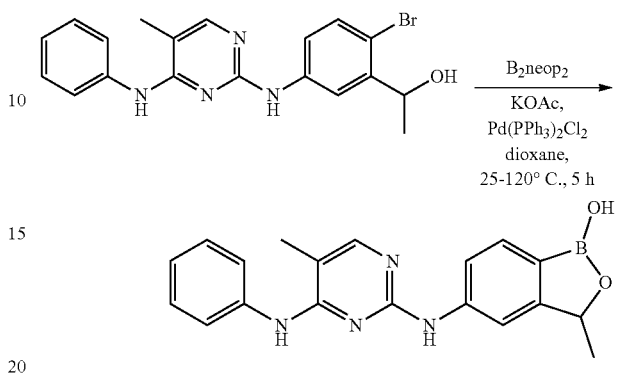

To a solution of 1-[5-[(4-anilino-5-methyl-pyrimidin-2-yl)amino]-2-bromo-phenyl]ethanol (600 mg, 1.50 mmol, 1 eq) and 2-(5,5-dimethyl-1,3,2-dioxaborinan-2-yl)-5,5-dimethyl-1,3,2-dioxaborinane (849 mg, 3.76 mmol, 2.5 eq) in dioxane (12 mL) was added Pd(PPh₃)₂Cl₂ (105 mg, 150 µmol, 0.1 eq) and KOAc (295 mg, 3.01 mmol, 2 eq) at 25° C. under N₂ atmosphere, the resulting mixture was stirred at 120° C. for 5 h. The reaction mixture was cooled to room temperature and filtered, the filtrate was concentrated in vacuo to give a residue. The residue was dissolved in H₂O (15 mL), and its pH was adjusted to 5 with 2N HCl, the aqueous phase was extracted with EtOAc (8 mL×3). The combined organic layers were washed with brine (5 mL×3), dried over Na₂SO₄, filtered and concentrated in vacuo to give the crude product, which was purified by prep-HPLC (column: Welch Xtimate C18 100*25 mm*3 um; mobile phase: [water (0.1% TFA)-MeOH]; B %: 35%-55%, 12 min) to give N2-(1-hydroxy-3-methyl-3H-2,1-benzoxaborol-5-yl)-5-methyl-N4-phenyl-pyrimidine-2,4-diamine (140 mg, 384 µmol, 25.54% yield, 94.91% purity) as a white solid. ¹H NMR (DMSO-d₆, 400 MHz) δ 10.26 (s, 1H), 9.69 (s, 1H), 8.98 (br s, 1H), 7.93 (s, 1H), 7.56-7.53 (m, 4H), 7.43 (t, J=8.4 Hz, 2H), 7.32-7.29 (m, 2H), 5.02 (q, J=6.8 Hz, 1H), 2.18 (s, 3H), 1.16 (d, J=6.4 Hz, 3H). MS (ESI): mass calcd. For C₁₉H₁₉BN₄O₂ 346.16, m/z found 347.1 [M+H]⁺. HPLC: 94.91% (220 nm), 93.77% (254 nm).

25. Preparation of N4-(1-ethylpropyl)-N2-[1-hydroxy-7-(trifluoromethyl)3H-2,1-benzoxaborol-5-yl]-5-methyl-pyrimidine-2,4-diamine

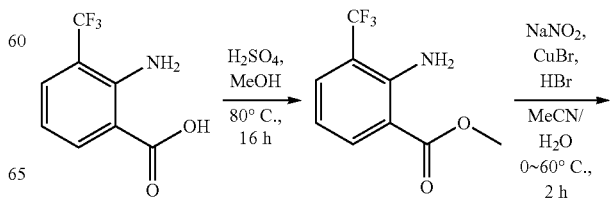

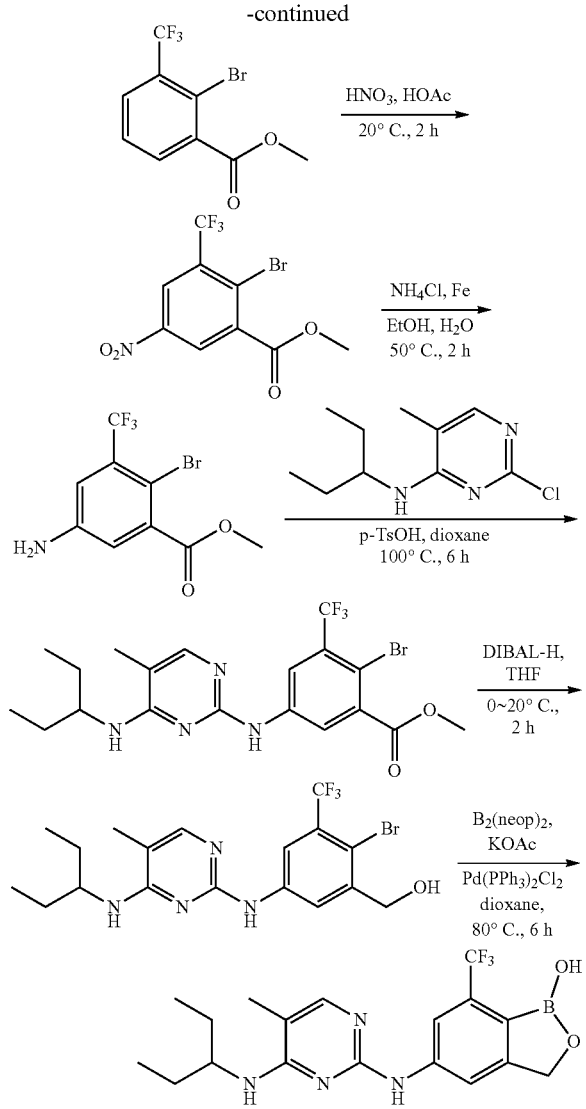

25.1 Preparation of methyl 2-amino-3-(trifluoromethyl)benzoate

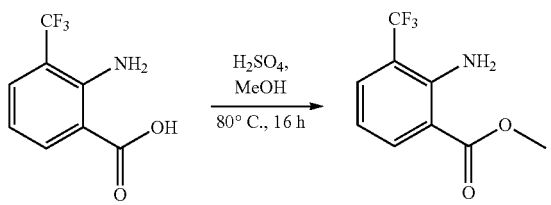

To a solution of 2-amino-3-(trifluoromethyl)benzoic acid (10.0 g, 48.75 mmol, 1 eq) in MeOH (150 mL) was added $H_2SO_4$ (4.00 g, 41.15 mmol, 2.2 mL) slowly at 0° C. After the addition, the resulting mixture was stirred for 16 h at 80° C. The reaction mixture was poured into ice/water (300 mL) at 0° C., and the aqueous phase was extracted with EtOAc (100 mL×3). The combined organic layers were washed with brine (100 mL), dried over anhydrous $Na_2SO_4$, filtered and concentrated in vacuo to give a residue, which was purified by column ($SiO_2$, Petroleum ether/Ethyl acetate=1/0 to 10/1) to give methyl 2-amino-3-(trifluoromethyl)benzoate (8.00 g, 36.50 mmol, 74.88% yield) as yellow oil. $^1$H NMR ($CDCl_3$, 400 MHz) δ 8.07 (d, J=8.0 Hz, 1H), 7.60 (d, J=8.0 Hz, 1H), 6.68 (t, J=8.0 Hz, 1H), 6.47 (br s, 2H), 3.89 (s, 3H).

25.2 Preparation of methyl 2-bromo-3-(trifluoromethyl)benzoate

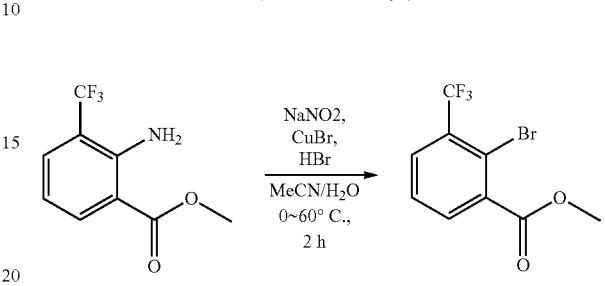

To a solution of methyl 2-amino-3-(trifluoromethyl)benzoate (5.00 g, 22.81 mmol, 1 eq) in MeCN (50 mL) and HBr (46.0 g, 228.14 mmol, 31 mL, 40% purity, 10 eq) was added $NaNO_2$ (1.90 g, 27.38 mmol, 1.2 eq, in 10 mL of $H_2O$) dropwise over 15 min at 0° C. Then CuBr (3.93 g, 27.38 mmol, 833.81 µL, 1.2 eq) was added in portions to the above mixture at 0° C., the resulting mixture was stirred for 2 h at 60° C. The reaction mixture was poured into ice/water (100 mL) at 0° C., and the aqueous phase was extracted with EtOAc (50 mL×3). The combined organic layers were washed with brine (100 mL×2), dried over $Na_2SO_4$, filtered and concentrated in vacuo to give a residue, which was purified by column chromatography ($SiO_2$, Petroleum ether/ Ethyl acetate=1/0 to 10/1) to give methyl 2-bromo-3-(trifluoro methyl)benzoate (5.20 g, 18.37 mmol, 80.53% yield) as yellow oil. $^1$H NMR ($CDCl_3$, 400 MHz) δ 7.80 (d, J=8.0 Hz, 1H), 7.74 (d, J=8.0 Hz, 1H), 7.49 (t, J=8.0 Hz, 1H), 3.98 (s, 3H).

25.3 Preparation of methyl 2-bromo-5-nitro-3-(trifluoromethyl)benzoate

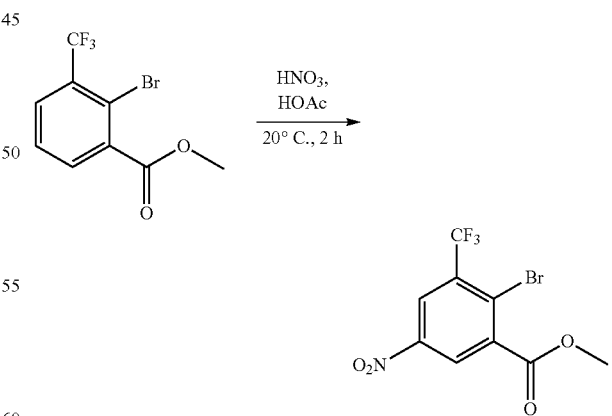

To a solution of methyl 2-bromo-3-(trifluoromethyl)benzoate (5.00 g, 17.67 mmol, 1 eq) in $H_2SO_4$ (50 mL) was added fuming $HNO_3$ (3.70 g, 53.05 mmol, 2.70 mL, 90% purity, 3.00 eq) dropwise at 0° C., the resulting mixture was stirred at 20° C. for 1 h. The reaction mixture was poured into ice/water (100 mL) at 0° C., and the formed yellow solid was collected by filtration, dried in vacuo to give methyl 2-bromo-5-nitro-3-(trifluoro methyl)benzoate (5.00 g, 15.24 mmol, 86.28% yield) as a yellow solid. $^1$H NMR (DMSO-$d_6$, 400 MHz) δ 8.77 (d, J=2.8 Hz, 1H), 8.57 (d, J=2.4 Hz, 1H), 3.95 (s, 3H).

25.4 Preparation of methyl 5-amino-2-bromo-3-(trifluoromethyl)benzoate

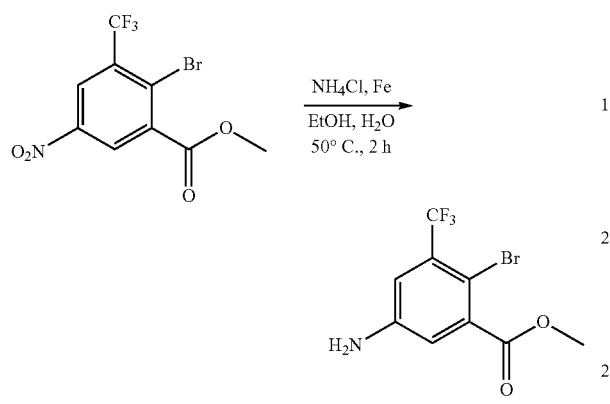

To a solution of methyl 2-bromo-5-nitro-3-(trifluoromethyl)benzoate (5.00 g, 15.24 mmol, 1 eq) in a mixture of H$_2$O (10 mL) and EtOH (100 mL) was added NH$_4$Cl (2.50 g, 45.7 mmol, 1.60 mL, 3 eq) and Fe (2.80 g, 45.7 mmol, 3 eq) sequentially at 20° C., the resulting mixture was stirred at 50° C. for 2 h. The reaction mixture was filtered, and the filtrate was concentrated in vacuo to give a residue, which was poured into ice/water (100 mL) at 0° C., and then extracted with EtOAc (100 mL×3). The combined organic layers were washed with brine (100 mL), dried over Na$_2$SO$_4$, filtered and concentrated in vacuo to give methyl 5-amino-2-bromo-3-(trifluoromethyl)benzoate (4.10 g, 13.76 mmol, 90.25% yield) as a white solid. $^1$H NMR (CDCl$_3$, 400 MHz) δ 7.08 (d, J=2.8 Hz, 1H), 6.99 (d, J=2.4 Hz, 1H), 3.99 (br s, 2H), 3.94 (s, 3H).

25.5 Preparation of methyl 2-bromo-5-[[4-(1-ethylpropylamino)-5-methyl-pyrimidin-2-yl] amino]-3-(trifluoromethyl)benzoate

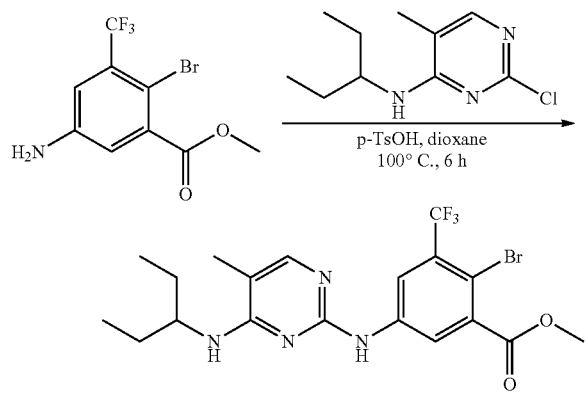

To a solution of methyl 5-amino-2-bromo-3-(trifluoromethyl)benzoate (1.50 g, 5.03 mmol, 1 eq) and 2-chloro-N-(1-ethylpropyl)-5-methyl-pyrimidin-4-amine (1.10 g, 5.0 mmol, 1 eq) in dioxane (30 mL) was added p-TsOH (1.30 g, 7.6 mmol, 1.5 eq) at 20° C., the resulting mixture was stirred at 100° C. for 6 h. The reaction mixture was poured into sat. NaHCO$_3$ (60 mL) at 0° C., and the aqueous phase was extracted with EtOAc (30 mL×3). The combined organic layers were washed with brine (20 mL), dried over Na$_2$SO$_4$, filtered and concentrated in vacuo to give a residue, which was purified by column chromatography (SiO$_2$, Petroleum ether/Ethyl acetate=1/0 to 1/1) to give methyl 2-bromo-5-[[4-(1-ethylpropylamino)-5-methyl-pyrimidin-2-yl]amino]-3-(trifluoromethyl)benzoate (1.60 g, 3.37 mmol, 66.89% yield) as a white solid. $^1$H NMR (DMSO-$d_6$, 400 MHz) δ 9.55 (s, 1H), 8.48 (d, J=2.8 Hz, 1H), 8.32 (d, J=2.4 Hz, 1H), 7.70 (s, 1H), 6.29 (d, J=8.8 Hz, 1H), 4.09-4.03 (m, 1H), 3.88 (s, 3H), 1.95 (s, 3H), 1.62-1.49 (m, 4H), 0.84 (t, J=7.6 Hz, 6H).

25.6 Preparation of [2-bromo-5-[[4-(1-ethylpropylamino)-5-methyl-pyrimidin-2-yl]amino]-3-(trifluoromethyl)phenyl]methanol

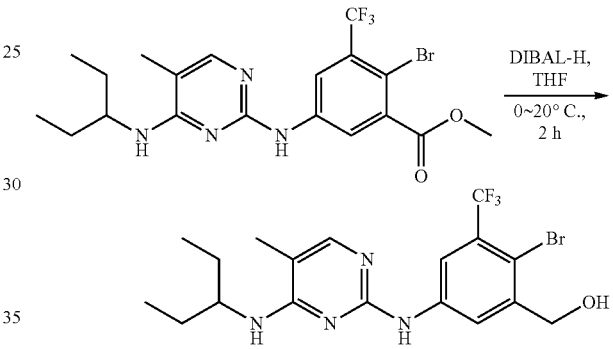

A mixture of methyl 2-bromo-5-[[4-(1-ethylpropylamino)-5-methyl-pyrimidin-2-yl]amino]-3-(trifluoromethyl)benzoate (1.00 g, 2.10 mmol, 1 eq) in THF (20 mL) was added DIBAL-H (1 M, 10.5 mL, 5 eq) dropwise at 0° C., and then the mixture was stirred at 20° C. for 2 h under N$_2$ atmosphere. The reaction was quenched by adding Na$_2$SO$_4$·10H$_2$O (20 g) at 0° C. The resulting mixture was filtered, and the filtrate was concentrated in vacuo to give [2-bromo-5-[[4-(1-ethylpropylamino)-5-methyl-pyrimidin-2-yl]amino]-3-(trifluoromethyl)phenyl]methanol (600 mg, 1.34 mmol, 63.76% yield) as yellow solid. $^1$H NMR (DMSO-$d_6$, 400 MHz) δ 9.35 (s, 1H), 8.51 (d, J=2.4 Hz, 1H), 8.09 (d, J=2.0 Hz, 1H), 7.68 (s, 1H), 6.19 (d, J=8.8 Hz, 1H), 5.52 (t, J=5.2 Hz, 1H), 4.53 (d, J=5.2 Hz, 2H), 4.23-4.13 (m, 1H), 1.95 (s, 3H), 1.60-1.42 (m, 4H), 0.84 (t, J=7.2 Hz, 6H).

25.7 Preparation of N4-(1-ethylpropyl)-N2-[1-hydroxy-7-(trifluoromethyl)3H-2,1-benzoxaborol-5-yl]-5-methyl-pyrimidine-2,4-diamine

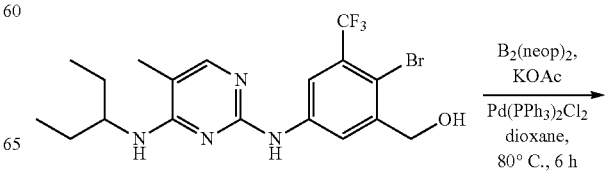

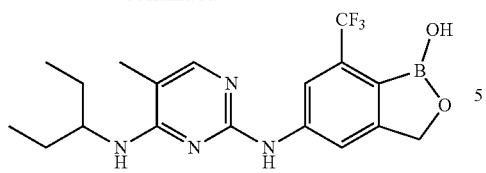
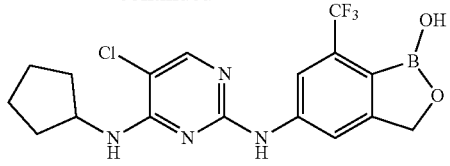

A mixture of [2-bromo-5-[[4-(1-ethylpropylamino)-5-methyl-pyrimidin-2-yl]amino]-3-(trifluoromethyl)phenyl]methanol (200 mg, 447.14 μmol, 1 eq), 2-(5,5-dimethyl-1,3,2-dioxaborinan-2-yl)-5,5-dimethyl-1,3,2-dioxaborinane (152 mg, 670.70 μmol, 1.5 eq), KOAc (132 mg, 1.34 mmol, 3 eq) and Pd(PPh$_3$)$_2$Cl$_2$ (32 mg, 44.71 μmol, 0.1 eq) in dioxane (10 mL) was degassed and purged with N$_2$ for 3 times, then the reaction mixture was stirred at 80° C. for 6 h under N$_2$ atmosphere. The reaction mixture was poured into sat. NH$_4$Cl (20 mL), and the aqueous phase was extracted with ethyl acetate (10 mL×3). The organic phase was washed with brine (20 mL), dried over anhydrous Na$_2$SO$_4$, concentrated in vacuo to give a residue, which was purified by prep-TLC (SiO$_2$, Petroleum ether/Ethyl acetate=2/1) and prep-HPLC (column: Nano-micro Kromasil C18 100*30 mm 8 um; mobile phase: [water(0.1% TFA)-ACN]; B %: 25%-55%, 10 min) to give N4-(1-ethylpropyl)-N2-[1-hydroxy-7-(trifluoromethyl)3H-2,1-benzoxaborol-5-yl]-5-methyl-pyrimidine-2,4-diamine (112 mg, 284.12 μmol, 21.18% yield) as a white solid. $^1$H NMR (DMSO-d$_6$, 400 MHz) δ 10.51 (s, 1H), 9.13 (s, 1H), 8.23 (s, 1H), 7.81 (br s, 1H), 7.80 (s, 1H), 7.78 (s, 1H), 5.06 (s, 2H), 4.11-4.06 (m, 1H), 2.04 (s, 3H), 1.65-1.55 (m, 4H), 0.83 (t, J=7.2 Hz, 6H). MS (ESI): mass calcd. For C$_{18}$H$_{22}$BF$_3$N$_4$O$_2$ 394.18, m/z found 395.1 [M+H]$^+$. HPLC: 98.77% (220 nm), 99.23% (254 nm).

26. Preparation of 5-((5-chloro-4-(cyclopentylamino)pyrimidin-2-yl)amino)-7-(trifluoromethyl)benzo[c][1,2]oxaborol-1(3H)-ol

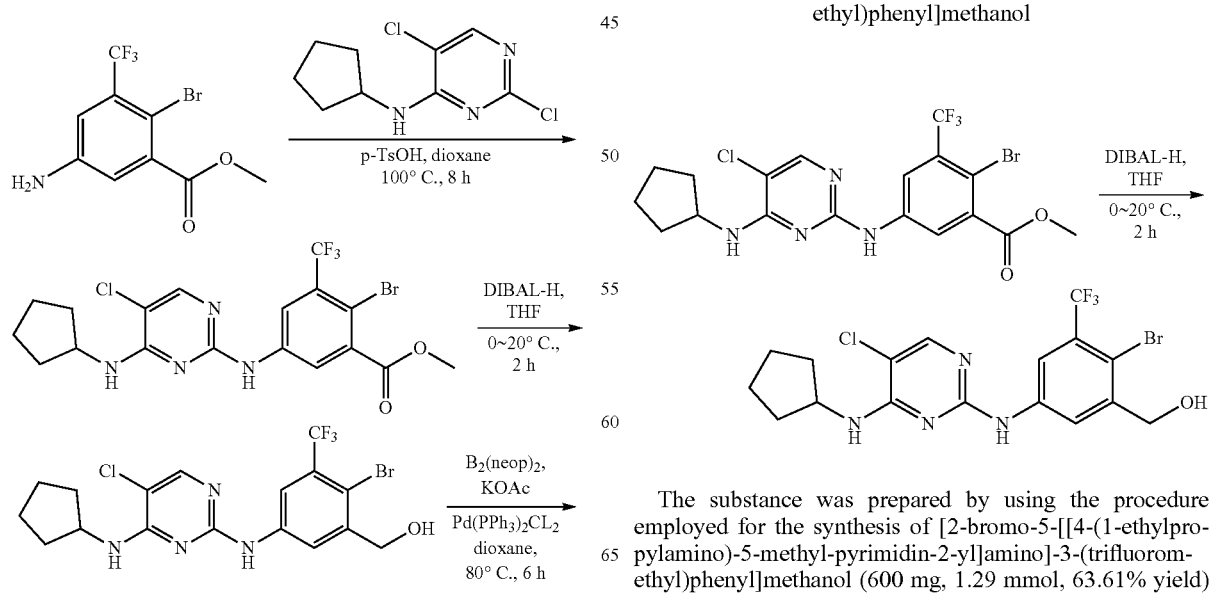

26.1 Preparation of methyl 2-bromo-5-[[5-chloro-4-(cyclopentylamino)pyrimidin-2-yl]amino]-3-(trifluoromethyl)benzoate

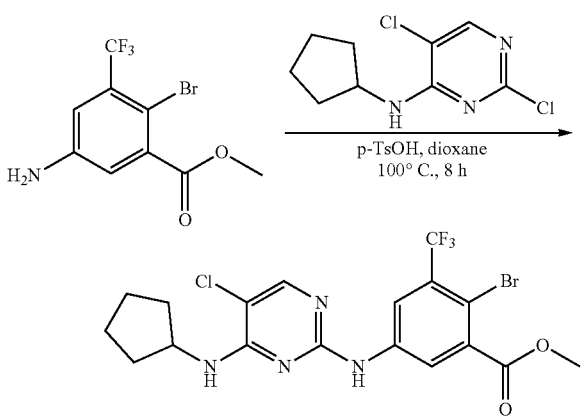

The substance was prepared by using the procedure employed for the synthesis of methyl 2-bromo-5-[[4-(1-ethylpropylamino)-5-methyl-pyrimidin-2-yl]amino]-3-methyl-benzoate (1.40 g, 2.84 mmol, 56.35% yield) as a white solid. $^1$H NMR (DMSO-d$_6$, 400 MHz) δ 9.89 (s, 1H), 8.42 (d, J=2.4 Hz, 1H), 8.29 (d, J=2.4 Hz, 1H), 8.01 (s, 1H), 7.06 (d, J=7.2 Hz, 1H), 4.41-4.28 (m, 1H), 3.89 (s, 3H), 1.94-1.73 (m, 2H), 1.72-1.62 (m, 2H), 1.59-1.53 (m, 4H).

26.2 Preparation of [2-bromo-5-[[5-chloro-4-(cyclopentylamino)pyrimidin-2-yl]amino]-3-(trifluoromethyl)phenyl]methanol The substance was prepared by using the procedure employed for the synthesis of [2-bromo-5-[[4-(1-ethylpropylamino)-5-methyl-pyrimidin-2-yl]amino]-3-(trifluoromethyl)phenyl]methanol (600 mg, 1.29 mmol, 63.61% yield) as a yellow solid. $^1$H NMR (DMSO-d$_6$, 400 MHz) δ 9.72 (s, 1H), 8.36 (d, J=2.4 Hz, 1H), 8.17 (d, J=2.4 Hz, 1H), 7.98 (s, 1H), 6.97 (d, J=7.6 Hz, 1H), 5.57 (t, J=5.6 Hz, 1H), 4.54 (d, J=5.6 Hz, 1H), 4.50-4.45 (m, 1H), 1.99-1.95 (m, 2H), 1.71-1.66 (m, 2H), 1.59-1.54 (m, 4H).

26.3 Preparation of 5-((5-chloro-4-(cyclopentylamino)pyrimidin-2-yl)amino)-7-(trifluoromethyl)benzo[c][1,2]oxaborol-1(3H)-ol

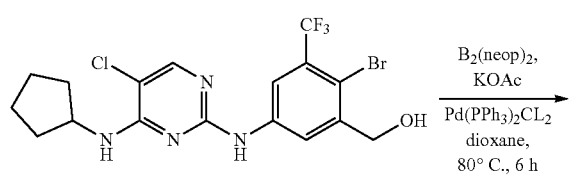

-continued

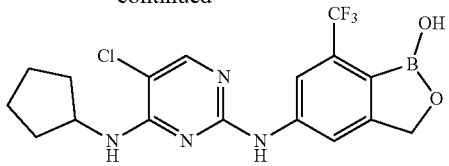

The substance was prepared by using the procedure employed for the synthesis of N4-(1-ethylpropyl)-N2-[1-hydroxy-7-(trifluoromethyl)3H-2,1-benzoxaborol-5-yl]-5-methyl-pyrimidine-2,4-diamine (60 mg, 145.42 μmol, 13.54% yield) as a white solid. $^1$H NMR (DMSO-$d_6$, 400 MHz) δ 9.92 (s, 1H), 8.98 (br s, 1H), 8.24 (s, 1H), 8.04 (s, 1H), 7.93 (s, 1H), 7.23 (d, J=7.2 Hz, 1H), 5.01 (s, 2H), 4.44-4.37 (m, 1H), 2.00-1.90 (m, 2H), 1.78-1.70 (m, 2H), 1.67-1.46 (m, 4H). MS (ESI): mass calcd. For $C_{17}H_{17}BClF_3N_4O_2$ 412.11, m/z found 413.0 [M+H]$^+$. HPLC: 98.46% (220 nm), 98.87% (254 nm).

27. Preparation of 7-methyl-5-((5-methyl-4-(phenylamino)pyrimidin-2-yl)amino)benzo[c][1,2]oxaborol-1(3H)-ol

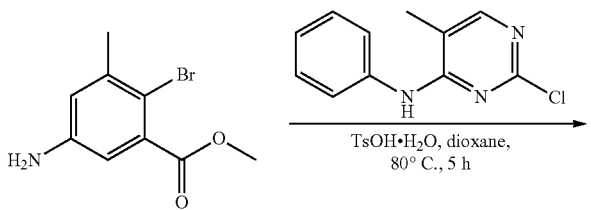

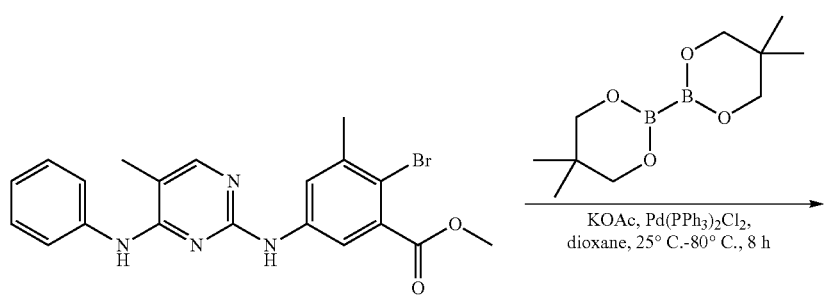

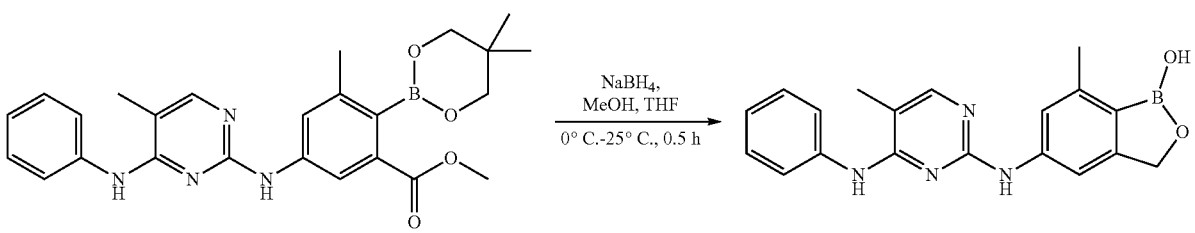

27.1 Preparation of methyl 5-[(4-anilino-5-methyl-pyrimidin-2-yl)amino]-2-bromo-3-methyl-benzoate

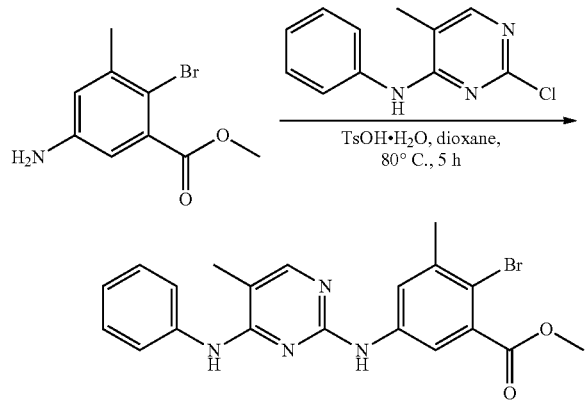

To a mixture of 2-chloro-5-methyl-N-phenyl-pyrimidin-4-amine (0.9 g, 4.10 mmol, 1 eq) and methyl 5-amino-2-bromo-3-methyl-benzoate (1.00 g, 4.10 mmol, 1 eq) in dioxane (20 mL) was added TsOH·H$_2$O (1.17 g, 6.15 mmol, 1.5 eq), the resulting mixture was stirred at 80° C. for 5 h. The reaction mixture was cooled to room temperature, and cold Na$_2$CO$_3$ solution (10 mL) was added, the aqueous phase was extracted with EtOAc (50 mL) twice. The combined organic layers were washed with cold water, dried over Na$_2$SO$_4$ and concentrated in vacuo to give the crude product. The crude product was purified by re-crystallization from EtOAc/petroleum ether (1:2) to give pure methyl 5-[(4-anilino-5-methyl-pyrimidin-2-yl)amino]-2-bromo-3-methyl-benzoate (1.71 g, 4.00 mmol, 97.68% yield) as a gray solid. 1H NMR (DMSO, 400 MHz) δ 9.26 (s, 1H), 8.34 (s, 1H), 7.93 (s, 1H), 7.80 (dd, J=8.0, 2.8 Hz, 2H), 7.66 (d, J=8.4 Hz, 2H), 7.30 (t, J=8.0 Hz, 2H), 7.06 (t, J=7.2 Hz, 2H) 3.78 (s, 3H), 2.24 (s, 3H), 2.12 (s, 3H).

27.2 Preparation of methyl 5-[(4-anilino-5-methyl-pyrimidin-2-yl)amino]-2-(5,5-dimethyl-1,3,2-dioxaborinan-2-yl)-3-methyl-benzoate

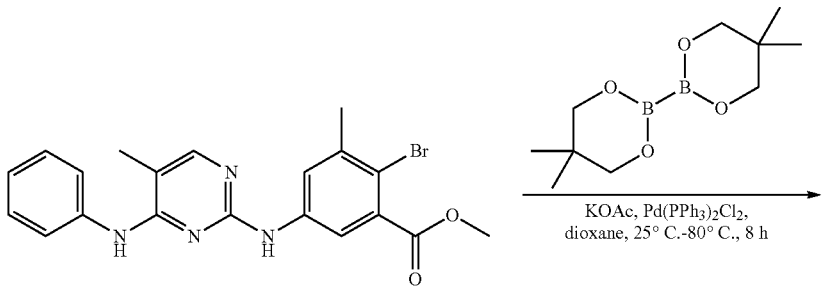

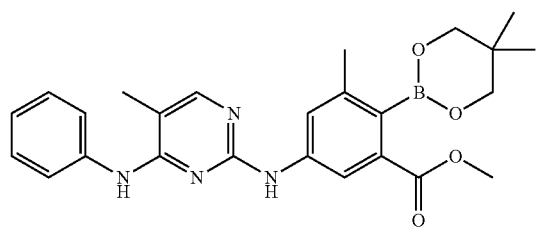

To a mixture of methyl 5-[(4-anilino-5-methyl-pyrimidin-2-yl)amino]-2-bromo-3-methyl-benzoate (380 mg, 889 μmol, 1 eq) and 2-(5,5-dimethyl-1,3,2-dioxaborinan-2-yl)-5,5-dimethyl-1,3,2-dioxaborinane (803 mg, 3.56 mmol, 4 eq) in anhydrous dioxane (20 mL) were added KOAc (175 mg, 1.78 mmol, 2 eq) and Pd(PPh₃)₂Cl₂ (31.2 mg, 44.4 μmol, 0.05 eq), the resulting mixture was bubbled with nitrogen for 10 mins, then sealed and stirred at 80° C. for 8 h. The reaction mixture was concentrated in vacuo to give a residue, which was purified by flash silica gel chromatography (ISCO®; 20 g SepaFlash® Silica Flash Column, Eluent of 20%-100% Ethyl acetate/Petroleum ethergradient @50 mL/min) to give methyl 5-[(4-anilino-5-methyl-pyrimidin-2-yl)amino]-2-(5,5-dimethyl-1,3,2-dioxaborinan-2-yl)-3-methyl-benzoate (290 mg, 630 μmol, 70.84% yield) as a light brown solid. 1H NMR (DMSO, 400 MHz) δ 9.12 (s, 1H), 8.27 (s, 1H), 7.95-7.91 (m, 2H), 7.80 (s, 1H), 7.72 (d, J=8.4 Hz, 2H), 7.29 (t, J=8.4 Hz, 2H), 7.05 (t, J=7.2 Hz, 1H), 3.78 (s, 3H), 3.67 (s, 4H), 2.22 (s, 3H), 2.12 (s, 3H), 1.06 (s, 6H).

27.3 Preparation of N2-(1-hydroxy-7-methyl-3H-2,1-benzoxaborol-5-yl)-5-methyl-N4-phenyl-pyrimidine-2,4-diamine

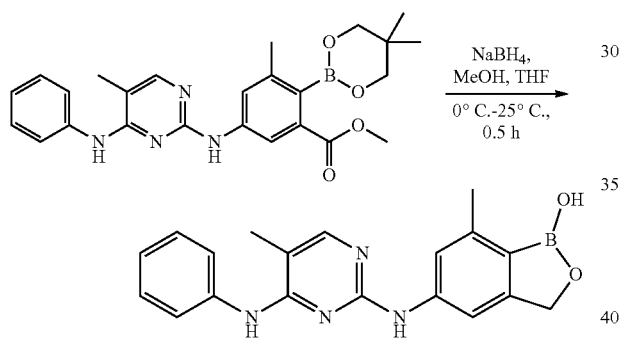

To a mixture of methyl 5-[(4-anilino-5-methyl-pyrimidin-2-yl)amino]-2-(5,5-dimethyl-1,3,2-dioxaborinan-2-yl)-3-methyl-benzoate (240 mg, 521.3 μmol, 1 eq) and MeOH (33 μL, 1.6 eq) in THF (6 mL) was added NaBH₄ (59 mg, 1.56 mmol, 3 eq) in portions at 0° C., the resulting mixture was stirred at 25° C. for 0.5 h. The reaction mixture was poured into ice-water (w/w=1/1) (8 mL), the pH of aqueous phase was adjusted to 3-4 with HCl (2N), extracted with (5 mL×3). The combined organic phase was washed with brine (5 mL×2), dried over anhydrous Na₂SO₄, filtered and concentrated in vacuo to give a residue, which was purified by prep-HPLC (column: Nano-micro Kromasil C18 100*30 mm 8 um; mobile phase: [water(0.1% TFA)-ACN]; B %: 15%-35%, 10 min) to give N2-(1-hydroxy-7-methyl-3H-2,1-benzoxaborol-5-yl)-5-methyl-N4-phenyl-pyrimidine-2,4-diamine (84 mg, 219 μmol, 42.0% yield, 90.25% purity) as a gray solid. ¹H NMR (DMSO-d₆, 400 MHz) δ 9.78 (br s, 1H), 9.01 (br s, 1H), 8.70 (s, 1H), 7.94 (s, 1H), 7.60 (d, J=7.6 Hz, 2H), 7.52 (s, 1H), 7.40 (t, J=7.6 Hz, 2H), 7.22-7.17 (m, 2H), 6.54 (s, 2H), 4.76 (s, 2H), 2.30 (s, 3H), 2.14 (s, 3H). MS (ESI): mass calcd. For $C_{19}H_{19}BN_4O_2$ 346.16, m/z found 347.1 [M+H]⁺. HPLC: 90.25% (220 nm), 88.74% (254 nm).

28. Preparation of 5-((5-methyl-4-(phenylamino)pyrimidin-2-yl)amino)-7-(trifluoro methyl) benzo[c][1,2]oxaborol-1(3H)-ol

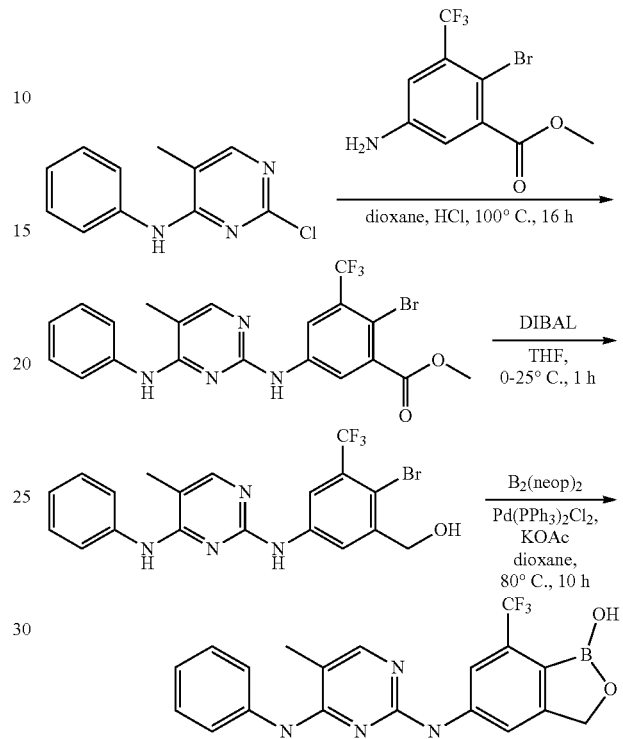

28.1 Preparation of methyl 2-bromo-5-((5-methyl-4-(phenylamino)pyrimidin-2-yl)amino)-3-(trifluoromethyl)benzoate

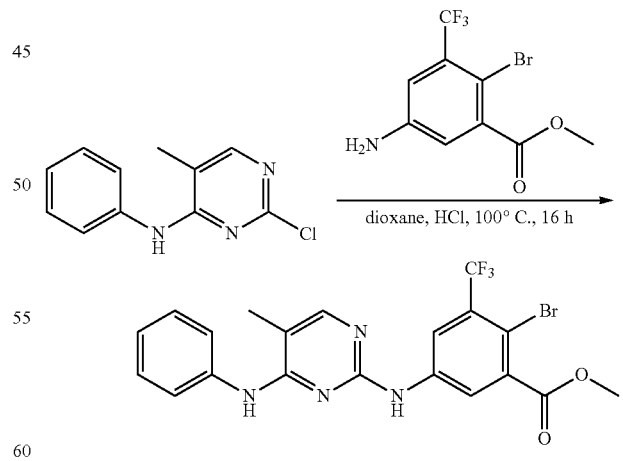

A mixture of 2-chloro-5-methyl-N-phenyl-pyrimidin-4-amine (500 mg, 2.28 mmol, 1 eq) and methyl 5-amino-2-bromo-3-(trifluoromethyl)benzoate (712 mg, 2.39 mmol, 1.05 eq) in dioxane (10 mL)/HCl (0.5 mL, 12 N) was stirred at 100° C. for 16 hr. The reaction mixture was cooled to room temperature, diluted with EtOAc (10 mL). The pH of the aqueous phase was adjusted to 9 with sat. NaHCO₃ (20 mL), the organic layer was separated, washed with brine, dried over Na₂SO₄, filtered and concentrated in vacuo to give the crude product. Then it was triturated with MTBE (10 mL), the precipitate was collected by filtration, dried in vacuo to give methyl 5-[(4-anilino-5-methyl-pyrimidin-2-yl)amino]-2-bromo-3-(trifluoromethyl)benzoate (670 mg, 1.39 mmol, 61.16% yield) as a gray solid. ¹H NMR (DMSO-d₆, 400 MHz) δ 9.65 (s, 1H), 8.40 (s, 1H), 8.29 (s, 1H), 8.23 (s, 1H), 7.96 (s, 1H), 7.64 (d, J=8.0 Hz, 2H), 7.28 (t, J=7.6 Hz, 1H), 7.06 (t, J=7.6 Hz, 1H), 3.81 (s, 3H), 2.12 (s, 3H).

28.2 Preparation of [5-[(4-anilino-5-methyl-pyrimidin-2-yl)amino]-2-bromo-3-(trifluoro methyl)phenyl]methanol

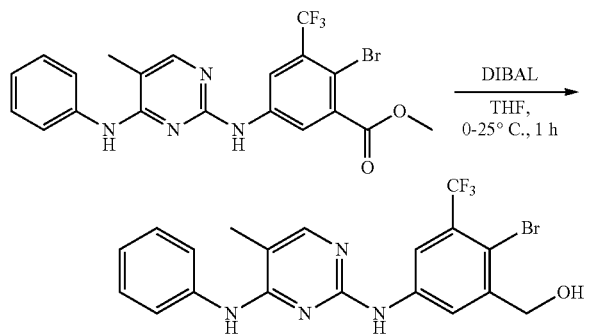

To a solution of methyl 5-[(4-anilino-5-methyl-pyrimidin-2-yl)amino]-2-bromo-3-(trifluoro methyl)benzoate (500 mg, 1.04 mmol, 1 eq) in THF (10 mL) was added DIBAL (1 M, 4.20 mL, 4 eq) dropwise at 0° C., the resulting mixture was stirred at 0-25° C. for 1 h. The reaction was quenched by adding Na₂SO₄·10H₂O (5 g) in portions at 0° C., the resulting suspension was passed through a pad of celite. The filter cake was washed with EtOAc (10 mL), and the filtrate was concentrated in vacuo to give [5-[(4-anilino-5-methyl-pyrimidin-2-yl)amino]-2-bromo-3-(trifluoromethyl)phenyl]methanol (420 mg, 926.63 μmol, 89.19% yield) as yellow oil.

28.3 Preparation of 5-((5-methyl-4-(phenylamino)pyrimidin-2-yl)amino)-7-(trifluoro methyl) benzo[c][1,2]oxaborol-1(3H)-ol

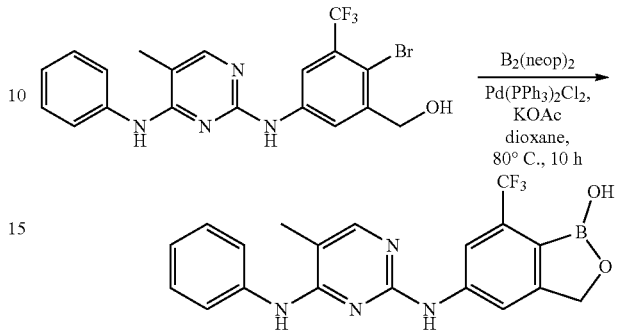

A mixture of [5-[(4-anilino-5-methyl-pyrimidin-2-yl)amino]-2-bromo-3-(trifluoromethyl) phenyl]methanol (400 mg, 882.51 μmol, 1 eq), 5,5,5',5'-tetramethyl-2,2'-bi(1,3,2-dioxabori nane) (997 mg, 4.41 mmol, 5 eq), Pd(PPh₃)₂Cl₂ (124 mg, 176.50 μmol, 0.2 eq) and KOAc (433. mg, 4.41 mmol, 5 eq) in dioxane (20 mL) was stirred at 80° C. for 10 h. The suspension was passed through a pad of celite, and the filtrate was concentrated in vacuo to give a residue, which was purified by prep-HPLC (column: Phenomenex Luna C18 150*30 mm*5 um; mobile phase: [water(0.05% HCl)-ACN]; B %: 15%-30%, 12 min) to give 5-((5-methyl-4-(phenylamino)pyri midin-2-yl)amino)-7-(trifluoromethyl) benzo[c][1,2]oxaborol-1(3H)-ol (54 mg, 134.95 μmol, 15.29% yield) as a white solid. ¹H NMR (DMSO-d₆, 400 MHz) δ 9.70 (s, 1H), 8.91 (s, 1H), 8.65 (s, 1H), 8.12 (s, 1H), 7.95 (s, 1H), 7.76 (s, 1H), 7.62 (d, J=8.0 Hz, 2H), 7.37 (t, J=8.0 Hz, 2H), 7.16 (t, J=8.0 Hz, 1H), 4.86 (s, 2H), 2.15 (s, 3H). MS (ESI): mass calcd. For C₁₉H₁₆BF₃N₄O₂ 400.13, m/z found 401.1 [M+H]⁺. HPLC: 99.28% (220 nm), 99.80% (254 nm).

29. Preparation of N2-(1-hydroxy-3,3,7-trimethyl-2,1-benzoxaborol-5-yl)-5-methyl-N4-phenyl-pyrimidine-2,4-diamine

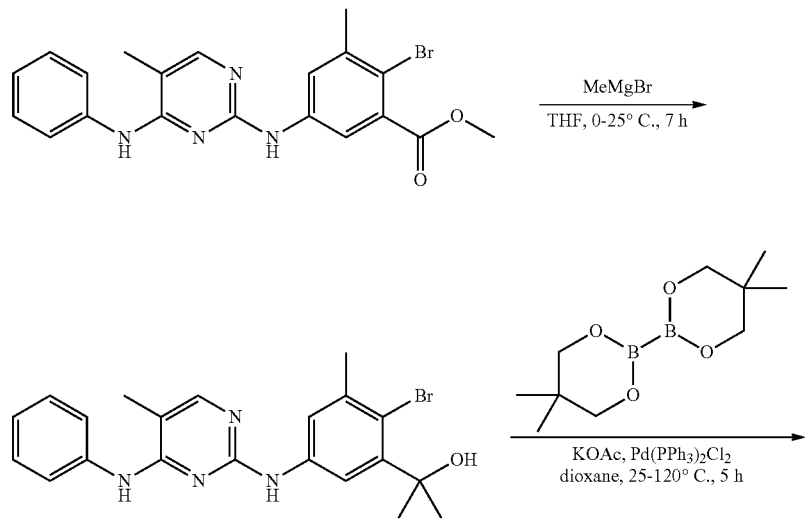

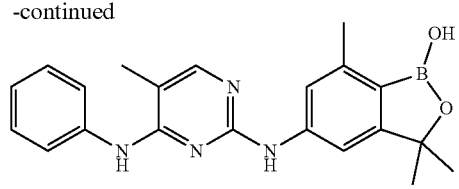

29.1 Preparation of 2-[5-[(4-anilino-5-methyl-pyrimidin-2-yl)amino]-2-bromo-3-methyl-phenyl]propan-2-ol

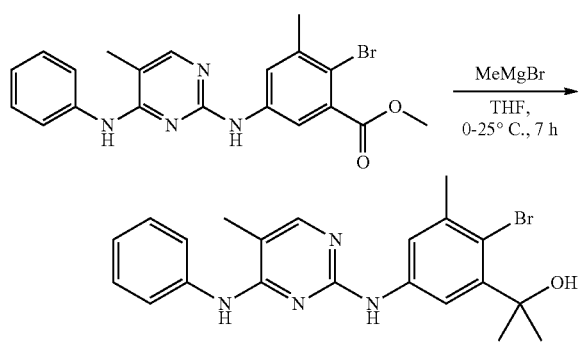

Methyl 5-[(4-anilino-5-methyl-pyrimidin-2-yl)amino]-2-bromo-3-methyl-benzoate (500 mg, 1.17 mmol, 1 eq) was added to MeMgBr (3 M, 7.80 mL, 20 eq) at 0° C. over a period of 30 min, the resulting mixture was stirred at 25° C. for 6.5 h. Then the reaction mixture was poured into sat. aq. NH$_4$Cl (15 mL), and the aqueous phase was extracted with EtOAc (8 mL×3). The combined organic layers were washed with brine (5 mL×3), dried over Na$_2$SO$_4$, filtered and concentrated in vacuo to give a residue. The residue was purified by flash silica gel chromatography (ISCO®; 12 g SepaFlash® Silica Flash Column, Eluent of 0-100% Ethyl acetate/Petroleum ethergradient @36 mL/min) to give 2-[5-[(4-anilino-5-methyl-pyrimidin-2-yl)amino]-2-bromo-3-methyl-phenyl]propan-2-ol (250 mg, 585 μmol, 49.99% yield) as a yellow solid.

29.2 Preparation of N2-(1-hydroxy-3,3,7-trimethyl-2,1-benzoxaborol-5-yl)-5-methyl-N4-phenyl-pyrimidine-2,4-diamine

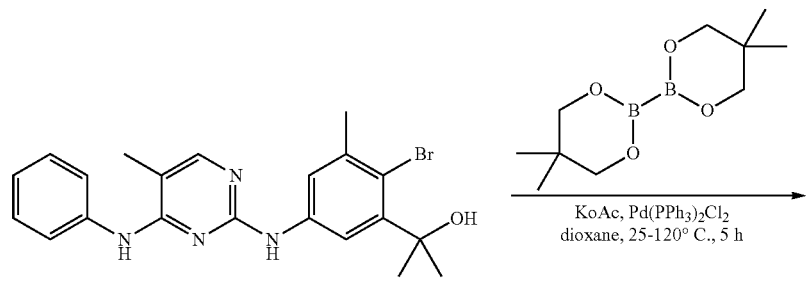

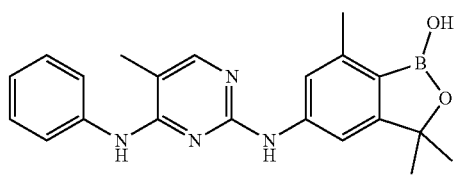

To a solution of 2-[5-[(4-anilino-5-methyl-pyrimidin-2-yl)amino]-2-bromo-3-methyl-phenyl]propan-2-ol (50 mg, 117 μmol, 1 eq) and 2-(5,5-dimethyl-1,3,2-dioxaborinan-2-yl)-5,5-dimethyl-1,3,2-dioxaborinane (66.1 mg, 293 μmol, 2.5 eq) in dioxane (3 mL) was added KOAc (23.0 mg, 234 μmol, 2 eq), Pd(PPh$_3$)$_2$Cl$_2$ (8.21 mg, 11.7 μmol, 0.1 eq) at 25° C. under N$_2$ atmosphere, the resulting mixture was stirred at 120° C. for 5 h. Then the reaction mixture was filtered, and the filtrate was concentrated in vacuo to give a residue. The residue was purified by prep-HPLC (column: Welch Xtimate C18 100*25 mm*3 um; mobile phase: [water(0.1% TFA)-ACN]; B %: 15%-35%, 12 min) to give N2-(1-hydroxy-3,3,7-trimethyl-2,1-benzoxaborol-5-yl)-5-methyl-N4-phenyl-pyrimidine-2,4-diamine (8.4 mg, 19.18% yield) as a white solid. $^1$H NMR (DMSO-d$_6$, 400 MHz) δ 10.00 (s, 1H), 9.49 (s, 1H), 8.66 (s, 1H), 7.91 (s, 1H), 7.58-7.56 (m, 2H), 7.42-7.38 (m, 2H), 7.26-7.25 (m, 2H), 7.23-7.16 (m, 1H), 2.29 (s, 3H), 2.17 (s, 3H), 3.83 (s, 6H). MS (ESI): mass calcd. For C$_{21}$H$_{23}$BN$_4$O$_2$ 374.19, m/z found 375.1 [M+H]$^+$. HPLC: 100.00% (220 nm), 100.00% (254 nm).

30. Preparation of 7-chloro-5-((5-methyl-4-(phenylamino)pyrimidin-2-yl)amino)benzo[c][1,2]oxaborol-1(3H)-ol

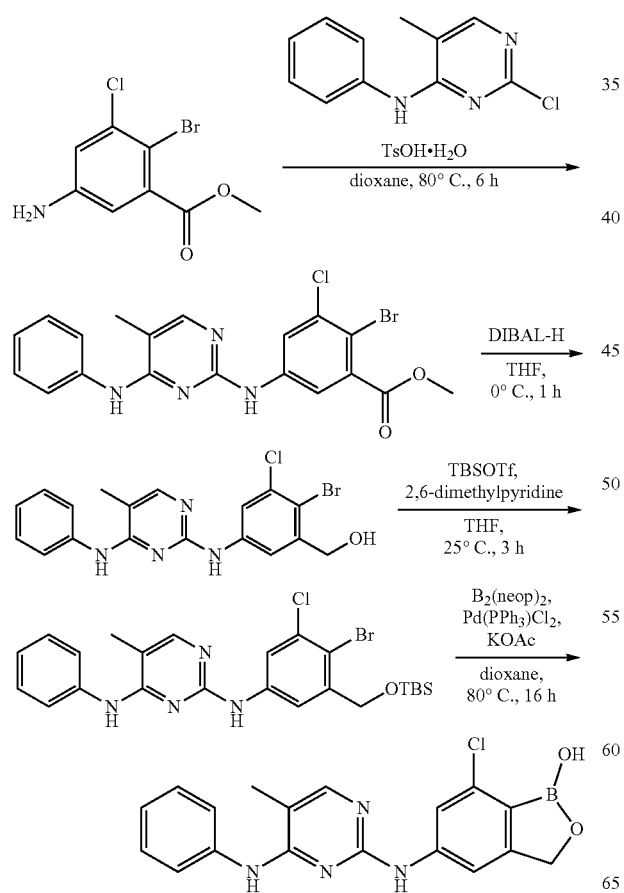

30.1 Preparation of methyl 5-[(4-anilino-5-methyl-pyrimidin-2-yl)amino]-2-bromo-3-chloro-benzoate

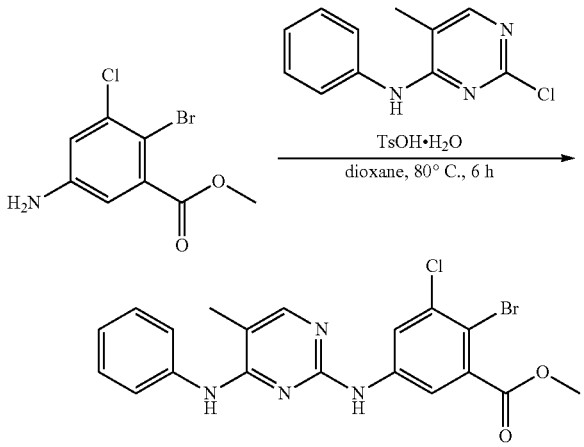

To a mixture of methyl 5-amino-2-bromo-3-chloro-benzoate (3.97 g, 15.0 mmol, 1.1 eq) and 2-chloro-5-methyl-N-phenyl-pyrimidin-4-amine (3 g, 13.7 mmol, 1 eq) in dioxane (30 mL) was added TsOH·H$_2$O (3.90 g, 20.49 mmol, 1.5 eq) in one portion at 25° C., the resulting mixture was stirred at 80° C. for 6 h. The reaction mixture was cooled to room temperature, and the organic solvent was removed in vacuo to give the crude product, which was neutralized by adding sat. aq. NaHCO$_3$, the precipitate from the mixture was collected by filtration, dried in vacuo to give methyl 5-[(4-anilino-5-methyl-pyrimidin-2-yl)amino]-2-bromo-3-chloro-benzoate (2.5 g, 5.58 mmol, 40.89% yield) as a yellow solid. $^1$H NMR (CDCl$_3$, 400 MHz) δ 8.15 (d, J=4.4 Hz, 1H), 8.07 (d, J=2.4 Hz, 1H), 7.94 (s, 1H), 7.62 (d, J=2.4 Hz, 1H), 7.54 (d, J=7.6 Hz, 2H), 7.42-7.36 (m, 3H), 7.15 (t, J=7.4 Hz, 1H), 6.38 (s, 1H), 3.88 (s, 3H), 2.15 (s, 3H).

30.2 Preparation of [5-[(4-anilino-5-methyl-pyrimidin-2-yl)amino]-2-bromo-3-chloro-phenyl]methanol

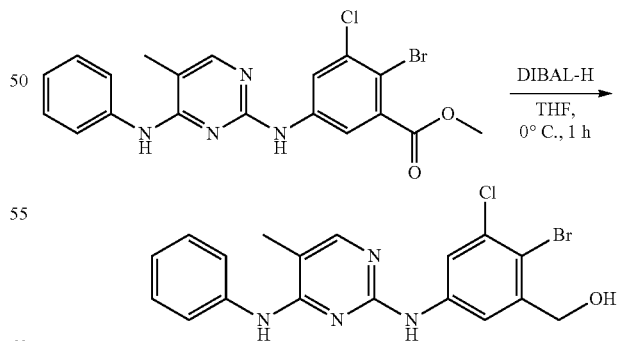

To a mixture of methyl 5-[(4-anilino-5-methyl-pyrimidin-2-yl)amino]-2-bromo-3-chloro-benzoate (1.2 g, 2.68 mmol, 1 eq) in THF (20 mL) was added DIBAL-H (1 M, 13.40 mL, 5 eq) dropwise at 0° C., the resulting mixture was stirred at 0° C. for 1 h. The reaction mixture was poured into H$_2$O (150 mL), Na$_2$SO$_4$·10H$_2$O (5 g) was added into above mixture, the resulting mixture stirred at 25° C. for 10 min. The insoluble substance was removed by filtration, and the filtrate was concentrated in vacuo to give [5-[(4-anilino-5-methyl-pyrimidin-2-yl)amino]-2-bromo-3-chloro-phenyl]methanol (0.7 g, 1.67 mmol, 62.23% yield) as a yellow solid. ¹H NMR (DMSO-de, 400 MHz) δ 9.36 (s, 1H), 8.31 (s, 1H), 8.20 (d, J=2.8 Hz, 1H), 8.06 (d, J=2.8 Hz, 1H), 7.94 (s, 1H), 7.73 (d, J=7.6 Hz, 2H), 7.62 (d, J=2.0 Hz, 1H), 7.34 (t, J=7.2 Hz, 2H), 7.06 (t, J=7.6 Hz, 1H), 5.47 (t, J=5.6 Hz, 1H), 4.45 (d, J=5.6 Hz, 2H), 2.13 (s, 3H).

30.3 Preparation of N2-[4-bromo-3-[[tert-butyl(dimethyl)silyl]oxymethyl]-5-chloro-phenyl]-5-methyl-N4-phenyl-pyrimidine-2,4-diamine

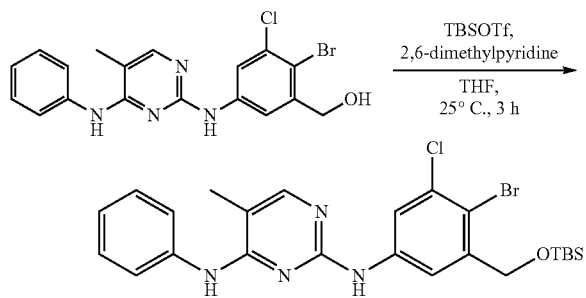

To a mixture of [5-[(4-anilino-5-methyl-pyrimidin-2-yl)amino]-2-bromo-3-chloro-phenyl]methanol (0.6 g, 1.43 mmol, 1 eq) in THF (10 mL) was added TBSOTf (567 mg, 2.14 mmol, 500 μL, 1.5 eq) and 2,6-dimethylpyridine (260 mg, 2.43 mmol, 280 μL, 1.7 eq) in one portion at 25° C., the resulting mixture was stirred at 25° C. for 3 h. The reaction mixture was poured into H₂O (10 mL), and the aqueous phase was extracted with EtOAc (10 mL×3). The combined organic layers were washed with brine (10 mL×2), dried over anhydrous Na₂SO₄, filtered and concentrated in vacuo to give a residue, which was purified by flash silica gel chromatography (ISCO®; 20 g SepaFlash® Silica Flash Column, Eluent of 0-30% Ethyl acetate/Petroleum ethergradient @75 mL/min) to give N2-[4-bromo-3-[[tert-butyl(dimethyl)silyl]oxymethyl]-5-chloro-phenyl]-5-methyl-N4-phenyl-pyrimidine-2,4-diamine (450 mg, 842.76 μmol, 58.95% yield) as a yellow solid. ¹H NMR (DMSO-d₆, 400 MHz) δ 9.44 (s, 1H), 8.34 (s, 1H), 8.08 (d, J=2.8 Hz, 1H), 7.92 (s, 1H), 7.74 (d, J=2.4 Hz, 1H), 7.69 (d, J=7.6 Hz, 2H), 7.34 (t, J=7.6 Hz, 2H), 7.07 (t, J=7.2 Hz, 1H), 4.63 (s, 2H), 2.13 (s, 3H), 0.93 (s, 9H), 0.11 (s, 6H).

30.4 Preparation of N2-(7-chloro-1-hydroxy-3H-2,1-benzoxaborol-5-yl)-5-methyl-N4-phenyl-pyrimidine-2,4-diamine

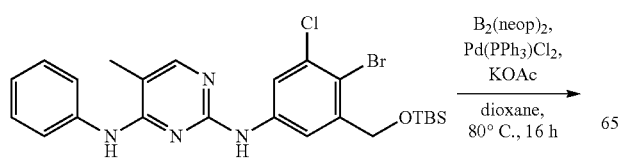

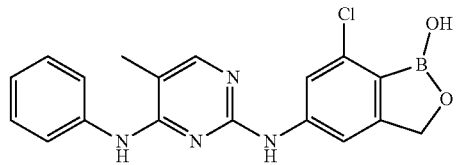

To a mixture of N2-[4-bromo-3-[[tert-butyl(dimethyl)silyl]oxymethyl]-5-chloro-phenyl]-5-methyl-N4-phenyl-pyrimidine-2,4-diamine (0.35 g, 655.48 μmol, 1 eq) and 2-(5,5-dimethyl-1,3,2-dioxaborinan-2-yl)-5,5-dimethyl-1,3,2-dioxaborinane (296 mg, 1.31 mmol, 2 eq) in dioxane (8 mL) was added KOAc (193 mg, 1.97 mmol, 3 eq) and Pd(PPh₃)₂Cl₂ (46 mg, 65.55 μmol, 0.1 eq) in one portion at 25° C., the resulting mixture was stirred at 80° C. for 16 h under N₂ atmosphere. The reaction mixture was cooled to room temperature, the precipitate was removed by filtration, then HCl (2N, 1 mL) was added into the filtrate, the mixture was concentrated in vacuo to give a residue. The residue was purified by prep-HPLC (column: Phenomenex Luna C₁₈ 150*30 mm*5 um; mobile phase: [water(0.1% TFA)-ACN]; B %: 15%-35%, 12 min) to give N2-(7-chloro-1-hydroxy-3H-2,1-benzoxaborol-5-yl)-5-methyl-N4-phenyl-pyrimidine-2,4-diamine (78 mg, 212.76 μmol, 32.46% yield) as a white solid. ¹H NMR (DMSO-d₆, 400 MHz) δ 9.98 (br s, 1H), 9.31 (br s, 1H), 8.98 (br s, 1H), 7.94 (s, 1H), 7.55 (d, J=8.0 Hz, 3H), 7.45-7.41 (m, 3H), 7.27-7.25 (m, 1H), 4.80 (s, 2H), 2.17 (s, 3H). MS (ESI): mass calcd. For C₁₈H₁BClN₄O₂ 366.11, m/z found 367.1 [M+H]⁺. HPLC: 96% (220 nm), 98.16% (254 nm).

31. Preparation of N2-(7-chloro-1-hydroxy-3,3-dimethyl-2,1-benzoxaborol-5-yl)-5-methyl-N4-phenyl-pyrimidine-2,4-diamine

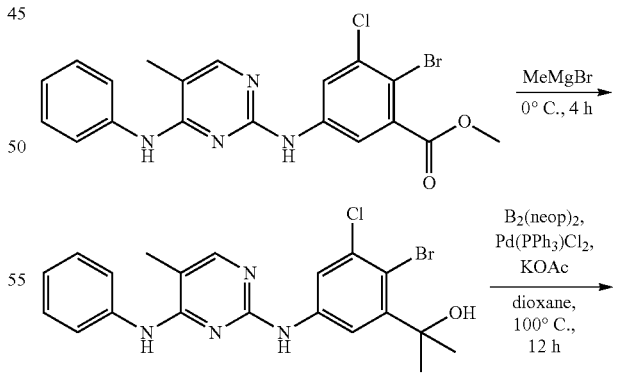

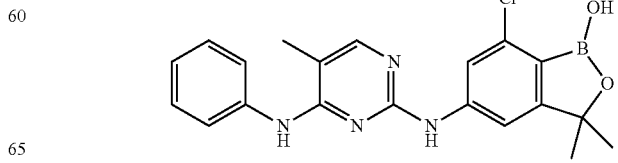

31.1 Preparation of 2-[5-[(4-anilino-5-methyl-pyrimidin-2-yl)amino]-2-bromo-3-chloro-phenyl]propan-2-ol

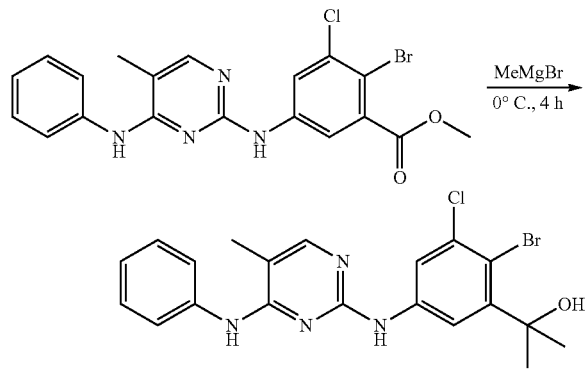

To a solution of methyl 5-[(4-anilino-5-methyl-pyrimidin-2-yl)amino]-2-bromo-3-chloro-benzoate (1 g, 2.23 mmol, 1 eq) in THF (10 mL) was added MeMgBr (3 M, 11.2 mL, 15 eq) at 0° C., the resulting mixture was stirred at 25° C. for 1 h. Then the reaction mixture was poured into sat. aq. NH$_4$Cl (20 mL), the aqueous phase was extracted with EtOAc (20 mL×3). The combined organic layers were washed with brine (20 mL×2), dried over anhydrous Na$_2$SO$_4$, filtered and concentrated in vacuo to give a residue, which was purified by flash silica gel chromatography (ISCO®; 20 g SepaFlash® Silica Flash Column, Eluent of 0-60% Ethyl acetate/Petroleum ethergradient @75 mL/min) to give 2-[5-[(4-anilino-5-methyl-pyrimidin-2-yl)amino]-2-bromo-3-chloro-phenyl]propan-2-ol (0.8 g, 1.79 mmol, 79.99% yield) as a yellow solid. $^1$H NMR (DMSO-d$_6$, 400 MHz) δ 9.34 (s, 1H), 8.29 (d, J=2.8 Hz, 2H), 7.94-7.93 (m, 1H), 7.85 (d, J=2.8 Hz, 1H), 7.75 (d, J=8.0 Hz, 2H), 7.34 (t, J=7.6 Hz, 2H), 7.07-7.04 (m, 1H), 5.23 (s, 1H), 2.13 (s, 3H), 1.61 (s, 6H).

31.2 Preparation of N2-(7-chloro-1-hydroxy-3,3-dimethyl-2,1-benzoxaborol-5-yl)-5-methyl-N4-phenyl-pyrimidine-2,4-diamine

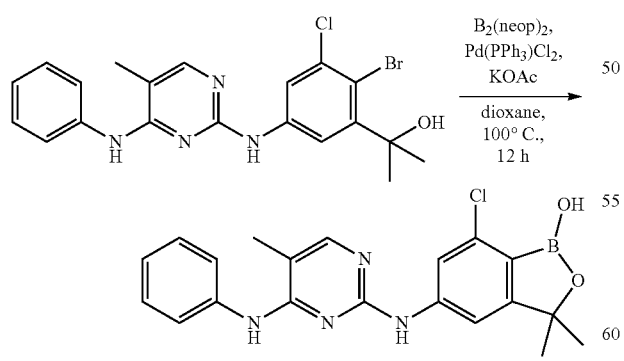

To a mixture of 2-[5-[(4-anilino-5-methyl-pyrimidin-2-yl)amino]-2-bromo-3-chloro-phenyl]propan-2-ol (0.7 g, 1.56 mmol, 1 eq) and 2-(5,5-dimethyl-1,3,2-dioxaborinan-2-yl)-5,5-dimethyl-1,3,2-dioxaborinane (706 mg, 3.13 mmol, 2 eq) in dioxane (10 mL) was added KOAc (460 mg, 4.69 mmol, 3 eq) and Pd(PPh$_3$)$_2$Cl$_2$ (110 mg, 156 μmol, 0.1 eq) in one portion at 25° C., the resulting mixture was stirred at 80° C. for 16 h under N$_2$ atmosphere. The reaction mixture was cooled to room temperature and filtered, HCl (2N, 1 mL) was added to the filtrate, the resulting mixture was concentrated in vacuo to give a residue. The residue was purified by prep-HPLC (column: Phenomenex Luna C18 150*30 mm*5 um; mobile phase: [water(0.1% TFA)-ACN]; B %: 20%-40%, 12 min) to give N2-(7-chloro-1-hydroxy-3,3-dimethyl-2,1-benzoxaborol-5-yl)-5-methyl-N4-phenyl-pyrimidine-2,4-diamine (220 mg, 557.44 μmol, 35.66% yield) as white solid. $^1$H NMR (DMSO-d$_6$, 400 MHz) δ 10.03 (br s, 1H), 9.30 (br s, 1H), 8.84 (br s, 1H), 7.95 (s, 1H), 7.58 (d, J=8.0 Hz, 3H), 7.41 (t, J=8.0 Hz, 2H), 7.35 (s, 1H), 7.23-7.19 (m, 1H), 2.17 (s, 3H), 1.32 (s, 6H). MS (ESI): mass calcd. For C$_{20}$H$_{20}$BClN$_4$O$_2$ 394.14, m/z found 395.1 [M+H]$^+$. HPLC: 96.13% (220 nm), 98.95% (254 nm).

32. Preparation of N2-(7-ethyl-1-hydroxy-3H-2,1-benzoxaborol-5-yl)-5-methyl-N4-phenyl-pyrimidine-2,4-diamine and N-(4-anilino-5-methyl-pyrimidin-2-yl)-N-(7-ethyl-1-hydroxy-3H-2,1-benzoxaborol-5-yl)-1,1,1-trifluoro-methanesulfonamide

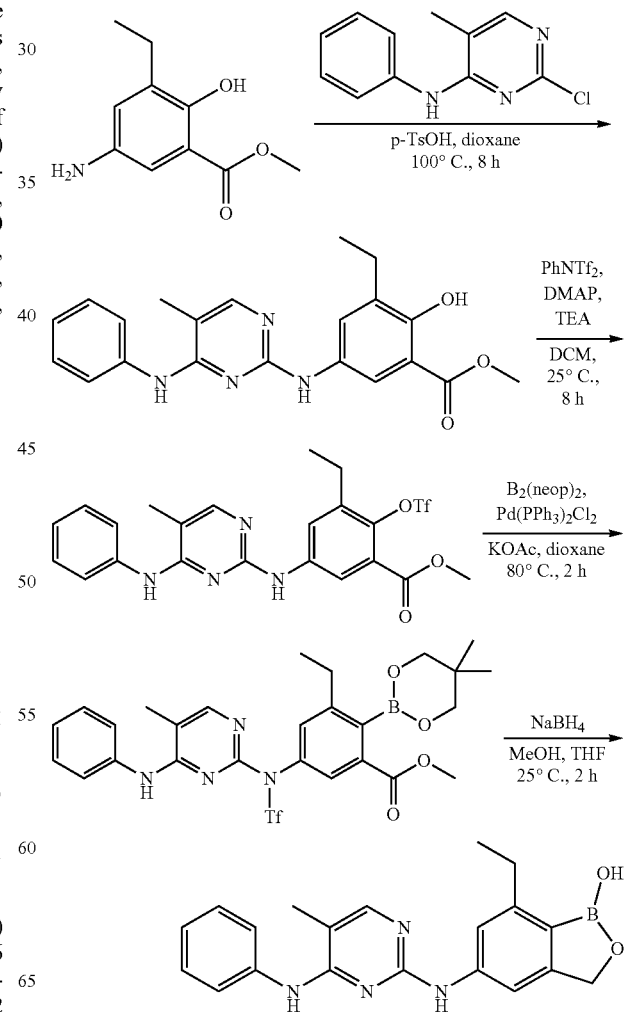

32.1 Preparation of 5-[(4-anilino-5-methyl-pyrimidin-2-yl)amino]-3-ethyl-2-hydroxy-benzoate

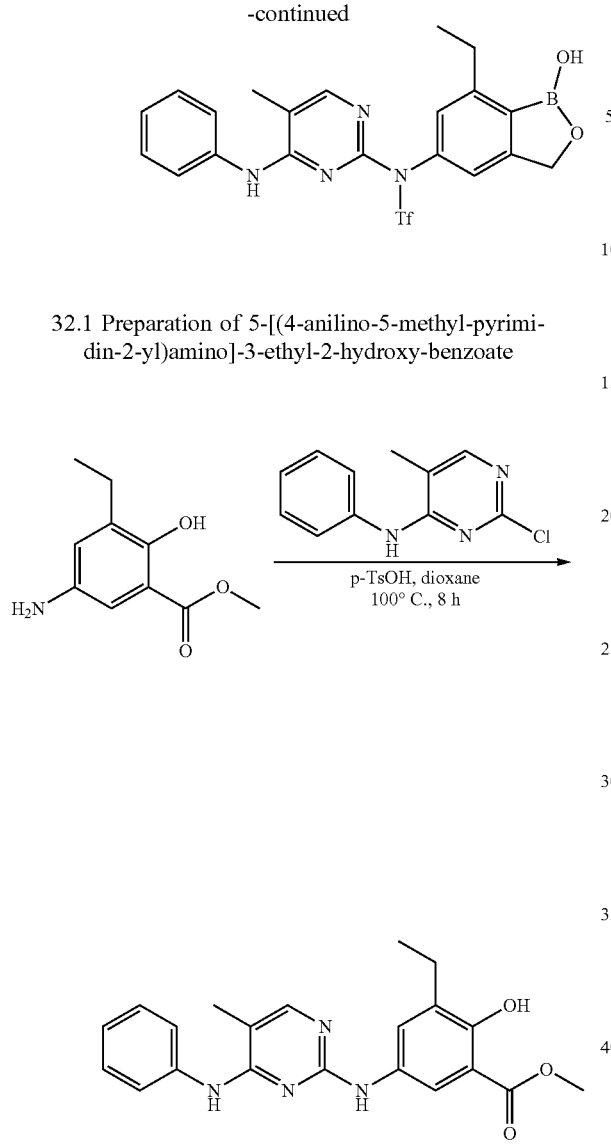

To a solution of methyl 5-amino-3-ethyl-2-hydroxy-benzoate (600 mg, 3.07 mmol, 1 eq) and 2-chloro-5-methyl-N-phenyl-pyrimidin-4-amine (675 mg, 3.07 mmol, 1 eq) in dioxane (20 mL) was added p-TsOH (793 mg, 4.60 mmol, 1.5 eq) at 20° C., the resulting mixture was stirred at 100° C. for 8 h. The reaction mixture was cooled to room temperature and filtered, the filtrate was concentrated in vacuo to give a residue, which was poured into sat. aq. NaHCO$_3$ (30 mL) at 0° C. The aqueous phase was extracted with EtOAc (30 mL×3), and the combined organic layers were washed with brine (100 mL), dried over anhydrous Na$_2$SO$_4$, filtered and concentrated in vacuo to give a residue, which was purified by column chromatography (SiO$_2$, Petroleum ether/Ethyl acetate=1/0 to 5/1) to give methyl 5-[(4-anilino-5-methyl-pyrimidin-2-yl)amino]-3-ethyl-2-hydroxy-benzoate (750 mg, 1.98 mmol, 64.56% yield) as a yellow solid. $^1$H NMR (CDCl$_3$, 400 MHz) δ 10.82 (s, 1H), 7.90 (s, 1H), 7.86 (d, J=2.4 Hz, 1H), 7.57 (d, J=7.6 Hz, 2H), 7.46 (d, J=2.4 Hz, 1H), 7.29 (t, J=7.6 Hz, 2H), 7.08 (t, J=7.6 Hz, 1H), 6.80 (s, 1H), 6.31 (s, 1H), 3.85 (s, 3H), 2.67 (q, J=7.2 Hz, 2H), 2.13 (s, 3H), 1.19 (t, J=7.2 Hz, 3H).

32.2 Preparation of methyl 5-[(4-anilino-5-methyl-pyrimidin-2-yl)-(trifluoromethylsulfonyl) amino]-3-ethyl-2-(trifluoromethylsulfonyloxy)benzoate

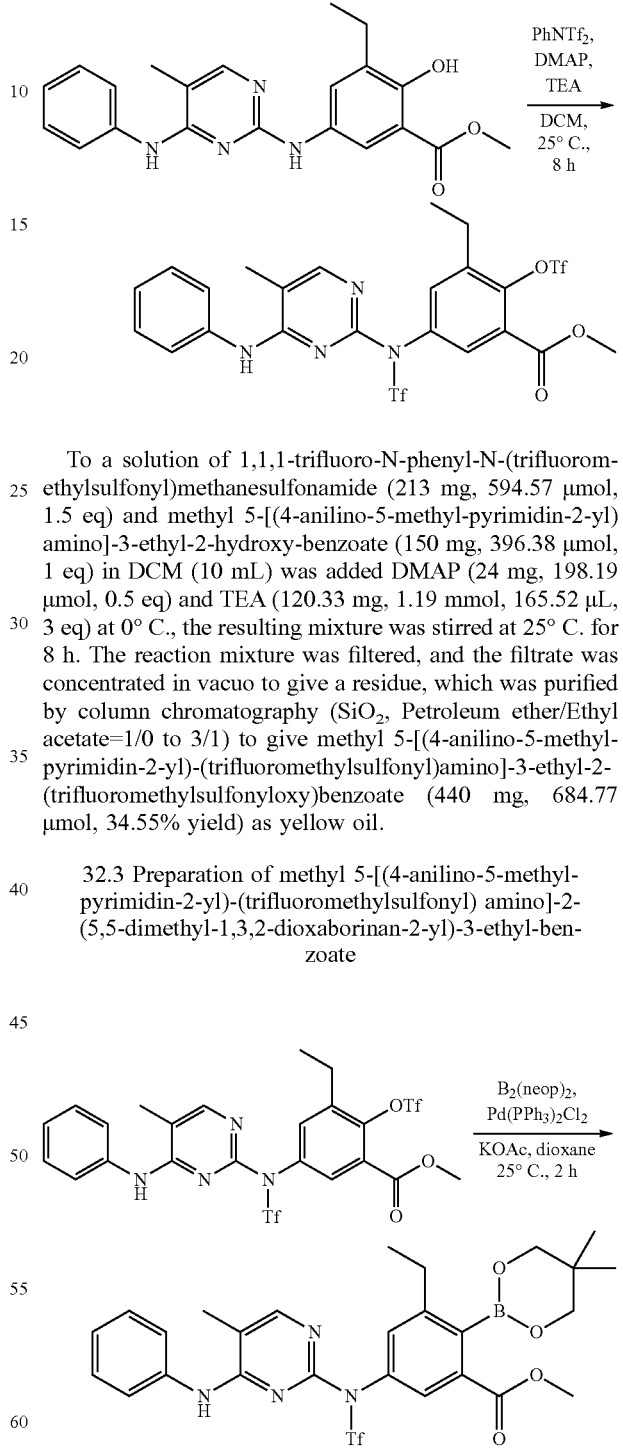

To a solution of 1,1,1-trifluoro-N-phenyl-N-(trifluoromethylsulfonyl)methanesulfonamide (213 mg, 594.57 μmol, 1.5 eq) and methyl 5-[(4-anilino-5-methyl-pyrimidin-2-yl)amino]-3-ethyl-2-hydroxy-benzoate (150 mg, 396.38 μmol, 1 eq) in DCM (10 mL) was added DMAP (24 mg, 198.19 μmol, 0.5 eq) and TEA (120.33 mg, 1.19 mmol, 165.52 μL, 3 eq) at 0° C., the resulting mixture was stirred at 25° C. for 8 h. The reaction mixture was filtered, and the filtrate was concentrated in vacuo to give a residue, which was purified by column chromatography (SiO$_2$, Petroleum ether/Ethyl acetate=1/0 to 3/1) to give methyl 5-[(4-anilino-5-methyl-pyrimidin-2-yl)-(trifluoromethylsulfonyl)amino]-3-ethyl-2-(trifluoromethylsulfonyloxy)benzoate (440 mg, 684.77 μmol, 34.55% yield) as yellow oil.

32.3 Preparation of methyl 5-[(4-anilino-5-methyl-pyrimidin-2-yl)-(trifluoromethylsulfonyl) amino]-2-(5,5-dimethyl-1,3,2-dioxaborinan-2-yl)-3-ethyl-benzoate A mixture of methyl 5-[(4-anilino-5-methyl-pyrimidin-2-yl)-(trifluoromethylsulfonyl)amino]-3-ethyl-2-(trifluoromethylsulfonyloxy)benzoate (100 mg, 157.09 μmol, 1 eq, 4 batch), 2-(5,5-dimethyl-1,3,2-dioxaborinan-2-yl)-5,5-dimethyl-1,3,2-dioxaborinane (107 mg, 471.27 μmol, 3 eq), KOAc (46.25 mg, 471.27 µmol, 3 eq) and Pd(PPh₃)₂Cl₂ (11.03 mg, 15.71 µmol, 0.1 eq) in dioxane (10 mL) was degassed and purged with N₂ for 3 times, then stirred at 80° C. for 2 h under N₂ atmosphere. The reaction mixture was cooled to room temperature and filtered, the filtrate was concentrated in vacuo to give methyl 5-[(4-anilino-5-methyl-pyrimidin-2-yl)-(trifluoromethylsulfonyl)amino]-2-(5,5-dimethyl-1,3,2-dioxaborinan-2-yl)-3-ethyl-benzoate (600 mg, 494.71 µmol, 78.73% yield, 50% purity) as black oil.

32.4 Preparation of N2-(7-ethyl-1-hydroxy-3H-2,1-benzoxaborol-5-yl)-5-methyl-N4-phenyl-pyrimidine-2,4-diamine and N-(4-anilino-5-methyl-pyrimidin-2-yl)-N-(7-ethyl-1-hydroxy-3H-2,1-benzoxaborol-5-yl)-1,1,1-trifluoro-methanesulfonamide

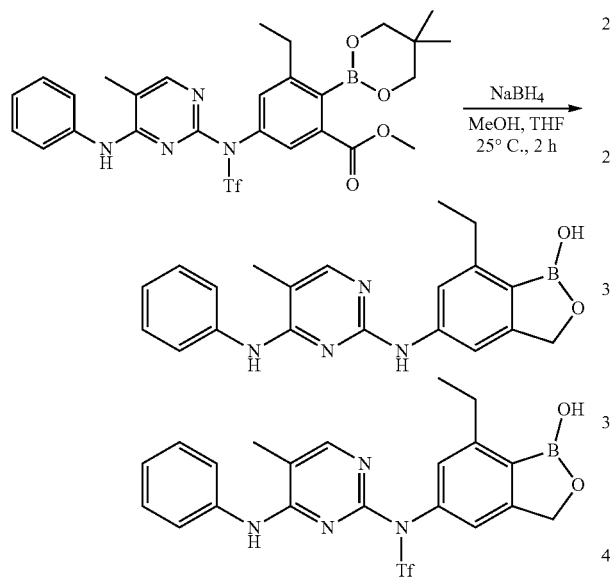

A mixture of [4-[(4-anilino-5-methyl-pyrimidin-2-yl)-(trifluoromethylsulfonyl)amino]-2-ethyl-6-methoxycarbonyl-phenyl]borinic acid (200 mg, 191.46 µmol, 1 eq) in MeOH (1 mL) and THF (10 mL) was added NaBH₄ (72.43 mg, 1.91 mmol, 10 eq) in portions at 0° C., the resulting mixture was stirred at 25° C. for 2 h under N₂ atmosphere. The reaction was quenched by adding HCl (1M, 5 mL) at 0° C., the mixture was concentrated in vacuo to give a residue, which was purified by prep-HPLC (column: Nano-micro Kromasil C18 100*30 mm 8 um; mobile phase: [water(0.1% TFA)-ACN]; B %: 50%-70%, 10 min and column: Welch Xtimate C18 150*25 mm*5 um; mobile phase: [water(10 mM NH₄HCO₃)-ACN]; B %: 50%-80%, 10.5 min) to give N2-(7-ethyl-1-hydroxy-3H-2,1-benzoxaborol-5-yl)-5-methyl-N4-phenyl-pyrimidine-2,4-diamine (10 mg, 27.76 µmol, 4.83% yield) as a yellow solid. ¹H NMR (DMSO-d₆, 400 MHz) δ 9.13 (s, 1H), 8.61 (s, 1H), 8.33 (s, 1H), 7.91 (s, 1H), 7.73 (s, 1H), 7.66 (d, J=8.0 Hz, 2H), 7.35 (t, J=8.0 Hz, 2H), 7.24 (s, 1H), 7.11 (t, J=8.0 Hz, 1H), 4.78 (s, 2H), 2.63 (q, J=7.6 Hz, 2H), 2.12 (s, 3H), 1.10 (t, J=7.6 Hz, 3H). MS (ESI): mass calcd. For C₂₀H₂₁BN₄O₂ 360.18, m/z found 361.1 [M+H]⁺. HPLC: 92.87% (220 nm), 94.53% (254 nm); and N-(4-anilino-5-methyl-pyrimidin-2-yl)-N-(7-ethyl-1-hydroxy-3H-2,1-benzoxaborol-5-yl)-1,1,1-trifluoro-methanesulfonamide (60 mg, 121.88 µmol, 21.22% yield, 20 mg has been delivered) as a white solid. ¹H NMR (DMSO-d₆, 400 MHz) δ 9.15 (s, 1H), 8.71 (s, 1H), 8.10 (s, 1H), 7.30-7.28 (m, 3H), 7.15 (s, 1H), 7.05 (t, J=7.2 Hz, 1H), 7.29 (t, J=7.2 Hz, 2H), 6.99 (t, J=7.2 Hz, 1H), 4.98 (s, 2H), 2.85 (q, J=7.6 Hz, 2H), 2.17 (s, 3H), 1.13 (t, J=7.6 Hz, 3H). MS (ESI): mass calcd. For C₂₁H₂₀BF₃N₄O₄S 492.13, m/z found 493.1 [M+H]⁺. HPLC: 99.84% (220 nm), 99.87% (254 nm).

Part 2-1: General Synthetic Teachings for Compounds of Formula (IA)

General Synthetic Scheme A

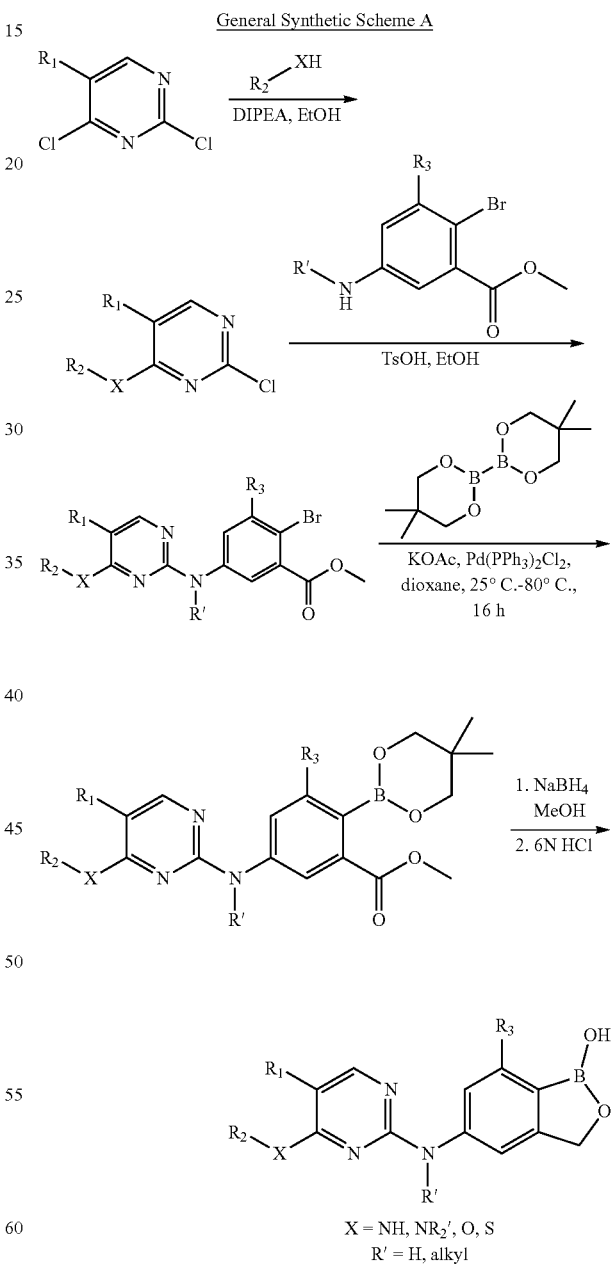

X = NH, NR₂', O, S
R' = H, alkyl

The detailed procedure is as shown in the preparation of 5-((5-fluoro-4-(hexan-3-ylamino) pyrimidin-2-yl)amino) benzo[c][1,2]oxaborol-1(3H)-ol. See also, below, Example 7.

General Synthetic Scheme B

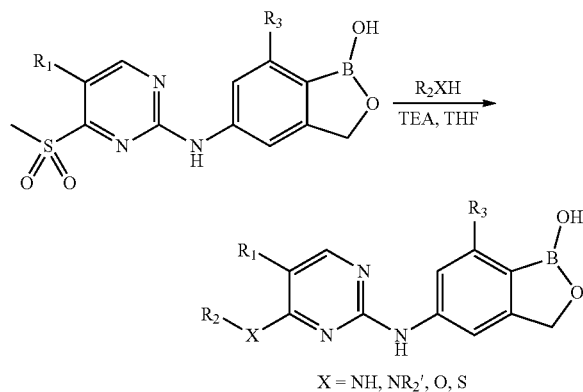

X = NH, NR₂', O, S

The detailed procedure is as shown in the preparation of 5-((5-chloro-4-(cyclohexylamino) pyrimidin-2-yl)amino) benzo[c][1,2]oxaborol-1(3H)-ol

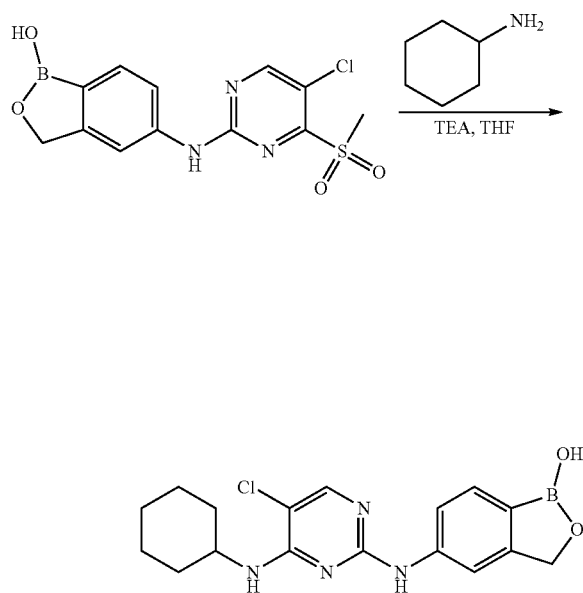

To a mixture of 5-chloro-N-(1-hydroxy-3H-2,1-benzoxaborol-5-yl)-4-methyl sulfonyl-pyrimidin-2-amine (200 mg, 588.99 μmol, 1 eq) and cyclohexanamine (64 mg, 647.89 μmol, 74.15 μL, 1.1 eq) in dioxane (3 mL) was added TEA (149 mg, 1.47 mmol, 204.95 μL, 2.5 eq) in one portion at 25° C. under N₂ atmosphere, the resulting reaction mixture was stirred at 25° C. for 2 h. Then H₂O (10 mL) was added into the reaction mixture, and its pH was adjusted to 5 with 2N HCl, the aqueous phase was extracted with EtOAc (20 mL×3). The combined organic layers were washed with brine (20 mL×2), dried over anhydrous Na₂SO₄, filtered and concentrated in vacuo to give a residue. The residue was purified by prep-HPLC (column: Nano-micro Kromasil C18 100*30 mm 5 um; mobile phase: [water(0.1% TFA)-ACN]; B %: 20%-45%, 10 min) to give 5-chloro-N4-cyclohexyl-N2-(1-hydroxy-3H-2,1-benzoxaborol-5-yl)pyrimidine-2,4-diamine (47 mg, 131.05 μmol, 22.25% yield) as a white solid.

Part 2-2: Synthetic Examples for Compounds of Formula (IA)

Example 1: 5-((5-chloro-4-(methylsulfonyl)pyrimidin-2-yl)amino)benzo[c][1,2]oxaborol-1(3H)-ol

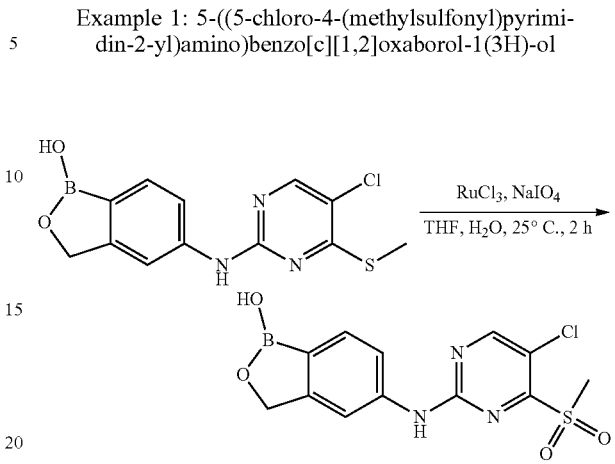

To a mixture of 5-chloro-N-(1-hydroxy-3H-2,1-benzoxaborol-5-yl)-4-methylsulfanyl-pyrimidin-2-amine (250 mg, 812.84 umol, 1 eq) in THF (8 mL) and H₂O (2 mL) was added NaIO₄ (522 mg, 2.44 mmol, 135.12 uL, 3 eq) and RuCl₃ (17 mg, 81.28 μmol, 5.42 μL, 0.1 eq) at room temperature under N₂ atmosphere. The resulting mixture was stirred at room temperature for 2 h. Then the reaction mixture was filtered, water (20 mL) was added into the obtained filtrate. The resulting mixture was extracted with EtOAc (20 mL×3), and the combined organic layers were washed with brine (20 mL×2), dried over Na2SO4, filtered and concentrated under reduced pressure to give a residue, which was purified by prep-HPLC (column: Welch Xtimate C18 100*25 mm*3 um; mobile phase: [water(0.1% TFA)-ACN]; B %: 40%-60%, 12 min to give 5-chloro-N-(1-hydroxy-3H-2,1-benzoxaborol-5-yl)-4-methylsulfonyl-pyrimidin-2-amine (0.041 g, 120.74 umol, 14.85% yield) as a white solid. ¹H NMR (DMSO-d6, 400 MHz) δ 10.56 (s, 1H), 9.07 (br s, 1H), 8.88 (s, 1H), 7.81 (s, 1H), 7.68 (d, J=8.0 Hz, 1H), 7.59 (d, J=8.0 Hz, 1H), 4.98 (s, 2H), 3.48 (s, 3H). MS (ESI): m/z found 338.0 [M−H]⁻. Purity by HPLC: 89.32% (220 nm), 88.4% (254 nm).

Example 2: 5-((5-chloro-4-(cyclohexylamino)pyrimidin-2-yl)amino)benzo[c][1,2]oxaborol-1(3H)-ol

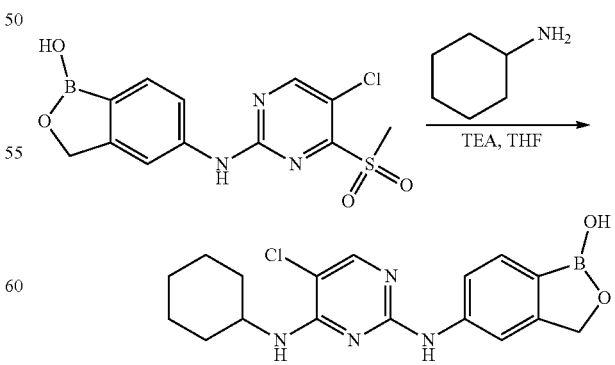

This substance was prepared following General Synthetic Scheme B by reacting 5-((5-chloro-4-(methylsulfonyl)pyrimidin-2-yl)amino)benzo[c][1,2]oxaborol-1(3H)-ol with cyclohexanamine in the presence of TEA in THF. $^1$H NMR (DMSO-d6, 400 MHz) δ (ppm) 9.61 (s, 1H), 8.99 (br, 1H), 8.01 (s, 1H), 7.88 (s, 1H), 7.63-7.58 (m, 2H), 7.13 (br, 1H), 4.95 (s, 2H), 3.98-3.96 (m, 1H), 1.93-1.90 (m, 2H), 1.82-1.79 (m, 2H), 1.70-1.66 (m, 1H), 1.46-1.40 (m, 2H), 1.34-1.31 (m, 2H), 1.20-1.15 (m, 1H) ppm. MS (ESI): m/z found 359.1 [M+H]$^+$. Purity by HPLC: 94.33% (220 nm), 96.85% (254 nm).

Example 3: 5-((5-chloro-4-(propylamino)pyrimidin-2-yl)amino)benzo[c][1,2]oxaborol-1(3H)-ol

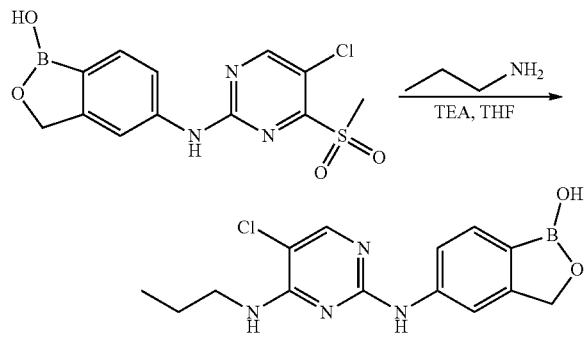

This substance was prepared following General Synthetic Scheme B starting with 5-((5-chloro-4-(methylsulfonyl)pyrimidin-2-yl)amino)benzo[c][1,2]oxaborol-1(3H)-ol with propylamine in the presence of TEA in THF. $^1$H NMR (DMSO-d6, 400 MHz) δ (ppm) 9.75 (s, 1H), 9.23 (br, 1H), 8.04 (s, 1H), 7.86 (s, 1H), 7.82 (br, 1H), 7.63 (d, J=8.4 Hz, 1H), 7.57 (d, J=8.4 Hz, 1H), 4.95 (s, 2H), 3.42-3.36 (m, 2H), 1.67-1.58 (m, 2H), 0.92 (t, J=7.2 Hz, 3H). MS (ESI): m/z found 319.1 [M+H]$^+$. Purity by HPLC: 98.74% (220 nm), 99% (254 nm).

Example 4: 5-chloro-2-((1-hydroxy-1,3-dihydrobenzo[c][1,2]oxaborol-5-yl)amino)pyrimidin-4-ol

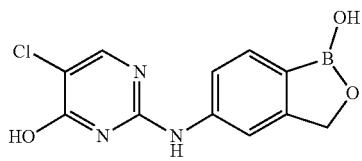 [SMILES: OB1OCc2cc(Nc3ncc(Cl)c(O)n3)ccc21]

This substance was prepared following General Synthetic Scheme A. $^1$H NMR (DMSO-d6, 400 MHz) δ (ppm) 7.98 (s, 1H), 7.79 (s, 1H), 7.69 (d, J=8.0 Hz, 1H), 7.46 (d, J=8.0 Hz, 1H), 4.96 (s, 2H). MS (ESI): m/z found 278.0 [M+H]$^+$. Purity by HPLC: 95.22% (220 nm), 93.22% (254 nm).

Example 5: 5-((4-(benzylamino)-5-chloropyrimidin-2-yl)amino)benzo[c][1,2]oxaborol-1(3H)-ol

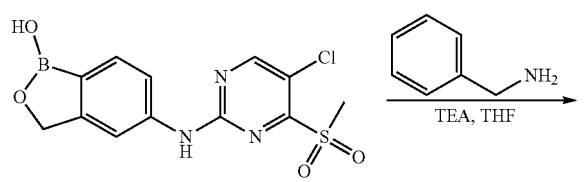

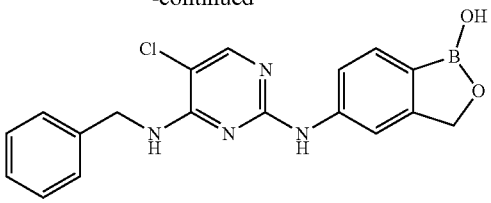

This substance was prepared following General Synthetic Scheme B, starting with 5-((5-chloro-4-(methylsulfonyl)pyrimidin-2-yl)amino)benzo[c][1,2]oxaborol-1(3H)-ol and benzylamine using the procedure in Example 2. $^1$H NMR (DMSO-d6, 400 MHz) δ (ppm) 9.52 (s, 1H), 8.09 (br, 1H), 8.04 (s, 1H), 7.70 (s, 1H), 7.51 (d, J=8.0 Hz, 1H), 7.41 (d, J=8.0 Hz, 1H), 7.34-7.33 (m, 4H), 7.25 (br, 1H), 4.79 (s, 2H), 4.66 (d, J=6.0 Hz, 1H). MS (ESI): m/z found 367.0 [M+H]$^+$. Purity by HPLC: 99.08% (220 nm), 98.63% (254 nm).

Example 6: 5-((5-chloro-4-(cyclopentylamino)pyrimidin-2-yl)amino)benzo[c][1,2]oxaborol-1(3H)-ol

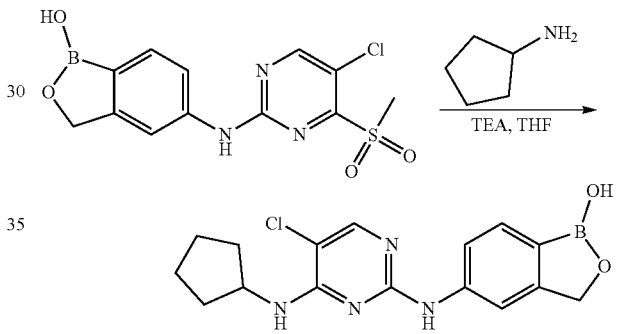

This substance was prepared following General Synthetic Scheme B, starting with 5-((5-chloro-4-(methylsulfonyl)pyrimidin-2-yl)amino)benzo[c][1,2]oxaborol-1(3H)-ol and cyclopentylamine using the procedure in Example 2. $^1$H NMR (DMSO-d6, 400 MHz) δ (ppm) 9.58 (s, 1H), 8.0 (s, 1H), 7.93 (s, 1H), 7.61-7.54 (m, 2H), 7.17 (br, 1H), 4.94 (s, 2H), 4.40-4.38 (m, 1H), 2.0-1.97 (m, 2H), 1.74-1.65 (m, 2H), 1.59-1.56 (m, 4H). MS (ESI): m/z found 345.1 [M+H]$^+$. Purity by HPLC: 84.75% (220 nm), 86.81% (254 nm).

Example 7: 5-((5-fluoro-4-(hexan-3-ylamino)pyrimidin-2-yl)amino)benzo[c][1,2]oxaborol-1(3H)-ol

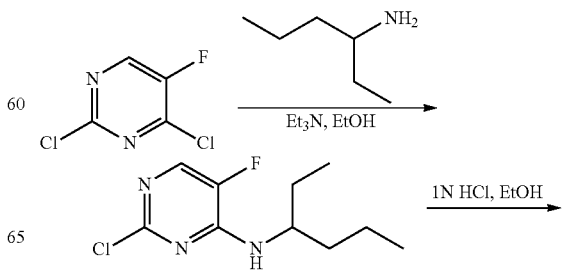

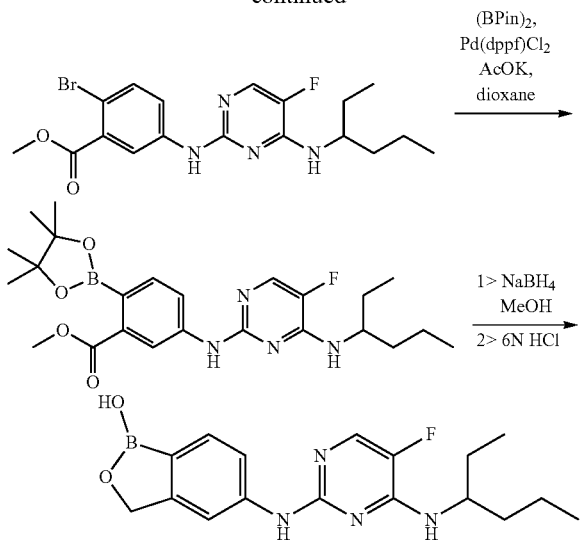

To a solution of 2,4-dichloro-5-fluoropyrimidine (1.6 g, 10.0 mmol) and hexan-3-amine (0.73 g, 10 mmol) in EtOH (15 mL) was added Et₃N (2.8 mL, 20.0 mmol) at room temperature. The reaction was heated to 50° C. for 2 h, then the reaction mixture was concentrated in vacuo to give a residue, which was purified by column chromatography (PE/EtOAc=10/1) to give 2-chloro-5-fluoro-N-(hexan-3-yl) pyrimidin-4-amine (1.1 g, yield 88%) as an off-white solid. ¹H NMR (400 MHz, CDCl₃): δ (ppm) 7.77 (s, 1H), 4.85 (br, 1H), 4.18-4.08 (m, 1H), 1.64-1.51 (m, 2H), 1.49-1.39 (m, 2H), 1.35-1.25 (m, 2H), 0.86 (t, J=7.5 Hz, 6H).

To a solution of 2-chloro-5-fluoro-N-(hexan-3-yl)pyrimidin-4-amine (1.1 g, 5 mmol) in EtOH (20 mL) was added methyl 5-amino-2-bromobenzoate (1.15 g, 5 mmol) and HCl (1.5 N, 4 mL). The resulting reaction mixture was heated to reflux for 3 h. Then the reaction was cooled to room temperature, diluted with water, extracted with EtOAc, and the combined organic phase was washed with water, brine, concentrated under reduce pressure to give a residue, which was triturated with EtOAc:PE=1:5 to give methyl 2-bromo-5-((5-fluoro-4-(hexan-3-ylamino)pyrimidin-2-yl)amino) benzoate (1.4 g, 80% yield) as a white solid. ¹H NMR (400 MHz, DMSO-d6): δ (ppm) 9.40 (s, 1H), 8.44 (d, J=2.7 Hz, 1H), 7.88 (d, J=3.9 Hz, 1H), 7.65 (dd, J=8.8, 2.7 Hz, 1H), 7.54 (d, J=8.8 Hz, 1H), 7.26 (dd, J=23.8, 8.7 Hz, 1H), 4.16-4.04 (m, 1H), 3.85 (s, 3H), 1.65-1.45 (m, 4H), 1.35-1.23 (m, 2H), 0.91-0.79 (m, 6H).

To a solution of methyl 2-bromo-5-((5-fluoro-4-(hexan-3-ylamino)pyrimidin-2-yl)amino)benzoate (1.2 g, 3 mmol) in THF (20 mL) was added KOAc (412 mg, 9 mol), (BPin)₂ (1.1 g, 4.2 mmol) and (dppf)PdCl2 (937 mg, 1.2 mmol) at room temperature under nitrogen atmosphere. The resulting mixture was heated to 100° C. overnight, then the solid was filtered and the filtrate was concentrated under reduce pressure to give a residue that was purified by silica chromatography with PE/EtOAc (100/1 to 20/1) to give the crude methyl 5-((5-fluoro-4-(hexan-3-ylamino)pyrimidin-2-yl) amino)-2-(4,4,5,5-tetramethyl-1,3,2-dioxaborolan-2-yl)benzoate (1.0 g, yield 52%) as a white solid. ¹H NMR (400 MHz, DMSO-d6): δ (ppm) 9.35 (s, 1H), 8.47 (d, J=2.0 Hz, 1H), 7.88 (d, J=3.9 Hz, 1H), 7.77 (dd, J=8.2, 2.1 Hz, 1H), 7.34 (d, J=8.1 Hz, 1H), 7.22-7.18 (m, 1H), 4.24-4.11 (m, 1H), 3.81 (s, 3H), 1.61-1.49 (m, 4H), 1.38-1.31 (m, 2H), 1.30 (s, 12H), 0.87 (d, J=7.0 Hz, 6H).

To a solution of crude methyl 5-((5-fluoro-4-(hexan-3-ylamino)pyrimidin-2-yl)amino)-2-(4,4,5,5-tetramethyl-1,3, 2-dioxaborolan-2-yl)benzoate (700 mg, 1.7 mmol) in MeOH (15 mL) was added NaBH₄ (532 mg, 14.0 mmol) at 30° C. in small portions. The reaction was stirred at 30° C. for 30 min, 6N HCl (3 mL) was added and stirred for another 20 min. Then it was neutralized with saturated aq. NaHCO₃ and filtered, the filter cake was purified by triturated with MeOH and water (v/v=5:1) to give 5-((5-fluoro-4-(hexan-3-ylamino)pyrimidin-2-yl)amino)benzo [c][1,2]oxaborol-1 (3H)-ol (117 mg, yield 20%) as a white solid. ¹H NMR (400 MHz, DMSO-d6) δ (ppm) 9.22 (s, 1H), 8.89 (s, 1H), 7.96-7.82 (m, 2H), 7.64-7.51 (m, 2H), 7.19 (d, J=8.6 Hz, 1H), 4.91 (s, 2H), 4.17-3.97 (m, 1H), 1.65-1.42 (m, 4H), 1.41-1.21 (m, 2H), 0.88 (t, J=7.3 Hz, 6H). Purity by HPLC: 97.79% at 210 nm and 97.96% at 254 nm. MS: m/z=345.2, (M+H)+.

Example 8: 5-((5-methyl-4-((3-methylcyclohexyl) amino)pyrimidin-2-yl)amino)benzo[c][1,2]oxaborol-1(3H)-ol

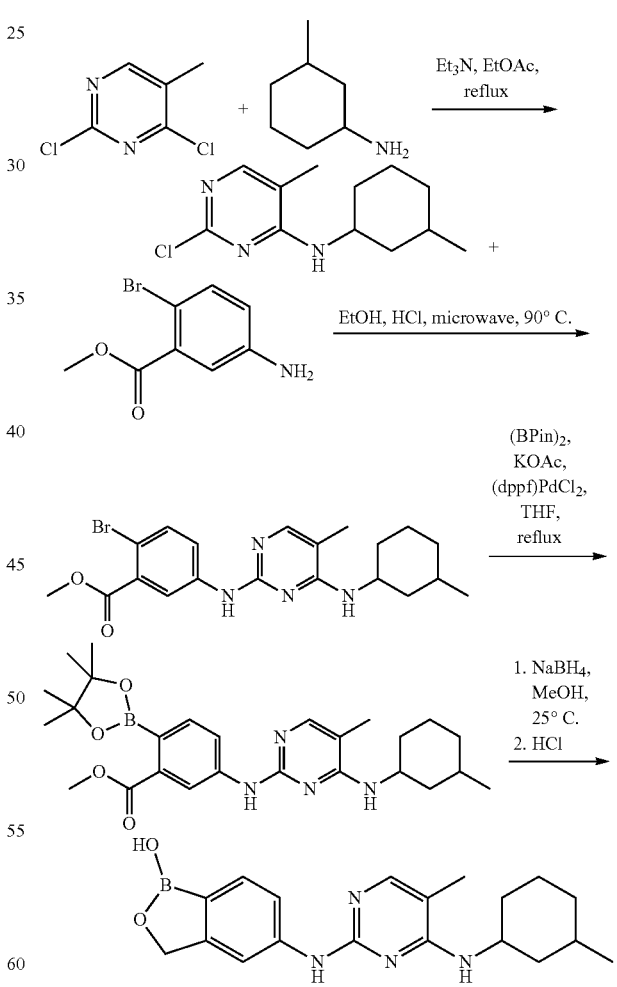

To a solution of 2,4-dichloro-5-methylpyrimidine (1.6 g, 10.0 mmol) in EtOAc (20 mL) was added 3-methylcyclohexan-1-amine (1.7 g, 15 mmol, cis-trans mixture) and Et₃N (2.0 g, 20.0 mmol) at room temperature. The reaction was heated to reflux overnight, then the solvent was removed in vacuo to give a residue that was purified by silica chromatography with PE/EtOAc (20/1 to 5/1) to give 2-chloro-5-methyl-N-(3-methylcyclohexyl)pyrimidin-4-amine (1.6 g, yield 67%, cis:trans=3:1) as a yellow solid, which was used directly to the next step.

To a solution of 2-chloro-5-methyl-N-(3-methylcyclohexyl)pyrimidin-4-amine (1.0 g, 4.2 mmol) in EtOH (6 mL) was added methyl 5-amino-2-bromobenzoate (1.0 g, 4.2 mmol) and HCl (1.5 N, 4 mL). The reaction was subjected to microwave irradiation (90° C., 30 min), then cooled to room temperature, poured into water and extracted with DCM, the combined organic phase was washed with water, brine, concentrated under reduce pressure to give a residue that was purified by silica chromatography with DCM/MeOH (100/1 to 10/1) to give methyl 2-bromo-5-((5-methyl-4-((3-methylcyclohexyl)amino)pyrimidin-2-yl)amino)benzoate (1.0 g, yield 56%) as a yellow solid.

To a solution of methyl 2-bromo-5-((5-methyl-4-((3-methylcyclohexyl)amino)pyrimidin-2-yl)amino)benzoate (1.0 g, 2.3 mmol) in THF (15 mL) was added KOAc (676 mg, 6.9 mmol), (BPin)$_2$ (864 mg, 3.4 mmol) and (dppf)PdCl$_2$ (734 mg, 0.9 mmol) at room temperature under nitrogen atmosphere. The resulting mixture was heated to reflux overnight, then the formed solid was filtered and the filtrate was concentrated under reduce pressure to give a residue that was purified by silica chromatography with DCM/MeOH (100/1 to 20/1) to give the crude methyl 5-((5-methyl-4-((3-methylcyclohexyl)amino)pyrimidin-2-yl)amino)-2-(4,4,5,5-tetramethyl-1,3,2-dioxaborolan-2-yl)benzoate (700 mg, contain 40% de-Br product in LCMS) as a black solid, which was used directly in the next step. MS: m/z=481.3, (M+H)$^+$.

To a solution of crude methyl 5-((5-methyl-4-((3-methylcyclohexyl)amino)pyrimidin-2-yl)amino)-2-(4,4,5,5-tetramethyl-1,3,2-dioxaborolan-2-yl)benzoate (700 mg, crude) in MeOH (20 mL) was added NaBH$_4$ (437 mg, 11.5 mmol) at 25° C. in small portions. The reaction was stirred at 25° C. for 30 min, 6N HCl (3 mL) was added and stirred for another 20 min. Then it was neutralized by adding saturated aq. NaHCO$_3$, extracted with DCM, and the combined organic phase was washed with water, brine, concentrated under reduce pressure to give a residue that was purified by silica chromatography with DCM/MeOH (100/1 to 20/1) to give the crude product, which was triturated with CH$_3$CN and water to give 5-((5-methyl-4-((3-methylcyclohexyl)amino)pyrimidin-2-yl)amino)benzo[c][1,2]oxaborol-1(3H)-ol (57 mg, yield 7%, cis:trans=1:1) as a white solid. $^1$H NMR (300 MHz, DMSO-d6): δ (ppm) 9.05 (s, 1H), 8.87 (s, 1H), 7.95 (d, J=10.7 Hz, 1H), 7.74-7.45 (m, 3H), 6.27 (d, J=7.4 Hz, 0.5H), 5.95 (d, J=7.4 Hz, 0.5H), 4.90 (s, 2H), 4.38-4.24 (m, 0.5H), 4.07-3.90 (m, 0.5H), 2.05-1.83 (m, 3H), 1.83-1.62 (m, 2H), 1.62-1.39 (m, 3H), 1.39-1.14 (m, 2H), 1.14-0.76 (m, 4H). Purity by HPLC: 98.33% at 210 nm and 99.03% at 254 nm. MS: m/z=353.2, (M+H)$^+$.

Example 9: 5-((4-((4-fluorobenzyl)amino)-5-methylpyrimidin-2-yl)amino)benzo[c][1,2]oxaborol-1(3H)-ol

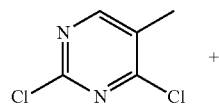
+

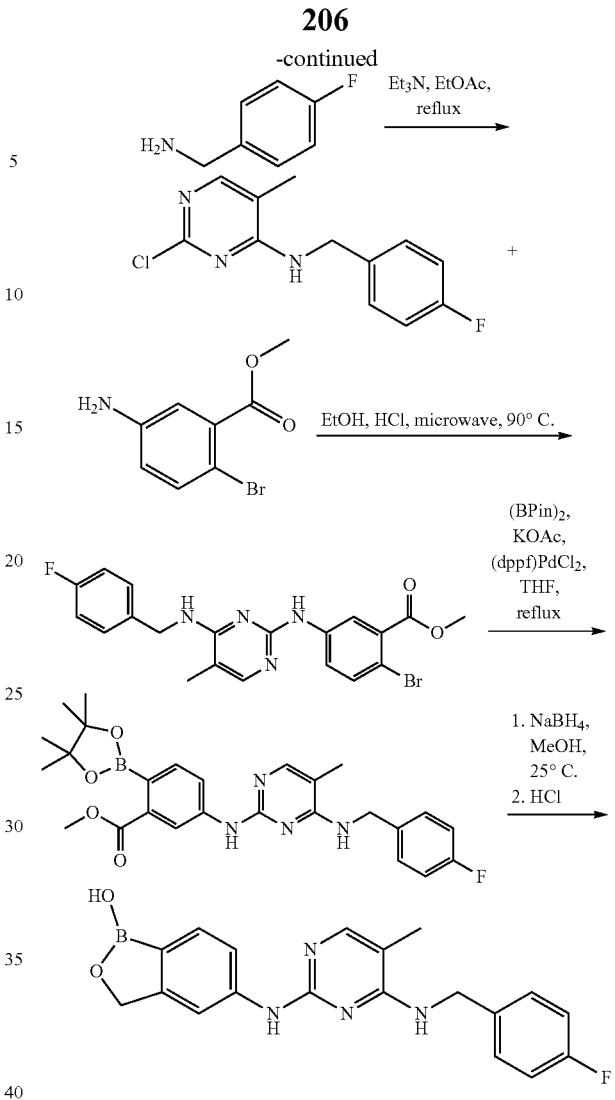

To a solution of 2,4-dichloro-5-methylpyrimidine (1.6 g, 10.0 mmol) in EtOAc (20 mL) was added (4-fluorophenyl)methanamine (1.9 g, 15 mmol) and Et$_3$N (2.0 g, 20.0 mmol) at room temperature. The reaction was heated to reflux overnight, then the solvent was removed in vacuo to give a residue that was purified by silica chromatography with PE/EtOAc (20/1 to 5/1) to give 2-chloro-N-(4-fluorobenzyl)-5-methylpyrimidin-4-amine (1.6 g, yield 64%) as a white solid. $^1$H NMR (400 MHz, DMSO-d6): δ 7.88 (t, J=5.9 Hz, 1H), 7.84 (s, 1H), 7.40-7.31 (m, 2H), 7.18-7.10 (m, 2H), 4.55 (d, J=6.0 Hz, 2H), 2.01 (s, 3H) ppm.

To a solution of 2-chloro-N-(4-fluorobenzyl)-5-methylpyrimidin-4-amine (1.6 g, 6.4 mmol) in EtOH (6 mL) was added methyl 5-amino-2-bromobenzoate (1.5 g, 6.4 mmol) and HCl (1.5 N, 4 mL). The reaction was subjected to microwave irradiation (90° C., 30 min), then cooled to room temperature, and poured into water, the formed solid was filtered and dried in vacuo to give methyl 2-bromo-5-((4-((4-fluorobenzyl)amino)-5-methylpyrimidin-2-yl)amino)benzoate (1.6 g, yield 57%) as a white solid. $^1$H NMR (400 MHz, DMSO-d$_6$): δ 10.92 (s, 1H), 9.13 (s, 1H), 8.12 (d, J=2.7 Hz, 1H), 7.85 (s, 1H), 7.68 (d, J=8.7 Hz, 1H), 7.51 (dd, J=8.8, 2.7 Hz, 1H), 7.39-7.27 (m, 2H), 7.18-7.05 (m, 2H), 4.68 (d, J=5.9 Hz, 2H), 3.76 (s, 3H), 2.06 (s, 3H) ppm.

To a solution of methyl 2-bromo-5-((4-((4-fluorobenzyl)amino)-5-methylpyrimidin-2-yl)amino)benzoate (1.6 g, 3.6 mmol) in THF (15 mL) was added KOAc (1.1 g, 10.8 mmol), (BPin)$_2$ (1.4 g, 5.4 mmol) and (dppf) PdCl$_2$ (1.1 g, 1.4 mmol) at room temperature under nitrogen atmosphere. The mixture was heated to reflux overnight, then the formed solid was filtered, and the filtrate was concentrated under reduce pressure to give a residue that was purified by silica chromatography with DCM/MeOH (100/1 to 20/1) to give methyl 5-((4-((4-fluorobenzyl)amino)-5-methylpyrimidin-2-yl)amino)-2-(4,4,5,5-tetramethyl-1,3,2-dioxaborolan-2-yl)benzoate (1.3 g, contain 30% de-Br product in LCMS) as a black solid, which was used directly to the next step. MS: m/z=493.3, (M+H)$^+$.

To a solution of crude methyl 5-((4-((4-fluorobenzyl)amino)-5-methylpyrimidin-2-yl)amino)-2-(4,4,5,5-tetramethyl-1,3,2-dioxaborolan-2-yl)benzoate (1.3 g, crude) in MeOH (20 mL) was added NaBH$_4$ (722 mg, 19.0 mmol) at 30° C. in small portions. The reaction was stirred at 30° C. for 30 min, then 6N HCl (3 mL) was added, the resulting mixture was kept stirring for another 20 min. The reaction mixture was neutralized with saturated aq. NaHCO$_3$, extracted with EtOAc, the combined organic phase was washed with water, brine, concentrated under reduce pressure to give a residue that was purified by silica chromatography with DCM/MeOH (100/1 to 20/1) to give the crude product, which was triturated with CH$_3$CN and water to give 5-((4-((4-fluorobenzyl)amino)-5-methylpyrimidin-2-yl)amino)benzo[c][1,2]oxaborol-1(3H)-ol (186 mg, yield 14%) as a yellow solid. $^1$H NMR (400 MHz, DMSO-d$_6$): δ 9.05 (s, 1H), 8.86 (s, 1H), 7.77 (d, J=26.9 Hz, 2H), 7.59-7.30 (m, 5H), 7.16 (t, J=8.8 Hz, 2H), 4.81 (s, 2H), 4.64 (d, J=5.4 Hz, 2H), 2.00 (s, 3H) ppm. Purity by HPLC: 99.55% at 210 nm and 98.97% at 254 nm. MS: (M+H)$^+$: m/z=365.1.

Example 10: 5-((5-methyl-4-((4-methylcyclohexyl)amino)pyrimidin-2-yl)amino)benzo[c][1,2]oxaborol-1(3H)-ol

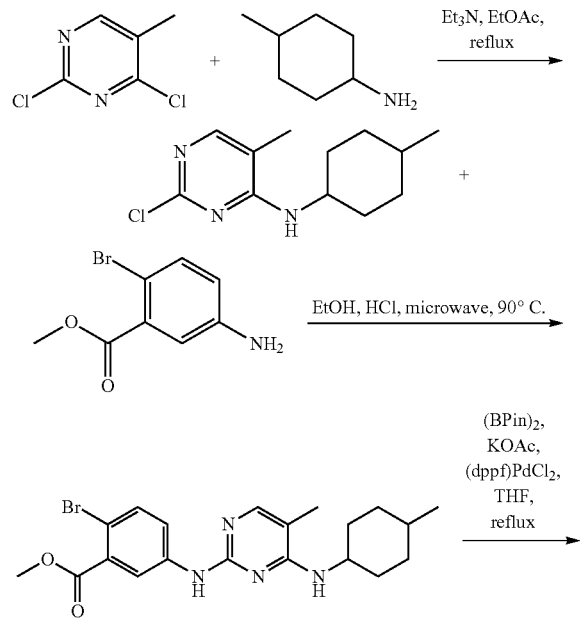

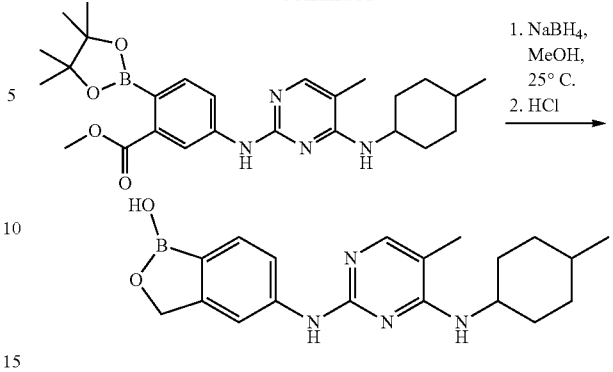

To a solution of 2,4-dichloro-5-methylpyrimidine (1.6 g, 10.0 mmol) in EtOAc (20 mL) was added 3-methylcyclohexan-1-amine (1.7 g, 15 mmol, cis-trans mixture) and Et$_3$N (2.0 g, 20.0 mmol) at room temperature. The reaction was heated to reflux overnight, then the solvent was moved in vacuo to give a residue that was purified by silica chromatography with PE/EtOAc (20/1 to 5/1) to give 2-chloro-5-methyl-N-(4-methylcyclohexyl)pyrimidin-4-amine (1.6 g, yield 67%, cis:trans=1:1) as a yellow solid.

To a solution of 2-chloro-5-methyl-N-(4-methylcyclohexyl)pyrimidin-4-amine (1.0 g, 4.2 mmol) in EtOH (6 mL) was added methyl 5-amino-2-bromobenzoate (1.0 g, 4.2 mmol) and HCl (1.5 N, 4 mL). The reaction was subjected to microwave irradiation (90° C., 30 min), then cooled to room temperature, poured into water, and the aqueous phase was extracted with DCM, the combined organic phase was washed with water, brine, concentrated under reduce pressure to give a residue that was purified by silica chromatography with DCM/MeOH (100/1 to 10/1) to give methyl 2-bromo-5-((5-methyl-4-((4-methylcyclohexyl)amino)pyrimidin-2-yl)amino)benzoate (1.0 g, yield 56%) as a yellow solid.

To a solution of methyl 2-bromo-5-((5-methyl-4-((4-methylcyclohexyl)amino)pyrimidin-2-yl)amino)benzoate (1.0 g, 2.3 mmol) in THF (15 mL) was added KOAc (676 mg, 6.9 mmol), (BPin)$_2$ (864 mg, 3.4 mmol) and (dppf) PdCl$_2$ (734 mg, 0.9 mmol) at room temperature under nitrogen atmosphere. The resulting mixture was heated to reflux overnight, then the solid was removed by filtration, and the filtrate was concentrated in vacuo to give a residue, which was purified by silica chromatography with DCM/MeOH (100/1 to 20/1) to give the crude methyl 5-((5-methyl-4-((4-methylcyclohexyl)amino)pyrimidin-2-yl)amino)-2-(4,4,5,5-tetramethyl-1,3,2-dioxaborolan-2-yl)benzoate (700 mg, contain 40% de-Br product in LCMS) as a black solid, which was used directly to the next step. MS: (M+H)$^+$: m/z=481.3.

To a solution of crude methyl 5-((5-methyl-4-((4-methylcyclohexyl)amino)pyrimidin-2-yl)amino)-2-(4,4,5,5-tetramethyl-1,3,2-dioxaborolan-2-yl)benzoate (700 mg, crude) in MeOH (20 mL) was added NaBH$_4$ (437 mg, 11.5 mmol) at 25° C. in small portions. The reaction was stirred at 25° C. for 30 min, then 6N HCl (3 mL) was added, and the resulting mixture was kept stirring for another 20 min. The reaction mixture was neutralized by adding saturated aq. NaHCO$_3$, extracted with DCM, the combined organic phase was washed with water, brine, concentrated under reduce pressure to give a residue that was purified by silica chromatography with DCM/MeOH (100/1 to 20/1) to give the crude product, which was triturated with CH$_3$CN and water to give 5-((5-methyl-4-((4-methylcyclohexyl)amino)pyrimidin-2-yl)amino)benzo[c][1,2]oxaborol-1(3H)-ol (99 mg, yield 7%, cis:trans=2:1) as a white solid. $^1$H NMR (400 MHz, DMSO-d$_6$): δ 9.08 (s, 1H), 8.89 (d, J=7.1 Hz, 1H), 8.00 (s, 1H), 7.69 (d, J=6.1 Hz, 1H), 7.64-7.58 (m, 1H), 7.54 (d, J=8.1 Hz, 1H), 6.29 (d, J=7.8 Hz, 0.35H), 6.11 (d, J=7.4 Hz, 0.67H), 4.93 (s, 2H), 4.14-3.89 (m, 1H), 2.06-1.89 (m, 3H), 1.86-1.33 (m, 8H), 1.14-0.90 (m, 4H) ppm. Purity by HPLC: 98.65% at 210 nm and 96.91% at 254 nm. MS: (M+H)$^+$: m/z=353.3.

Example 11: 5-((4-(cyclobutylamino)-5-methylpyrimidin-2-yl)amino)benzo[c][1,2]oxaborol-1(3H)-ol

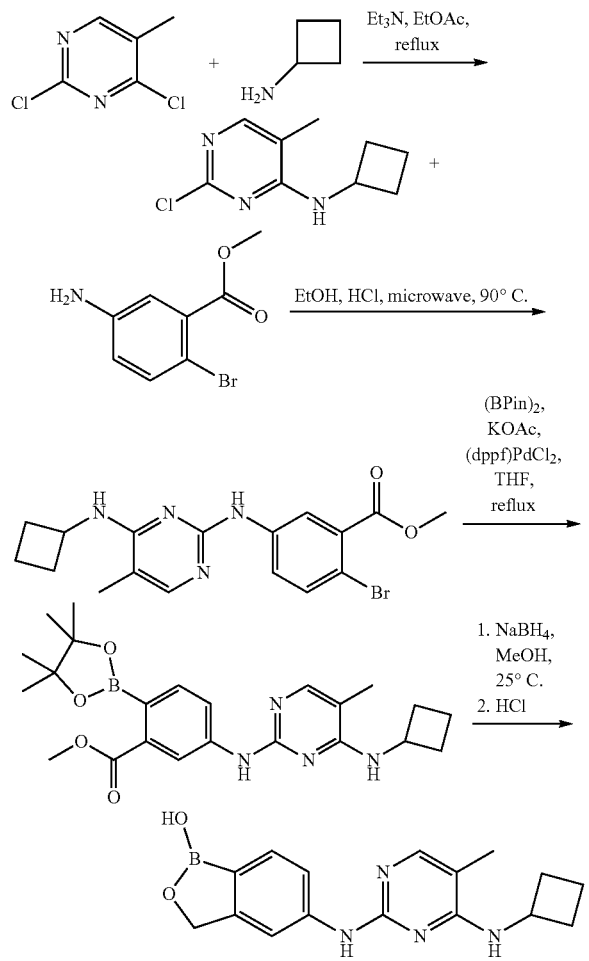

To a solution of 2,4-dichloro-5-methylpyrimidine (1.6 g, 10.0 mmol) in EtOAc (20 mL) was added cyclobutanamine (1.1 g, 15 mmol) and Et$_3$N (2.0 g, 20.0 mmol) at room temperature. The reaction was heated to reflux overnight, then the solvent was removed in vacuo to give a residue, which was triturated with CH$_3$CN and H$_2$O to give 2-chloro-N-cyclobutyl-5-methylpyrimidin-4-amine (1.6 g, yield 80%) as a light yellow solid. $^1$H NMR (300 MHz, CDCl$_3$): δ 7.80 (s, 1H), 4.84 (s, 1H), 4.76-4.52 (m, 1H), 2.58-2.30 (m, 3H), 2.06-1.50 (m, 6H) ppm.

To a solution of 2-chloro-N-cyclobutyl-5-methylpyrimidin-4-amine (1.6 g, 8.1 mmol) in EtOH (6 mL) was added methyl 5-amino-2-bromobenzoate (1.9 g, 8.1 mmol) and HCl (1.5 N, 4 mL). The reaction was subjected to microwave irradiation (90° C., 30 min), then cooled to room temperature, poured into water, the formed solid was collected by filtration, dried in vacuo to give methyl 2-bromo-5-((4-(cyclobutylamino)-5-methylpyrimidin-2-yl)amino)benzoate (2.1 g, yield 68%) as a yellow solid. $^1$H NMR (400 MHz, CDCl$_3$): δ 10.73 (s, 1H), 8.27 (d, J=2.7 Hz, 1H), 7.59-7.50 (m, 1H), 7.50-7.29 (m, 2H), 6.23 (d, J=6.3 Hz, 1H), 4.66-4.44 (m, 1H), 3.86 (s, 3H), 2.47-2.32 (m, 2H), 2.32-1.58 (m, 7H) ppm.

To a solution of methyl 2-bromo-5-((4-(cyclobutylamino)-5-methylpyrimidin-2-yl)amino)benzoate (1.6 g, 4.1 mmol) in THF (15 mL) was added KOAc (1.2 g, 12.3 mmol), (BPin)$_2$ (1.5 g, 6.1 mmol) and (dppf)PdCl$_2$ (1.3 g, 1.6 mmol) at room temperature under nitrogen atmosphere. The mixture was heated to reflux overnight, then the solid was removed by filtration, and the filtrate was concentrated under reduce pressure to give a residue, which was purified by silica chromatography with DCM/MeOH (100/1 to 20/1) to give the crude methyl 5-((4-(cyclobutylamino)-5-methylpyrimidin-2-yl)amino)-2-(4,4,5,5-tetramethyl-1,3,2-dioxaborolan-2-yl)benzoate (1.1 g, 70% purity in LCMS) as a black solid, which was used directly to the next step. MS: (M+H)$^+$: m/z=439.3.

To a solution of crude methyl 5-((4-(cyclobutylamino)-5-methylpyrimidin-2-yl)amino)-2-(4,4,5,5-tetramethyl-1,3,2-dioxaborolan-2-yl)benzoate (1.1 g, crude) in MeOH (20 mL) was added NaBH$_4$ (760 mg, 20.0 mmol) at 30° C. in small portions. The reaction was stirred at 30° C. for 30 min, then 6N HCl (3 mL) was added, and the resulting mixture was kept stirring for another 20 min. The reaction mixture was neutralized by adding saturated aq. NaHCO$_3$, and the aqueous phase was extracted with EtOAc. The combined organic phase was washed with water, brine, concentrated under reduce pressure to give a residue, which was purified by silica chromatography with DCM/MeOH (100/1 to 20/1) to give the crude product which triturated with CH$_3$CN and water to give 5-((4-(cyclobutylamino)-5-methylpyrimidin-2-yl)amino)benzo[c][1,2]oxaborol-1(3H)-ol (260 mg, yield 20%) as a yellow solid. $^1$H NMR (300 MHz, DMSO-d$_6$): δ 9.03 (s, 1H), 8.85 (s, 1H), 8.03 (s, 1H), 7.69 (s, 1H), 7.55 (q, J=8.0 Hz, 2H), 6.73 (d, J=7.0 Hz, 1H), 4.92 (s, 2H), 4.65-4.45 (m, 1H), 2.33-2.18 (m, 2H), 2.18-2.01 (m, 2H), 1.93 (s, 3H), 1.81-1.57 (m, 2H) ppm. HPLC purity: 98.57% at 210 nm and 98.69% at 254 nm. MS: (M+H)$^+$: m/z=311.1.

Example 12: 5-((4-(sec-butylamino)-5-chloropyrimidin-2-yl)amino)benzo[c][1,2]oxaborol-1(3H)-ol

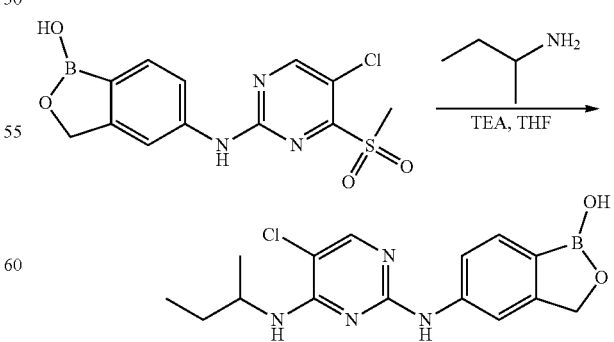

This substance was prepared following General Synthetic Scheme B, starting with 5-((5-chloro-4-(methylsulfonyl) pyrimidin-2-yl)amino)benzo[c][1,2]oxaborol-1(3H)-ol and butan-2-amine using the procedure in Example 2. ¹H NMR (DMSO-d6, 400 MHz) δ (ppm) 9.61 (s, 1H), 8.20 (br, 1H), 8.02 (s, 1H), 7.85 (s, 1H), 7.62-7.55 (m, 2H), 4.94 (s, 2H), 4.16-4.11 (m, 2H), 1.70-1.65 (m, 1H), 1.56-1.52 (m, 1H), 1.22 (d, J=6.8 Hz, 3H), 0.89 (t, J=3.4 Hz, 3H). MS (ESI): m/z found 333.1 [M+H]⁺. Purity by HPLC: 97.93% (220 nm), 95.61% (254 nm).

Example 13: 5-((5-methyl-4-((1-phenylpropyl)amino)pyrimidin-2-yl)amino)benzo[c][1,2]oxaborol-1(3H)-ol

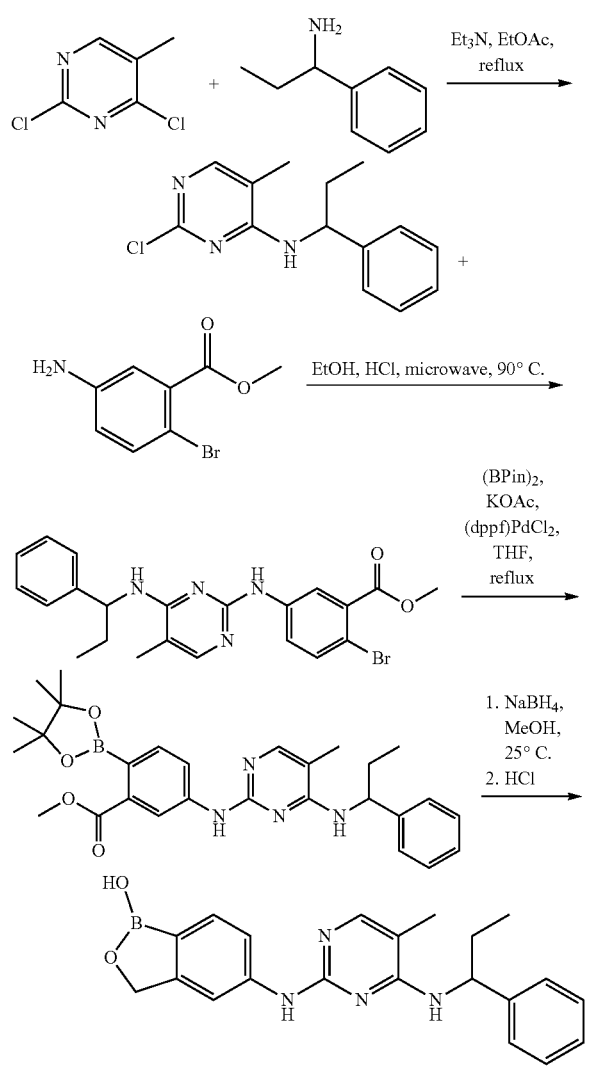

To a solution of 2,4-dichloro-5-methylpyrimidine (1.1 g, 7.0 mmol) in EtOAc (10 mL) was added 1-phenylpropan-1-amine (945 mg, 7.0 mmol) and Et₃N (1.4 g, 14.0 mmol) at room temperature. The reaction was heated to reflux overnight, then the solvent was removed in vacuo to give a residue, which was triturated with CH₃CN and H₂O to give 2-chloro-5-methyl-N-(1-phenylpropyl)pyrimidin-4-amine (1.2 g, yield 67%) as a white solid. ¹H NMR (400 MHz, CDCl₃): δ 7.73 (s, 1H), 7.37-7.20 (m, 5H), 5.16-5.10 (m, 1H), 4.84-4.82 (m, 1H), 2.02-1.75 (m, 5H), 0.86 (t, J=7.4 Hz, 3H) ppm.

To a solution of 2-chloro-5-methyl-N-(1-phenylpropyl)pyrimidin-4-amine (1.2 g, 4.6 mmol) in EtOH (6 mL) was added methyl 5-amino-2-bromobenzoate (1.1 g, 4.6 mmol) and HCl (1.5 N, 4 mL). The reaction was subjected to microwave irradiation (90° C., 30 min), then cooled to room temperature, poured into water. The aqueous phase was extracted with DCM, the combined organic phase was washed with water, brine, concentrated under reduce pressure to give a residue, which was purified by silica chromatography with DCM/MeOH (100/1 to 20/1) to give methyl 2-bromo-5-((5-methyl-4-((1-phenylpropyl)amino)pyrimidin-2-yl)amino)benzoate (1.0 g, yield 48%) as a yellow solid. ¹H NMR (400 MHz, CDCl₃): δ 7.94 (d, J=2.4 Hz, 1H), 7.60 (s, 1H), 7.45-7.41 (m, 2H), 7.33-7.20 (m, 5H), 5.10-5.05 (m, 1H), 4.93-4.91 (m, 1H), 3.83 (s, 3H), 2.02-1.73 (m, 5H), 0.89 (t, J=7.4 Hz, 3H) ppm.

To a solution of methyl 2-bromo-5-((5-methyl-4-((1-phenylpropyl)amino)pyrimidin-2-yl)amino)benzoate (1.0 g, 2.1 mmol) in THF (15 mL) was added KOAc (617 mg, 6.3 mmol), (BPin)₂ (787 mg, 3.1 mmol) and (dppf)PdCl₂ (653 mg, 0.8 mmol) at room temperature under nitrogen atmosphere. The mixture was heated to reflux overnight, then the solid was removed by filtration, and the filtrate was concentrated under reduce pressure to give a residue, which was purified by silica chromatography with DCM/MeOH (100/1 to 20/1) to give the crude methyl 5-((5-methyl-4-((1-phenylpropyl)amino)pyrimidin-2-yl)amino)-2-(4,4,5,5-tetramethyl-1,3,2-dioxaborolan-2-yl)benzoate (800 mg, 30% de-Br product in LCMS) as a black solid, which was used directly to the next step. MS: (M+H)⁺: m/z=503.3.

To a solution of crude methyl 5-((5-methyl-4-((1-phenylpropyl)amino)pyrimidin-2-yl)amino)-2-(4,4,5,5-tetramethyl-1,3,2-dioxaborolan-2-yl)benzoate (800 mg, crude) in MeOH (10 mL) was added NaBH₄ (380 mg, 10.0 mmol) at 30° C. in small portions. The reaction was stirred at 30° C. for 30 min, then 6N HCl (3 mL) was added, and the resulting mixture was kept stirring for another 20 min. The reaction mixture was neutralized by adding saturated aq. NaHCO₃, and the aqueous phase was extracted with EtOAc, the combined organic phase was washed with water, brine, concentrated under reduce pressure to give a residue, which was purified by silica chromatography with DCM/MeOH (100/1 to 20/1) to give the crude product, which was triturated with CH₃CN and water to give 5-((5-methyl-4-((1-phenylpropyl)amino)pyrimidin-2-yl)amino)benzo[c][1,2]oxaborol-1(3H)-ol (77 mg, yield 10%) as a white solid. ¹H NMR (400 MHz, DMSO-d₆): δ 9.00 (s, 1H), 8.86 (s, 1H), 7.79 (s, 1H), 7.69 (s, 1H), 7.55-7.41 (m, 4H), 7.32 (t, J=7.6 Hz, 2H), 7.19 (t, J=7.3 Hz, 1H), 6.82 (d, J=8.2 Hz, 1H), 5.14 (dd, J=14.6, 8.6 Hz, 1H), 5.10-4.80 (m, 2H), 2.04 (s, 3H), 1.99-1.75 (m, 2H), 0.93 (t, J=7.3 Hz, 3H) ppm. Purity by HPLC: 96.48% at 210 nm and 98.14% at 254 nm. MS: (M+H)⁺: m/z=375.2.

Example 14: 5-((5-chloro-4-(pentan-3-ylamino)pyrimidin-2-yl)amino)benzo[c][1,2]oxaborol-1(3H)-ol

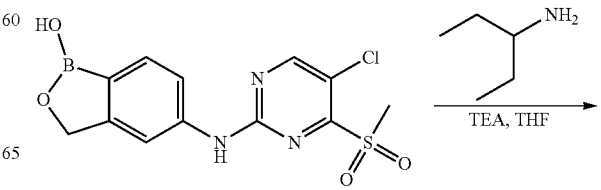

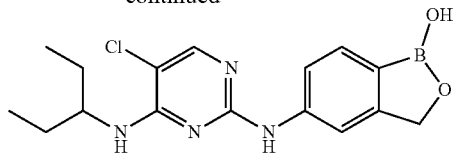

This substance was prepared following General Synthetic Scheme B, starting with 5-((5-chloro-4-(methylsulfonyl)pyrimidin-2-yl)amino)benzo[c][1,2]oxaborol-1(3H)-ol and pentan-3-amine using the procedure in Example 2. $^1$H NMR (DMSO-d6, 400 MHz) δ (ppm) 9.39 (s, 1H), 8.93 (s, 1H), 7.96 (s, 1H), 7.89 (s, 1H), 7.61-7.56 (m, 2H), 6.70 (d, J=8.8 Hz, 1H), 4.93 (s, 2H), 4.05-4.0 (m, 1H), 1.64-1.57 (m, 4H), 0.90-0.86 (m, 6H). MS (ESI): m/z found 347.0 [M+H]$^+$. Purity by HPLC: 95.31% (220 nm), 99.07% (254 nm).

Example 15: 5-((5-chloro-4-((1-hydroxybutan-2-yl)amino)pyrimidin-2-yl)amino)benzo[c][1,2]oxaborol-1(3H)-ol

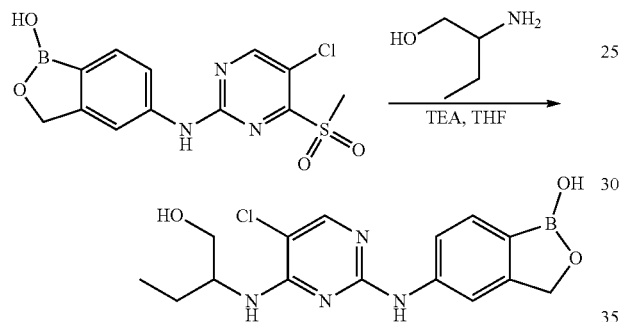

This substance was prepared following General Synthetic Scheme B, starting with 5-((5-chloro-4-(methylsulfonyl)pyrimidin-2-yl)amino)benzo[c][1,2]oxaborol-1(3H)-ol and 2-aminobutan-1-ol using the procedure in Example 2. $^1$H NMR (DMSO-d6, 400 MHz) δ (ppm) 9.47 (s, 1H), 8.95 (br, 1H), 7.99 (s, 1H), 7.89 (s, 1H), 7.59-7.57 (m, 2H), 6.64-6.63 (m, 1H), 4.93 (s, 2H), 4.10-4.09 (m, 1H), 3.59-3.55 (m, 1H), 3.52-3.51 (m, 1H) 1.71-1.66 (m, 1H), 1.62-1.57 (m, 1H), 0.92-0.89 (m, 3H). MS (ESI): m/z found 349 [M+H]$^+$. Purity by HPLC: 91.87% (220 nm), 95.66% (254 nm).

Example 16: 5-((4-(cyclopentylamino)-5-methylpyrimidin-2-yl)amino)benzo[c][1,2]oxaborol-1(3H)-ol

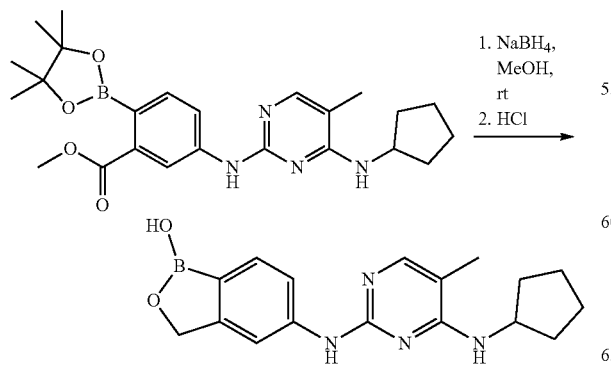

To a solution of methyl 5-((4-(cyclopentylamino)-5-methylpyrimidin-2-yl)amino)-2-(4,4,5,5-tetramethyl-1,3,2-dioxaborolan-2-yl)benzoate (5.4 g, crude), which was prepared using the general experimental procedure, in MeOH (50 mL) was added NaBH$_4$ (4.6 g, 0.12 mol) at room temperature in small portions. The reaction was stirred at room temperature for 1 h, then 6N HCl (10 mL) was added and stirred for another 20 min. The reaction mixture was neutralized by adding saturated NaHCO$_3$, and the aqueous phase was extracted with EtOAc, the combined organic phase was washed with water, brine, concentrated under reduce pressure to give a residue, which was purified by silica chromatography with MeOH/DCM (100/1 to 50/1) to give the crude product, which was triturated with MeCN/H$_2$O (10/1) to give 5-((4-(cyclopentylamino)-5-methylpyrimidin-2-yl)amino)benzo[c][1,2]oxaborol-1(3H)-ol (1.43 g, yield 29%) as a white solid. $^1$H NMR (400 MHz, DMSO-d$_6$): δ 9.06 (s, 1H), 8.87 (s, 1H), 8.04 (s, 1H), 7.68 (s, 1H), 7.56 (dd, J=19.7, 8.1 Hz, 2H), 6.36 (d, J=6.9 Hz, 1H), 4.91 (s, 2H), 4.51-4.32 (m, 1H), 2.09-1.87 (m, 2H), 1.93 (s, 3H), 1.81-1.65 (m, 2H), 1.65-1.46 (m, 4H). HPLC purity: 98.40% at 210 nm and 97.77% at 254 nm. MS: (M+H)$^+$: m/z=325.1.

Example 17: 5-((4-((1-hydroxybutan-2-yl)amino)-5-methylpyrimidin-2-yl)amino)benzo[c][1,2]oxaborol-1(3H)-ol

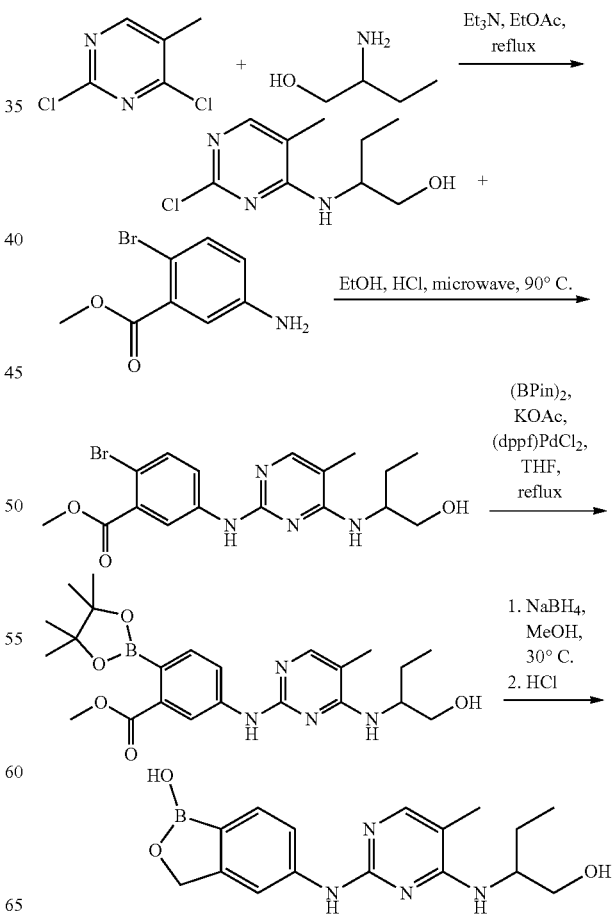

To a solution of 2,4-dichloro-5-methylpyrimidine (2.0 g, 12.3 mmol) in EtOAc (20 mL) was added 2-aminobutan-1-ol (2.2 g, 24.6 mmol) and Et$_3$N (2.5 g, 24.6 mmol) at room temperature. The reaction was heated to reflux overnight, then the solvent was removed in vacuo to give a residue, which was triturated with water and MeOH to give 2-((2-chloro-5-methylpyrimidin-4-yl)amino)butan-1-ol (2.1 g, yield 81%) as a light yellow solid. $^1$H NMR (300 MHz, CDCl$_3$): δ 7.81 (s, 1H), 4.91 (d, J=6.5 Hz, 1H), 4.29-4.06 (m, 1H), 3.88-3.65 (m, 2H), 2.03 (s, 3H), 1.80-1.56 (m, 2H), 1.01 (t, J=7.4 Hz, 3H) ppm.

To a solution of 2-((2-chloro-5-methylpyrimidin-4-yl)amino)butan-1-ol (1.3 g, 6.0 mmol) in EtOH (6 mL) was added methyl 5-amino-2-bromobenzoate (1.4 g, 6.0 mmol) and HCl (1.5 N, 4 mL). The reaction was subjected to microwave irradiation (90° C., 30 min), then cooled to room temperature and extracted with EtOAc, the organic was washed with water, brine, concentrated under reduce pressure to give a residue, which was purified by silica chromatography with DCM/MeOH (100/1 to 10/1) to give methyl 2-bromo-5-((4-((1-hydroxybutan-2-yl)amino)-5-methylpyrimidin-2-yl)amino)benzoate (1.4 g, yield 58%) as a yellow solid. $^1$H NMR (300 MHz, CDCl$_3$): δ 9.76 (s, 1H), 8.27 (s, 1H), 7.60-7.33 (m, 3H), 6.01 (d, J=8.4 Hz, 1H), 4.47-4.24 (m, 1H), 4.03-3.73 (m, 5H), 2.05 (s, 3H), 1.87-1.56 (m, 2H), 0.97 (t, J=7.3 Hz, 3H) ppm.

To a solution of methyl 2-bromo-5-((4-((1-hydroxybutan-2-yl)amino)-5-methylpyrimidin-2-yl)amino)benzoate (1.4 g, 3.4 mmol) in THF (15 mL) was added KOAc (1.0 g, 10.2 mmol), (BPin)$_2$ (1.3 g, 5.1 mmol) and (dppf)PdCl$_2$ (1.1 g, 1.3 mmol) at room temperature under nitrogen atmosphere. The mixture was heated to reflux overnight, then the solid was removed by filtration, and the filtrate was concentrated under reduce pressure to give a residue, which was purified by silica chromatography with DCM/MeOH (100/1 to 20/1) to give the crude methyl 5-((4-((1-hydroxybutan-2-yl)amino)-5-methylpyrimidin-2-yl)amino)-2-(4,4,5,5-tetramethyl-1,3,2-dioxaborolan-2-yl)benzoate (1.0 g, contain 45% de-Br product in LCMS) as a black solid. MS: (M+H)$^+$: m/z=457.2.

To a solution of methyl 5-((4-((1-hydroxybutan-2-yl)amino)-5-methylpyrimidin-2-yl)amino)-2-(4,4,5,5-tetramethyl-1,3,2-dioxaborolan-2-yl)benzoate (1.0 g, crude) in MeOH (20 mL) was added NaBH$_4$ (570 mg, 15.0 mmol) at 30° C. in small portions. The reaction was stirred at 30° C. for 30 min, then 6N HCl (3 mL) was added and stirred for another 20 min. The reaction mixture was neutralized by adding saturated NaHCO$_3$ and extracted with EtOAc, the combined organic phase was washed with water, brine, concentrated under reduce pressure to give a residue, which was purified by silica chromatography with DCM/MeOH (100/1 to 20/1) to give the crude product, which was further purification by pre-HPLC (0.1% TFA in MeCN and H$_2$O) to give 5-((4-((1-hydroxybutan-2-yl)amino)-5-methylpyrimidin-2-yl)amino)benzo[c][1,2]oxaborol-1(3H)-ol (90 mg, yield 9%) as a white solid. $^1$H NMR (400 MHz, DMSO-d$_6$): δ 9.01 (s, 1H), 8.83 (s, 1H), 7.97 (s, 1H), 7.68 (s, 1H), 7.55 (dd, J=21.2, 8.1 Hz, 2H), 6.02 (d, J=8.1 Hz, 1H), 4.91 (s, 2H), 4.67 (s, 1H), 4.21-4.04 (m, 1H), 3.63-3.41 (m, 2H), 1.94 (s, 3H), 1.78-1.66 (m, 1H), 1.63-1.49 (m, 1H), 0.91 (t, J=7.3 Hz, 3H) ppm. HPLC purity: 98.18% at 210 nm and 99.94% at 254 nm. MS: (M+H)$^+$: m/z=329.2.

Example 18: 5-((4-((3-(hydroxymethyl)phenyl)amino)-5-methylpyrimidin-2-yl)amino)benzo[c][1,2]oxaborol-1(3H)-ol

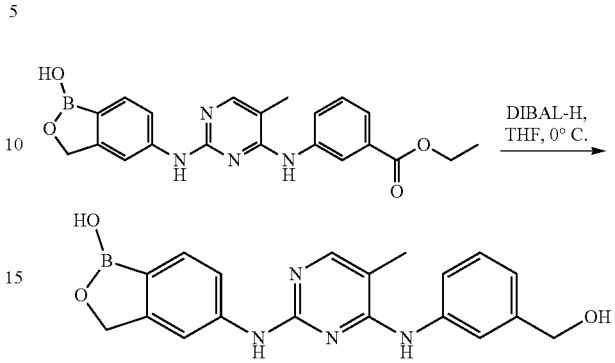

To a solution of ethyl 3-((2-((1-hydroxy-1,3-dihydrobenzo[c][1,2]oxaborol-5-yl)amino)-5-methylpyrimidin-4-yl)amino)benzoate (500 mg, 1.2 mmol), which was prepared as shown in Example 61, in THF (10 mL) was added DIBAL-H (1.5 N, 4 mL) at 0° C. under N$_2$ atmosphere, the reaction was stirred at 0° C. for 2 h, then it was quenched by adding 6N HCl, poured into water, neutralized by adding aq. NaHCO$_3$, extracted with EtOAc. The combined organic phase was washed with water, brine, concentrated under reduce pressure to give a residue, which was purified by silica chromatography with DCM/MeOH (100/1 to 10/1) to give the crude product, which was further purified by pre-HPLC (0.1% TFA in MeCN) to give 5-((4-((3-(hydroxymethyl)phenyl)amino)-5-methylpyrimidin-2-yl)amino)benzo[c][1,2] oxaborol-1(3H)-ol (62 mg, yield 14%) as a white solid. $^1$H NMR (400 MHz, DMSO-d$_6$): δ 9.20 (s, 1H), 8.85 (s, 1H), 8.38 (s, 1H), 7.91 (s, 1H), 7.84 (s, 1H), 7.62 (d, J=7.9 Hz, 1H), 7.49 (s, 2H), 7.32 (t, J=7.8 Hz, 1H), 7.07 (d, J=7.6 Hz, 1H), 5.21 (s, 1H), 4.79 (s, 2H), 4.51 (s, 2H), 2.12 (s, 3H) ppm. HPLC purity: 98.72% at 210 nm and 98.83% at 254 nm. MS: (M+H)$^+$: m/z=363.1.

Example 19: 5-((4-(cyclopentyloxy)-5-methylpyrimidin-2-yl)amino)benzo[c][1,2]oxaborol-1(3H)-ol

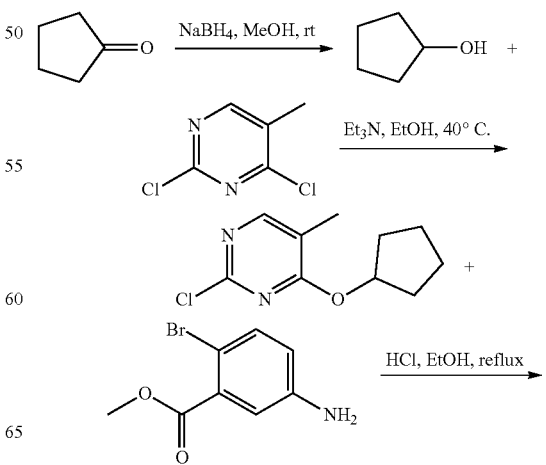

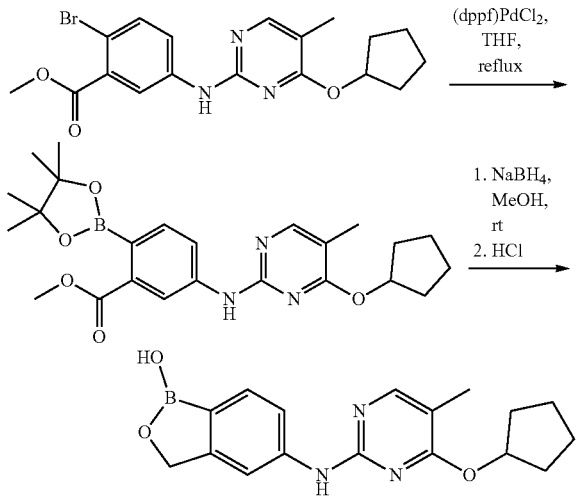

To a solution of cyclopentanone (5.0 g, 59.5 mmol) in MeOH (50 mL) was added NaBH₄ (4.5 g, 0.12 mol). The reaction was stirred at room temperature overnight, then it was poured into water and extracted with DCM, and the combined organic phase was washed with water, brine, concentrated in vacuo to give the crude cyclopentanol (3.0 g, yield 51%) as a light oil. $^1$H NMR (400 MHz, CDCl$_3$): δ 4.56 (s, 1H), 3.27-3.01 (m, 1H), 2.53 (d, J=3.4 Hz, 3H), 2.09-1.88 (m, 2H), 1.88-1.68 (m, 2H), 1.68-1.37 (m, 4H) ppm.

To a solution of 2,4-dichloro-5-methylpyrimidine (3.7 g, 23.0 mmol) in DMF (20 mL) was added cyclopentanol (2.0 g, 23 mmol) and NaH (1.8 g, 46 mmol) at room temperature. The reaction was heated at 60° C. overnight, then the mixture was quenched by adding water, extracted with EA, and the combined organic phase was washed with brine (3×50 mL), concentrated in vacuo to give residue, which was purified by silica chromatography with PE/EtOAc (20/1 to 10/1) to give 2-chloro-4-(cyclopentyloxy)-5-methylpyrimidine (2.2 g, yield 45%) as a yellow solid. $^1$H NMR (400 MHz, CDCl$_3$): δ 8.07 (s, 1H), 5.61-5.47 (m, 1H), 2.08 (s, 3H), 2.03-1.93 (m, 2H), 1.86-1.78 (m, 4H), 1.70-1.62 (m, 2H) ppm.

To a solution of 2-chloro-4-(cyclopentyloxy)-5-methylpyrimidine (1.1 g, 5 mmol) in EtOH (10 mL) was added methyl 5-amino-2-bromobenzoate (1.15 g, 5 mmol) and HCl (1.5 N, 4 mL). The resulting mixture was heat up to 80° C. for 5 h, then cooled to room temperature, poured into water, the solid was collected by filtration, dried in vacuo to give methyl 2-bromo-5-((4-(cyclopentyloxy)-5-methylpyrimidin-2-yl)amino)benzoate (1.0 g, yield 61%) as a white solid. $^1$H NMR (400 MHz, CDCl$_3$): δ 11.09 (s, 1H), 8.32 (d, J=2.6 Hz, 1H), 7.83 (s, 1H), 7.65 (d, J=8.7 Hz, 1H), 7.53 (dd, J=8.7, 2.6 Hz, 1H), 5.66-5.50 (m, 1H), 3.92 (s, 3H), 2.09 (s, 3H), 2.04-2.03 (m, 2H), 1.98-1.66 (m, 6H) ppm.

To a solution of methyl 2-bromo-5-((4-(cyclopentyloxy)-5-methylpyrimidin-2-yl)amino)benzoate (1.0 g, 2.4 mmol) in dioxane (15 mL) was added KOAc (706 mg, 7.2 mmol), (BPin)$_2$ (914 mg, 3.6 mmol) and (dppf)PdCl$_2$ (800 mg, 1.0 mmol) at room temperature under nitrogen atmosphere. The mixture was heated to reflux overnight, then the solid was removed by filtration, and the filtrate was concentrated under reduce pressure to give a residue, which was purified by silica chromatography with PE/EA (10/1 to 3/1) to give crude methyl 5-((4-(cyclopentyloxy)-5-methylpyrimidin-2-yl)amino)-2-(4,4,5,5-tetramethyl-1,3,2-dioxaborolan-2-yl)benzoate (650 mg, 70% purity) as a colorless oil. $^1$H NMR (400 MHz, DMSO): δ 9.62 (s, 1H), 8.45 (d, J=2.1 Hz, 1H), 8.07 (d, J=0.6 Hz, 1H), 7.93 (s, 1H), 7.83 (dd, J=8.2, 2.1 Hz, 1H), 7.39 (d, J=8.1 Hz, 1H), 5.57-5.41 (m, 1H), 3.82 (s, 3H), 2.08-1.94 (m, 5H), 1.82-1.69 (m, 4H), 1.63 (t, J=6.7 Hz, 2H), 1.30 (s, 12H) ppm.

To a solution of methyl 5-((4-(cyclopentyloxy)-5-methylpyrimidin-2-yl)amino)-2-(4,4,5,5-tetramethyl-1,3,2-dioxaborolan-2-yl)benzoate (650 mg, 1.3 mmol) in MeOH (10 mL) was added NaBH$_4$ (380 mg, 10.0 mmol) at room temperature in small portions. The reaction was kept stirring at room temperature for 30 min, then 6N HCl (3 mL) was added and stirred for another 20 min. The reaction mixture was neutralized by adding saturated NaHCO$_3$, extracted with EtOAc, the combined organic phase was washed with water, brine, concentrated under reduce pressure to give a residue, which was purified by silica chromatography with DCM/MeOH (100/1 to 20/1) to give the crude product, which was triturated with CH$_3$CN and water to give 5-((4-(cyclopentyloxy)-5-methylpyrimidin-2-yl)amino)benzo[c][1,2]oxaborol-1(3H)-ol (236 mg, yield 56%) as a white solid. $^1$H NMR (400 MHz, DMSO-d$_6$): δ 9.50 (s, 1H), 8.91 (s, 1H), 8.05 (s, 1H), 7.95 (s, 1H), 7.68-7.48 (m, 2H), 5.56-5.37 (m, 1H), 4.94 (s, 2H), 2.08-1.87 (m, 5H), 1.84-1.67 (m, 4H), 1.67-1.52 (m, 2H). ppm. HPLC purity: 96.53% at 210 nm and 95.01% at 254 nm. MS: (M+H)$^+$: m/z=326.2.

Example 20: 5-((4-(cyclopentyl(methyl)amino)-5-methylpyrimidin-2-yl)amino)benzo[c][1,2]oxaborol-1(3H)-ol

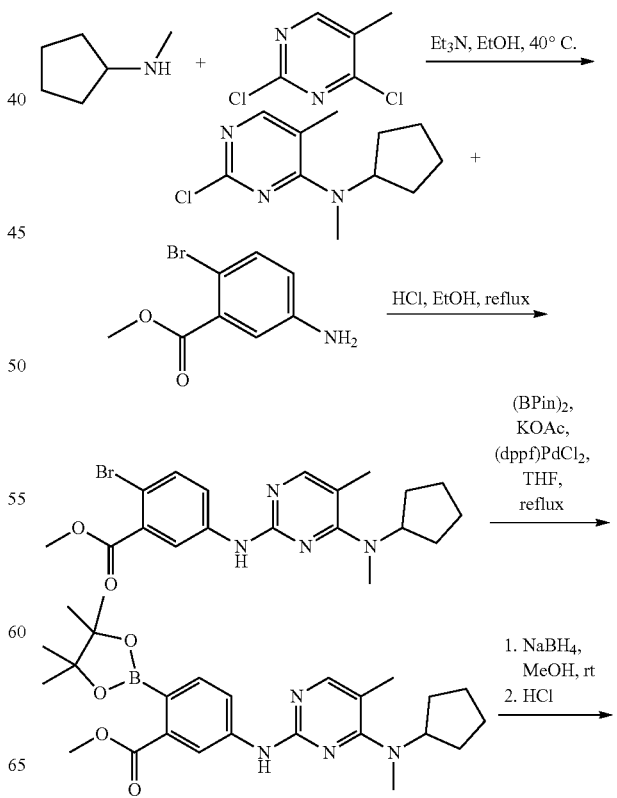

-continued

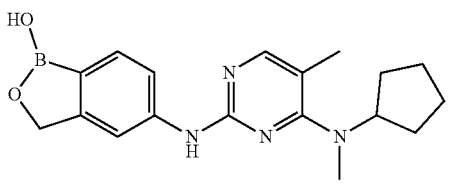

This substance was prepared using the scheme above and the general procedure described in General Synthetic Scheme A. $^1$H NMR (300 MHz, DMSO-$d_6$): δ 9.14 (s, 1H), 8.88 (s, 1H), 7.95 (s, 1H), 7.83 (s, 1H), 7.66-7.43 (m, 2H), 4.91 (s, 2H), 4.68-4.48 (m, 1H), 2.90 (s, 3H), 2.16 (s, 3H), 1.95-1.75 (m, 2H), 1.75-1.44 (m, 6H) ppm. HPLC purity: 98.74% at 210 nm and 98.51% at 254 nm. MS: (M+H)$^+$: m/z=339.2.

Example 21: 5-((5-chloro-4-((2-cyclopropylethyl)amino)pyrimidin-2-yl)amino)benzo[c][1,2]oxaborol-1(3H)-ol

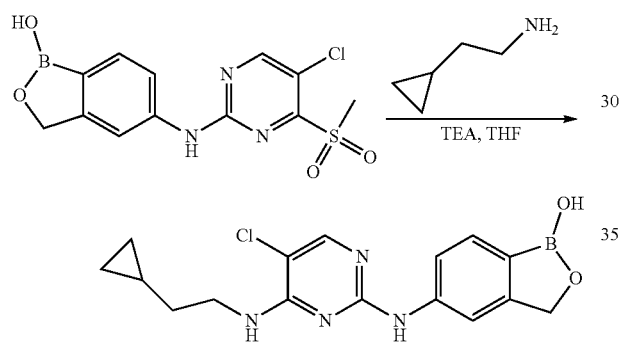

This substance was prepared following General Synthetic Scheme B, starting with 5-((5-chloro-4-(methylsulfonyl)pyrimidin-2-yl)amino)benzo[c][1,2]oxaborol-1(3H)-ol and pentan-3-amine using the procedure in Example 2. $^1$H NMR (DMSO-d6, 400 MHz) δ (ppm) 9.47 (s, 1H), 8.88 (s, 1H), 7.92 (s, 1H), 7.79 (s, 1H), 7.57-7.52 (m, 2H), 7.41-7.39 (m, 1H), 4.87 (s, 2H), 3.47-3.41 (m, 2H), 1.47-1.41 (m, 2H), 0.65-0.64 (m, 1H), 0.37-0.35 (m, 2H), 0.02-0.01 (m, 2H). MS (ESI): m/z found 345.1 [M+H]$^+$. Purity by HPLC: 97.31% (220 nm), 98.41% (254 nm).

Example 22: 5-((5-chloro-4-(2-ethylaziridin-1-yl)pyrimidin-2-yl)amino)benzo[c][1,2]oxaborol-1(3H)-ol

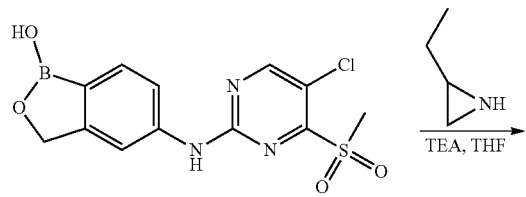

-continued

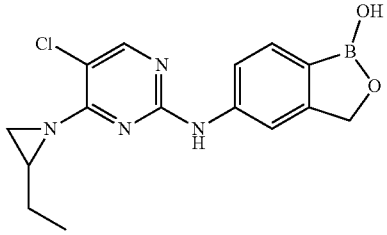

This substance was prepared following General Synthetic Scheme B, from 5-((5-chloro-4-(methylsulfonyl)pyrimidin-2-yl)amino)benzo[c][1,2]oxaborol-1(3H)-ol, which was prepared using the procedure in Example 2, and 2-ethylaziridine. $^1$H NMR (DMSO-d6, 400 MHz) δ (ppm) 10.55 (s, 1H), 9.95 (s, 1H), 9.22 (s, 1H), 8.31 (s, 1H), 7.76 (d, J=7.6 Hz, 1H), 7.62 (s, 1H), 7.51 (d, J=7.6 Hz, 1H), 5.01 (s, 2H), 4.69-4.64 (m, 1H), 4.41-4.40 (m, 1H), 4.28-4.26 (m, 1H), 1.81-1.72 (m, 2H), 0.98 (t, J=7.4 Hz, 3H). MS (ESI): m/z found 331.0 [M+H]$^+$. Purity by HPLC: 99.26% (220 nm), 99% (254 nm).

Example 23: 5-((4-(cyclopentylamino)pyrimidin-2-yl)amino)benzo[c][1,2]oxaborol-1(3H)-ol

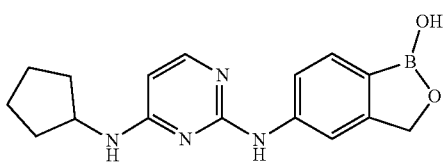 [SMILES: OB1OCc2cc(Nc3nccc(NC4CCCC4)n3)ccc21]

This substance was prepared using the general experimental procedure as shown in General Synthetic Scheme A. $^1$H NMR (400 MHz, DMSO-$d_6$): δ 9.15 (s, 1H), 8.87 (s, 1H), 8.02 (s, 1H), 7.79 (br, 1H), 7.61-7.53 (m, 2H), 7.24 (br, 1H), 5.95 (d, J=6.0 Hz, 1H), 4.91 (s, 2H), 4.23-4.22 (m, 1H), 1.99-1.93 (m, 2H), 1.70-1.24 (m, 6H) ppm. HPLC purity: 98.05% at 210 nm and 98.18% at 254 nm. MS: (M+H)$^+$: m/z=311.1.

Example 24: 5-((4-(cyclohexylamino)pyrimidin-2-yl)amino)benzo[c][1,2]oxaborol-1(3H)-ol

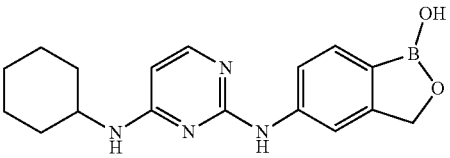 [SMILES: OB1OCc2cc(Nc3nccc(NC4CCCCC4)n3)ccc21]

This substance was prepared using the general experimental procedure as shown in General Synthetic Scheme A. $^1$H NMR (400 MHz, DMSO-$d_6$): δ 9.14 (s, 1H), 8.89 (s, 1H), 8.01 (s, 1H), 7.61 (d, J=8.0 Hz, 1H), 7.55-7.53 (m, 2H), 7.12 (br, 1H), 5.94 (d, J=5.6 Hz, 1H), 4.92 (s, 2H), 3.82-3.81 (m, 1H), 1.98-1.95 (m, 2H), 1.78-1.75 (m, 2H), 1.66-1.63 (m, 1H), 1.36-1.17 (m, 5H) ppm. HPLC purity: 99.34% at 210 nm and 98.18% at 254 nm. MS: (M+H)$^+$: m/z=325.2.

Example 25: 5-((5-methyl-4-((2-(trifluoromethyl)phenyl)amino)pyrimidin-2-yl)amino)benzo[c][1,2]oxaborol-1(3H)-ol

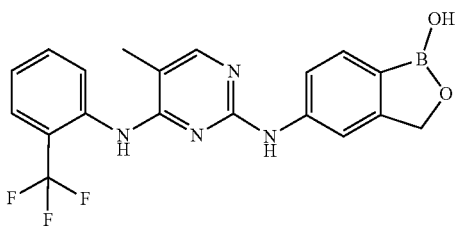 [SMILES: Cc1cnc(Nc2ccc3c(c2)COB3O)nc1Nc1ccccc1C(F)(F)F]

This substance was prepared using the general experimental procedure as shown in General Synthetic Scheme A. $^1$H NMR (400 MHz, DMSO-d$_6$): δ 9.15 (s, 1H), 8.80 (s, 1H), 8.35 (s, 1H), 7.89-7.78 (m, 3H), 7.63-7.58 (m, 2H), 7.49 (s, 1H), 7.34 (d, J=8.0 Hz, 1H), 7.19 (dd, J=8.8, 1.6 Hz, 1H), 4.61 (s, 2H), 2.11 (s, 3H) ppm. HPLC purity: 99.85% at 210 nm and 99.84% at 254 nm. MS: (M+H)$^+$: m/z=401.1.

Example 26: 5-((4-((2-ethylphenyl)amino)-5-methylpyrimidin-2-yl)amino)benzo[c][1,2]oxaborol-1(3H)-ol

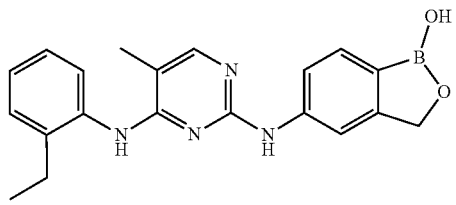 [SMILES: CCc1ccccc1Nc1nc(Nc2ccc3c(c2)COB3O)ncc1C]

This substance was prepared using the general experimental procedure as shown in following General Synthetic Scheme A. $^1$H NMR (400 MHz, DMSO-d$_6$): δ 9.08 (s, 1H), 8.79 (s, 1H), 8.23 (s, 1H), 7.83 (s, 1H), 7.56 (s, 1H), 7.39-7.19 (m, 6H), 4.62 (s, 2H), 2.59-2.49 (m, 2H), 2.11 (s, 3H), 1.08 (t, J=7.8 Hz, 3H) ppm. HPLC purity: 98.66% at 210 nm and 98.32% at 254 nm. MS: (M+H)$^+$: m/z=361.2.

Example 27: 5-((4-((2-fluorophenyl)amino)-5-methylpyrimidin-2-yl)amino)benzo[c][1,2]oxaborol-1(3H)-ol

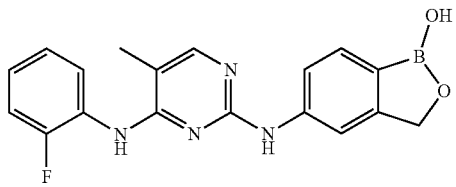 [SMILES: Cc1cnc(Nc2ccc3c(c2)COB3O)nc1Nc1ccccc1F]

This substance was prepared using the general experimental procedure as shown in General Synthetic Scheme A. $^1$H NMR (400 MHz, DMSO-d$_6$): δ 9.19 (s, 1H), 8.82 (s, 1H), 8.38 (s, 1H), 7.90 (s, 1H), 7.66 (s, 1H), 7.51-7.47 (m, 1H), 7.40-7.34 (m, 3H), 7.29-7.24 (m, 2H), 4.68 (s, 2H), 2.12 (s, 3H) ppm. HPLC purity: 97.19% at 210 nm and 97.7% at 254 nm. MS: (M+H)$^+$: m/z=351.1.

Example 28: 5-((4-((2-methoxyphenyl)amino)-5-methylpyrimidin-2-yl)amino)benzo[c][1,2]oxaborol-1(3H)-ol

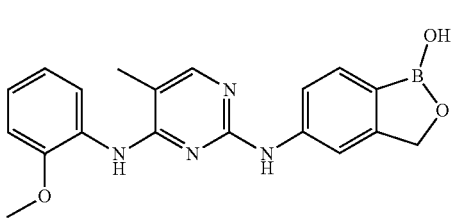 [SMILES: COc1ccccc1Nc1nc(Nc2ccc3c(c2)COB3O)ncc1C]

This substance was prepared using the general experimental procedure as shown in General Synthetic Scheme A. $^1$H NMR (400 MHz, DMSO-d$_6$): δ 9.19 (s, 1H), 8.86 (s, 1H), 7.89 (s, 1H), 7.82-7.77 (m, 3H), 7.46 (d, J=8.0 Hz, 1H), 7.36 (d, J=8.0 Hz, 1H), 7.21-7.19 (m, 1H), 7.13 (d, J=7.6 Hz, 1H), 7.02-6.98 (m, 1H), 4.77 (s, 2H), 3.79 (s, 3H), 2.10 (s, 3H) ppm. HPLC purity: 99.72% at 210 nm and 99.74% at 254 nm. MS: (M+H)$^+$: m/z=363.1.

Example 29: 5-((4-(cyclohexyloxy)pyrimidin-2-yl)amino)benzo[c][1,2]oxaborol-1(3H)-ol

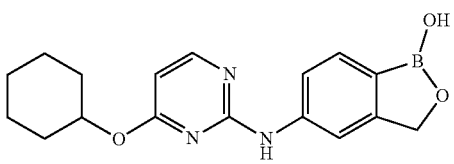 [SMILES: OB1OCc2cc(Nc3nccc(OC4CCCCC4)n3)ccc21]

This substance was prepared using the general experimental procedure as shown in General Synthetic Scheme A. $^1$H NMR (DMSO-d6, 400 MHz) δ 9.69 (s, 1H), 8.95 (s, 1H), 8.20 (d, J=6.0 Hz, 1H), 7.93 (s, 1H), 7.60 (s, 1H), 6.25 (d, J=5.6 Hz, 1H), 5.04-5.03 (m, 1H), 4.95 (s, 2H), 2.05-2.03 (m, 2H), 1.79-1.76 (m, 2H), 1.59-1.57 (m, 1H), 1.49-1.38 (m, 4H), 1.27-1.24 (m, 1H) ppm. HPLC purity: 98.35% at 210 nm and 98.69% at 254 nm. MS: (M+H)$^+$: m/z=326.1.

Example 30: 5-((4-((2-chlorophenyl)amino)-5-methylpyrimidin-2-yl)amino)benzo[c][1,2]oxaborol-1(3H)-ol

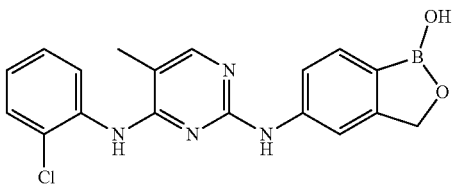 [SMILES: Cc1cnc(Nc2ccc3c(c2)COB3O)nc1Nc1ccccc1Cl]

This substance was prepared using the general experimental procedure as shown in General Synthetic Scheme A. $^1$H NMR (DMSO-d6, 400 MHz) δ 9.43 (s, 1H), 8.87 (s, 1H), 8.71 (br, 1H), 7.93 (s, 1H), 7.65-7.57 (m, 3H), 7.48-7.38 (m, 3H), 7.23 (d, J=8.0 Hz, 1H), 4.68 (s, 2H), 2.14 (s, 3H) ppm. HPLC purity: 97.04% at 210 nm and 96.10% at 254 nm. MS: (M+H)⁺: m/z=367.1.

Example 31: 5-((5-methyl-4-((2-(trifluoromethoxy)phenyl)amino)pyrimidin-2-yl)amino)benzo[c][1,2]oxaborol-1(3H)-ol

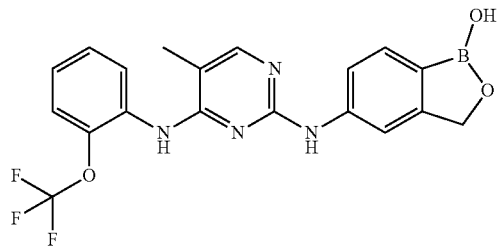 [SMILES: Cc1cnc(Nc2ccc3c(c2)COB3O)nc1Nc1ccccc1OC(F)(F)F]

This substance was prepared using the general experimental procedure as shown in General Synthetic Scheme A. ¹H NMR (DMSO-d6, 400 MHz) δ 9.18 (s, 1H), 8.83 (s, 1H), 8.38 (s, 1H), 7.92 (s, 1H), 7.64-7.62 (m, 2H), 7.51-7.38 (m, 4H), 7.28-7.26 (m, 1H), 4.67 (s, 2H), 2.11 (s, 3H) ppm. HPLC purity: 99.7% at 210 nm and 99.81% at 254 nm. MS: (M+H)⁺: m/z=417.1.

Example 32: 5-((5-chloro-4-(hexan-3-ylamino)pyrimidin-2-yl)amino)benzo[c][1,2]oxaborol-1(3H)-ol

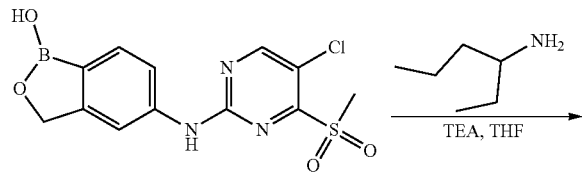

This substance was prepared following General Synthetic Scheme, starting with 5-((5-chloro-4-(methylsulfonyl)pyrimidin-2-yl)amino)benzo[c][1,2]oxaborol-1(3H)-ol and hexan-3-amine using the procedure in Example 2. ¹H NMR (DMSO-d6, 400 MHz) δ (ppm) 9.56 (br, 1H), 8.99 (br, 1H), 8.00 (s, 1H), 7.83 (s, 1H), 7.61-7.57 (m, 2H), 6.98 (br, 1H), 4.94 (s, 2H), 4.14-4.13 (m, 1H), 1.63-1.54 (m, 4H), 1.32-1.29 (m, 2H), 0.87 (t, J=7.4 Hz, 6H). MS (ESI): m/z found 361.1 [M+H]⁺. Purity by HPLC: 92.39% (220 nm), 96.9% (254 nm).

Example 33: 5-((5-methyl-4-(o-tolylamino)pyrimidin-2-yl)amino)benzo[c][1,2]oxaborol-1(3H)-ol

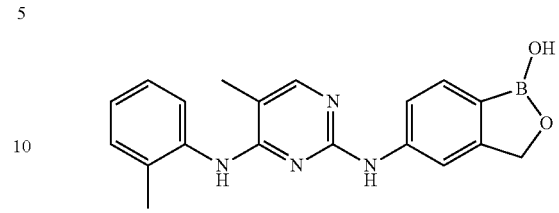

This substance was prepared using the general experimental procedure as shown in General Synthetic Scheme A. ¹H NMR (DMSO-d6, 400 MHz) δ 9.11 (s, 1H), 8.80 (s, 1H), 8.23 (s, 1H), 7.85 (s, 1H), 7.62 (s, 1H), 7.37-7.34 (m, 2H), 7.31-7.22 (m, 3H), 4.64 (s, 2H), 2.50 (s, 3H), 2.12 (s, 3H) ppm. HPLC purity: 96.72% at 210 nm and 97.15% at 254 nm. MS: (M+H)⁺: m/z=347.2.

Example 34: 5-((5-chloro-4-(cyclopentylamino)pyrimidin-2-yl)amino)-7-fluorobenzo[c][1,2]oxaborol-1(3H)-ol

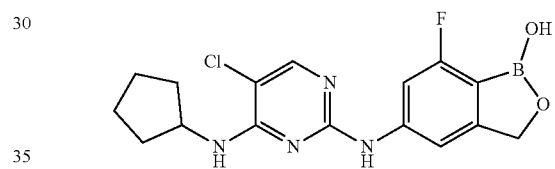

This substance was prepared using the general experimental procedure as shown in General Synthetic Scheme A. ¹H NMR (DMSO-d6, 400 MHz) δ (ppm) 9.98 (br, 1H), 8.07 (s, 1H), 7.55 (s, 1H), 7.52 (s, 1H), 7.45 (br, 1H), 4.95 (s, 2H), 4.40-4.35 (m, 1H), 1.98-1.96 (m, 2H), 1.74-1.72 (m, 2H), 1.65-1.56 (m, 4H). MS (ESI): m/z found 363.1 [M+H]⁺. Purity by HPLC: 94.06% (220 nm), 87.79% (254 nm).

Example 35: 7-fluoro-5-((5-methyl-4-(phenylamino)pyrimidin-2-yl)amino)benzo[c][1,2]oxaborol-1(3H)-ol

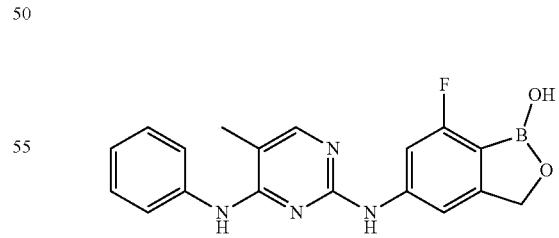

This substance was prepared using the general experimental procedure as shown in General Synthetic Scheme A. ¹H NMR (DMSO-d6, 400 MHz) δ (ppm) 9.99 (s, 1H), 9.26 (br, 1H), 9.09 (br, 1H), 7.95 (s, 1H), 7.56 (d, J=8.0 Hz, 2H), 7.44-7.40 (m, 3H), 7.26-7.24 (m, 2H), 4.83 (s, 2H), 2.16 (s, 3H). MS (ESI): m/z found 351.1 [M+H]⁺. Purity by HPLC: 98.78% (220 nm), 99.78% (254 nm).

Example 36: 7-fluoro-5-((5-methyl-4-(pentan-3-ylamino)pyrimidin-2-yl)amino)benzo[c][1,2]oxaborol-1(3H)-ol

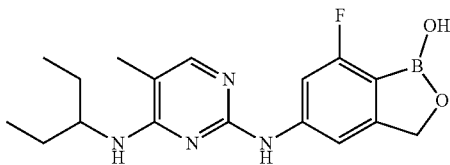 [SMILES: CCC(CC)Nc1nc(Nc2cc(F)c3c(c2)COB3O)ncc1C]

This substance was prepared using the general experimental procedure as shown in General Synthetic Scheme A. $^1$H NMR (DMSO-d6, 400 MHz) δ (ppm) 10.37 (s, 1H), 9.19 (s, 1H), 7.81 (s, 1H), 7.75 (s, 1H), 7.45 (d, J=10.8 Hz, 1H), 7.37 (s, 1H), 5.00 (s, 2H), 4.03-3.98 (m, 1H), 2.03 (s, 3H), 1.64-1.57 (m, 4H), 0.87 (t, J=7.4 Hz, 6H). MS (ESI): m/z found 345.1 [M+H]$^+$. Purity by HPLC: 98.43% (220 nm), 98.38% (254 nm).

Example 37: 2-(2-fluoroethyl)-7-((2-((1-hydroxy-1,3-dihydrobenzo[c][1,2]oxaborol-5-yl)amino)-5-methylpyrimidin-4-yl)amino)isoindolin-1-one

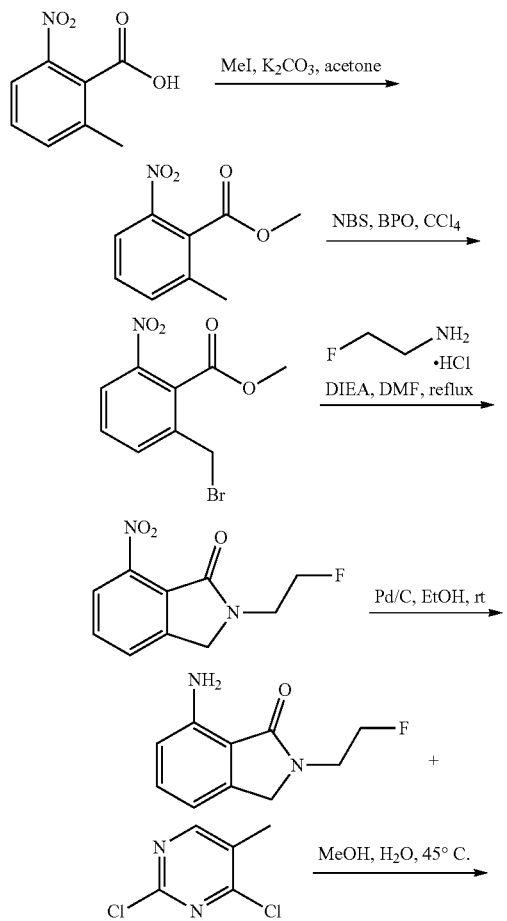

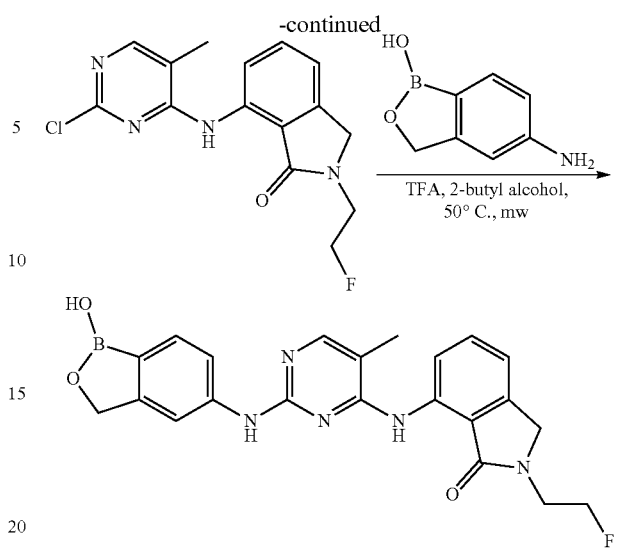

To a solution of 2-methyl-6-nitrobenzoic acid (5.0 g, 27.6 mmol) in acetone (60 mL) was added K$_2$CO$_3$ (5.7 g, 41.4 mmol) and MeI (4.3 g, 30.4 mmol), the resulting reaction mixture was heated to reflux overnight. Then it was quenched with water, extracted with EtOAc, and the combined organic phase was concentrated in vacuo to give a residue, which was purified by column chromatography (PE/EtOAc=50/1 to 10/1) to give methyl 2-methyl-6-nitrobenzoate (5.1 g, yield 94%) as a light oil. $^1$H NMR (300 MHz, DMSO-d6): δ 8.03 (d, J=8.1 Hz, 1H), 7.76 (d, J=7.6 Hz, 1H), 7.65 (dd, J=8.1, 7.6 Hz, 1H), 3.87 (s, 3H) ppm.

To a suspension of methyl 2-methyl-6-nitrobenzoate (5.1 g, 26.1 mmol) in CCl$_4$ (50 ml) was added NBS (4.6 g, 26.1 mol) and BPO (629 mg, 2.6 mmol), the resulting mixture was heated to reflux overnight. Then it was concentrated in vacuo to give a residue that was purified by silica-gel chromatography to give methyl 2-(bromomethyl)-6-nitrobenzoate (2.8 g, yield 39%) as a yellow solid. $^1$H NMR (400 MHz, DMSO-d$_6$): δ 8.22 (d, J=8.2 Hz, 1H), 8.07 (d, J=7.6 Hz, 1H), 7.85 (dd, J=8.2, 7.6 Hz, 1H), 4.81 (s, 2H), 3.95 (s, 3H) ppm.

To a solution of methyl 2-(bromomethyl)-6-nitrobenzoate (2.5 g, 9.1 mmol) in DMF (20 mL) was added 2-fluoroethanamine hydrochloride (0.9 g, 9.1 mmol) and DIEA (1.8 g, 13.7 mmol), the resulting reaction mixture was stirred at 80° C. overnight. Then it was poured into water, extracted with EtOAc. The combined organic phase was washed with brine, dried over sodium sulfate, concentrated in vacuo to give a residue, which was purified by silica-gel chromatography to give 2-(2-fluoroethyl)-7-nitroisoindolin-1-one (1.3 g, yield 65%) as a yellow solid. $^1$H NMR (300 MHz, CDCl$_3$): δ 7.87-7.59 (m, 3H), 4.79 (t, J=4.5 Hz, 1H), 4.63 (s, 3H), 3.94 (dt, J=29.0, 4.4 Hz, 2H) ppm.

To a solution of 2-(2-fluoroethyl)-7-nitroisoindolin-1-one (1.3 g, 5.8 mmol) in EtOH (10 mL) was added Pd/C (400 mg) and backfilled with H$_2$ three times. The reaction was stirred at room temperature for 4 h, then filtered, and the filtrate was concentrated to give 7-amino-2-(2-fluoroethyl)isoindolin-1-one (1.0 g, yield 91%) as a yellow solid. $^1$H NMR (300 MHz, DMSO-d$_6$): δ 7.20 (t, J=7.7 Hz, 1H), 6.60 (dd, J=20.5, 7.7 Hz, 2H), 6.04 (s, 2H), 4.71 (t, J=4.9 Hz, 1H), 4.55 (t, J=4.9 Hz, 1H), 4.39 (s, 2H), 3.78 (t, J=4.8 Hz, 1H), 3.69 (t, J=4.8 Hz, 1H) ppm.

To a solution of 7-amino-2-(2-fluoroethyl)isoindolin-1-one (600 mg, 3.1 mmol) in MeOH/H$_2$O (15 mL, 2:3) was added 2,4-dichloro-5-methylpyrimidine (502 mg, 3.1 mmol)). The reaction was stirred at 45° C. for 1 d, the formed solid was collected by filtration, which was dried in vacuo to give 7-((2-chloro-5-methylpyrimidin-4-yl)amino)-2-(2-fluoroethyl)isoindolin-1-one (800 mg, yield 80%) as a white solid. MS: (M+H)⁺: m/z=321.0.

To a solution of 7-((2-chloro-5-methylpyrimidin-4-yl)amino)-2-(2-fluoroethyl)isoindolin-1-one (320 mg, 1.0 mmol) in 2-butyl alcohol (10 mL) was added 5-aminobenzo[c][1,2]oxaborol-1(3H)-ol (149 mg, 1.0 mmol) and TFA (342 mg, 3.0 mmol). The reaction was subjected to irradiation microwave (50° C., 15 min), then it was poured into water, neutralized with aq. NaHCO₃, extracted with EtOAc, and the combined organic phase was concentrated in vacuo to give a residue, which was purified by pre-HPLC (TFA in CH₃CN) to give 2-(2-fluoroethyl)-7-((2-((1-hydroxy-1,3-dihydrobenzo[c][1,2]oxaborol-5-yl)amino)-5-methylpyrimidin-4-yl)amino)isoindolin-1-one (28.9 mg, yield 7%) as a white solid. ¹H NMR (400 MHz, DMSO-d₆): δ 10.34 (s, 1H), 9.76 (s, 1H), 9.02 (s, 1H), 8.68 (s, 1H), 8.06 (s, 1H), 7.85 (s, 1H), 7.66 (d, J=8.0 Hz, 1H), 7.53 (t, J=7.8 Hz, 2H), 7.26 (d, J=7.3 Hz, 1H), 4.96 (s, 2H), 4.81-4.71 (m, 1H), 4.65-4.61 (m, 3H), 3.95-3.87 (m, 1H), 3.87-3.80 (m, 1H), 2.20 (s, 3H) ppm. HPLC purity: 99.60% at 210 nm and 99.36% at 254 nm. MS (ESI): m/z found 434.1 [M+H]⁺.

Example 38 is intentionally blank to preserve numbering.

Example 39: 5-((5-methyl-4-(pentan-3-ylamino)pyrimidin-2-yl)amino)benzo[c][1,2]oxaborol-1(3H)-ol

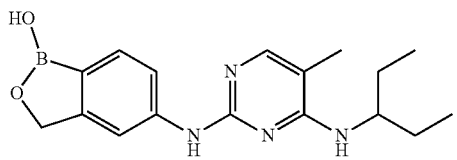 [SMILES: CCC(CC)Nc1nc(Nc2ccc3c(c2)COB3O)ncc1C]

The title compound was prepared by using the scheme and procedures shown below:

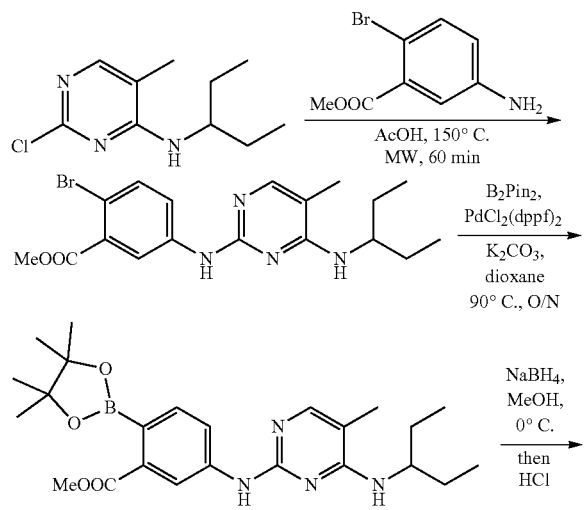

A mixture of 2-chloro-5-methyl-N-(pentan-3-yl)pyrimidin-4-amine (400 mg, 1.87 mmol) and methyl 5-amino-2-bromobenzoate (430 mg, 1.87 mmol) in acetic acid (10 mL) was stirred at 150° C. under microwave for 60 minutes. The reaction mixture was concentrated and purified by column chromatography by elution with ethyl acetate/methanol (100/1, v/v) to obtain methyl 2-bromo-5-((5-methyl-4-(pentan-3-ylamino)pyrimidin-2-yl)amino)benzoate (440 mg, 52% yield) as a white powder. MS: m/z=407.0 [M+H]⁺. A mixture of this intermediate (50 mg, 0.123 mmol), Pin₂B₂ (156 mg, 0.61 mmol), PdCl₂dppf (50 mg, 0.068 mmol) and K₂CO₃ (253 mg, 1.83 mmol) in 1,4-dioxane (5 mL) was stirred at 90° C. under N₂ for 6 h. The reaction was concentrated and purified by column chromatography to give methyl 5-((5-methyl-4-(pentan-3-ylamino)pyrimidin-2-yl)amino)-2-(4,4,5,5-tetramethyl-1,3,2-dioxaborolan-2-yl)benzoate (50 mg, crude). It was used in the next step without further purification. To a solution of methyl 5-((5-methyl-4-(pentan-3-ylamino)pyrimidin-2-yl)amino)-2-(4,4,5,5-tetramethyl-1,3,2-dioxaborolan-2-yl)benzoate (200 mg, crude) in methanol (10 mL) was added NaBH₄ (20 mg, 0.52 mmol) at 0° C. The reaction mixture was stirred at room temperature for 1 hour. The reaction mixture was quenched with aqeuous HCl (6 N, 10 mL) and stirred for 1 hour. The methanol was removed, and the residue aqueous phase was extracted with ethyl acetate (2*20 mL). The organic layer was combined, dried over Na₂SO₄, filtered and concentrated to get the crude. It was purified by prep-HPLC to give 5-((5-methyl-4-(pentan-3-ylamino)pyrimidin-2-yl)amino)benzo[c][1,2]oxaborol-1(3H)-ol formic acid salt (8 mg, 4.9% yield) as a white powder. ¹H NMR (400 MHz, DMSO-d₆): δ 9.04 (s, 1H), 8.87 (s, 1H), 8.14 (s, 1H), 7.95 (s, 1H), 7.67 (s, 1H), 7.61 (d, J=12.0 Hz, 1H), 7.53 (d, J=8.0 Hz, 1H), 6.19-6.17 (m, 1H), 4.91 (s, 2H), 4.08-4.03 (m, 1H). 1.95 (s, 3H), 1.63-1.55 (m, 4H), 0.89 (t, J=8.0 Hz, 6H) ppm. HPLC purity: 99.7% at 214 nm and 99.5% at 254 nm; MS: m/z=327.1 [M+H]⁺.

Example 40: 5-((4-(cyclohexylamino)-5-methylpyrimidin-2-yl)amino)benzo[c][1,2]oxaborol-1(3H)-ol

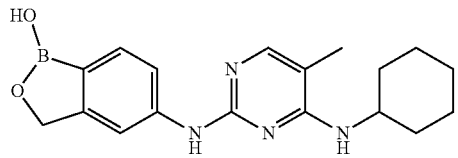

The title compound was prepared by using the scheme and procedures shown below:

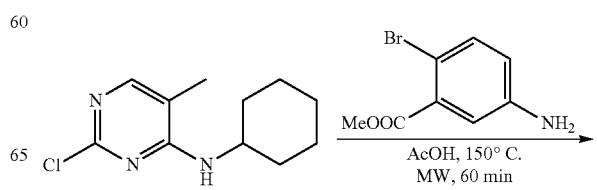

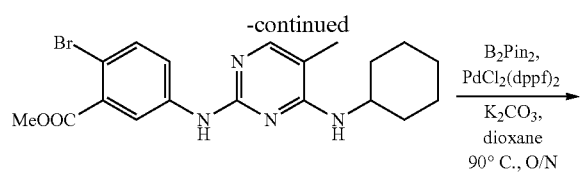

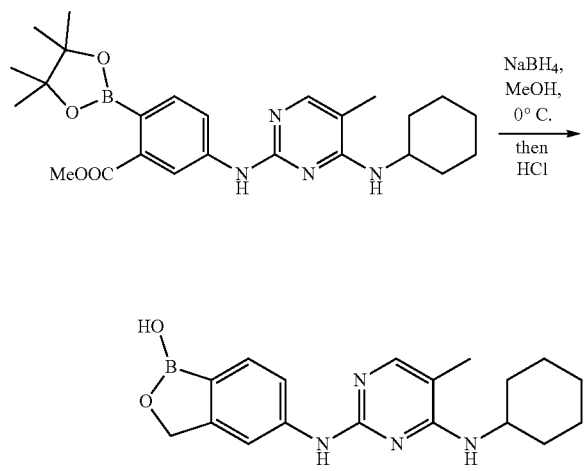

A mixture of 2-chloro-N-cyclohexyl-5-methylpyrimidin-4-amine (112 mg, 0.5 mmol) and methyl 5-amino-2-bromobenzoate (120 mg, 0.5 mmol) in acetic acid (3 mL) was stirred at 150° C. under microwave for 60 minutes. The reaction mixture was concentrated and purified by column chromatography by elution with ethyl acetate/methanol (100/1, v/v) to obtain methyl 2-bromo-5-((4-(cyclohexylamino)-5-methylpyrimidin-2-yl)amino)benzoate (100 mg, 48% yield) as a white powder. MS: m/z=419.0, 421.0 [M+H]$^+$. A mixture of this intermediate (100 mg, 0.238 mmol), Pin$_2$B$_2$ (181 mg, 0.714 mmol), PdCl$_2$dppf (87 mg, 0.12 mmol) and K$_2$CO$_3$ (295.6 mg, 2.14 mmol) in dioxane (5 mL) was stirred at 90° C. under N$_2$ overnight. The reaction was concentrated and purified by column chromatography to give methyl 5-((4-(cyclohexylamino)-5-methylpyrimidin-2-yl)amino)-2-(4,4,5,5-tetramethyl-1,3,2-dioxaborolan-2-yl)benzoate (100 mg, crude). It was used in the next step without further purification. To a solution of this boron-containing intermediate (500 mg, 1.0 mmol) in methanol (20 mL) was added NaBH$_4$ (200 mg, 5.0 mmol) at 0° C. The reaction mixture was stirred at room temperature for 1 hour. The reaction mixture was quenched with aqeuous HCl (6 N, 15 mL) and stirred for 1 hour. Methanol was removed, and the residue aqueous phase was extracted with ethyl acetate (2*30 mL). The organic layer was combined, dried over Na$_2$SO$_4$, filtered and concentrated to give the crude product. It was purified by prep-HPLC to give 5-((4-(cyclohexylamino)-5-methylpyrimidin-2-yl)amino)benzo[c][1,2]oxaborol-1(3H)-ol formic acid salt (30 mg, 8.9% yield) as a white powder. $^1$H NMR (300 MHz, DMSO-d$_6$): δ 9.14 (s, 1H), 8.87 (s, 1H), 7.93 (s, 1H), 7.65 (s, 1H), 7.59-7.51 (m, 2H), 6.40-6.37 (m, 1H), 4.91 (s, 2H), 4.03-3.95 (m, 1H). 1.98-1.88 (m, 2H), 1.91 (s, 3H), 1.88-1.73 (m, 2H), 1.69-1.66 (m, 1H), 1.41-1.31 (m, 5H) ppm. HPLC purity: 90.9% at 214 nm; MS: m/z=339.1 [M+H]$^+$.

Example 41: 5-((4-(benzylamino)-5-methylpyrimidin-2-yl)amino)benzo[c][1,2]oxaborol-1(3H)-ol

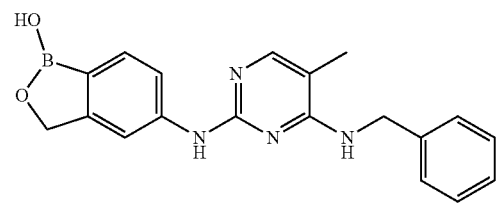 [SMILES: Cc1cnc(Nc2ccc3c(c2)COB3O)nc1NCc1ccccc1]

The title compound was prepared by using the scheme and procedures shown below:

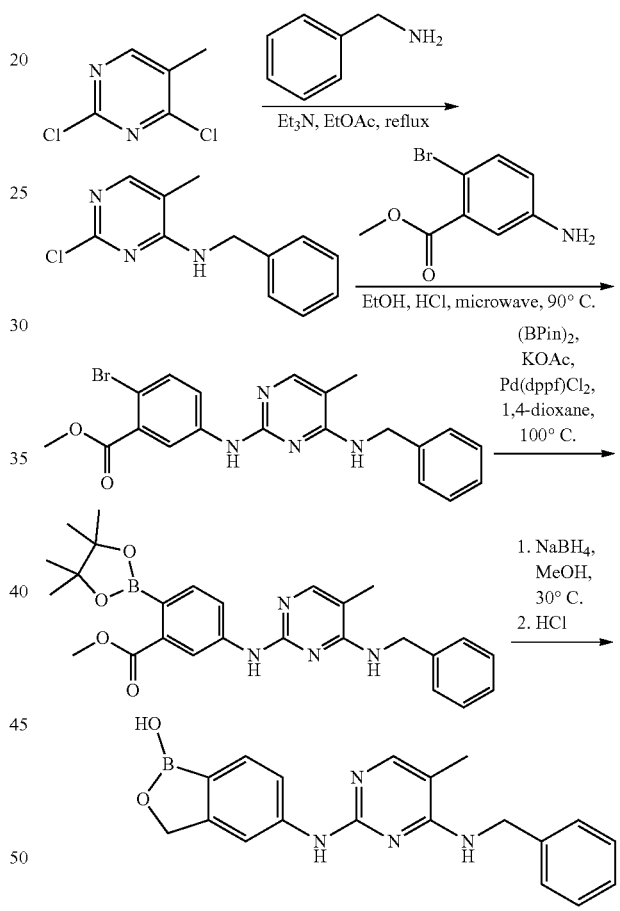

To a solution of 2,4-dichloro-5-methylpyrimidine (1.6 g, 10.0 mmol) in ethyl acetate (20 mL) was added benzylamine (1.6 g, 15.0 mmol) and triethylamine (1.5 g, 15.0 mmol) at room temperature. The reaction was refluxed overnight, and then the solvent was concentrated to ⅓ volume. It was filtered, and the solid was washed with ethyl acetate, water and dried to give the intermediate N-benzyl-2-chloro-5-methylpyrimidin-4-amine (1.0 g, yield 44%) as a white solid. $^1$H NMR (300 MHz, CDCl$_3$): δ 7.86 (s, 1H), 7.51-7.30 (m, 5H), 4.97 (s, 1H), 4.72 (d, J=5.3 Hz, 2H), 2.01 (s, 3H) ppm. To a solution of this intermediate (1.0 g, 4.3 mmol) in ethanol (6 mL) was added methyl 5-amino-2-bromobenzoate (989 mg, 4.3 mmol) and HCl (1.5 N, 4 mL). The reaction was subjected to microwave irradiation (90° C., 30 minutes), cooled to room temperature and extracted with ethyl acetate. The organic was washed with water, brine, concentrated under reduce pressure. The residue was purified by silica gel chromatography eluting with dichloromethane/methanol (100/1 to 10/1) to give methyl 5-((4-(benzylamino)-5-methylpyrimidin-2-yl)amino)-2-bromobenzoate (1.0 g, yield 56%) as a brown solid. $^1$H NMR (300 MHz, CDCl$_3$): δ 10.85 (s, 1H), 8.33 (d, J=2.5 Hz, 1H), 7.52 (d, J=8.7 Hz, 1H), 7.48-7.30 (m, 7H), 6.68 (br. s, 1H), 4.81 (d, J=5.3 Hz, 2H), 3.75 (s, 3H), 2.09 (s, 3H) ppm. To a solution of this intermediate (600 mg, 1.4 mmol) in 1,4-dioxane (10 mL) was added potassium acetate (412 mg, 4.2 mol), (BPin)$_2$ (533 mg, 2.1 mmol) and Pd(dppf)Cl$_2$ (457 mg, 0.6 mmol) at room temperature under nitrogen atmosphere. The mixture was stirred at 100° C. overnight and filtered. The filtrate was concentrated under reduced pressure. The residue was purified by silica gel chromatography eluting with petroleum ether/ethyl acetate (100/1 to 20/1, v/v) to give the crude product methyl 5-((4-(benzylamino)-5-methylpyrimidin-2-yl)amino)-2-(4,4,5,5-tetramethyl-1,3,2-dioxaborolan-2-yl)benzoate (1.1 g) as a black solid. MS: m/z=475.2 (M+H)$^+$. To a solution of this intermediate (1.1 g, crude) in methanol (15 mL) was added NaBH$_4$ (532 mg, 14.0 mmol) at 30° C. in small portions. The reaction was stirred at 30° C. for 30 minutes, and then 6N HCl (3 mL) was added and stirred for another 20 minutes. It was neutralized with saturated NaHCO$_3$ and extracted with ethyl acetate. The organic was washed with water, brine, concentrated under reduced pressure. The residue was purified by prep-HPLC (0.1% TFA in MeCN and H$_2$O) to give the product 5-((4-(benzylamino)-5-methylpyrimidin-2-yl)amino)benzo[c][1,2]oxaborol-1 (3H)-ol trifluoroacetic acid salt (67 mg, yield 10%) as a white solid. $^1$H NMR (400 MHz, DMSO-d$_6$): δ 12.15 (s, 1H), 10.20 (s, 1H), 9.11 (s, 1H), 8.89 (s, 1H), 7.79 (s, 1H), 7.61 (d, J=8.0 Hz, 1H), 7.50 (s, 1H), 7.39-7.22 (m, 6H), 4.83 (s, 2H), 4.68 (d, J=5.8 Hz, 2H), 2.08 (s, 3H) ppm. HPLC purity: 97.1% at 210 nm and 96.7% at 254 nm. MS: m/z=347.2 (M+H)$^+$.

Example 42: 5-((4-(sec-butylamino)-5-methylpyrimidin-2-yl)amino)benzo[c][1,2]oxaborol-1(3H)-ol

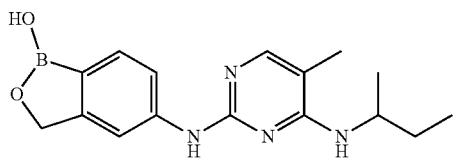 [SMILES: CCC(C)Nc1nc(Nc2ccc3c(c2)COB3O)ncc1C]

The title compound was prepared by using the scheme and procedures shown below:

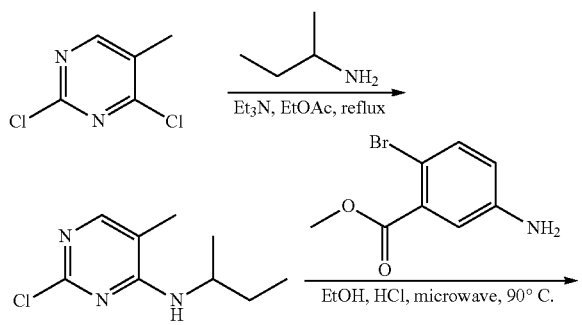

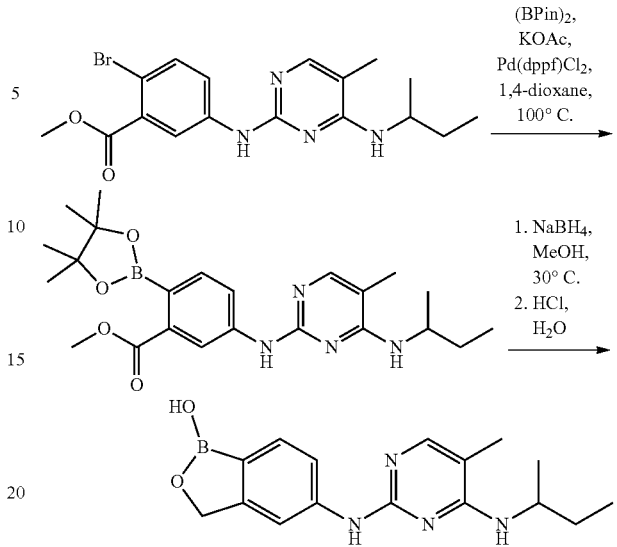

To a solution of 2,4-dichloro-5-methylpyrimidine (4.8 g, 30.0 mmol) in ethyl acetate (30 mL) were added butan-2-amine (11 g, 0.15 mol) and triethylamine (4.5 g, 45.0 mmol) at room temperature. The reaction was refluxed overnight, and then the solvent was concentrated to ⅓. It was filtered, and the solid was washed with ethyl acetate, water and dried to give N-(sec-butyl)-2-chloro-5-methylpyrimidin-4-amine (6.0 g, yield 100%) as a white solid. $^1$H NMR (300 MHz, CDCl$_3$): δ 7.79 (s, 1H), 4.46 (br. s, 1H), 4.31-4.14 (m, 1H), 1.99 (s, 3H), 1.65-1.46 (m, 2H), 1.23 (d, J=6.5 Hz, 3H), 0.95 (t, J=7.4 Hz, 3H) ppm. To a solution of N-(sec-butyl)-2-chloro-5-methylpyrimidin-4-amine (500 mg, 2.5 mmol) in ethanol (6 mL) were added methyl 5-amino-2-bromobenzoate (570 mg, 2.5 mmol) and HCl (1.5 N, 4 mL). The reaction was subjected to microwave irradiation (90° C., 30 minutes), cooled to room temperature and extracted with ethyl acetate. The organic was washed with water, brine, and concentrated under reduce pressure. The residue was purified by silica chromatography by elution with dichloromethane/methanol (100/1 to 10/1) to give methyl 2-bromo-5-((4-(sec-butylamino)-5-methylpyrimidin-2-yl)amino)benzoate (480 mg, yield 49%) as a brown solid. $^1$H NMR (300 MHz, CDCl$_3$): δ 9.92 (br. s, 1H), 8.33 (s, 1H), 7.70-7.44 (m, 3H), 4.98 (d, J=7.7 Hz, 1H), 4.36-4.15 (m, 1H), 3.93 (s, 3H), 2.02 (s, 3H), 1.71-1.54 (m, 2H), 1.38-1.20 (m, 3H), 0.99 (t, J=7.4 Hz, 3H) ppm. To a solution of this intermediate (480 mg, 1.2 mmol) in 1,4-dioxane (10 mL) were added potassium acetate (353 mg, 3.6 mmol), Pin$_2$B$_2$ (457 mg, 1.8 mmol) and Pd(dppf)Cl$_2$ (408 mg, 0.5 mmol) at room temperature under nitrogen atmosphere. The mixture was stirred at 100° C. overnight and then filtered. The filtrate was concentrated under reduce pressure. The residue was purified by silica chromatography by elution with petroleum ether/ethyl acetate (100/1 to 20/1) to give methyl 5-((4-(sec-butylamino)-5-methylpyrimidin-2-yl)amino)-2-(4,4,5,5-tetramethyl-1,3,2-dioxaborolan-2-yl)benzoate (500 mg) as a black solid. MS: m/z=441.3 (M+H)$^+$. To a solution of this boron intermediate (500 mg) in methanol (10 mL) was added NaBH$_4$ (228 mg, 6.0 mmol) at 30° C. in small portions. The reaction was stirred at 30° C. for 30 minutes, and 6N HCl (3 mL) was added. It was stirred for another 20 minutes. Then it was neutralized with saturated NaHCO$_3$ and extracted with ethyl acetate. The organic was washed with water, brine, and concentrated under reduce pressure. The residue was purified by pre-HPLC (0.1% trifluoroacetic acid in acetonitrile and H₂O) to give the product 5-((4-(sec-butylamino)-5-methylpyrimidin-2-yl)amino)benzo[c][1,2]oxaborol-1(3H)-ol trifluoroacetic acid salt (24 mg, yield 5%) as a white solid. $^1$H NMR (400 MHz, DMSO-d₆): δ 12.06 (br. s, 1H), 10.28 (br. s, 1H), 9.14 (br. s, 1H), 7.99 (br. s, 1H), 7.80-7.57 (m, 3H), 7.46 (d, J=8.1 Hz, 1H), 4.99 (s, 2H), 4.23-4.03 (m, 1H), 2.02 (s, 3H), 1.78-1.61 (m, 1H), 1.61-1.43 (m, 1H), 1.22 (d, J=6.5 Hz, 3H), 0.88 (t, J=7.3 Hz, 3H) ppm. HPLC purity: 95.9% at 210 nm and 95.4% at 254 nm. MS: m/z=313.2 (M+H)⁺.

Example 43: 5-((5-methyl-4-(propylamino)pyrimidin-2-yl)amino)benzo[c][1,2]oxaborol-1(3H)-ol

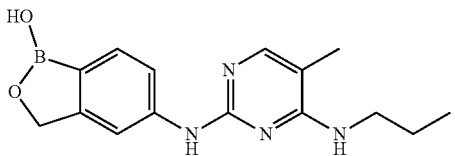 [SMILES: CCCNc1nc(Nc2ccc3c(c2)COB3O)ncc1C]

The title compound was prepared by using the scheme and procedures shown below:

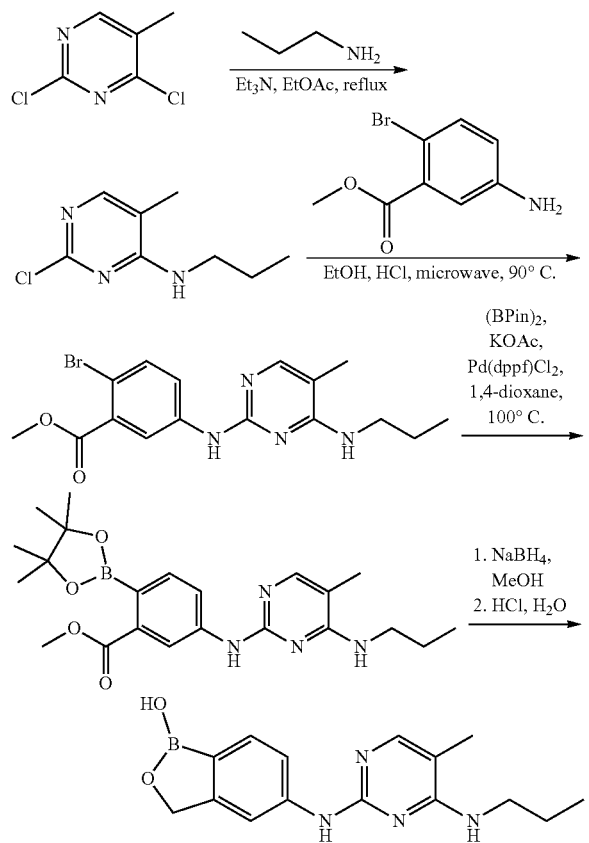

To a solution of 2,4-dichloro-5-methylpyrimidine (4.8 g, 30.0 mmol) in ethyl acetate (20 mL) were added propan-1-amine (10 mL) and triethylamine (4.5 g, 45.0 mmol) at room temperature. The reaction was refluxed overnight. The solvent was concentrated, and the residue was purified by silica chromatography to give 2-chloro-5-methyl-N-propylpyrimidin-4-amine (3.0 g, yield 54%) as a white solid. $^1$H NMR (300 MHz, CDCl₃): δ 7.80 (s, 1H), 4.73 (br. s, 1H), 3.52-3.46 (m, 2H), 2.01 (s, 3H), 1.71-1.63 (m, 2H), 1.00 (t, J=7.3 Hz, 3H) ppm. To a solution of this amine intermediate (1.0 g, 5.4 mmol) in ethanol (6 mL) were added methyl 5-amino-2-bromobenzoate (1.2 g, 5.4 mmol) and HCl (1.5 N, 4 mL). The reaction was subjected to microwave irradiation (90° C., 30 minutes). Normal work-up generated the residue, which was purified by silica chromatography by elution with dichloromethane/methanol (100/1 to 10/1) to give methyl 2-bromo-5-((5-methyl-4-(propylamino) pyrimidin-2-yl)amino)benzoate (1.3 g, yield 65%) as a white solid. $^1$H NMR (300 MHz, CDCl₃): δ 10.94 (br. s, 1H), 8.35 (s, 1H), 7.64-7.54 (m, 2H), 7.43 (s, 1H), 5.85 (br. s, 1H), 3.94 (s, 3H), 3.70-3.60 (m, 2H), 2.09 (s, 3H), 1.79-1.71 (m, 2H), 1.03 (t, J=7.1 Hz, 3H) ppm. To a solution of this intermediate (1.3 g, 3.4 mmol) in 1,4-dioxane (15 mL) were added potassium acetate (1.0 g, 10.2 mol), (BPin)₂ (1.3 g, 5.1 mmol) and Pd(dppf)Cl₂ (1.1 g, 1.4 mmol) at room temperature under N₂ atmosphere. The mixture was stirred at 100° C. overnight. Normal work-up as described in Example 41 generated the residue, which was purified by silica chromatography by elution with petroleum ether/ethyl acetate (100/1 to 20/1) to give methyl 5-((5-methyl-4-(propylamino)pyrimidin-2-yl)amino)-2-(4,4,5,5-tetramethyl-1,3,2-dioxaborolan-2-yl)benzoate (1.1 g) as a black solid. MS: m/z=427.3 (M+H)⁺. To a solution of this boron intermediate (1.1 g) in MeOH (20 mL) was added NaBH₄ (646 mg, 17.0 mmol) at 30° C. in small portions. The reaction was stirred at 30° C. for 30 minutes, and 6N HCl (3 mL) was added. It was stirred for another 20 minutes. Then it was neutralized with saturated NaHCO₃ and extracted with ethyl acetate. Normal work-up as described in Example 41 provided the residue, which was purified by pre-HPLC (0.1% trifluoroacetic acid in acetonitrile and H₂O) and further purification by pre-TLC (dichloromethane/methanol=20/1) to give the final product 5-((5-methyl-4-(propylamino)pyrimidin-2-yl)amino)benzo[c][1,2]oxaborol-1(3H)-ol (43 mg, yield 4%) as a white solid. $^1$H NMR (300 MHz, DMSO-d₆): δ 9.62 (br. s, 1H), 9.00 (s, 1H), 7.85 (s, 1H), 7.68-7.53 (m, 4H), 4.94 (s, 2H), 3.46-3.38 (m, 2H), 1.94 (s, 3H), 1.69-1.57 (m, 2H), 0.92 (t, J=7.1 Hz, 3H) ppm. HPLC purity: 96.9% at 210 nm and 98.8% at 254 nm. MS: m/z=299.2 (M+H)⁺.

Example 44: 5-((4-((2-cyclopropylethyl)amino)-5-methylpyrimidin-2-yl)amino)benzo[c][1,2]oxaborol-1(3H)-ol

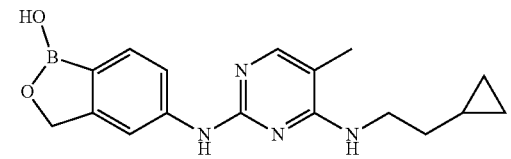 [SMILES: Cc1cnc(Nc2ccc3c(c2)COB3O)nc1NCCC1CC1]

The title compound was prepared by using the scheme and procedures shown below:

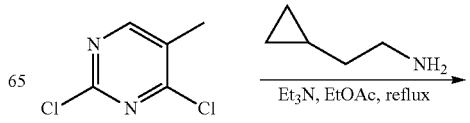

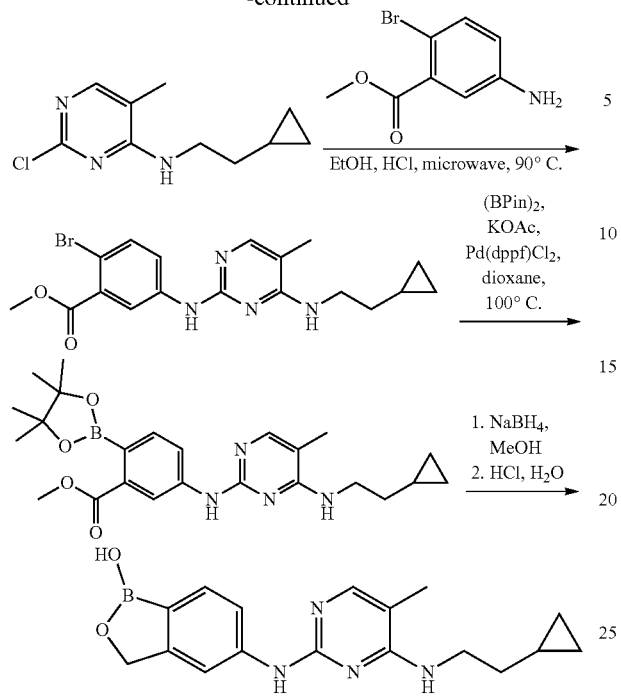

To a solution of 2,4-dichloro-5-methylpyrimidine (1.1 g, 7.0 mmol) in ethyl acetate (10 mL) were added 2-cyclopropylethan-1-amine hydrogen chloride (847 mg, 7.0 mmol) and triethylamine (980 mg, 10.0 mmol) at room temperature. The reaction was refluxed overnight. The mixture was concentrated to ⅓ and filtered to collect the solid. The solid was washed with ethyl acetate, water and dried to give the product (1.4 g, yield 93%) as a white solid. $^1$H NMR (300 MHz, CDCl$_3$): δ 7.81 (s, 1H), 4.90 (br. s, 1H), 3.62 (q, J=8.7 Hz, 2H), 2.01 (s, 3H), 1.59-1.52 (m, 2H), 0.91-0.67 (m, 1H), 0.60-0.40 (m, 2H), 0.20-0.08 (m, 2H) ppm. To a solution of this amine intermediate (1.0 g, 4.7 mmol) in ethanol (6 mL) were added methyl 5-amino-2-bromobenzoate (1.1 g, 4.7 mmol) and HCl (1.5 N, 4 mL). The reaction was subjected to microwave irradiation (90° C., 30 minutes), cooled to room temperature and extracted with ethyl acetate. Normal work-up as described in Example 41 provided a residue, which was purified by silica gel chromatography by elution with dichloromethane/methanol (100/1 to 10/1) to give methyl 2-bromo-5-((4-((2-cyclopropylethyl)amino)-5-methylpyrimidin-2-yl)amino)benzoate (1.3 g, yield 68%) as a brown solid. MS: m/z=405.1 (M+H)$^+$. To a solution of this intermediate (1.3 g, 3.2 mmol) in 1,4-dioxane (15 mL) were added potassium acetate (941 mg, 9.6 mol), (PinB)$_2$ (1.2 g, 4.8 mmol) and Pd(dppf)Cl$_2$ (1.0 g, 1.3 mmol) at room temperature under nitrogen atmosphere. The mixture was heated to 100° C. overnight, and then the solid was removed by filtration. After evaporation of the filtrate, the residue was purified by silica gel chromatography by elution with petroleum ether/ethyl acetate (100/1 to 20/1) to give methyl 5-((4-((2-cyclopropyl ethyl)amino)-5-methylpyrimidin-2-yl)amino)-2-(4,4,5,5-tetramethyl-1,3,2-dioxaborolan-2-yl)benzoate (1.1 g) as a black solid. MS: m/z=453.3 (M+H)$^+$. To a solution of this boron intermediate (1.1 g, crude) in methanol (20 mL) was added NaBH$_4$ (608 mg, 16.0 mmol) at 30° C. in small portions. The reaction was stirred at 30° C. for 30 minutes, and 6N HCl (3 mL) was added. It was stirred for another 20 minutes. Then it was neutralized with saturated NaHCO$_3$ and extracted with ethyl acetate. Normal work-up as described in Example 41 generated the residue, which was purified by prep-HPLC (0.1% trifluoroacetic acid in acetonitrile and H$_2$O) to give the product 5-((4-((2-cyclopropylethyl) amino)-5-methyl pyrimidin-2-yl)amino)benzo[c][1,2]oxaborol-1(3H)-ol trifluoroacetic acid salt (52.9 mg, yield 5%) as a white solid. $^1$H NMR (400 MHz, DMSO-d$_6$): δ 12.30 (br. s, 1H), 10.32 (s, 1H), 9.14 (s, 1H), 8.38 (s, 1H), 7.79-7.61 (m, 3H), 7.60-7.50 (m, 1H), 4.98 (s, 2H), 3.53 (q, J=7.2 Hz, 2H), 1.98 (s, 3H), 1.50 (q, J=7.2 Hz, 2H), 0.79-0.63 (m, 1H), 0.50-0.40 (m, 2H), 0.05-0.01 (m, 2H) ppm. HPLC purity: 96.2% at 210 nm and 94.2% at 254 nm. MS: m/z=325.2 (M+H)$^+$.

Example 45: 5-((4-(hexan-3-ylamino)-5-methylpyrimidin-2-yl)amino)benzo[c][1,2]oxaborol-1(3H)-ol

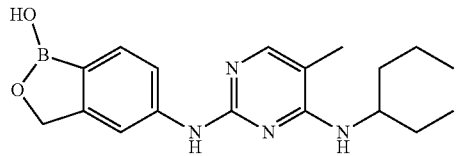

The title compound was prepared by using the scheme and procedures shown below:

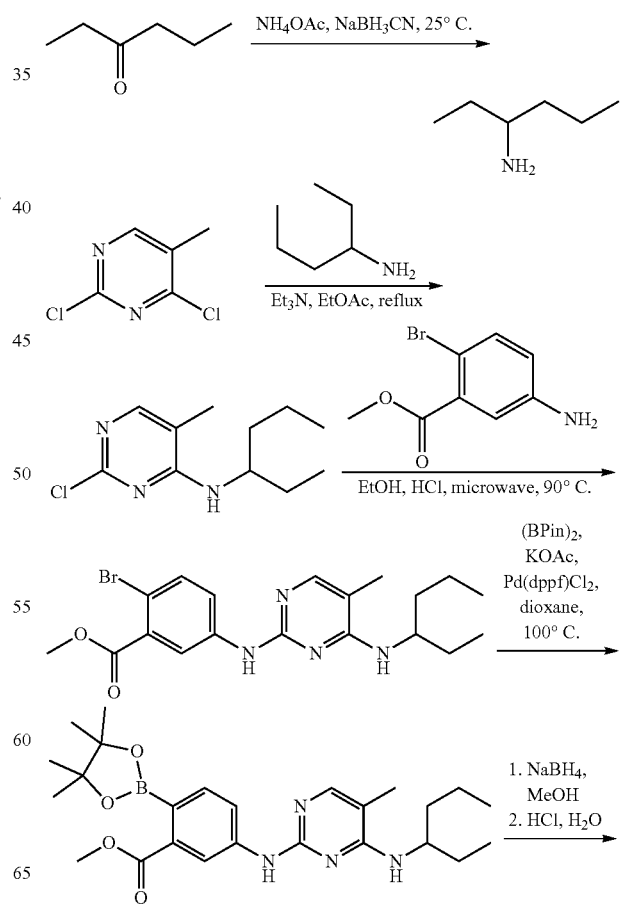

237

-continued

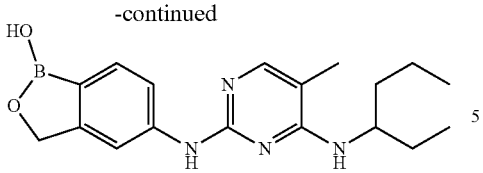

To a solution of hexan-3-one (4.2 g, 33.1 mmol) in methanol (60 mL) were added ammonium acetate (25.5 g, 0.33 mol) and sodium cyanoborohydride (2.1 g, 33.1 mmol). The reaction mixture was stirred at room temperature for 24 hours. The solvent was removed under reduced pressure and the residue was diluted with water. It was basified with 15% NaOH aqueous and extracted with dichloromethane. The extract was washed with brine, dried over anhydrous magnesium sulfate, filtered and evaporated to give hexan-3-amine (1.6 g, yield 38%) as a light oil. $^1$H NMR (300 MHz, CDCl$_3$): δ 2.77-2.56 (m, 1H), 1.58-1.18 (m, 6H), 1.00-0.80 (m, 6H) ppm. To a solution of 2,4-dichloro-5-methylpyrimidine (1.6 g, 10.0 mmol) in ethyl acetate (20 mL) were added hexan-3-amine (1.6 g, 16.0 mmol) and triethylamine (2.0 g, 20 mmol) at room temperature. The reaction was refluxed overnight. The solvent was concentrated and the residue was purified by silica gel chromatography to give 2-chloro-N-(hexan-3-yl)-5-methylpyrimidin-4-amine (1.9 g, yield 83%) as a white solid. $^1$H NMR (300 MHz, CDCl$_3$): δ 7.79 (s, 1H), 4.51-4.16 (m, 1H), 1.99 (s, 3H), 1.82-1.21 (m, 6H), 1.00-0.82 (m, 6H) ppm. To a solution of this amine intermediate (1.9 g, 8.4 mmol) in ethanol (6 mL) were added methyl 5-amino-2-bromobenzoate (1.9 g, 8.4 mmol) and HCl (1.5 N, 4 mL). The reaction was subjected to microwave irradiation (90° C., 30 minutes). Normal work-up as described in Example 41 generated a residue, which was purified by silica gel chromatography by elution with dichloromethane/methanol (100/1 to 10/1) to give methyl 2-bromo-5-((4-(hexan-3-ylamino)-5-methylpyrimidin-2-yl)amino)benzoate (1.6 g, yield 46%) as a brown solid. MS: m/z=421.1 (M+H)$^+$. To a solution of this intermediate (1.6 g, 3.8 mmol) in 1,4-dioxane (20 mL) were added potassium acetate (1.1 g, 11.4 mmol), (BPin)$_2$ (1.4 g, 5.7 mmol) and Pd(dppf)Cl$_2$ (1.2 g, 1.5 mmol) at room temperature under nitrogen atmosphere. The mixture was stirred at 100° C. overnight, and then the solid was filtered off. The filtrate was concentrated and the residue was purified by silica gel chromatography by elution with dichloromethane/methanol (100/1 to 20/1) to give methyl 5-((4-(hexan-3-yl-amino)-5-methylpyrimidin-2-yl)amino)-2-(4,4,5,5-tetramethyl-1,3,2-dioxaborolan-2-yl)benzoate (1.8 g) as a black solid. MS: m/z=469.3 (M+H)$^+$. To a solution of this boron intermediate (1.8 g, crude) in methanol (20 mL) was added NaBH$_4$ (722 mg, 19.0 mmol) at 30° C. in small portions. The reaction was stirred at 30° C. for 30 minutes, and 6N HCl (5 mL) was added. It was stirred for another 20 minutes. Normal work-up provided a residue, which was purified by prep-HPLC (0.1% trifluoroacetic acid in acetonitrile and H$_2$O). The trifluoroacetic acid in the material was removed using aqueous NaHCO$_3$ to give 5-((4-(hexan-3-ylamino)-5-methylpyrimidin-2-yl)amino) benzo[c][1,2]oxaborol-1(3H)-ol (83.8 mg, yield 7%) as a white solid. $^1$H NMR (400 MHz, DMSO-d$_6$): δ 9.48 (br. s, 1H), 8.97 (s, 1H), 7.82 (s, 1H), 7.68 (d, J=0.7 Hz, 1H), 7.64-7.48 (m, 2H), 6.86 (br. s, 1H), 4.93 (s, 2H), 4.24-4.09 (m, 1H), 1.98 (s, 3H), 1.66-1.50 (m, 4H), 1.41-1.21 (m, 2H), 0.88-0.84 (m, 6H) ppm. HPLC purity: 97.6% at 210 nm and 98.0% at 254 nm. MS: m/z=341.2 (M+H)$^+$.

238

Example 46: 5-((4-(cyclohexylamino)-5-(trifluoromethyl)pyrimidin-2-yl)amino)benzo[c][1,2]oxaborol-1(3H)-ol

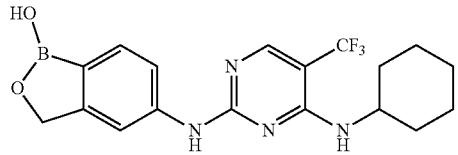 [SMILES: OB1OCc2cc(Nc3ncc(C(F)(F)F)c(NC4CCCCC4)n3)ccc21]

The title compound was prepared by using the scheme and procedures shown below:

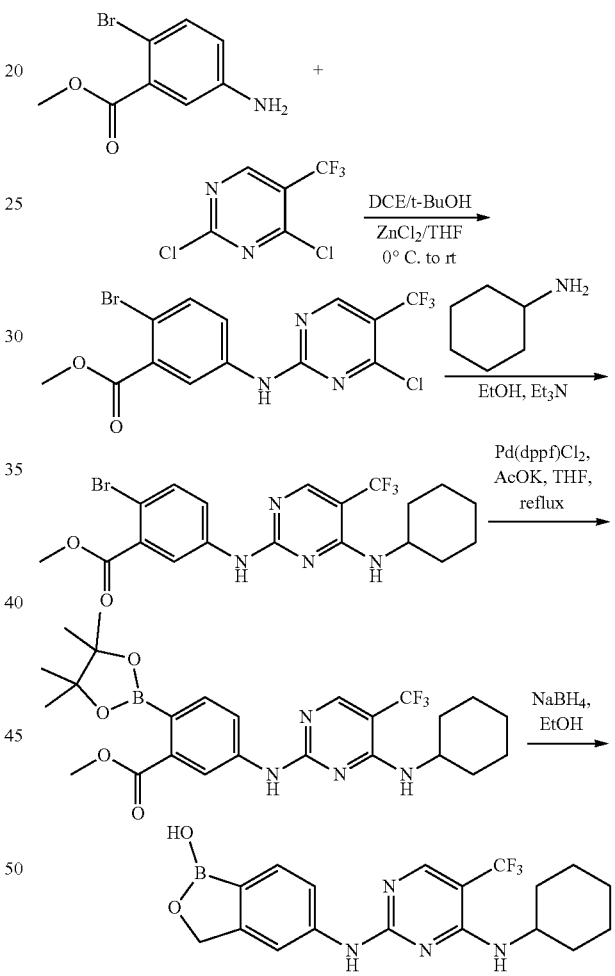

To a solution of 2,4-dichloro-5-(trifluoromethyl)pyrimidine (18 g, 83.3 mmol) in 600 mL of a mixed solvent of t-butanol/1,2-dichloroethane (DCE, 1/1, v/v) was added zinc chloride tetrahydrofuran solution (1M, 125 mL, 1.5 equivalents). After one hour, methyl 5-amino-2-bromobenzoate (19.0 g, 83.3 mmol) was added, followed by dropwise addition of triethylamine (12.9 mL, 91.6 mmol) in 80 mL of 1,2-dichloroethane/t-butanol. After stirring overnight, the solvents were removed under reduced pressure and the residue was dissolved in ethyl acetate (250 mL) and washed with brine (100 mL). The organic layer was dried over sodium sulphate, filtered and concentrated in vacuo. The residue was triturated in a mixed solvent of petroleum ether/ethyl acetate (150 mL, v/v=3/1). The solid was collected by filtration and dried in vacuo to give methyl 2-bromo-5-((4-chloro-5-(trifluoromethyl)pyrimidin-2-yl)amino)benzoate (15.0 g, 44%) as an off-white solid. $^1$H NMR (400 MHz, CDCl$_3$): δ 10.94 (s, 1H), 8.88 (s, 1H), 8.17 (d, J=2.6 Hz, 1H), 7.82 (dd, J=8.8, 2.7 Hz, 1H), 7.75 (d, J=8.8 Hz, 1H), 3.88 (s, 3H) ppm. To a solution of methyl 2-bromo-5-((4-chloro-5-(trifluoromethyl)pyrimidin-2-yl)amino)benzoate (2.0 g, 5 mmol) and cyclohexanamine (0.6 g, 12 mmol) in ethanol (15 mL) was added triethylamine (1.01 g, 10.0 mmol) at room temperature. The reaction was refluxed for 3 hours, and then the reaction mixture was cooled to room temperature and concentrated in vacuo. The residue was triturated with water and dried in air to give methyl 2-bromo-5-((4-(cyclohexylamino)-5-(trifluoromethyl)pyrimidin-2-yl)amino)benzoate (2.3 g, yield 91%) as a white solid. $^1$H NMR (400 MHz, CDCl$_3$): δ 8.10 (s, 1H), 8.00 (br. s, 1H), 7.92 (s, 1H), 7.66 (d, J=8.7 Hz, 1H), 7.50 (d, J=8.7 Hz, 1H), 5.03 (d, J=6.2 Hz, 1H), 4.06-3.89 (m, 1H), 3.86 (s, 3H), 2.03-1.88 (m, 2H), 1.76-1.63 (m, 2H), 1.64-1.53 (m, 1H), 1.43-1.27 (m, 2H), 1.27-1.09 (m, 3H) ppm. To a solution of the obtained intermediate (1.1 g, 2.3 mmol) in tetrahydrofuran (10 mL) were added potassium acetate (474 mg, 4.8 mol), (BPin)$_2$ (701 mg, 2.76 mmol) and Pd(dppf)Cl$_2$ (457 mg, 0.6 mmol) at room temperature under nitrogen atmosphere. The mixture was stirred at 100° C. overnight, and then the solid was filtered off. The filtrate was concentrated and the residue was purified by silica gel chromatography by elution with petroleum ether/ethyl acetate (100/1 to 50/1) to give methyl 5-((4-(cyclohexylamino)-5-(trifluoromethyl)pyrimidin-2-yl)amino)-2-(4,4,5,5-tetramethyl-1,3,2-dioxaborolan-2-yl)benzoate (0.62 g, yield 45%) as a white solid. $^1$H NMR (400 MHz, CDCl$_3$): δ 8.10-8.05 (m, 2H), 7.75 (d, J=8.1 Hz, 1H), 7.40 (d, J=8.1 Hz, 1H), 5.03 (d, J=6.8 Hz, 1H), 4.10-4.00 (m, 1H), 3.84 (s, 3H), 2.03-1.88 (m, 2H), 1.73-1.63 (m, 2H), 1.59-1.57 (m, 1H), 1.42-1.10 (m, 19H) ppm. To a solution of this boron intermediate (620 mg, 1.1 mmol) in methanol (15 mL) was added NaBH$_4$ (266 mg, 7 mmol) at 30° C. in small portions. The reaction was stirred at 30° C. for 30 minutes, and 6N HCl (3 mL) was added. It was stirred for another 20 minutes, neutralized with saturated NaHCO$_3$ and filtered to collect the solid. The filter cake was triturated with acetonitrile to give 5-((4-(cyclohexyl amino)-5-(trifluoromethyl)pyrimidin-2-yl)amino)benzo[c][1,2]oxaborol-1(3H)-ol (230 mg, yield 60%) as a white solid. $^1$H NMR (400 MHz, DMSO-d$_6$): δ 10.16 (br. s, 1H), 9.04 (br. s, 1H), 8.29 (s, 1H), 7.84 (s, 1H), 7.68-7.62 (m, 2H), 6.96 (br. s, 1H), 4.97 (s, 2H), 4.12-4.05 (m, 1H), 1.88-1.77 (m, 4H), 1.66 (d, J=12.4 Hz, 1H), 1.55-1.42 (m, 2H), 1.38-1.23 (m, 2H), 1.21-1.10 (m, 1H) ppm. HPLC purity: 98.6% at 210 nm and 98.3% at 254 nm. MS: m/z=393.1 (M+H)$^+$.

Example 47: 5-((4-(propylamino)-5-(trifluoromethyl)pyrimidin-2-yl)amino)benzo[c][1,2]oxaborol-1(3H)-ol

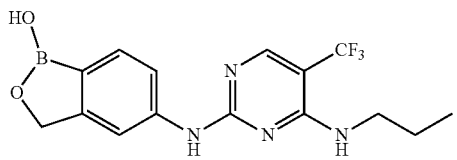

The title compound was prepared by using the scheme and procedures shown below:

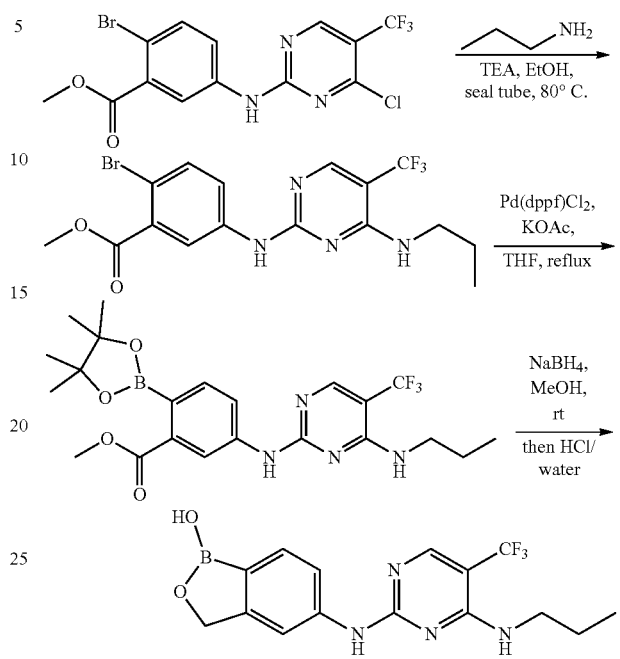

To a solution of methyl 2-bromo-5-((4-chloro-5-(trifluoromethyl)pyrimidin-2-yl)amino)benzoate (820 mg, 2.0 mmol) and propan-1-amine (590 mg, 10.0 mmol) in ethanol (10 mL) was added triethyamine (684 mg, 6.0 mmol) at room temperature. The reaction was stirred at 80° C. for 2 hours in a sealed tube, and then the reaction was cooled to room temperature and concentrated in vacuo. The residue was dissolved in ethyl acetate, then washed with water and brine. It was concentrated under reduce pressure to give methyl 2-bromo-5-((4-(propylamino)-5-(trifluoromethyl)pyrimidin-2-yl)amino)benzoate (900 mg, yield 100%) as a light oil. $^1$H NMR (300 MHz, CDCl$_3$): δ 8.24 (s, 1H), 8.18 (s, 1H), 7.59 (s, 2H), 7.43 (s, 1H), 5.28 (s, 1H), 3.95 (s, 3H), 3.53 (q, J=6.5 Hz, 2H), 1.78-1.57 (m, 2H), 1.01 (t, J=7.4 Hz, 3H) ppm. To a solution of this obtained intermediate (900 mg, 2.1 mmol) in tetrahydrofuran (15 mL) were added potassium acetate (617 mg, 6.3 mmol), (BPin)$_2$ (787 mg, 3.1 mmol) and Pd(dppf)Cl$_2$ (653 mg, 0.8 mmol) at room temperature under nitrogen atmosphere. The mixture was stirred at 80° C. for 4 hours, and then the solid was filtered. The filtrate was concentrated under reduce pressure and the residue was purified by silica gel chromatography by elution with petroleum ether/ethyl acetate (100/1 to 20/1, v/v) to give methyl 5-((4-(propylamino)-5-(trifluoromethyl)pyrimidin-2-yl)amino)-2-(4,4,5,5-tetramethyl-1,3,2-dioxaborolan-2-yl)benzoate (550 mg, yield 55%) as a light yellow solid. $^1$H NMR (300 MHz, CDCl$_3$): δ 8.36 (s, 1H), 8.16 (s, 1H), 7.74-7.61 (m, 2H), 7.48 (d, J=8.0 Hz, 1H), 5.29 (br. s, 1H), 3.92 (s, 3H), 3.66-3.44 (m, 2H), 1.79-1.59 (m, 2H), 1.43 (s, 12H), 1.01 (t, J=7.4 Hz, 3H) ppm. To a solution of this boron intermediate (550 mg, 1.1 mmol) in methanol (15 mL) was added NaBH$_4$ (210 mg, 5.5 mmol) at room temperature in small portions. The reaction was stirred at room temperature for 30 minutes, and 6N HCl (3 mL) was added. It was stirred for another 20 minutes, neutralized with saturated NaHCO$_3$ and filtered to collect the solid. The filter cake was triturated with acetonitrile and water to give the product 5-((4-(propylamino)-5-(trifluoromethyl)pyrimidin-2-yl)amino)benzo[c][1,2]oxaborol-1(3H)-ol (183 mg, yield 47%) as a white solid. $^1$H NMR (300 MHz, DMSO-d$_6$): δ 9.82 (br. s, 1H), 9.01 (br. s, 1H), 8.20 (s, 1H), 7.92 (s, 1H), 7.65 (d, J=8.0 Hz, 1H), 7.60 (d, J=8.1 Hz, 1H), 7.35-7.26 (m, 1H), 4.93 (s, 2H), 3.50-3.36 (m, 2H), 1.65-1.57 (m, 2H), 0.90 (t, J=7.4 Hz, 3H) ppm. HPLC purity: 96.3% at 210 nm and 97.8% at 254 nm. MS: m/z=353.2 (M+H)$^+$.

Example 48: 5-((4-(sec-butylamino)-5-(trifluoromethyl)pyrimidin-2-yl)amino)benzo[c][1,2]oxaborol-1(3H)-ol

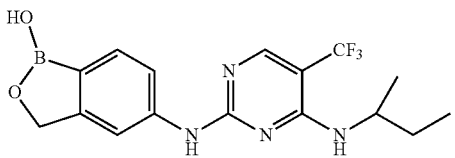 [SMILES: CCC(C)Nc1nc(Nc2ccc3c(c2)COB3O)ncc1C(F)(F)F]

The title compound was prepared by using the scheme and procedures shown below:

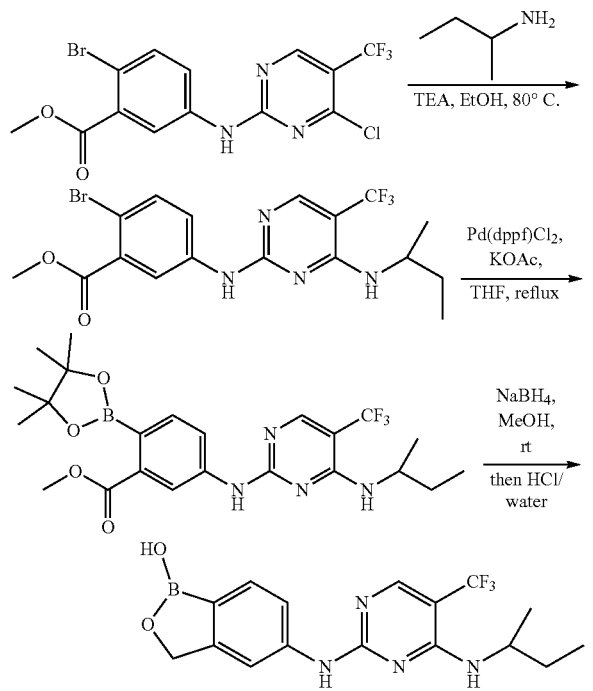

To a solution of methyl 2-bromo-5-((4-chloro-5-(trifluoromethyl)pyrimidin-2-yl)amino)benzoate (1 g, 2.4 mmol) and butan-2-amine (876 mg, 12.0 mmol) in ethanol (10 mL) was added triethylamine (727 mg, 7.2 mmol) at room temperature. The reaction was stirred at 80° C. for 2 hours. Normal work-up as described in Example 41 gave methyl 2-bromo-5-((4-(sec-butylamino)-5-(trifluoromethyl)pyrimidin-2-yl)amino)benzoate (1.0 g, yield 99%) as a white solid. $^1$H NMR (300 MHz, CDCl$_3$): δ 8.18 (s, 2H), 7.96 (br. s, 1H), 7.60 (s, 2H), 5.00 (d, J=6.7 Hz, 1H), 4.36-4.19 (m, 1H), 3.94 (s, 3H), 1.70-1.55 (m, 2H), 1.35-1.20 (m, 3H), 0.97 (t, J=7.4 Hz, 3H) ppm. To a solution of this obtained intermediate (1 g, 2.3 mmol) in tetrahydrofuran (15 mL) were added potassium acetate (676 mg, 6.9 mmol), (BPin)$_2$ (863 mg, 3.4 mmol) and Pd(dppf)Cl$_2$ (734 mg, 0.9 mmol) at room temperature under nitrogen atmosphere. The mixture was stirred at 80° C. overnight, and then the solid was filtered. The filtrate was concentrated under reduced pressure and the residue was purified by silica gel chromatography by elution with petroleum ether/ethyl acetate (100/1 to 20/1, v/v) to give methyl 5-((4-(sec-butyl-amino)-5-(trifluoromethyl)pyrimidin-2-yl)amino)-2-(4,4,5,5-tetramethyl-1,3,2-dioxaboro-lan-2-yl)benzoate (500 mg, yield 45%) as a light yellow solid. $^1$H NMR (300 MHz, CDCl$_3$): δ 8.33 (d, J=1.5 Hz, 1H), 8.16 (s, 1H), 7.77 (br. s, 1H), 7.72-7.68 (m, 1H), 7.48 (d, J=8.0 Hz, 1H), 4.98 (d, J=7.5 Hz, 1H), 4.40-4.20 (m, 1H), 3.92 (s, 3H), 1.71-1.52 (m, 2H), 1.43 (s, 12H), 1.35-1.20 (m, 3H), 0.97 (t, J=7.4 Hz, 3H) ppm. To a solution of this boron intermediate (500 mg, 1.0 mmol) in methanol (10 mL) was added NaBH$_4$ (190 mg, 5.0 mmol) at room temperature in small portions. The reaction was stirred at room temperature for 30 minutes, and 6N HCl (3 mL) was added. It was stirred for additional 20 minutes, neutralized with saturated NaHCO$_3$ and filtered to collect the solid. The filter cake was triturated with acetonitrile and water to give the product (183 mg, yield 50%) as a white solid. $^1$H NMR (300 MHz, DMSO-d$_6$): δ 9.78 (br. s, 1H), 9.02 (s, 1H), 8.22 (s, 1H), 7.90 (s, 1H), 7.62 (d, J=0.9 Hz, 2H), 6.50 (d, J=8.1 Hz, 1H), 4.95 (s, 2H), 4.35-4.25 (m, 1H), 1.78-1.62 (m, 1H), 1.62-1.50 (m, 1H), 1.21 (d, J=7.4 Hz, 3H), 0.88 (t, J=7.4 Hz, 3H) ppm. HPLC purity: 98.5% at 210 nm and 98.2% at 254 nm. MS: m/z=367.2 (M+H)$^+$.

Example 49: 5-((4-(benzylamino)-5-(trifluoromethyl)pyrimidin-2-yl)amino)benzo[c][1,2]oxaborol-1(3H)-ol

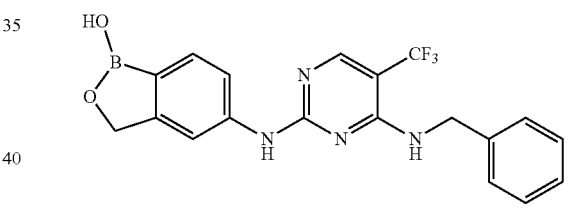

The title compound was prepared by using the scheme and procedures shown below:

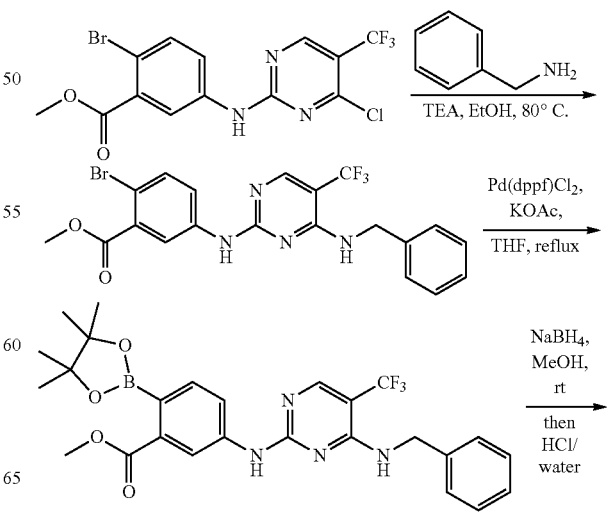

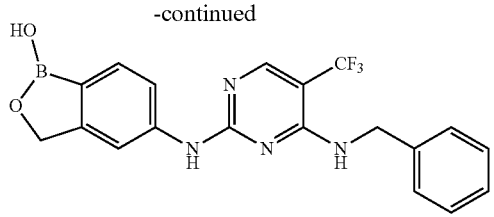

To a solution of methyl 2-bromo-5-((4-chloro-5-(trifluoromethyl)pyrimidin-2-yl)amino)benzoate (820 mg, 2.0 mmol) and benzylamine (642 mg, 6.0 mmol) in ethanol (10 mL) was added triethylamine (684 mg, 6.0 mmol) at room temperature. The reaction was stirred at 80° C. overnight, and then the reaction was cooled to room temperature, poured into water and filtered to collect the solid, which was dried to give methyl 5-((4-(benzylamino)-5-(trifluoromethyl)pyrimidin-2-yl)amino)-2-bromobenzoate (950 mg, yield 99%) as a white solid. $^1$H NMR (300 MHz, DMSO-$d_6$): δ 9.92 (br. s, 1H), 8.35-8.14 (m, 2H), 7.97-7.79 (m, 1H), 7.68-7.57 (m, 1H), 7.57-7.38 (m, 1H), 7.36-7.15 (m, 5H), 4.69 (d, J=5.7 Hz, 2H), 3.78 (s, 3H) ppm. To a solution of this obtained intermediate (950 mg, 2.0 mmol) in tetrahydrofuran (15 mL) were added potassium acetate (588 mg, 6.0 mmol), (BPin)$_2$ (762 mg, 3.0 mmol) and Pd(dppf)Cl$_2$ (653 mg, 0.8 mmol) at room temperature under nitrogen atmosphere. The mixture was stirred at 80° C. overnight, and then the solid was filtered. The filtrate was concentrated to give the residue was purified by silica gel chromatography by elution with petroleum ether/ethyl acetate (100/1 to 20/1, v/v) to give methyl 5-((4-(benzylamino)-5-(trifluoromethyl)pyrimidin-2-yl)amino)-2-(4,4,5,5-tetramethyl-1,3,2-dioxaborolan-2-yl)benzoate (900 mg, yield 86%) as a light yellow solid. $^1$H NMR (300 MHz, CDCl$_3$): δ 8.39 (s, 1H), 8.22 (s, 1H), 7.79-7.52 (m, 2H), 7.48-7.20 (m, 7H), 5.53 (s, 1H), 4.80 (d, J=5.2 Hz, 2H), 3.79 (s, 3H), 1.42 (s, 12H) ppm. To a solution of this boron intermediate (900 mg, 1.7 mmol) in methanol (10 mL) was added NaBH$_4$ (323 mg, 8.5 mmol) at room temperature in small portions. The reaction was stirred at room temperature for 30 min and then 6N HCl (3 mL) was added. It was stirred for additional 20 minutes, neutralized with saturated NaHCO$_3$ and filtered to collect the solid. The filter cake was triturated with acetonitrile and water to give the product 5-((4-(benzylamino)-5-(trifluoromethyl)pyrimidin-2-yl)amino)benzo[c][1,2]oxaborol-1(3H)-ol (269 mg, yield 40%) as a white solid. $^1$H NMR (400 MHz, DMSO-$d_6$): δ 9.79 (br. s, 1H), 8.97 (s, 1H), 8.27 (s, 1H), 7.85 (t, J=5.6 Hz, 1H), 7.69 (s, 1H), 7.52 (d, J=8.0 Hz, 1H), 7.43 (d, J=8.0 Hz, 1H), 7.38-7.27 (m, 4H), 7.27-7.20 (m, 1H), 4.79 (s, 2H), 4.71 (d, J=5.8 Hz, 2H) ppm. HPLC purity: 97.7% at 210 nm and 97.9% at 254 nm. MS: m/z=401.1 (M+H)$^+$.

Example 50: 5-((4-(cyclopentylamino)-5-(trifluoromethyl)pyrimidin-2-yl)amino)benzo[c][1,2]oxaborol-1(3H)-ol

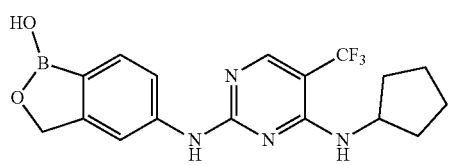 [SMILES: OB1OCc2cc(Nc3ncc(C(F)(F)F)c(NC4CCCC4)n3)ccc21]

The title compound was prepared by using the scheme and procedures shown below:

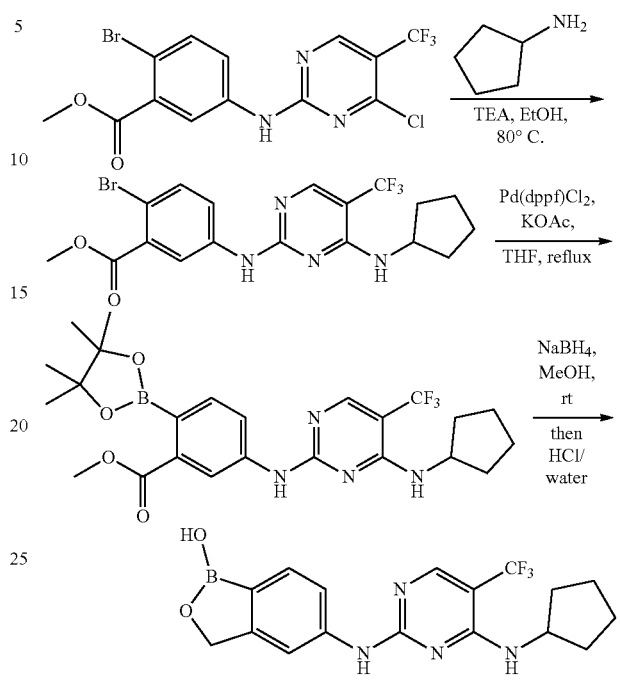

To a solution of methyl 2-bromo-5-((4-chloro-5-(trifluoromethyl)pyrimidin-2-yl)amino)benzoate (1.0 g, 2.3 mmol) and cyclopentanamine (587 mg, 6.9 mmol) in ethanol (10 mL) was added triethylamine (698 mg, 6.9 mmol) at room temperature. The reaction mixture was stirred at 80° C. for 3 hours, cooled to room temperature, poured into water and filtered. The solid was dried to give methyl 2-bromo-5-((4-(cyclopentylamino)-5-(trifluoromethyl)pyrimidin-2-yl)amino)benzoate (1.1 g, yield 100%) as a white solid. $^1$H NMR (300 MHz, CDCl$_3$): δ 8.22 (s, 1H), 8.17 (s, 1H), 7.59 (s, 2H), 7.55 (s, 1H), 5.16 (d, 1H), 4.50-4.43 (m, 1H), 3.94 (s, 3H), 2.20-2.05 (m, 2H), 1.80-1.60 (m, 4H), 1.60-1.45 (m, 2H) ppm. To a solution of this obtained intermediate (1.1 g, 2.4 mmol) in tetrahydrofuran (15 mL) were added potassium acetate (706 mg, 7.2 mmol), (BPin)$_2$ (914 mg, 3.6 mmol) and Pd(dppf)Cl$_2$ (734 mg, 0.9 mmol) at room temperature under nitrogen atmosphere. The mixture was stirred at 80° C. overnight, and then the solid was filtered. The filtrate was concentrated, and the residue was purified by silica gel chromatography by elution with petroleum ether/ethyl acetate (100/1 to 20/1) to give the product (650 mg, yield 54%) as a white solid. $^1$H NMR (300 MHz, CDCl$_3$): δ 8.34 (br. s, 1H), 8.15 (s, 1H), 7.89 (br. s, 1H), 7.78-7.60 (m, 1H), 7.48 (d, J=8.0 Hz, 1H), 5.16 (d, J=5.7 Hz, 1H), 4.59-4.45 (m, 1H), 3.91 (s, 3H), 2.24-2.05 (m, 2H), 1.83-1.60 (m, 4H), 1.60-1.36 (m, 14H) ppm. To a solution of this boron intermediate (650 mg, 1.3 mmol) in methanol (10 mL) was added NaBH$_4$ (247 mg, 6.5 mmol) at room temperature in portions. The reaction was stirred at room temperature for 30 minutes, and 6N HCl (3 mL) was added. It was stirred for another 20 minutes, neutralized with saturated NaHCO$_3$ and filtered to collect the solid. The filter cake was triturated with acetonitrile and water to give the product 5-((4-(cyclopentylamino)-5-(trifluoromethyl)pyrimidin-2-yl)amino)benzo[c][1,2]oxaborol-1(3H)-ol (253 mg, yield 51%) as a white solid. $^1$H NMR (300 MHz, DMSO-$d_6$): δ 9.79 (s, 1H), 8.99 (s, 1H), 8.21 (s, 1H), 7.96 (s, 1H), 7.60 (s, 2H), 6.57 (d, J=6.9 Hz, 1H), 4.93 (s, 2H), 4.61-4.40 (m, 1H), 2.05-1.90 (m, 2H), 1.80-1.50 (m, 6H) ppm. HPLC purity: 97.4% at 210 nm and 97.1% at 254 nm. MS: m/z=379.2 (M+H)$^+$.

Example 51: 5-((4-(pentan-3-ylamino)-5-(trifluoromethyl)pyrimidin-2-yl)amino)benzo[c][1,2]oxaborol-1(3H)-ol

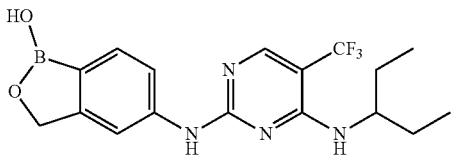

The title compound was prepared by using the scheme and procedures shown below:

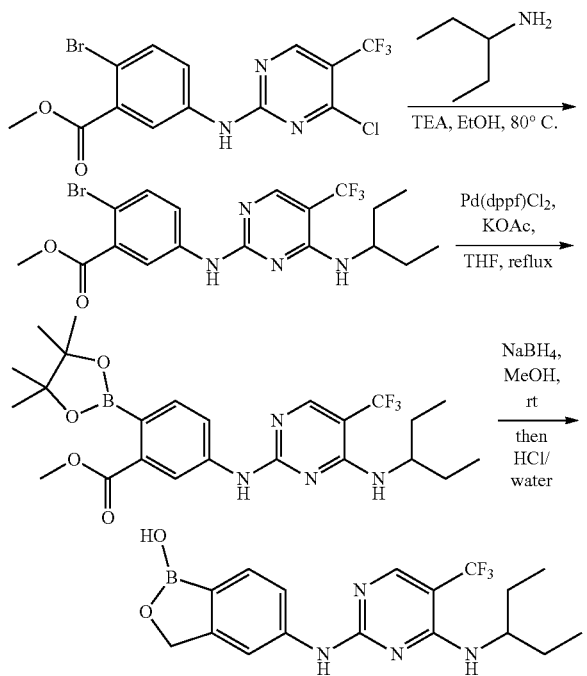

To a solution of methyl 2-bromo-5-((4-chloro-5-(trifluoromethyl)pyrimidin-2-yl)amino)benzoate (2.0 g, 5 mmol) and pentan-3-amine (880 mg, 10 mmol) in ethanol (15 mL) was added triethylamine (1.01 g, 10.0 mmol) at room temperature. The reaction was refluxed for 3 hours, and then the reaction was cooled to room temperature. After rotary evaporation, the residue was triturated with water and dried in air to give the product (1.8 g, yield 78%) as a white solid. $^1$H NMR (400 MHz, CDCl$_3$): δ 8.10 (d, J=0.5 Hz, 1H), 8.06 (d, J=2.5 Hz, 1H), 8.00-7.85 (br. s, 1H), 7.54-7.50 (m, 2H), 4.85 (d, J=8.1 Hz, 1H), 4.16-3.99 (m, 1H), 3.86 (s, 3H), 1.71-1.54 (m, 2H), 1.53-1.38 (m, 2H), 0.87 (t, J=7.4 Hz, 6H) ppm. To a solution of this bromo intermediate (1.8 g, 3.9 mmol) in tetrahydrofuran (10 mL) were added potassium acetate (955 mg, 9.75 mol), (BPin)$_2$ (1.18 g, 4.68 mmol) and Pd(dppf)Cl$_2$ (293 mg, 0.4 mmol) at room temperature under nitrogen atmosphere. The mixture was stirred at 100° C. overnight, and then the solid was filtered. After evaporation, the residue was purified by silica gel chromatography by elution with petroleum ether/ethyl acetate (100/1 to 50/1) to give methyl 5-((4-(pentan-3-ylamino)-5-(trifluoromethyl)pyrimidin-2-yl)amino)-2-(4,4,5,5-tetramethyl-1,3,2-dioxaborolan-2-yl)benzoate (1.31 g, yield 66%) as an off-white solid. $^1$H NMR (400 MHz, CDCl$_3$): δ 8.23 (d, J=2.0 Hz, 1H), 8.11 (br. s, 1H), 8.07 (d, J=0.4 Hz, 1H), 7.64 (dd, J=8.1, 2.1 Hz, 1H), 7.39 (d, J=8.0 Hz, 1H), 4.83 (d, J=8.3 Hz, 1H), 4.27-4.09 (m, 1H), 3.83 (s, 3H), 1.71-1.55 (m, 2H), 1.52-1.39 (m, 2H), 1.35 (s, 12H), 0.86 (t, J=7.4 Hz, 6H) ppm. To a solution of this boron intermediate (1.1 g, 2 mmol) in methanol (15 mL) was added NaBH$_4$ (370 mg, 10 mmol) at 30° C. in small portions. The reaction was stirred at 30° C. for 30 minutes, and 6N HCl (3 mL) was added. It was stirred for another 20 minutes and neutralized with saturated NaHCO$_3$. It was filtered to collect the solid, which was triturated with acetonitrile to give the product 5-((4-(pentan-3-ylamino)-5-(trifluoromethyl)pyrimidin-2-yl)amino)benzo[c][1,2]oxaborol-1(3H)-ol (328 mg, yield 45%) as a white solid. $^1$H NMR (400 MHz, DMSO-d$_6$): δ 9.77 (s, 1H), 8.99 (s, 1H), 8.21 (s, 1H), 7.88 (s, 1H), 7.66-7.60 (m, 2H), 6.42 (d, J=8.4 Hz, 1H), 4.94 (s, 2H), 4.29-4.05 (m, 1H), 1.64-1.59 (m, 4H), 0.87 (t, J=7.4 Hz, 6H) ppm. HPLC purity: 96.48% at 210 nm and 95.77% at 254 nm. MS: m/z=381.2 (M+H)$^+$.

Example 52: 5-((4-((2-cyclopropylethyl)amino)-5-(trifluoromethyl)pyrimidin-2-yl)amino)benzo[c][1,2]oxaborol-1(3H)-ol

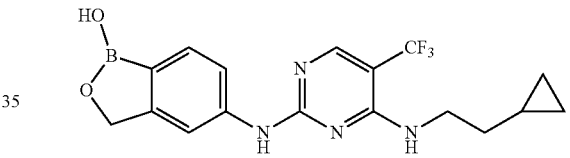

The title compound was prepared by using the scheme and procedures shown below:

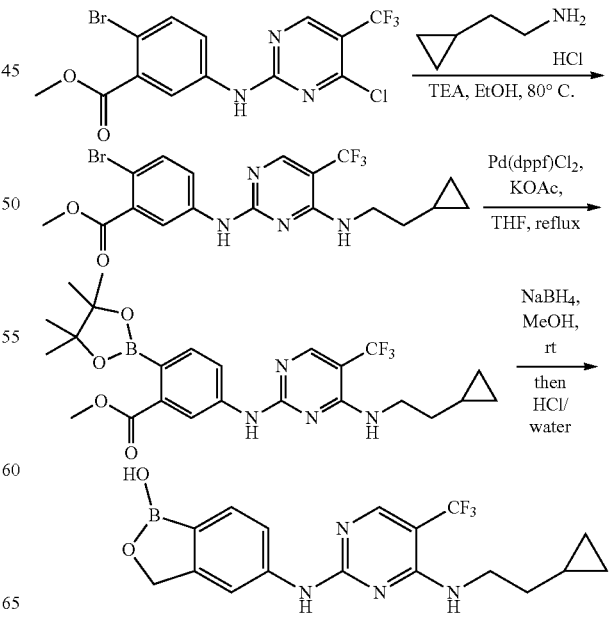

To a solution of methyl 2-bromo-5-((4-chloro-5-(trifluoromethyl)pyrimidin-2-yl)amino)benzoate (1 g, 2.4 mmol) and 2-cyclopropylethanamine hydrochloride (436 mg, 3.6 mmol) in ethanol (10 mL) was added triethylamine (485 mg, 4.8 mmol) at room temperature. The reaction was heated to 80° C. for 2 hours, and then the reaction was cooled to room temperature. Normal work-up as described in Example 41 gave methyl 2-bromo-5-((4-((2-cyclopropylethyl) amino)-5-(trifluoromethyl)pyrimidin-2-yl)amino)benzoate (1.1 g, yield 100%) as a yellow solid. $^1$H NMR (400 MHz, CDCl$_3$): δ 8.12 (s, 1H), 8.07 (s, 1H), 7.48 (d, J=1.5 Hz, 2H), 7.36 (br. s, 1H), 5.37 (br. s, 1H), 3.82 (s, 3H), 3.56-3.51 (m, 2H), 1.47-1.43 (m, J=6.7 Hz, 2H), 0.63-0.58 (m, 1H), 0.43-0.41 (m, 2H), 0.10-0.01 (m, 2H) ppm. To a solution of this bromo intermediate (1.1 g, 2.4 mmol) in tetrahydrofuran (15 mL) were added potassium acetate (705 mg, 7.2 mmol), (BPin)$_2$ (914 mg, 3.6 mmol) and Pd(dppf)Cl$_2$ (734 mg, 0.9 mmol) at room temperature under nitrogen atmosphere. The mixture was stirred at 80° C. overnight, and then the solid was filtered. After evaporation of the filtrate, the residue was purified by silica gel chromatography by elution with petroleum ether/ethy acetate (100/1 to 20/1, v/v) to give methyl 5-((4-((2-cyclopropylethyl)amino)-5-(trifluoromethyl)pyrimidin-2-yl)amino)-2-(4,4,5,5-tetramethyl-1,3,2-dioxaborolan-2-yl)benzoate (950 mg, yield 78%) as a light yellow solid. $^1$H NMR (300 MHz, CDCl$_3$): δ 8.40 (s, 1H), 8.16 (s, 1H), 7.89 (s, 1H), 7.71 (dd, J=8.0, 1.9 Hz, 1H), 7.48 (d, J=8.0 Hz, 1H), 5.50 (s, 1H), 3.92 (s, 3H), 3.72-3.66 (m, 2H), 1.62-1.55 (m, 2H), 1.43 (s, 12H), 0.80-0.65 (m, 1H), 0.55-0.48 (m, 2H), 0.14-0.08 (m, 2H) ppm. To a solution of this boron intermediate (950 mg, 1.9 mmol) in methanol (15 mL) was added NaBH$_4$ (361 mg, 9.5 mmol) at room temperature in small portions. The reaction was stirred at room temperature for 30 minutes, and then 6N HCl (3 mL) was added. It was stirred for another 20 minutes, neutralized with saturated NaHCO$_3$ and filtered to collect the solid. The filter cake was triturated with acetonitrile and water to give the product 5-((4-((2-cyclopropylethyl) amino)-5-(trifluoromethyl)pyrimidin-2-yl)amino)benzo[c] [1,2]oxaborol-1(3H)-ol (247 mg, yield 34%) as a white solid. $^1$H NMR (400 MHz, DMSO-d$_6$): δ 9.74 (s, 1H), 8.95 (s, 1H), 8.15 (s, 1H), 7.84 (s, 1H), 7.64 (dd, J=8.1, 1.2 Hz, 1H), 7.57 (d, J=8.1 Hz, 1H), 7.20-7.07 (m, 1H), 4.90 (s, 2H), 3.66-3.42 (m, 2H), 1.48-1.42 (m, 2H), 0.66-0.62 (m, 1H), 0.39-0.35 (m, 2H), 0.06 to −0.05 (m, 2H) ppm. HPLC purity: 98.21% at 210 nm and 98.29% at 254 nm. MS: m/z=379.1 (M+H)$^+$.

Example 53: 5-((4-(hexan-3-ylamino)-5-(trifluoromethyl)pyrimidin-2-yl)amino)benzo[c][1,2]oxaborol-1(3H)-ol

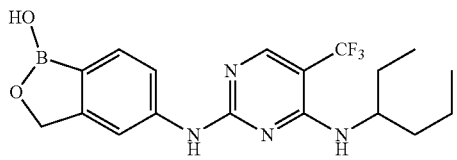 [SMILES: CCCC(CC)Nc1nc(Nc2ccc3c(c2)COB3O)ncc1C(F)(F)F]

The title compound was prepared by using the scheme and procedures shown below:

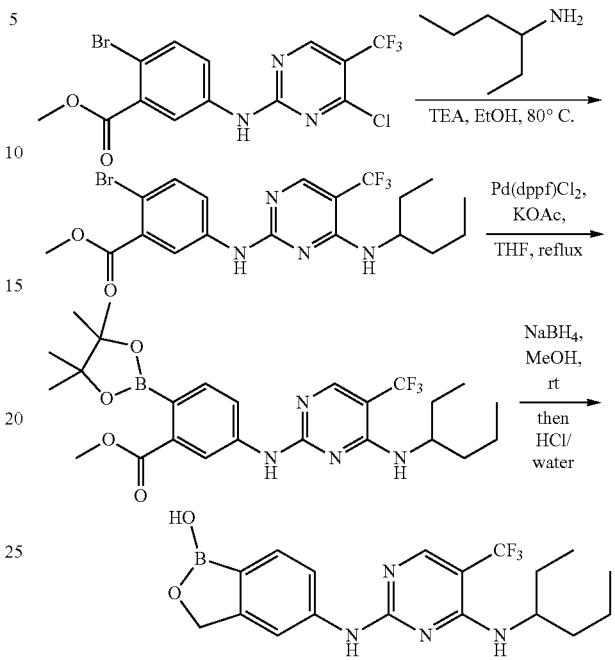

To a solution of methyl 2-bromo-5-((4-chloro-5-(trifluoromethyl)pyrimidin-2-yl)amino)benzoate (2.0 g, 5 mmol) and hexan-3-amine (1.1 g, 10 mmol) in ethanol (15 mL) was added triethylamine (1.01 g, 10.0 mmol) at room temperature. The reaction was refluxed for 3 hours, and then the reaction was cooled to room temperature and concentrated in vacuo. The residue was triturated with water and dried in air to give the product (2.3 g, yield 91%) as a white solid. $^1$H NMR (400 MHz, CDCl$_3$): δ 8.09 (d, J=0.7 Hz, 1H), 8.06 (d, J=2.6 Hz, 1H), 7.68-7.61 (m, 1H), 7.54-7.49 (m, 2H), 4.83 (d, J=8.3 Hz, 1H), 4.21-4.16 (m, 1H), 3.86 (s, 3H), 1.60-1.31 (m, 6H), 0.88-0.83 (m, 6H) ppm. To a solution of this bromo intermediate (1.1 g, 2.3 mmol) in tetrahydrofuran (10 mL) were added potassium acetate (474 mg, 4.8 mol), (BPin)$_2$ (701 mg, 2.76 mmol) and Pd(dppf)Cl$_2$ (457 mg, 0.6 mmol) at room temperature under N$_2$. The mixture was stirred at 100° C. overnight, and then the solid was filtered. The filtrate was concentrated, and the residue was purified by silica gel chromatography by elution with petroleum ether/ethyl acetate (100/1 to 50/1, v/v) to give methyl 5-((4-(hexan-3-ylamino)-5-(trifluoromethyl)pyrimidin-2-yl)amino)-2-(4,4,5,5-tetra-methyl-1,3,2-dioxaborolan-2-yl)benzoate (0.62 g, yield 45%) as a white solid. $^1$H NMR (400 MHz, CDCl$_3$): δ 8.21 (d, J=2.0 Hz, 1H), 8.09 (s, 1H), 7.96-7.85 (m, 1H), 7.66 (dd, J=8.3, 1.7 Hz, 1H), 7.39 (d, J=8.0 Hz, 1H), 4.80 (d, J=8.5 Hz, 1H), 4.34-4.17 (m, 1H), 3.83 (s, 3H), 1.65-1.30 (m, 6H), 1.35 (s, 12H), 0.90-0.82 (m, 6H) ppm. To a solution of this boron intermediate (620 mg, 1.1 mmol) in methanol (15 mL) was added NaBH$_4$ (266 mg, 7 mmol) at 30° C. in small portions. The reaction was stirred at 30° C. for 30 minutes, and then 6N HCl (3 mL) was added. It was stirred for another 20 minutes, neutralized with saturated NaHCO$_3$ and filtered to collect the solid. The filter cake was triturated with acetonitrile to give the product 5-((4-(hexan-3-ylamino)-5-(trifluoromethyl) pyrimidin-2-yl)amino)benzo[c][1,2]oxaborol-1(3H)-ol (154 mg, yield 58%) as a white solid. ¹H NMR (400 MHz, DMSO-d₆): δ 10.32 (s, 1H), 9.00 (br. s, 1H), 8.32 (s, 1H), 7.78 (s, 1H), 7.67 (d, J=8.0 Hz, 1H), 7.60 (d, J=8.0 Hz, 1H), 7.15 (s, 1H), 4.96 (s, 2H), 4.30-4.20 (m, 1H), 1.73-1.45 (m, 4H), 1.40-1.20 (m, 2H), 0.85 (t, J=7.1 Hz, 6H) ppm. HPLC purity: 95.97% at 210 nm and 96.79% at 254 nm. MS: m/z=395.1 (M+H)⁺.

Example 54: 5-((5-methyl-4-(pentan-3-yloxy)pyrimidin-2-yl)amino)benzo[c][1,2]oxaborol-1(3H)-ol

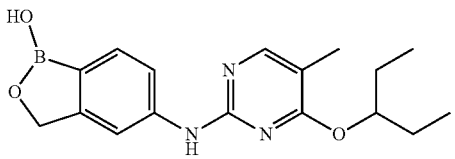

The title compound was prepared by using the scheme and procedures shown below:

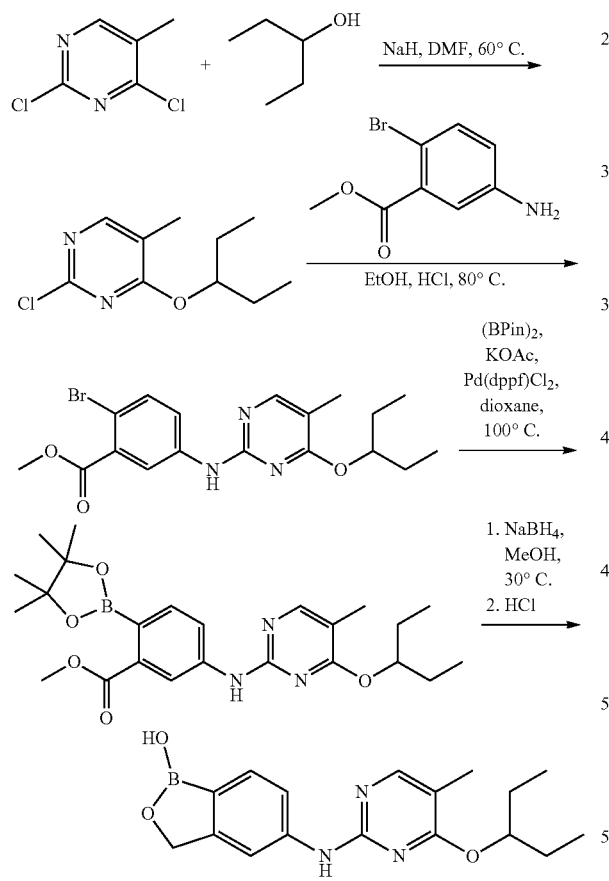

To a solution of 2,4-dichloro-5-methylpyrimidine (1.6 g, 10.0 mmol) and pentan-3-ol (0.88 g, 10 mmol) in dimethylformamide (20 mL) was added NaH (0.6 g, 20.0 mmol) in portions at room temperature. The reaction was stirred at 60° C. overnight, and then the reaction was quenched by water. Normal work-up as described in Example 41 gave a residue, which was purified by column chromatography to give 2-chloro-5-methyl-4-(pentan-3-yloxy)pyrimidine (1.0 g, yield 44%) as a white solid. ¹H NMR (400 MHz, CDCl₃):

δ 8.01 (s, 1H), 5.13 (quintet, J=5.9 Hz, 1H), 2.03 (s, 3H), 1.68-1.61 (m, 4H), 0.85 (t, J=7.5 Hz, 6H) ppm. To a solution of this intermediate (1.0 g, 4.6 mmol) in ethanol (8 mL) were added methyl 5-amino-2-bromobenzoate (1.05 g, 4.6 mmol) and HCl (1.5 N, 4 mL). The reaction was refluxed for 3 hours. The reaction was monitored by TLC, then reaction was cooled to room temperature and diluted with water. Normal work-up as described in Example 41 gave the residue, which was triturated with ethyl acetate:petroleum ether (1:5, v/v) to give methyl 2-bromo-5-((5-methyl-4-(pentan-3-yloxy)pyrimidin-2-yl)amino)benzoate as a white solid. ¹H NMR (400 MHz, DMSO-d₆): δ 10.16 (br. s, 1H), 8.28 (s, 1H), 8.14 (s, 1H), 7.67 (s, 2H), 5.23-5.04 (m, 1H), 3.86 (s, 3H), 2.01 (s, 3H), 1.73-1.66 (m, 4H), 0.88 (t, J=7.3 Hz, 6H) ppm. To a solution of this bromo intermediate (600 mg, 1.4 mmol) in 1,4-dioxane (10 mL) were added potassium acetate (412 mg, 4.2 mol), (BPin)₂ (533 mg, 2.1 mmol) and Pd(dppf)Cl₂ (457 mg, 0.6 mmol) at room temperature under nitrogen atmosphere. The mixture was stirred at 100° C. overnight, and then the solid was filtered. The filtrate was concentrated, and the residue was purified by silica gel column chromatography by elution with petroleum ether/ethyl acetate (100/1 to 20/1) to give methyl 5-((5-methyl-4-(pentan-3-yloxy)pyrimidin-2-yl)amino)-2-(4,4,5,5-tetramethyl-1,3,2-dioxaborolan-2-yl)benzoate (0.8 g) as a white solid. MS: m/z=456.3 (M+H)⁺. To a solution of this boron intermediate (800 mg) in methanol (15 mL) was added NaBH₄ (532 mg, 14.0 mmol) at 30° C. in small portions. The reaction was stirred at 30° C. for 30 minutes, and 6N HCl (3 mL) was added. It was stirred for another 20 minutes, neutralized with saturated NaHCO₃ and extracted with ethyl acetate. Normal work-up as described in Example 41 gave the residue, which was purified by pre-HPLC to give the product 5-((5-methyl-4-(pentan-3-yloxy)pyrimidin-2-yl)amino)benzo[c][1,2]oxaborol-1(3H)-ol (89.4 mg, yield 20%) as a white solid. ¹H NMR (400 MHz, DMSO-d₆): δ 9.78 (s, 1H), 8.94 (br. s, 1H), 8.09 (s, 1H), 7.82 (s, 1H), 7.63-7.55 (m, 2H), 5.09 (quintet, J=6.0 Hz, 1H), 4.95 (s, 2H), 2.00 (s, 3H), 1.75-1.67 (m, 4H), 0.91 (t, J=7.4 Hz, 6H) ppm. HPLC purity: 99.59% at 210 nm and 99.63% at 254 nm. MS: m/z=328.2 (M+H)⁺.

Example 55: 5-((4-(cyclohexyloxy)-5-methylpyrimidin-2-yl)amino)benzo[c][1,2]oxaborol-1(3H)-ol

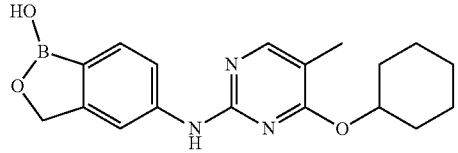 [SMILES: Cc1cnc(Nc2ccc3c(c2)COB3O)nc1OC1CCCCC1]

The title compound was prepared by using the scheme and procedures shown below:

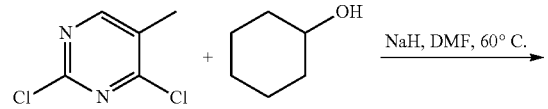

251

-continued

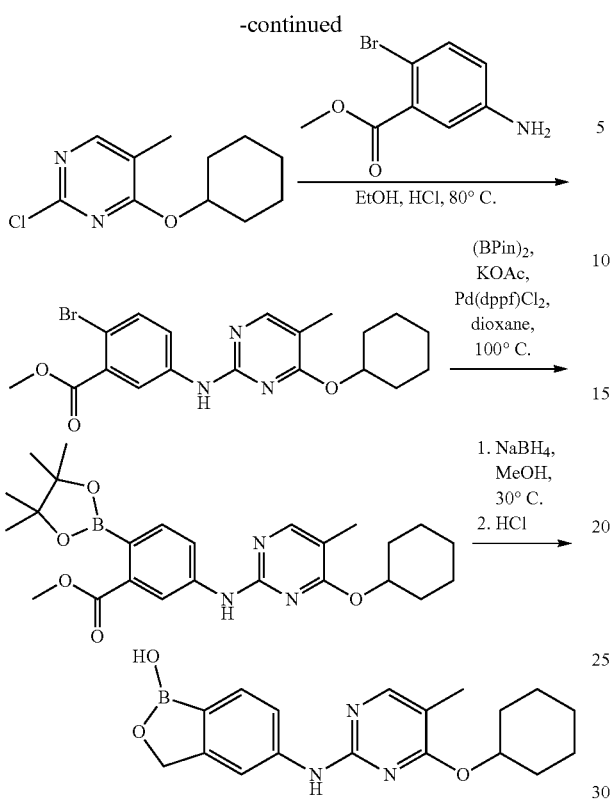

To a solution of 2,4-dichloro-5-methylpyrimidine (1.6 g, 10.0 mmol) and cyclohexanol (1.0 g, 10 mmol) in dimethylformamide (20 mL) was added NaH (0.6 g, 20.0 mmol) in portions at room temperature. The reaction was stirred at 60° C. overnight, and then quenched with water. Normal work-up as described in Example 41 provided a residue, which was purified by column chromatography to give 2-chloro-4-(cyclohexyloxy)-5-methyl-pyrimidine (1.5 g, yield 68%) as a colorless oil. $^1$H NMR (400 MHz, CDCl$_3$): δ 8.00 (s, 1H), 5.16-5.10 (m, 1H), 2.02 (s, 3H), 1.93-1.81 (m, 2H), 1.76-1.63 (m, 2H), 1.57-1.45 (m, 3H), 1.45-1.34 (m, 2H), 0.85-0.73 (m, 1H) ppm. To a solution of this intermediate (1.0 g, 4.4 mmol) in ethanol (8 mL) were added methyl 5-amino-2-bromobenzoate (1.05 g, 4.6 mmol) and HCl (1.5 N, 4 mL). The reaction mixture was refluxed for 3 hours. Normal work-up as described in Example 41 generated the residue, which was triturated with ethyl acetate:petroleum ether (1:5, v/v) to give methyl 2-bromo-5-((4-(cyclohexyloxy)-5-methyl pyrimidin-2-yl)amino)benzoate as a white solid (0.8 g, yield 44%). $^1$H NMR (400 MHz, DMSO-d$_6$): δ 10.29 (s, 1H), 8.19 (s, 1H), 8.15 (s, 1H), 7.68 (s, 2H), 5.20-5.02 (m, 1H), 3.87 (s, 3H), 2.01 (s, 3H), 1.97-1.87 (m, 2H), 1.77-1.64 (m, 2H), 1.62-1.47 (m, 3H), 1.45-1.28 (m, 3H) ppm. To a solution of this bromo intermediate (600 mg, 1.4 mmol) in 1,4-dioxane (10 mL) were added potassium acetate (412 mg, 4.2 mol), (BPin)$_2$ (533 mg, 2.1 mmol) and Pd(dppf)Cl$_2$ (457 mg, 0.6 mmol) at room temperature under nitrogen atmosphere. The mixture was stirred at 100° C. overnight, and then the solid was filtered. The filtrate was concentrated, and the residue was purified by silica gel chromatography by elution with petroleum ether/ethyl acetate (100/1 to 20/1) to give methyl 5-((4-(cyclohexyloxy)-5-methyl-pyrimidin-2-yl)amino)-2-(4,4,5,5-tetramethyl-1,3,2-dioxaborolan-2-yl)benzoate (0.6 g) as a white solid. MS: m/z=468.3 (M+H)$^+$. To a solution of this boron

252 intermediate (600 mg) in methanol (15 mL) was added NaBH$_4$ (532 mg, 14.0 mmol) at 30° C. in small portions. The reaction was stirred at 30° C. for 30 minutes, and 6N HCl (3 mL) was added. It was stirred for another 20 minutes, neutralized with saturated NaHCO$_3$ and filtered to collect the solid. It was triturated with dichloromethane to give the product 5-((4-(cyclohexyloxy)-5-methyl-pyrimidin-2-yl)amino)benzo[c][1,2]oxaborol-1(3H)-ol (255 mg, yield 53%) as a white solid. $^1$H NMR (400 MHz, DMSO-d$_6$): δ 9.57 (s, 1H), 8.94 (br. s, 1H), 8.07 (s, 1H), 7.91 (s, 1H), 7.58 (s, 2H), 5.20-5.00 (m, 1H), 4.94 (s, 2H), 1.99 (s, 3H), 2.10-1.90 (m, 2H), 1.85-1.70 (m, 2H), 1.64-1.25 (m, 6H) ppm. HPLC purity: 97.81% at 210 nm and 97.45% at 254 nm. MS: m/z=340.2 (M+H)$^+$.

Example 56: 5-((4-(cyclohexylthio)-5-methylpyrimidin-2-yl)amino)benzo[c][1,2]oxaborol-1(3H)-ol

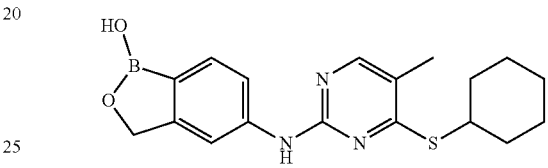

The title compound was prepared by using the scheme and procedures shown below:

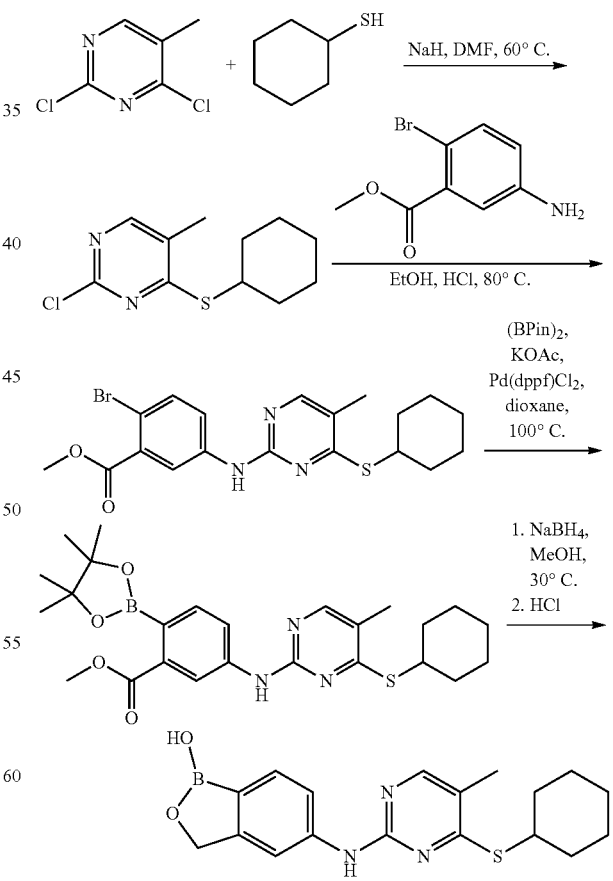

To a solution of 2,4-dichloro-5-methylpyrimidine (1.6 g, 10.0 mmol) and cyclohexanethiol (1.16 g, 10 mmol) in dimethylformamide (20 mL) was added NaH (0.6 g, 20.0 mmol) in portions at room temperature. The reaction mixture was stirred at 60° C. overnight. Normal work-up as described in Example 41 provided a residue, which was purified by column chromatography (petroleum ether/ethyl acetate from 100:1 to 5:1) to give 2-chloro-4-(cyclohexylthio)-5-methylpyrimidine (1.4 g, yield 58%) as oil. $^1$H NMR (400 MHz, CDCl$_3$): δ 8.01 (s, 1H), 4.08-3.92 (m, 1H), 2.13 (s, 3H), 1.81-1.76 (m, 2H), 1.68-1.62 (m, 1H), 1.57-1.45 (m, 6H), 1.37-1.32 (m, 1H). ppm. To a solution of this intermediate (1.0 g, 4.1 mmol) in ethanol (8 mL) were added methyl 5-amino-2-bromobenzoate (1.05 g, 4.6 mmol) and HCl (1.5 N, 4 mL). The reaction was refluxed for 3 hours. Normal work-up as described in Example 41 provided a residue, which was triturated with ethyl acetate: petroleum ether (1:5, v/v) to give methyl 2-bromo-5-((4-(cyclohexylthio)-5-methylpyrimidin-2-yl)amino)benzoate as a white solid (0.9 g, yield 47%). $^1$H NMR (400 MHz, DMSO-d$_6$): δ 9.74 (s, 1H), 8.15 (d, J=2.7 Hz, 1H), 8.07 (s, 1H), 7.84 (dd, J=8.8, 2.7 Hz, 1H), 7.62 (d, J=8.8 Hz, 1H), 4.02-3.91 (m, 1H), 3.87 (s, 3H), 2.02 (s, 3H), 2.06-1.97 (m, 2H), 1.74-1.66 (m, 2H), 1.64-1.55 (m, 1H), 1.54-1.29 (m, 5H) ppm. To a solution of this bromo intermediate (600 mg, 1.4 mmol) in 1,4-dioxane (10 mL) were added potassium acetate (412 mg, 4.2 mol), (BPin)$_2$ (533 mg, 2.1 mmol) and Pd(dppf)Cl$_2$ (457 mg, 0.6 mmol) at room temperature under nitrogen atmosphere. The mixture was stirred at 100° C. overnight, and then the solid was filtered. The filtrate was concentrated and the residue was purified by silica gel chromatography by elution with petroleum ether/ethyl acetate (100/1 to 20/1, v/v) to give methyl 5-((4-(cyclohexylthio)-5-methylpyrimidin-2-yl) amino)-2-(4,4,5,5-tetramethyl-1,3,2-dioxaborolan-2-yl)benzoate (0.61 g) as a white solid. MS: m/z=484.3 (M+H)$^+$. To a solution of this boron intermediate (600 mg, crude) in methanol (15 mL) was added NaBH$_4$ (532 mg, 14.0 mmol) at 30° C. in small portions. The reaction mixture was stirred at 30° C. for 30 minutes, and 6N HCl (3 mL) was added. It was stirred for another 20 minutes, neutralized with saturated NaHCO$_3$ and filtered to collect the solid. It was purified by prep-HPLC to give the product 5-((4-(cyclohexylthio)-5-methylpyrimidin-2-yl)amino)benzo[c] [1,2]oxaborol-1(3H)-ol (66 mg, yield 53%) as a white solid. $^1$H NMR (400 MHz, DMSO-d$_6$): δ 9.64 (s, 1H), 8.89 (br. s, 1H), 8.05 (s, 1H), 7.78 (s, 1H), 7.73-7.67 (m, 1H), 7.63 (d, J=8.1 Hz, 1H), 4.96 (s, 2H), 4.02-3.97 (m, 1H), 2.11-2.04 (m, 2H), 2.02 (s, 3H), 1.80-1.70 (m, 2H), 1.70-1.60 (m, 1H), 1.56-1.38 (m, 4H), 1.37-1.20 (m, 1H). ppm. HPLC purity: 99.75% at 210 nm and 98.72% at 254 nm. MS: m/z=356.2 (M+H)$^+$.

Example 57: 5-((5-methyl-4-(pentan-3-ylthio)pyrimidin-2-yl)amino)benzo[c][1,2]oxaborol-1(3H)-ol

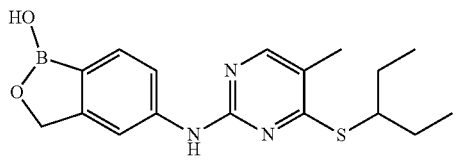

The title compound was prepared by using the scheme and procedures shown below:

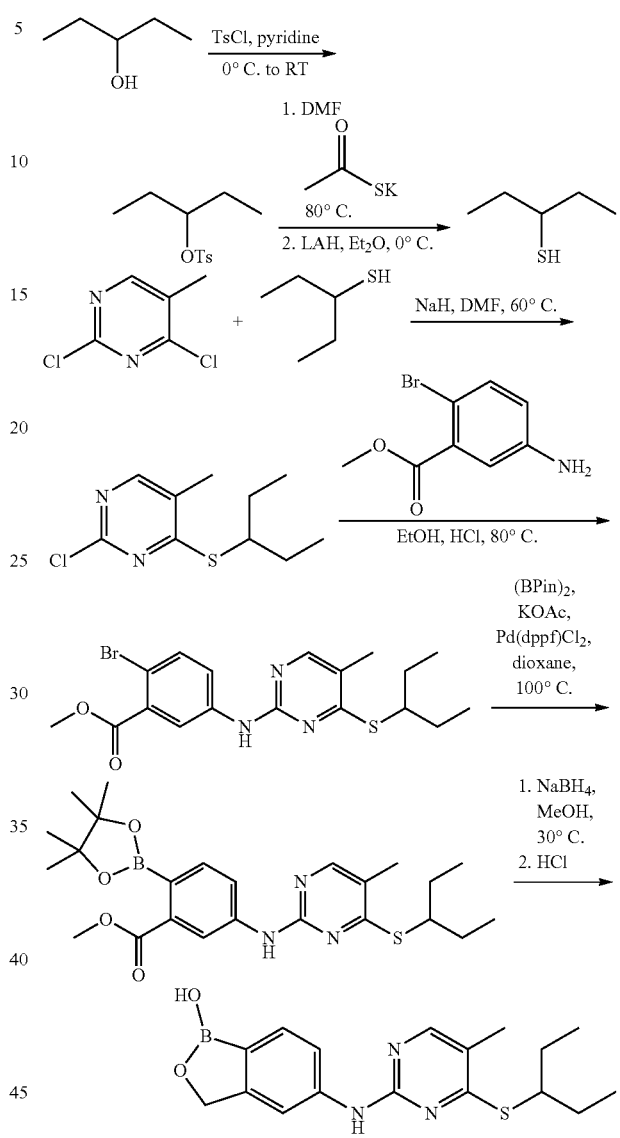

To a solution of pentan-3-ol (5.7 g, 60 mmol) in anhydrous pyridine (40 mL) was added slowly p-toluenesulfonyl chloride (13.6 g: 66 mmol) at 0° C. The solution was warmed to room temperature and the mixture was stirred overnight. Hexane (30 mL) was added and the solution was filtered. The solid was washed with hexane (30 mL). The combined organic layers were washed with aqueous hydrochloric acid (5N, 2×30 mL). After drying over anhydrous sodium sulfate and filtration, the solvent was removed by rotary evaporation to give pentan-3-yl 4-methylbenzene sulfonate as a white solid (11.7 g, yield 86%). Potassium thioacetate (571 g, 50 mmol) was dissolved in dimethylformamide (20 mL). Pentan-3-yl 4-methylbenzene sulfonate (11.4 g, 50 mmol) was added and the solution was stirred at 80° C. for 2 hours. Then saturated aqueous sodium chloride solution (100 mL) was added. The aqueous solution was extracted with diethyl ether (3×100 mL) and the combined organic layers were washed with saturated aqueous sodium chloride solution (5×50 mL). After drying over anhydrous sodium sulfate and filtration, the solvent was removed by rotary evaporation to give S-(pentan-3-yl) ethanethioate as a red oil (5.6 g, yield 72%). $^1$H NMR (400 MHz, CDCl$_3$): δ 3.38-3.31 (m, 1H), 2.25 (s, 3H), 1.64-1.45 (m, 4H), 0.87 (t, J=7.4 Hz, 6H) ppm. This ester intermediate (5.6 g, 38 mmol) was dissolved in anhydrous diethyl ether (15 mL), and was reduced by slowly adding a suspension of lithium aluminum hydride (2.81 g, 76 mmol) in anhydrous diethyl ether (20 mL) at 0° C. The solution was stirred for 2 hours at room temperature. Saturated aqueous ammonium chloride solution (20 mL) was added slowly at 0° C., and then Na$_2$SO$_4$ was added. The mixture was stirred for 10 minutes and then filtered through a Celite pad. The filter cake was washed with diethyl ether (3×20 mL), and the filtrate was concentrated in vacuo under low temperature to remove the solvent and to give the residue, pentane-3-thiol, as a colorless oil (2.78 g, yield 71%) which was used in the next step without further purification, To a solution of 2,4-dichloro-5-methylpyrimidine (4.0 g, 25.0 mmol) and pentane-3-thiol (2.78 g, 25 mmol) in dimethylformamide (20 mL) was added NaH (2.0 g, 50.0 mmol) in portions at room temperature. The reaction was stirred at 60° C. overnight, and then the reaction was quenched by water. Normal work-up as described in Example 41 gave a residue, which was purified by column chromatography to give 2-chloro-5-methyl-4-(pentan-3-ylthio)pyrimidine (2.45 g, yield 44%) as a white solid. $^1$H NMR (400 MHz, CDCl$_3$): δ 7.93 (s, 1H), 3.97-3.89 (m, 1H), 2.08 (s, 3H), 1.78-1.60 (m, 4H), 0.94 (t, J=7.4 Hz, 6H) ppm. To a solution of this thioether intermediate (1.0 g, 4.6 mmol) in ethanol (8 mL) were added methyl 5-amino-2-bromobenzoate (1.05 g, 4.6 mmol) and HCl (1.5 N, 4 mL). The reaction was refluxed for 3 hours. Normal work-up as described in Example 41 generated the residue, which was triturated with ethyl acetate:petroleum ether (1:5, v/v) to give methyl 2-bromo-5-((5-methyl-4-(pentan-3-ylthio)pyrimidin-2-yl)amino)benzoate as a white solid. $^1$H NMR (400 MHz, CDCl$_3$): δ 8.08 (d, J=2.7 Hz, 1H), 8.06 (br. s, 1H), 7.85 (s, 1H), 7.65 (dd, J=8.7, 2.7 Hz, 1H), 7.59 (d, J=8.7 Hz, 1H), 4.10-3.96, (m, 1H), 3.95 (s, 3H), 2.14 (s, 3H), 1.88-1.66 (m, 4H), 1.02 (t, J=7.4 Hz, 6H) ppm. To a solution of this bromo intermediate (1.2 g, 2.8 mmol) in 1,4-dioxane (10 mL) were added potassium acetate (824 mg, 8.4 mol), (BPin)$_2$ (1.06 mg, 4.2 mmol) and Pd(dppf)Cl$_2$ (457 mg, 0.6 mmol) at room temperature under nitrogen atmosphere. The mixture was stirred at 100° C. overnight, and then the solid was filtered. The residue after evaporation of the filtrate was purified by silica gel chromatography by elution with petroleum ether/ethyl acetate (100/1 to 20/1, v/v) to give methyl 5-((5-methyl-4-(pentan-3-ylthio)pyrimidin-2-yl)amino)-2-(4,4,5,5-tetramethyl-1,3,2-dioxaborolan-2-yl)benzoate (1.1 g) as a white solid. $^1$H NMR (400 MHz, CDCl$_3$) δ 8.09 (d, J=2.1 Hz, 1H), 7.81 (s, 1H), 7.70 (dd, J=8.1, 2.2 Hz, 1H), 7.39 (d, J=8.1 Hz, 1H), 7.22 (s, 1H), 4.05-3.96, (m, 1H), 3.84 (s, 3H), 2.03 (s, 3H), 1.77-1.60 (m, 4H), 1.34 (s, 12H), 0.93 (t, J=7.4 Hz, 6H) ppm. To a solution of this boron intermediate (1.1 g, 2.3 mmol) in methanol (15 mL) was added NaBH$_4$ (532 mg, 14.0 mmol) at 30° C. in small portions. The reaction was stirred at 30° C. for 30 minutes, and 6N HCl (3 mL) was added. It was stirred for another 20 minutes, and then neutralized with saturated NaHCO$_3$. Normal work-up as described in Example 41 generated the residue, which was recrystallized with dimethyl sulfoxide and water to give the product 5-((5-methyl-4-(pentan-3-ylthio)pyrimidin-2-yl)amino)benzo[c][1,2] oxaborol-1(3H)-ol (208 mg, yield 25%) as a white solid. $^1$H NMR (400 MHz, DMSO-d$_6$): δ 9.65 (s, 1H), 8.88 (br. s, 1H), 8.05 (s, 1H), 7.87 (s, 1H), 7.61 (d, J=0.7 Hz, 2H), 4.95 (s, 2H), 4.12-3.98 (m, 1H), 2.05 (s, 3H), 1.86-1.62 (m, 4H), 0.97 (t, J=7.3 Hz, 6H) ppm. HPLC purity: 96.56% at 210 nm and 96.81% at 254 nm. MS: m/z=344.1 (M+H)$^+$.

Example 58: 5-((5-fluoro-4-(pentan-3-ylamino)pyrimidin-2-yl)amino)benzo[c][1,2]oxaborol-1(3H)-ol

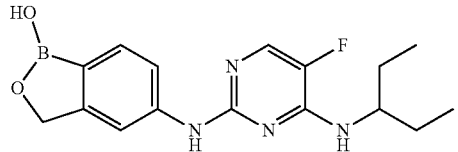

The title compound was prepared by using the scheme and procedures shown below:

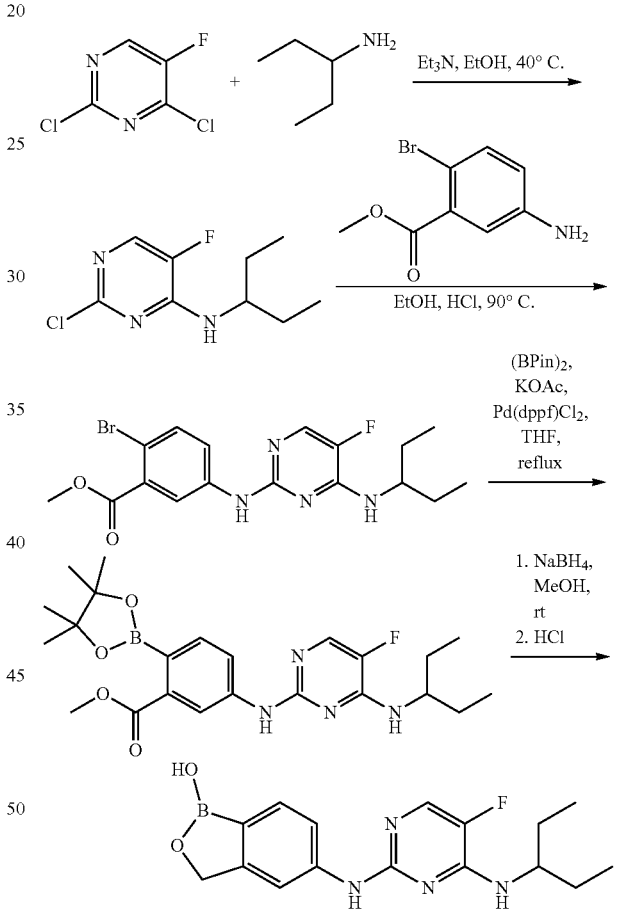

To a solution of 2,4-dichloro-5-fluoropyrimidine (1.7 g, 10.0 mmol) in ethanol (20 mL) was added pentan-3-amine (1.7 g, 20.0 mmol) and triethylamine (2.0 g, 20 mmol) at room temperature. The reaction was stirred at 40° C. for 3 hours, and then the reaction was poured into water and filtered to collect the solid. It was dried to give 2-chloro-5-fluoro-N-(pentan-3-yl)pyrimidin-4-amine (1.3 g, yield 60%) as a white solid. $^1$H NMR (400 MHz, CDCl$_3$): δ 7.78 (d, J=2.9 Hz, 1H), 4.82 (d, J=6.0 Hz, 1H), 4.10-3.95 (m, 1H), 1.72-1.52 (m, 2H), 1.52-1.33 (m, 2H), 0.87 (t, J=7.4 Hz, 6H) ppm. To a solution of this intermediate (1.3 g, 6.0 mmol) in ethanol (6 mL) were added methyl 5-amino-2-bromo-benzoate (1.4 g, 6.0 mmol) and HCl (1.5 N, 4 mL). The reaction mixture was subjected to microwave irradiation (90° C., 30 minutes), cooled to room temperature, and poured into water. The solid was collected by filtration and dried to give methyl 2-bromo-5-((5-fluoro-4-(pentan-3-ylamino)-pyrimidin-2-yl)amino)benzoate (1.0 g, yield 41%) as a brown solid. $^1$H NMR (400 MHz, DMSO-$d_6$): δ 10.71 (s, 1H), 8.73 (s, 1H), 8.27 (d, J=2.5 Hz, 1H), 8.19 (d, J=5.3 Hz, 1H), 7.73 (d, J=8.7 Hz, 1H), 7.56 (dd, J=8.7, 2.6 Hz, 1H), 4.05-3.92 (m, 1H), 3.86 (s, 3H), 1.68-1.50 (m, 4H), 0.87 (t, J=7.4 Hz, 6H) ppm. To a solution of this bromo intermediate (1.0 g, 2.4 mmol) in tetrahydrofuran (15 mL) was added potassium acetate (705 mg, 7.2 mmol), (BPin)$_2$ (914 mg, 3.6 mmol) and Pd(dppf)Cl$_2$ (734 mg, 0.9 mmol) at room temperature under N$_2$. The mixture was refluxed overnight, and then the solid was filtered. The filtrate was concentrated, and the residue was purified by silica gel chromatography by elution with petroleum ether/ethyl acetate (100/1 to 10/1, v/v) to give the crude product (500 mg, yield 45%) as a yellow solid. $^1$H NMR (400 MHz, DMSO-$d_6$): δ 9.36 (s, 1H), 8.45 (d, J=1.9 Hz, 1H), 7.89 (d, J=3.9 Hz, 1H), 7.76 (dd, J=8.2, 2.0 Hz, 1H), 7.34 (d, J=8.2 Hz, 1H), 7.22 (d, J=8.7 Hz, 1H), 4.11-3.99 (m, 1H), 3.81 (s, 3H), 1.72-1.44 (m, 4H), 1.33 (s, 12H), 0.88 (t, J=7.3 Hz, 6H) ppm. To a solution of this boron intermediate (500 mg, 1.1 mmol) in methanol (10 mL) was added NaBH$_4$ (418 mg, 11.0 mmol) at room temperature in small portions. It was stirred for 30 minutes, and 6N HCl (5 mL) was added. The mixture was stirred for another 20 minutes, neutralized with saturated NaHCO$_3$ and filtered. The solid obtained was triturated with acetonitrile and H$_2$O to give the product 5-((5-fluoro-4-(pentan-3-ylamino)pyrimidin-2-yl)amino)benzo[c][1,2]oxaborol-1(3H)-ol (95.0 mg, yield 26%) as a white solid. $^1$H NMR (300 MHz, DMSO-$d_6$): δ 9.21 (s, 1H), 8.91 (s, 1H), 8.00-7.75 (m, 2H), 7.56 (s, 2H), 7.19 (d, J=8.1 Hz, 1H), 4.91 (s, 2H), 4.05-3.85 (m, 1H), 1.70-1.50 (m, 4H), 0.88 (t, J=7.1 Hz, 6H) ppm. HPLC purity: 97.05% at 210 nm and 96.78% at 254 nm. MS: m/z=331.2 (M+H)$^+$.

Example 59: 5-((4-(cyclohexylamino)-5-fluoropyrimidin-2-yl)amino)benzo[c][1,2]oxaborol-1(3H)-ol

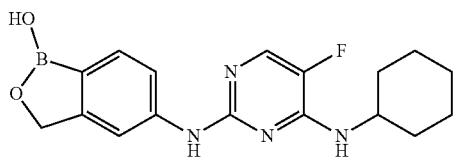 [SMILES: OB1OCc2cc(Nc3ncc(F)c(NC4CCCCC4)n3)ccc21]

The title compound was prepared by using the scheme and procedures shown below:

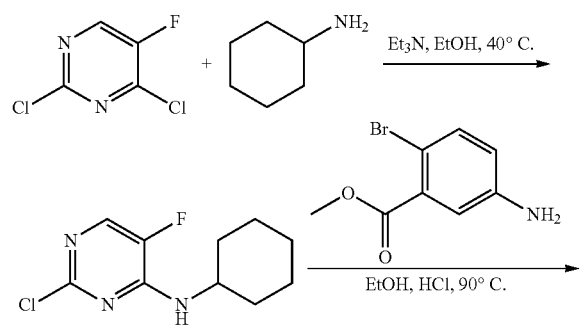

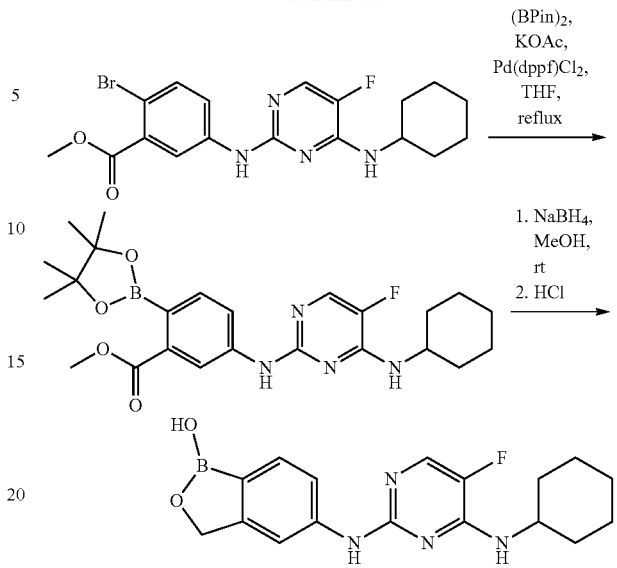

To a solution of 2,4-dichloro-5-fluoropyrimidine (1.7 g, 10.0 mmol) in ethanol (20 mL) were added cyclohexanamine (2.0 g, 20.0 mmol) and triethylamine (2.0 g, 20 mmol) at room temperature. The reaction mixture was stirred at 40° C. for 3 hours, poured into water, and filtered. The solid obtained was dried to provide 2-chloro-N-cyclohexyl-5-fluoropyrimidin-4-amine (1.6 g, yield 70%) as a white solid. $^1$H NMR (400 MHz, CDCl$_3$): δ 7.77 (d, J=2.9 Hz, 1H), 4.97 (br. s, 1H), 4.02-3.85 (m, 1H), 2.04-1.89 (m, 2H), 1.75-1.65 (m, 2H), 1.65-1.51 (m, 1H), 1.46-1.28 (m, 2H), 1.28-1.04 (m, 3H) ppm. To a solution of this intermediate (1.6 g, 7.0 mmol) in ethanol (6 mL) were added methyl 5-amino-2-bromo-benzoate (1.6 g, 7.0 mmol) and HCl (1.5 N, 4 mL). The mixture was subjected to microwave irradiation (90° C., 30 min), cooled to room temperature and poured into water. The solid after filtration was dried to give methyl 2-bromo-5-((4-(cyclohexylamino)-5-fluoropyrimidin-2-yl)amino)benzoate (1.4 g, yield 48%) as a white solid. $^1$H NMR (400 MHz, DMSO-$d_6$): δ 9.45 (s, 1H), 8.25 (d, J=2.7 Hz, 1H), 7.90 (d, J=3.9 Hz, 1H), 7.73 (dd, J=8.9, 2.7 Hz, 1H), 7.56 (d, J=8.8 Hz, 1H), 7.40 (d, J=7.9 Hz, 1H), 3.95-3.80 (m, 1H), 3.86 (s, 3H), 1.93-1.83 (m, 2H), 1.83-1.67 (m, 2H), 1.68-1.57 (m, 1H), 1.41-1.20 (m, 4H), 1.20-1.10 (m, 1H) ppm. To a solution of this bromo intermediate (1.4 g, 3.3 mmol) in tetrahydrofuran (15 mL) were added potassium acetate (970 mg, 9.9 mmol), (BPin)$_2$ (1.1 g, 4.4 mmol), and Pd(dppf)Cl$_2$ (1.0 g, 1.3 mmol) at room temperature under N$_2$. The mixture was refluxed overnight, cooled to room temperature, and filtered. The filtrate was concentrated, and the residue was purified by silica gel chromatography by elution with petroleum ether/ethyl acetate (100/1 to 10/1, v/v) to give methyl 5-((4-(cyclohexyl-amino)-5-fluoropyrimidin-2-yl)amino)-2-(4,4,5,5-tetra-methyl-1,3,2-dioxaborolan-2-yl)benzoate (1.0 g, yield 65%) as a yellow solid. $^1$H NMR (400 MHz, DMSO-$d_6$): δ 9.37 (s, 1H), 8.29 (d, J=2.0 Hz, 1H), 7.89 (d, J=3.8 Hz, 1H), 7.83 (dd, J=8.2, 2.1 Hz, 1H), 7.36 (d, J=8.0 Hz, 1H), 7.32 (d, J=8.0 Hz, 1H), 4.00-3.90 (br. s, 1H), 3.81 (s, 3H), 1.95-1.82 (m, 2H), 1.82-1.70 (m, 2H), 1.70-1.59 (m, 1H), 1.41-1.22 (m, 16H), 1.22-1.11 (m, 1H) ppm. To a solution of this boron intermediate (1.0 g, 2.1 mmol) in methanol (10 mL) was added NaBH$_4$ (798 mg, 21.0 mmol) at room temperature in small portions. The reaction mixture was stirred for 30 minutes, and 6N HCl (5 mL) was added.

It was stirred for another 20 minutes, neutralized with saturated NaHCO₃ and filtered to give the solid. It was triturated with acetonitrile and H₂O to generate the product 5-((4-(cyclohexylamino)-5-fluoro-pyrimidin-2-yl)amino)benzo[c][1,2]oxaborol-1(3H)-ol (195.0 mg, yield 27%) as a white solid. ¹H NMR (300 MHz, DMSO-d₆): δ 9.29 (s, 1H), 8.91 (s, 1H), 7.93 (s, 1H), 7.88 (d, J=4.8 Hz, 1H), 7.60-7.50 (m, 2H), 7.34 (d, J=7.3 Hz, 1H), 4.92 (s, 2H), 4.00-3.80 (m, 1H), 2.00-1.86 (m, 2H), 1.86-1.75 (m, 2H), 1.70-1.60 (m, 1H), 1.40-1.05 (m, 5H) ppm. HPLC purity: 98.92% at 210 nm and 98.60% at 254 nm. MS: m/z=343.2 (M+H)⁺.

Example 60: 5-((5-methyl-4-(phenylamino)pyrimidin-2-yl)amino)benzo[c][1,2]oxaborol-1(3H)-ol

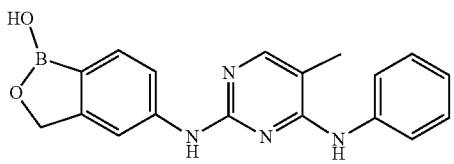 [SMILES: Cc1cnc(Nc2ccc3c(c2)COB3O)nc1Nc1ccccc1]

The title compound was prepared by using the scheme and procedures shown below:

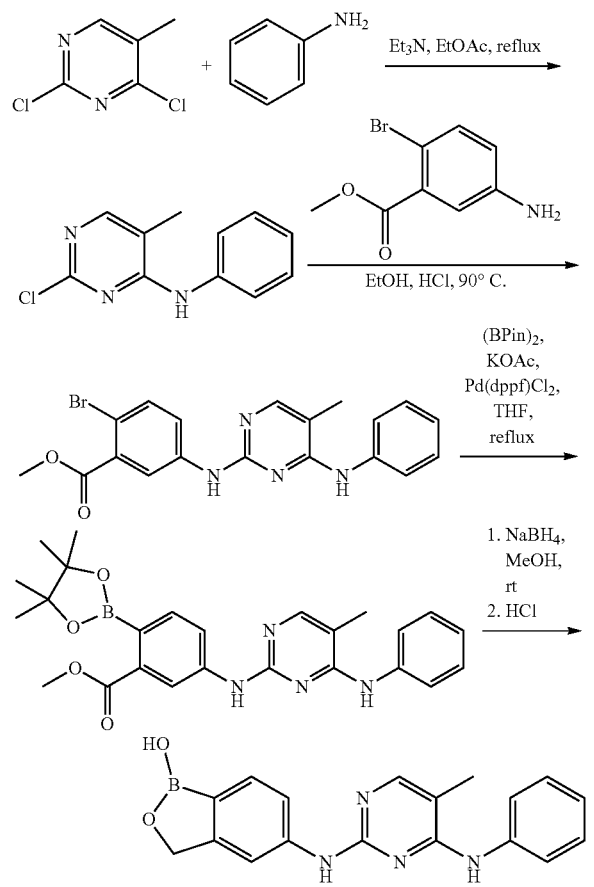

To a solution of 2,4-dichloro-5-methylpyrimidine (1.6 g, 10.0 mmol) in ethyl acetate (20 mL) were added aniline (1.9 g, 20 mmol) and triethylamine (2.0 g, 20.0 mmol) at room temperature. The reaction mixture was refluxed for 1 day and concentrated to provide the residue, which was purified by silica gel chromatography to give 2-chloro-5-methyl-N-phenylpyrimidin-4-amine (1.5 g, yield 54%) as a white solid. ¹H NMR (300 MHz, CDCl₃): δ 8.01 (s, 1H), 7.63 (d, J=8.0 Hz, 2H), 7.39 (t, J=7.8 Hz, 2H), 7.16 (t, J=7.3 Hz, 1H), 6.53 (s, 1H), 2.19 (s, 3H) ppm. To a solution of this intermediate (1.5 g, 6.8 mmol) in ethanol (6 mL) were added methyl 5-amino-2-bromobenzoate (1.6 g, 6.8 mmol) and HCl (1.5 N, 4 mL). The mixture was subjected to microwave irradiation (90° C., 30 minutes), cooled to room temperature and extracted with ethyl acetate. The organic layer was washed with water, brine, and concentrated. The residue obtained was purified by silica gel chromatography by elution with dichloromethane/methanol (100/1 to 10/1, v/v) to give methyl 2-bromo-5-((5-methyl-4-(phenylamino)-pyrimidin-2-yl)amino)benzoate (2.5 g, yield 89%) as a yellow solid. ¹H NMR (300 MHz, DMSO-d₆): δ 11.10 (s, 1H), 10.03 (s, 1H), 8.00 (s, 1H), 7.78 (d, J=2.1 Hz, 1H), 7.59-7.43 (m, 4H), 7.38 (t, J=7.6 Hz, 2H), 7.34-7.23 (m, 1H), 3.79 (s, 4H), 2.18 (s, 3H) ppm. To a solution of this bromo intermediate (1.2 g, 2.9 mmol) in tetrahydrofuran (15 mL) were added potassium acetate (853 mg, 8.7 mmol), (BPin)₂ (1.1 g, 4.5 mmol) and Pd(dppf)Cl₂ (898 mg, 1.1 mmol) at room temperature under N₂. The mixture was refluxed overnight, cooled to room temperature and filtered. The filtrate was concentrated and the residue was purified by silica gel chromatography by elution with dichloromethane/methanol (100/1 to 20/1, v/v) to give methyl 5-((5-methyl-4-(phenylamino)pyrimidin-2-yl)amino)-2-(4,4,5,5-tetramethyl-1,3,2-dioxaborolan-2-yl)benzoate (1.0 g) as a black solid. MS: m/z=461.2 (M+H)⁺. To a solution of this boron intermediate (1.0 g) in methanol (20 mL) was added NaBH₄ (570 mg, 15.0 mmol) at 30° C. in small portions. The mixture was stirred at 30° C. for 30 minutes, and 6N HCl (3 mL) was added. It was stirred for another 20 minutes, neutralized with saturated NaHCO₃ and extracted with ethyl acetate. The organic layer was washed with water, brine, and concentrated under reduced pressure. The residue was purified by silica gel chromatography by elution with dichloromethane/methanol (100/1 to 20/1, v/v) to provide the solid, which was triturated with acetonitrile and water to generate the product (90 mg, yield 9%) as a white solid. ¹H NMR (400 MHz, DMSO-d₆): δ 9.23 (s, 1H), 8.88 (s, 1H), 8.37 (s, 1H), 7.93 (s, 1H), 7.90 (s, 1H), 7.66 (d, J=7.6 Hz, 2H), 7.53-7.41 (m, 2H), 7.37 (t, J=7.9 Hz, 2H), 7.13 (t, J=7.3 Hz, 1H), 4.81 (s, 2H), 2.13 (s, 3H) ppm. HPLC purity: 95.03% at 210 nm and 96.33% at 254 nm. MS: m/z=333.2 (M+H)⁺.

Example 61: Ethyl 3-((2-((1-hydroxy-1,3-dihydrobenzo[c][1,2]oxaborol-5-yl)amino)-5-methylpyrimidin-4-yl)amino)benzoate

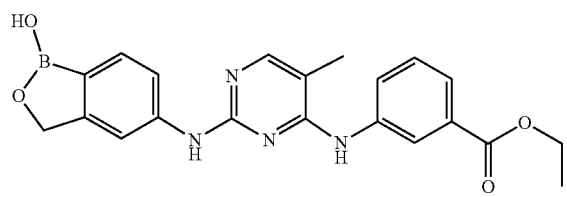 [SMILES: CCOC(=O)c1cccc(Nc2nc(Nc3ccc4c(c3)COB4O)ncc2C)c1]

The title compound was prepared by using the scheme and procedures shown below:

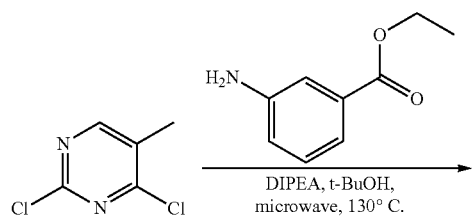

Example 62: 5-((5-fluoro-4-(propylamino)pyrimidin-2-yl)amino)benzo[c][1,2]oxaborol-1(3H)-ol

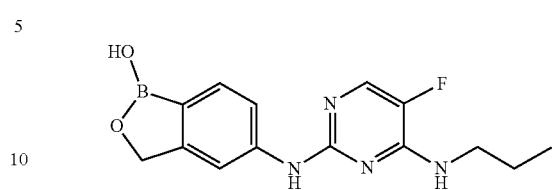

The title compound was prepared by using the scheme and procedures shown below:

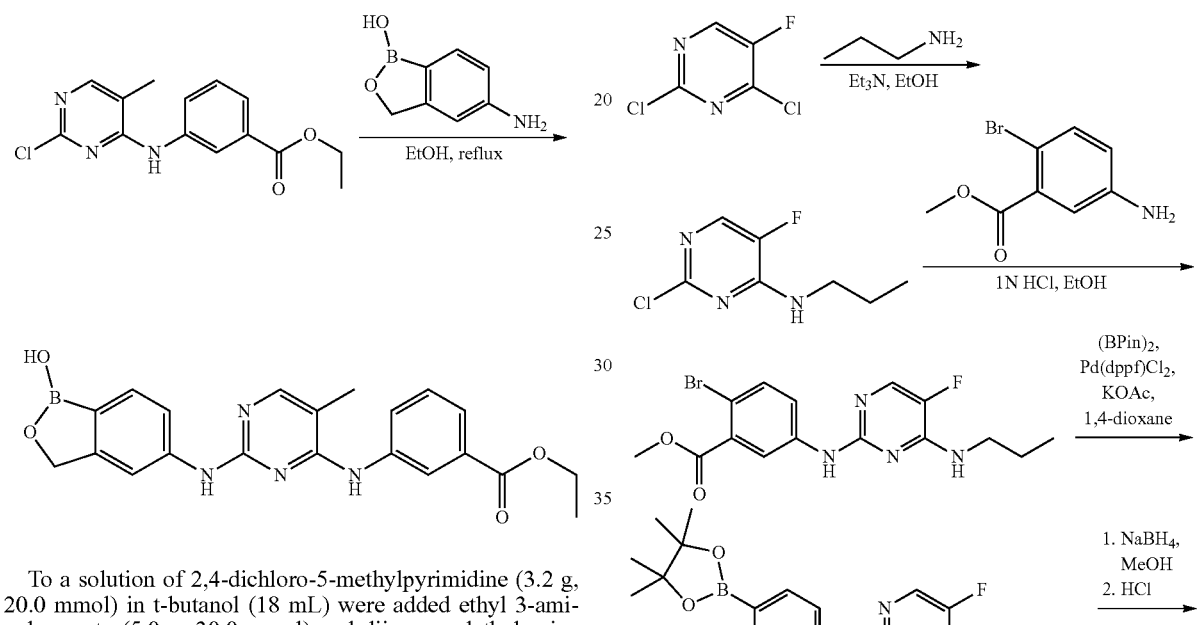

To a solution of 2,4-dichloro-5-methylpyrimidine (3.2 g, 20.0 mmol) in t-butanol (18 mL) were added ethyl 3-aminobenzoate (5.0 g, 30.0 mmol) and diisopropylethylamine (12 mL) at room temperature. The mixture was subjected to microwave irradiation (130° C., 4 hours), cooled to room temperature, and concentrated. The residue was purified by silica gel chromatography by elution with petroleum ether/ethyl acetate (20/1 to 5/1, v/v) to give ethyl 3-((2-chloro-5-methylpyrimidin-4-yl)amino)benzoate (2.0 g, yield 34%) as a yellow solid. $^1$H NMR (300 MHz, CDCl$_3$): δ 8.13-8.05 (m, 3H), 7.82 (d, J=7.7 Hz, 1H), 7.48 (t, J=7.9 Hz, 1H), 6.65 (s, 1H), 4.40 (q, J=7.1 Hz, 2H), 2.22 (s, 3H), 1.42 (t, J=7.1 Hz, 3H) ppm. To a solution of this chloro intermediate (1 g, 3.4 mmol) in ethanol (20 mL) was added 5-aminobenzo[c][1,2]oxaborol-1(3H)-ol (944 mg, 5.1 mmol). The mixture was stirred at 30° C. for 3 days, quenched by 6N HCl and poured into water. Normal work-up as described in Example 41 provided the residue, which was purified by silica gel chromatography by elution with dichloromethane/methanol (100/1 to 10/1, v/v) to give the crude product. It was triturated with acetonitrile and H$_2$O to generate the product ethyl 3-((2-((1-hydroxy-1,3-dihydro-benzo[c][1,2]oxaborol-5-yl)amino)-5-methylpyrimidin-4-yl)amino)benzoate (85.5 mg, yield 6%) as a white solid. $^1$H NMR (400 MHz, DMSO-d$_6$): δ 9.29 (s, 1H), 8.87 (s, 1H), 8.63 (s, 1H), 8.14 (d, J=2.0 Hz, 1H), 8.13-8.06 (m, 1H), 7.97 (s, 1H), 7.81 (s, 1H), 7.70 (d, J=7.8 Hz, 1H), 7.51 (t, J=7.9 Hz, 1H), 7.46 (s, 2H), 4.75 (s, 2H), 4.27 (q, J=7.1 Hz, 2H), 2.14 (s, 3H), 1.25 (t, J=7.1 Hz, 3H) ppm. HPLC purity: 95.65% at 210 nm and 96.51% at 254 nm. MS: m/z=405.2 (M+H)$^+$.

To a solution of 2,4-dichloro-5-fluoropyrimidine (1.6 g, 10.0 mmol) and propan-1-amine (0.6 g, 10 mmol) in ethanol (15 mL) was added triethylamine (2.8 mL, 20.0 mmol) at room temperature. The mixture was stirred at 50° C. for 2 hours and concentrated in vacuo. It was purified by column chromatography (petroleum ether/ethyl acetate=20/1, v/v) to give 2-chloro-5-fluoro-N-propylpyrimidin-4-amine (1.4 g, yield 74%) as a white solid. $^1$H NMR (400 MHz, DMSO-d$_6$): δ 8.20 (br. s, 1H), 8.05 (d, J=3.5 Hz, 1H), 3.33-3.27 (m, 2H), 1.59-1.52 (m, 2H), 0.89 (t, J=7.4 Hz, 3H) ppm. To a solution of this intermediate (1.0 g, 5 mmol) in ethanol (8 mL) were added methyl 5-amino-2-bromobenzoate (1.15 g, 5 mmol) and HCl (1.5 N, 4 mL). It was refluxed for 3 hours and cooled to room temperature. Normal work-up as described in Example 41 provided the residue, which was triturated with ethyl acetate:petroleum ether=1:5 to give methyl 2-bromo-5-((5-fluoro-4-(propylamino)-pyrimidin-2- yl)amino)benzoate (1.15 g, 60% yield) as a white solid. $^1$H NMR (400 MHz, DMSO-d$_6$): δ 9.44 (s, 1H), 8.41 (d, J=2.7 Hz, 1H), 7.90 (d, J=3.8 Hz, 1H), 7.69 (dd, J=8.8, 2.7 Hz, 1H), 7.62-7.51 (m, 2H), 3.85 (s, 3H), 3.38-3.35 (m, 2H), 1.66-1.50 (m, 2H), 0.90 (t, J=7.4 Hz, 3H) ppm. To a solution of this bromo intermediate (1.15 g, 3 mmol) in tetrahydrofuran (20 mL) were added potassium acetate (412 mg, 9 mol), (BPin)$_2$ (1.1 g, 4.2 mmol) and Pd(dppf)Cl$_2$ (937 mg, 1.2 mmol) at room temperature under N$_2$. The mixture was stirred at 100° C. overnight, cooled to room temperature and then filtered. The filtrate was concentrated and the residue was purified by silica gel chromatography by elution with petroleum ether/ethyl acetate (100/1 to 20/1, v/v) to give methyl 5-((5-fluoro-4-(propylamino)pyrimidin-2-yl)amino)-2-(4,4,5,5-tetramethyl-1,3,2-dioxaborolan-2-yl)benzoate (0.8 g) as a white solid. $^1$H NMR (400 MHz, DMSO-d$_6$): δ 10.69 (s, 1H), 9.10 (s, 1H), 8.39 (d, J=2.1 Hz, 1H), 8.23 (d, J=5.3 Hz, 1H), 7.74 (dd, J=8.1, 2.1 Hz, 1H), 7.52 (d, J=8.1 Hz, 1H), 3.88 (s, 3H), 3.51-3.46 (m, 2H), 1.73-1.62 (m, 2H), 1.36 (s, 12H), 0.95 (t, J=7.4 Hz, 3H) ppm. To a solution of this boron intermediate (800 mg) in methanol (15 mL) was added NaBH$_4$ (532 mg, 14.0 mmol) at 30° C. in small portions. The mixture was stirred at 30° C. for 30 minutes, and 6N HCl (3 mL) was added. It was stirred for another 20 minutes, neutralized with saturated NaHCO$_3$ and filtered. The filter cake was triturated with methanol and water (v/v=5:1) to give the product 5-((5-fluoro-4-(propylamino)pyrimidin-2-yl)amino)benzo[c][1,2]oxaborol-1(3H)-ol (85.1 mg, yield 28%) as a white solid. $^1$H NMR (400 MHz, DMSO-d$_6$): δ 10.81 (s, 1H), 9.14 (s, 1H), 8.22 (d, J=5.3 Hz, 1H), 7.76-7.73 (m, 2H), 7.53 (dd, J=8.1, 1.4 Hz, 1H), 4.97 (s, 2H), 3.43-3.37 (m, 2H), 1.66-1.60 (m, 2H), 0.92 (t, J=7.4 Hz, 3H) ppm. HPLC purity: 97.39% at 210 nm and 97.00% at 254 nm. MS: m/z=303.2 (M+H)$^+$.

Example 63: 5-((4-(sec-butylamino)-5-fluoropyrimidin-2-yl)amino)benzo[c][1,2]oxaborol-1(3H)-ol

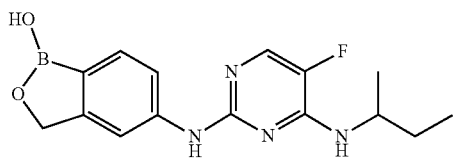

The title compound was prepared by using the scheme and procedures shown below:

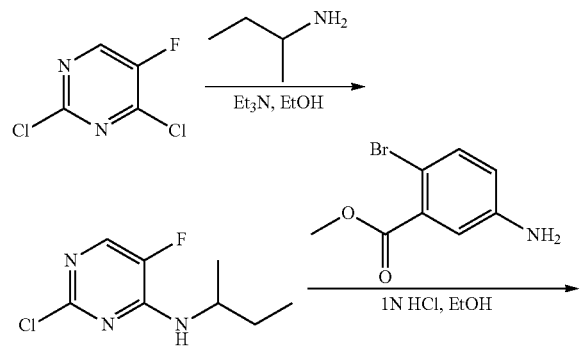

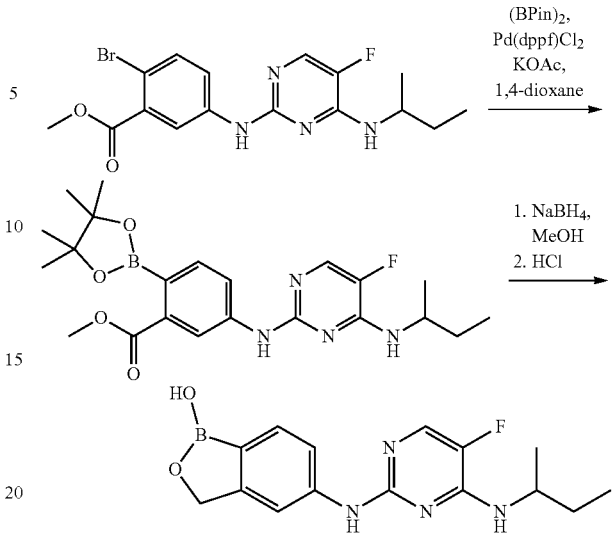

To a solution of 2,4-dichloro-5-fluoropyrimidine (1.6 g, 10.0 mmol) and butan-2-amine (0.73 g, 10 mmol) in ethanol (15 mL) was added triethylamine (2.8 mL, 20.0 mmol) at room temperature. The mixture was stirred at 50° C. for 2 hours and concentrated in vacuo. The residue was purified by column chromatography (petroleum ether/ethyl acetate=20/1, v/v) to give N-(sec-butyl)-2-chloro-5-fluoropyrimidin-4-amine (1.8 g, yield 88%) as a white solid. $^1$H NMR (400 MHz, DMSO-d$_6$): δ 8.04 (d, J=3.6 Hz, 1H), 7.96 (d, J=8.0 Hz, 1H), 4.06-3.97 (m, 1H), 1.58-1.51 (m, 2H), 1.15 (d, J=8.0 Hz, 3H), 0.86 (t, J=7.4 Hz, 3H) ppm. To a solution of this intermediate (1.02 g, 5 mmol) in ethanol (8 mL) were added methyl 5-amino-2-bromobenzoate (1.15 g, 5 mmol) and HCl (1.5 N, 4 mL). The reaction was refluxed for 3 hours. Normal work-up as described in Example 41 provided the residue, which was triturated with ethyl acetate:petroleum ether=1:5 to give the product (1.6 g, 80% yield) as a white solid. $^1$H NMR (400 MHz, DMSO-d$_6$): δ 9.92 (s, 1H), 8.34 (d, J=2.0 Hz, 1H), 8.01 (d, J=8.0 Hz, 1H), 7.95 (br. s, 1H), 7.65-7.59 (m, 2H), 4.14-4.04 (m, 1H), 3.86 (s, 3H), 1.66-1.51 (m, 2H), 1.20 (d, J=6.6 Hz, 3H), 0.88 (t, J=7.4 Hz, 3H) ppm. To a solution of this bromo intermediate (1.15 g, 3 mmol) in tetrahydrofuran (20 mL) were added potassium acetate (412 mg, 9 mol), (BPin)$_2$ (1.1 g, 4.2 mmol) and Pd(dppf)Cl$_2$ (937 mg, 1.2 mmol) at room temperature under N$_2$. The mixture was stirred at 100° C. overnight, cooled to room temperature and filtered. The filtrate was concentrated and the residue was purified by silica gel chromatography by elution with petroleum ether/ethyl acetate (100/1 to 20/1) to give methyl 5-((4-(sec-butylamino)-5-fluoropyrimidin-2-yl)amino)-2-(4,4,5,5-tetramethyl-1,3,2-dioxaborolan-2-yl)-benzoate (0.7 g, yield 52%) as a white solid. $^1$H NMR (400 MHz, DMSO-d$_6$): δ 9.37 (s, 1H), 8.44 (d, J=2.0 Hz, 1H), 7.89 (d, J=3.9 Hz, 1H), 7.77 (dd, J=8.2, 2.1 Hz, 1H), 7.35 (d, J=8.1 Hz, 1H), 7.29 (d, J=8.3 Hz, 1H), 4.18-4.14 (m, 1H), 3.81 (s, 3H), 1.66-1.51 (m, 2H), 1.30 (s, 12H), 1.20 (d, J=6.6 Hz, 3H), 0.89 (t, J=7.4 Hz, 3H) ppm. To a solution of this boron intermediate (700 mg, 1.7 mmol) in methanol (15 mL) was added NaBH$_4$ (532 mg, 14.0 mmol) at 30° C. in small portions. The reaction mixture was stirred at 30° C. for 30 minutes, and then 6N HCl (3 mL) was added. It was stirred for another 20 minutes, neutralized with saturated NaHCO$_3$ and filtered. The filter cake was purified by trituration with methanol and water (v/v=5:1) to give the product 5-((4-(sec-butylamino)-5-fluoropyrimidin-2-yl)amino)benzo[c][1,2]oxaborol-1(3H)-ol (167 mg, yield %) as a white solid. $^1$H NMR (400 MHz, DMSO-$d_6$): δ 9.24 (s, 1H), 8.98 (s, 1H), 7.92 (d, J=3.6 Hz, 1H), 7.88 (d, J=3.6 Hz, 1H), 7.60-7.55 (m, 2H), 7.27 (d, J=8.0 Hz, 1H), 4.91 (s, 2H), 4.10-4.07 (m, 1H), 1.66-1.61 (m, 1H), 1.55-1.50 (m, 1H), 1.19 (d, J=6.4 Hz, 3H), 0.90 (t, J=7.4 Hz, 3H) ppm. HPLC purity: 98.82% at 210 nm and 98.71% at 254 nm. MS: m/z=317.2 (M+H)$^+$.

Example 64: 5-((4-(benzylamino)-5-fluoropyrimidin-2-yl)amino)benzo[c][1,2]oxaborol-1(3H)-ol

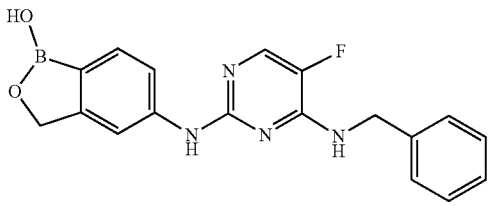 [SMILES: OB1OCc2cc(Nc3ncc(F)c(NCc4ccccc4)n3)ccc21]

The title compound was prepared by using the scheme and procedures shown below:

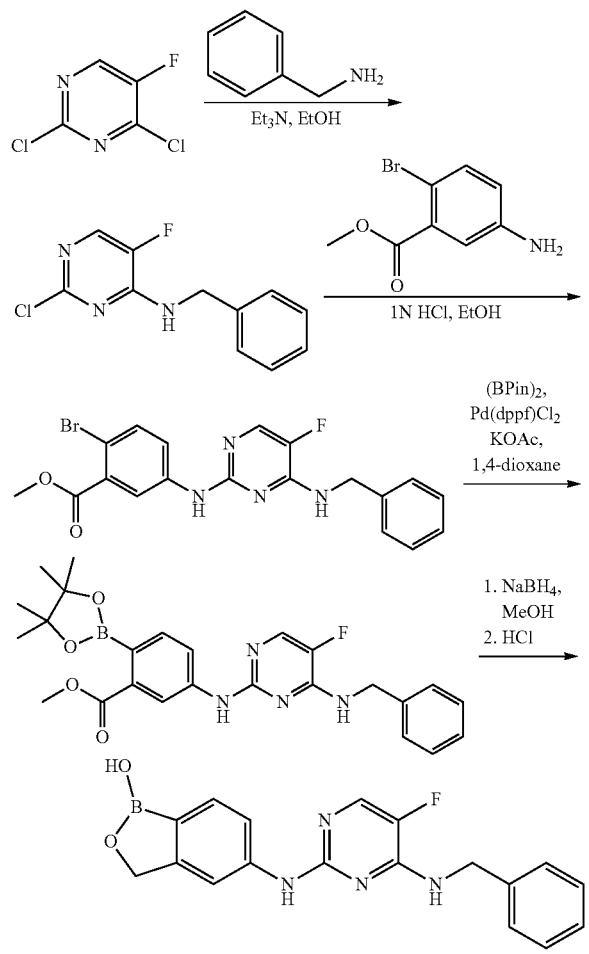

To a solution of 2,4-dichloro-5-fluoropyrimidine (1.6 g, 10.0 mmol) and benzylamine (0.73 g, 10 mmol) in ethanol (15 mL) was added triethylamine (2.8 mL, 20.0 mmol) at room temperature. The mixture was stirred at 50° C. for 2 hours and concentrated in vacuo. The residue was purified by column chromatography (petroleum ether/ethyl acetate=20/1, v/v) to give N-benzyl-2-chloro-5-fluoropyrimidin-4-amine (1.6 g, yield 68%) as a white solid. $^1$H NMR (400 MHz, DMSO-$d_6$): δ 8.75 (t, J=5.7 Hz, 1H), 8.11 (d, J=3.4 Hz, 1H), 7.41-7.20 (m, 5H), 4.57 (d, J=6.1 Hz, 2H) ppm. To a solution of this intermediate (1.19 g, 5 mmol) in ethanol (8 mL) were added methyl 5-amino-2-bromobenzoate (1.15 g, 5 mmol) and HCl (1.5 N, 4 mL). The reaction mixture was refluxed for 3 hours and cooled to room temperature. Normal work-up as described in Example 41 provided a residue, which was triturated with ethyl acetate:petroleum ether=1:5 to give methyl 5-((4-(benzylamino)-5-fluoropyrimidin-2-yl)amino)-2-bromobenzoate (1.25 g, 58% yield) as a white solid. $^1$H NMR (400 MHz, DMSO-$d_6$): δ 9.47 (s, 1H), 8.30 (d, J=2.7 Hz, 1H), 8.21 (t, J=6.1 Hz, 1H), 7.96 (d, J=3.7 Hz, 1H), 7.66 (dd, J=8.9, 2.7 Hz, 1H), 7.50 (d, J=8.8 Hz, 1H), 7.40-7.26 (m, 4H), 7.27-7.18 (m, 1H), 4.64 (d, J=6.1 Hz, 2H), 3.77 (s, 3H) ppm. To a solution of this bromo intermediate (1.25 g, 3 mmol) in tetrahydrofuran (20 mL) were added potassium acetate (882 mg, 9 mol), (BPin)$_2$ (1.1 g, 4.2 mmol) and Pd(dppf)Cl$_2$ (937 mg, 1.2 mmol) at room temperature under N$_2$. The mixture was stirred at 100° C. overnight, cooled to room temperature and filtered. The filtrate was concentrated and the residue was purified by silica gel chromatography by elution with petroleum ether/ethyl acetate (100/1 to 20/1, v/v) to give methyl 5-((4-(benzylamino)-5-fluoropyrimidin-2-yl)amino)-2-(4,4,5,5-tetramethyl-1,3,2-dioxaborolan-2-yl)benzoate (0.62 g, yield 49%) as a white solid. $^1$H NMR (400 MHz, DMSO-$d_6$): δ 9.46 (s, 1H), 8.42 (d, J=2.1 Hz, 1H), 8.19 (t, J=6.1 Hz, 1H), 8.01 (d, J=3.7 Hz, 1H), 7.82 (dd, J=8.2, 2.1 Hz, 1H), 7.42 (d, J=7.2 Hz, 2H), 7.40-7.32 (m, 3H), 7.28 (t, J=7.2 Hz, 1H), 4.71 (d, J=6.1 Hz, 2H), 3.80 (s, 3H), 1.34 (s, 12H) ppm. To a solution of this boron intermediate (620 mg, 1.3 mmol) in methanol (15 mL) was added NaBH$_4$ (532 mg, 14.0 mmol) at 30° C. in small portions. The reaction was stirred at 30° C. for 30 minutes, and 6N HCl (3 mL) was added. It was stirred for another 20 minutes, neutralized with saturated NaHCO$_3$ and filtered to collect the solid. The filter cake was purified by trituration with methanol and water (v/v=5:1) to give the product 5-((4-(benzylamino)-5-fluoropyrimidin-2-yl)amino)benzo[c][1,2]-oxaborol-1(3H)-ol (172 mg, yield 37%) as a white solid. $^1$H NMR (400 MHz, DMSO-$d_6$): δ 9.27 (s, 1H), 8.89 (s, 1H), 8.13 (t, J=6.0 Hz, 1H), 7.95 (d, J=3.7 Hz, 1H), 7.79 (s, 1H), 7.52-7.40 (m, 2H), 7.39-7.29 (m, 4H), 7.28-7.20 (m, 1H), 4.82 (s, 2H), 4.64 (d, J=6.1 Hz, 2H) ppm. HPLC purity: 98.96% at 210 nm and 99.07% at 254 nm. MS: m/z=351.1 (M+H)$^+$.

Example 65: 5-((4-(cyclopentylamino)-5-fluoropyrimidin-2-yl)amino)benzo[c][1,2]oxaborol-1(3H)-ol

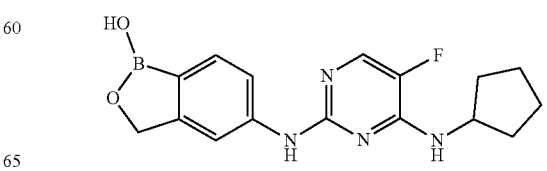

The title compound was prepared by using the scheme and procedures shown below:

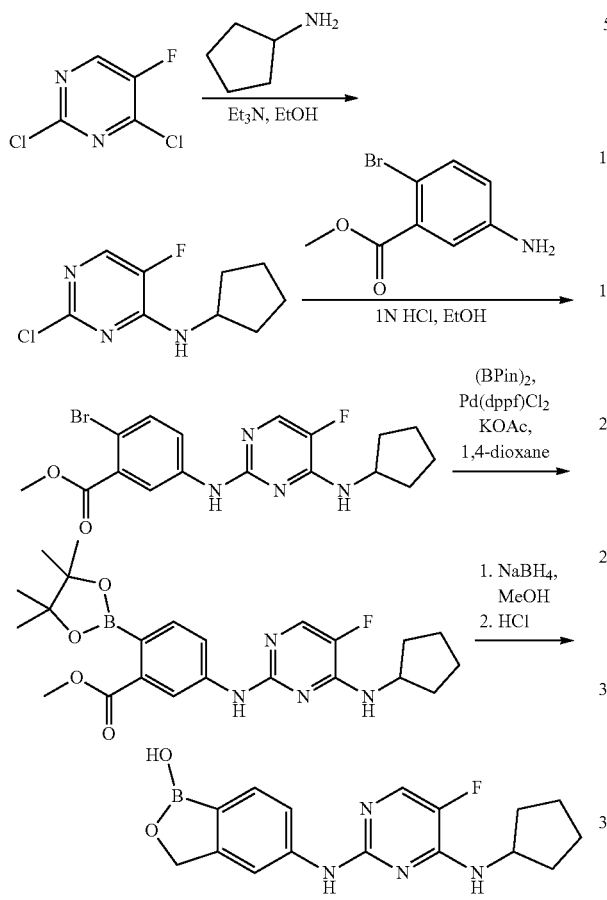

To a solution of 2,4-dichloro-5-fluoropyrimidine (1.6 g, 10.0 mmol) and cyclopentylamine (0.73 g, 10 mmol) in ethanol (15 mL) was added triethylamine (2.8 mL, 20.0 mmol) at room temperature. The reaction mixture was stirred at 50° C. for 2 hours and concentrated in vacuo. The residue was purified by column chromatography (petroleum ether/ethyl acetate=10/1, v/v) to give 2-chloro-N-cyclopentyl-5-fluoropyrimidin-4-amine (1.41 g, yield 68%) as a white solid. $^1$H NMR (400 MHz, CDCl$_3$): δ 7.83 (d, J=2.9 Hz, 1H), 5.18 (s, 1H), 4.50-4.35 (m, 1H), 2.19-2.05 (m, 2H), 1.80-1.59 (m, 4H), 1.55-1.40 (m, 2H) ppm. To a solution of this intermediate (1.41 g, 5 mmol) in ethanol (8 mL) were added methyl 5-amino-2-bromobenzoate (1.15 g, 5 mmol) and HCl (1.5 N, 4 mL). The reaction mixture was refluxed for 3 hours and cooled to room temperature. Normal work-up as described in Example 41 generated the residue, which was triturated with ethyl acetate:petroleum ether (1:5, v/v) to give methyl 2-bromo-5-((4-(cyclopentylamino)-5-fluoropyrimidin-2-yl)amino)-benzoate (1.55 g, 58% yield) as a white solid. $^1$H NMR (400 MHz, DMSO-d$_6$): δ 10.13 (s, 1H), 8.32 (br. s, 1H), 8.31 (d, J=2.5 Hz, 1H), 8.15-7.96 (m, 1H), 7.74-7.53 (m, 2H), 4.40-4.25 (m, 1H), 1.99-1.89 (m, 2H), 1.76-1.67 (m, 2H), 1.67-1.52 (m, 4H) ppm. To a solution of this bromo inter-mediate (1.23 g, 3 mmol) in 1,4-dioxane (20 mL) were added potassium acetate (882 mg, 9 mol), (BPin)$_2$ (1.1 g, 4.2 mmol) and Pd(dppf)Cl$_2$ (937 mg, 1.2 mmol) at room temperature under N$_2$. The mixture was stirred at 100° C. overnight, cooled to room temperature and filtered. The filtrate was concentrated and the residue was purified by silica gel chromatography by elution with petroleum ether/ethyl acetate (100/1 to 20/1, v/v) to give methyl 5-((4-(cyclopentylamino)-5-fluoropyrimidin-2-yl)amino)-2-(4,4,5,5-tetramethyl-1,3,2-dioxa-borolan-2-yl)benzoate (0.43 g, yield 31%) as a white solid. $^1$H NMR (400 MHz, DMSO-d$_6$): δ 9.38 (s, 1H), 8.44 (d, J=2.0 Hz, 1H), 7.89 (d, J=3.8 Hz, 1H), 7.77 (dd, J=8.2, 2.1 Hz, 1H), 7.39 (dd, J=35.7, 7.6 Hz, 2H), 4.42-4.36 (m, 1H), 3.80 (s, 3H), 2.03-1.94 (m, 2H), 1.74-1.67 (m, 2H), 1.62-1.52 (m, 4H), 1.29 (s, 12H) ppm. To a solution of this boron intermediate (620 mg, 1.3 mmol) in methanol (15 mL) was added NaBH$_4$ (532 mg, 14.0 mmol) at 30° C. in small portions. The reaction was stirred at 30° C. for 30 minutes, and 6N HCl (3 mL) was added. It was stirred for another 20 minutes, neutralized with saturated NaHCO$_3$ and filtered to collect the solid. The filter cake was triturated with methanol and water (v/v=5:1) to give the product 5-((4-(cyclopentylamino)-5-fluoropyrimidin-2-yl)amino)benzo[c][1,2]oxaborol-1(3H)-ol (96 mg, yield 27%) as a white solid. $^1$H NMR (400 MHz, DMSO-d$_6$): δ 9.27 (s, 1H), 8.91 (s, 1H), 7.98 (s, 1H), 7.89 (d, J=3.8 Hz, 1H), 7.55 (s, 2H), 7.42 (d, J=7.0 Hz, 1H), 4.91 (s, 2H), 4.42-4.26 (m, 1H), 2.09-1.90 (m, 2H), 1.82-1.65 (m, 2H), 1.67-1.46 (m, 4H) ppm. HPLC purity: 96.11% at 210 nm and 95.72% at 254 nm. MS: m/z=329.1 (M+H)$^+$.

Example 66: 5-((5-chloro-4-(methylthio)pyrimidin-2-yl)amino)benzo[c][1,2]oxaborol-1(3H)-ol

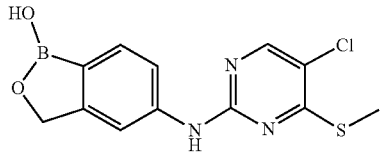 [SMILES: CSc1nc(Nc2ccc3c(c2)COB3O)ncc1Cl]

The title compound was prepared by using the scheme and procedures shown below:

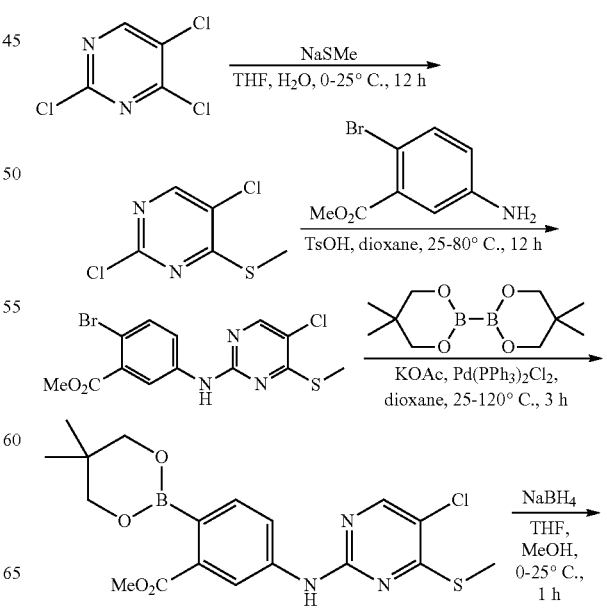

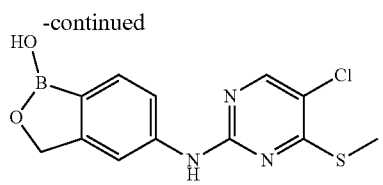

To a mixture of 2,4,5-trichloropyrimidine (80 g, 436.15 mmol, 1 eq) in tetrahydrofuran (800 mL) and H$_2$O (800 mL) was added NaSCH$_3$ (36.68 g, 523.38 mmol, 33.35 mL, 1.2 equivalents) at 0° C. under N$_2$. The mixture was stirred at 25° C. for 12 hours. The reaction mixture was added with H$_2$O (100 mL), and extracted with ethyl acetate (200 mL×3). The combined organic layers were washed with brine (200 mL×2), dried over Na$_2$SO$_4$, filtered and concentrated under reduced pressure to give a residue. The residue was purified by column chromatography (SiO$_2$, petroleum ether/ethyl acetate=10/1 to 5/1, v/v) to give 2,5-dichloro-4-(methylthio) pyrimidine (72 g, 369.10 mmol, 84.63% yield) as a white solid. $^1$H NMR (CDCl$_3$, 400 MHz): δ 8.22 (s, 1H), 2.60 (s, 3H) ppm. To a mixture of methyl 5-amino-2-bromobenzoate (5 g, 21.73 mmol, 1 equivalents) and 2,5-dichloro-4-(methylthio)-pyrimidine (5.09 g, 26.08 mmol, 1.2 equivalents) in 1,4-dioxane (100 mL) was added p-toluenesulfonic acid (7.49 g, 43.47 mmol, 2 equivalents) at 25° C. under N$_2$. The mixture was heated to 80° C. and stirred for 12 hours. The reaction mixture was filtered and the filter cake was washed by ethyl acetate (20 mL×3) to give methyl 2-bromo-5-((5-chloro-4-(methylthio)pyrimidin-2-yl)amino)benzoate (4 g, 10.29 mmol, 47.35% yield) as a white solid. $^1$H NMR (DMSO-d$_6$, 400 MHz): δ 10.11 (s, 1H), 8.39 (s, 1H), 8.29 (d, J=3.2 Hz, 1H), 7.75-7.60 (m, 2H), 3.83 (s, 3H), 2.57 (s, 3H) ppm. To a mixture of this bromo intermediate (2 g, 5.15 mmol, 1 equivalents) and 2-(5,5-dimethyl-1,3,2-dioxaborinan-2-yl)-5,5-dimethyl-1,3,2-dioxaborinane (2.91 g, 12.86 mmol, 2.5 equivalents) in 1,4-dioxane (40 mL) were added potassium acetate (1.26 g, 12.86 mmol, 2.5 equivalents) and Pd(PPh$_3$)$_2$Cl$_2$ (722.36 mg, 1.03 mmol, 0.2 equivalents) at 25° C. under N$_2$. The mixture was heated to 120° C. and stirred for 3 hours. The reaction mixture was filtered and concentrated under reduced pressure to give a residue. The residue was purified by column chromatography (SiO$_2$, petroleum ether/ethyl acetate=10/1 to 5/1, v/v) to give methyl 5-((5-chloro-4-(methylthio)pyrimidin-2-yl)amino)-2-(5,5-dimethyl-1,3,2-dioxaborinan-2-yl)benzoate (1.8 g, 4.27 mmol, 82.95% yield) as a yellow solid. $^1$H NMR (CDCl$_3$, 400 MHz): δ 8.39 (s, 1H), 8.05 (s, 1H), 7.58 (d, J=8.0 Hz, 1H), 7.49 (d, J=8.4 Hz, 1H), 7.33 (s, 1H), 3.93 (s, 3H), 3.66 (s, 4H), 2.60 (s, 3H), 1.12 (s, 6H) ppm. To a mixture of this boron intermediate (500 mg, 1.15 mmol, 1 equivalents) in tetrahydrofuran (10 mL) and methanol (1 mL) was added NaBH$_4$ (108 mg, 2.87 mmol, 2.5 equivalents) at 0° C. under N$_2$. The mixture was stirred at 25° C. for 1 hours. The reaction mixture was adjusted to pH 5 with 2N HCl, and extracted with ethyl acetate (20 mL×3). The combined organic layers were washed with brine (20 mL×2), dried over Na$_2$SO$_4$, filtered and concentrated under reduced pressure to give a residue. The residue was purified by prep-HPLC (column: Nano-micro Kromasil C18 100*30 mm Sum; mobile phase: [water (0.1% trifluoroacetic acid)-acetonitrile]; B %: 40%-65%, 10 minutes). The eluent was directly dried over lyophilization to give the product 5-((5-chloro-4-(methylthio)pyrimidin-2-yl)amino)benzo[c][1,2]oxaborol-1(3H)-ol (101 mg, 328.39 mol, 28.6% yield) as a white solid. $^1$H NMR (DMSO-d$_6$, 400 MHz): δ 9.99 (s, 1H), 8.97 (br. s, 1H), 8.31 (s, 1H), 7.91 (s, 1H), 7.65-7.60 (m, 2H), 4.97 (s, 2H), 2.60 (s, 3H) ppm. MS (ESI): m/z=306.0 [M−H]$^-$. HPLC purity: 98.75% (220 nm), and 98.16% (254 nm).

Example 67: 5-((4-((2-cyclopropylethyl)amino)-5-fluoropyrimidin-2-yl)amino)benzo[c][1,2]oxaborol-1(3H)-ol

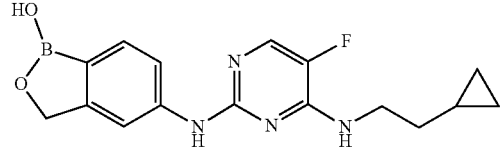 [SMILES: OB1OCc2cc(Nc3ncc(F)c(NCCC4CC4)n3)ccc21]

The title compound was prepared by using the scheme and procedure shown below:

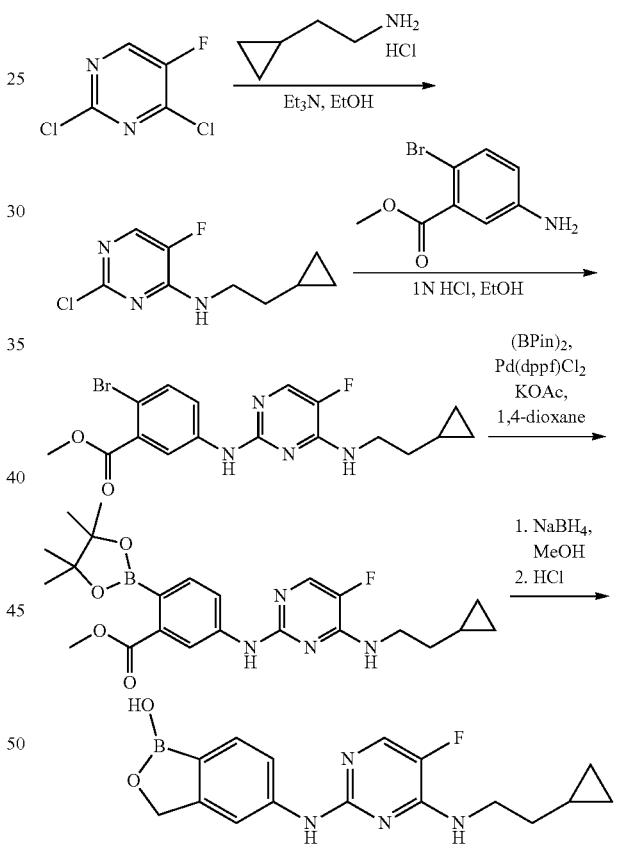

To a solution of 2,4-dichloro-5-fluoropyrimidine (1.6 g, 10.0 mmol) and 2-cyclopropylethan-1-amine HCl salt (1.21 g, 10 mmol) in ethanol (15 mL) was added triethylamine (2.8 mL, 20.0 mmol) at room temperature. The reaction mixture was stirred at 50° C. for 2 hours and concentrated in vacuo. It was purified by column chromatography to give 2-chloro-N-(2-cyclopropylethyl)-5-fluoropyrimidin-4-amine (1.72 g, yield 80%) as an off-white solid. $^1$H NMR (400 MHz, CDCl$_3$): δ 7.75 (d, J=2.8 Hz, 1H), 5.31 (br. s, 1H), 3.53-3.48 (m, 2H), 1.45 (q, J=7.0 Hz, 2H), 0.69-0.54 (m, 1H), 0.41-0.39 (m, 2H), 0.03 to −0.01 (m, 2H) ppm. To a solution of this intermediate (1.72 g, 8 mmol) in ethanol (20 mL) were added methyl 5-amino-2-bromobenzoate (1.8 g, 8 mmol) and HCl (1.5 N, 4 mL). The reaction mixture was refluxed for 3 hours. Normal work-up as described in Example 41 provided the residue, which was triturated with ethyl acetate:petroleum ether=1:5 to give methyl 2-bromo-5-((4-((2-cyclopropylethyl)amino)-5-fluoropyrimidin-2-yl)amino)-benzoate (2.05 g, 62.8% yield) as a white solid. ¹H NMR (400 MHz, CDCl₃): δ 10.88 (s, 1H), 8.17 (d, J=2.6 Hz, 1H), 7.58 (d, J=4.3 Hz, 1H), 7.52 (d, J=8.7 Hz, 1H), 7.42 (d, J=4.0 Hz, 1H), 6.54 (br. s, 1H), 3.81 (s, 3H), 3.66-3.59 (m, 2H), 1.51 (q, J=6.9 Hz, 2H), 0.63-0.58 (m, 1H), 0.44-0.39 (m, 2H), 0.01 to −0.03 (m, 2H) ppm. To a solution of this bromo intermediate (1.15 g, 3 mmol) in tetrahydrofuran (20 mL) were added potassium acetate (412 mg, 9 mol), (BPin)₂ (1.1 g, 4.2 mmol) and Pd(dppf)Cl₂ (937 mg, 1.2 mmol) at room temperature under N₂. The mixture was stirred at 100° C. overnight, cooled to room temperature and filtered. The filtrate was concentrated and the residue was purified by silica gel chromatography by elution with petroleum ether/ethyl acetate (100/1 to 20/1, v/v) to give methyl 5-((4-((2-cyclopropylethyl)amino)-5-fluoropyrimidin-2-yl)amino)-2-(4,4,5,5-tetramethyl-1,3,2-dioxaboro-lan-2-yl)benzoate (0.7 g, 52% yield) as a white solid. ¹H NMR (400 MHz, CDCl₃): δ 8.18 (d, J=2.1 Hz, 1H), 7.66 (d, J=3.4 Hz, 1H), 7.59 (dd, J=8.1, 2.2 Hz, 1H), 7.34 (d, J=8.1 Hz, 1H), 7.22 (br. s, 1H), 5.08-5.02 (m, 1H), 3.78 (s, 3H), 3.54-3.49 (m, 2H), 1.45 (q, J=6.9 Hz, 2H), 1.30 (s, 12H), 0.68-0.62 (m, 1H), 0.39-0.37 (m, 2H), 0.01 to −0.02 (m, 2H) ppm. To a solution of this boron intermediate (700 mg, 1.7 mmol) in methanol (15 mL) was added NaBH₄ (532 mg, 14.0 mmol) at 30° C. in small portions. It was stirred at 30° C. for 30 minutes, and 6N HCl (3 mL) was added. The mixture was stirred for another 20 minutes, neutralized with saturated NaHCO₃ and filtered to collect the solid. The filter cake was triturated with methanol and water (v/v=5:1) to give the product 5-((4-((2-cyclopropylethyl)amino)-5-fluoropyrimidin-2-yl)amino)benzo[c][1,2]-oxaborol-1(3H)-ol (167 mg) as a white solid. ¹H NMR (400 MHz, DMSO-d₆): δ 9.24 (s, 1H), 8.90 (s, 1H), 7.91-7.87 (m, 2H), 7.61-7.50 (m, 3H), 4.91 (s, 2H), 3.47-3.44 (m, 2H), 1.53-1.47 (m, 2H), 0.80-0.65 (m, 1H), 0.45-0.40 (m, 2H), 0.09 to 0.05 (m, 2H) ppm. HPLC purity: 96.41% at 210 nm and 96.31% at 254 nm. MS: m/z=329.2 (M+H)⁺.

Example 68: 5-((5-methyl-4-((1-phenylethyl)amino)pyrimidin-2-yl)amino)benzo[c][1,2]oxaborol-1(3H)-ol

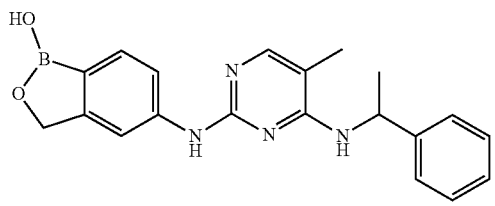 [SMILES: Cc1cnc(Nc2ccc3c(c2)COB3O)nc1NC(C)c1ccccc1]

The title compound was prepared by using the scheme and procedure shown below:

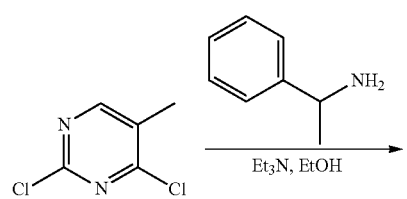

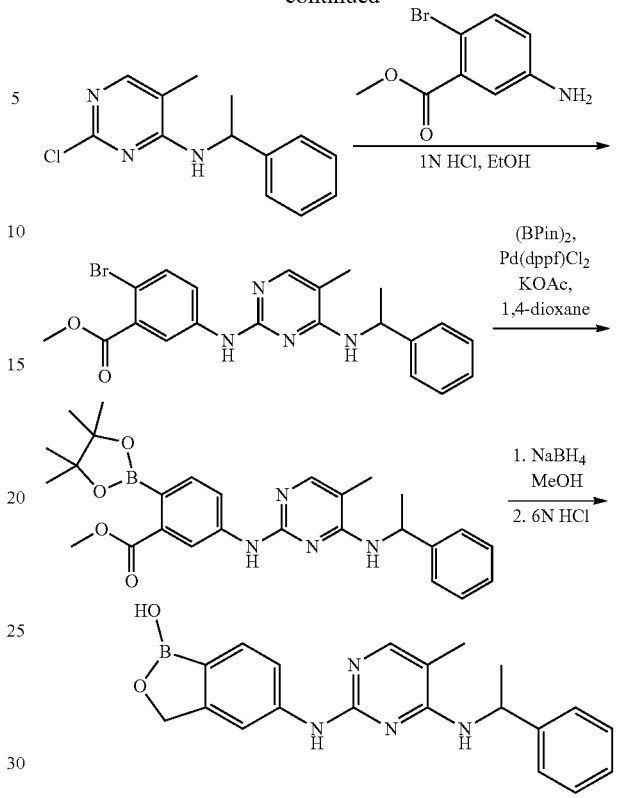

To a solution of 2,4-dichloro-5-methylpyrimidine (1.6 g, 10.0 mmol) and 1-phenylethan-1-amine (1.21 g, 10 mmol) in ethanol (15 mL) was added triethylamine (2.8 mL, 20.0 mmol) at room temperature. The mixture was stirred at 50° C. for 2 hours and concentrated in vacuo. The residue was washed with water and triturated with petroleum ether/ethyl acetate (10:1, v/v) to give 2-chloro-5-methyl-N-(1-phenylethyl)pyrimidin-4-amine (1.8 g, yield 75%) as a white solid. ¹H NMR (400 MHz, CDCl₃): δ 7.74 (s, 1H), 7.34-7.26 (m, 4H), 7.25-7.20 (m, 1H), 5.41-5.34 (m, 1H), 4.82 (d, J=6.9 Hz, 1H), 1.92 (s, 3H), 1.54 (d, J=6.8 Hz, 3H) ppm. To a solution of this intermediate (1.8 g, 7.2 mmol) in ethanol (20 mL) were added methyl 5-amino-2-bromobenzoate (1.67 g, 7.2 mmol) and HCl (1.5 N, 4 mL). The mixture was refluxed for 3 hours and cooled to room temperature. Normal work-up as described in Example 41 generated the residue, which was triturated with ethyl acetate:petroleum ether=1:5 to give methyl 2-bromo-5-((5-methyl-4-((1-phenylethyl)amino)pyrimidin-2-yl)amino)-benzoate (2.4 g, 75% yield) as an off-white solid. ¹H NMR (400 MHz, CDCl₃): δ 10.76 (s, 1H), 8.12 (d, J=2.7 Hz, 1H), 7.46 (d, J=8.7 Hz, 1H), 7.36 (s, 1H), 7.30-7.20 (m, 6H), 6.05 (d, J=7.3 Hz, 1H), 5.37-5.30 (m, 1H), 3.78 (s, 3H), 2.03 (s, 3H), 1.62 (d, J=6.9 Hz, 3H) ppm. To a solution of this bromo intermediate (1.23 g, 3 mmol) in tetrahydrofuran (20 mL) were added potassium acetate (882 mg, 9 mol), (BPin)₂ (1.1 g, 4.2 mmol) and Pd(dppf)Cl₂ (937 mg, 1.2 mmol) at room temperature under N₂. The mixture was stirred at 100° C. overnight, cooled to room temperature and then filtered. The filtrate was concentrated and the residue was purified by silica gel chromatography by elution with dichloromethane and methanol (100/1 to 20/1, v/v) to give methyl 5-((5-methyl-4-((1-phenylethyl)amino)pyrimidin-2-yl)amino)-2-(4,4,5,5-tetramethyl-1,3,2-dioxaborolan-2-yl)benzoate (1.1 g, crude) as a brown solid. LCMS:

m/z=489.3 (M+H)+. To a solution of this boron intermediate (1.1 g, crude) in methanol (15 mL) was added NaBH4 (532 mg, 14.0 mmol) at 30° C. in portions. It was stirred at 30° C. for 30 minutes, and 6N HCl (3 mL) was added. It was stirred for another 20 minutes, neutralized with saturated NaHCO3 and filtered to collect the solid. The filter cake was purified by column chromatography by elution with dichloromethane and methanol (100:1 to 40:1, v/v) to give the product 5-((5-methyl-4-((1-phenylethyl)amino)pyrimidin-2-yl)amino)benzo-[c][1,2]oxaborol-1(3H)-ol (60 mg) as a white solid. $^1$H NMR (400 MHz, DMSO-d$_6$): $^1$H NMR (400 MHz, DMSO-d$_6$): δ 9.01 (s, 1H), 8.85 (s, 1H), 7.76 (s, 1H), 7.71 (s, 1H), 7.49 (d, J=8.1 Hz, 1H), 7.46-7.39 (m, 3H), 7.32 (t, J=7.7 Hz, 2H), 7.19 (t, J=7.3 Hz, 1H), 6.90 (d, J=7.9 Hz, 1H), 5.45-5.34 (m, 1H), 4.94 (d, J=14.2 Hz, 1H), 4.84 (d, J=14.2 Hz, 1H), 2.04 (s, 3H), 1.53 (d, J=7.1 Hz, 3H) ppm. HPLC purity: 97.78% at 210 nm and 97.00% at 254 nm. MS: m/z=361.2 (M+H)+.

Example 69: 5-((4-((3-chlorobenzyl)amino)-5-methylpyrimidin-2-yl)amino)benzo[c][1,2]oxaborol-1(3H)-ol

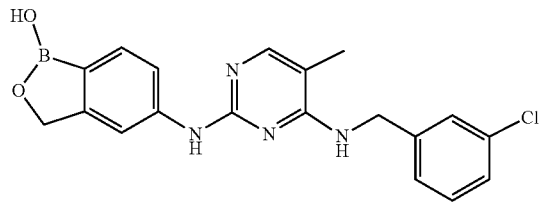 [SMILES: Cc1cnc(Nc2ccc3c(c2)COB3O)nc1NCc1cccc(Cl)c1]

The title compound was prepared by using the scheme and procedure shown below:

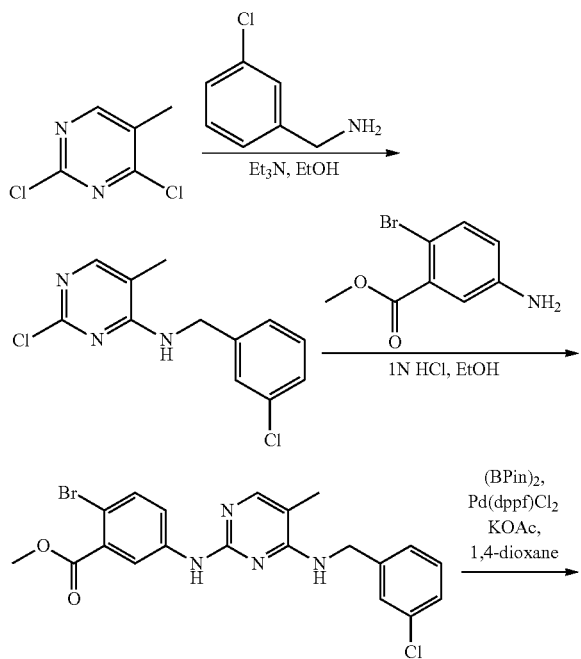

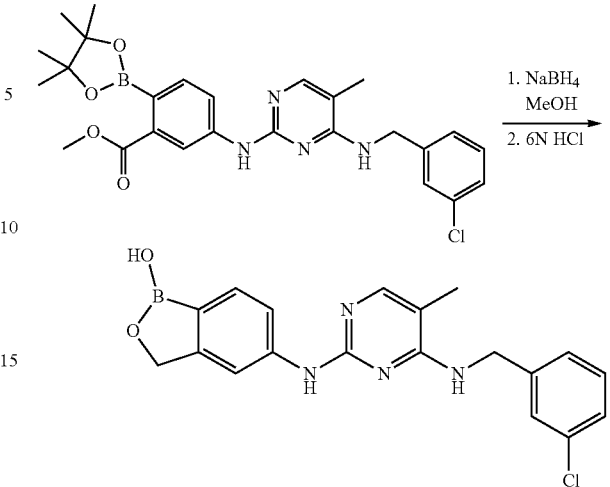

To a solution of 2,4-dichloro-5-methylpyrimidine (1.6 g, 10.0 mmol) and (3-chlorophenyl)-methanamine (1.21 g, 10 mmol) in ethanol (15 mL) was added triethylamine (2.8 mL, 20.0 mmol) at room temperature. The reaction mixture was heated to 50° C. for 2 hours and concentrated in vacuo. The residue was washed with water and triturated with petroleum ether/ethyl acetate (10:1, v/v) to give 2-chloro-N-(3-chlorobenzyl)-5-methylpyrimidin-4-amine (1.9 g, yield 75%) as a white solid. $^1$H NMR (400 MHz, CDCl$_3$): δ 7.76 (d, J=0.8 Hz, 1H), 7.24-7.15 (m, 4H), 5.07 (br. s, 1H), 4.62 (d, J=5.7 Hz, 2H), 1.95 (d, J=0.7 Hz, 3H) ppm. To a solution of this intermediate (1.9 g, 7.2 mmol) in ethanol (20 mL) were added methyl 5-amino-2-bromobenzoate (1.67 g, 7.2 mmol) and HCl (1.5 N, 4 mL). It was refluxed for 3 hours and cooled to room temperature. Normal work-up as described in Example 41 provided the residue, which was triturated with ethyl acetate:petroleum ether (1:5, v/v) to acquire methyl 2-bromo-5-((4-((3-chlorobenzyl)amino)-5-methylpyrimidin-2-yl)amino)benzoate (2.3 g, 70% yield) as an off-white solid. $^1$H NMR (400 MHz, CDCl$_3$): δ 10.67 (s, 1H), 8.57 (s, 1H), 8.00 (d, J=2.8 Hz, 1H), 7.38-7.25 (m, 2H), 7.22 (dd, J=8.6, 2.8 Hz, 1H), 7.14-7.02 (m, 3H), 6.99 (d, J=4.6 Hz, 1H), 4.53 (d, J=5.4 Hz, 2H), 3.60 (d, J=3.5 Hz, 3H), 1.91 (d, J=2.4 Hz, 3H) ppm. To a solution of this bromo intermediate (1.3 g, 3 mmol) in tetrahydrofuran (20 mL) were added potassium acetate (882 mg, 9 mol), (BPin)$_2$ (1.1 g, 4.2 mmol) and Pd(dppf)Cl$_2$ (937 mg, 1.2 mmol) at room temperature under nitrogen atmosphere. The mixture was stirred at 100° C. overnight, cooled to room temperature and then filtered. The filtrate was concentrated and the residue was purified by silica gel chromatography by elution with dichloromethane and methanol (100/1 to 20/1, v/v) to give methyl 5-((4-((3-chlorobenzyl)amino)-5-methyl-pyrimidin-2-yl)amino)-2-(4,4,5,5-tetramethyl-1,3,2-dioxa-borolan-2-yl)benzoate (1.4 g) as a brown solid. MS: m/z=509.3 (M+H)+. To a solution of this boron intermediate (1.4 g, crude) in methanol (15 mL) was added NaBH4 (532 mg, 14.0 mmol) at 30° C. in portions. The mixture was stirred at 30° C. for 30 minutes, and 6N HCl (3 mL) was added. It was stirred for another 20 minutes, neutralized with saturated NaHCO3 and filtered to collect the solid. The filter cake was purified by column chromatography by elution with dichloromethane and methanol (100:1 to 40:1, v/v) to give the product 5-((4-((3-chlorobenzyl)amino)-5-methylpyrimidin-2-yl)amino)-benzo[c][1,2]oxaborol-1(3H)-ol (307 mg) as an-off white solid. $^1$H NMR (400 MHz, DMSO-d$_6$): δ 9.08

(s, 1H), 8.85 (s, 1H), 7.80 (s, 1H), 7.75 (s, 1H), 7.48-7.27 (m, 7H), 4.80 (s, 2H), 4.66 (d, J=5.7 Hz, 2H), 2.02 (s, 3H) ppm. HPLC purity: 99.46% at 210 nm and 99.17% at 254 nm. MS: m/z=381.1 (M+H)⁺.

Example 70: 5-((4-((3-fluorobenzyl)amino)-5-methylpyrimidin-2-yl)amino)benzo[c][1,2]oxaborol-1(3H)-ol

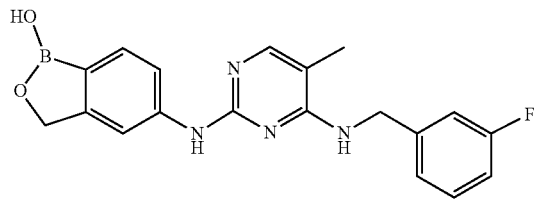 [SMILES: Cc1cnc(Nc2ccc3c(c2)COB3O)nc1NCc1cccc(F)c1]

The title compound was prepared by using the scheme and procedure shown below:

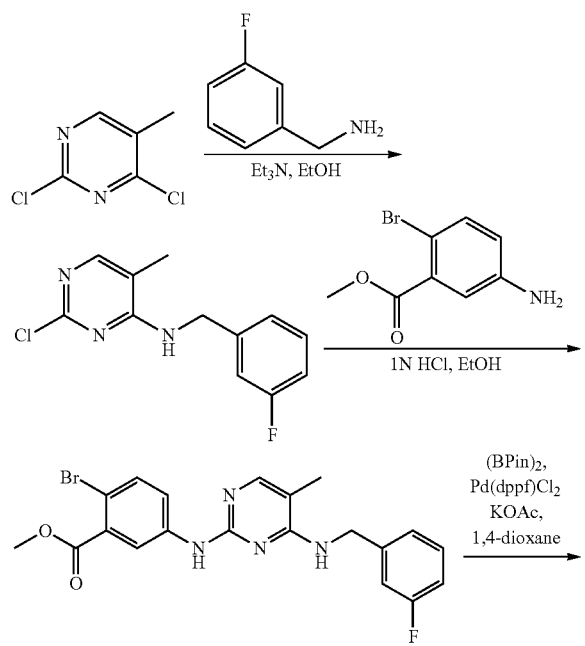

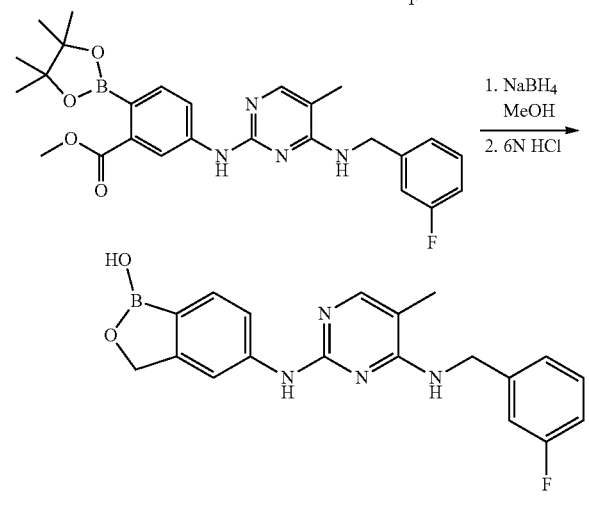

The procedures used for the synthesis of the analogs above such as Example 69 were adapted for the preparation of the title compound. Yields and analytical data of intermediates and final compound are shown below. In the 1$^{st}$ step, 2-chloro-N-(3-fluorobenzyl)-5-methylpyrimidin-4-amine was obtained by trituration with petroleum ether/ethyl acetate (10:1, v/v) in 75% yield as a white solid. ¹H NMR (400 MHz, CDCl₃): δ 7.77 (s, 1H), 7.28-7.22 (m, 1H), 7.05 (d, J=7.6 Hz, 1H), 6.98-6.90 (m, 2H), 5.02 (br. s, 1H), 4.64 (d, J=5.6 Hz, 2H), 1.95 (s, 3H) ppm. In the 2$^{nd}$ step, methyl 2-bromo-5-((4-((3-fluorobenzyl)amino)-5-methylpyrimidin-2-yl)amino)-benzoate was acquired as an off-white solid with 70% yield. ¹H NMR (400 MHz, CDCl₃): δ 10.71 (s, 1H), 8.52 (s, 1H), 8.03 (d, J=2.6 Hz, 1H), 7.38-7.30 (m, 2H), 7.24 (dd, J=8.7, 2.7 Hz, 1H), 7.19-7.09 (m, 1H), 6.79-7.84 (m, 3H), 4.58 (d, J=5.6 Hz, 2H), 3.62 (s, 3H), 1.94 (s, 3H) ppm. In the 3$^{rd}$ step, methyl 5-((4-((3-fluorobenzyl)amino)-5-methylpyrimidin-2-yl)amino)-2-(4,4,5,5-tetramethyl-1,3,2-dioxaborolan-2-yl)benzoate was obtained by purification using silica gel chromatography by elution with dichloromethane and methanol (100/1 to 20/1, v/v). MS: m/z=493.2 (M+H)⁺. In the 4$^{th}$ step, the final compound (150 mg, yield 14% over two steps) was obtained as an off-white solid by purification using column chromatography by elution with dichloromethane and methanol (100:1 to 40:1, v/v). ¹H NMR (400 MHz, DMSO-d₆): δ 9.07 (s, 1H), 8.85 (s, 1H), 7.78-7.75 (m, 2H), 7.46-7.35 (m, 4H), 7.19 (d, J=7.6 Hz, 1H), 7.14 (d, J=10.4 Hz, 1H), 7.04 (td, J=8.5, 2.3 Hz, 1H), 4.79 (s, 2H), 4.67 (d, J=6.0 Hz, 2H), 2.02 (s, 3H) ppm. HPLC purity: 98.14% at 210 nm and 98.80% at 254 nm. MS: m/z=365.2 (M+H)⁺.

Example 71: 5-((4-(cyclopropylamino)-5-methylpyrimidin-2-yl)amino)benzo[c][1,2]oxaborol-1(3H)-ol

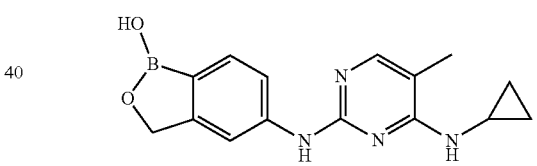

The title compound was prepared by using the scheme and procedure shown below:

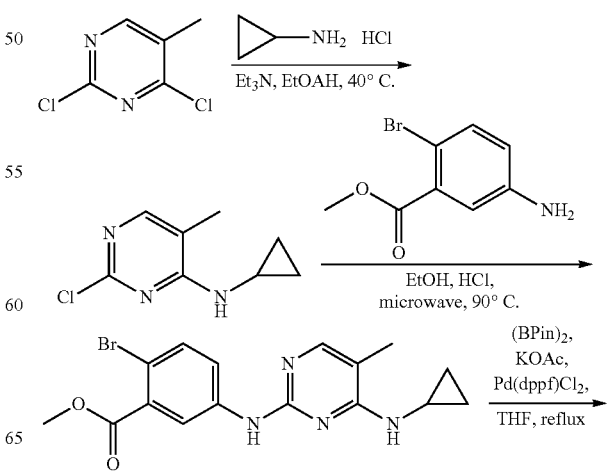

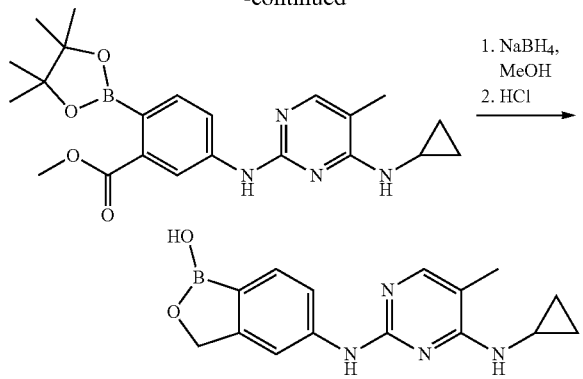

The procedures used for the synthesis of the analogs above such as Example 69 were adapted for the preparation of the title compound. Yields and analytical data of intermediates and final compound are shown below. In the 1st step, 2-chloro-N-cyclopropyl-5-methylpyrimidin-4-amine was purified by silica gel chromatography by elution with petroleum ether/ethyl acetate (20/1 to 5/1, v/v) and obtained in 56% yield as a white solid. MS: m/z=184.2 (M+H)+. In the 2nd step, methyl 2-bromo-5-((4-(cyclopropylamino)-5-methylpyrimidin-2-yl)amino)benzoate was purified by trituration with methanol and H$_2$O, and obtained in 68% yield as a white solid. $^1$H NMR (300 MHz, DMSO-d$_6$): δ 11.03 (s, 1H), 8.56 (s, 1H), 8.36 (s, 1H), 7.80-7.75 (m, 3H), 3.82 (s, 3H), 2.95-2.90 (m, 1H), 1.98 (s, 3H), 0.86-0.73 (m, 4H) ppm.

In the 3rd step, methyl 5-((4-(cyclopropylamino)-5-methylpyrimidin-2-yl)amino)-2-(4,4,5,5-tetra-methyl-1,3,2-dioxaborolan-2-yl)benzoate was purified by silica gel chromatography by elution with dichloromethane/methanol (100/1 to 20/1, v/v) and obtained as a dark solid. MS: m/z=425.3 (M+H)+. In the 4th step, the crude final compound was purified by silica gel chromatography by elution with dichloromethane/methanol (100/1 to 20/1) and further, trituration with acetonitrile and water. 5-((4-(cyclopropylamino)-5-methylpyrimidin-2-yl)amino)benzo[c][1,2]oxaborol-1(3H)-ol was obtained in 15% yield as a white solid. $^1$H NMR (300 MHz, DMSO-d$_6$): δ 9.13 (s, 1H), 8.84 (s, 1H), 8.21 (s, 1H), 7.68 (s, 1H), 7.62 (d, J=8.0 Hz, 1H), 7.52 (d, J=8.0 Hz, 1H), 6.81 (s, 1H), 4.91 (s, 2H), 2.89-2.78 (m, 1H), 1.89 (s, 3H), 0.85-0.70 (m, 2H), 0.67-0.50 (m, 2H) ppm. HPLC purity: 97.34% at 210 nm and 97.40% at 254 nm. MS: m/z=297.1 (M+H)+.

Example 72: 5-((4-((4-chlorobenzyl)amino)-5-methylpyrimidin-2-yl)amino)benzo[c][1,2]oxaborol-1(3H)-ol

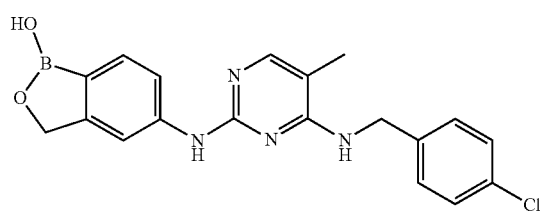 [SMILES: Cc1cnc(Nc2ccc3c(c2)COB3O)nc1NCc1ccc(Cl)cc1]

The title compound was prepared by using the scheme and procedure shown below:

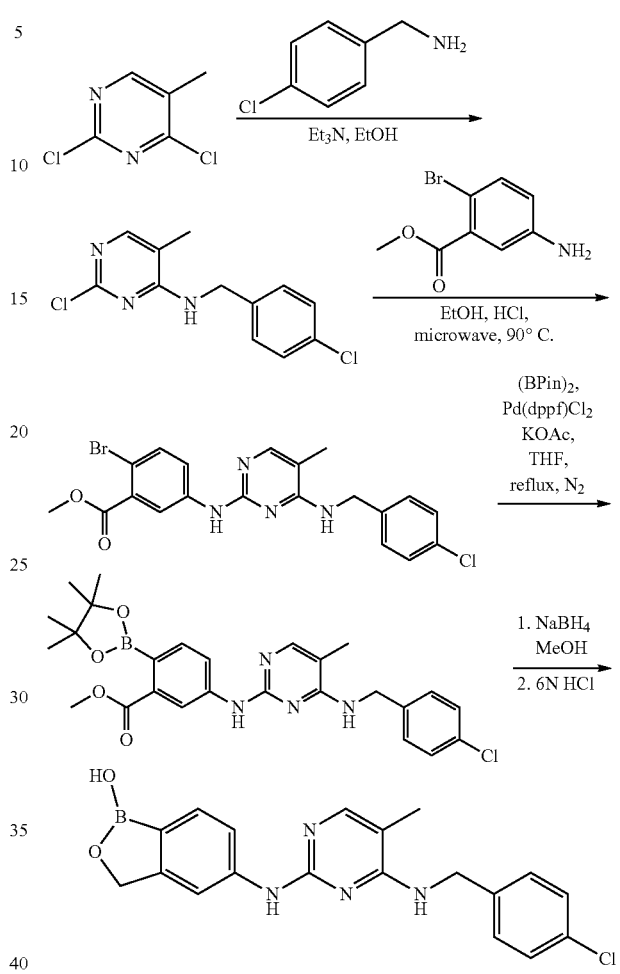

The procedures used for the synthesis of the analogs above such as Example 69 were adapted for the preparation of the title compound. Yields and analytical data of intermediates and final compound are shown below. In the 1st step, the crude product was purified by silica gel chromatography by elution with petroleum ether/ethyl acetate (20/1 to 5/1, v/v) to give 2-chloro-N-(4-chlorobenzyl)-5-methylpyrimidin-4-amine in 67% yield as a white solid. MS: m/z=268.0 (M+H)+. In the 2nd step, methyl 2-bromo-5-((4-((4-chlorobenzyl)amino)-5-methylpyrimidin-2-yl)amino) benzoate was purified by trituration with methanol and H$_2$O, and obtained in 58% yield as a white solid. $^1$H NMR (300 MHz, DMSO-d$_6$): δ 10.87 (s, 1H), 9.12 (s, 1H), 8.07 (d, J=2.4 Hz, 1H), 7.84 (s, 1H), 7.65 (d, J=8.7 Hz, 1H), 7.48 (dd, J=8.8, 2.4 Hz, 1H), 7.38-7.29 (m, 4H), 4.66 (d, J=5.6 Hz, 2H), 3.76 (s, 3H), 2.06 (s, 3H) ppm. In the 3rd step, the crude product was purified by silica gel chromatography by elution with dichloromethane/methanol (100/1 to 20/1, v/v) to give methyl 5-((4-((4-chlorobenzyl)amino)-5-methyl-pyrimidin-2-yl)amino)-2-(4,4,5,5-tetramethyl-1,3,2-dioxaborolan-2-yl)benzoate as a dark solid. MS: m/z=509.2 (M+H)+. In the 4th step, the final compound, 5-((4-((4-chlorobenzyl)amino)-5-methylpyrimidin-2-yl)amino)benzo[c][1,2]oxaborol-1(3H)-ol, was obtained by purification using silica gel chromatography by elution with dichloromethane/methanol (100/1 to 20/1) and further, trituration with acetonitrile and water in 17% yield as a white solid. $^1$H NMR (300 MHz, DMSO-$d_6$): δ 9.06 (s, 1H), 8.85 (s, 1H), 7.77 (s, 1H), 7.74 (s, 1H), 7.44-7.36 (m, 7H), 4.78 (s, 2H), 4.63 (d, J=5.4 Hz, 2H), 2.00 (s, 3H) ppm. HPLC purity: 96.29% at 210 nm and 98.76% at 254 nm. MS: m/z=381.1 (M+H)$^+$.

Comparative Example A: 5-((4-(cyclohexyloxy)-5-methylpyrimidin-2-yl)(methyl)amino)benzo[c][1,2]oxaborol-1(3H)-ol

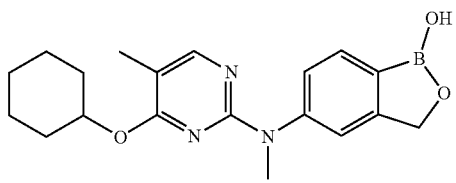 [SMILES: Cc1cnc(N(C)c2ccc3c(c2)COB3O)nc1OC1CCCCC1]

This substance was prepared following General Synthetic Scheme A. $^1$H NMR (300 MHz, DMSO-$d_6$): δ 9.12 (s, 1H), 7.98 (s, 1H), 7.68 (d, J=8.0 Hz, 1H), 7.37-7.33 (m, 2H), 4.97 (s, 2H), 4.79-4.74 (m, 1H), 3.46 (s, 3H), 1.94 (s, 3H), 1.86-1.83 (m, 2H), 1.67-1.64 (m, 2H), 1.49-1.38 (m, 3H), 1.24-1.22 (m, 3H) ppm. HPLC purity: 97.57% at 210 nm and 97.55% at 254 nm. MS: (M+H)$^+$: m/z=354.2.

Comparative Example B: 5-((4-(cyclopentylamino)-5-methylpyrimidin-2-yl)(methyl)amino)benzo[c][1,2]oxaborol-1(3H)-ol

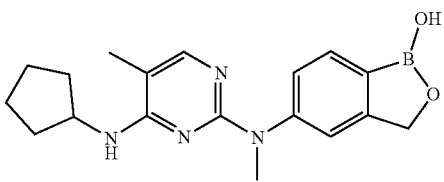 [SMILES: Cc1cnc(N(C)c2ccc3c(c2)COB3O)nc1NC1CCCC1]

This substance was prepared following General Synthetic Scheme A. $^1$H NMR (400 MHz, DMSO-$d_6$): δ 11.59 (br, 1H), 9.41 (br, 1H), 8.05 (d, J=7.2 Hz, 1H), 7.87 (d, J=7.2 Hz, 1H), 7.50 (d, J=1.6 Hz, 1H), 7.46 (s, 1H), 7.40 (dd, J=7.6, 1.6 Hz, 1H), 5.02 (s, 2H), 4.33-4.32 (m, 1H), 3.48 (s, 3H), 1.99 (s, 3H), 1.91-1.90 (m, 2H), 1.72-1.53 (m, 6H) ppm. HPLC purity: 99.38% at 210 nm and 99.88% at 254 nm. MS: (M+H)$^+$: m/z=339.2.

Part 2-3: Synthetic Examples for Compounds of Formula (IA)

Example 2-3-1: 2-((1-hydroxy-1,3-dihydrobenzo[c][1,2]oxaborol-5-yl)amino)-4-(propylamino) pyrimidine-5-carbaldehyde

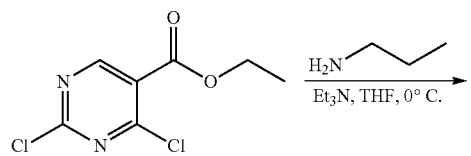

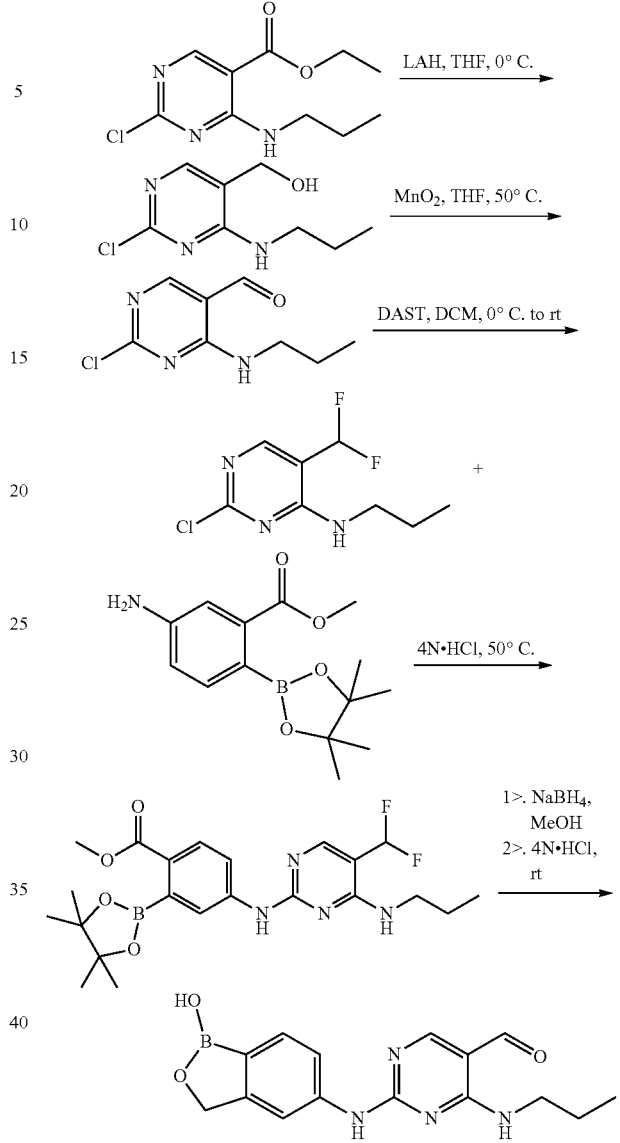

To a solution of compound ethyl 2,4-dichloropyrimidine-5-carboxylate (5.0 g, 22.7 mmol) and Et$_3$N (3.8 mL, 27.2 mmol) in THF (40 mL) was added propan-1-amine (1.34 g, 22.7 mmol) dropwise at 0° C., the resulting mixture was stirred at room temperature for 2 h. Then the reaction was quenched by adding water, and the aqueous phase was extracted by EtOAc. The combined organic layer was washed with brine, dried over anhydrous Na$_2$SO$_4$, filtered and concentrated in vacuo to give a residue, which was purified by column chromatography to give ethyl 2-chloro-4-(propylamino)pyrimidine-5-carboxylate as a white solid (3.1 g, yield 56%). $^1$H NMR (400 MHz, CDCl$_3$): δ 8.65 (s, 1H), 8.41 (s, 1H), 4.36 (q, J=7.1 Hz, 2H), 3.55-3.46 (m, 2H), 1.69-1.64 (m, 2H), 1.39 (t, J=7.1 Hz, 3H), 1.00 (t, J=7.4 Hz, 3H) ppm.

To a solution of ethyl 2-chloro-4-(propylamino)pyrimidine-5-carboxylate (2.6 g, 10.7 mmol) in dry THF (100 mL) was added LAH (488 mg, 12.8 mmol) in portions at 0° C., then the reaction mixture was warmed up to rt and kept stirring for 2 h. Then the reaction was quenched by adding H$_2$O (~3 mL) at 0° C., and anhydrous Na$_2$SO$_4$ solid was added to the mixture. The resulting mixture was filtered through a pad of Celite, and the filtrate was concentrated in vacuo to give a residue, which was purified by column chromatography (PE/EtOAc=30/1) to give (2-chloro-4-(propylamino)pyrimidin-5-yl)methanol (1.6 g, yield 74%). $^1$HNMR (400 MHz, CDCl$_3$): δ 7.64 (s, 1H), 6.30 (s, 1H), 4.54 (s, 2H), 1.65 (q, J=14.5, 7.3 Hz, 2H), 1.21 (t, J=7.0 Hz, 2H), 0.98 (t, J=7.4 Hz, 3H) ppm.

A solution of (2-chloro-4-(propylamino)pyrimidin-5-yl) methanol (1.6 g, 8.0 mmol) and MnO$_2$ (7.0 g, 80 mmol) in dry THF (50 mL) was heated up to 50° C., and kept stirring overnight. Then the reaction mixture was filtered through a pad of Celite, and the filtrate was concentrated in vacuo to give a residue, which was purified by column chromatography (PE/EtOAc=50/1) to give 2-chloro-4-(propylamino) pyrimidine-5-carbaldehyde (1.3 g, yield 81%). $^1$HNMR (400 MHz, CDCl$_3$): δ 9.81 (s, 1H), 8.71 (s, 1H), 8.39 (s, 1H), 3.54 (q, J=13.3, 6.8 Hz, 2H), 1.67 (dt, J=14.6, 7.3 Hz, 2H), 0.99 (t, J=7.4 Hz, 3H) ppm.

To a solution of 2-chloro-4-(propylamino)pyrimidine-5-carbaldehyde (4.1 g, 20.6 mmol) in dry DCM (20 mL) was added DAST (27.3 mL, 206 mmol) dropwise at 0° C., then slowly warmed to rt, and kept stirring at rt overnight. Then the reaction mixture was poured into ice water, the organic layer was dried over anhydrous Na$_2$SO$_4$, concentrated in vacuo to give a residue, which was purified by column chromatography (100% PE) to give 2-chloro-5-(difluoromethyl)-N-propylpyrimidin-4-amine (2.1 g, yield 46%). $^1$HNMR (400 MHz, DMSO-d$_6$): δ 8.18 (s, 1H), 7.81 (s, 1H), 7.03 (t, J=53.8 Hz, 1H), 3.33-3.27 (m, 2H), 1.62-1.51 (m, 2H), 0.92-0.81 (m, 3H) ppm.

To a solution of 2-chloro-5-(difluoromethyl)-N-propylpyrimidin-4-amine (221 mg, 1.0 mmol), methyl 5-amino-2-(4,4,5,5-tetramethyl-1,3,2-dioxaborolan-2-yl)benzoate (277 mg, 1.0 mmol) in MeOH (20 mL) was added 4N HCl (5 mL), the resulting mixture was heated to 50° C. for 2 h. The reaction mixture was then cooled to room temperature, a solid was formed after removal of organic solvents, the solid was collected by filtration, dried in vacuo to give methyl 4-((5-(difluoromethyl)-4-(propylamino)pyrimidin-2-yl) amino)-2-(4,4,5,5-tetramethyl-1,3,2-dioxaborolan-2-yl) benzoate (110 mg, yield 23.8%) as a white solid. MS: (M+H)$^+$: m/z=463.2.

A solution of methyl 4-((5-(difluoromethyl)-4-(propylamino)pyrimidin-2-yl)amino)-2-(4,4,5,5-tetramethyl-1,3,2-dioxaborolan-2-yl)benzoate (110 mg, 0.24 mmol) in MeOH (5 mL) was added NaBH$_4$ (190 mg, 5 mmol), the resulting mixture was stirred at room temperature for 30 min. 4N. HCl (3.0 mL) was added, and the reaction mixture was stirred at rt for another 30 min, concentrated in vacuo to give a residue, which was purified by prep-HPLC to give 2-((1-hydroxy-1,3-dihydrobenzo[c][1,2]oxaborol-5-yl)amino)-4-(propylamino)pyrimidine-5-carbaldehyde (26.5 mg, 36%) as a yellow solid. $^1$HNMR (400 MHz, DMSO-d$_6$): δ 10.15 (s, 1H), 9.57 (s, 1H), 9.02 (s, 1H), 8.74 (s, 1H), 8.50 (s, 1H), 7.98 (s, 1H), 7.70 (d, J=8.0 Hz, 1H), 7.64 (d, J=8.0 Hz, 1H), 4.96 (s, 2H), 3.48 (dd, J=13.9, 6.4 Hz, 2H), 1.73-1.55 (m, 2H), 0.94 (t, J=7.4 Hz, 3H) ppm. HPLC purity: 86.71% at 210 nm and 98.87% at 254 nm. MS: (M+H)$^+$: m/z=313.2

Example 2-3-2: 5-((4-((1-methoxypentan-3-yl) amino)-5-(trifluoromethyl)pyrimidin-2-yl)amino) benzo[c][1,2] oxaborol-1(3H)-ol

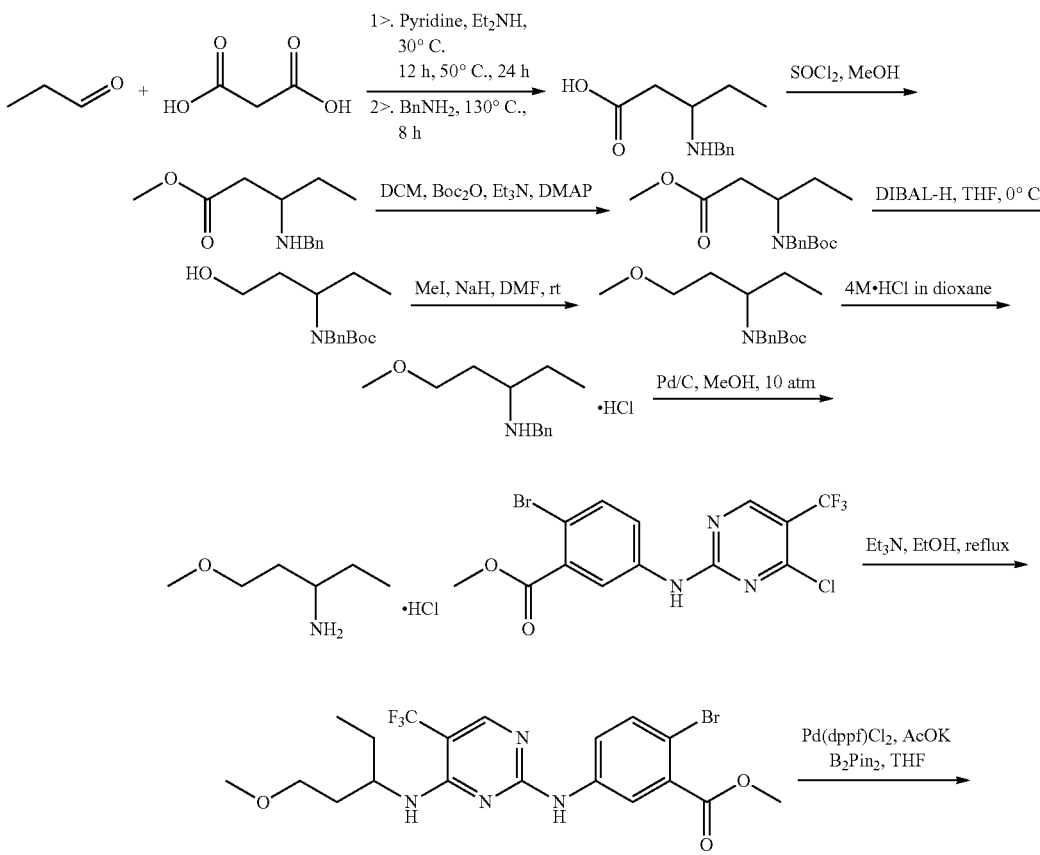

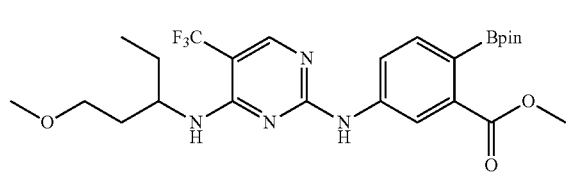 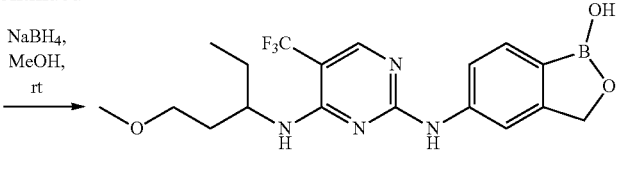

A mixture of propionaldehyde (58 g, 1.0 mol), malonic acid (104 g, 1.0 mol) and Et$_2$NH (10.0 mL, 0.1 mol) in pyridine (1.0 L) was heated up to 30° C., and kept stirring for 12 h. Then the reaction mixture was heated up to 50° C., and kept stirring for 24 h. BnNH$_2$ (107 g, 1.0 mol) was added to the above mixture, and the resulting mixture was heated to 130° C. and kept stirring for 8 h. The reaction mixture was cooled to rt, the formed solid was collected by filtration, dried in vacuo to give 3-(benzylamino)pentanoic acid (57 g, 28%). MS (ESI$^+$): m/z=208.2 (M+H)$^+$ To a solution of 3-(benzylamino)pentanoic acid (30 g, 145 mmol) in MeOH (500 mL) was added SOCl$_2$ (30 mL) dropwise at 0° C., then the resulting mixture was heated to reflux for 1 h. The reaction mixture was cooled down to room temperature, diluted with EtOAc, washed with sat. NaHCO$_3$, dried over anhydrous Na$_2$SO$_4$, concentrated in vacuo to give methyl 3-(benzylamino)pentanoate (22.0 g, yield 69%) as a yellow oil. $^1$HNMR (400 MHz, DMSO-d$_6$): δ 7.39-7.18 (m, 5H), 3.69 (s, 2H), 3.57 (s, 3H), 2.84-2.75 (m, 1H), 2.46-2.33 (m, 2H), 1.48-1.36 (m, 2H), 0.84 (t, J=7.4 Hz, 3H) ppm.

To a solution of methyl 3-(benzylamino)pentanoate (22 g, 100 mmol), Et$_3$N (36 mL, 200 mmol) and DMAP (610 mg, 5 mmol) in DCM (400 mL) was added Boc$_2$O (32.4 g, 150 mmol) in portions, and the reaction mixture was stirred overnight. 500 mL of H$_2$O was added into the above mixture, the organic layer was separated, dried over anhydrous Na$_2$SO$_4$, concentrated in vacuo to give a residue, which was purified by silica gel chromatography (petroleum ether:ethylacetate=95:5) to give methyl 3-(benzyl(tert-butoxycarbonyl)amino)pentanoate (11.0 g, yield 36%). $^1$HNMR (400 MHz, DMSO-d$_6$): δ 7.34-7.18 (m, 5H), 4.51-4.30 (m, 1H), 4.28-3.94 (m, 2H), 3.48 (s, 3H), 1.51-1.21 (m, 13H), 0.70 (s, 3H) ppm.

To a solution of methyl 3-(benzyl(tert-butoxycarbonyl)amino)pentanoate (10.0 g, 31 mmol) in dry THF (75 mL) was added DIBAL-H (31 mL, 46.5 mmol, 1.5 M in toluene) dropwise at 0° C. under N$_2$ atmosphere, the resulting mixture was stirred at 0° C. for 1 h. The reaction was quenched by adding 5 mL of H$_2$O, stirred at rt for additional 30 min. The reaction mixture was diluted by EtOAc, and the organic phase was separated, dried over anhydrous Na$_2$SO$_4$, filtered through a pad of Celite. The filtrate was concentrated in vacuo to give the crude product, which was purified by silica gel chromatography (petroleum ether:ethylacetate=10:1) to give tert-butyl benzyl(1-hydroxypentan-3-yl)carbamate (7.5 g, yield 83%). $^1$HNMR (400 MHz, DMSO-d$_6$): δ 7.39-7.17 (m, 5H), 4.46-4.16 (m, 2H), 4.02-3.64 (m, 1H), 3.33-3.24 (m, 2H), 1.72-1.60 (m, 1H), 1.57-1.24 (m, 12H), 0.77-0.59 (m, 3H) ppm.

To a solution of tert-butyl benzyl(1-hydroxypentan-3-yl) carbamate (7.0 g, 23.9 mmol) in dry DMF (100 mL) was added NaH (1.4 g, 35.8 mmol) in portions at 0° C. under N$_2$ atmosphere, and the resulting mixture was stirred for 30 min at 0° C. MeI (3.1 mL, 47.8 mmol) was then added dropwise at 0° C., and the reaction mixture was warmed up to rt for 3 h. The reaction was quenched by adding 5 mL of sat. NH$_4$Cl at 0° C., diluted by 100 mL of EtOAc. The organic layer was separated, washed with brine (100 mL×3), dried over anhydrous Na$_2$SO$_4$, filtered and concentrated in vacuo to give the crude product, which was purified by silica gel chromatography (petroleum ether:ethylacetate=30:1) to give tert-butyl benzyl(1-methoxypentan-3-yl)carbamate (7.5 g, yield 83%). $^1$HNMR (400 MHz, DMSO-d$_6$): δ 7.41-7.08 (m, 5H), 4.44-4.16 (m, 2H), 3.96-3.61 (m, 1H), 3.32 (s, 1H), 3.20-3.05 (m, 4H), 1.78-1.54 (m, 2H), 1.52-1.23 (m, 11H), 0.77-0.61 (m, 3H) ppm.

A mixture of tert-butyl benzyl(1-methoxypentan-3-yl)carbamate (6.1 g, 19.9 mmol) in dioxane (50 mL, 4M. HCl in dioxane) was stirred overnight, then concentrated in vacuo to give the crude product N-benzyl-1-methoxypentan-3-amine HCl salt (4.8 g, crude) as a white solid, which was used directly in the next step without further purification. $^1$HNMR (400 MHz, DMSO-d$_6$): δ 9.17 (s, 2H), 7.65-7.57 (m, 2H), 7.49-7.36 (m, 3H), 4.14 (t, J=5.5 Hz, 2H), 3.48-3.36 (m, 2H), 3.22 (s, 3H), 3.09-2.99 (m, 1H), 2.06-1.94 (m, 1H), 1.92-1.81 (m, 1H), 1.80-1.65 (m, 2H), 0.90 (t, J=7.5 Hz, 3H) ppm.

A mixture of N-benzyl-1-methoxypentan-3-amine HCl salt (4.8 g, 19.8 mmol) and Pd—C (10%, 500 mg) in MeOH (25 mL) was hydrogenated under H$_2$ atmosphere (150 Psi) for 8 hours at room temperature. The reaction mixture was then passed through a pad of Celite, and the filtrate was concentrated in vacuo to give 1-methoxypentan-3-amine HCl (3.1 g, crude) as a yellow oil, it was used directly in the next step without further purification.

A mixture of 1-methoxypentan-3-amine HCl (500 mg, 3.3 mmol), methyl 2-bromo-5-((4-chloro-5-(trifluoromethyl) pyrimidin-2-yl)amino)benzoate (1.0 g, 2.5 mmol) and Et$_3$N (1.0 mL, 7.5 mmol) in EtOH (25 mL) was heated to reflux for 3 h. The reaction mixture was cooled to room temperature, diluted with DCM (50 mL), washed with brine (100 mL×3), dried over anhydrous Na$_2$SO$_4$, filtered and concentrated in vacuo to give the crude product, which was purified by silica gel chromatography (petroleum ether:ethylacetate=1:1) to give methyl 2-bromo-5-((4-((1-methoxypentan-3-yl)amino)-5-(trifluoromethyl)pyrimidin-2-yl)amino) benzoate (630 mg, yield 52%). $^1$HNMR (400 MHz, DMSO-d$_6$): δ 9.93 (s, 1H), 8.40 (s, 1H), 8.22 (s, 1H), 7.70 (d, J=8.7 Hz, 1H), 7.64-7.56 (m, 1H), 6.68 (d, J=8.4 Hz, 1H), 4.45-4.31 (m, 1H), 3.85 (s, 3H), 3.39-3.34 (m, 2H), 3.14 (s, 3H), 1.90-1.73 (m, 2H), 1.70-1.51 (m, 2H), 0.83 (t, J=7.4 Hz, 3H) ppm.

To a solution of methyl 2-bromo-5-((4-((1-methoxypentan-3-yl)amino)-5-(trifluoromethyl) pyrimidin-2-yl)amino) benzoate (300 mg, 0.61 mmol) in THF (15 mL) was added KOAc (179 mg, 1.83 mmol), (BPin)$_2$ (185 g, 0.73 mmol) and (dppf)PdCl$_2$ (44 mg, 0.06 mmol) at room temperature under nitrogen atmosphere, the resulting mixture was heated to reflux overnight. The solid was filtered, and the filtrate was concentrated in vacuo to give a residue, which was purified by silica chromatography (DCM/MeOH (100/1 to 20/1)) to give methyl 5-((4-((1-methoxypentan-3-yl)amino)-5-(trifluoromethyl)pyrimidin-2-yl)amino)-2-(4,4,5,5-tetramethyl-1,3,2-dioxaborolan-2-yl)benzoate (280 mg, contain 5% de-Br product in LCMS) as a white solid. $^1$HNMR (400 MHz, DMSO-$d_6$): δ 9.88 (s, 1H), 8.40 (s, 1H), 8.22 (s, 1H), 7.87 (d, J=8.1 Hz, 1H), 7.39 (d, J=8.1 Hz, 1H), 6.65 (d, J=8.2 Hz, 1H), 4.49-4.40 (m, 1H), 3.82 (s, 3H), 3.41-3.35 (m, 2H), 3.15 (s, 3H), 1.89-1.79 (m, 2H), 1.67-1.57 (m, 2H), 1.30 (s, 12H), 0.84 (t, J=7.4 Hz, 3H) ppm.

To a solution of methyl 5-((4-((1-methoxypentan-3-yl)amino)-5-(trifluoromethyl) pyrimidin-2-yl)amino)-2-(4,4,5,5-tetramethyl-1,3,2-dioxaborolan-2-yl)benzoate (280 mg, crude) in MeOH (20 mL) in MeOH was added NaBH$_4$ (722 mg, 19.0 mmol) at 30° C. in portions, the resulting reaction mixture was stirred at 30° C. for 30 min. 6N HCl (3 mL) was added into above mixture, which was kept stirring for 20 min. The reaction mixture was neutralized with sat. NaHCO$_3$, extracted with EtOAc, and the combined organic phase was washed with water, brine, concentrated in vacuo to give a residue, which was purified by prep-HPLC (0.1% TFA in MeCN and H$_2$O) to give 5-((4-((1-methoxypentan-3-yl)amino)-5-(trifluoromethyl)pyrimidin-2-yl) amino) benzo[c][1,2]oxaborol-1(3H)-ol (52.6 mg, yield 13%) as a yellow solid. $^1$HNMR (400 MHz, DMSO-$d_6$): δ 9.79 (s, 1H), 8.98 (s, 1H), 8.21 (s, 1H), 7.88 (s, 1H), 7.63 (q, J=18.8, 8.1 Hz, 2H), 6.66 (d, J=8.1 Hz, 1H), 4.94 (s, 2H), 4.37 (q, J=13.8, 6.8 Hz, 1H), 3.39 (t, J=5.6 Hz, 2H), 3.17 (s, 3H), 1.85 (q, J=12.4, 6.1 Hz, 2H), 1.71-1.54 (m, 2H), 0.86 (t, J=7.4 Hz, 3H) ppm. HPLC purity: 96.66% at 210 nm and 97.27% at 254 nm. MS (ESI$^+$): m/z=411.2 (M+H)$^+$.

Example 2-3-3: 2-((1-hydroxy-1,3-dihydrobenzo[c][1,2]oxaborol-5-yl)amino)-4-(pentan-3-ylamino)pyrimidine-5-carbonitrile

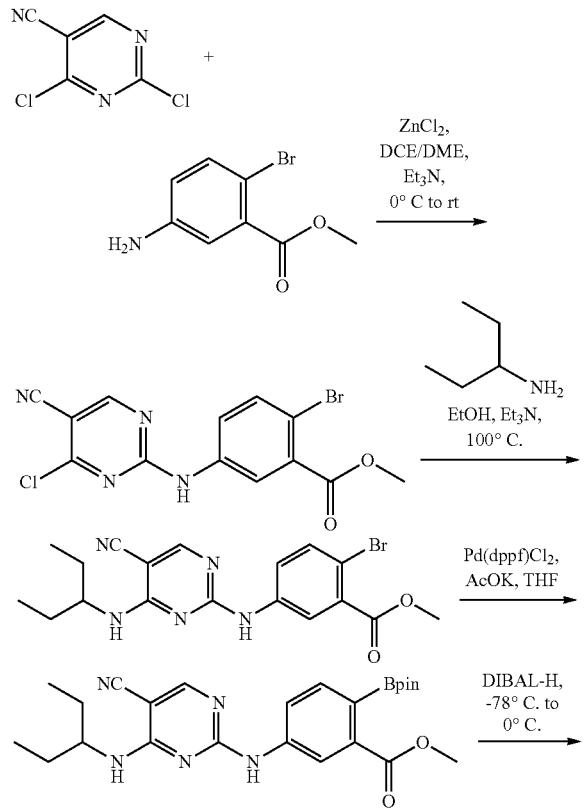

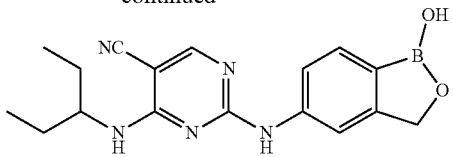

To a solution of 2,4-dichloropyrimidine-5-carbonitrile (1.0 g, 5.8 mmol) in a mixture of t-BuOH/DCE (30 mL, v/v=1:1) was added zinc chloride (8.7 mL, 1 M solution in THF, 1.5 eq) at 0° C., the resulting mixture was stirred for 1 h. Methyl 5-amino-2-bromobenzoate (19.0 g, 1.3 mmol) and triethylamine (0.9 mL, 6.4 mmol) in 3 mL of DCE/t-BuOH was then added to the above mixture sequentially, and the reaction mixture was stirred overnight. The solvents were removed under reduced pressure to obtain a residue, which was dissolved in ethyl acetate (25 mL), washed with brine (10 mL), dried over sodium sulphate, filtered and concentrated in vacuo to give the crude product, which was triturated in a mixture of PE/EtOAc (150 mL, v/v=3/1). The formed solid was collected by filtration, dried in vacuo to give methyl 2-bromo-5-((4-chloro-5-cyanopyrimidin-2-yl) amino)benzoate (2.0 g, 94%) as an off-white solid. MS (ESI$^-$): m/z=367.0 (M+H)$^+$.

To a solution of methyl 2-bromo-5-((4-chloro-5-cyanopyrimidin-2-yl)amino)benzoate (1.8 g, 4.9 mmol) and pentan-3-amine (0.6 g, 12 mmol) in EtOH (15 mL) was added Et$_3$N (1.01 g, 10.0 mmol) at room temperature, the resulting mixture was heated to reflux for 3 h. Then the reaction mixture was cooled to room temperature, concentrated in vacuo to give a residue, which was triturated with water, and the formed solid was collected by filtration, and dried in air to give methyl 2-bromo-5-((5-cyano-4-(pentan-3-ylamino)pyrimidin-2-yl)amino)benzoate (1.8 g, yield 90%) as a white solid. MS (ESI$^+$): m/z=418.1, 420.1 (M+H)$^+$ To a solution of methyl 2-bromo-5-((5-cyano-4-(pentan-3-ylamino)pyrimidin-2-yl)amino)benzoate (1.1 g, 2.6 mmol) in THF (10 mL) was added KOAc (474 mg, 4.8 mol), (BPin)$_2$ (701 mg, 2.76 mmol) and (dpp)PdCl$_2$ (457 mg, 0.6 mmol) at room temperature under nitrogen atmosphere, the resulting mixture was heated to 100° C. overnight. The solid was removed by filtration, and the filtrate was concentrated in vacuo to give a residue, which was purified by silica chromatography (PE/EtOAc (100/1 to 50/1)) to give methyl 5-((5-cyano-4-(pentan-3-ylamino)pyrimidin-2-yl)amino)-2-(4,4,5,5-tetramethyl-1,3,2-dioxaborolan-2-yl)benzoate (1.1 g, yield 92%) as a yellow solid. MS (ESI$^+$): m/z=466.3 (M+H)$^+$ DIBAL-H (2.0 mL, 3.0 mmol, 1.5 M in toluene) was added dropwise to a solution of 5-((5-cyano-4-(pentan-3-ylamino)pyrimidin-2-yl)amino)-2-(4,4,5,5-tetramethyl-1,3,2-dioxaborolan-2-yl)benzoate (500 mg, 0.93 mmol) in THF at −78° C., the resulting mixture was stirred at −78° C. for 30 min. The reaction mixture was warmed up to 0° C., stirred for additional 30 min, then warmed up to room temperature and kept stirring for 2 h. The reaction mixture was re-cooled to 0° C., quenched by adding 1N HCl (10 mL), stirred at rt for 1 h, diluted with DCM (50 mL), the organic layer was separated and dried over anhydrous Na$_2$SO$_4$, filtered and concentrated in vacuo to give the crude product, which was purified by prep-HPLC (0.1% TFA in MeCN and H$_2$O) to give 2-((1-hydroxy-1,3-dihydrobenzo[c][1,2]oxaborol-5-yl)amino)-4-(pentan-3-ylamino) pyrimidine-5-carbonitrile (12.3 mg, yield 4%). $^1$H NMR (400 MHz, DMSO-$d_6$): δ 9.94 (s, 1H), 9.01 (s, 1H), 8.35 (s, 1H), 7.87 (s, 1H), 7.62 (s, 1H), 7.50-7.38 (m, 1H), 4.94 (s, 2H), 4.10-4.00 (m, 1H), 1.69-1.55 (m, 4H), 0.87 (t, J=7.2 Hz, 6H) ppm. HPLC purity: 92.93% at 210 nm and 94.87% at 254 nm. MS (ESI⁺): m/z=338.2 (M+H)⁺

Example 2-3-4: 5-((4-(pentan-3-ylamino)pyrimidin-2-yl)amino)benzo[c][1,2]oxaborol-1(3H)-ol

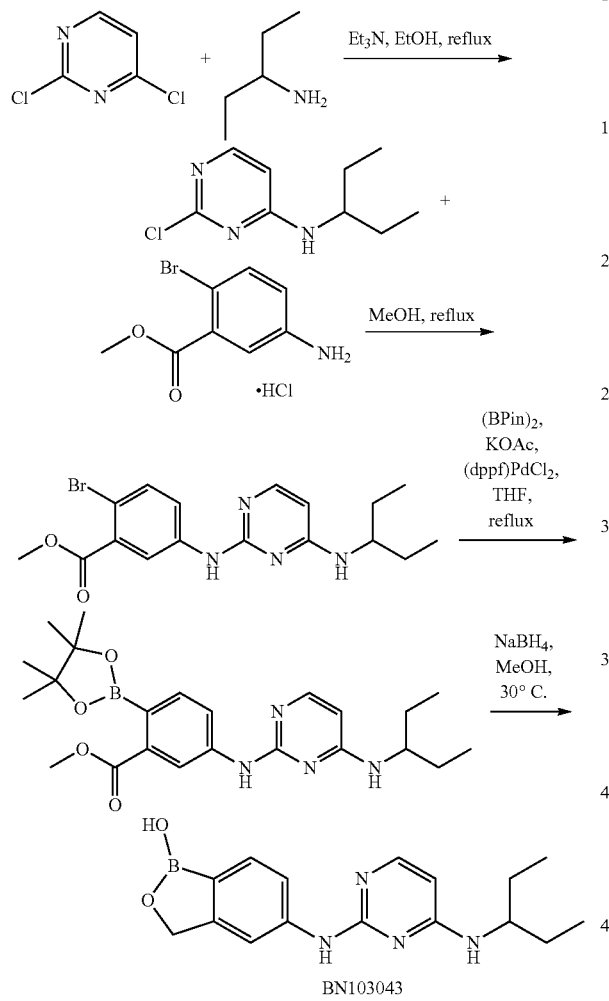

To a solution of 2,4-dichloropyrimidine (5.0 g, 33.6 mmol) in EtOH (50 mL) was added pentan-3-amine (4.4 g, 50.0 mmol) and Et₃N (10.0 g, 0.1 mol) at room temperature, the resulting mixture was heated to reflux overnight. Then the reaction mixture was concentrated in vacuo to give a residue, which was purified by silica chromatography to give 2-chloro-N-(pentan-3-yl)pyrimidin-4-amine (4.4 g, yield 66%) as a white solid. ¹H NMR (300 MHz, CDCl₃): δ 7.85 (d, J=5.9 Hz, 1H), 7.69 (d, J=7.6 Hz, 1H), 6.43 (d, J=5.9 Hz, 1H), 3.83 (d, J=7.4 Hz, 1H), 1.62-1.33 (m, 4H), 0.84 (t, J=7.4 Hz, 6H) ppm.

To a solution of 2-chloro-N-(pentan-3-yl)pyrimidin-4-amine (4.4 g, 22.0 mmol) in MeOH (30 mL) was added methyl 5-amino-2-bromobenzoate hydrochloride (5.9 g, 22.0 mmol), the resulting mixture was heated to reflux overnight. Then the reaction mixture was concentrated in vacuo to give a residue, which was purified by silica chromatography (DCM/MeOH (100/1 to 10/1)) to give methyl 2-bromo-5-((4-(pentan-3-ylamino)pyrimidin-2-yl)amino)benzoate (4.6 g, yield 53%) as a white solid. ¹H NMR (400 MHz, CDCl₃): δ 10.14 (s, 1H), 8.18 (s, 1H), 7.75-7.37 (m, 3H), 6.84 (s, 1H), 6.23 (s, 1H), 4.13-3.91 (m, 1H), 3.85 (s, 3H), 1.70-1.39 (m, 4H), 0.87 (t, J=7.4 Hz, 6H) ppm.

To a solution of methyl 2-bromo-5-((4-(pentan-3-ylamino)pyrimidin-2-yl)amino)benzoate (1.6 g, 4.0 mmol) in THF (30 mL) was added KOAc (1.2 g, 12.0 mmol), (BPin)₂ (1.5 g, 6.0 mmol) and (dppf)PdCl₂ (1.2 g, 1.6 mmol) at room temperature under nitrogen atmosphere, the resulting mixture was heated to reflux for 2 days. Then the solid was removed by filtration, and the filtrate was concentrated in vacuo to give a residue, which was purified by silica chromatography (DCM/MeOH (100/1 to 20/1)) to give crude methyl 5-((4-(pentan-3-ylamino)pyrimidin-2-yl)amino)-2-(4,4,5,5-tetramethyl-1,3,2-dioxaborolan-2-yl)benzoate (1.4 g, contain 30% de-Br product in LCMS) as a yellow solid. MS (ESI⁺): m/z=441.4 (M+H)⁺

To a solution of methyl 5-((4-(pentan-3-ylamino)pyrimidin-2-yl)amino)-2-(4,4,5,5-tetramethyl-1,3,2-dioxaborolan-2-yl)benzoate (1.4 g, crude) in MeOH (30 mL) was added NaBH₄ (1.0 g, 27.0 mmol) at 30° C. in portions, the resulting reaction mixture was stirred for 30 min. Then it was quenched by adding water, the aqueous phase was extracted with DCM/MeOH (10:1). The combined organic phase was washed with water, brine, concentrated in vacuo to give a residue, which was purified by silica chromatography (DCM/MeOH (100/1 to 20/1)) to give the crude product, which was triturated with MeCN and water to give 5-((4-(pentan-3-ylamino)pyrimidin-2-yl)amino)benzo[c][1,2]oxaborol-1(3H)-ol (103 mg, yield 8%) as an off-white solid. ¹H NMR (400 MHz, DMSO-d₆): δ 9.09 (s, 1H), 8.87 (s, 1H), 7.96 (s, 1H), 7.78 (s, 1H), 7.63 (d, J=7.9 Hz, 1H), 7.54 (d, J=8.1 Hz, 1H), 7.00 (s, 1H), 5.97 (d, J=5.8 Hz, 1H), 4.91 (s, 2H), 4.00-3.78 (m, 1H), 1.66-1.36 (m, 4H), 0.89 (t, J=7.3 Hz, 6H) ppm. HPLC purity: 98.83% at 210 nm and 99.00% at 254 nm. MS (ESI⁺): m/z=313.2 (M+H)⁺

Example 2-3-5: 7-fluoro-5-((4-(pentan-3-ylamino)-5-(trifluoromethyl)pyrimidin-2-yl)amino)benzo[c][1,2]oxaborol-1(3H)-ol

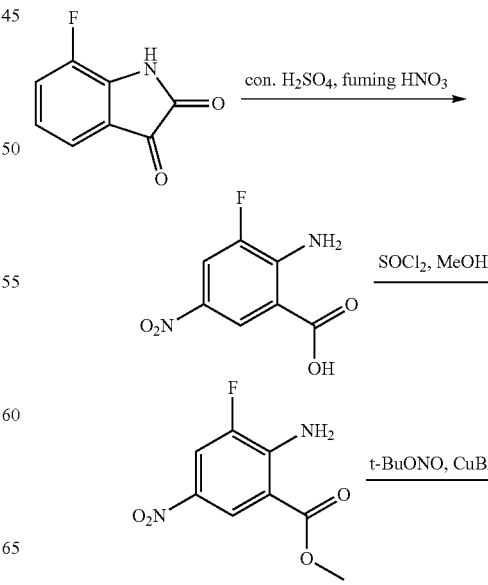

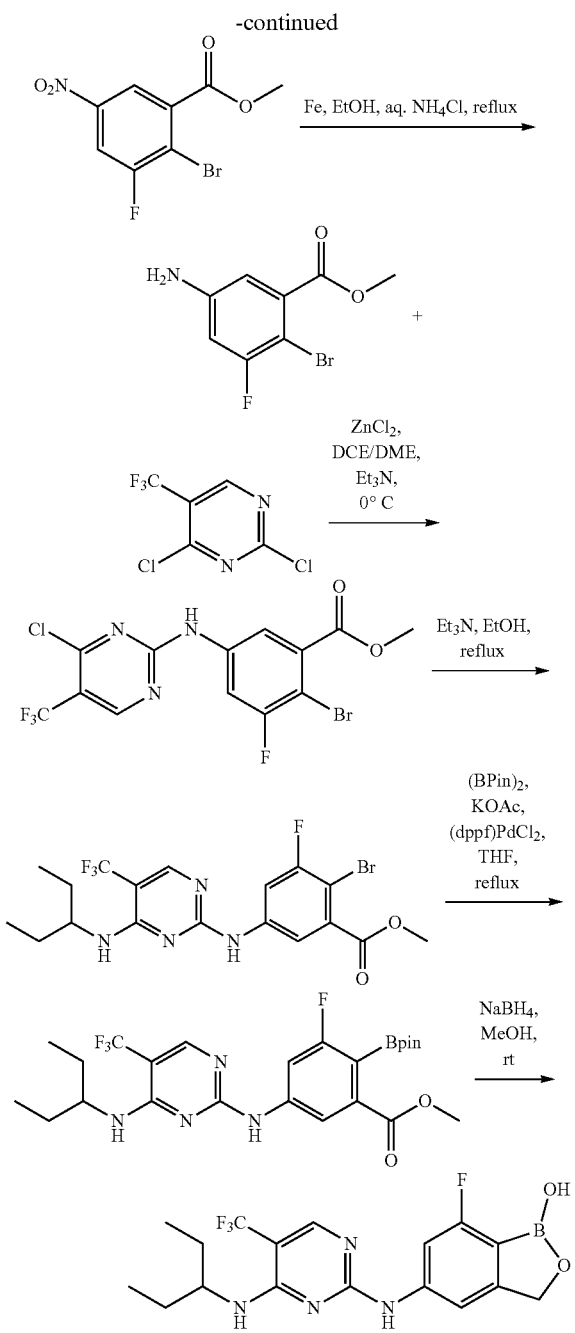

To a solution of 7-fluoroindoline-2,3-dione (10.0 g, 60.0 mmol) in concentrated $H_2SO_4$ (25 mL) was added fuming $HNO_3$ (2.5 mL) at 0° C. dropwise, the resulting reaction mixture was stirred at 0° C. for 1 h. Then the mixture was poured into 45% NaOH ice-water solution, and 30% $H_2O_2$ (10 mL) was added to above mixture dropwise at room temperature, the resulting mixture was stirred for another 30 min. The pH of this mixture was adjusted to 2 by adding aq. HCl, and the formed solid was collected by filtration, washed with water, dried in vacuo to give 2-amino-3-fluoro-5-nitrobenzoic acid (11.2 g, crude) as a yellow solid, which was used directly in the next step without further purification.

To a solution of 2-amino-3-fluoro-5-nitrobenzoic acid (10.0 g, crude) in MeOH (100 mL) was added $SOCl_2$ (10 mL), the resulting mixture was heated to 70° C. and kept stirring overnight. The reaction mixture was cooled to room temperature, concentrated in vacuo to give the crude product, which was suspended in ethyl acetate, and its pH was adjust to 8-9 by adding cold sat. Sodium bicarbonate solution. The aqueous phase is extracted twice with ethyl acetate, and the combined organic phase was washed with saturated sodium bicarbonate solution and brine sequentially, dried over anhydrous sodium sulfate, filtered and concentrated in vacuo to give a residue, which was purified by silica chromatography (PE/EtOAc (50/1 to 10/1)) to give methyl 2-amino-3-fluoro-5-nitrobenzoate (6.0 g, yield 47%) as a yellow solid. $^1$H NMR (300 MHz, DMSO-$d_6$): δ 8.46 (s, 1H), 8.14 (d, J=11.2 Hz, 1H), 7.80 (s, 2H), 3.88 (s, 3H) ppm.

A suspension of cuprous bromide (6.24 g, 43.4 mmol) and 5 mL of tert-butyl nitrite in 50 mL of anhydrous acetonitrile was heated to 70° C. Then a solution of 6.0 g of methyl-2-amino-3-fluoro-5-nitrobenzoate (27.6 mmol) in 30 mL of anhydrous acetonitrile was added to above mixture dropwise, the resulting reaction mixture was stirred at 70° C. overnight. After cooled to room temperature, the reaction mixture was poured into 1 N hydrochloric acid solution, the aqueous phase was extracted with ethyl acetate three times. The combined organic phase was washed twice with saturated sodium chloride solution, dried over magnesium sulfate, filtered and concentrated in vacuo to give the crude product, which is purified by column chromatography to give methyl 2-bromo-3-fluoro-5-nitrobenzoate (4.3 g, yield 56%) as a yellow solid. $^1$H NMR (300 MHz, DMSO-$d_6$): δ 8.60-8.30 (m, 2H), 3.92 (s, 3H) ppm.

To a solution of a methyl 2-bromo-3-fluoro-5-nitrobenzoate (4.3 g, 15.5 mmol) in EtOH (30 mL) was added Fe powder (8.4 g, 0.15 mol) and sat. $NH_4Cl$ (10 mL), the resulting mixture was stirred at 80° C. for 4 h. Then the solid was removed by filtration, and the filtrate was poured into water, extracted with EtOAc. The combined organic phase was washed with water, brine, concentrated in vacuo to give a residue, which was purified by silica chromatography (PE/EtOAc (50/1 to 10/1)) to give methyl 5-amino-2-bromo-3-fluorobenzoate (1.8 g, yield 47%) as a yellow solid. $^1$H NMR (400 MHz, DMSO-$d_6$): δ 6.81 (d, J=1.8 Hz, 1H), 6.63 (dd, J=11.4, 2.6 Hz, 1H), 5.89 (s, 2H), 3.82 (d, J=6.3 Hz, 3H) ppm.

To a solution of 2,4-dichloro-5-(trifluoromethyl)pyrimidine (1.5 g, 6.9 mmol) in a mixture of DCE/t-BuOH (54 mL, v/v: 1/1) was added $ZnCl_2$ (8.3 mL, 1 N in THF) at 0° C., the resulting mixture was stirred at 0° C. for 1 h. Then methyl 5-amino-2-bromo-3-fluorobenzoate (1.7 g, 6.9 mmol) and $Et_3N$ (766 mg, 7.6 mmol) in DCE/t-BuOH (1:1, 10 mL) were added, the reaction mixture was stirred at 30° C. for 24 h. The mixture was poured into water, and the aqueous phase was extracted with ethyl acetate. The combined organic phase was washed with water, brine, concentrated in vacuo to give a residue, which was purified by silica chromatography (PE/EtOAc (50/1 to 10/1)) to give methyl 2-bromo-5-((4-chloro-5-(trifluoromethyl)pyrimidin-2-yl)amino)-3-fluorobenzoate (1.4 g, yield 47%) as a yellow solid. $^1$H NMR (300 MHz, DMSO-$d_6$) δ 11.13 (s, 1H), 8.93 (s, 1H), 8.04 (d, J=11.2 Hz, 1H), 7.93 (s, 1H), 3.89 (s, 3H) ppm. MS (ESI$^+$): m/z=425.8, 427.8 (M–H)$^-$ To a solution of methyl 2-bromo-5-((4-chloro-5-(trifluoromethyl)pyrimidin-2-yl)amino)-3-fluorobenzoate (1.2 g, 2.8 mmol) in EtOH (20 mL) was added pentan-3-amine (365 mg, 4.2 mmol) and $Et_3N$ (840 mg, 8.4 mmol). The reaction mixture was stirred at 80° C. for 6 h, then it was concentrated in vacuo to give a residue, which was purified by silica chromatography (PE/EtOAc (50/1 to 20/1)) to give methyl 2-bromo-3-fluoro-5-((4-(pentan-3-ylamino)-5-(trifluoromethyl)pyrimidin-2-yl)amino)benzoate (1.4 g, yield 100%) as a light yellow solid. $^1$H NMR (300 MHz, DMSO-$d_6$): δ 10.11 (s, 1H), 8.25 (s, 1H), 8.10 (s, 1H), 7.94 (d, J=11.7 Hz, 1H), 6.62 (d, J=7.5 Hz, 1H), 4.27-4.04 (m, 1H), 3.84 (d, J=15.5 Hz, 3H), 1.72-1.47 (m, 4H), 0.84 (t, J=7.3 Hz, 6H) ppm.

To a solution of methyl 2-bromo-3-fluoro-5-((4-(pentan-3-ylamino)-5-(trifluoromethyl) pyrimidin-2-yl)amino)benzoate (1.3 g, 2.7 mmol) in THF (30 mL) was added KOAc (804 mg, 8.1 mmol), (BPin)$_2$ (1.4 g, 5.4 mmol) and (dppf) PdCl$_2$ (810 mg, 1.1 mmol) at room temperature under nitrogen atmosphere. The mixture was heated to reflux for 1 d, then the solid was removed by filtration, and the filtrate was concentrated in vacuo to give a residue, which was purified by silica chromatography (PE/EtOAc (100/1 to 20/1)) to give methyl 3-fluoro-5-((4-(pentan-3-ylamino)-5-(trifluoromethyl)pyrimidin-2-yl)amino)-2-(4,4,5,5-tetramethyl-1,3,2-dioxaborolan-2-yl) benzoate (840 mg, contain B$_2$Pin$_2$) as a yellow solid. $^1$H NMR (400 MHz, CDCl$_3$): δ 8.06 (s, 1H), 7.83 (s, 1H), 7.73 (d, J=10.6 Hz, 1H), 4.88 (d, J=8.4 Hz, 1H), 4.20-4.09 (m, 1H), 3.82 (s, 3H), 1.72-1.56 (m, 2H), 1.53-1.42 (m, 2H), 1.23-1.18 (m, 12H), 0.87 (t, J=7.4 Hz, 6H) ppm.

To a solution of give methyl 3-fluoro-5-((4-(pentan-3-ylamino)-5-(trifluoromethyl) pyrimidin-2-yl)amino)-2-(4,4,5,5-tetramethyl-1,3,2-dioxaborolan-2-yl)benzoate (840 mg, contain B$_2$Pin$_2$) in MeOH (20 mL) was added NaBH$_4$ (800 gm) at room temperature in portions. The reaction was stirred at room temperature for 30 min, then it was quenched by water, and the aqueous phase was extracted with EtOAc. The combined organic layer was washed with water, brine, concentrated in vacuo to give a residue, which was triturated with MeCN and water to give 7-fluoro-5-((4-(pentan-3-ylamino)-5-(trifluoromethyl)pyrimidin-2-yl)amino)benzo[c][1,2]oxaborol-1(3H)-ol (66.1 mg, yield 6%) as white solid. $^1$H NMR (400 MHz, DMSO-$d_6$): δ 9.97 (s, 1H), 9.07 (s, 1H), 8.24 (s, 1H), 7.67-7.50 (m, 2H), 6.52 (d, J=8.3 Hz, 1H), 4.96 (s, 2H), 4.25-4.09 (m, 1H), 1.72-1.52 (m, 4H), 0.87 (t, J=7.3 Hz, 6H) ppm. HPLC purity: 95.38% at 210 nm and 96.29% at 254 nm. MS (ESI$^+$): m/z=399.1 (M+H)$^+$.

Example 2-3-6: 3-((2-((1-hydroxy-1,3-dihydrobenzo[c][1,2]oxaborol-5-yl)amino)-5-methylpyrimidin-4-yl)amino)pentane-1,5-diol and 5-((4-((2-hydroxytetrahydro-2H-pyran-4-yl)amino)-5-methylpyrimidin-2-yl)amino)benzo[c][1,2]oxaborol-1(3H)-ol

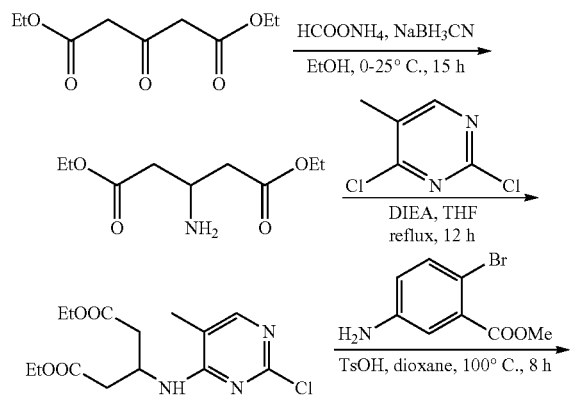

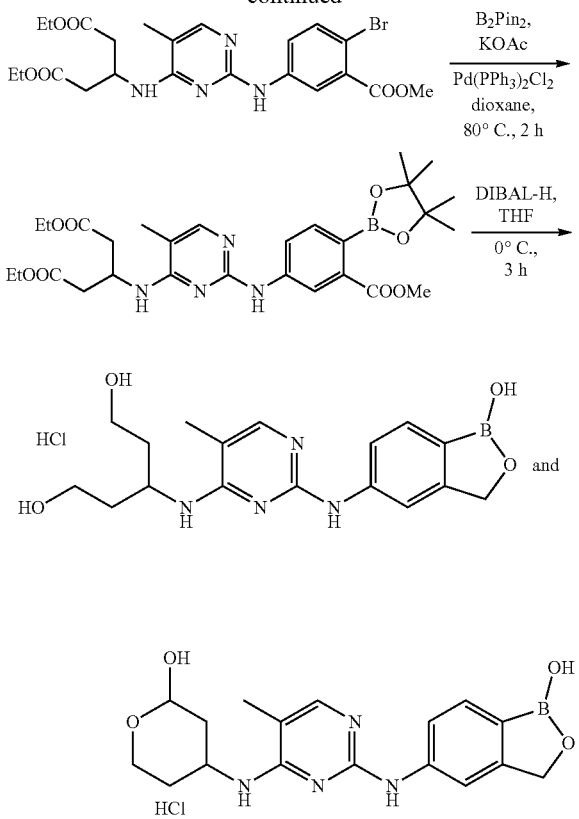

Preparation of diethyl 3-aminopentanedioate

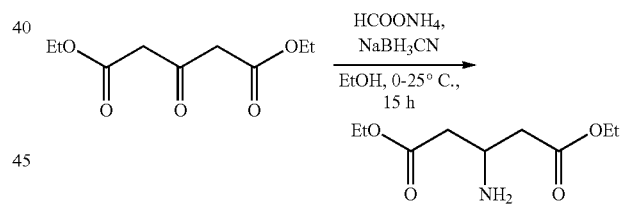

To a mixture of diethyl 3-oxopentanedioate (20.0 g, 98.91 mmol, 18.02 mL, 1 eq) in EtOH (500 mL) was added ammonia-formic acid (50.0 g, 791.28 mmol, 8 eq) and NaBH$_3$CN (6.90 g, 108.80 mmol, 1.1 eq) in one portion at 0° C. The mixture was stirred at 25° C. for 15 h. The mixture was poured into H$_2$O (100 mL). After removal of the organic solvent, the pH of the aqueous phase was adjusted to pH=3 with 3N HCl, and the aqueous phase was extracted with EtOAc (200 mL×2), and the combined organic layer was discarded. The pH of the aqueous layer was then adjusted to pH=10 with K$_2$CO$_3$, extracted with EtOAc (200 mL×2). The organic layer was washed with brine (200 mL×2), dried over anhydrous Na$_2$SO$_4$, filtered and concentrated in vacuo to yield diethyl 3-aminopentanedioate (5.00 g, 24.60 mmol, 4.97% yield) as colorless oil. $^1$H NMR (CDCl$_3$, 400 MHz) δ 4.16 (q, J=7.2 Hz, 4H), 3.67-3.63 (m, 1H), 2.52 (dd, J=16, 4.8 Hz, 2H), 2.42 (dd, J=16, 4.4 Hz, 2H), 2.02 (br s, 2H), 1.03 (d, J=7.2 Hz, 6H).

Preparation of diethyl 3-[(2-chloro-5-methyl-pyrimidin-4-yl)amino]pentanedioate

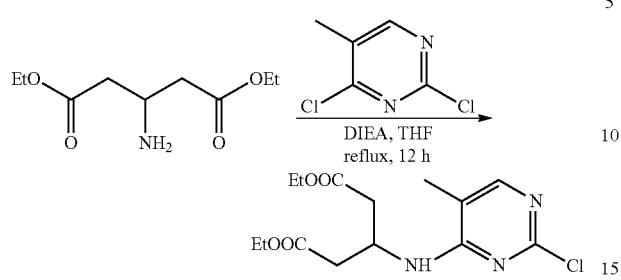

To a solution of ethyl 3-amino-5-ethoxy-4-oxo-pentanoate (8.0 g, 39.36 mmol, 1 eq) in THF (120 mL) was added DIEA (20.4 g, 157.45 mmol, 27.42 mL, 4 eq) and 2,4-dichloro-5-methyl-pyrimidine (6.4 g, 39.36 mmol, 1 eq) at 20° C. The reaction mixture was stirred at 90° C. for 12 h. The reaction mixture was filtered, and the filtrate was concentrated in vacuo to give a residue, which was purified by column (SiO$_2$, Petroleum ether:Ethyl acetate=30:1) to give diethyl 3-[(2-chloro-5-methyl-pyrimidin-4-yl)amino]pentanedioate (6 g, 18.19 mmol, 46.22% yield) as yellow gum. $^1$H NMR (MeOD, 400 MHz) δ 7.77 (s, 1H), 5.06-4.98 (m, 1H), 4.09 (q, J=7.2 Hz, 4H), 2.71 (d, J=6.8 Hz, 4H), 2.01 (s, 3H), 1.20 (t, J=7.2 Hz, 6H).

Preparation of diethyl 3-[[2-(4-bromo-3-methoxy-carbonyl-anilino)-5-methyl-pyrimidin-4-yl]amino]pentanedioate

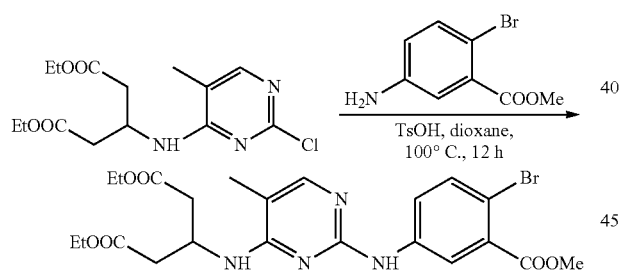

To a solution of diethyl 3-[(2-chloro-5-methyl-pyrimidin-4-yl)amino]pentanedioate (1.0 g, 3.03 mmol, 1 eq) in dioxane (20 mL) was added TsOH·H$_2$O (577 mg, 3.03 mmol, 1 eq) and methyl 5-amino-2-bromo-benzoate (698 mg, 3.03 mmol, 1 eq) at 20° C. The mixture was stirred at 100° C. for 12 h. Then the reaction mixture was partitioned between EtOAc (20 mL) and sat. aq. NaHCO$_3$ (20 mL). The organic phase was separated, washed with brine (10 mL), dried over anhydrous Na$_2$SO$_4$, filtered and concentrated in vacuo to give a residue, which was purified by column (SiO$_2$, Petroleum ether/Ethyl acetate=5/1 to 1/1) to give diethyl3-[[2-(4-bromo-3-methoxycarbonyl-anilino)-5-methyl-pyrimidin-4-yl]amino]pentanedioate (900 mg, 1.72 mmol, 56.71% yield) as a white solid. $^1$H NMR (CDCl$_3$, 400 MHz) δ 8.02 (d, J=2.4 Hz, 1H), 7.76 (s, 1H), 7.72 (dd, J=8.8 Hz, 2.4 Hz, 1H), 7.55 (d, J=8.8 Hz, 1H), 7.05 (s, 1H), 5.76-5.72 (m, 1H), 4.98-4.93 (m, 1H), 4.15 (q, J=7.2 Hz, 4H), 3.94 (s, 3H), 2.85-2.70 (m, 4H), 1.98 (s, 3H), 1.25 (t, J=7.2 Hz, 6H).

Preparation of diethyl 3-[[2-[4-(5,5-dimethyl-1,3,2-dioxaborinan-2-yl)-3-_methoxycarbonyl-anilino]-5-methyl-pyrimidin-4-yl]amino]pentanedioate

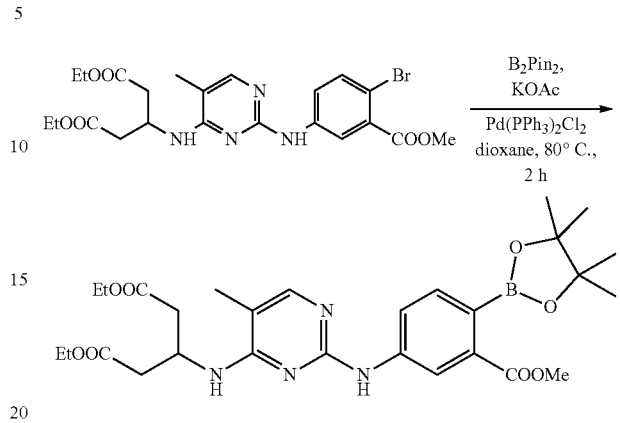

A mixture of diethyl 3-[[2-(4-bromo-3-methoxycarbonyl-anilino)-5-methyl-pyrimidin-4-yl]amino]pentanedioate (450 mg, 859.80 µmol, 1 eq), 2-(5,5-dimethyl-1,3,2-dioxaborinan-2-yl)-5,5-dimethyl-1,3,2-dioxaborinane (583 mg, 2.58 mmol, 3 eq), KOAc (253 mg, 2.58 mmol, 3 eq), Pd(PPh$_3$)$_2$Cl$_2$ (121 mg, 171.96 µmol, 0.2 eq) in dioxane (10 mL) was degassed and purged with N$_2$ for 3 times, then the reaction mixture was stirred at 80° C. for 2 h under N$_2$ atmosphere. The reaction mixture was filtered, and the filtrate was concentrated in vacuo to give a residue, which was purified by column chromatography (SiO$_2$, Petroleum ether/Ethyl acetate=1/0 to 1/1) to give diethyl 3-[[2-[4-(5,5-dimethyl-1,3,2-dioxaborinan-2-yl)-3-methoxycarbonyl-anilino]-5-methyl-pyrimidin-4-yl]amino]pentanedioate (600 mg, 808.75 µmol, 47.03% yield, 75% purity) as a white solid.

Preparation of 3-[[2-[(1-hydroxy-3H-2,1-benzoxaborol-5-yl)amino]-5-methyl-pyrimidin-4-yl]amino]pentane-1,5-diol hydrochloride and 4-[[2-[(1-hydroxy-3H-2,1-benzoxaborol-5-yl) amino]-5-methyl-pyrimidin-4-yl]amino]tetrahydropyran-2-ol hydrochloride

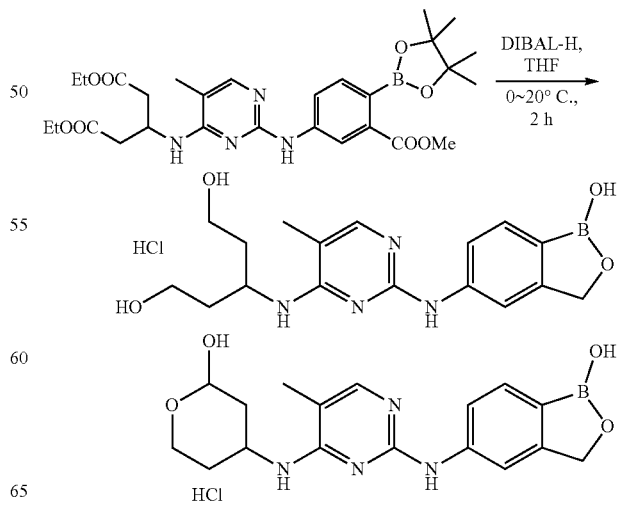

A mixture of diethyl 3-[[2-[4-(5,5-dimethyl-1,3,2-dioxaborinan-2-yl)-3-methoxycarbonyl-anilino]-5-methyl-pyrimidin-4-yl]amino]pentanedioate (600 mg, 647.00 μmol, 1 eq) in THF (10 mL) was added DIBAL-H (1 M, 3.9 mL, 6 eq) dropwise at 0° C., and then the mixture was stirred at 20° C. for 2 h under $N_2$ atmosphere. The reaction was quenched with $Na_2SO_4 \cdot 10H_2O$, and the resulting mixture was filtered, the filtrate was concentrated in vacuo to give a residue, which was purified by prep-HPLC (column: Phenomenex Synergi C18 150*25*10 um; mobile phase: [water(0.1% TFA)-ACN]; B %: 10%-30%, 8 min). The collections from prep-HPLC were treated with 0.5 mL of HCl (1N), which were freeze-dried to give 3-[[2-[(1-hydroxy-3H-2,1-benzoxaborol-5-yl)amino]-5-methyl-pyrimidin-4-yl]amino]pentane-1,5-diol; hydrochloride (58 mg, 146.96 μmol, 22.71% yield) as a white solid $^1H$ NMR (DMSO-$d_6$+$D_2O$, 400 MHz) δ 7.76 (s, 1H), 7.69 (dd, J=8.0 Hz, 1H), 7.61 (s, 1H), 7.41 (d, J=8.0 Hz, 1H), 4.96 (s, 2H), 4.51-4.47 (m, 1H), 3.43-3.35 (m, 4H), 1.96 (s, 3H), 1.78-1.72 (m, 4H). MS (ESI): mass calcd. For $C_{17}H_{23}BN_4O_4$ 358.18, m/z found 359.1 [M+H]$^+$. HPLC: 97.34% (220 nm), 98.86% (254 nm), and 4-[[2-[(1-hydroxy-3H-2,1-benzoxaborol-5-yl)amino]-5-methyl-pyrimidin-4-yl]amino] tetrahydropyran-2-ol; hydrochloride (8.5 mg, 21.65 μmol, 3.35% yield) as a white solid. $^1H$ NMR (DMSO-$d_6$+$D_2O$, 400 MHz) δ 7.83 (s, 0.5H), 7.72-7.67 (m, 1.5H), 7.45 (s, 1H), 7.38 (m, 1H), 5.22 (s, 0.5H), 4.99-4.97 (m, 2H), 4.65-4.55 (m, 1H), 4.25-4.15 (m, 0.5H), 3.95-3.91 (m, 1H), 3.61-3.57 (m, 0.5H), 3.50-3.35 (m, 0.5H), 1.99-1.94 (m, 0.5H), 1.97 (s, 4H), 1.82-1.46 (m, 3.5H). MS (ESI): mass calcd. For $C_{17}H_{21}BN_4O_4$ 356.17, m/z found 357.1 [M+H]$^+$. HPLC: 95.01% (220 nm), 96.45% (254 nm).

Example 2-3-7: 5-((4-((1,5-difluoropentan-3-yl)amino)-5-methylpyrimidin-2-yl)amino)benzo[c][1,2]oxaborol-1(3H)-ol

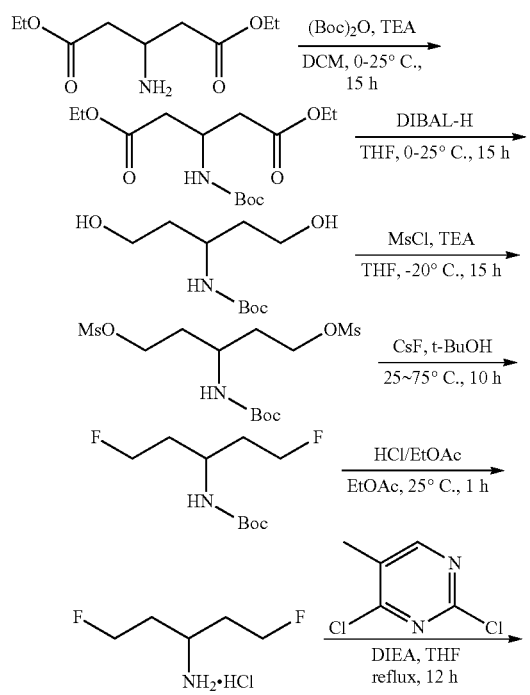

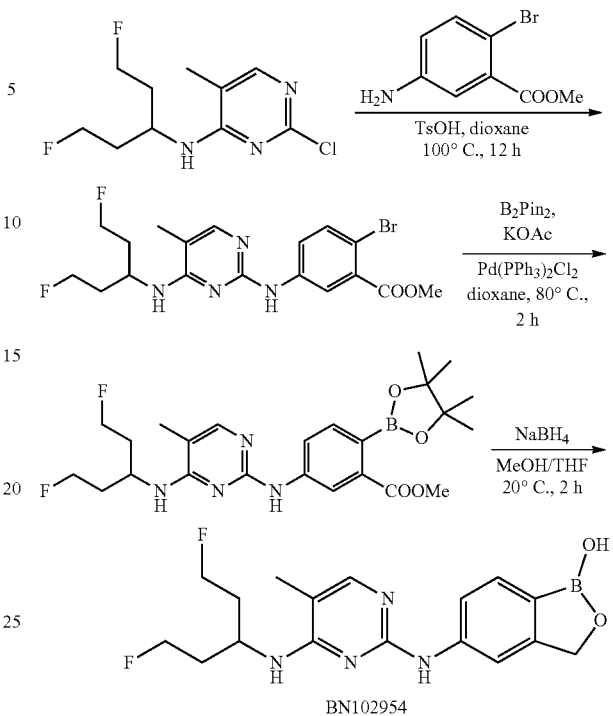

Preparation of diethyl 3-(tert-butoxycarbonylamino)pentanedioate

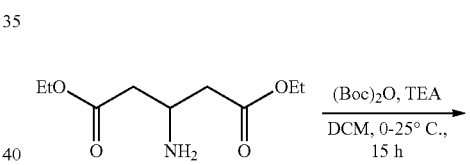

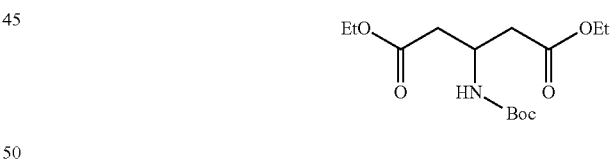

To a mixture of diethyl 3-aminopentanedioate (12.5 g, 61.51 mmol, 1 eq) and $Et_3N$ (24.9 g, 246.02 mmol, 34.24 mL, 4 eq) in DCM (150 mL) was added (Boc)$_2$O (26.9 g, 123.01 mmol, 28.26 mL, 2 eq) in one portion at 0° C. under $N_2$ atmosphere. The reaction mixture was stirred at 25° C. for 15 h. The mixture was poured into $H_2O$ (80 mL), and the aqueous phase was extracted with DCM (50 mL×2). The combined organic layer was washed with brine (50 mL×2), dried over anhydrous $Na_2SO_4$, filtered and concentrated in vacuo to give a residue, which was purified by column chromatography (SiO$_2$, Petroleum ether/Ethyl acetate=10/1 to 5/1) to give diethyl 3-(tert-butoxycarbonylamino)pentanedioate (16.0 g, 52.74 mmol, 42.88% yield) as colorless oil. $^1H$ NMR (CDCl$_3$, 400 MHz) δ 5.35 (s, 1H), 4.34-4.31 (m, 1H), 4.15 (q, J=7.2 Hz, 4H), 2.71-2.59 (m, 4H), 1.44 (s, 9H), 1.27 (d, J=7.2 Hz, 6H).

Preparation of tert-butyl N-[3-hydroxy-1-(2-hydroxyethyl)propyl]carbamate

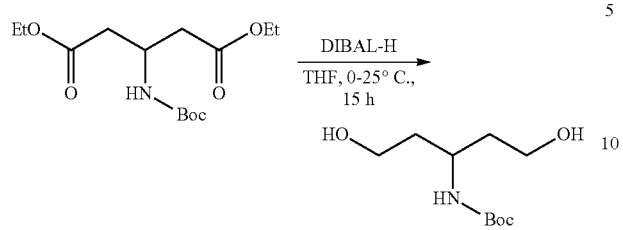

To a mixture of diethyl 3-(tert-butoxycarbonylamino) pentanedioate (8.00 g, 26.37 mmol, 1 eq) in THF (100 mL) was added DIBAL-H (1 M, 105.5 mL, 4 eq) dropwise at 0° C. under N₂ atmosphere. The mixture was stirred at 25° C. for 15 h. The reaction was quenched with Na₂SO₄·10H₂O (30 g) at 0° C., and the solid was removed by filtration. The filtrate was concentrated in vacuo to give tert-butyl N-[3-hydroxy-1-(2-hydroxyethyl)propyl]carbamate (7.00 g, 31.92 mmol, 60.52% yield) as colorless oil. ¹H NMR (CDCl₃, 400 MHz) δ 4.93 (d, J=4.4 Hz, 1H), 4.01-3.97 (m, 1H), 3.73 (dd, J=7.6, 3.6 Hz, 4H), 2.76 (br s, 1H), 1.89-1.80 (m, 2H), 1.57-1.50 (m, 2H) 1.46 (s, 9H).

Preparation of [3-(tert-butoxycarbonylamino)-5-methyl sulfonyloxy-pentyl]methanesulfonate

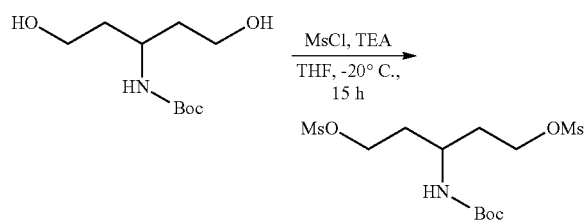

To a mixture of tert-butyl N-[3-hydroxy-1-(2-hydroxyethyl)propyl]carbamate (4.00 g, 18.24 mmol, 1 eq) and TEA (7.40 g, 72.97 mmol, 10.2 mL, 4 eq) in THF (30 mL) was added MsCl (5.20 g, 45.60 mmol, 3.50 mL, 2.5 eq) dropwise at −20° C. under N₂ atmosphere. The reaction mixture was stirred for 15 h at −20° C. Then H₂O (20 mL) was added to the above reaction mixture, and the aqueous phase was extracted with EtOAc (15 mL×2). The combined organic layer was washed with brine (15 mL×2), dried over anhydrous Na₂SO₄, filtered and concentrated in vacuo to give [3-(tert-butoxycarbonylamino)-5-methyl sulfonyloxy-pentyl]methanesulfonate (3.00 g, crude) as a yellow solid. ¹H NMR (CDCl₃, 400 MHz) δ 4.77 (d, J=5.2 Hz, 1H), 4.30-4.21 (m, 4H), 3.85-3.83 (m, 1H), 3.01 (s, 6H), 1.96-1.85 (m, 4H), 1.40 (s, 9H)

Preparation of tert-butyl N-[3-fluoro-1-(2-fluoroethyl)propyl] carbamate

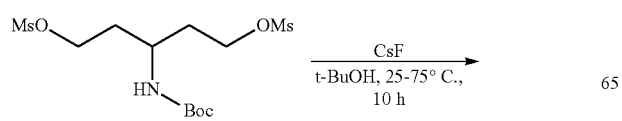

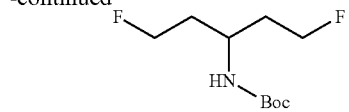

To a mixture of [3-(tert-butoxycarbonylamino)-5-methylsulfonyloxy-pentyl]methanesulfonate (3.00 g, 6.39 mmol, 1 eq) in t-BuOH (30 mL) was added CsF (5.80 g, 38.35 mmol, 1.40 mL, 6 eq) in one portion at 25° C., the resulting mixture was heated up to 75° C. and kept stirring for 10 h. The reaction mixture was then cooled to room temperature, concentrated in vacuo to give a residue, to which H₂O (20 mL) was added, extracted with EtOAc (10 mL×2). The combined organic layer was washed by brine (10 mL×2), dried over Na₂SO₄, filtered and concentrated in vacuo to give a residue, which was purified by column chromatography (SiO₂, Petroleum ether/Ethyl acetate=10/1 to 3/1) to give tert-butyl N-[3-fluoro-1-(2-fluoroethyl)propyl]carbamate (0.7 g, 3.14 mmol, 49.05% yield) as a white solid. ¹H NMR (CDCl₃, 400 MHz) δ 4.65-4.61 (m, 2H), 4.53-4.49 (m, 2H), 3.91-3.88 (m, 1H), 2.04-1.86 (m, 4H), 1.45 (s, 9H).

1,5-difluoropentan-3-amine

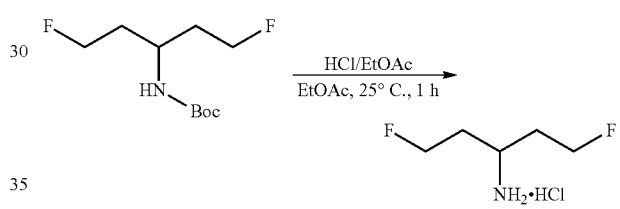

To a mixture of tert-butyl N-[3-fluoro-1-(2-fluoroethyl) propyl]carbamate (700 mg, 3.14 mmol, 1 eq) in EtOAc (5 mL) was added HCl/EtOAc (15 mL) in one portion at 25° C. The mixture was stirred at 25° C. for 1 h. The reaction mixture was concentrated in vacuo to give the 1,5-difluoropentan-3-amine (450 mg, 2.82 mmol, 89.92% yield, HCl) as a yellow solid. ¹H NMR (CDCl₃, 400 MHz) δ 8.27 (s, 3H), 4.69-4.67 (m, 2H), 4.57-4.54 (m, 2H), 3.38-3.35 (m, 1H), 2.08-2.03 (dd, J=12, 6 Hz, 2H), 2.01-1.97 (dd, J=12, 6 Hz, 2H).

Preparation of 2-chloro-N-[3-fluoro-1-(2-fluoroethyl)propyl]-5-methyl-pyrimidin-4-amine

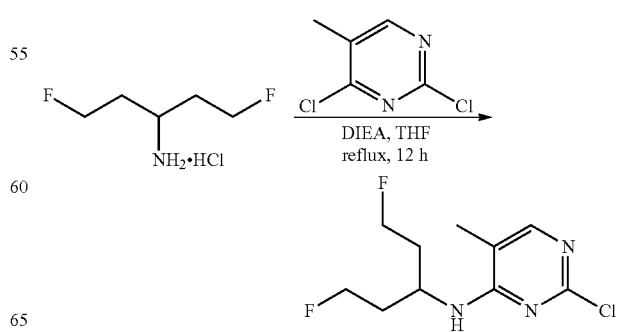

This substance was prepared by following the procedure employed for synthesis of diethyl 3-[(2-chloro-5-methyl-pyrimidin-4-yl)amino]pentanedioate as a white solid. Yield: 38.35%. $^1$H NMR (CDCl$_3$, 400 MHz) δ 7.84 (s, 1H), 5.03 (t, J=5.2 Hz, 1H), 4.74-4.55 (m, 5H), 2.17-2.11 (m, 4H), 1.99 (s, 3H).

Preparation of methyl 2-bromo-5-[[4-[[3-fluoro-1-(2-fluoroethyl)propyl]amino]-5-methyl-pyrimidin-2-yl]amino]benzoate

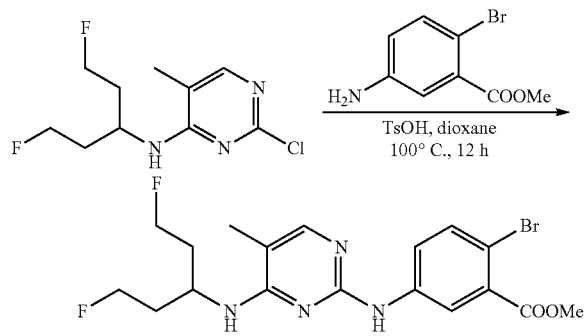

The substance was prepared by following the procedure employed for the synthesis of diethyl 3-[[2-(4-bromo-3-methoxycarbonyl-anilino)-5-methyl-pyrimidin-4-yl]amino]pentanedioate as a white solid. Yield: 45.06%. $^1$H NMR (CDCl$_3$, 400 MHz) δ 8.12 (d, J=2.4 Hz, 1H), 7.76 (s, 1H), 7.60 (dd, J=8.8 Hz, 2.8 Hz, 1H), 7.53 (d, J=2.4 Hz, 1H), 6.95 (s, 1H), 4.72-4.55 (m, 6H), 3.93 (m, 3H), 2.23-1.98 (m, 4H), 1.97 (s, 3H).

Preparation of methyl 2-(5,5-dimethyl-1,3,2-dioxaborinan-2-yl)-5-[[4-[[3-fluoro-1-(2-fluoroethyl)propyl]amino]-5-methyl-pyrimidin-2-yl]amino]benzoate

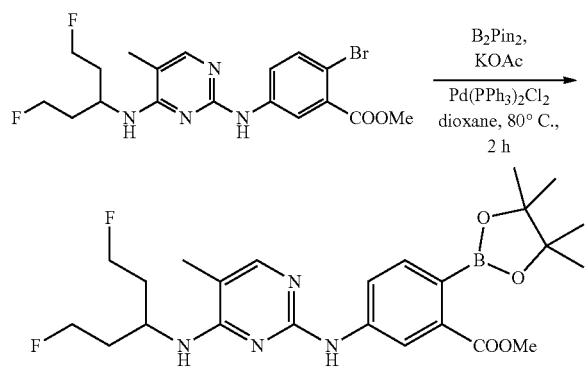

This substance was prepared by following the procedure employed for the synthesis of diethyl 3-[[2-[4-(5,5-dimethyl-1,3,2-dioxaborinan-2-yl)-3-methoxycarbonyl-anilino]-5-methyl-pyrimidin-4-yl]amino]pentanedioate as a white solid. Yield: 59.56% with 60% purity.

Preparation of 5-((4-((1,5-difluoropentan-3-yl)amino)-5-methylpyrimidin-2-yl)amino) benzo[c][1,2]oxaborol-1(3H)-ol

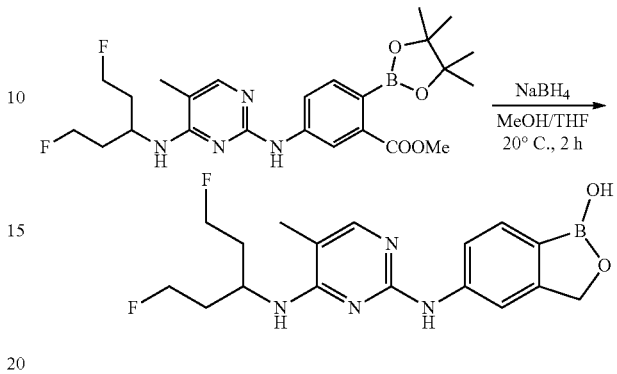

The substance was prepared by following the procedure employed for the synthesis of 3-[[2-[(1-hydroxy-3H-2,1-benzoxaborol-5-yl)amino]-5-methyl-pyrimidin-4-yl]amino]pentane-1,5-diol; hydrochloride and 4-[[2-[(1-hydroxy-3H-2,1-benzoxaborol-5-yl) amino]-5-methyl-pyrimidin-4-yl]amino]tetrahydropyran-2-ol; hydrochloride as a white solid. Yield: 23.29%. $^1$H NMR (DMSO-d$_6$, 400 MHz) δ 10.18 (s, 1H), 9.13 (s, 1H), 8.03 (s, 1H), 7.75 (s, 1H), 7.69 (d, J=8.0 Hz, 1H), 7.70 (s, 1H), 7.44 (d, J=8.0 Hz, 1H), 4.95 (s, 2H), 4.61-4.39 (m, 5H), 2.09-1.99 (m, 4H), 2.03 (m, 3H). MS (ESI): mass calcd. For $C_{17}H_{21}BF_2N_4O_2$ 362.17, m/z found 363.1 [M+H]$^+$. HPLC: 96.02% (220 nm), 97.78% (254 nm).

BIOLOGICAL EXAMPLES

The compounds of the present disclosure were tested in multiple assays. The results are compiled in the Figures, as noted.

Biochemical Kinase Assay Protocol (JAK, TrkA, Syk, Tyk2)
Reagent: Base Reaction buffer; 20 mM Hepes (pH 7.5), 10 mM MgCl2, 1 mM EGTA, 0.02% Brij™ 35, 0.02 mg/ml BSA, 0.1 mM Na3VO4, 2 mM DTT, 1% DMSO, where required cofactors are added individually to each kinase reaction.

Reaction Procedure:
1. Prepare indicated substrate in freshly prepared Base Reaction Buffer
2. Deliver any required cofactors to the substrate solution above
3. Deliver indicated kinase (JAK or TrkA) into the substrate solution and gently mix
4. Deliver compounds in DMSO into the kinase reaction mixture by Acoustic technology (Echo550; nanoliter range), incubate for 20 minutes at room temperature
5. Deliver 33P-ATP into the reaction mixture to initiate the reaction.
6. Incubate kinase reaction for 2 hours at room temperature
7. Reactions are spotted onto P81 ion exchange paper
8. Detect kinase activity by filter-binding method.

PDE4B Phosphodiesterase Assay

The assay is based on the fluorescence polarization measuring AMP/GMP production as a result of the enzyme activity by displacement of Tracer binding to the AMP/GMP antibody.

Reaction Buffer: 10 mM Tris-HCl, pH 7.5, 5 mM MgCl2, 0.01% Brij 35, 1 mM DTT and 1% DMSO.

Enzyme: Recombinant human PDE4B (Gene Accession #NM_002600; aa 305-end) was expressed by baculovirus in Sf9 insect cells using an N-terminal GST tag. Mw=78 kDa.

Substrate: 1 μM cAMP

Detection: Transcreener® AMP2/GMP2 Antibody AMP2/GMP2 AlexaFluor 633 Tracer

Reaction Procedure:
1. Prepared indicated enzyme and substrate in freshly prepared Reaction Buffer
2. Delivered enzyme solution into the reaction well
3. Delivered compounds in 100% DMSO into the enzyme solution by Acoustic technology (Echo550; nanoliter range), incubated for 10 min at room temperature
4. Delivered substrate solution into the reaction well to initiate the reaction
5. Incubated for 1 h at room temperature
6. Added detection mixture (Tracer and antibody in the stop buffer) to stop the reaction and incubated for 90 min with gentle mixing. The fluorescence polarization was measured at Ex/Em 620/688.

Data Analysis: The FP signals were converted into nM product based on an AMP/GMP standard curve and calculated % Enzyme activity relative to DMSO control by Excel. The curve fit was performed using GraphPad prism.

T-Cell Inflammation Inhibition Assay for IL-4, IL-13 and TNFa

The test compounds were solubilized in DMSO, then diluted to make appropriate stocks for use in the assay, and diluted in culture medium to 20× assay concentrations. PBMC's were plated and allowed to settle for 1 hour at 37° C., 5% $C_{O2}$. Test compounds and controls were added to the settled PBMC's and incubated for 1 hour at 37° C., 5% CO2. The PBMC's were then be treated with PHA (10 μg/mL) and incubated for 24 hours at 37° C., 5% CO2. Vehicle was used as a positive control and dexamethasone (100 nM) was used as a reference inhibitor control. After the main incubation, cell culture supernatants were harvested and assayed for the cytokines listed above, using standard Luminex protocols. Levels of cytokine induction were interpolated from standard curves using 5-parameter non-linear regression analyses, where $y=(A+((B-A)/(1+(((B-E)/(E-A))*((x/C)^{\wedge}D)))))$. The interpolated data was then normalized to vehicle controls and analyzed to determine IC50 values using 4-parameter non-linear regression analyses, where $y=(A+((B-A)/(1+((C/x)^{\wedge}D))))$ Cytokine Function Assay Protocol for IL-4/pSTAT6 and GM-CSF/pSTAT5

GM-CSF/pSTAT5: Whole blood from a healthy donor was lysed to remove red blood cells. Cells were plated onto a 96w plate. Compound was added and incubated for 1 hour (at 370 C). After 1 hour, cells were stimulated with GM-CSF for 15 minutes. Cells were fixed and stained with anti pSTAT5 antibody. After staining, cells were read on Beckman-Coulter CytoFLEX.

IL-4/pSTAT6: PBMC from a healthy donor was plated onto a 96w plate. Compound was added and incubated for 1 hour (at 370 C). After 1 hour, cells were stimulated with IL-4 for 15 minutes. Cells were fixed and stained with anti-pSTAT6 antibody. After staining, cells were read on Beckman-Coulter CytoFLEX.

Results: Results of the biological examples are provided in the Figure. As demonstrated, embodiments of compounds of the present disclosure demonstrate activity as: (i) inhibitors of one or more JAK kinases, (ii) selective inhibitors of JAK1, (iii) dual modulators of one or more JAK kinases and PDE4, and (iv) dual modulators selective for JAK1 along with inhibition of PDE4. Additionally, the compounds of the present disclosure may have additional activity to modulate one or more additional tyrosine kinase, including inhibition of Tropomyosin receptor kinase A (TrkA) or Spleen tyrosine kinase (Syk).

Accordingly, the compounds of the present disclosure demonstrate potential as therapeutics agents for one or more of atopic dermatitis, psoriasis, psoriatic arthritis, Bechet's disease, *pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer.

All publications, patents, and patent applications cited in this specification are incorporated herein by reference for the teaching to which such citation is used.

Test compounds for the experiments described herein were employed in free or salt form.

The specific responses observed may vary according to and depending on the particular active compound selected or whether there are present carriers, as well as the type of formulation and mode of administration employed, and such expected variations or differences in the results are contemplated in accordance with practice of the present disclosure.

Although specific embodiments of the present disclosure are herein illustrated and described in detail, the disclosure is not limited thereto. The above detailed descriptions are provided as exemplary of the present disclosure and should not be construed as constituting any limitation of the disclosure. Modifications will be obvious to those skilled in the art, and all modifications that do not depart from the spirit of the disclosure are intended to be included with the scope of the appended claims.

The invention claimed is:

1. A compound of formula (IB):

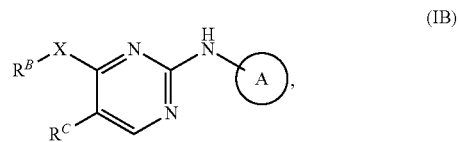

wherein:

A is selected from the group consisting of:

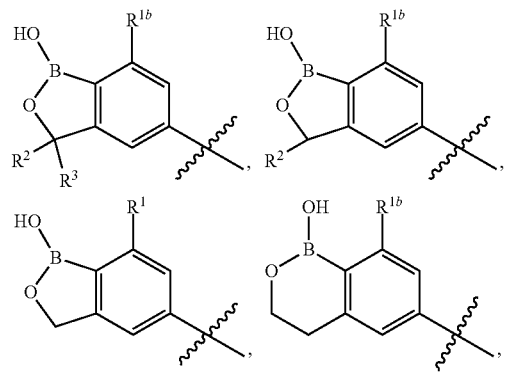

-continued

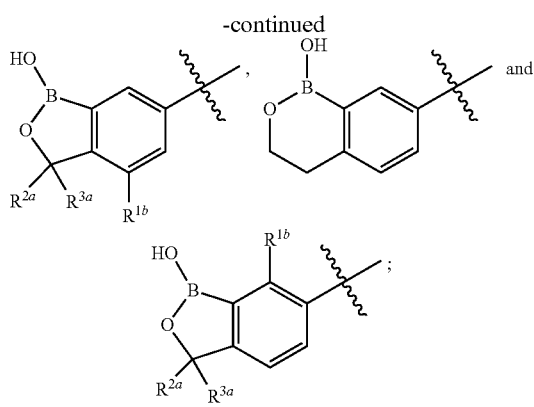

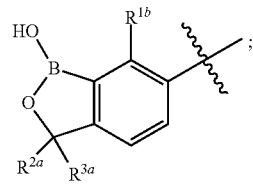

X is selected from the group consisting of: NH, O, and S;

RB is selected from the group consisting of: unsubstituted phenyl, substituted phenyl, unsubstituted $C_1$-$C_6$ alkyl, substituted $C_1$-$C_6$ alkyl, unsubstituted $C_3$-$C_6$ cycloalkyl, and substituted $C_3$-$C_6$ cycloalkyl, wherein substituted is selected from one or more $CH_2OH$, $C_1$-$C_3$ alkyl and $SO_2(C_1$-$C_3$ alkyl);

$R^C$ is selected from the group consisting of: hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, and partially or fully halogenated cyclopropyl;

each $R^1$, when present, is selected from the group consisting of: chlorine, bromine, iodine, $C_1$-$C_3$ alkyl, $C_2$-$C_3$ alkenyl, $C_2$-$C_5$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, $O(C_1$-$C_3$ alkyl), and $O(C_1$-$C_3$ haloalkyl);

each $R^{1b}$, when present, independently is selected from the group consisting of: hydrogen, halogen, $C_1$-$C_3$ alkyl, $C_2$-$C_3$ alkenyl, $C_2$-$C_3$ alkynyl, cyclopropyl, $C_1$-$C_3$ haloalkyl, $C_2$-$C_3$ haloalkenyl, $C_2$-$C_3$ haloalkynyl, partially or fully halogenated cyclopropyl, $O(C_1$-$C_3$ alkyl), and $O(C_1$-$C_3$ haloalkyl);

each of $R^2$ and $R^3$, when present, independently is selected from the group consisting of: $C_1$-$C_3$ alkyl, $C_2$-$C_3$ alkenyl, $C_2$-$C_3$ alkynyl, and, when present, $R^2$ and $R^3$ taken together form a 3 membered cycloalkyl ring; and each of $R^{2a}$ and $R^{3a}$, when present, independently is selected from the group consisting of: hydrogen, $C_1$-$C_3$ alkyl, $C_2$-$C_3$ alkenyl, $C_2$-$C_3$ alkynyl, and $R^{2a}$ and $R^{3a}$ taken together form a 3 membered cycloalkyl ring, or a stereoisomer, enantiomer, or tautomer thereof, or a veterinary or pharmaceutically acceptable salt thereof.

2. The compound of claim 1, wherein A is selected from the group consisting of

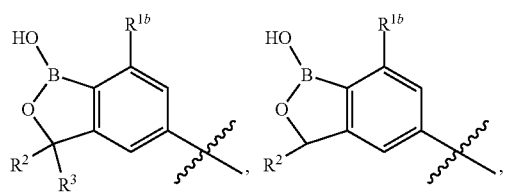

-continued

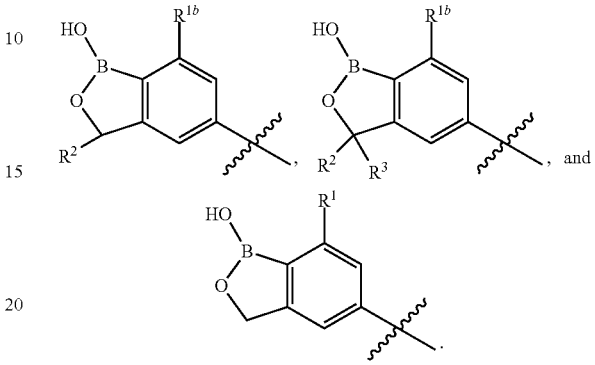

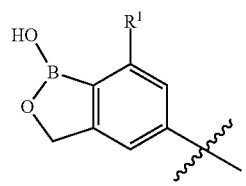

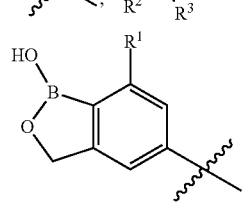

3. The compound of claim 1, wherein X is NH.

4. A compound selected from the group consisting of:

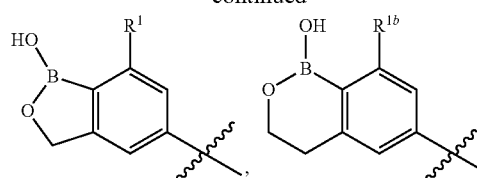

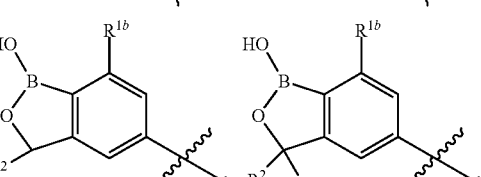

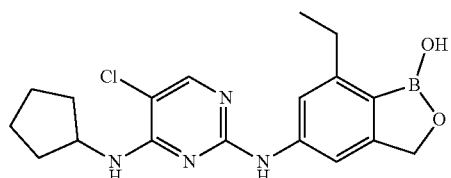

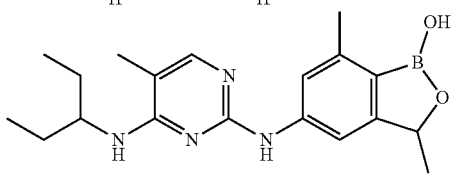

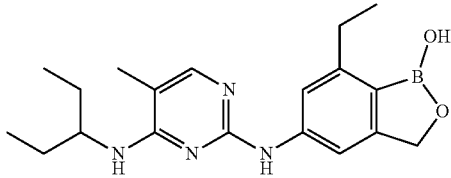

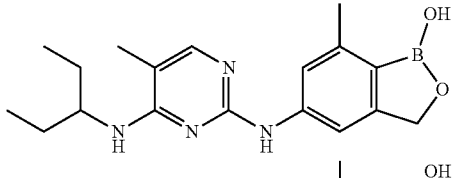

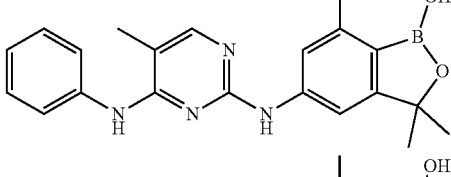

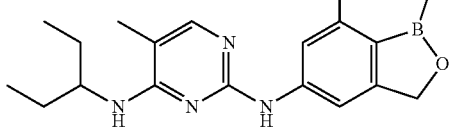

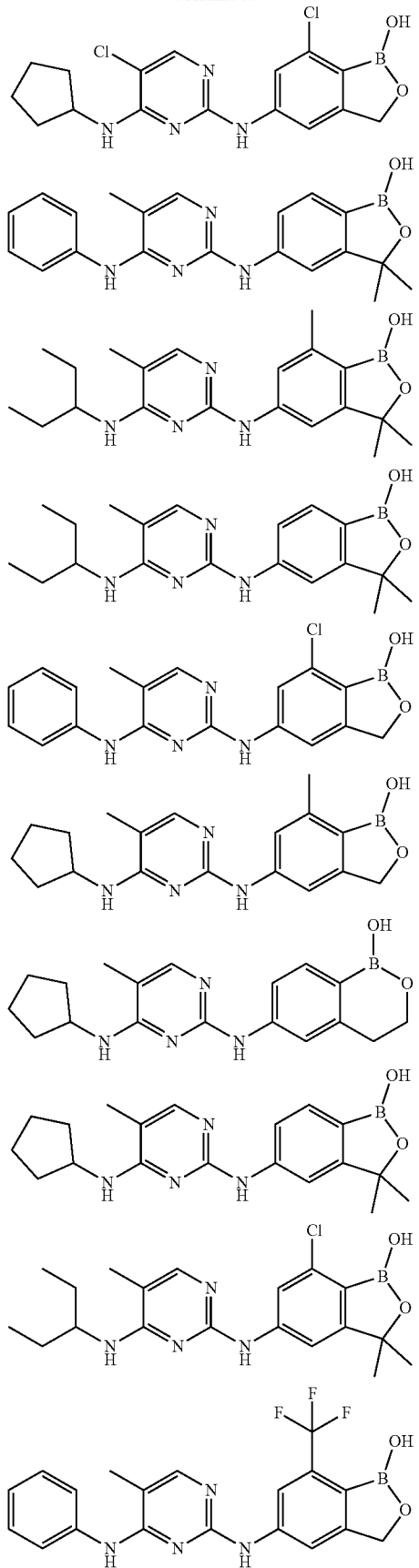
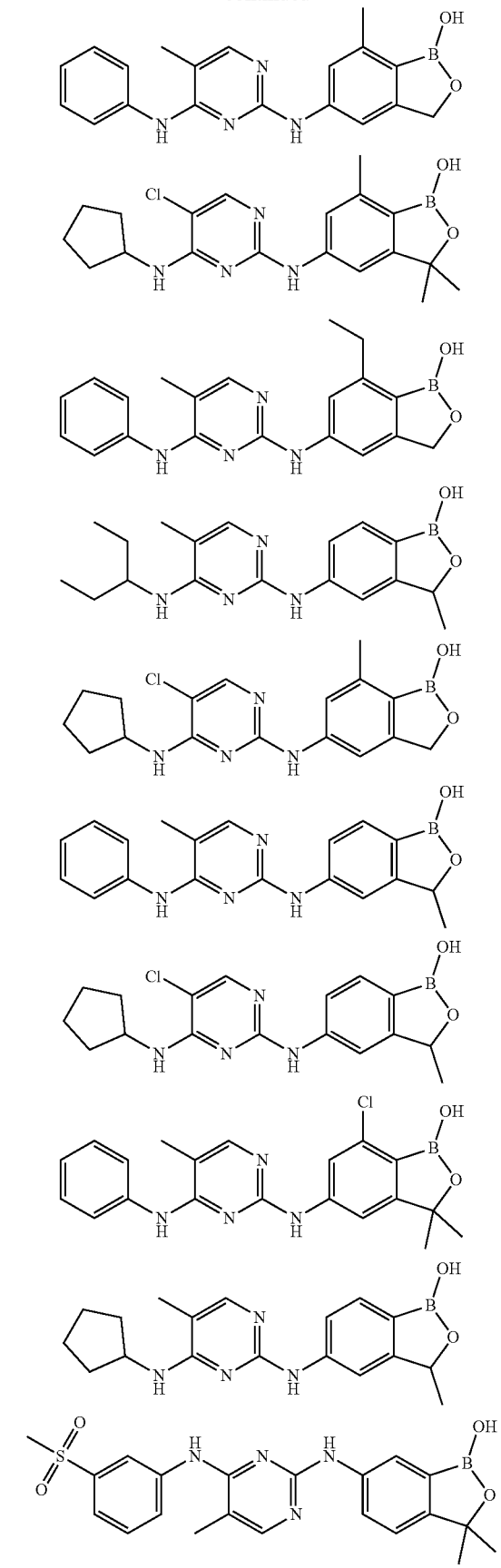

-continued

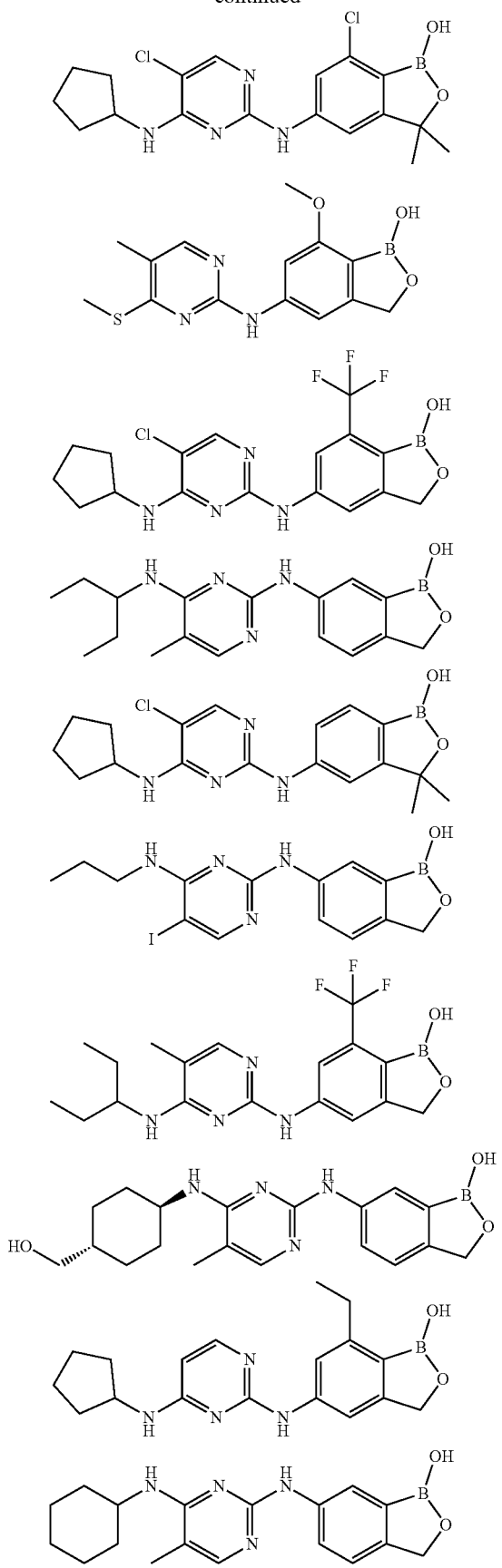

-continued

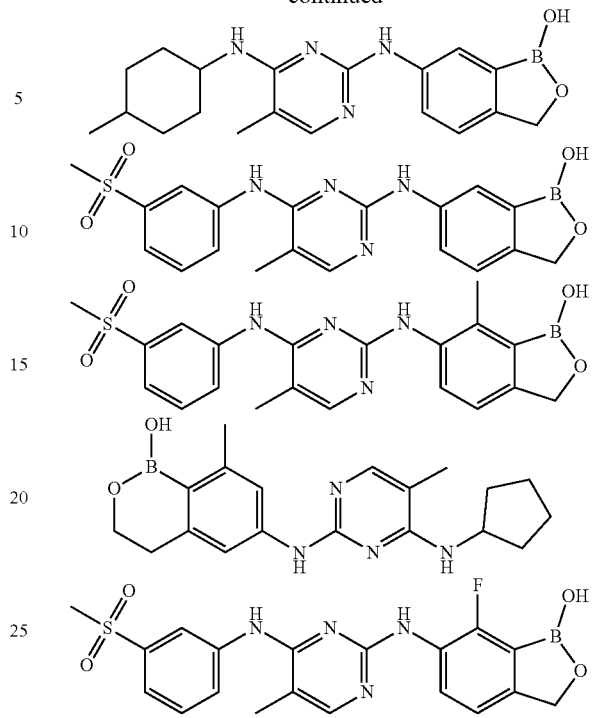

or a stereoisomer, enantiomer, or tautomer thereof, or a veterinary or pharmaceutically acceptable salt thereof.

5. A method for treating a patient having a disease or disorder susceptible to modulation of one or more of (i) JAK, and (ii) JAK and an additional enzyme, comprising administering a therapeutically effective amount of a compound of claim 1,
wherein the additional enzyme is a tyrosine kinase or PDE4.

6. The method of claim 5, wherein the additional tyrosine kinase is one or more of TrkA and Syk.

7. The method of claim 5, wherein the disease or disorder is one or more of atopic dermatitis, psoriasis, psoriatic arthritis, Bechet's disease, *pityriasis rubra* pilaris, alopecia areata, discoid lupus erythematosus, vitiligo, palmoplantar pustulosis, mucocutaneous disease erythema multiforme, mycosis fungoides, graft-versus-host disease, cutaneous lupus, rheumatoid arthritis (RA), arthritis, ulcerative colitis, Crohn's disease, inflammatory bowel disease (IBD), transplant rejection, systemic lupus erythematosus (SLE), dermatomyositis, Sjogren's syndrome, dry eye disease, secondary hypereosinophilic syndrome (HES), allergy, allergic dermatitis, asthma, vasculitis, multiple sclerosis, diabetic nephropathy, cardiovascular disease, artherosclerosis, and cancer.

8. The method of claim 7, wherein the disease or disorder is one or more of atopic dermatitis, psoriasis, and rheumatoid arthritis.

9. The method according to any one of claims 5-8, wherein the compound is administered in an amount to perturb an immune regulatory pathway in a cell, wherein the perturbation results in an effect on the JAK-STAT pathway.

10. A method of inhibiting JAK in combination with PDE4, in a mammalian cell comprising contacting the mammalian cell with a compound of claim 1,
wherein the mammalian cell is a cell from a subject having an inflammatory condition.

11. The method according to claim 10, wherein the inhibition is selective for JAK-1.

12. A method of inhibiting JAK alone or with one or more of TrkA and Syk, in a mammalian cell comprising contacting the mammalian cell with a compound any one of claim 1, wherein the mammalian cell is a cell from a subject having an inflammatory condition.

13. The method according to claim 12, wherein the inhibition is selective for JAK-1.

14. A method for treating one or more diseases or disorders of inflammation, auto-immune dysfunction, and cancer comprising administering to a subject in need thereof an effective amount of a compound of claim 1,
wherein the disease or disorder is atopic dermatitis, psoriasis, or rheumatoid arthritis, and
wherein the subject is a mammal.

15. The method of claim 14, wherein the mammal is selected from humans, livestock mammals, domestic mammals, or companion mammals.

16. A composition comprising a compound of claim 1, and a pharmaceutically or veterinary acceptable carrier.

17. A combination comprising a compound of claim 1, and one or more other pharmaceutical or veterinary active substances.

18. A compound is selected from the group consisting of:

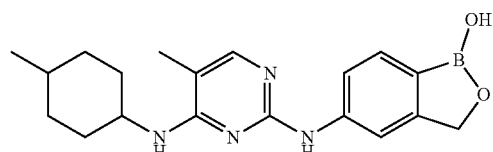

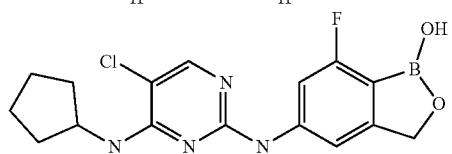

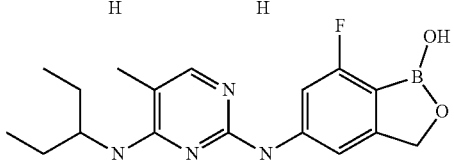

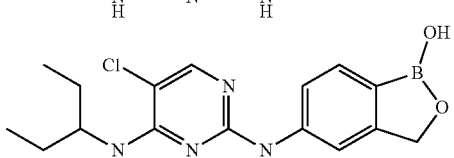

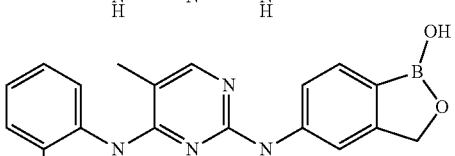

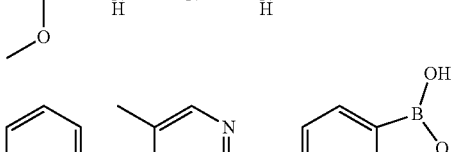

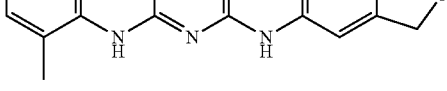

-continued

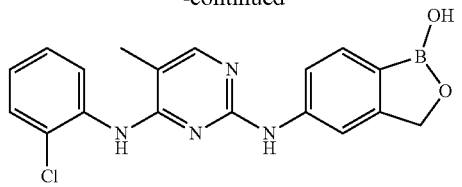

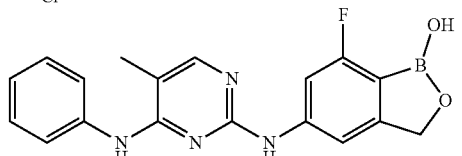

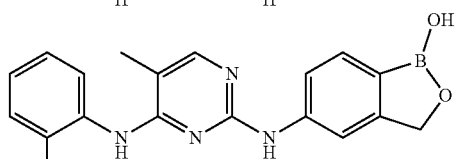

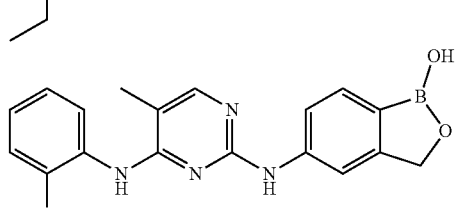

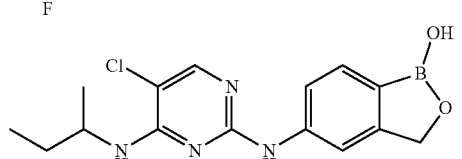

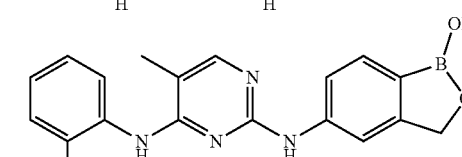

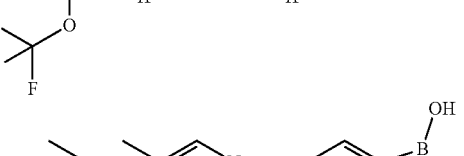

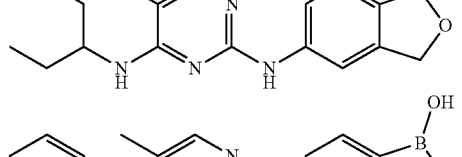

311
-continued
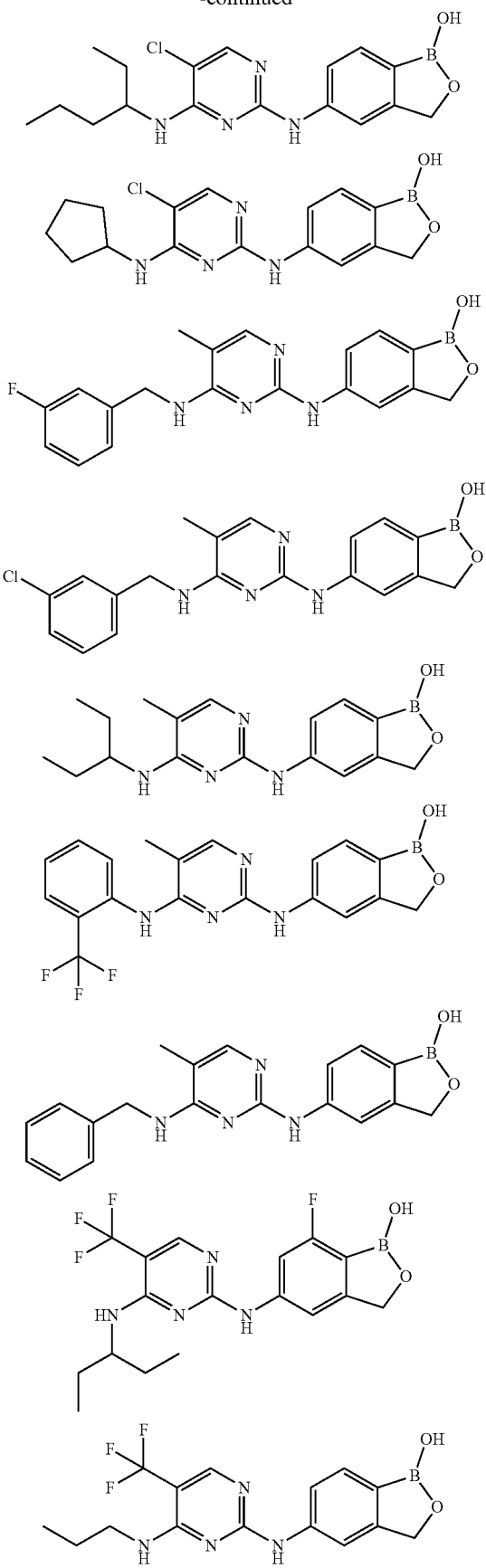
312
-continued
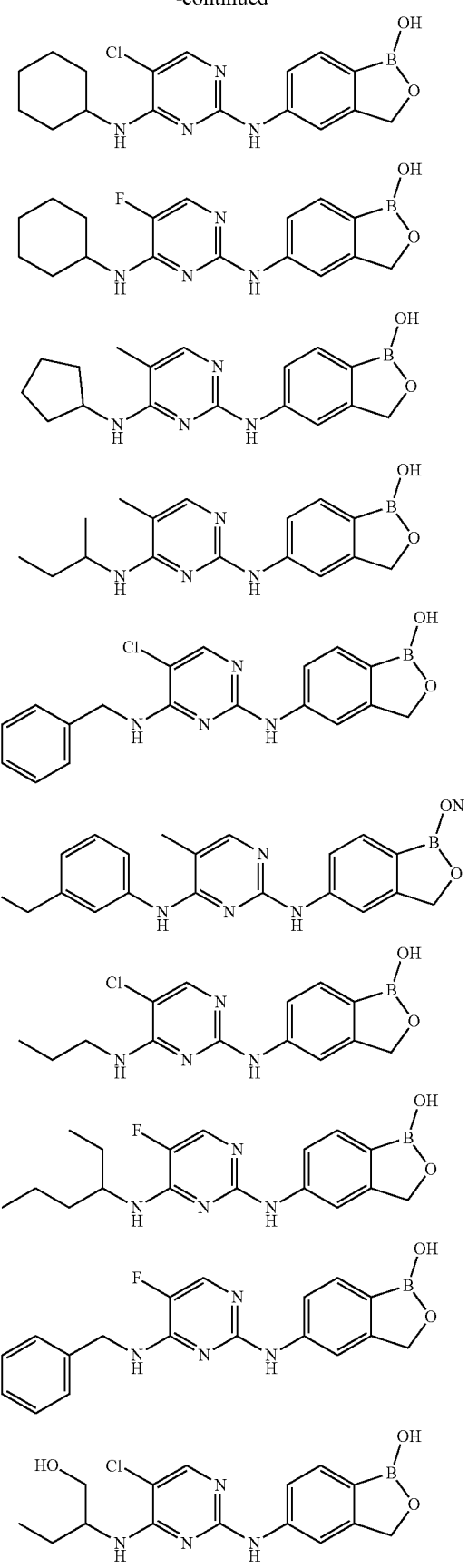

-continued
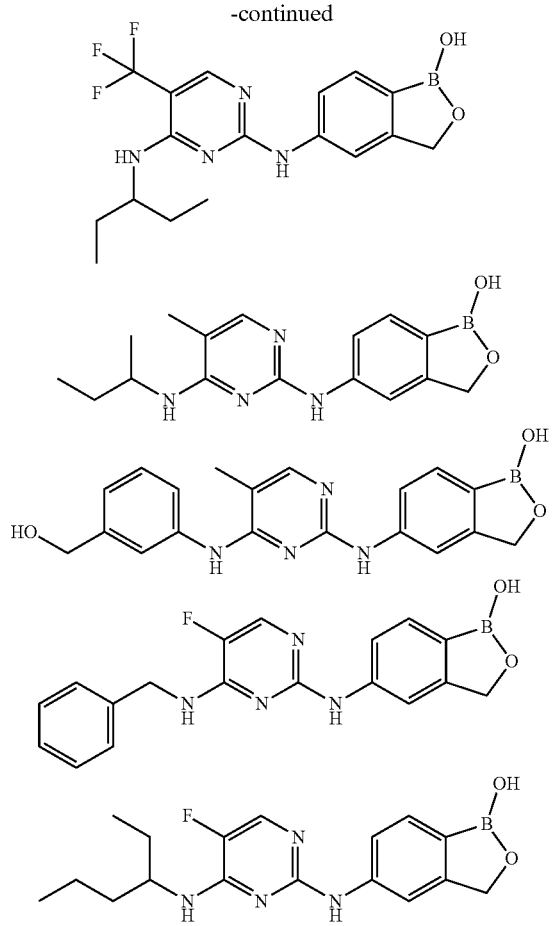
-continued
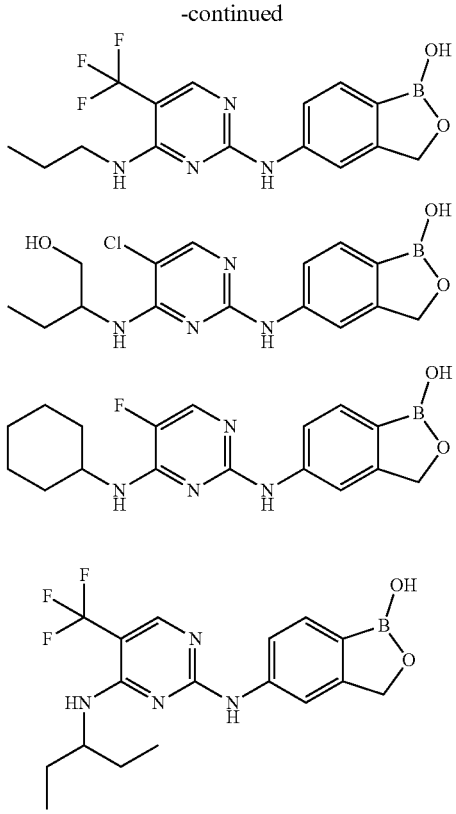
or a stereoisomer, enantiomer, or tautomer thereof, or a veterinary or pharmaceutically acceptable salt thereof.
* * * * *

UNITED STATES PATENT AND TRADEMARK OFFICE
CERTIFICATE OF CORRECTION

PATENT NO. : 12,358,932 B2
APPLICATION NO. : 17/623961
DATED : July 15, 2025
INVENTOR(S) : Zhou et al.

Page 1 of 1

It is certified that error appears in the above-identified patent and that said Letters Patent is hereby corrected as shown below:

In the Claims

Column 303, Claim 1, Line 19, please delete "RB is selected from the" and insert --$R^B$ is selected from the--.

Signed and Sealed this
Nineteenth Day of August, 2025

Coke Morgan Stewart
*Acting Director of the United States Patent and Trademark Office*